(12) United States Patent
Barsanti et al.

(10) Patent No.: US 7,470,709 B2
(45) Date of Patent: Dec. 30, 2008

(54) BENZIMIDAZOLE QUINOLINONES AND USES THEREOF

(75) Inventors: Paul A. Barsanti, Pleasant Hill, CA (US); Dirksen Bussiere, San Leandro, CA (US); Stephen D. Harrison, Albany, CA (US); Carla C. Heise, Benicia, CA (US); Johanna M. Jansen, San Francisco, CA (US); Elisa Jazan, Richmond, CA (US); Timothy D. Machajewski, Martinez, CA (US); Christopher McBride, Oakland, CA (US); William R. McCrea, Jr., Berkeley, CA (US); Simon Ng, Walnut Creek, CA (US); Zhi-Jie Ni, Fremont, CA (US); Sabina Pecchi, Oakland, CA (US); Keith B. Pfister, San Ramon, CA (US); Savithri Ramurthy, Walnut Creek, CA (US); Paul A. Renhowe, Danville, CA (US); Cynthia M. Shafer, El Sobrante, CA (US); Joel B. Silver, Santa Cruz, CA (US); Allan S. Wagman, Belmont, CA (US); Marion Wiesmann, Brisbane, CA (US); Kelly Wayman, San Rafael, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 392 days.

(21) Appl. No.: 10/644,055

(22) Filed: Aug. 19, 2003

(65) Prior Publication Data

US 2004/0092535 A1 May 13, 2004

Related U.S. Application Data

(60) Provisional application No. 60/405,729, filed on Aug. 23, 2002, provisional application No. 60/426,107, filed on Nov. 13, 2002, provisional application No. 60/426,226, filed on Nov. 13, 2002, provisional application No. 60/426,282, filed on Nov. 13, 2002, provisional application No. 60/428,210, filed on Nov. 21, 2002, provisional application No. 60/460,328, filed on Apr. 3, 2003, provisional application No. 60/460,493, filed on Apr. 3, 2003, provisional application No. 60/460,327, filed on Apr. 3, 2003, provisional application No. 60/478,916, filed on Jun. 16, 2003, provisional application No. 60/484,048, filed on Jul. 1, 2003.

(51) Int. Cl.
*A61K 31/47* (2006.01)
(52) U.S. Cl. .......... 514/312; 514/314; 514/313
(58) Field of Classification Search .......... 514/312, 514/314, 313; 546/270.1
See application file for complete search history.

(56) References Cited

U.S. PATENT DOCUMENTS 4,659,657 A 4/1987 Harnisch et al.

(Continued)

FOREIGN PATENT DOCUMENTS

DE 2363459 6/1975

(Continued)

OTHER PUBLICATIONS

Salmon, S. E. et al., *Basic & Clinical Pharmacology, Seventh Edition*, edited by B. Katzung, Appleton & Lange, pp. 29, 881-884 (1998).

(Continued)

*Primary Examiner*—D. Margaret Seaman
(74) *Attorney, Agent, or Firm*—Joseph P. Meara; Foley & Lardner LLP

(57) ABSTRACT

Methods of inhibiting various enzymes and treating various conditions are provided that include administering to a subject a compound of Structure I or IB, a pharmaceutically acceptable salt thereof, a tautomer thereof, or a pharmaceutically acceptable salt of the tautomer. Compounds having the Structure I and IB have the following structures and have the variables described herein. Such compounds may be used to prepare medicaments for use in inhibiting various enzymes and for use in treating conditions mediated by such enzymes.

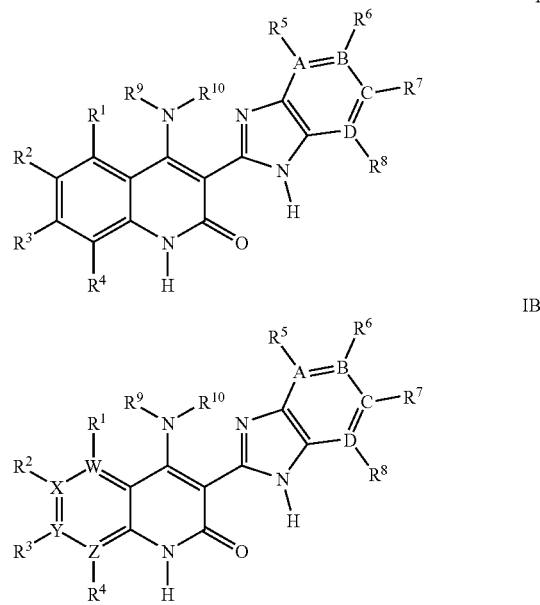

17 Claims, 14 Drawing Sheets

U.S. PATENT DOCUMENTS

| | | | |
|---|---|---|---|
| 5,073,492 | A | 12/1991 | Chen et al. |
| 5,151,360 | A | 9/1992 | Handa et al. |
| 5,330,992 | A | 7/1994 | Eissenstat et al. |
| 5,414,088 | A | 5/1995 | Von Der Saal et al. |
| 5,585,380 | A | 12/1996 | Bianco et al. |
| 5,646,153 | A | 7/1997 | Spada et al. |
| 5,710,158 | A | 1/1998 | Myers et al. |
| 5,763,441 | A | 6/1998 | App et al. |
| 5,792,771 | A | 8/1998 | App et al. |
| 5,801,212 | A | 9/1998 | Okamoto et al. |
| 5,855,866 | A | 1/1999 | Thorpe et al. |
| RE36,256 | E | 7/1999 | Spada et al. |
| 5,942,385 | A | 8/1999 | Hirth |
| 5,981,569 | A | 11/1999 | App et al. |
| 6,057,320 | A | 5/2000 | Spada et al. |
| 6,137,010 | A | 10/2000 | Joo et al. |
| 6,174,912 | B1 | 1/2001 | Beck et al. |
| 6,258,951 | B1 | 7/2001 | Lohmann et al. |
| 6,303,600 | B1 | 10/2001 | Cox et al. |
| 6,306,874 | B1 | 10/2001 | Fraley et al. |
| 6,313,138 | B1 | 11/2001 | Fraley et al. |
| RE37,650 | E | 4/2002 | Myers et al. |
| 6,420,382 | B2 | 7/2002 | Fraley et al. |
| 6,479,512 | B1 | 11/2002 | Fraley et al. |
| 6,593,344 | B1 | 7/2003 | Biedermann et al. |
| 6,605,617 | B2 * | 8/2003 | Renhowe et al. ............ 514/312 |
| 6,759,417 | B2 | 7/2004 | Renhowe et al. |
| 6,762,194 | B2 | 7/2004 | Renhowe et al. |
| 6,774,237 | B2 | 8/2004 | Renhowe et al. |
| 6,774,327 | B1 | 8/2004 | Wong |
| 6,800,760 | B2 * | 10/2004 | Renhowe et al. ......... 546/270.1 |
| 2002/0103230 | A1 | 8/2002 | Renhowe et al. |
| 2002/0107392 | A1 * | 8/2002 | Renhowe et al. ............. 544/60 |
| 2003/0028018 | A1 | 2/2003 | Renhowe et al. |
| 2003/0087854 | A1 | 5/2003 | Monia et al. |
| 2003/0158224 | A1 | 8/2003 | Renhowe et al. |
| 2003/0207883 | A1 | 11/2003 | Renhowe et al. |
| 2004/0220196 | A1 | 11/2004 | Hannah et al. |
| 2005/0261307 | A1 | 11/2005 | Cai et al. |

FOREIGN PATENT DOCUMENTS

| | | |
|---|---|---|
| DE | 3634066 | 4/1988 |
| DE | 19841985 | 3/2000 |
| EP | 0290153 | 11/1988 |
| EP | 0 509 717 | 4/1992 |
| EP | 0 508 800 | 10/1992 |
| EP | 0 747 771 | 12/1996 |
| EP | 0 797 376 | 9/1997 |
| EP | 0 290 153 | 11/1998 |
| EP | 1 086 705 | 3/2001 |
| HU | P0104752 | 7/2002 |
| JP | 63230687 | 9/1988 |
| JP | 6-9952 | 1/1994 |
| JP | 7-43896 | 2/1995 |
| JP | 8-29973 | 2/1996 |
| JP | 63-258903 | 10/1998 |
| WO | 92/18483 | 10/1992 |
| WO | 92/20642 | 11/1992 |
| WO | 95/15758 | 6/1995 |
| WO | 95/18801 | 7/1995 |
| WO | 97/03069 | 1/1997 |
| WO | 97/34876 | 9/1997 |
| WO | 97/48694 | 12/1997 |
| WO | 98/13350 | 4/1998 |
| WO | 99/10349 | 3/1999 |
| WO | 99/50263 | 10/1999 |
| WO | 99/65897 | 12/1999 |
| WO | WO 00/03990 | 1/2000 |
| WO | WO 00/20400 | 4/2000 |
| WO | 00/27379 | 5/2000 |
| WO | WO 00/58315 | 10/2000 |
| WO | WO 00/71129 | 11/2000 |
| WO | 01/02369 | 1/2001 |
| WO | WO 01/12169 | 2/2001 |
| WO | 01/28993 | 4/2001 |
| WO | 01/29025 | 4/2001 |
| WO | WO 01/28993 | 4/2001 |
| WO | 01/52904 | 7/2001 |
| WO | 01/55114 | 8/2001 |
| WO | 01/62251 | 8/2001 |
| WO | 01/62252 | 8/2001 |
| WO | WO 01/74296 | 10/2001 |
| WO | 02/18383 | 3/2002 |
| WO | 02/22598 | * 3/2002 |
| WO | WO 02/18383 | 3/2002 |
| WO | WO 02/22598 | 3/2002 |
| WO | 02/32861 | 4/2002 |
| WO | WO 02/26716 | 4/2002 |
| WO | WO 02/058697 | 8/2002 |
| WO | 03/004488 | 1/2003 |
| WO | WO 03/033472 | 4/2003 |
| WO | WO 03/087095 | 10/2003 |
| WO | WO 2004/018419 | 3/2004 |
| WO | WO 2004/030620 | 4/2004 |
| WO | WO 2004/031401 | 4/2004 |
| WO | WO 2004/043389 | 5/2004 |
| WO | WO 2004/063151 | 7/2004 |
| WO | WO 2004/087153 | 10/2004 |
| WO | WO 2005/046589 | 5/2005 |
| WO | WO 2005/053692 | 6/2005 |
| WO | WO 2006/081445 | 8/2006 |

OTHER PUBLICATIONS

Milauer, B. et al., "Glioblastoma Growth Inhibited In Vivo by a Dominant-Negative Flk-1 Mutant," *Nature*, vol. 367, pp. 576-579 (1994); published by Nature Publishing Group.

Pinedo, H. M. et al., "Translational Research: The Role of VEGF in Tumor Angiogenesis," *The Oncologist 2000*, vol. 5 (suppl. 1), pp. 1-2 (2000).

McMahon, G., "VEGF Receptor Signaling in Tumor Angiogenesis," *The Oncologist 2000*, vol. 5 (suppl. 1), pp. 3-10 (2000).

European Search Report dated Feb. 28, 2006 for EP 05017665.0.

Ukrainets, et al., "Effective Synthesis of 3-(Benzimidazol-2-yl)-4-Hydroxy-2-Oxo-1,2-Dihydroquinolines," *Tetrahedron Letters*, vol. 36, No. 42, 1995, pp. 7747-7748.

Carla Heise, et al., "In vivo Preclinical Evaluation of Tyrosine Kinase Inhibitors with Potent Effects on Tumor Angiogenesis, Growth and Metastasis," Abstract and presentation material for a presentation at the American Association for Cancer Research meeting held in Apr. 2002.

U.S. Appl. No. 10/644,055, Barsanti, et al., Aug. 2003.

U.S. Appl. No. 10/839,793, Barsanti, et al., May 2004.

U.S. Appl. No. 10/982,543, Cai, et al., Nov. 2004.

Cecil, Textbook of Medicine, 21$^{st}$ Edition (2000), Goldman & Bennett (Editors), W.B. Saunders Company (Publisher), Chapter 198, pp. 1060-1074).

International Search Report for PCT/US2005/005316 dated Nov. 28, 2005.

Zetter, B. R., "Angiogenesis and Tumor Metastasis," *Annu. Rev. Med.*, 1998, vol. 49, pp. 407-424; published by Annual Review Inc.

MSNBC News Services, "Mixed results on new cancer drug," Nov. 9, 2000.

Gura, T., "Systems for Identifying New Drugs Are Often Faulty," *Science*, 1997, vol. 278, pp. 1041-1042.

Dermer, G. B., "Another Anniversary for the War on Cancer," *Biotechnology*, 1994, vol. 12, p. 320.

Freshney, R. I., *Culture of Animal Cells—A Manual of Basic Technique*, 1983, pp. 1-4; published by Alan R. Liss, Inc.

Angiogenesis Foundation, "New Study Shows That Acute Myeloid Leukemia is Angiogenesis-Dependent," Jan. 4, 2000; www.angio.org/newsandviews/ archive2000/jan_4_2000.html.

Hussong, J. W. et al., "Evidence of increased angiogenesis in acute myeloid leukemia," *Blood*, 2000, vol. 95(1), pp. 309-313; The American Society of Hematology.

Kerbel, R. S., "Tumor Angiogenesis: Past, Present and Near Future," *Carcinogenesis*, 2000, vol. 21(3), pp. 505-515; Oxford University Press.

Lundberg, L. G. et al., "Bone Marrow in Polycythemia Vera, Chronic Myelocytic Leukemia, and Myelofibrosis Has an Increased Vascularity," *American Journal of Pathology*, 2000, vol. 157(1), pp. 15-19.

Dankbar, B. et al., "Vascular endothelial growth factor and interleukin-6 in paracrine tumor-stromal cell interactions in multiple myeloma," *Blood*, 2000, vol. 5(8), pp. 2630-2636.

Menzel, T. et al., "Elevated Intracellular Level of Basic Fibroblast Growth Factor Correlates with Stage of Chronic Lymphocytic Leukemia and is Associated With Resistance to Fludarabine," *Blood*, 1996, vol. 87(3), pp. 1056-1063.

Gruber, G. et al., "Basic Fibroblast Growth Factor is Expressed in CD19/CD11c-Positive Cells in Hairy Cell Leukemia," *Blood*, 1999, vol. 94(3), pp. 1077-1085.

Grand, et al., Targeting FGFR3 in Multiple Myeloma: Inhibition of t(4;14) Positive Cells by SU5402 and PD173074, Leukemia, 2004, vol. 18, pp. 962-966.

Dalton, et al., "Multiple Myeloma," Hematology, Am. Soc. Hematol. Educ. Program, 2001, 157-77.

International Search Report for PCT/US04/36956 dated Oct. 2, 2006.

Gontero et al., "Metastasis Markers in Bladder Cancer: A Review of the Literature and Clinical Considerations", European Urology, vol. 46, pp. 296-311 (2004).

Kirstein, CA 145:201781, abstract only of Recent Patents on Anticancer Drug Discovery, vol. 1(2), pp. 153-161 (2006).

Bastin, et al., "Salt Selection and Optimisation Procedures for Parmaceutical New Chemical Entities," *Organic Process Research & Development*, vol. 4, pp. 427-435, 2000.

Winstead, E., "p53 Gene May Help Fight Tumors," *NCI Cancer Bulletin*, vol. 4, No. 5, pp. 1-2, 2007.

Yao, et al., "Cell-specific but p53-independent Regulation of Vascular Endothelial Growth Factor Expression of Interferons in Human Glioblastoma Cells," *Journal of Neuro-Oncology*, vol. 76, pp. 219-225, 2006.

Yoo, et al., "Synchronous Elevation of Soluble Intercellular Adhesion Molecule-1 (ICAM-1) and Vascular Cell Adhesion Molecule-1 (VCAM-1) Correlates with Gastric Cancer Progression," *Yonsei Medical Journal*, vol. 39, No. 1, pp. 27-36, 1998.

Zeng, et al., "HDAC3 is crucial in shear- and VEGF-induced stem cell differentiation toward endothelial cells," *The Journal of Cell Biology*, vol. 174, No. 7, pp. 1059-1069, 2006.

Aprelikova, O., et al., "FLT4, a novel Class III Receptor Tyrosine Kinase in chromosome 5q33-qter1," *Cancer Res.*, vol. 52, pp. 746-748, Feb. 1, 1992, published by The American Association for Cancer Research, Stanford University Libraries' High Wire Press, California, United States of America.

Beals, C. R. et al., "Nuclear Export of NF-ATc Enhanced by Glycogen Synthase Kinase-3," *Science*, vol. 275, pp. 1903-1933, Mar. 28, 1997.

Brownlees, J. et al., "Tau phosphorylation in transgenic mice expressing glycogen synthase kinase-3β transgenes," *NeuroReport*, vol. 8, No. 15, pp. 3251-3255, Oct. 20, 1997; published by Rapid Science Publishers.

Chan, T. A. et al., "14-3-3σ is required to prevent mitotic catastrophe after DNA damage," *Nature*, vol. 401, pp. 616-620, Oct. 7, 1999; published by Macmillan Magazines Ltd.

Chen, G. et al., "The Mood-Stabilizing Agent Valproate Inhibits the Activity of Glycogen Synthase Kinase-3," *J. Neurochem.*, vol. 72, No. 3, 1999, pp. 1327-1330; published by Lippincott Williams & Wilkins, Inc., Philadelphia.

Chesi, M. et al., "Activated fibroblast growth factor receptor 3 is an oncogene that contributes to tumor progression in multiple myeloma," *Blood*, 2001, vol. 97, No. 3, pp. 729-736, Feb. 1, 2001; published by The American Society of Hematology.

Connolly, D., et al., "Human Vascular Permeability Factor," *J. Biol. Chem.*, vol. 264, pp. 20017-20024, 1989, published by The American Society for Biochemistry and Molecular Biology, Inc., Stanford University Libraries' High Wire Press, California, United States of America.

Connolly, D., et al., "Tumor Vascular Permeability Factor Stimulates Endothelial Cell Growth and Angiogenesis," *J. Clin. Invest.*, vol. 84, pp. 1470-1478, Nov. 1989, published by The American Society for Clinical Investigation, Inc., Stanford University Libraries' High Wire Press, California, United States of America.

Cross, A. E. et al., "The inhibition of glycogen synthase kinase-3 by insulin or insulin-like growth factor 1 in the rat skeletal muscle cell line L6 blocked by wortmannin, but not by rapamycin: evidence that wortmannin blocks activation of the mitogen-activated protein kinase pathway in L6 cells between Ras and Raf," *Biochem J.*, vol. 303, pp. 21-26, 1994; (printed in Great Britain).

DeVries, C., et al., "The fms-Like Tyrosine Kinase, a Receptor for Vascular Endothelial Growth Factor," *Science*, vol. 255, pp. 989-991, Feb. 21, 1992, published by The American Society for the Advancement of Science, Stanford University Libraries' High Wire Press, California, United States of America.

Doukas, M. A. et al., "Effect of Lithium on Stem Cell and Stromal Cell Proliferation in vitro," *Exp. Hematol.*, vol. 14, pp. 215-221, 1986; published by International Society for Experimental Hematology.

Ferrara, N., et al., "The Biology of Vascular Endothelial Growth Factor," *Endocrinol. Rev.*, vol. 18, No. 1, pp. 4-25, 1997, published by The Endocrine Society, Stanford University Libraries' High Wire Press, California, United States of America.

Flückiger-Isler, R. E. et al., "Stimulation of rat liver glycogen systhesis by the adenosine kinase inhibitor 5-iodotubercidin," *Biochem. J.*, vol. 292, pp. 85-91, 1993; (printed in Great Britain).

Folkman, J., "Fighting Cancer by Attacking Its Blood Supply," *Scientific American*, vol. 275, pp. 150-154, Sep. 1996, published by Scientific American, Inc., New York, New York, United States of America.

Hammond, W. P. et al., "Lithium Therapy of Canine Cyclic Hematopoiesis," *Blood*, vol. 55, No. 1, pp. 26-28, Jan. 1980.

Heinrich, M. C. et al., "Inhibition of KIT Tyrosine Kinase Activity: A Novel Molecular Approach to the Treatment of KIT-Positive Malignancies," *J. Clin. Oncol.*, vol. 20, No. 6, pp. 1692-1703, Mar. 15, 2002.

Hennequin, L. F., et al., Design and Structure—Activity Relationship of a New Class of Potent VEGF Receptor Tyrosine Kinase Inhibitors,: *J. Med. Chem.*, vol. 42, No. 26, pp. 5369-5389, 1999; published by American Chemical Society, Washington, D.C.

Hirao, A. et al., "DNA Damage-Induced Activation of p53 by the Checkpoint Kinase CHk2," *Science*, vol. 287, pp. 1824-1827, Mar. 10, 2000.

Klein, P. S. et al., "A molecular mechanism for the effect of lithium on development," *Proc. Natl. Acad. Sci. USA*, vol. 93, pp. 8455-8459, Aug. 1996.

Lee, J. et al., "Positive Regulation of Wee1 by Chk1 and 14-3-3 Proteins," *Molecular Biology of the Cell*, vol. 12, pp. 551-563, Mar. 2001; published by The American Society for Cell Biology.

Leung, D., et al., "Vascular Endothelial Growth Factor Is a Secreted Angiogenic Mitogen," *Science*, vol. 246, pp. 1306-1309, Dec. 8, 1989, published by The American Society for the Advancement of Science, Stanford University Libraries' High Wire Press, California, United States of America.

Levis, M. et al., "A FLT3-targeted tyrosine kinase inhibitor is cytotoxic to leukemia cells in vitro and in vivo," *Blood*, vol. 99, No. 11, pp. 3885-3891, Jun. 1, 2002; published by the American Society of Hematology.

Liu, Q. et al., "Chk1 is an essential kinase that is regulated by Atr and required for the $G_2$/M DNA damage checkpoint," *Genes & Development*, vol. 14, 2000, pp. 1448-1459; published by Cold Springs Harbor Laboratory Press.

Lopez-Girona, A. et al., "Nuclear localization of Cdc25 is regulated by DNA damage and a 14-3-3 protein," *Nature*, vol. 397, pp. 172-175, Jan. 14, 1999; published by Macmillan Magazines Ltd.

Lovestone, S. et al., "Alzheimer's disease-like phosphorylation of the microtubule-associated protein tau by glycogen synthase kinase-3 in transfected mammalian cells," *Current Biology*, vol. 4, pp. 1077-1086, Dec. 1, 1994; published by Elsevier Science Ltd.

Lymboussaki, A., "Vascular endothelial growth factors and their receptors in embryos, adults, and in tumors," Academic Dissertation, University of Helsinki, Molecular/Cancer Biology Laboratory and Department of Pathology, Haartman Institute, 1999.

Maguire, M.P., et al., "A New Series of PDGF Receptor Tyrosine Kinase Inhibitors: 3-Substituted Quinoline Derivatives," *J. Med. Chem.*, vol. 37, No. 14, pp. 2129-2137, 1994; published by American Chemical Society, Washington, D.C.

Massillon, D. et al., "Identification of the glycogenic compound 5-iodotubercidin as a general protein kinase inhibitor," *Biochem. J.*, vol. 299, pp. 123-128, 1994; printed in Great Britain.

Matei, S., et al., "Condensation of ethyl 2-benzimidazoleacetate with carbonyl compounds," *Rev. Chim.*, vol. 33, No. 6, pp. 527-530, 1989, published by the Central Institute of Chemistry, Bucharest, Romania.

Mustonen, T., et al., "Endothelial Receptor Tyrosine Kinases Involved in Angiogenesis," *J. Cell Biology*, vol. 129, No. 4, pp. 895-898, May, 1995, published by The Rockfeller University Press, New York, New York, United States of America.

Nonaka, S. et al., "Chronic lithium treatment robustly protects neurons in the central nervous system against excitotoxicity by inhibiting N-methyl-D-aspartate receptor-mediated calcium influx," *Proc. Natl. Acad. Sci. USA*, vol. 95, pp. 2642-2647, Mar. 1998.

Parker, L. L. et al., "Inactivation of the p34cdc2-Cyclin B Complex by the Human WEE1 Tyrosine Kinase," *Science*, vol. 257, pp. 1955-1957, Sep. 25, 1992.

Pei, J.-J. et al., "Distribution, Levels, and Activity of Glycogen Synthase Kinase-3 in the Alzheimer Disease Brain," *Journal of Neuropathology and Experimental Neurology*, vol. 56, No. 1, pp. 70-78, Jan. 1997; published by the American Association of Neuropathologists.

Peng, C.-Y. et al., "Mitotic and $G_2$ Checkpoint Control: Regulation of 14-3-3 Protein Binding by Phosphorylation of Cdc25C on Serine-216," *Science*, vol. 277, pp. 1501-1505, Sep. 5, 1997.

Plouet, J., et al., "Isolation and characterization of a newly identified endothelial cell mitogen produced by AtT-20 cells," *EMBO J.*, vol. 8, No. 12, pp. 3801-3806, 1989, published by IRL Press.

Quinn, T., et al., "Fetal liver kinase 1 is a receptor for vascular endothelial growth factor and is selectively expressed in vascular endothelium," *Proc. Natl. Acad. Sci. USA*, vol. 90, pp. 7533-7537, Aug. 1993.

Saito, Y. et al., "The mechanism by which epidermal growth factor inhibits glycogen synthase kinase 3 in A431 cells," *Biochem. J.*, vol. 303, pp. 27-31, 1994; printed in Great Britain.

Sanchez, Y. et al., "Conservation of the Chk1 Checkpoint Pathway in Mammals: Linkage of DNA Damage to Cdk Regulation Through Cdc25," *Science*, vol. 277, pp. 1497-1501, Sep. 5, 1997.

Shibuya, M., et al., "Nucleotide sequence and expression of a novel human receptor-type tyrosine kinase gene (flt) closely related to the fms family," *Oncogene*, vol. 5, pp. 519-524, 1990, published by Macmillan Press Ltd., Stockton Press Company, Great Britain.

Smolich, B.D. et al., "The antiangiogenic protein kinase inhibitors SU5416 and SU6668 Inhibit the SCF receptor (c-kit) in a human myeloid leukemia cell line and in acute myeloid leukemia blasts," *Blood*, vol. 97, No. 5, pp. 1413-1421, Mar. 1, 2001; published by The American Society of Hematology.

Stambolic, V. et al., "Lithium inhibits glycogen synthase kinase-3 activity and mimics Wingless signaling in intact cells," *Current Biology*, vol. 6, No. 12, pp. 1664-1668, 1996; published by Current Biology Ltd. ISSN 0960-9822.

Stover, D. R., "Recent advances in protein kinase inhibition: Current molecular scaffolds used for inhibitor synthesis," *Current Opinion in Drug Discovery & Development*, vol. 2, No. 4, pp. 274-285, 1999; published by PharmaPress Ltd., London, United Kingdom.

Sun, T-Q. et al.. "PAR-1 is a Dishevelled-associated kinase and a positive regulator of Wnt signalling," *Nature Cell Biology*, vol. 3, pp. 628-636, Jul. 2001; published by Macmillan Magazines Ltd.

Takashima, A. et al., "tau protein kinase I is essential for amyloid β-protein-induced neurotoxicity," *Proc. Natl. Acad. Sci. USA*, vol. 90, pp. 7789-7793, Aug. 1993.

Takashima, A. et al., "Presenilin 1 associates with glycogen synthase kinase-3β and its substrate tau," *Proc. Natl. Acad. Sci. USA*, vol. 95, pp. 9637-9641, Aug. 1998; published by The National Academy of Sciences.

Terman, B., et al., "Identification of a new endothelial cell growth factor receptor tyrosine kinase," *Oncogene*, vol. 6, pp. 1677-1683, 1991, published by Macmillan Press Ltd., Stockton Press Company, Great Britain.

Thomas, M.D., R. J. et al., "Progress in Geriatrics: Excitatory Amino Acids in Health and Disease," *J. of the American Geriatrics Society*, vol. 43, No. 11, Nov. 1995; published by American Geriatrics Society.

Ukrainets, I., "Effective Synthesis of 3-(Benzimidazol-2-yl)-4-Hydroxy-2-Oxo-1,2-Dihydroquinolines," *Tet. Lett.*, vol. 36, No. 42, pp. 7747-7748, 1995, published by Elsevier Science Ltd., Great Britain.

Ukrainets, I., et al., "2-Carbethoxymethyl-4H-3,1-Benzoxazin-4-One. 3.*Condensation of o-Phenylenediamine," pp. 198-200, translated from *Khimiya Geterotsiklicheskikh Soedinii*, No. 2, pp. 239-241, Feb. 1992, published by Plenum Publ. Corp., London, Great Britain.

Ukrainets, I., et al., "4-Hydroxy-2-Quinolones 7.* Synthesis and Biological Properties of 1-R-3-(2-Benzimidazolyl)-4-Hydroxy-2-Quinolones," pp. 92-94, translated from *Khimiya Geterotsiklicheskikh Soedinii*, No. 1, pp. 105-108, Jan. 1993, published by Plenum Publ. Corp., London, Great Britain.

Ukrainets, I., et al., "4-Hydroxy-2-Quinolones. 16.* Condensation of N-R-Substituted Amides of 2-Carboxy-Malonanilic Acid With o-Phenylenediamine," pp. 941-944, translated from *Khimiya Geterotsiklicheskikh Soedinii*, vol. 8, pp. 1105-1108, Aug. 1993, published by Plenum Publ. Corp., London, Great Britain.

Ukrainets, I., et al., "4-Hydroxy-2-Quinolones. 32.* Synthesis and Antithyroid Activity of Thio Analogs of 1H-2-OXO-3-(2-Benzimidazolyl)-4-HydroxyQuinoline," *Chem. Heterocyclic Comp.*, vol. 33, No. 5, pp. 600-604, 1997, published by Kluwer Academic Publishers, London, Great Britain.

Ullrich, A., et al., "Signal Transduction by Receptors with Tyrosine Kinase Activity," *Cell*, vol. 61, pp. 203-212, Apr. 20, 1990, published by Cell Press, Cambridge, Massachusetts, United States of America.

van der Geer, P., et al., "Receptor Protein-Tyrosine Kinases and Their Signal Transduction Pathways," *Annu. Rev. Cell Biol.*, vol. 10, pp. 251-337, 1994, published by Annual Reviews, Inc., Palo Alto, California, United States of America.

Vogelstein, B. et al., "Surfing the p53 network," *Nature*, vol. 408, pp. 307-310, Nov. 16, 2000; published by Macmillan Magazines Ltd.

Welsh, G. I. et al., "Glycogen synthase kinase-3 is rapidly inactivated in response to insulin and phosphorylates eukaryotic initiation factor eIF-2B," *Biochem. J.*, vol. 294, pp. 625-629, 1993; printed in Great Britain.

Yamasaki, Y. et al., "Pioglitazone (AD-4833) Ameliorates Insulin Resistance in Patients with NIDDM," *Tohoku J. Exp. Med.*, vol. 183, pp. 173-183, 1997.

Zhao, H. et al., "ATR-Mediated Checkpoint Pathways Regulate Phosphorylation and Activation of Human Chk1," *Molecular and Cellular Biology*, vol. 21, No. 13, pp. 4129-4139, Jul. 2001; published by American Society for Microbiology.

Zhang, Z. et al., "Destabilization of β-catenin by mutations in presenilin-1 potentiates neuronal apoptosis," *Nature*, vol. 395, pp. 698-702, Oct. 15, 1998; published by Macmillan Publishers Ltd.

List of compounds purchased from various vendors (3 pages).

CAS printout for 304876-79-7 Registry File, entry date into Registry File Nov. 29, 2000.

CAS printout for 300591-52-0 Registry File, entry date into Registry File Oct. 31, 2000.

Majolini, M. B. et al., "Dysregulation of the Protein Tyrosine Kinase LCK in Lymphoproliferative Disorders and in Other Neoplasias," *Leukemia and Lymphoma*, vol. 35(3-4), 1999, pp. 245-254; published by OPA (Overseas Publishers Association) N.V.

Śuśa, M. et al., "Src inhibitors: drugs for the treatment of osteoporosis, cancer or both?," *TiPS*, vol. 21, Dec. 2000, pp. 489-495; published by Elsevier Science Ltd.

Berwanger, B. et al., "Loss of a *FYN*-regulated differentiation and growth arrest pathway in advanced stage neuroblastoma," *Cancer Cell*, vol. 2, Nov. 2002, pp. 377-386; published by Cell Press.

Siemeister, G. et al., "Two Independent Mechanisms Essential for Tumor Angiogenesis: Inhibition of Human Melanoma Xenograft Growth by interfering with either the Vascular Endothelial Growth Factor Receptor Pathway or the Tie-2 Pathway," *Cancer Research*, vol. 59, Jul. 1, 1999, pp. 3185-3191.

Valtola, R. et al., "VEGFR-3 and Its Ligand VEGF-C Are Associated with Angiogenesis in Breast Cancer," *American Journal of Pathology*, vol. 154, No. 5, May 1999, pp. 1381-1390; published by American Society for Investigative Pathology.

Trudel, S. et al., "CHIR-258, a novel, multitargeted tyrosine kinase inhibitor for the potential treatment of t(4;14) multiple myeloma," *Blood*, Apr. 1, 2005, vol. 105, No. 7, pp. 2941-2948.

Lee, S. H. et al., "In vivo Target Modulation and Biological Activity of CHIR-258, a Multitargeted Growth Factor Receptor Kinase Inhibitor, in Colon Cancer Models," *Clin. Cancer. Res.*, May 15, 2005, vol. 11, No. 10; pp. 3633-3641.

Lopes de Menezes, D. E. et al., "CHIR-258: A Potent Inhibitor of FLT3 Kinase in Experimental Tumor Xenograft Models of Human Acute Myelogenous Leukemia," *Clin. Cancer. Res.*, Jul. 15, 2005, vol. 11, No. 14, pp. 5281-5291.

Carmeliet, P. et al. "Angiogenesis in Cancer and Other Diseases," Nature, 407, pp. 249-257 (2000).

* cited by examiner

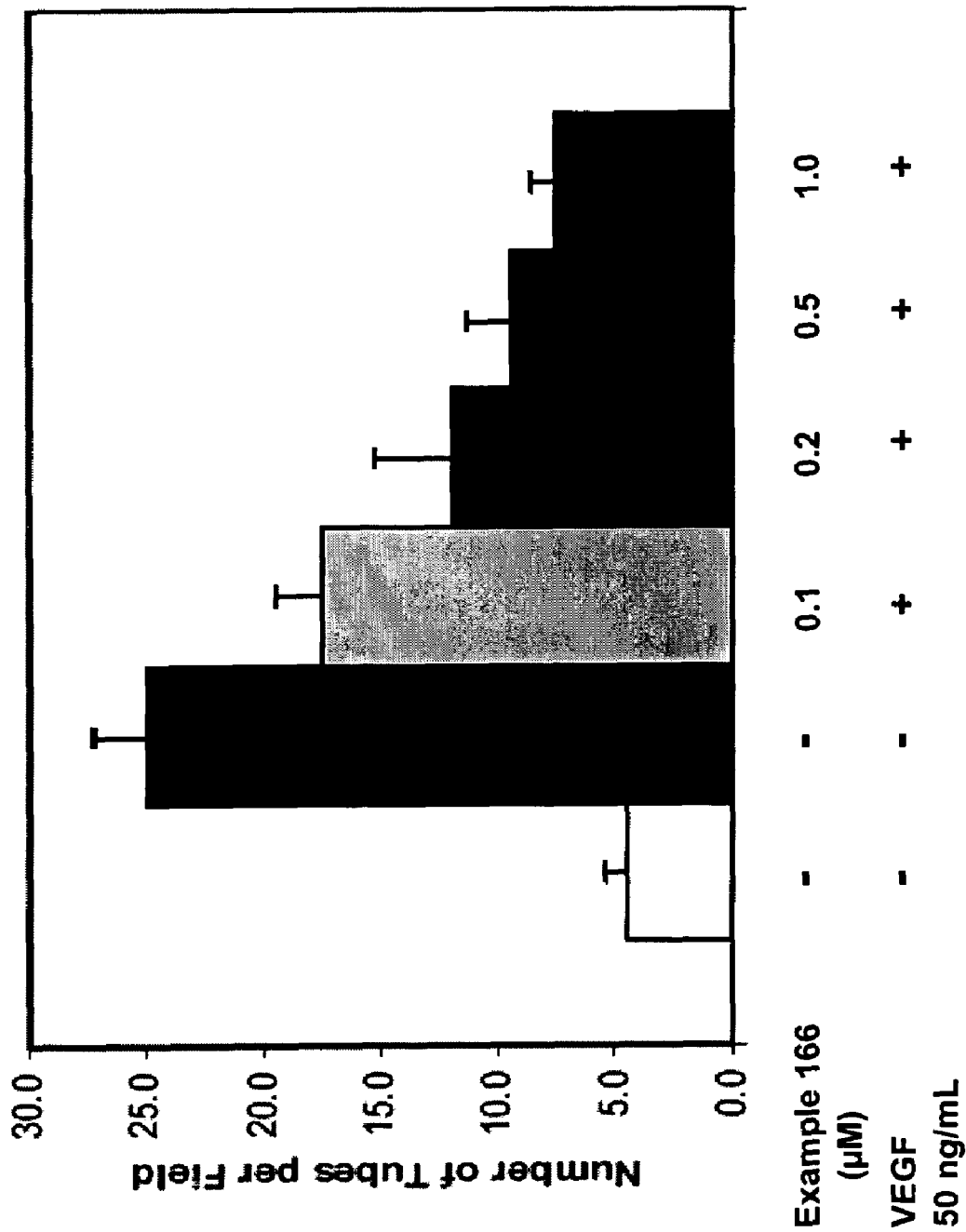

BENZIMIDAZOLE QUINOLINONES AND USES THEREOF

CROSS-REFERENCES TO RELATED APPLICATIONS

This application claims priority to the following U.S. provisional applications: U.S. Provisional Application No. 60/405,729, filed on Aug. 23, 2002; U.S. Provisional Application No. 60/428,210, filed on Nov. 21, 2002; U.S. Provisional Application No. 60/484,048 filed on Jul. 1, 2003; U.S. Provisional Application No. 60/426,282, filed on Nov. 13, 2002; U.S. Provisional Application No. 60/460,493, filed on Apr. 3, 2003; U.S. Provisional Application No. 60/426,226, filed on Nov. 13, 2002; U.S. Provisional Application No. 60/460,327, filed on Apr. 3, 2003; U.S. Provisional Application No. 60/478,916, filed on Jun. 16, 2003; U.S. Provisional Application No. 60/426,107, filed on Nov. 13, 2002; and U.S. Provisional Application No. 60/460,328, filed on Apr. 3, 2003. The disclosure of each of the above provisional applications is herein incorporated by reference in its entirety and for all purposes as if fully set forth herein.

FIELD OF THE INVENTION

This invention pertains generally to methods and compositions for treating a variety of patients and cell subjects. More particularly, the present invention provides novel compositions of matter and methods for angiogenesis inhibition, treating cancer, treating diabetes, stimulating insulin-dependent processes, treating Alzheimer's disease, treating bipolar disorder, treating central nervous system disorders, prolonging immune responses, reducing the splitting of centrosomes, blocking DNA repair, modulating cell cycle arrest, and inhibiting enzymes such as serine/threonine kinases and tyrosine kinases. The present invention thus has application in the areas of oncology, diabetes, immunology, and medicinal chemistry.

BACKGROUND OF THE INVENTION

Capillaries reach into almost all tissues of the human body and supply tissues with oxygen and nutrients as well as removing waste products. Under typical conditions, the endothelial cells lining the capillaries do not divide, and capillaries, therefore, do not normally increase in number or size in a human adult. Under certain normal conditions, however, such as when a tissue is damaged, or during certain parts of the menstrual cycle, the capillaries begin to proliferate rapidly. This process of forming new capillaries from pre-existing blood vessels is known as angiogenesis or neovascularization. See Folkman, J. Scientific American 275, 150-154 (1996). Angiogenesis during wound healing is an example of pathophysiological neovascularization during adult life. During wound healing, the additional capillaries provide a supply of oxygen and nutrients, promote granulation tissue, and aid in waste removal. After termination of the healing process, the capillaries normally regress. Lymboussaki, A. "Vascular Endothelial Growth Factors and their Receptors in Embryos, Adults, and in Tumors" Academic Dissertation, University of Helsinki, Molecular/Cancer Biology Laboratory and Department of Pathology, Haartman Institute, (1999).

Angiogenesis also plays an important role in the growth of cancer cells. It is known that once a nest of cancer cells reaches a certain size, roughly 1 to 2 mm in diameter, the cancer cells must develop a blood supply in order for the tumor to grow larger as diffusion will not be sufficient to supply the cancer cells with enough oxygen and nutrients. Thus, inhibition of angiogenesis is expected to halt the growth of cancer cells.

Receptor tyrosine kinases (RTKs) are transmembrane polypeptides that regulate developmental cell growth and differentiation, remodeling and regeneration of adult tissues. Mustonen, T. et al., J. Cell Biology 129, 895-898 (1995); van der Geer, P. et al. Ann Rev. Cell Biol. 10, 251-337 (1994). Polypeptide ligands known as growth factors or cytokines, are known to activate RTKs. Signaling RTKs involves ligand binding and a shift in conformation in the external domain of the receptor resulting in its dimerization. Lymboussaki, A. "Vascular Endothelial Growth Factors and their Receptors in Embryos, Adults, and in Tumors" Academic Dissertation, University of Helsinki, Molecular/Cancer Biology Laboratory and Department of Pathology, Haartman Institute, (1999); Ullrich, A. et al., Cell 61, 203-212 (1990). Binding of the ligand to the RTK results in receptor trans-phosphorylation at specific tyrosine residues and subsequent activation of the catalytic domains for the phosphorylation of cytoplasmic substrates. Id.

Two subfamilies of RTKs are specific to the vascular endothelium. These include the vascular endothelial growth factor (VEGF) subfamily and the Tie receptor subfamily. Class V RTKs include VEGFR1 (FLT-1), VEGFR2 (KDR (human), Flk-1 (mouse)), and VEGFR3 (FLT-4). Shibuya, M. et al., Oncogene 5, 519-525 (1990); Terman, B. et al., Oncogene 6, 1677-1683 (1991); Aprelikova, O. et al., Cancer Res. 52, 746-748 (1992).

Members of the VEGF subfamily have been described as being able to induce vascular permeability and endothelial cell proliferation and further identified as a major inducer of angiogenesis and vasculogenesis. Ferrara, N. et al., Endocrinol. Rev. 18, 4-25 (1997). VEGF is known to specifically bind to RTKs including FLT-1 and Flk-1. DeVries, C. et al., Science 255, 989-991 (1992); Quinn, T. et al., Proc. Natl. Acad. Sci. 90, 7533-7537 (1993). VEGF stimulates the migration and proliferation of endothelial cells and induces angiogenesis both in vitro and in vivo. Connolly, D. et al., J. Biol. Chem. 264, 20017-20024 (1989); Connolly, D. et al., J. Clin. Invest. 84, 1470-1478 (1989); Ferrara, N. et al., Endocrino. Rew. 18, 4-25 (1997); Leung, D. et al., Science 246, 1306-1309 (1989); Plouet, J. et al., EMBO J 8, 3801-3806 (1989).

Because angiogenesis is known to be critical to the growth of cancer and to be controlled by VEGF and VEGF-RTK, substantial efforts have been undertaken to develop compounds which inhibit or retard angiogenesis and inhibit VEGF-RTK.

Platelet derived growth factor receptor kinase (PDGFR) is another type of RTK. PDGF expression has been shown in a number of different solid tumors, from glioblastomas to prostate carcinomas. In these various tumor types, the biological role of PDGF signaling can vary from autocrine stimulation of cancer cell growth to more subtle paracrine interactions involving adjacent stroma and angiogenesis. Therefore, inhibiting the PDGFR kinase activity with small molecules may interfere with tumor growth and angiogenesis.

Tie-2 is a membrane RTK. Upon binding to its ligand, Tie-2 is activated and phosphorylates its downstream signal proteins. Tie-2 kinase activity may then trigger a pathway of cellular response that leads to stabilization of vascular vessels in cancer. Therefore, blocking kinase activity of Tie-2, in synergy with blockage of activity of other angiogenic kinases such as VEGF and FGFR1 receptor kinases, may be effective in cutting off the blood supply to cancer cells and in treating the disease.

FLT-3 is a receptor tyrosine kinase belonging to the PDGF Receptor family expressed on acute myelogenous leukemia (AML) cells in a majority of patients and can be present in wildtype form or have activating mutations that result in constitutively active kinase function. An internal tandem repeat (ITD) mutation is expressed in about 25% of AML patients and has been associated with poor prognosis in AML patients. Levis, M et al Blood 99, 11; 2002.

c-Kit is another receptor tyrosine kinase belonging to PDGF Receptor family and is normally expressed in hematopoietic progenitor, mast and germ cells. C-kit expression has been implicated in a number of cancers including mast cell leukemia, germ cell tumors, small-cell lung carcinoma, gastrointestinal stromal tumors, acute myelogenous leukemia (AML), neuroblastoma, melanoma, ovarian carcinoma, breast carcinoma. Heinrich, M. C. et al; J. Clin. Onc. 20, 6 1692-1703, 2002 (review article); Smolich, B. D. et al Blood, 97, 5; 1413-1421.

c-ABL is a tyrosine kinase that was originally identified as an oncogene product from the genome of the Abelson murine leukemia virus. About 90% of chronic myelogenous leukemia (CML), 20-30% of acute lymphoblastic leukemia (ALL) and about 1% of acute myeloblastic leukemia (AML) have a reciprocal translocation between chromsome 9 and 22. The translocation results in the 'Philadelphia' chromosome and is the reason for the expression of a chimeric BCR/ABL transcript.

FGFR3 is a tyrosine kinase associated with various cancers. Fibroblast growth factor receptor 3 (FGFR3) is a class IV receptor tyrosine kinase. FGFR3 is deregulated due to a t(4, 14) translocation in about 15% of multiple myeloma patients. This translocation causes the expression of a functional FGFR3 that can respond to FGF1 in e.g. the bone microenvironment. In some cases, activating mutations that make FGFR3 ligand independent have been identified. These activating FGFR3 mutations have been found to cause Ras-like tumor progression and evidence exists that similar signaling pathways are utilized (Chesi et al Blood 2001 97 729-736.).

Glycogen synthase kinase 3 (GSK-3) is a serine/threonine kinase for which two isoforms, α and β, have been identified. Woodgett, *Trends Biochem. Sci.*, 16:177-81 (1991). Both GSK-3 isoforms are constitutively active in resting cells. GSK-3 was originally identified as a kinase that inhibits glycogen synthase by direct phosphorylation. Upon insulin activation, GSK-3 is inactivated, thereby allowing the activation of glycogen synthase and possibly other insulin-dependent events, such glucose transport. Subsequently, it has been shown that GSK-3 activity is also inactivated by other growth factors that, like insulin, signal through receptor tyrosine kinases (RTKs). Examples of such signaling molecules include IGF-1 and EGF. Saito et al., *Biochem. J.*, 303:27-31 (1994); Welsh et al., *Biochem. J.* 294:625-29 (1993); and Cross et al., *Biochem. J.*, 303:21-26 (1994).

Agents that inhibit GSK-3 activity are useful in the treatment of disorders that are mediated by GSK-3 activity. In addition, inhibition of GSK-3 mimics the activation of growth factor signaling pathways and consequently GSK-3 inhibitors are useful in the treatment of diseases in which such pathways are insufficiently active. Examples of diseases that can be treated with GSK-3 inhibitors are described below.

Diabetes mellitus is a serious metabolic disease that is defined by the presence of chronically elevated levels of blood glucose (hyperglycemia). This state of hyperglycemia is the result of a relative or absolute lack of activity of the peptide hormone, insulin. Insulin is produced and secreted by the β cells of the pancreas. Insulin is reported to promote glucose utilization, protein synthesis, and the formation and storage of carbohydrate energy as glycogen. Glucose is stored in the body as glycogen, a form of polymerized glucose, which may be converted back into glucose to meet metabolism requirements. Under normal conditions, insulin is secreted at both a basal rate and at enhanced rates following glucose stimulation, all to maintain metabolic homeostasis by the conversion of glucose into glycogen.

The term diabetes mellitus encompasses several different hyperglycemic states. These states include Type 1 (insulin-dependent diabetes mellitus or IDDM) and Type 2 (non-insulin dependent diabetes mellitus or NIDDM) diabetes. The hyperglycemia present in individuals with Type 1 diabetes is associated with deficient, reduced, or nonexistent levels of insulin that are insufficient to maintain blood glucose levels within the physiological range. Conventionally, Type 1 diabetes is treated by administration of replacement doses of insulin, generally by a parental route. Since GSK-3 inhibition stimulates insulin-dependent processes, it is useful in the treatment of type 1 diabetes.

Type 2 diabetes is an increasingly prevalent disease of aging. It is initially characterized by decreased sensitivity to insulin and a compensatory elevation in circulating insulin concentrations, the latter of which is required to maintain normal blood glucose levels. Increased insulin levels are caused by increased secretion from the pancreatic beta cells, and the resulting hyperinsulinemia is associated with cardiovascular complications of diabetes. As insulin resistance worsens, the demand on the pancreatic beta cells steadily increases until the pancreas can no longer provide adequate levels of insulin, resulting in elevated levels of glucose in the blood. Ultimately, overt hyperglycemia and hyperlipidemia occur, leading to the devastating long-term complications associated with diabetes, including cardiovascular disease, renal failure and blindness. The exact mechanism(s) causing type 2 diabetes are unknown, but result in impaired glucose transport into skeletal muscle and increased hepatic glucose production, in addition to inadequate insulin response. Dietary modifications are often ineffective, therefore the majority of patients ultimately require pharmaceutical intervention in an effort to prevent and/or slow the progression of the complications of the disease. Many patients can be treated with one or more of the many oral anti-diabetic agents available, including sulfonylureas, to increase insulin secretion. Examples of sulfonylurea drugs include metformin for suppression of hepatic glucose production, and troglitazone, an insulin-sensitizing medication. Despite the utility of these agents, 30-40% of diabetics are not adequately controlled using these medications and require subcutaneous insulin injections. Additionally, each of these therapies has associated side effects. For example, sulfonylureas can cause hypoglycemia and troglitazone can cause severe hepatoxicity. Presently, there is a need for new and improved drugs for the treatment of prediabetic and diabetic patients.

As described above, GSK-3 inhibition stimulates insulin-dependent processes and is consequently useful in the treatment of type 2 diabetes. Recent data obtained using lithium salts provides evidence for this notion. The lithium ion has recently been reported to inhibit GSK-3 activity. Klein et al., *PNAS* 93:8455-9 (1996). Since 1924, lithium has been reported to have antidiabetic effects including the ability to reduce plasma glucose levels, increase glycogen uptake, potentiate insulin, up-regulate glucose synthase activity and to stimulate glycogen synthesis in skin, muscle and fat cells. However, lithium has not been widely accepted for use in the inhibition of GSK-3 activity, possibly because of its documented effects on molecular targets other than GSK-3. The purine analog 5-iodotubercidin, also a GSK-3 inhibitor, likewise stimulates glycogen synthesis and antagonizes inactivation of glycogen synthase by glucagon and vasopressin in rat liver cells. Fluckiger-Isler et al., *Biochem J.* 292:85-91 (1993); and Massillon et al., *Biochem J.* 299:123-8 (1994). However, this compound has also been shown to inhibit other serine/threonine and tyrosine kinases. Massillon et al., *Biochem J.* 299:123-8 (1994).

One of the main goals in the management of patients with diabetes mellitus is to achieve blood glucose levels that are as close to normal as possible. In general, obtaining normal postprandial blood glucose levels is more difficult than normalizing fasting hyperglycemia. In addition, some epidemiological studies suggest that postprandial hyperglycemia (PPHG) or hyperinsulinemia are independent risk factors for the development of macrovascular complications of diabetes mellitus. Recently, several drugs with differing pharmacodynamic profiles have been developed which target PPHG. These include insulin lispro, amylin analogues, alpha-glucosidase inhibitors and meglitinide analogues. Insulin lispro has a more rapid onset of action and shorter duration of efficacy compared with regular human insulin. In clinical trials, the use of insulin lispro has been associated with improved control of PPHG and a reduced incidence of hypoglycemic episodes. Repaglinide, a meglitinide analogue, is a short-acting insulinotropic agent which, when given before meals, stimulates endogenous insulin secretions and lowers postprandial hyperglycaemic excursions. Both insulin lispro and repaglinide are associated with postprandial hyperinsulinaemia. In contrast, amylin analogues reduce PPHG by slowing gastric emptying and delivery of nutrients to the absorbing surface of the gut. Alpha-glucosidase inhibitors such as acarbose, miglitol and voglibose also reduce PPHG primarily by interfering with the carbohydrate-digesting enzymes and delaying glucose absorption. Yamasaki et al., *Tohoku J Exp Med* 1997; 183(3):173-83. The GSK inhibitors of the present invention are also useful, alone or in combination with the agents set forth above, in the treatment of postprandial hyperglycemia as well as in the treatment of fasting hyperglycemia.

GSK-3 is also involved in biological pathways relating to Alzheimer's disease (AD). The characteristic pathological features of AD are extracellular plaques of an abnormally processed form of the amyloid precursor protein (APP), so called β-amyloid peptide (β-AP) and the development of intracellular neurofibrillary tangles containing paired helical filaments (PHF) that consist largely of hyperphosphorylated tau protein. GSK-3 is one of a number of kinases that have been found to phosphorylate tau protein in vitro on the abnormal sites characteristic of PHF tau, and is the only kinase also demonstrated to do this in living cells and in animals. Lovestone et al., *Current Biology* 4:1077-86 (1994); and Brownlees et al., *Neuroreport* 8: 3251-3255 (1997). Furthermore, the GSK-3 kinase inhibitor, LiCI, blocks tau hyperphosphorylation in cells. Stambolic et al., *Current Biology* 6:1664-8 (1996). Thus GSK-3 activity may contribute to the generation of neurofibrillary tangles and consequently to disease progression. Recently it has been shown that GSK-3β associates with another key protein in AD pathogenesis, presenillin 1 (PS1). Takashima et al., *PNAS* 95:9637-9641 (1998). Mutations in the PS1 gene lead to increased production of β-AP, but the authors also demonstrate that the mutant PS1 proteins bind more tightly to GSK-3β and potentiate the phosphorylation of tau, which is bound to the same region of PS1.

It has also been shown that another GSK-3 substrate, β-catenin, binds to PS1. Zhong et al., *Nature* 395:698-702 (1998). Cytosolic β-catenin is targeted for degradation upon phosphorylation by GSK-3 and reduced β-catenin activity is associated with increased sensitivity of neuronal cells to β-AP induced neuronal apoptosis. Consequently, increased association of GSK-3β with mutant PS1 may account for the reduced levels of β-catenin that have been observed in the brains of PS1-mutant AD patients and to the disease related increase in neuronal cell-death. Consistent with these observations, it has been shown that injection of GSK-3 antisense but not sense, blocks the pathological effects of β-AP on neurons in vitro, resulting in a 24 hour delay in the onset of cell death and increased cell survival at 1 hour from 12 to 35%. Takashima et al., *PNAS* 90:7789-93. (1993). In these latter studies, the effects on cell-death are preceded (within 3-6 hours of β-AP administration) by a doubling of intracellular GSK-3 activity, suggesting that in addition to genetic mechanisms that increase the proximity of GSK-3 to its substrates, β-AP may actually increase GSK-3 activity. Further evidence for a role for GSK-3 in AD is provided by the observation that the protein expression level (but, in this case, not specific activity) of GSK-3 is increased by 50% in postsynaptosomal supernatants of AD vs. normal brain tissue. Pei et al., *J. Neuropathol Exp.*, 56:70-78 (1997). Thus, specific inhibitors of GSK-3 should slow the progression of Alzheimer's Disease.

In addition to the effects of lithium described above, there is a long history of the use of lithium to treat bipolar disorder (manic depressive syndrome). This clinical response to lithium may reflect an involvement of GSK-3 activity in the etiology of bipolar disorder, in which case GSK-3 inhibitors could be relevant to that indication. In support of this notion it was recently shown that valproate, another drug commonly used in the treatment of bipolar disorder, is also a GSK-3 inhibitor. Chen et al., *J. Neurochemistry*, 72:1327-1330 (1999). One mechanism by which lithium and other GSK-3 inhibitors may act to treat bipolar disorder is to increase the survival of neurons subjected to aberrantly high levels of excitation induced by the neurotransmitter, glutamate. Nonaka et al., *PNAS* 95: 2642-2647 (1998). Glutamate-induced neuronal excitotoxicity is also believed to be a major cause of neurodegeneration associated with acute damage, such as in cerebral ischemia, traumatic brain injury and bacterial infection. Furthermore it is believed that excessive glutamate signaling is a factor in the chronic neuronal damage seen in diseases such as Alzheimer's, Huntingdon's, Parkinson's, AIDS associated dementia, amyotrophic lateral sclerosis (ALS) and multiple sclerosis (MS). Thomas, *J. Am. Geriatr. Soc.* 43: 1279-89 (1995). Consequently, GSK-3 inhibitors should provide a useful treatment in these and other neurodegenerative disorders.

GSK-3 phosphorylates transcription factor NF-AT and promotes its export from the nucleus, in opposition to the effect of calcineurin. Beals et al., *Science* 275:1930-33 (1997). Thus, GSK-3 blocks early immune response gene activation via NF-AT, and GSK-3 inhibitors may tend to permit or prolong activation of immune responses. Thus, GSK-3 inhibitors are believed to prolong and potentiate the immunostimulatory effects of certain cytokines, and such an effect may enhance the potential of those cytokines for tumor immunotherapy or indeed for immunotherapy in general.

Lithium has other biological effects. It is a potent stimulator of hematopoiesis, both in vitro and in vivo. Hammond et al., *Blood* 55: 26-28 (1980). In dogs, lithium carbonate eliminated recurrent neutropenia and normalized other blood cell counts. Doukas et al. *Exp. Hematol.* 14: 215-221 (1986). If these effects of lithium are mediated through the inhibition of GSK-3, GSK-3 inhibitors may have even broader applications. Since inhibitors of GSK-3 are useful in the treatment of many diseases, the identification of new inhibitors of GSK-3 would be highly desirable.

NEK-2 is a mammalian serine threonine kinase, which is structurally related to the NimA kinase from the fungus *Aspergillus nidulans*. Mutations in NimA result in G2 phase arrest of cells and overexpression of wt NimA results in premature chromatin condensation, even when ectopically expressed in mammalian cells. Both protein and kinase levels peak in S/G2 phase of the cell cycle. NimA also appears to be required for the localization of cdk1/cyclinB complex to the nucleus and spindle pole body. Histone H3 has been shown to be an in vitro substrate for the kinase, and if this is also the case in vivo, it may explain the role of the kinase in chromosome condensation. Six NimA kinases have been identified to date in mammals, and of these, NEK-2 appears to be the most closely related to NimA. It's activity is also cell cycle regulated, peaking in S/G2 phase. Overexpression of NEK-2, however, does not affect chromatin condensation but instead results in a pronounced splitting of centrosomes, possibly due to the loss of centriole/centriole adhesion. There is evidence that NEK-2 is regulated by phosphorylation and can interact with protein phosphatase PP1. NEK-2 is ubiquitously expressed and appears to be most abundant in testis. Hyseq cluster 374113, containing only NEK-2 sequences shows dramatic overexpression of NEK-2 in lymph node metastasis (13.3×) and in primary tumor (6.5×). Inhibition of NEK-2 by antisense oligonucleotides inhibited cell proliferation and reduced the capability of cells to grow in soft agar. In addition, increased cell death was observed in these cells both in the presence and absence of cisplatin.

Ultraviolet light, ionizing radiation, environmental agents and cytotoxic drugs can result in damage to cellular DNA integrity. When such damage occurs during DNA replication or cell division it is potentially catastrophic and may result in cell death. The cellular response is to arrest the cell cycle at one of two checkpoints (G1/S or G2/M) to either permit DNA repair or initiate apoptosis.

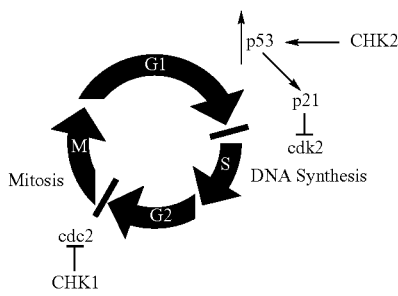

The G1/S checkpoint is regulated by the p53 transcriptional activator protein and the absence of this critical protein is often an important step in tumorigenesis, thus defining p53 as a tumor suppressor. In fact, nearly 50% of all cancers are p53 defective due to mutation. T. Soussi, *Ann. N.Y. Acad Sci.*, 910, 121 (2001). In response to DNA damage, checkpoint kinase 2 (CHK-2) phosphorylates p53 and this results in stabilization of the protein and an elevation in p53 levels. A. Hirao et al., *Science*, 287, 1824 (2000). Consequently, negative cell cycle regulators, such as p21Waf1/Cip1, are activated and halt the cell cycle at the G1/S checkpoint. B. Vogelstein et al., *Nature*, 408, 307 (2000).

The G2/M checkpoint is monitored by the serine/threonine checkpoint kinase 1 (CHK1). Upon DNA damage, the protein kinase ATR (ataxia-telangiectasia mutated—rad53 related kinase) is activated. H. Zhao et al., *Mol. Cell Biol.*, 21, 4129 (2001); Q. Liu et al., *Genes Dev.*, 14, 1448 (2000). SATR-dependent phosphorylation of CHK1 promotes its phosphorylation of Cdc25 and Wee1 and ultimately inactivation of Cdc2. Thus, CHK1 phosphorylation of Cdc25c targets it for nuclear export to the cytoplasm and as a result the Cdc25c phosphatase is rendered unavailable to activate Cdc2 by dephosphorylation. Y. Sanchez et al., *Science*, 277, 1497 (1997); C. Y. Peng et al., *Science*, 277, 1501 (1997); T. A. Chen et al., *Nature*, 401, 616 (1999); and A. Lopez-Girona et al., *Nature*, 397, 172 (1999). In addition, CHK1 activates the protein kinase Wee1, which phosphorylates and inactivates Cdc2. J. Lee et al. *Mol. Biol. Cell*, 12, 551 (2001); L. L. Parker et al., *Science*, 257, 1955 (1992). These dual pathways thus converge to result in cell cycle arrest. Because cell cycle arrest is a potential mechanism by which tumor cells can overcome the damage induced by cytotoxic agents, abrogation of these checkpoints with novel therapeutic agents should increase the sensitivity of tumors to chemotherapy. The presence of two checkpoints, coupled with the tumor specific abrogation of one of these by p53 mutations in 50% of cancers, can be exploited to design tumor-selective agents. Thus, in p53 minus tumors, therapeutic inhibition of G2/M arrest leaves cancerous cells no options for DNA damage repair and results in apoptosis. Normal cells have wild type p53 and retain an intact G1/S checkpoint. Thus these cells have an opportunity to correct DNA damage and survive. One approach to the design of chemosensitizers that abrogate the G2/M checkpoint is to identify inhibitors of the key G2/M regulatory kinase, CHK1.

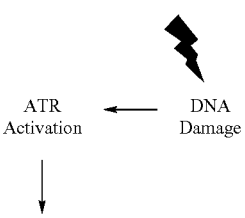

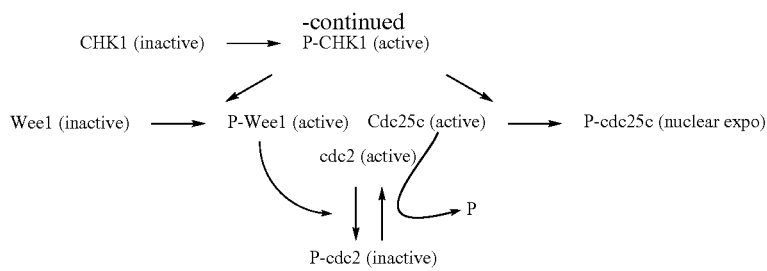

It has been shown that PAR-1, also known as HDAK, a regulator of polarity, is a modulator of Wnt-β-catenin signaling, indicating a link between two important developmental pathways. See Sun, T-Q. et al. *Nature Cell Biology*, 3, 628-636 (2001). An important function of β-catenin, namely its role in cell signaling, has been elucidated in the past few years. β-Catenin is the vertebrate homologue of the Drosophila segment polarity gene armadillo, an important element in the Wingless/Wnt (Wg/Wnt) signaling pathway. Wingless is a cell-cell signal in Drosophila that triggers many key developmental processes, Wnt being the vertebrate homologue. In the absence of a mitotic signal from outside the cell β-catenin is sequestered in a complex with the adenomatous polyposis coli (APC) gene product, a serine threonine glycogen synthetase kinase (GSK-3β) and an adapter protein axin (or a homologue conductin), enabling phosphorylation and degradation of free β-catenin by the ubiquitin-proteasome system. The function of and interactions between the proteins in the complex was something of a mystery until recently. Axin, a recently recognized component of the complex, acts as a scaffold protein in the multiprotein structure. Formation of an axin regulatory complex is critical for GSK-3β activity and β-catenin phosphorylation and degradation, since GSK-3β does not bind directly to β-catenin but requires the presence of axin, which binds to both proteins. This complex formation leads to the maintenance of low levels of free cytoplasmic β-catenin. Residual catenins hold cells together by binding to cadherins, both at the adherens junctions and the actin cytoskeleton.

When a mitotic signal is delivered by the Wnt pathway, by association of the Wg/Wnt family of secreted glycoproteins and their membrane receptor frizzled, it leads to activation of the dishevelled (Dsh) protein, which is recruited to the cell membrane. The activated Dsh downregulates the protein complex, so that it can no longer phosphorylate β-catenin, which then is not degraded. How exactly Wnt signaling leads to the stabilization of β-catenin remains unclear, although the critical step is possibly the dissociation of GSK-3β from axin with the help of Dsh. With GSK-3β no longer bound to axin, it cannot phosphorylate β-catenin, leading to an increase in β-catenin levels. Another proposed model is that inhibition of GSK-3β activity upon Wnt signaling by Dsh leads to the dephosphorylation of axin, resulting in a reduced efficiency of binding to β-catenin. The release of β-catenin from the phosphorylation and degradation complex promotes β-catenin stabilization and signaling. The resulting increase in free cytosolic β-catenin then enters the nucleus. This results in an increase of free cytosolic β-catenin which translocates to the nucleus and directly binds the transcription factors Lef and Tcf, leading to the activation of gene expression. Recently, the target genes of these transcription factors have been identified. They are thought to be involved in inhibiting apoptosis and promoting cellular proliferation and migration, and include the c-myc oncogene and one of the cell cycle regulators cyclin D1.

Transformation of adult mammalian cells into malignant tumors is believed to reflect an exaggeration of the Wg/Wnt pathway, at least in some tumors. The PAR-1 gene is involved in Wg/Wnt activity levels as well as production of free β-catenin in the cell. Down regulating of Wg/Wnt has been shown to limit β-catenin, which is involved in anti-apoptosis signaling. Small molecule inhibitors capable of inhibiting PAR-1 such as those disclosed herein, have been shown to be efficacious in cancer cell lines. Screens monitoring PAR-1 (HDAK) inhibition depict effective reduction of Wnt activity, with EC50 values below 10 μM in cell-based assays. Therefore, a need remains for small molecule inhibitors of the PAR-1, capable of inhibiting Wg/Wnt signaling and β-catenin production in order to reduce growth of tumor cell lines and tumors via stimulation of cellular apoptosis.

Various indolyl substituted compounds have recently been disclosed in WO 01/29025, WO 01/62251, and WO 01/62252, and various benzimidazolyl compounds have recently been disclosed in WO 01/28993. These compounds are reportedly capable of inhibiting, modulating, and/or regulating signal transduction of both receptor-type and non-receptor tyrosine kinases. Some of the disclosed compounds contain a quinolone fragment bonded to the indolyl or benzimidazolyl group.

The synthesis of 4-hydroxy quinolone and 4-hydroxy quinoline derivatives is disclosed in a number of references which are being incorporated by reference in their entirety for all purposes as if fully set forth herein. For example, Ukrainets et al. have disclosed the synthesis of 3-(benzimidazol-2-yl)-4-hydroxy-2-oxo-1,2-dihydroquinoline. Ukrainets, I. et al., Tet. Lett. 42, 7747-7748 (1995); Ukrainets, I. et al., Khimiya Geterotsiklicheskikh Soedinii, 2, 239-241(1992). Ukrainets has also disclosed the synthesis, anticonvulsive and antithyroid activity of other 4-hydroxy quinolones and thio analogs such as 1H-2-oxo-3-(2-benzimidazolyl)-4-hydoxyquinoline. Ukrainets, I. et al., Khimiya Geterotsiklicheskikh Soedinii, 1, 105-108 (1993); Ukrainets, I. et al., Khimiya Geterotsiklicheskikh Soedinii, 8, 1105-1108 (1993); Ukrainets, I. et al., Chem. Heterocyclic Comp. 33, 600-604, (1997).

The synthesis of various quinoline derivatives is disclosed in WO 97/48694. These compounds are disclosed as capable of binding to nuclear hormone receptors and being useful for stimulating osteoblast proliferation and bone growth. The compounds are also disclosed as being useful in the treatment or prevention of diseases associated with nuclear hormone receptor families.

Various quinoline derivatives in which the benzene ring of the quinolone is substituted with a sulfur group are disclosed in WO 92/18483. These compounds are disclosed as being useful in pharmaceutical formulations and as medicaments.

Quinolone and coumarin derivatives have been disclosed as having use in a variety of applications unrelated to medicine and pharmaceutical formulations. References that describe the preparation of quinolone derivatives for use in photopolymerizable compositions or for luminescent properties include: U.S. Pat. No. 5,801,212 issued to Okamoto et al.; JP 8-29973; JP 7-43896; JP 6-9952; JP 63-258903; EP 797376; and DE 23 63 459 which are all herein incorporated by reference in their entirety for all purposes as if fully set forth herein.

Various quinolinone benzimidazole compounds described as useful in inhibiting angiogenesis and vascular endothelial growth factor receptor tyrosine kinases are disclosed in U.S. patent application Ser. No. 09/951,265 and WO 02/22598 (published on Mar. 21, 2002), U.S. patent application Ser. No. 09/943,382 and WO 02/18383 (published on Mar. 7, 2002), and U.S. patent application Ser. No. 10/116,117 filed (published on Feb. 6, 2003 as US 20030028018 A1) each of which is incorporated herein by reference in its entirety for all purposes as if fully set forth herein.

Each of the following documents to which this application claims priority is also herein incorporated by reference in its entirety and for all purposes as if the references were fully set forth herein: U.S. Ser. No. 60/405,729 filed on Aug. 23, 2002; U.S. Ser. No. 60/426,107 filed on Nov. 13, 2002; U.S. Ser. No. 60/426,226 filed on Nov. 13, 2002; U.S. Ser. No. 60/426,282 filed on Nov. 13, 2002; U.S. Ser. No. 60/428,210 filed on Nov. 21, 2002; U.S. Ser. No. 60/460,327 filed on Apr. 3, 2003 U.S. Ser. No. 60/460,328 filed on Apr. 3, 2003; U.S. Ser. No. 60/460,493 filed on Apr. 3, 2003; U.S. Ser. No. 60/478,916 filed on Jun. 16, 2003; and U.S. Ser. No. 60/484,048 filed on Jul. 1, 2003.

A continuing need exists for compounds that inhibit the proliferation of capillaries, inhibit the growth of tumors, treat cancer, treat diabetes, stimulate insulin-dependent processes, treat Alzheimer's disease, treat central nervous system disorders, prolong immune responses, reduce the splitting of centrosomes, block DNA repair, modulate cell cycle arrest, and/or inhibit enzymes such as FLT-1 (VEGFR1), VEGFR2 (KDR, Flk-1), VEGFR3, FGFR1, GSK-3, Cdk2, Cdk4, MEK1, CHK2, CK1ε, Raf, c-Kit, c-ABL, p60src, FGFR3, FLT-3, NEK-2, CHK1, Rsk2, PAR-1, Cdc2, Fyn, Lck, Tie-2, PDGFRα, and PDGFRβ, and pharmaceutical formulations and medicaments that contain such compounds. A need also exists for methods for administering such compounds, pharmaceutical formulations, and medicaments to patients or subjects in need thereof.

SUMMARY OF THE INVENTION

The present invention provides methods of inhibiting serine/threonine and tyrosine kinases, and methods of treating biological conditions mediated by serine/threonine and tyrosine kinases. In particular, the present invention provides methods of inhibiting serine/threonine kinases, including glycogen synthase kinase 3 (GSK-3), cyclin dependent kinase 2 (Cdk2), cyclin dependent kinase 4 (Cdk4), MEK1, NEK-2, CHK2, CK1ε, Raf, checkpoint kinase 1 (CHK1), ribosomal S6 kinase 2 (Rsk2), and PAR-1 and methods of inhibiting tyrosine kinases, including cell division cycle 2 kinase (Cdc2 kinase), FYN oncogene kinase related to SRC, FGR, YES (Fyn), lymphocyte-specific protein tyrosine kinase (Lck), c-Kit, c-ABL, p60src, VEGFR3, PDGFRα, PDGFRβ, FGFR3, FLT-3 and tyrosine kinase with Ig and EGF homology domains (Tie-2). The present invention also provides methods of treating biological conditions mediated by serine/threonine kinases, including GSK-3, Cdk2, Cdk4, MEK1, NEK-2, CHK2, CK1ε, Raf, CHK1, Rsk2, and PAR-1, and methods of treating biological conditions mediated by tyrosine kinases, including Cdc2 kinase, c-Kit, c-ABL, p60src, VEGFR3, PDGFRα, PDGFRβ, FGFR3, FLT-3, Fyn, Lck, and Tie-2. Finally, the present invention provides compounds and pharmaceutical formulations including the compounds that are used in the above methods.

Serine/Threonine Kinase Inhibition

In one aspect, the present invention provides a method of inhibiting a serine/threonine kinase in a subject and/or a method of treating a biological condition mediated by serine/threonine kinase activity in a subject. The methods include administering to the subject a compound of Structure I, a tautomer of the compound, a pharmaceutically acceptable salt of the compound, a pharmaceutically acceptable salt of the tautomer, or mixtures thereof. In the method of inhibiting a serine/threonine kinase, the serine/threonine kinase is inhibited in the subject after administration. Structure I has the following formula:

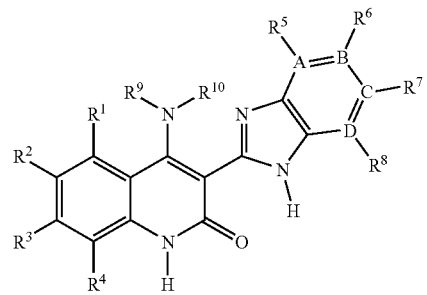

where:
A, B, C, and D are independently selected from carbon or nitrogen;
$R^1$ is selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted alkynyl groups having from 1 to 8 carbon atoms, substituted and unsubstituted heterocyclyl groups, substituted and unsubstituted heterocyclylalkyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)-alkyl groups, —S(=O)—NH$_2$, substituted and unsubstituted —S(=O)—N(H)(alkyl) groups, substituted and unsubstituted —S(=O)—N(alkyl)$_2$ groups, —OH, substituted and unsubstituted alkoxy groups, substituted and unsubstituted aryloxy groups, substituted and unsubstituted arylalkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(H)—C(=O)-heterocyclyl groups, substituted and unsubstituted —N(H)—C(=O)-heterocyclylalkyl groups, substituted and unsubstituted —N(H)—S(=O)-alkyl groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(aralkyl) groups, substituted and unsubstituted —C(=O)—N(H)(heterocyclyl) groups, —C(=O)—N(H)(heterocyclylalkyl) groups, —CO$_2$H, substituted and unsubstituted —C(=O)—O-alkyl groups, substituted and unsubstituted —C(=O)—O-heterocyclyl groups, or substituted and unsubstituted —C(=O)—O-heterocyclylalkyl groups;

R$^2$ and R$^3$ are independently selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted alkynyl groups having from 1 to 8 carbon atoms, substituted and unsubstituted aryl groups, substituted and unsubstituted aralkyl groups, substituted and unsubstituted heterocyclyl groups, substituted and unsubstituted heterocyclylalkyl groups, —SH, substituted and unsubstituted —S-alkyl groups, substituted and unsubstituted —S-aryl groups, substituted and unsubstituted —S-aralkyl groups, substituted and unsubstituted —S(=O)$_2$—O-alkyl groups, substituted and unsubstituted —S(=O)$_2$-alkyl groups, substituted and unsubstituted —S(=O)$_2$-heterocyclyl groups, substituted and unsubstituted —S(=O)-alkyl groups, substituted and unsubstituted —S(=O)-heterocyclyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, substituted and unsubstituted —S(=O)$_2$—N(H)(aryl) groups, substituted and unsubstituted —S(=O)$_2$—N(alkyl)(aryl) groups, substituted and unsubstituted —S(=O)$_2$—N(aryl)$_2$ groups, substituted and unsubstituted —S(=O)$_2$—N(H)(aralkyl) groups, substituted and unsubstituted —S(=O)$_2$—N(alkyl)(aralkyl) groups, substituted and unsubstituted —S(=O)$_2$—N(aralkyl)$_2$ groups, —OH, substituted and unsubstituted alkoxy groups, substituted and unsubstituted aryloxy groups, substituted and unsubstituted aralkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, substituted and unsubstituted —N(aryl)$_2$ groups, substituted and unsubstituted —N(H)(aralkyl) groups, substituted and unsubstituted —N(alkyl)(aralkyl) groups, substituted and unsubstituted —N(aralkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—S(=O)$_2$-alkyl groups, substituted and unsubstituted —N(H)—S(=O)$_2$-aryl groups, substituted and unsubstituted —N(H)—S(=O)$_2$-aralkyl groups, substituted and unsubstituted —N(H)—S(=O)$_2$-heterocyclyl groups, substituted and unsubstituted —N(H)—S(=O)$_2$-heterocyclylalkyl groups, substituted and unsubstituted —N(H)—C(=O)-alkyl groups, substituted and unsubstituted —N(H)—C(=O)-aryl groups, substituted and unsubstituted —N(H)—C(=O)-aralkyl groups, substituted and unsubstituted —N(H)—C(=O)-heterocyclyl groups, substituted and unsubstituted —N(H)—C(=O)-heterocyclylalkyl groups, substituted and unsubstituted —N(alkyl)-C(=O)-alkyl groups, substituted and unsubstituted —N(alkyl)-C(=O)-aryl groups, substituted and unsubstituted —N(alkyl)-C(=O)-aralkyl groups, substituted and unsubstituted —N(alkyl)-C(=O)-heterocyclyl groups, substituted and unsubstituted —N(alkyl)-C(=O)-heterocyclylalkyl groups, substituted and unsubstituted —N(alkyl)-S(=O)$_2$-alkyl groups, substituted and unsubstituted —N(alkyl)-S(=O)$_2$-aryl groups, substituted and unsubstituted —N(alkyl)-S(=O)$_2$-aralkyl groups, substituted and unsubstituted —N(alkyl)-S(=O)$_2$-heterocyclyl groups, substituted and unsubstituted —N(alkyl)-S(=O)$_2$-heterocyclylalkyl groups, —N(H)—C(=O)—NH$_2$, substituted and unsubstituted —N(H)—C(=O)—N(H)(alkyl) groups, substituted and unsubstituted —N(H)—C(=O)—N(alkyl)$_2$ groups, substituted and unsubstituted —N(H)—C(=O)—N(H)(aryl) groups, substituted and unsubstituted —N(H)—C(=O)—N(alkyl)(aryl) groups, substituted and unsubstituted —N(H)—C(=O)—N(aryl)$_2$ groups, substituted and unsubstituted —N(H)—C(=O)—N(H)(aralkyl) groups, substituted and unsubstituted —N(H)—C(=O)—N(alkyl)(aralkyl) groups, substituted and unsubstituted —N(H)—C(=O)—N(aralkyl)$_2$ groups, substituted and unsubstituted —N(H)—C(=O)—N(H)(heterocyclyl) groups, substituted and unsubstituted —N(H)—C(=O)—N(alkyl)(heterocyclyl) groups, substituted and unsubstituted —N(H)—C(=O)—N(heterocyclyl)$_2$ groups, substituted and unsubstituted —N(H)—C(=O)—N(H)(heterocyclylalkyl) groups, substituted and unsubstituted —N(H)—C(=O)—N(alkyl)(heterocyclylalkyl) groups, substituted and unsubstituted —N(H)—C(=O)—N(heterocyclylalkyl)$_2$ groups, substituted and unsubstituted —N(alkyl)-C(=O)—NH$_2$ groups, substituted and unsubstituted —N(alkyl)-C(=O)—N(H)(alkyl) groups, substituted and unsubstituted —N(alkyl)-C(=O)—N(alkyl)$_2$ groups, substituted and unsubstituted —N(alkyl)-C(=O)—N(H)(aryl) groups, substituted and unsubstituted —N(alkyl)-C(=O)—N(alkyl)(aryl) groups, substituted and unsubstituted —N(alkyl)-C(=O)—N(aryl)$_2$ groups, substituted and unsubstituted —N(alkyl)-C(=O)—N(H)(aralkyl) groups, substituted and unsubstituted —N(alkyl)-C(=O)—N(alkyl)(aralkyl) groups, substituted and unsubstituted —N(alkyl)-C(=O)—N(aralkyl)$_2$ groups, substituted and unsubstituted —N(alkyl)-C(=O)—N(H)(heterocyclyl) groups, substituted and unsubstituted —N(alkyl)-C(=O)—N(alkyl)(heterocyclyl) groups, substituted and unsubstituted —N(alkyl)-C(=O)—N(heterocyclyl)$_2$ groups, substituted and unsubstituted —N(alkyl)-C(=O)—N(H)(heterocyclylalkyl) groups, substituted and unsubstituted —N(alkyl)-C(=O)—N(alkyl)(heterocyclylalkyl) groups, substituted and unsubstituted —N(alkyl)-C(=O)—N(heterocyclylalkyl)$_2$ groups, substituted and unsubstituted —C(=O)-alkyl groups, substituted and unsubstituted —C(=O)-aryl groups, substituted and unsubstituted —C(=O)-aralkyl groups, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(aryl) groups, substituted and unsubstituted —C(=O)—N(alkyl)(aryl) groups, substituted and unsubstituted —C(=O)—N(aryl)$_2$ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)$_2$ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)$_2$ groups, —CO$_2$H, substituted and unsubstituted —C(=O)—O-alkyl groups, substituted and unsubstituted —C(=O)—O-aryl groups, substituted and unsubstituted —C(=O)—O-heterocyclyl groups, or substituted and unsubstituted —C(=O)—O-heterocyclylalkyl groups;

$R^4$ is selected from —H, —F, —Cl, —Br, —I, —CN, —NO$_2$, substituted and unsubstituted alkyl groups having from 1 to 12 carbon atoms, substituted and unsubstituted alkenyl groups having from 1 to 8 carbon atoms, substituted and unsubstituted alkynyl groups having from 1 to 8 carbon atoms, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)-alkyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, —OH, substituted and unsubstituted alkoxy groups, —NH$_2$, substituted and unsubstituted —N(H)(alkyl) groups, substituted and unsubstituted —N(alkyl)$_2$ groups, substituted and unsubstituted —N(H)—C(=O)-alkyl groups, substituted and unsubstituted —N(H)—S(=O)-alkyl groups, —C(=O)—NH$_2$, substituted and unsubstituted —C(=O)—N(H)(alkyl) groups, substituted and unsubstituted —C(=O)—N(alkyl)$_2$ groups, or substituted and unsubstituted —C(=O)—O-alkyl groups;

$R^5$ and $R^8$ are independently selected from —H, —F, —Cl, —Br, —I, —CN, —NO$_2$, substituted and unsubstituted straight and branched chain alkyl groups having from 1 to 8 carbon atoms, substituted and unsubstituted alkenyl groups having from 1 to 8 carbon atoms, substituted and unsubstituted alkynyl groups having from 1 to 8 carbon atoms, substituted and unsubstituted heterocyclyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)-alkyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, —OH, substituted and unsubstituted alkoxy groups, —NH$_2$, substituted and unsubstituted —N(H)(alkyl) groups, substituted and unsubstituted —N(alkyl)$_2$ groups, substituted and unsubstituted —N(H)—C(=O)-alkyl groups, substituted and unsubstituted —N(H)—S(=O)-alkyl groups, —C(=O)—NH$_2$, substituted and unsubstituted —C(=O)—N(H)(alkyl) groups, substituted and unsubstituted —C(=O)—N(alkyl)$_2$ groups, or substituted and unsubstituted —C(=O)—O-alkyl groups; or $R^5$ may be absent if A is nitrogen; or $R^8$ may be absent if D is nitrogen;

$R^6$ and $R^7$ are independently selected from —H, —F, —Cl, —Br, —I, —NO$_2$, —CN, substituted and unsubstituted alkyl groups having from 1 to 12 carbon atoms, substituted and unsubstituted alkenyl groups having from 1 to 12 carbon atoms, substituted and unsubstituted alkynyl groups having from 1 to 8 carbon atoms, substituted and unsubstituted heterocyclyl groups, substituted and unsubstituted heterocyclylalkyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)$_2$-heterocyclyl groups, substituted and unsubstituted —S(=O)-alkyl groups, substituted and unsubstituted —S(=O)-heterocyclyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, substituted and unsubstituted —S(=O)$_2$—N(H)(heterocyclyl) groups, substituted and unsubstituted —S(=O)$_2$—N(alkyl)(heterocyclyl) groups, substituted and unsubstituted —S(=O)$_2$—N(heterocyclyl)$_2$ groups, substituted and unsubstituted —S(=O)$_2$—N(H)(heterocyclylalkyl) groups, substituted and unsubstituted —S(=O)$_2$—N(alkyl)(heterocyclylalkyl) groups, substituted and unsubstituted —S(=O)$_2$—N(heterocyclylalkyl)$_2$ groups, —OH, substituted and unsubstituted alkoxy groups, substituted and unsubstituted aryloxy groups, substituted and unsubstituted arylalkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, substituted and unsubstituted —N(aryl)$_2$ groups, substituted and unsubstituted —N(H)(aralkyl) groups, substituted and unsubstituted —N(alkyl)(aralkyl) groups, substituted and unsubstituted —N(aralkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—S(=O)$_2$-alkyl groups, substituted and unsubstituted —N(H)—S(=O)$_2$-heterocyclyl groups, substituted and unsubstituted —N(H)—S(=O)$_2$-heterocyclylalkyl groups, substituted and unsubstituted —N(H)—C(=O)-alkyl groups, substituted and unsubstituted —N(H)—C(=O)-heterocyclyl groups, substituted and unsubstituted —N(H)—C(=O)-heterocyclylalkyl groups, substituted and unsubstituted —N(alkyl)-C(=O)-alkyl groups, substituted and unsubstituted —N(alkyl)-C(=O)-heterocyclyl groups, substituted and unsubstituted —N(alkyl)-C(=O)-heterocyclylalkyl groups, substituted and unsubstituted —N(alkyl)-S(=O)$_2$-alkyl groups, substituted and unsubstituted —N(alkyl)-S(=O)$_2$-heterocyclyl groups, substituted and unsubstituted —N(alkyl)-S(=O)$_2$-heterocyclylalkyl groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(aryl) groups, substituted and unsubstituted —C(=O)—N(alkyl)(aryl) groups, substituted and unsubstituted —C(=O)—N(aryl)$_2$ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)$_2$ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)$_2$ groups, —CO$_2$H, substituted and unsubstituted —C(=O)—O-alkyl groups, substituted and unsubstituted —C(=O)—O-heterocyclyl groups, or substituted and unsubstituted —C(=O)—O-heterocyclylalkyl groups; or $R^6$ may be absent if B is nitrogen; or $R^7$ may be absent if C is nitrogen;

$R^9$ is selected from —H, substituted and unsubstituted alkyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, substituted and unsubstituted heterocyclylaminoalkyl groups, substituted and unsubstituted alkoxy groups, or —NH$_2$, or $R^9$ and $R^{10}$ join together to form one or more rings, each having 5, 6, or 7 ring members; and $R^{10}$ is —H, or $R^9$ and $R^{10}$ join together to form one or more rings, each having 5, 6, or 7 ring members.

In some embodiments of the method of inhibiting a serine/threonine kinase using a compound of Structure I, a tautomer of the compound, a pharmaceutically acceptable salt of the compound, a pharmaceutically acceptable salt of the tautomer, or mixtures thereof, the serine/threonine kinase is selected from glycogen synthase kinase 3, cyclin dependent kinase 2, cyclin dependent kinase 4, MEK1, NEK-2, CHK2, CK1ε, Raf, checkpoint kinase 1, ribosomal S6 kinase 2, or PAR-1.

Tyrosine Kinase Inhibition

In another aspect, the present invention provides a method of inhibiting a tyrosine kinase in a subject and/or a method of treating a biological condition mediated by a tyrosine kinase in a subject. The tyrosine kinase is Cdc2 kinase, Fyn, Lck, c-Kit, c-ABL, VEGFR3, PDGFα, PDGFβ, FGFR3, FLT-3, or Tie-2. In some embodiments, the tyrosine kinase is Cdc2 kinase, Fyn, Lck, or Tie-2 and in some other embodiments, the tyrosine kinase is c-Kit, c-ABL, p60src, VEGFR3, PDGFα, PDGFβ, FGFR3, or FLT-3. The methods include administering to the subject a compound of Structure I, a tautomer of the compound, a pharmaceutically acceptable salt of the compound, a pharmaceutically acceptable salt of the tautomer, or mixtures thereof. In the method of inhibiting a tyrosine kinase, the tyrosine kinase is inhibited in the subject after administration. Structure I has the following formula:

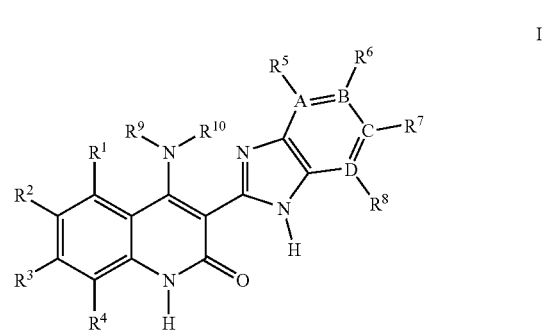

where,

A, B, C, and D are independently selected from carbon or nitrogen;

$R^1$ is selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —SH, substituted and unsubstituted —S-alkyl groups, substituted and unsubstituted —S-heterocyclyl groups, —OH, substituted and unsubstituted alkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(H)—C(=O)-heterocyclyl groups, substituted and unsubstituted —N(H)—C(=O)-heterocyclylalkyl groups, substituted and unsubstituted —N(alkyl)-S(=O)$_2$-alkyl groups, substituted and unsubstituted —N(alkyl)-S(=O)$_2$-heterocyclyl groups, substituted and unsubstituted —N(alkyl)-S(=O)$_2$-heterocyclylalkyl groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)$_2$ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)$_2$ groups, —CO$_2$H, substituted and unsubstituted —C(=O)—O-alkyl groups, substituted and unsubstituted —C(=O)—O-heterocyclyl groups, or substituted and unsubstituted —C(=O)—O-heterocyclylalkyl groups;

$R^2$ and $R^3$ are independently selected from —H, —F, —Cl, —Br, —I, —NO$_2$, —CN, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)$_2$-heterocyclyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, substituted and unsubstituted —S(=O)-alkyl groups, substituted and unsubstituted —S(=O)-heterocyclyl groups, —OH, substituted and unsubstituted alkoxy groups, substituted and unsubstituted aryloxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, substituted and unsubstituted —N(aryl)$_2$ groups, substituted and unsubstituted —N(H)(aralkyl) groups, substituted and unsubstituted —N(alkyl)(aralkyl) groups, substituted and unsubstituted —N(aralkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(alkyl)-C(=O)-alkyl groups, substituted and unsubstituted —N(H)—C(=O)-aryl groups, substituted and unsubstituted —N(alkyl)-C(=O)-aryl groups, substituted and unsubstituted —N(H)—C(=O)-aralkyl groups, substituted and unsubstituted —N(alkyl)-C(=O)-aralkyl groups, substituted and unsubstituted —N(H)—C(=O)-heterocyclyl groups, substituted and unsubstituted —N(alkyl)-C(=O)-heterocyclyl groups, substituted and unsubstituted —N(H)—C(=O)-heterocyclylalkyl groups, substituted and unsubstituted —N(alkyl)-C(=O)-heterocyclylalkyl groups, substituted and unsubstituted —N(H)—S(=O)$_2$-alkyl groups, substituted and unsubstituted —N(H)—S(=O)$_2$-aryl, substituted and unsubstituted —N(H)—S(=O)$_2$-heterocyclyl groups, substituted and unsubstituted —C(=O)-alkyl groups, substituted and unsubstituted —C(=O)-aryl, substituted and unsubstituted —C(=O)-aralkyl, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(aryl) groups, substituted and unsubstituted —C(=O)—N(alkyl)(aryl) groups, substituted and unsubstituted —C(=O)—N(aryl)$_2$ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)$_2$ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)$_2$ groups, —CO$_2$H, substituted and unsubstituted —C(=O)—O-alkyl groups, C(=O)—O-aryl groups —C(=O)—O-aralkyl groups, substituted and unsubstituted —C(=O)—O-heterocyclyl groups, or substituted and unsubstituted —C(=O)—O-heterocyclylalkyl groups;

$R^4$ is selected from —H or substituted and unsubstituted alkyl groups having from 1 to 12 carbon atoms;

$R^5$ and $R^8$ are independently selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —OH, substituted and unsubstituted alkoxy groups, substituted and unsubstituted heterocyclyloxy groups, substituted and unsubstituted heterocyclylalkoxy groups; or $R^5$ may be absent if A is nitrogen; or $R^8$ may be absent if D is nitrogen;

$R^6$ and $R^7$ are independently selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted arylakyl groups, substituted and unsubstituted heterocyclyl groups, substituted and unsubstituted heterocyclylalkyl groups, —SH, substituted and unsubstituted —S-alkyl groups, substituted and unsubstituted —S-heterocyclyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, —OH, substituted and unsubstituted alkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(H)—C(=O)-heterocyclyl groups, substituted and unsubstituted —N(H)—C(═O)-heterocyclylalkyl groups, substituted and unsubstituted —N(alkyl)-C(═O)-alkyl groups, substituted and unsubstituted —N(alkyl)-C(═O)-heterocyclyl groups, substituted and unsubstituted —N(alkyl)-C(═O)-heterocyclylalkyl, substituted and unsubstituted —N(H)—S(═O)$_2$-alkyl groups, substituted and unsubstituted —N(H)—S(═O)$_2$-heterocyclyl groups, substituted and unsubstituted —N(H)—S(═O)$_2$-heterocyclylalkyl groups, substituted and unsubstituted —C(═O)-alkyl groups, substituted and unsubstituted —C(═O)-heterocyclyl groups, substituted and unsubstituted —C(═O)-heterocyclylalkyl groups, —C(═O)—NH$_2$, substituted and unsubstituted —C(═O)—N(H)(alkyl) groups, substituted and unsubstituted —C(═O)—N(alkyl)$_2$ groups, substituted and unsubstituted —C(═O)—N(H)(heterocyclyl) groups, substituted and unsubstituted —C(═O)—N(alkyl)(heterocyclyl) groups, substituted and unsubstituted —C(═O)—N(heterocyclyl)$_2$ groups, substituted and unsubstituted —C(═O)—N(H)(heterocyclylalkyl) groups, substituted and unsubstituted —C(═O)—N(alkyl)(heterocyclylalkyl) groups, substituted and unsubstituted —C(═O)—N(heterocyclylalkyl)$_2$ groups, —CO$_2$H, substituted and unsubstituted —C(═O)—O-alkyl groups, substituted and unsubstituted —C(═O)—O-heterocyclyl groups, or substituted and unsubstituted —C(═O)—O-heterocyclylalkyl groups; or $R^6$ is absent if B is nitrogen; or $R^7$ is absent if C is nitrogen;

$R^9$ is selected from —H, substituted and unsubstituted alkyl groups having from 1 to 12 carbon atoms, substituted and unsubstituted alkenyl groups having from 1 to 12 carbons, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted heterocyclyloxy groups, —NH$_2$, or substituted and unsubstituted heterocyclylaminoalkyl; and $R^{10}$ is —H.

The present invention further provides methods of inhibiting serine/threonine kinases and tyrosine kinases and treating biological conditions mediated by such kinases using compounds of Structure IB. In some such embodiments, the invention provides a method of inhibiting GSK-3 and treating biological conditions mediated by GSK-3 in a subject. The invention also provides the use of a compound of Structure IB in preparing a medicament for use in inhibiting a serine/threonine kinase such as GSK-3 or a tyrosine kinase in a subject and/or for use in treating a biological condition mediated by a serine/threonine kinase such as GSK-3 or a tyrosine kinase. In one aspect, a method of inhibiting a serine/threonine kinase or a tyrosine kinase or treating a biological condition mediated by a serine/threonine kinase or a tyrosine kinase includes administering to the subject a compound of Structure IB, a tautomer of the compound, a pharmaceutically acceptable salt of the compound, a pharmaceutically acceptable salt of the tautomer, or mixtures thereof. In some embodiments, a kinase such as a serine/threonine kinase such as GSK-3 or a tyrosine kinase is inhibited in the subject after administration. Structure IB has the following formula:

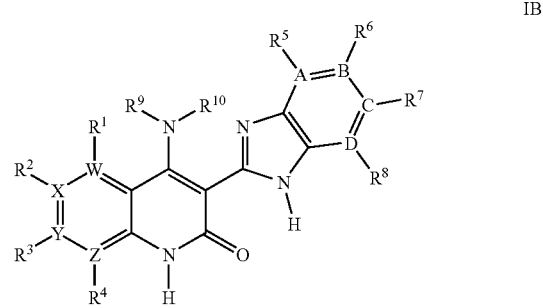

where:
A, B, C, and D are independently selected from carbon or nitrogen;
W, X, Y, and Z are independently selected from the group consisting of carbon and nitrogen and at least one of W, X, Y, and Z is a nitrogen;
$R^1$ is selected from —H, —F, —Cl, —Br, —I, substituted or unsubstituted straight or branched chain alkyl groups having from 1 to 8 carbon atoms, substituted or unsubstituted alkenyl groups having from 1 to 8 carbon atoms, substituted or unsubstituted alkynyl groups having from 1 to 8 carbon atoms, —CN, —NO$_2$, —OH, —SH, substituted or unsubstituted alkoxy groups, substituted or unsubstituted —S-alkyl groups, substituted or unsubstituted —S(═O)$_2$—O-alkyl groups, substituted or unsubstituted —S(═O)$_2$-alkyl groups, substituted or unsubstituted —S(═O)-alkyl groups, —S(═O)—NH$_2$, substituted or unsubstituted —S(═O)—N(H)(alkyl) groups, substituted or unsubstituted —S(═O)—N(alkyl)$_2$ groups, —C(═O)—NH$_2$, substituted or unsubstituted —C(═O)—N(H)(alkyl) groups, substituted or unsubstituted —C(═O)—N(alkyl)$_2$ groups, substituted or unsubstituted —C(═O)—O-alkyl groups, —NH$_2$, substituted or unsubstituted —N(H)(alkyl) groups, substituted or unsubstituted —N(alkyl)$_2$ groups, substituted or unsubstituted —N(H)—C(═O)-alkyl groups, or substituted or unsubstituted —N(H)—S(═O)-alkyl groups; or $R^1$ may be absent if W is nitrogen;

$R^2$ is selected —H, —F, —Cl, —Br, —I, —NO$_2$, —CN, —NH$_2$, —CO$_2$H, —OH, substituted or unsubstituted straight or branched chain alkyl groups having from 1 to 8 carbon atoms, substituted or unsubstituted cycloalkenyl groups, substituted or unsubstituted cycloalkyl groups, substituted or unsubstituted alkoxy groups, substituted or unsubstituted —N(H)(alkyl) groups, substituted or unsubstituted —N(alkyl)$_2$ groups, substituted or unsubstituted heterocyclyl groups, substituted or unsubstituted aryl groups, substituted or unsubstituted alkenyl groups having from 1 to 8 carbon atoms, substituted or unsubstituted alkynyl groups having from 1 to 8 carbon atoms, —SH, substituted or unsubstituted —S-alkyl groups, substituted or unsubstituted —S(═O)$_2$—O-alkyl groups, substituted or unsubstituted —S(═O)$_2$-alkyl groups, substituted or unsubstituted —S(═O)$_2$-heterocyclyl groups, substituted or unsubstituted —S(═O)-alkyl groups, substituted or unsubstituted —S(═O)-heterocyclyl groups, —S(═O)—NH$_2$, substituted or unsubstituted —S(═O)—N(H)(alkyl) groups, substituted or unsubstituted —S(═O)—N(alkyl)$_2$ groups, —C(═O)—NH$_2$, substituted or unsubstituted —C(═O)—N(H)(alkyl) groups, substituted or unsubstituted —C(═O)—N(alkyl)₂ groups, substituted or unsubstituted —C(═O)-alkyl groups, substituted or unsubstituted —C(═O)-heterocyclyl groups, substituted or unsubstituted —C(═O)—O-alkyl groups, substituted or unsubstituted —N(H)—C(═O)-alkyl groups, substituted or unsubstituted —N(H)—C(═O)-heterocyclyl groups, substituted or unsubstituted —N(H)—S(═O)-alkyl groups, substituted or unsubstituted —N(H)—S(═O)-heterocyclyl groups, —N(alkyl)-C(═O)-alkyl groups, substituted or unsubstituted —N(alkyl)-C(═O)-heterocyclyl groups, substituted or unsubstituted —N(alkyl)-S(═O)-alkyl groups, substituted or unsubstituted —N(alkyl)-S(═O)-heterocyclyl groups, —N(H)—C(═O)—NH₂, substituted or unsubstituted —N(H)—C(═O)—N(H)(alkyl) groups, substituted or unsubstituted —N(H)—C(═O)—N(alkyl)₂ groups, —N(alkyl)-C(═O)—NH₂, substituted or unsubstituted —N(alkyl)-C(═O)—N(H)(alkyl) groups, or substituted or unsubstituted —N(alkyl)-C(═O)—N(alkyl)₂ groups; or $R^2$ and $R^3$ may join together to form a cyclic group when X and Y are both carbon; or $R^2$ may be absent if X is nitrogen;

$R^3$ is selected from —H, —F, —Cl, —Br, —I, —OH, substituted or unsubstituted straight or branched chain alkyl groups having from 1 to 8 carbon atoms, substituted or unsubstituted alkoxy groups, —CO₂H, —CN, substituted or unsubstituted —N(H)(alkyl) groups, substituted or unsubstituted —N(H)(cycloalkyl) groups, substituted or unsubstituted —N(alkyl)₂ groups, substituted or unsubstituted heterocyclyl groups, substituted or unsubstituted aryl groups, substituted or unsubstituted —C(═O)-heterocyclyl groups, substituted or unsubstituted —C(═O)-alkyl groups, substituted or unsubstituted —C(═O)—N(H)(alkyl) groups, substituted or unsubstituted —C(═O)—N(alkyl)₂ groups, —C(═O)—NH₂ groups, substituted or unsubstituted —C(═O)—N(H)(heterocyclyl) groups, substituted or unsubstituted —C(═O)—N(H)(aryl) groups, substituted or unsubstituted alkenyl groups having from 1 to 8 carbon atoms, substituted or unsubstituted alkynyl groups having from 1 to 8 carbon atoms, —NO₂, —SH, substituted or unsubstituted —S-alkyl groups, substituted or unsubstituted —S(═O)₂—O-alkyl groups, substituted or unsubstituted —S(═O)₂-alkyl groups, substituted or unsubstituted —S(═O)₂-heterocyclyl groups, substituted or unsubstituted —S(═O)-alkyl groups, substituted or unsubstituted —S(═O)-heterocyclyl groups, —S(═O)—NH₂, substituted or unsubstituted —S(═O)—N(H)(alkyl) groups, substituted or unsubstituted —S(═O)—N(alkyl)₂ groups, substituted or unsubstituted —C(═O)—O-alkyl groups, —NH₂, substituted or unsubstituted —N(H)—C(═O)-alkyl groups, substituted or unsubstituted —N(H)—C(═O)-heterocyclyl groups, substituted or unsubstituted —N(H)—S(═O)-alkyl groups, substituted or unsubstituted —N(H)—S(═O)-heterocyclyl groups, substituted or unsubstituted —N(alkyl)-C(═O)-alkyl groups, substituted or unsubstituted —N(alkyl)-C(═O)-heterocyclyl groups, substituted or unsubstituted —N(alkyl)-S(═O)-alkyl groups, substituted or unsubstituted —N(alkyl)-S(═O)-heterocyclyl groups, —N(H)—C(═O)—NH₂, substituted or unsubstituted —N(H)—C(═O)—N(H)(alkyl) groups, substituted or unsubstituted —N(H)—C(═O)—N(alkyl)₂ groups, —N(alkyl)-C(═O)—NH₂, substituted or unsubstituted —N(alkyl)-C(═O)—N(H)(alkyl) groups, or substituted or unsubstituted —N(alkyl)-C(═O)—N(alkyl)₂ groups; or $R^2$ and $R^3$ may join together to form a cyclic group when X and Y are both carbon; or $R^3$ may be absent if Y is nitrogen;

$R^4$ is selected from of —H, —F, —Cl, —Br, —I, substituted or unsubstituted straight or branched chain alkyl groups having from 1 to 8 carbon atoms, substituted or unsubstituted alkenyl groups having from 1 to 8 carbon atoms, substituted or unsubstituted alkynyl groups having from 1 to 8 carbon atoms, —CN, —NO₂, —OH, —SH, substituted or unsubstituted alkoxy groups, substituted or unsubstituted —S-alkyl groups, substituted or unsubstituted —S(═O)₂—O-alkyl groups, substituted or unsubstituted —S(═O)₂-alkyl groups, substituted or unsubstituted —S(═O)-alkyl groups, —S(═O)—NH₂, substituted or unsubstituted —S(═O)—N(H)(alkyl) groups, substituted or unsubstituted —S(═O)—N(alkyl)₂ groups, —C(═O)—NH₂, substituted or unsubstituted —C(═O)—N(H)(alkyl) groups, substituted or unsubstituted —C(═O)—N(alkyl)₂ groups, substituted or unsubstituted —C(═O)—O-alkyl groups, —NH₂, substituted or unsubstituted —N(H)(alkyl) groups, substituted or unsubstituted —N(alkyl)₂ groups, substituted or unsubstituted —N(H)—C(═O)-alkyl groups, or substituted or unsubstituted —N(H)—S(═O)-alkyl groups; or $R^4$ may be absent if Z is nitrogen;

$R^5$ is selected from —H, —F, —Cl, —Br, —I, substituted or unsubstituted straight or branched chain alkyl groups having from 1 to 8 carbon atoms, substituted or unsubstituted heterocyclyl groups, substituted or unsubstituted alkenyl groups having from 1 to 8 carbon atoms, substituted or unsubstituted alkynyl groups having from 1 to 8 carbon atoms, —CN, —NO₂, —OH, —SH, substituted or unsubstituted alkoxy groups, substituted or unsubstituted —S-alkyl groups, substituted or unsubstituted —S(═O)₂—O-alkyl groups, substituted or unsubstituted —S(═O)₂-alkyl groups, substituted or unsubstituted —S(═O)-alkyl groups, —S(═O)—NH₂, substituted or unsubstituted —S(═O)—N(H)(alkyl) groups, substituted or unsubstituted —S(═O)—N(alkyl)₂ groups, —C(═O)—NH₂, substituted or unsubstituted —C(═O)—N(H)(alkyl) groups, substituted or unsubstituted —C(═O)—N(alkyl)₂ groups, substituted or unsubstituted —C(═O)—O-alkyl groups, —NH₂, substituted or unsubstituted —N(H)(alkyl) groups, substituted or unsubstituted —N(alkyl)₂ groups, substituted or unsubstituted —N(H)—C(═O)-alkyl groups, or substituted or unsubstituted —N(H)—S(═O)-alkyl groups; or $R^5$ may be absent if A is nitrogen;

$R^6$ is selected from —H, —Cl, —F, —Br, —OH, substituted or unsubstituted heterocyclyl groups, substituted or unsubstituted —N(H)(alkyl) groups, substituted or unsubstituted —N(H)(heterocyclyl) groups, substituted or unsubstituted —N(alkyl)(heterocyclyl) groups, substituted or unsubstituted alkoxy groups, substituted or unsubstituted alkyl groups having from 1 to 8 carbon atoms, substituted or unsubstituted alkenyl groups having from 1 to 8 carbon atoms, substituted or unsubstituted alkynyl groups having from 1 to 8 carbon atoms, —CN, —NO₂, —OH, —SH, substituted or unsubstituted —S-alkyl groups, substituted or unsubstituted —S(═O)₂—O-alkyl groups, substituted or unsubstituted —S(═O)₂-alkyl groups, substituted or unsubstituted —S(═O)₂-heterocyclyl groups, substituted or unsubstituted —S(═O)-alkyl groups, substituted or unsubstituted —S(═O)-heterocyclyl groups, —S(═O)—NH₂, substituted or unsubstituted —S(=O)—N(H)(alkyl) groups, substituted or unsubstituted —S(=O)—N(alkyl)₂ groups, —C(=O)—NH₂, substituted or unsubstituted —C(=O)—N(H)(alkyl) groups, substituted or unsubstituted —C(=O)—N(alkyl)₂ groups, substituted or unsubstituted —C(=O)-alkyl groups, substituted or unsubstituted —C(=O)-heterocyclyl groups, substituted or unsubstituted —C(=O)—O-alkyl groups, —NH₂, substituted or unsubstituted —N(alkyl)₂ groups, substituted or unsubstituted —N(H)—C(=O)-alkyl groups, substituted or unsubstituted —N(H)—C(=O)-heterocyclyl groups, substituted or unsubstituted —N(alkyl)-C(=O)-alkyl groups, substituted or unsubstituted —N(alkyl)-C(=O)-heterocyclyl groups, substituted or unsubstituted —N(H)—S(=O)-alkyl groups, substituted or unsubstituted —N(H)—S(=O)-heterocyclyl groups, substituted or unsubstituted —N(alkyl)-S(=O)-alkyl groups, or substituted or unsubstituted —N(alkyl)-S(=O)-heterocyclyl groups; or $R^6$ may be absent if B is nitrogen;

$R^7$ is selected from —H, —Cl, —F, —Br, —OH, substituted or unsubstituted heterocyclyl groups, substituted or unsubstituted —N(H)(alkyl) groups, substituted or unsubstituted —N(H)(heterocyclyl) groups, substituted or unsubstituted —N(alkyl)(heterocyclyl) groups, substituted or unsubstituted alkoxy groups, substituted or unsubstituted alkyl groups having from 1 to 8 carbon atoms, substituted or unsubstituted alkenyl groups having from 1 to 8 carbon atoms, substituted or unsubstituted alkynyl groups having from 1 to 8 carbon atoms, —CN, —NO₂, —OH, —SH, substituted or unsubstituted —S-alkyl groups, substituted or unsubstituted —S(=O)₂—O-alkyl groups, substituted or unsubstituted —S(=O)₂-alkyl groups, substituted or unsubstituted —S(=O)₂-heterocyclyl groups, substituted or unsubstituted —S(=O)-alkyl groups, substituted or unsubstituted —S(=O)-heterocyclyl groups, —S(=O)—NH₂, substituted or unsubstituted —S(=O)—N(H)(alkyl) groups, substituted or unsubstituted —S(=O)—N(alkyl)₂ groups, —C(=O)—NH₂, substituted or unsubstituted —C(=O)—N(H)(alkyl) groups, substituted or unsubstituted —C(=O)—N(alkyl)₂ groups, substituted or unsubstituted —C(=O)-alkyl groups, substituted or unsubstituted —C(=O)-heterocyclyl groups, substituted or unsubstituted —C(=O)—O-alkyl groups, —NH₂, substituted or unsubstituted —N(alkyl)₂ groups, substituted or unsubstituted —N(H)—C(=O)-alkyl groups, substituted or unsubstituted —N(H)—C(=O)-heterocyclyl groups, substituted or unsubstituted —N(alkyl)-C(=O)-alkyl groups, substituted or unsubstituted —N(alkyl)-C(=O)-heterocyclyl groups, substituted or unsubstituted —N(H)—S(=O)-alkyl groups, substituted or unsubstituted —N(H)—S(=O)-heterocyclyl groups, substituted or unsubstituted —N(alkyl)-S(=O)-alkyl groups, or substituted or unsubstituted —N(alkyl)-S(=O)-heterocyclyl groups; or $R^7$ may be absent if C is nitrogen;

$R^8$ is selected from —H, —F, —Cl, —Br, —I, substituted or unsubstituted straight or branched chain alkyl groups having from 1 to 8 carbon atoms, substituted or unsubstituted heterocyclyl groups, substituted or unsubstituted alkenyl groups having from 1 to 8 carbon atoms, substituted or unsubstituted alkynyl groups having from 1 to 8 carbon atoms, —CN, —NO₂, —OH, —SH, substituted or unsubstituted alkoxy groups, substituted or unsubstituted —S-alkyl groups, substituted or unsubstituted —S(=O)₂—O-alkyl groups, substituted or unsubstituted —S(=O)₂-alkyl groups, substituted or unsubstituted —S(=O)-alkyl groups, —S(=O)—NH₂, substituted or unsubstituted —S(=O)—N(H)(alkyl) groups, substituted or unsubstituted —S(=O)—N(alkyl)₂ groups, —C(=O)—NH₂, substituted or unsubstituted —C(=O)—N(H)(alkyl) groups, substituted or unsubstituted —C(=O)—N(alkyl)₂ groups, substituted or unsubstituted —C(=O)—O-alkyl groups, —NH₂, substituted or unsubstituted —N(H)(alkyl) groups, substituted or unsubstituted —N(alkyl)₂ groups, substituted or unsubstituted —N(H)—C(=O)-alkyl groups, or substituted or unsubstituted —N(H)—S(=O)-alkyl groups; or $R^8$ may be absent if D is nitrogen;

$R^9$ is selected from of substituted or unsubstituted heterocyclyl groups, substituted or unsubstituted aryl groups, substituted or unsubstituted alkoxy groups, —NH₂, substituted or unsubstituted cycloalkyl groups, or substituted or unsubstituted straight or branched chain alkyl groups having from 1 to 8 carbon atoms, or $R^9$ and $R^{10}$ join together to form a ring having 5, 6, or 7 ring members; or $R^{10}$ is —H, or $R^9$ and $R^{10}$ join together to form a ring having 5, 6, or 7 ring members.

The invention further provides the use of the compounds of Structure I and IB, tautomers of the compounds, pharmaceutically acceptable salts of the compounds, pharmaceutically acceptable salts of the tautomers, and mixtures thereof in the preparation and manufacture of medicaments for inhibiting any of the serine/threonine kinases or tyrosine kinases or for use in treating any biological conditions mediated by such kinases. In some embodiments, the compounds may be used to prepare medicaments in containers such as vials, ampoules, or other pharmaceutical formulation storage devices and such storage devices may include labels which may include directions for application such as directions for inhibiting a kinase or directions for treating a subject that has a biological condition mediated by a kinase.

The invention also provides novel compounds of Structure I and IB that may be used to inhibit the kinases described herein or may be used to treat biological conditions mediated by such kinases.

Further objects, features and advantages of the invention will be apparent from the following detailed description.

BRIEF DESCRIPTION OF THE DRAWINGS

FIGS. 9A and 9B are graphs showing inhibition of VEGF-mediated migration of HUVEC and VEGF-mediated tube formation in the presence of 4-amino-5-fluoro-3-[5-(4-methylpiperazin-1-yl)-1H-benzimidazol-2-yl]quinolin-2(1H)-one.

DETAILED DESCRIPTION OF THE INVENTION

Figure 1:
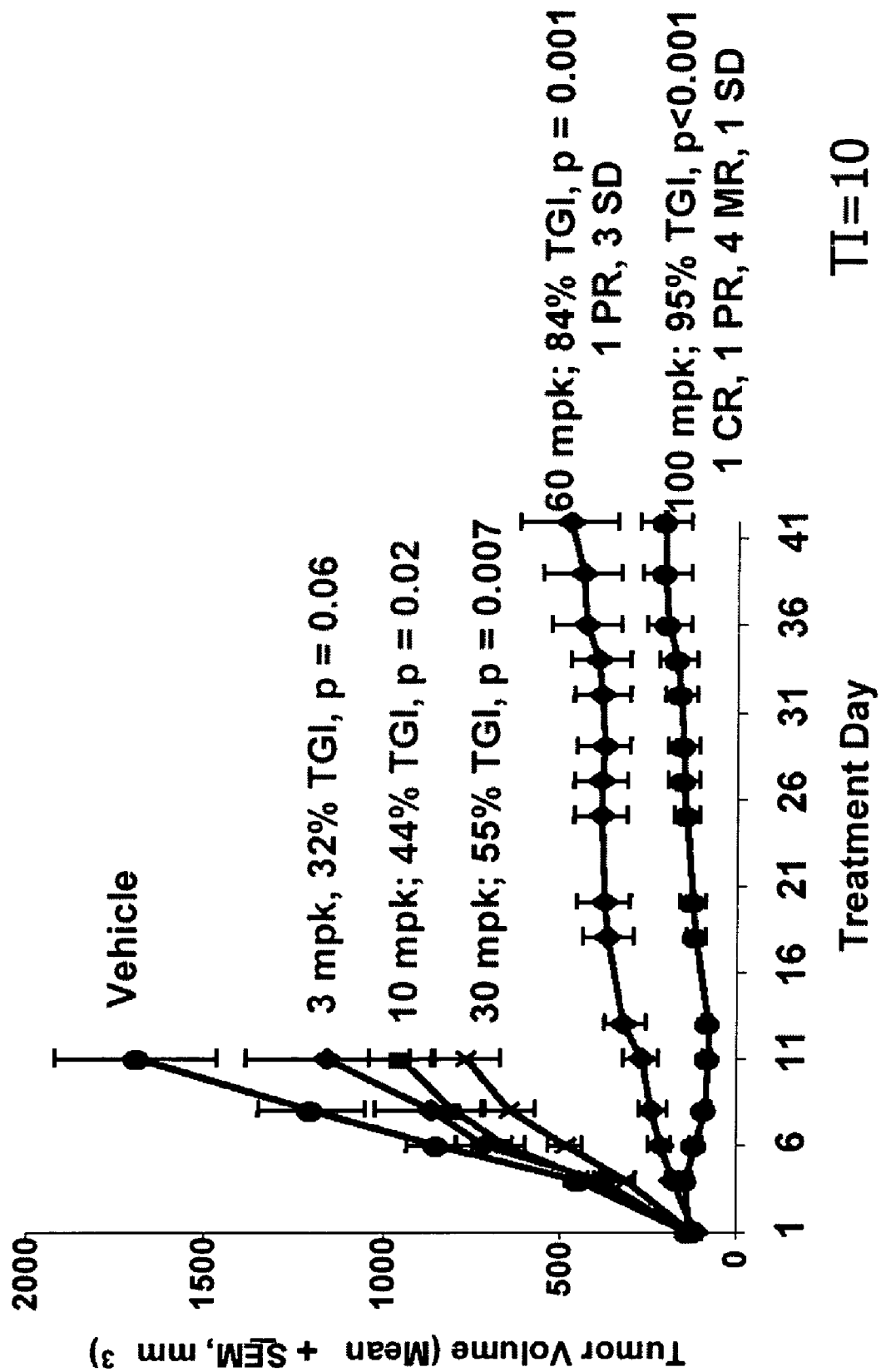
FIG. 1 is a graph of tumor growth inhibition in the presence of 4amino-5-fluoro-3-[5-(4-methylpiperazin-1-yl)-1H-benzimidazol-2-yl]quinolin-2(1H)-one in the KM12L4a colon tumor model in nu/nu mice.

The present invention relates to a novel class of compounds which act as inhibitors of serine/threonine kinases and tyrosine kinases, including inhibitors of GSK-3, Cdk2, Cdk4, MEK1, NEK-2, CHK2, CK1ε, Raf, CHK1, Rsk2, PAR-1, Cdc2 kinase, c-Kit, c-ABL, p60src, FGFR3, FLT-3, Fyn, Lck, and Tie-2. The present invention further relates to the compounds used in these methods. These compounds can be formulated into pharmaceutical formulations that are useful in treating patients with a need for such inhibitors (e.g., those suffering from cancer). The compounds described herein are also useful for reducing capillary proliferation and in the treatment of cancer and other medical or cellular conditions in human and cell subjects.

The following abbreviations and definitions are used throughout this application:

"ALS" is an abbreviation that stands for amyotropic lateral sclerosis.

"AD" is an abbreviation that stands for Alzheimer Disease.

"APP" is an abbreviation that stands for amyloid precursor protein.

"bFGF" is an abbreviation that stands for basic fibroblast growth factor.

"FGFR1", also referred to as bFGFR, is an abbreviation that stands for a tyrosine kinase that interacts with the fibroblast growth factor FGF.

"Cdc 2" is an abbreviation that stands for cell division cycle 2.

"Cdk 2" is an abbreviation that stands for cyclin dependent kinase 2.

"Cdk 4" is an abbreviation that stands for cyclin dependent kinase 4.

"Chk 1" is an abbreviation that stands for checkpoint kinase 1.

"CK1ε" is a serine/threonine kinase that stands for Casein kinase 1 (epsilon).

"c-ABL" is an abbreviation for a tyrosine kinase that stands for an oncogene product originally isolated from the Abelson leukemia virus.

"C-Kit" is also known as stem cell factor receptor or mast cell growth factor receptor.

"FGF" is an abbreviation for the fibroblast growth factor that interacts with FGFR1.

"FGFR3" is an abbreviation that stands for the tyrosine kinase fibroblast growth factor receptor 3 that is often expressed in multiple myeloma-type cancers.

"Flk-1" is an abbreviation that stands for fetal liver tyrosine kinase 1, also known as kinase-insert domain tyrosine kinase or KDR (human), also known as vascular endothelial growth factor receptor-2 or VEGFR2 (KDR (human), Flk-1 (mouse)).

"FLT-1" is an abbreviation that stands for fms-like tyrosine kinase-1, also known as vascular endothelial growth factor receptor-1 or VEGFR1.

"FLT-3" is an abbreviation that stands for fms-like tyrosine kinase-3, also known as stem cell tyrosine kinase I (STK I).

"FLT-4" is an abbreviation that stands for fms-like tyrosine kinase-4, also known as VEGFR3.

"Fyn" is an abbreviation that stands for FYN oncogene kinase related to SRC, FGR, YES.

"GSK-3" is an abbreviation that stands for glycogen synthase kinase 3.

"p60src" is a tyrosine kinase originally identified as the v-src oncogene of the rous sarcoma virus.

"PAR-1" is an abbreviation that stands for a kinase also known as disheveled associated kinase, also known as HDAK.

"Lck" is an abbreviation that stands for lymphocyte-specific protein tyrosine kinase.

"MEK1" is an abbreviation that stands for a serine threonine kinase in the MAPK (Mitogen activated protein kinase) signal transduction pathway in a module that is formed of the Raf-MEK1-ERK. MEK1 phosphorylates ERK (extracellular regulated kinase).

"MS" is an abbreviation that stands for multiple sclerosis.

"NEK-2" is an abbreviation that stands for NIM-A related kinase.

"NIM-A" is an abbreviation that stands for never in mitosis.

"PDGF" is an abbreviation that stands for platelet derived growth factor. PDGF interacts with tyrosine kinases PDGFRα and PDGFRβ.

"PHF" is an abbreviation that stands for paired helical filaments.

"PS 1" is an abbreviation that stands for presenelin 1.

"Rsk2" is an abbreviation that stands for ribosomal S6 kinase 2.

"Raf" is a serine/threonine kinase in the MAPK signal transduction pathway.

"RTK" is an abbreviation that stands for receptor tyrosine kinase.

"Tie-2" is an abbreviation that stands for tyrosine kinase with Ig and EGF homology domains.

"VEGF" is an abbreviation that stands for vascular endothelial growth factor.

"VEGF-RTK" is an abbreviation that stands for vascular endothelial growth factor receptor tyrosine kinase.

Generally, reference to a certain element such as hydrogen or H is meant to include all isotopes of that element. For example, if an R group is defined to include hydrogen or H, it also includes deuterium and tritium.

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: $-CH(CH_3)_2$, $-CH(CH_3)(CH_2CH_3)$, $-CH(CH_2CH_3)_2$, $-C(CH_3)_3$, $-C(CH_2CH_3)_3$, $-CH_2CH(CH_3)_2$, $-CH_2CH(CH_3)(CH_2CH_3)$, $-CH_2CH(CH_2CH_3)_2$, $-CH_2C(CH_3)_3$, $-CH_2C(CH_2CH_3)_3$, $-CH(CH_3)CH(CH_3)(CH_2CH_3)$, $-CH_2CH_2CH(CH_3)_2$, $-CH_2CH_2CH(CH_3)(CH_2CH_3)$, $-CH_2CH_2CH(CH_2CH_3)_2$, $-CH_2CH_2C(CH_3)_3$, $-CH_2CH_2C(CH_2CH_3)_3$, $-CH(CH_3)CH_2CH(CH_3)_2$, $-CH(CH_3)CH(CH_3)CH(CH_3)_2$, $-CH(CH_2CH_3)CH(CH_3)CH(CH_3)(CH_2CH_3)$, and others. The phrase also includes cyclic alkyl groups such as cycloalkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Preferred unsubstituted alkyl groups include straight and branched chain alkyl groups and cyclic alkyl groups having 1 to 20 carbon atoms. More preferred such unsubstituted alkyl groups have from 1 to 10 carbon atoms while even more preferred such groups have from 1 to 5 carbon atoms. Most preferred unsubstituted alkyl groups include straight and branched chain alkyl groups having from 1 to 3 carbon atoms and include methyl, ethyl, propyl, and $-CH(CH_3)_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Preferred substituted alkyl groups include, among others, alkyl groups in which one or more bonds to a carbon or hydrogen atom is/are replaced by one or more bonds to fluorine atoms.

One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The phrase "unsubstituted aryl" refers to aryl groups that do not contain heteroatoms. Thus the phrase includes, but is not limited to, groups such as phenyl, biphenyl, anthracenyl, naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A preferred unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others.

The phrase "unsubstituted alkenyl" refers to straight and branched chain and cyclic groups such as those described with respect to unsubstituted alkyl groups as defined above, except that at least one double bond exists between two carbon atoms. Examples include, but are not limited to, vinyl, $-CH=C(H)(CH_3)$, $-CH=C(CH_3)_2$, $-C(CH_3)=C(H)_2$, $-C(CH_3)=C(H)(CH_3)$, $-C(CH_2CH_3)=CH_2$, cyclohexenyl, cyclopentenyl, cyclohexadienyl, butadienyl, pentadienyl, and hexadienyl among others.

The phrase "substituted alkenyl" has the same meaning with respect to unsubstituted alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "unsubstituted alkynyl" refers to straight and branched chain groups such as those described with respect to unsubstituted alkyl groups as defined above, except that at least one triple bond exists between two carbon atoms. Examples include, but are not limited to $-C\equiv C(H)$, $-C\equiv C(CH_3)$, $-C\equiv C(CH_2CH_3)$, $-(H_2)C\equiv C(H)$, $-C(H)_2C\equiv C(CH_3)$, and $-C(H)_2C\equiv C(CH_2CH_3)$ among others.

The phrase "substituted alkynyl" has the same meaning with respect to unsubstituted alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "unsubstituted aralkyl" refers to unsubstituted alkyl groups as defined above in which a hydrogen or carbon bond of the unsubstituted alkyl group is replaced with a bond to an aryl group as defined above. For example, methyl (—$CH_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group). Thus the phrase includes, but is not limited to, groups such as benzyl, diphenylmethyl, and 1-phenylethyl (—$CH(C_6H_5)(CH_3)$) among others.

The phrase "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom. Examples of substituted aralkyl groups include, but are not limited to, —$CH_2C(=O)(C_6H_5)$, and —$CH_2$(2-methylphenyl) among others.

The phrase "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridinyl, dihydropyridinyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g., 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g., 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene oxide and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiophene, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to an unsubstituted heterocyclyl group as defined above in which one or more of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, N-alkyl piperazinyl groups such as 1-methyl piperazinyl, piperazine-N-oxide, N-alkyl piperazine N-oxides, 2-phenoxy-thiophene, and 2-chloropyridinyl among others. In addition, substituted heterocyclyl groups also include heterocyclyl groups in which the bond to the non-hydrogen atom is a bond to a carbon atom that is part of a substituted and unsubstituted aryl, substituted and unsubstituted aralkyl, or unsubstituted heterocyclyl group. Examples include but are not limited to 1-benzylpiperidinyl, 3-phenythiomorpholinyl, 3-(pyrrolidin-1-yl)-pyrrolidinyl, and 4-(piperidin-1-yl)-piperidinyl. Groups such as N-alkyl substituted piperazine groups such as N-methyl piperazine, substituted morpholine groups, and piperazine N-oxide groups such as piperazine N-oxide and N-alkyl piperazine N-oxides are examples of some substituted heterocyclyl groups. Groups such as substituted piperazine groups such as N-alkyl substituted piperazine groups such as N-methyl piperazine and the like, substituted morpholine groups, piperazine N-oxide groups, and N-alkyl piperazine N-oxide groups are examples of some substituted heterocyclyl groups that are especially suited as $R^6$ or $R^7$ groups.

The phrase "unsubstituted heterocyclylalkyl" refers to unsubstituted alkyl groups as defined above in which a hydrogen or carbon bond of the unsubstituted alkyl group is replaced with a bond to a heterocyclyl group as defined above. For example, methyl (—$CH_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

The phrase "substituted heterocyclylalkyl" has the same meaning with respect to unsubstituted heterocyclylalkyl groups that substituted aralkyl groups had with respect to unsubstituted aralkyl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group. In addition, a substituted heterocyclylalkyl group also includes groups in which a carbon bond or a hydrogen bond of the alkyl part of the group is replaced by a bond to a substituted and unsubstituted aryl or substituted and unsubstituted aralkyl group. Examples include but are not limited to phenyl-(piperidin-1-yl)-methyl and phenyl-(morpholin4-yl)-methyl.

The phrase "unsubstituted alkylaminoalkyl" refers to an unsubstituted alkyl group as defined above in which a carbon or hydrogen bond is replaced by a bond to a nitrogen atom that is bonded to a hydrogen atom and an unsubstituted alkyl group as defined above. For example, methyl (—$CH_3$) is an unsubstituted alkyl group. If a hydrogen atom of the methyl group is replaced by a bond to a nitrogen atom that is bonded to a hydrogen atom and an ethyl group, then the resulting compound is —$CH_2$—N(H)($CH_2CH_3$) which is an unsubstituted alkylaminoalkyl group.

The phrase "substituted alkylaminoalkyl" refers to an unsubstituted alkylaminoalkyl group as defined above except where one or more bonds to a carbon or hydrogen atom in one or both of the alkyl groups is replaced by a bond to a non-carbon or non-hydrogen atom as described above with respect to substituted alkyl groups except that the bond to the nitrogen atom in all alkylaminoalkyl groups does not by itself qualify all alkylaminoalkyl groups as being substituted. However, substituted alkylaminoalkyl groups does include groups in which the hydrogen bonded to the nitrogen atom of the group is replaced with a non-carbon and non-hydrogen atom.

The phrase "unsubstituted dialkylaminoalkyl" refers to an unsubstituted alkyl group as defined above in which a carbon bond or hydrogen bond is replaced by a bond to a nitrogen atom which is bonded to two other similar or different unsubstituted alkyl groups as defined above.

The phrase "substituted dialkylaminoalkyl" refers to an unsubstituted dialkylaminoalkyl group as defined above in which one or more bonds to a carbon or hydrogen atom in one or more of the alkyl groups is replaced by a bond to a non-carbon and non-hydrogen atom as described with respect to substituted alkyl groups. The bond to the nitrogen atom in all dialkylaminoalkyl groups does not by itself qualify all dialkylaminoalkyl groups as being substituted.

The phrase "unsubstituted alkoxy" refers to a hydroxyl group (—OH) in which the bond to the hydrogen atom is replaced by a bond to a carbon atom of an otherwise unsubstituted alkyl group as defined above.

The phrase "substituted alkoxy" refers to a hydroxyl group (—OH) in which the bond to the hydrogen atom is replaced by a bond to a carbon atom of an otherwise substituted alkyl group as defined above.

The phrase "unsubstituted heterocyclyloxy" refers to a hydroxyl group (—OH) in which the bond to the hydrogen atom is replaced by a bond to a ring atom of an otherwise unsubstituted heterocyclyl group as defined above.

The phrase "substituted heterocyclyloxy" refers to a hydroxyl group (—OH) in which the bond to the hydrogen atom is replaced by a bond to a ring atom of an otherwise substituted heterocyclyl group as defined above.

The phrase "unsubstituted heterocyclyloxyalkyl" refers to an unsubstituted alkyl group as defined above in which a carbon bond or hydrogen bond is replaced by a bond to an oxygen atom which is bonded to an unsubstituted heterocyclyl group as defined above.

The phrase "substituted heterocyclyloxyalkyl" refers to an unsubstituted heterocyclyloxyalkyl group as defined above in which a bond to a carbon or hydrogen group of the alkyl group of the heterocyclyloxyalkyl group is bonded to a non-carbon and non-hydrogen atom as described above with respect to substituted alkyl groups or in which the heterocyclyl group of the heterocyclyloxyalkyl group is a substituted heterocyclyl group as defined above.

The phrase "unsubstituted heterocyclylalkoxy" refers to an unsubstituted alkyl group as defined above in which a carbon bond or hydrogen bond is replaced by a bond to an oxygen atom which is bonded to the parent compound, and in which another carbon or hydrogen bond of the unsubstituted alkyl group is bonded to an unsubstituted heterocyclyl group as defined above.

The phrase "substituted heterocyclylalkoxy" refers to an unsubstituted heterocyclylalkoxy group as defined above in which a bond to a carbon or hydrogen group of the alkyl group of the heterocyclylalkoxy group is bonded to a non-carbon and non-hydrogen atom as described above with respect to substituted alkyl groups or in which the heterocyclyl group of the heterocyclylalkoxy group is a substituted heterocyclyl group as defined above. Further, a substituted heterocyclylalkoxy group also includes groups in which a carbon bond or a hydrogen bond to the alkyl moiety of the group may be substituted with one or more additional substituted and unsubstituted heterocycles. Examples include but are not limited to pyrid-2-ylmorpholin-4-ylmethyl and 2-pyrid-3-yl-2-morpholin-4-ylethyl.

The phrase "unsubstituted arylaminoalkyl" refers to an unsubstituted alkyl group as defined above in which a carbon bond or hydrogen bond is replaced by a bond to a nitrogen atom which is bonded to at least one unsubstituted aryl group as defined above.

The phrase "substituted arylaminoalkyl" refers to an unsubstituted arylaminoalkyl group as defined above except where either the alkyl group of the arylaminoalkyl group is a substituted alkyl group as defined above or the aryl group of the arylaminoalkyl group is a substituted aryl group except that the bonds to the nitrogen atom in all arylaminoalkyl groups does not by itself qualify all arylaminoalkyl groups as being substituted. However, substituted arylaminoalkyl groups does include groups in which the hydrogen bonded to the nitrogen atom of the group is replaced with a non-carbon and non-hydrogen atom.

The phrase "unsubstituted heterocyclylaminoalkyl" refers to an unsubstituted alkyl group as defined above in which a carbon or hydrogen bond is replaced by a bond to a nitrogen atom which is bonded to at least one unsubstituted heterocyclyl group as defined above.

The phrase "substituted heterocyclylaminoalkyl" refers to unsubstituted heterocyclylaminoalkyl groups as defined above in which the heterocyclyl group is a substituted heterocyclyl group as defined above and/or the alkyl group is a substituted alkyl group as defined above. The bonds to the nitrogen atom in all heterocyclylaminoalkyl groups does not by itself qualify all heterocyclylaminoalkyl groups as being substituted. However, substituted heterocyclylaminoalkyl groups do include groups in which the hydrogen bonded to the nitrogen atom of the group is replaced with a non-carbon and non-hydrogen atom.

The phrase "unsubstituted alkylaminoalkoxy" refers to an unsubstituted alkyl group as defined above in which a carbon or hydrogen bond is replaced by a bond to an oxygen atom which is bonded to the parent compound and in which another carbon or hydrogen bond of the unsubstituted alkyl group is bonded to a nitrogen atom which is bonded to a hydrogen atom and an unsubstituted alkyl group as defined above.

The phrase "substituted alkylaminoalkoxy" refers to unsubstituted alkylaminoalkoxy groups as defined above in which a bond to a carbon or hydrogen atom of the alkyl group bonded to the oxygen atom which is bonded to the parent compound is replaced by one or more bonds to a non-carbon and non-hydrogen atoms as discussed above with respect to substituted alkyl groups and/or if the hydrogen bonded to the amino group is bonded to a non-carbon and non-hydrogen atom and/or if the alkyl group bonded to the nitrogen of the amine is bonded to a non-carbon and non-hydrogen atom as described above with respect to substituted alkyl groups. The presence of the amine and alkoxy functionality in all alkylaminoalkoxy groups does not by itself qualify all such groups as substituted alkylaminoalkoxy groups.

The phrase "unsubstituted dialkylaminoalkoxy" refers to an unsubstituted alkyl group as defined above in which a carbon or hydrogen bond is replaced by a bond to an oxygen atom which is bonded to the parent compound and in which another carbon or hydrogen bond of the unsubstituted alkyl group is bonded to a nitrogen atom which is bonded to two other similar or different unsubstituted alkyl groups as defined above.

The phrase "substituted dialkylaminoalkoxy" refers to an unsubstituted dialkylaminoalkoxy group as defined above in which a bond to a carbon or hydrogen atom of the alkyl group bonded to the oxygen atom which is bonded to the parent compound is replaced by one or more bonds to a non-carbon and non-hydrogen atoms as discussed above with respect to substituted alkyl groups and/or if one or more of the alkyl groups bonded to the nitrogen of the amine is bonded to a non-carbon and non-hydrogen atom as described above with respect to substituted alkyl groups. The presence of the amine and alkoxy functionality in all dialkylaminoalkoxy groups does not by itself qualify all such groups as substituted dialkylaminoalkoxy groups.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

The present invention provides methods of inhibiting serine/threonine and tyrosine kinases, and methods of treating biological conditions mediated by serine/threonine and tyrosine kinases. In particular, the present invention provides methods of inhibiting serine/threonine kinases, including glycogen synthase kinase 3 (GSK-3), cyclin dependent kinase 2 (Cdk2), cyclin dependent kinase 4 (Cdk4), MEK1, NEK-2, CHK2, CK1ε, Raf, checkpoint kinase 1 (CHK1), ribosomal S6 kinase 2 (Rsk2), and PAR-1 and methods of inhibiting tyrosine kinases, including cell division cycle 2 kinase (Cdc2 kinase), c-Kit, c-ABL, p60src, VEGFR3, PDGFRα, PDGFRβ, FGFR3, FLT-3, FYN oncogene kinase related to SRC, FGR, and YES (Fyn), lymphocyte-specific protein tyrosine kinase (Lck), and tyrosine kinase with Ig and EGF homology domains (Tie-2). The present invention also provides methods of treating biological conditions mediated by serine/threonine kinases, including GSK-3, Cdk2, Cdk4, MEK1, NEK-2, CHK2, CK1ε, Raf, CHK1, Rsk2, and PAR-1, and methods of treating biological conditions mediated by tyrosine kinases, including Cdc2 kinase, c-Kit, c-ABL, p60src, VEGFR3, PDGFRα, PDGFRβ, FGFR3, FLT-3, Fyn, Lck, and Tie-2.

Methods Relating to Serine/Threonine Kinases

In one aspect, the present invention provides a method of inhibiting a serine/threonine kinase in a subject and/or a method of treating a biological condition mediated by serine/threonine kinase activity in a subject. The methods include administering to the subject a compound of Structure I, a tautomer of the compound, a pharmaceutically acceptable salt of the compound, a pharmaceutically acceptable salt of the tautomer, or mixtures thereof. In the method of inhibiting a serine/threonine kinase, the serine/threonine kinase is inhibited in the subject after administration. Structure I has the following formula:

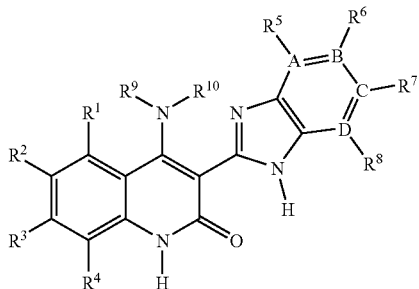

where,
- A, B, C, and D are independently selected from carbon or nitrogen;
- $R^1$ is selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted alkynyl groups having from 1 to 8 carbon atoms, substituted and unsubstituted heterocyclyl groups, substituted and unsubstituted heterocyclylalkyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)-alkyl groups, —S(=O)—NH$_2$, substituted and unsubstituted —S(=O)—N(H)(alkyl) groups, substituted and unsubstituted —S(=O)—N(alkyl)$_2$ groups, —OH, substituted and unsubstituted alkoxy groups, substituted and unsubstituted aryloxy groups, substituted and unsubstituted aralkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(H)—C(=O)-heterocyclyl groups, substituted and unsubstituted —N(H)—C(=O)-heterocyclylalkyl groups, substituted and unsubstituted —N(H)—S(=O)-alkyl groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(aralkyl) groups, substituted and unsubstituted —C(=O)—N(H)(heterocyclyl) groups, —C(=O)—N(H)(heterocyclylalkyl) groups, —CO$_2$H, substituted and unsubstituted —C(=O)—O-alkyl groups, substituted and unsubstituted —C(=O)—O-heterocyclyl groups, or substituted and unsubstituted —C(=O)—O-heterocyclylalkyl groups;
- $R^2$ and $R^3$ are independently selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted alkynyl groups having from 1 to 8 carbon atoms, substituted and unsubstituted aryl groups, substituted and unsubstituted aralkyl groups, substituted and unsubstituted heterocyclyl groups, substituted and unsubstituted heterocyclylalkyl groups, —SH, substituted and unsubstituted —S-alkyl groups, substituted and unsubstituted —S-aryl groups, substituted and unsubstituted —S-aralkyl groups, substituted and unsubstituted —S(=O)$_2$—O-alkyl groups, substituted and unsubstituted —S(=O)$_2$-alkyl groups, substituted and unsubstituted —S(=O)$_2$-heterocyclyl groups, substituted and unsubstituted —S(=O)-alkyl groups, substituted and unsubstituted —S(=O)-heterocyclyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, substituted and unsubstituted —S(=O)$_2$—N(H)(aryl) groups, substituted and unsubstituted —S(=O)$_2$—N(alkyl)(aryl) groups, substituted and unsubstituted —S(=O)$_2$—N(aryl)$_2$ groups, substituted and unsubstituted —S(=O)$_2$—N(H)(aralkyl) groups, substituted and unsubstituted —S(=O)$_2$—N(alkyl)(aralkyl) groups, substituted and unsubstituted —S(=O)$_2$—N(aralkyl)$_2$ groups, —OH, substituted and unsubstituted alkoxy groups, substituted and unsubstituted aryloxy groups, substituted and unsubstituted aralkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, substituted and unsubstituted —N(aryl)$_2$ groups, substituted and unsubstituted —N(H)(aralkyl) groups, substituted and unsubstituted —N(alkyl)(aralkyl) groups, substituted and unsubstituted —N(aralkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—S(=O)$_2$-alkyl groups, substituted and unsubstituted —N(H)—S(=O)$_2$-aryl groups, substituted and unsubstituted —N(H)—S(=O)$_2$-aralkyl groups, substituted and unsubstituted —N(H)—S(=O)$_2$-heterocyclyl groups, substituted and unsubstituted —N(H)—S(=O)$_2$-heterocyclylalkyl groups, substituted and unsubstituted —N(H)—C(=O)-alkyl groups, substituted and unsubstituted —N(H)—C(=O)-aryl groups, substituted and unsubstituted —N(H)—C(=O)-aralkyl groups, substituted and unsubstituted —N(H)—C(=O)-heterocyclyl groups, substituted and unsubstituted —N(H)—C(=O)-heterocyclylalkyl groups, substituted and unsubstituted —N(alkyl)-C(=O)-alkyl groups, substituted and unsubstituted —N(alkyl)-C(=O)-aryl groups, substituted and unsubstituted —N(alkyl)-C(=O)-aralkyl groups, substituted and unsubstituted —N(alkyl)-C(=O)-heterocyclyl groups, substituted and unsubstituted —N(alkyl)-C(=O)-heterocyclylalkyl groups, substituted and unsubstituted —N(alkyl)-S(=O)₂-alkyl groups, substituted and unsubstituted —N(alkyl)-S(=O)₂-aryl groups, substituted and unsubstituted —N(alkyl)-S(=O)₂-aralkyl groups, substituted and unsubstituted —N(alkyl)-S(=O)₂-heterocyclyl groups, substituted and unsubstituted —N(alkyl)-S(=O)₂-heterocyclylalkyl groups, —N(H)—C(=O)—NH₂, substituted and unsubstituted —N(H)—C(=O)—N(H)(alkyl) groups, substituted and unsubstituted —N(H)—C(=O)—N(alkyl)₂ groups, substituted and unsubstituted —N(H)—C(=O)—N(H)(aryl) groups, substituted and unsubstituted —N(H)—C(=O)—N(alkyl)(aryl) groups, substituted and unsubstituted —N(H)—C(=O)—N (aryl)₂ groups, substituted and unsubstituted —N(H)—C(=O)—N(H)(aralkyl) groups, substituted and unsubstituted —N(H)—C(=O)—N(alkyl)(aralkyl) groups, substituted and unsubstituted —N(H)—C(=O)—N(aralkyl)₂ groups, substituted and unsubstituted —N(H)—C(=O)—N(H)(heterocyclyl) groups, substituted and unsubstituted —N(H)—C(=O)—N(alkyl)(heterocyclyl) groups, substituted and unsubstituted —N(H)—C(=O)—N(heterocyclyl)₂ groups, substituted and unsubstituted —N(H)—C(=O)—N(H)(heterocyclylalkyl) groups, substituted and unsubstituted —N(H)—C(=O)—N(alkyl)(heterocyclylalkyl) groups, substituted and unsubstituted —N(H)—C(=O)—N(heterocyclylalkyl)₂ groups, substituted and unsubstituted —N(alkyl)-C(=O)—NH₂ groups, substituted and unsubstituted —N(alkyl)-C(=O)—N(H)(alkyl) groups, substituted and unsubstituted —N(alkyl)-C(=O)—N(alkyl)₂ groups, substituted and unsubstituted —N(alkyl)-C(=O)—N(H)(aryl) groups, substituted and unsubstituted —N(alkyl)-C(=O)—N(alkyl)(aryl) groups, substituted and unsubstituted —N(alkyl)-C(=O)—N (aryl)₂ groups, substituted and unsubstituted —N(alkyl)-C(=O)—N(H)(aralkyl) groups, substituted and unsubstituted —N(alkyl)-C(=O)—N(alkyl)(aralkyl) groups, substituted and unsubstituted —N(alkyl)-C(=O)—N(aralkyl)₂ groups, substituted and unsubstituted —N(alkyl)-C(=O)—N(H)(heterocyclyl) groups, substituted and unsubstituted —N(alkyl)-C(=O)—N(alkyl)(heterocyclyl) groups, substituted and unsubstituted —N(alkyl)-C(=O)—N(heterocyclyl)₂ groups, substituted and unsubstituted —N(alkyl)-C(=O)—N(H)(heterocyclylalkyl) groups, substituted and unsubstituted —N(alkyl)-C(=O)—N(alkyl)(heterocyclylalkyl) groups, substituted and unsubstituted —N(alkyl)-C(=O)—N(heterocyclylalkyl)₂ groups, substituted and unsubstituted —C(=O)-alkyl groups, substituted and unsubstituted —C(=O)-aryl groups, substituted and unsubstituted —C(=O)-aralkyl groups, substituted and unsubstituted —C(=O)-heterocyclyl groups, substituted and unsubstituted —C(=O)-heterocyclylalkyl groups, —C(=O)—NH₂, substituted and unsubstituted —C(=O)—N(H)(alkyl) groups, substituted and unsubstituted —C(=O)—N(alkyl)₂ groups, substituted and unsubstituted —C(=O)—N(H)(aryl) groups, substituted and unsubstituted —C(=O)—N(alkyl)(aryl) groups, substituted and unsubstituted —C(=O)—N(aryl)₂ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)₂ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)₂ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)₂ groups, —CO₂H, substituted and unsubstituted —C(=O)—O-alkyl groups, substituted and unsubstituted —C(=O)—O-aryl groups, substituted and unsubstituted —C(=O)—O-heterocyclyl groups, or substituted and unsubstituted —C(=O)—O-heterocyclylalkyl groups;

$R^4$ is selected from —H, —F, —Cl, —Br, —I, —CN, —NO₂, substituted and unsubstituted alkyl groups having from 1 to 12 carbon atoms, substituted and unsubstituted alkenyl groups having from 1 to 8 carbon atoms, substituted and unsubstituted alkynyl groups having from 1 to 8 carbon atoms, —SH, substituted and unsubstituted —S-alkyl groups, substituted and unsubstituted —S(=O)₂—O-alkyl groups, substituted and unsubstituted —S(=O)₂-alkyl groups, substituted and unsubstituted —S(=O)-alkyl groups, —S(=O)₂—NH₂, substituted and unsubstituted —S(=O)₂—N(H)(alkyl) groups, substituted and unsubstituted —S(=O)₂—N(alkyl)₂ groups, —OH, substituted and unsubstituted alkoxy groups, —NH₂, substituted and unsubstituted —N(H)(alkyl) groups, substituted and unsubstituted —N(alkyl)₂ groups, substituted and unsubstituted —N(H)—C(=O)-alkyl groups, substituted and unsubstituted —N(H)—S(=O)-alkyl groups, —C(=O)—NH₂, substituted and unsubstituted —C(=O)—N(H)(alkyl) groups, substituted and unsubstituted —C(=O)—N(alkyl)₂ groups, or substituted and unsubstituted —C(=O)—O-alkyl groups;

$R^5$ and $R^8$ are independently selected from —H, —F, —Cl, —Br, —I, —CN, —NO₂, substituted and unsubstituted straight and branched chain alkyl groups having from 1 to 8 carbon atoms, substituted and unsubstituted alkenyl groups having from 1 to 8 carbon atoms, substituted and unsubstituted alkynyl groups having from 1 to 8 carbon atoms, substituted and unsubstituted heterocyclyl groups, —SH, substituted and unsubstituted —S-alkyl groups, substituted and unsubstituted —S(=O)₂—O-alkyl groups, substituted and unsubstituted —S(=O)₂-alkyl groups, substituted and unsubstituted —S(=O)-alkyl groups, —S(=O)₂—NH₂, substituted and unsubstituted —S(=O)₂—N(H)(alkyl) groups, substituted and unsubstituted —S(=O)₂—N(alkyl)₂ groups, —OH, substituted and unsubstituted alkoxy groups, —NH₂, substituted and unsubstituted —N(H)(alkyl) groups, substituted and unsubstituted —N(alkyl)₂ groups, substituted and unsubstituted —N(H)—C(=O)-alkyl groups, substituted and unsubstituted —N(H)—S(=O)-alkyl groups, —C(=O)—NH₂, substituted and unsubstituted —C(=O)—N(H)(alkyl) groups, substituted and unsubstituted —C(=O)—N(alkyl)₂ groups, or substituted and unsubstituted —C(=O)—O-alkyl groups; or $R^5$ may be absent if A is nitrogen; or $R^8$ may be absent if D is nitrogen;

$R^6$ and $R^7$ are independently selected from —H, —F, —Cl, —Br, —I, —NO₂, —CN, substituted and unsubstituted alkyl groups having from 1 to 12 carbon atoms, substituted and unsubstituted alkenyl groups having from 1 to 12 carbon atoms, substituted and unsubstituted alkynyl groups having from 1 to 8 carbon atoms, substituted and unsubstituted heterocyclyl groups, substituted and unsubstituted heterocyclylalkyl groups, —SH, substituted and unsubstituted —S-alkyl groups, substituted and unsubstituted —S(=O)₂—O-alkyl groups, substituted and unsubstituted —S(=O)₂-alkyl groups, substituted and unsubstituted —S(=O)₂-heterocyclyl groups, substituted and unsubstituted —S(=O)-alkyl groups, substituted and unsubstituted —S(=O)-heterocyclyl groups, —S(=O)₂—NH₂, substituted and unsubstituted —S(=O)₂—N(H)(alkyl) groups, substituted and unsubstituted —S(=O)₂—N(alkyl)₂ groups, substituted and unsubstituted —S(=O)₂—N(H)(heterocyclyl) groups, substituted and unsubstituted —S(=O)₂—N(alkyl)(heterocyclyl) groups, substituted and unsubstituted —S(=O)₂—N(heterocyclyl)₂ groups, substituted and unsubstituted —S(=O)₂—N(H)(heterocyclylalkyl) groups, substituted and unsubstituted —S(=O)₂—N(alkyl)(heterocyclylalkyl) groups, substituted and unsubstituted —S(=O)₂—N(heterocyclylalkyl)₂ groups, —OH, substituted and unsubstituted alkoxy groups, substituted and unsubstituted aryloxy groups, substituted and unsubstituted arylalkoxy groups, substituted and unsubstituted heterocyclyloxy groups, substituted and unsubstituted heterocyclylalkoxy groups, —NH₂, substituted and unsubstituted —N(H)(alkyl) groups, substituted and unsubstituted —N(alkyl)₂ groups, substituted and unsubstituted —N(H)(aryl) groups, substituted and unsubstituted —N(alkyl)(aryl) groups, substituted and unsubstituted —N(aryl)₂ groups, substituted and unsubstituted —N(H)(aralkyl) groups, substituted and unsubstituted —N(alkyl)(aralkyl) groups, substituted and unsubstituted —N(aralkyl)₂ groups, substituted and unsubstituted —N(H)(heterocyclyl) groups, substituted and unsubstituted —N(alkyl)(heterocyclyl) groups, substituted and unsubstituted —N(heterocyclyl)₂ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)₂ groups, substituted and unsubstituted —N(H)—S(=O)₂-alkyl groups, substituted and unsubstituted —N(H)—S(=O)₂-heterocyclyl groups, substituted and unsubstituted —N(H)—S(=O)₂-heterocyclylalkyl groups, substituted and unsubstituted —N(H)—C(=O)-alkyl groups, substituted and unsubstituted —N(H)—C(=O)-heterocyclyl groups, substituted and unsubstituted —N(H)—C(=O)-heterocyclylalkyl groups, substituted and unsubstituted —N(alkyl)-C(=O)-alkyl groups, substituted and unsubstituted —N(alkyl)-C(=O)-heterocyclyl groups, substituted and unsubstituted —N(alkyl)-C(=O)-heterocyclylalkyl groups, substituted and unsubstituted —N(alkyl)-S(=O)₂-alkyl groups, substituted and unsubstituted —N(alkyl)-S(=O)₂-heterocyclyl groups, substituted and unsubstituted —N(alkyl)-S(=O)₂-heterocyclylalkyl groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH₂, substituted and unsubstituted —C(=O)—N(H)(alkyl) groups, substituted and unsubstituted —C(=O)—N(alkyl)₂ groups, substituted and unsubstituted —C(=O)—N(H)(aryl) groups, substituted and unsubstituted —C(=O)—N(alkyl)(aryl) groups, substituted and unsubstituted —C(=O)—N(aryl)₂ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)₂ groups, substituted and unsubstituted —C(=O)—N(H) (heterocyclyl) groups, substituted and unsubstituted —C(=O)—N(alkyl)(heterocyclyl) groups, substituted and unsubstituted —C(=O)—N(heterocyclyl)₂ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)₂ groups, —CO₂H, substituted and unsubstituted —C(=O)—O-alkyl groups, substituted and unsubstituted —C(=O)—O-heterocyclyl groups, or substituted and unsubstituted —C(=O)—O-heterocyclylalkyl groups; or R⁶ may be absent if B is nitrogen; or R⁷ may be absent if C is nitrogen;

R⁹ is selected from —H, substituted and unsubstituted alkyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, substituted and unsubstituted heterocyclylaminoalkyl groups, substituted and unsubstituted alkoxy groups, or —NH₂, or R⁹ and R¹⁰ join together to form one or more rings, each having 5, 6, or 7 ring members; and R¹⁰ is —H, or R⁹ and R¹⁰ join together to form one or more rings, each having 5, 6, or 7 ring members.

In some embodiments of the method of inhibiting a serine/threonine kinase in a subject and/or the method of treating a biological condition mediated by serine/threonine kinase activity in a subject, the serine/threonine kinase is selected from glycogen synthase kinase 3, cyclin dependent kinase 2, cyclin dependent kinase 4, MEK1, NEK-2, CHK2, CK1ε, Raf, checkpoint kinase 1, ribosomal S6 kinase 2, or dishevel ed associated kinase (PAR-1).

Methods Relating to Glycogen Synthase Kinase 3

In some embodiments of the method of inhibiting a serine/threonine kinase in a subject and/or the method of treating a biological condition mediated by serine/threonine kinase activity in a subject using a compound of Structure I, a tautomer of the compound, a pharmaceutically acceptable salt of the compound, a pharmaceutically acceptable salt of the tautomer, or mixtures thereof, the serine/threonine kinase is GSK-3. In some such methods the GSK-3 is inhibited in the subject after administration. Structure I has the following formula:

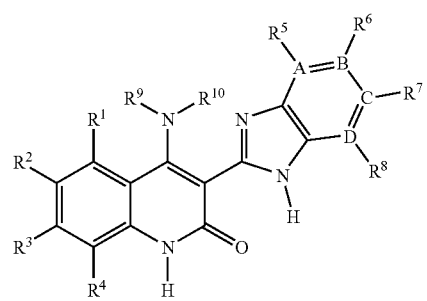

where:
A, B, C, and D are independently selected from carbon or nitrogen;
R¹ is selected from —H, —F, —Cl, —Br, —I, —CN, —NO₂, substituted and unsubstituted straight and branched chain alkyl groups having from 1 to 8 carbon atoms, substituted and unsubstituted alkenyl groups having from 1 to 8 carbon atoms, substituted and unsubstituted alkynyl groups having from 1 to 8 carbon atoms, substituted and unsubstituted heterocyclyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)-alkyl groups, —S(=O)—NH$_2$, substituted and unsubstituted —S(=O)—N(H)(alkyl) groups, substituted and unsubstituted —S(=O)—N(alkyl)$_2$ groups, —OH, substituted and unsubstituted alkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)—C(=O)-alkyl groups, substituted and unsubstituted —N(H)—S(=O)-alkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(aralkyl) groups, —CO$_2$H, or substituted and unsubstituted —C(=O)—O-alkyl groups;

R$^2$ is selected from —H, —F, —Cl, —Br, —I, —CN, —NO$_2$, substituted and unsubstituted straight and branched chain alkyl groups having from 1 to 8 carbon atoms, substituted and unsubstituted alkenyl groups having from 1 to 8 carbon atoms, substituted and unsubstituted alkynyl groups having from 1 to 8 carbon atoms, substituted and unsubstituted cycloalkyl groups, substituted and unsubstituted cycloalkenyl groups, substituted and unsubstituted aryl groups, substituted and unsubstituted heterocyclyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)$_2$-heterocyclyl groups, substituted and unsubstituted —S(=O)-alkyl groups, substituted and unsubstituted —S(=O)-heterocyclyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, —OH, substituted and unsubstituted alkoxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)—C(=O)-alkyl groups, substituted and unsubstituted —N(H)—C(=O)-heterocyclyl groups, substituted and unsubstituted —N(H)—S(=O)-alkyl groups, substituted and unsubstituted —N(H)—S(=O)-heterocyclyl groups, —N(alkyl)-C(=O)-alkyl groups, substituted and unsubstituted —N(alkyl)-C(=O)-heterocyclyl groups, substituted and unsubstituted —N(alkyl)-S(=O)-alkyl groups, substituted and unsubstituted —N(alkyl)-S(=O)-heterocyclyl groups, —N(H)—C(=O)—NH$_2$, substituted and unsubstituted —N(H)—C(=O)—N(H)(alkyl) groups, substituted and unsubstituted —N(H)—C(=O)—N(alkyl)$_2$ groups, —N(alkyl)-C(=O)—NH$_2$, substituted and unsubstituted —N(alkyl)-C(=O)—N(H)(alkyl) groups, substituted and unsubstituted —N(alkyl)-C(=O)—N(alkyl)$_2$ groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)-alkyl groups, substituted and unsubstituted —C(=O)-heterocyclyl groups, —CO$_2$H, or substituted and unsubstituted —C(=O)—O-alkyl groups; or R$^2$ and R$^3$ may join together to form a cyclic group;

R$^3$ is selected from —H, —F, —Cl, —Br, —I, —CN, —NO$_2$, substituted and unsubstituted straight and branched chain alkyl groups having from 1 to 8 carbon atoms, substituted and unsubstituted alkenyl groups having from 1 to 8 carbon atoms, substituted and unsubstituted alkynyl groups having from 1 to 8 carbon atoms, substituted and unsubstituted aryl groups, substituted and unsubstituted aralkyl groups, substituted and unsubstituted heterocyclyl groups, substituted and unsubstituted heterocyclylalkyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)$_2$-heterocyclyl groups, substituted and unsubstituted —S(=O)-alkyl groups, substituted and unsubstituted —S(=O)-heterocyclyl groups, —S(=O)—NH$_2$, substituted and unsubstituted —S(=O)—N(H)(alkyl) groups, substituted and unsubstituted —S(=O)—N(alkyl)$_2$ groups, —OH, substituted and unsubstituted alkoxy groups, substituted and unsubstituted heterocyclyloxy groups, substituted and unsubstituted heterocyclylalkoxy groups, substituted and unsubstituted —N(H)(alkyl) groups, substituted and unsubstituted —N(H)(cycloalkyl) groups, substituted and unsubstituted —N(H)(heterocyclyl) groups, substituted and unsubstituted —N(H)(heterocyclylalkyl) groups, substituted and unsubstituted —N(alkyl)$_2$ groups, —NH$_2$, substituted and unsubstituted —N(H)—C(=O)-alkyl groups, substituted and unsubstituted —N(H)—C(=O)-heterocyclyl groups, substituted and unsubstituted —N(H)—S(=O)-alkyl groups, substituted and unsubstituted —N(H)—S(=O)-heterocyclyl groups, substituted and unsubstituted —N(alkyl)-C(=O)-alkyl groups, substituted and unsubstituted —N(alkyl)-C(=O)-heterocyclyl groups, substituted and unsubstituted —N(alkyl)-S(=O)-alkyl groups, substituted and unsubstituted —N(alkyl)-S(=O)-heterocyclyl groups, —N(H)—C(=O)—NH$_2$, substituted and unsubstituted —N(H)—C(=O)—N(H)(alkyl) groups, substituted and unsubstituted —N(H)—C(=O)—N(alkyl)$_2$ groups, —N(alkyl)-C(=O)—NH$_2$, substituted and unsubstituted —N(alkyl)-C(=O)—N(H)(alkyl) groups substituted and unsubstituted —N(alkyl)-C(=O)—N(alkyl)$_2$ groups, substituted and unsubstituted —C(=O)-alkyl groups, substituted and unsubstituted —C(=O)-heterocyclyl groups, —C(=O)—NH$_2$ groups, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, substituted and unsubstituted —C(=O)—N(H)(aryl) groups, —CO$_2$H, or substituted and unsubstituted —C(=O)—O-alkyl groups, or R$^2$ and R$^3$ may join together to form a cyclic group;

R$^4$ is selected from —H, —F, —Cl, —Br, —I, —CN, —NO$_2$, substituted and unsubstituted straight and branched chain alkyl groups having from 1 to 8 carbon atoms, substituted and unsubstituted alkenyl groups having from 1 to 8 carbon atoms, substituted and unsubstituted alkynyl groups having from 1 to 8 carbon atoms, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)-alkyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, —OH, substituted and unsubstituted alkoxy groups, —NH$_2$, substituted and unsubstituted —N(H)(alkyl) groups, substituted and unsubstituted —N(alkyl)$_2$ groups, substituted and unsubstituted —N(H)—C(=O)-alkyl groups, substituted and unsubstituted —N(H)—S(=O)-alkyl groups, —C(=O)—NH$_2$, substituted and unsubstituted —C(=O)—N(H)(alkyl) groups, substituted and unsubstituted —C(=O)—N(alkyl)$_2$ groups, or substituted and unsubstituted —C(=O)—O-alkyl groups;

$R^5$ is selected from —H, —F, —Cl, —Br, —I, —CN, —NO$_2$, substituted and unsubstituted straight and branched chain alkyl groups having from 1 to 8 carbon atoms, substituted and unsubstituted alkenyl groups having from 1 to 8 carbon atoms, substituted and unsubstituted alkynyl groups having from 1 to 8 carbon atoms, substituted and unsubstituted heterocyclyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)-alkyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, —OH, substituted and unsubstituted alkoxy groups, —NH$_2$, substituted and unsubstituted —N(H)(alkyl) groups, substituted and unsubstituted —N(alkyl)$_2$ groups, substituted and unsubstituted —N(H)—C(=O)-alkyl groups, substituted and unsubstituted —N(H)—S(=O)-alkyl groups, —C(=O)—NH$_2$, substituted and unsubstituted —C(=O)—N(H)(alkyl) groups, substituted and unsubstituted —C(=O)—N(alkyl)$_2$ groups, or substituted and unsubstituted —C(=O)—O-alkyl groups; or $R^5$ may be absent if A is nitrogen;

$R^6$ is selected from —H, —F, —Cl, —Br, —I, —CN, —NO$_2$, substituted and unsubstituted alkyl groups having from 1 to 8 carbon atoms, substituted and unsubstituted alkenyl groups having from 1 to 8 carbon atoms, substituted and unsubstituted alkynyl groups having from 1 to 8 carbon atoms, substituted and unsubstituted heterocyclyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)$_2$-heterocyclyl groups, substituted and unsubstituted —S(=O)-alkyl groups, substituted and unsubstituted —S(=O)-heterocyclyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, —OH, substituted and unsubstituted alkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(H)—C(=O)-alkyl groups, substituted and unsubstituted —N(H)—C(=O)-heterocyclyl groups, substituted and unsubstituted —N(alkyl)-C(=O)-alkyl groups, substituted and unsubstituted —N(alkyl)-C(=O)-heterocyclyl groups, substituted and unsubstituted —N(H)—S(=O)$_2$-alkyl groups, substituted and unsubstituted —N(H)—S(=O)$_2$-heterocyclyl groups, and unsubstituted —N(alkyl)-S(=O)$_2$-alkyl groups, substituted and unsubstituted —N(alkyl)-S(=O)$_2$-heterocyclyl groups, substituted and unsubstituted —C(=O)-alkyl groups, substituted and unsubstituted —C(=O)-heterocyclyl groups, —C(=O)—NH$_2$, substituted and unsubstituted —C(=O)—N(H)(alkyl) groups, substituted and unsubstituted —C(=O)—N(alkyl)$_2$ groups, —CO$_2$H, or substituted and unsubstituted —C(=O)—O-alkyl groups; or $R^6$ may be absent if B is nitrogen;

$R^7$ is selected from —H, —F, —Cl, —Br, —I, —CN, —NO$_2$, substituted and unsubstituted alkyl groups having from 1 to 8 carbon atoms, substituted and unsubstituted alkenyl groups having from 1 to 8 carbon atoms, substituted and unsubstituted alkynyl groups having from 1 to 8 carbon atoms, substituted and unsubstituted heterocyclyl groups, substituted and unsubstituted heterocyclylalkyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)$_2$-heterocyclyl groups, substituted and unsubstituted —S(=O)-alkyl groups, substituted and unsubstituted —S(=O)-heterocyclyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, —OH, substituted and unsubstituted alkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(H)—C(=O)-alkyl groups, substituted and unsubstituted —N(H)—C(=O)-heterocyclyl groups, substituted and unsubstituted —N(alkyl)-C(=O)-alkyl groups, substituted and unsubstituted —N(alkyl)-C(=O)-heterocyclyl groups, substituted and unsubstituted —N(H)—S(=O)-alkyl groups, substituted and unsubstituted —N(H)—S(=O)-heterocyclyl groups, substituted and unsubstituted —N(alkyl)-S(=O)-alkyl groups, substituted and unsubstituted —N(alkyl)-S(=O)-heterocyclyl groups, substituted and unsubstituted amidine groups, —C(=O)—NH$_2$, substituted and unsubstituted —C(=O)—N(H)(alkyl) groups, substituted and unsubstituted —C(=O)—N(alkyl)$_2$ groups, and unsubstituted —C(=O)—N(H)(heterocyclyl) groups, substituted and unsubstituted —C(=O)—N(H)(alkyl)(heterocyclyl) groups, substituted and unsubstituted —C(=O)—N(heterocyclyl)$_2$ groups, substituted and unsubstituted —C(=O)-alkyl groups, substituted and unsubstituted —C(=O)-heterocyclyl groups, —CO$_2$H, or substituted and unsubstituted —C(=O)—O-alkyl groups; or $R^7$ may be absent if C is nitrogen;

$R^8$ is selected from —H, —F, —Cl, —Br, —I, —CN, —NO$_2$, substituted and unsubstituted straight and branched chain alkyl groups having from 1 to 8 carbon atoms, substituted and unsubstituted alkenyl groups having from 1 to 8 carbon atoms, substituted and unsubstituted alkynyl groups having from 1 to 8 carbon atoms, substituted and unsubstituted heterocyclyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)-alkyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, —OH, substituted and unsubstituted alkoxy groups, —NH$_2$, substituted and unsubstituted —N(H)(alkyl) groups, substituted and unsubstituted —N(alkyl)$_2$ groups, substituted and unsubstituted —N(H)—C(=O)-alkyl groups, substituted and unsubstituted —N(H)—S(=O)$_2$-alkyl groups, —C(=O)—NH$_2$, substituted and unsubstituted —C(=O)—N(H)(alkyl) groups, substituted and unsubstituted —C(=O)—N(alkyl)$_2$ groups, or substituted and unsubstituted —C(=O)—O-alkyl groups; or R$^8$ may be absent if D is nitrogen;

R$^9$ is selected from —H, substituted and unsubstituted straight and branched chain alkyl groups having from 1 to 8 carbon atoms, substituted and unsubstituted cycloalkyl groups, substituted and unsubstituted aryl groups, substituted and unsubstituted aralkyl groups, substituted and unsubstituted heterocyclyl groups, substituted and unsubstituted heterocyclylalkyl groups, substituted and unsubstituted heterocyclylaminoalkyl groups, substituted and unsubstituted alkoxy groups, or —NH$_2$, or R$^9$ and R$^{10}$ join together to form a ring having 5, 6, or 7 ring members; and R$^{10}$ is —H, or R$^9$ and R$^{10}$ join together to form a ring having 5, 6, or 7 ring members.

In some embodiments of the method of inhibiting GSK-3 in a subject and/or the method of treating a biological condition mediated by GSK-3 activity in a subject, A, B, C, and D are independently selected from carbon or nitrogen;

R$^1$ is selected from —H, —F, —Cl, —Br, —I, substituted or unsubstituted straight or branched chain alkyl groups having from 1 to 8 carbon atoms, substituted or unsubstituted alkenyl groups having from 1 to 8 carbon atoms, substituted or unsubstituted alkynyl groups having from 1 to 8 carbon atoms, —CN, —NO$_2$, —OH, —SH, substituted or unsubstituted alkoxy groups, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)-alkyl groups, —S(=O)—NH$_2$, substituted or unsubstituted —S(=O)—N(H)(alkyl) groups, substituted or unsubstituted —S(=O)—N(alkyl)$_2$ groups, —C(=O)—NH$_2$, substituted or unsubstituted —C(=O)—N(H)(alkyl) groups, substituted or unsubstituted —C(=O)—N(alkyl)$_2$ groups, substituted or unsubstituted —C(=O)—O-alkyl groups, —NH$_2$, substituted or unsubstituted —N(H)(alkyl) groups, substituted or unsubstituted —N(alkyl)$_2$ groups, substituted or unsubstituted —N(H)—C(=O)-alkyl groups, or substituted or unsubstituted —N(H)—S(=O)-alkyl groups;

R$^2$ is selected —H, —F, —Cl, —Br, —I, —NO$_2$, —CN, —NH$_2$, —CO$_2$H, —OH, substituted or unsubstituted straight or branched chain alkyl groups having from 1 to 8 carbon atoms, substituted or unsubstituted cycloalkenyl groups, substituted or unsubstituted cycloalkyl groups, substituted or unsubstituted alkoxy groups, substituted or unsubstituted —N(H)(alkyl) groups, substituted or unsubstituted —N(alkyl)$_2$ groups, substituted or unsubstituted heterocyclyl groups, substituted or unsubstituted aryl groups, substituted or unsubstituted alkenyl groups having from 1 to 8 carbon atoms, substituted or unsubstituted alkynyl groups having from 1 to 8 carbon atoms, —SH, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)$_2$-heterocyclyl groups, substituted or unsubstituted —S(=O)-alkyl groups, substituted or unsubstituted —S(=O)-heterocyclyl groups, —S(=O)—NH$_2$, substituted or unsubstituted —S(=O)—N(H)(alkyl) groups, substituted or unsubstituted —S(=O)—N(alkyl)$_2$ groups, —C(=O)—NH$_2$, substituted or unsubstituted —C(=O)—N(H)(alkyl) groups, substituted or unsubstituted —C(=O)—N(alkyl)$_2$ groups, substituted or unsubstituted —C(=O)-alkyl groups, substituted or unsubstituted —C(=O)-heterocyclyl groups, substituted or unsubstituted —C(=O)—O-alkyl groups, substituted or unsubstituted —N(H)—C(=O)-alkyl groups, substituted or unsubstituted —N(H)—C(=O)-heterocyclyl groups, substituted or unsubstituted —N(H)—S(=O)-alkyl groups, substituted or unsubstituted —N(H)—S(=O)-heterocyclyl groups, —N(alkyl)-C(=O)-alkyl groups, substituted or unsubstituted —N(alkyl)-C(=O)-heterocyclyl groups, substituted or unsubstituted —N(alkyl)-S(=O)-alkyl groups, substituted or unsubstituted —N(alkyl)-S(=O)-heterocyclyl groups, —N(H)—C(=O)—NH$_2$, substituted or unsubstituted —N(H)—C(=O)—N(H)(alkyl) groups, substituted or unsubstituted —N(H)—C(=O)—N(alkyl)$_2$ groups, —N(alkyl)-C(=O)—NH$_2$, substituted or unsubstituted —N(alkyl)-C(=O)—N(H)(alkyl) groups, or substituted or unsubstituted —N(alkyl)-C(=O)—N(alkyl)$_2$ groups; or R$^2$ and R$^3$ may join together to form a cyclic group;

R$^3$ is selected from —H, —F, —Cl, —Br, —I, —OH, substituted or unsubstituted straight or branched chain alkyl groups having from 1 to 8 carbon atoms, substituted or unsubstituted alkoxy groups, —CO$_2$H, —CN, substituted or unsubstituted —N(H)(alkyl) groups, substituted or unsubstituted —N(H)(cycloalkyl) groups, substituted or unsubstituted —N(alkyl)$_2$ groups, substituted or unsubstituted heterocyclyl groups, substituted or unsubstituted aryl groups, substituted or unsubstituted —C(=O)-heterocyclyl groups, substituted or unsubstituted —C(=O)-alkyl groups, substituted or unsubstituted —C(=O)—N(H)(alkyl) groups, substituted or unsubstituted —C(=O)—N(alkyl)$_2$ groups, —C(=O)—NH$_2$ groups, substituted or unsubstituted —C(=O)—N(H)(heterocyclyl) groups, substituted or unsubstituted —C(=O)—N(H)(aryl) groups, substituted or unsubstituted alkenyl groups having from 1 to 8 carbon atoms, substituted or unsubstituted alkynyl groups having from 1 to 8 carbon atoms, —NO$_2$, —SH, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)$_2$-heterocyclyl groups, substituted or unsubstituted —S(=O)-alkyl groups, substituted or unsubstituted —S(=O)-heterocyclyl groups, —S(=O)—NH$_2$, substituted or unsubstituted —S(=O)—N(H)(alkyl) groups, substituted or unsubstituted —S(=O)—N(alkyl)$_2$ groups, substituted or unsubstituted —C(=O)—O-alkyl groups, —NH$_2$, substituted or unsubstituted —N(H)—C(=O)-alkyl groups, substituted or unsubstituted —N(H)—C(=O)-heterocyclyl groups, substituted or unsubstituted —N(H)—S(=O)-alkyl groups, substituted or unsubstituted —N(H)—S(=O)-heterocyclyl groups, substituted or unsubstituted —N(alkyl)-C(=O)-alkyl groups, substituted or unsubstituted —N(alkyl)-C(=O)-heterocyclyl groups, substituted or unsubstituted —N(alkyl)-S(=O)-alkyl groups, substituted or unsubstituted —N(alkyl)-S(=O)-heterocyclyl groups, —N(H)—C(=O)—NH$_2$, substituted or unsubstituted —N(H)—C(=O)—N(H)(alkyl) groups, substituted or unsubstituted —N(H)—C(=O)—N(alkyl)$_2$ groups, —N(alkyl)-C(=O)—NH$_2$, substituted or unsubstituted —N(alkyl)-C(=O)—N(H)(alkyl) groups, or substituted or unsubstituted —N(alkyl)-C(=O)—N(alkyl)$_2$ groups; or $R^2$ and $R^3$ may join together to form a cyclic group;

$R^4$ is selected from of —H, —F, —Cl, —Br, —I, substituted or unsubstituted straight or branched chain alkyl groups having from 1 to 8 carbon atoms, substituted or unsubstituted alkenyl groups having from 1 to 8 carbon atoms, substituted or unsubstituted alkynyl groups having from 1 to 8 carbon atoms, —CN, —NO$_2$, —OH, —SH, substituted or unsubstituted alkoxy groups, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)-alkyl groups, —S(=O)—NH$_2$, substituted or unsubstituted —S(=O)—N(H)(alkyl) groups, substituted or unsubstituted —S(=O)—N(alkyl)$_2$ groups, —C(=O)—NH$_2$, substituted or unsubstituted —C(=O)—N(H)(alkyl) groups, substituted or unsubstituted —C(=O)—N(alkyl)$_2$ groups, substituted or unsubstituted —C(=O)—O-alkyl groups, —NH$_2$, substituted or unsubstituted —N(H)(alkyl) groups, substituted or unsubstituted —N(alkyl)$_2$ groups, substituted or unsubstituted —N(H)—C(=O)-alkyl groups, or substituted or unsubstituted —N(H)—S(=O)-alkyl groups;

$R^5$ is selected from —H, —F, —Cl, —Br, —I, substituted or unsubstituted straight or branched chain alkyl groups having from 1 to 8 carbon atoms, substituted or unsubstituted heterocyclyl groups, substituted or unsubstituted alkenyl groups having from 1 to 8 carbon atoms, substituted or unsubstituted alkynyl groups having from 1 to 8 carbon atoms, —CN, —NO$_2$, —OH, —SH, substituted or unsubstituted alkoxy groups, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)-alkyl groups, —S(=O)—NH$_2$, substituted or unsubstituted —S(=O)—N(H)(alkyl) groups, substituted or unsubstituted —S(=O)—N(alkyl)$_2$ groups, —C(=O)—NH$_2$, substituted or unsubstituted —C(=O)—N(H)(alkyl) groups, substituted or unsubstituted —C(=O)—N(alkyl)$_2$ groups, substituted or unsubstituted —C(=O)—O-alkyl groups, —NH$_2$, substituted or unsubstituted —N(H)(alkyl) groups, substituted or unsubstituted —N(alkyl)$_2$ groups, substituted or unsubstituted —N(H)—C(=O)-alkyl groups, or substituted or unsubstituted —N(H)—S(=O)-alkyl groups; or $R^5$ may be absent if A is nitrogen;

$R^6$ is selected from —H, —Cl, —F, —Br, —OH, substituted or unsubstituted heterocyclyl groups, substituted or unsubstituted —N(H)(alkyl) groups, substituted or unsubstituted —N(H)(heterocyclyl) groups, substituted or unsubstituted —N(alkyl)(heterocyclyl) groups, substituted or unsubstituted alkoxy groups, substituted or unsubstituted alkyl groups having from 1 to 8 carbon atoms, substituted or unsubstituted alkenyl groups having from 1 to 8 carbon atoms, substituted or unsubstituted alkynyl groups having from 1 to 8 carbon atoms, —CN, —NO$_2$, —OH, —SH, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)$_2$-heterocyclyl groups, substituted or unsubstituted —S(=O)-alkyl groups, substituted or unsubstituted —S(=O)-heterocyclyl groups, —S(=O)—NH$_2$, substituted or unsubstituted —S(=O)—N(H)(alkyl) groups, substituted or unsubstituted —S(=O)—N(alkyl)$_2$ groups, —C(=O)—NH$_2$, substituted or unsubstituted —C(=O)—N(H)(alkyl) groups, substituted or unsubstituted —C(=O)—N(alkyl)$_2$ groups, substituted or unsubstituted —C(=O)-alkyl groups, substituted or unsubstituted —C(=O)-heterocyclyl groups, substituted or unsubstituted —C(=O)—O-alkyl groups, —NH$_2$, substituted or unsubstituted —N(alkyl)$_2$ groups, substituted or unsubstituted —N(H)—C(=O)-alkyl groups, substituted or unsubstituted —N(H)—C(=O)-heterocyclyl groups, substituted or unsubstituted —N(alkyl)-C(=O)-alkyl groups, substituted or unsubstituted —N(alkyl)-C(=O)-heterocyclyl groups, substituted or unsubstituted —N(H)—S(=O)-alkyl groups, substituted or unsubstituted —N(H)—S(=O)-heterocyclyl groups, substituted or unsubstituted —N(alkyl)-S(=O)-alkyl groups, or substituted or unsubstituted —N(alkyl)-S(=O)-heterocyclyl groups; or $R^6$ may be absent if B is nitrogen;

$R^7$ is selected from —H, —Cl, —F, —Br, —OH, substituted or unsubstituted heterocyclyl groups, substituted or unsubstituted —N(H)(alkyl) groups, substituted or unsubstituted —N(H)(heterocyclyl) groups, substituted or unsubstituted —N(alkyl)(heterocyclyl) groups, substituted or unsubstituted alkoxy groups, substituted or unsubstituted alkyl groups having from 1 to 8 carbon atoms, substituted or unsubstituted alkenyl groups having from 1 to 8 carbon atoms, substituted or unsubstituted alkynyl groups having from 1 to 8 carbon atoms, —CN, —NO$_2$, —OH, —SH, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)$_2$-heterocyclyl groups, substituted or unsubstituted —S(=O)-alkyl groups, substituted or unsubstituted —S(=O)-heterocyclyl groups, —S(=O)—NH$_2$, substituted or unsubstituted —S(=O)—N(H)(alkyl) groups, substituted or unsubstituted —S(=O)—N(alkyl)$_2$ groups, —C(=O)—NH$_2$, substituted or unsubstituted —C(=O)—N(H)(alkyl) groups, substituted or unsubstituted —C(=O)—N(alkyl)$_2$ groups, substituted or unsubstituted —C(=O)-alkyl groups, substituted or unsubstituted —C(=O)-heterocyclyl groups, substituted or unsubstituted —C(=O)—O-alkyl groups, —NH$_2$, substituted or unsubstituted —N(alkyl)$_2$ groups, substituted or unsubstituted —N(H)—C(=O)-alkyl groups, substituted or unsubstituted —N(H)—C(=O)-heterocyclyl groups, substituted or unsubstituted —N(alkyl)-C(=O)-alkyl groups, substituted or unsubstituted —N(alkyl)-C(=O)-heterocyclyl groups, substituted or unsubstituted —N(H)—S(=O)-alkyl groups, substituted or unsubstituted —N(H)—S(=O)-heterocyclyl groups, substituted or unsubstituted —N(alkyl)-S(=O)-alkyl groups, or substituted or unsubstituted —N(alkyl)-S(=O)-heterocyclyl groups; or $R^7$ may be absent if C is nitrogen;

$R^8$ is selected from —H, —F, —Cl, —Br, —I, substituted or unsubstituted straight or branched chain alkyl groups having from 1 to 8 carbon atoms, substituted or unsubstituted heterocyclyl groups, substituted or unsubstituted alkenyl groups having from 1 to 8 carbon atoms, substituted or unsubstituted alkynyl groups having from 1 to 8 carbon atoms, —CN, —NO$_2$, —OH, —SH, substituted or unsubstituted alkoxy groups, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)-alkyl groups, —S(=O)—NH$_2$, substituted or unsubstituted —S(=O)—N(H)(alkyl) groups, substituted or unsubstituted —S(=O)—N(alkyl)$_2$ groups, —C(=O)—NH$_2$, substituted or unsubstituted —C(=O)—N(H)(alkyl) groups, substituted or unsubstituted —C(=O)—N(alkyl)$_2$ groups, substituted or unsubstituted —C(=O)—O-alkyl groups, —NH$_2$, substituted or unsubstituted —N(H)(alkyl) groups, substituted or unsubstituted —N(alkyl)$_2$ groups, substituted or unsubstituted —N(H)—C(=O)-alkyl groups, or substituted or unsubstituted —N(H)—S(=O)-alkyl groups; or $R^8$ may be absent if D is nitrogen;

$R^9$ is selected from of substituted or unsubstituted heterocyclyl groups, substituted or unsubstituted aryl groups, substituted or unsubstituted alkoxy groups, —NH$_2$, substituted or unsubstituted cycloalkyl groups, or substituted or unsubstituted straight or branched chain alkyl groups having from 1 to 8 carbon atoms, or $R^9$ and $R^{10}$ join together to form a ring having 5, 6, or 7 ring members; or $R^{10}$ is —H, or $R^9$ and $R^{10}$ join together to form a ring having 5, 6, or 7 ring members.

In some embodiments of the method of inhibiting GSK-3 in a subject and/or the method of treating a biological condition mediated by GSK-3 activity in a subject, $R^1$ is selected from —H, —F, —Cl, —Br, —I, and straight and branched chain alkyl groups having from 1 to 8 carbon atoms;

$R^2$ is selected from —H, —F, —Cl, —Br, —I, —CN, —CO$_2$H, —NO2, straight and branched chain alkyl groups having from 1 to 8 carbon atoms, substituted and unsubstituted cycloalkyl groups, substituted and unsubstituted cycloalkenyl groups, substituted and unsubstituted aryl groups, substituted and unsubstituted heterocyclyl groups, —OH, substituted and unsubstituted alkoxy groups, —NH$_2$, substituted and unsubstituted —N(H)(alkyl) groups, or substituted and unsubstituted —N(alkyl)$_2$ groups;

$R^3$ is selected from —H, —F, —Cl, —Br, —I, —CN, straight and branched chain alkyl groups having from 1 to 8 carbon atoms, substituted and unsubstituted aryl groups, substituted and unsubstituted heterocyclyl groups, —OH, substituted and unsubstituted alkoxy groups, substituted and unsubstituted —N(H)(alkyl) groups, substituted and unsubstituted —N(H)(cycloalkyl) groups, substituted and unsubstituted —N(H)(heterocyclyl) groups, substituted and unsubstituted —N(H)(heterocyclylalkyl) groups, substituted and unsubstituted —N(alkyl)$_2$ groups, —CO$_2$H, substituted and unsubstituted —C(=O)-heterocyclyl groups, substituted and unsubstituted —C(=O)-alkyl groups, substituted and unsubstituted —C(=O)N(H)(alkyl) groups, substituted and unsubstituted —C(=O)—N(alkyl)$_2$ groups, —C(=O)—NH$_2$ groups, substituted and unsubstituted —C(=O)—N(H)(heterocyclyl) groups, or substituted and unsubstituted —C(=O)—N(H)(aryl) groups;

$R^4$ is selected from —H, —F, —Cl, —Br, —I, and straight and branched chain alkyl groups having from 1 to 8 carbon atoms;

$R^5$ is selected from —H, —F, —Cl, —Br, —I, straight and branched chain alkyl groups having from 1 to 8 carbon atoms, or substituted and unsubstituted heterocyclyl groups; or $R^5$ may be absent if A is nitrogen;

$R^6$ is selected from —H, —F, —Cl, —Br, substituted and unsubstituted alkyl groups having from 1 to 8 carbon atoms, substituted and unsubstituted heterocyclyl groups, —OH, substituted and unsubstituted alkoxy groups, substituted and unsubstituted —N(H)(alkyl) groups, substituted and unsubstituted —N(H)(heterocyclyl) groups, or substituted and unsubstituted —N(alkyl)(heterocyclyl) groups; or $R^6$ may be absent if B is nitrogen;

$R^7$ is selected from —H, —Cl, —F, —Br, substituted and unsubstituted alkyl groups having from 1 to 8 carbon atoms, —OH, substituted and unsubstituted alkoxy groups, substituted and unsubstituted heterocyclyl groups, substituted and unsubstituted —N(H)(alkyl) groups, substituted and unsubstituted —N(H)(heterocyclyl) groups, or substituted and unsubstituted —N(alkyl)(heterocyclyl) groups; or $R^7$ may be absent if C is nitrogen; and $R^8$ is selected from —H, —F, —Cl, —Br, —I, straight and branched chain alkyl groups having from 1 to 8 carbon atoms, or substituted and unsubstituted heterocyclyl groups; or $R^8$ may be absent if D is nitrogen.

In some embodiments of the method of inhibiting GSK-3 in a subject and/or the method of treating a biological condition mediated by GSK-3 activity in a subject, A, B, C, and D are all carbon.

In some embodiments of the method of inhibiting GSK-3 in a subject and/or the method of treating a biological condition mediated by GSK-3 activity in a subject, one of A or D is nitrogen, and B and C are both carbon.

In some embodiments of the method of inhibiting GSK-3 in a subject and/or the method of treating a biological condition mediated by GSK-3 activity in a subject, $R^{10}$ is —H, and $R^9$ is selected from substituted and unsubstituted straight and branched chain alkyl groups having from 1 to 8 carbon atoms, substituted and unsubstituted cycloalkyl groups, substituted and unsubstituted aryl groups, substituted and unsubstituted aralkyl groups, substituted and unsubstituted heterocyclyl groups, substituted and unsubstituted heterocyclylalkyl groups, substituted and unsubstituted heterocyclylaminoalkyl groups, substituted and unsubstituted alkoxy groups, or —NH$_2$.

In some embodiments of the method of inhibiting GSK-3 in a subject and/or the method of treating a biological condition mediated by GSK-3 activity in a subject, $R^9$ is selected from unsubstituted straight and branched chain alkyl groups having from 1 to 8 carbon atoms, substituted and unsubstituted cycloalkyl groups, substituted and unsubstituted aryl groups, substituted and unsubstituted aralkyl groups, substituted and unsubstituted heterocyclyl groups, substituted and unsubstituted heterocyclylalkyl groups wherein the heterocyclyl group is saturated, substituted and unsubstituted heterocyclylalkyl groups wherein the heterocyclyl group is unsaturated, substituted and unsubstituted alkoxy groups, —NH$_2$, substituted and unsubstituted alkoxyalkyl groups, substituted and unsubstituted hydroxyalkyl groups, substituted and unsubstituted dialkylaminoalkyl groups, substituted and unsubstituted alkylaminoalkyl groups, substituted and unsubstituted aminoalkyl groups, substituted and unsubstituted heterocyclylaminoalkyl groups, substituted and unsubstituted (heterocyclyl)(alkyl)aminoalkyl groups, or substituted and unsubstituted alkyl-(SO$_2$)-alkyl groups.

In some embodiments of the method of inhibiting GSK-3 in a subject and/or the method of treating a biological condition mediated by GSK-3 activity in a subject, $R^{10}$ is —H, and $R^9$ is selected from substituted and unsubstituted cycloalkyl groups, substituted and unsubstituted saturated heterocyclyl groups, substituted and unsubstituted heterocyclylalkyl groups, or substituted and unsubstituted aminoalkyl groups.

In some embodiments of the method of inhibiting GSK-3 in a subject and/or the method of treating a biological condition mediated by GSK-3 activity in a subject, $R^9$ is selected from quinuclidinyl groups, piperidinyl groups, piperidinylalkyl groups, pyrrolidinyl groups, or aminocyclohexyl groups. In some such embodiments, $R^9$ is a quinuclidinyl group, and in further such embodiments $R^9$ is a quinuclidin-3-yl group.

In some embodiments of the method of inhibiting GSK-3 in a subject and/or the method of treating a biological condition mediated by GSK-3 activity in a subject, $R^9$ is selected from monocyclic, bicyclic, or polycyclic saturated heterocyclyl groups.

In some embodiments of the method of inhibiting GSK-3 in a subject and/or the method of treating a biological condition mediated by GSK-3 activity in a subject, $R^1$ is selected from —H, —F, —Cl, or —CH$_3$ groups. In some such embodiments $R^1$ is —H or —F, and in further such embodiments, $R^1$ is —H.

In some embodiments of the method of inhibiting GSK-3 in a subject and/or the method of treating a biological condition mediated by GSK-3 activity in a subject, $R^2$ is selected from —H, —Cl, —F, —Br, —I, —CH$_3$, —NO$_2$, —OMe, —CN, —CO$_2$H, substituted and unsubstituted 1,2,3,6-tetrahydropyridine groups, substituted and unsubstituted thiophene groups, substituted and unsubstituted imidazole groups, substituted and unsubstituted pyrrole groups, substituted and unsubstituted 3-pyridinyl groups, substituted and unsubstituted 4-pyridinyl groups, phenyl, 2-substituted phenyl groups, 2,4-disubstituted phenyl groups, 4-substituted phenyl groups, 3-substituted phenyl groups, 2,6-disubstituted phenyl groups, 3,4-disubstituted phenyl groups, substituted and unsubstituted dialkylamino groups, or substituted and unsubstituted alkylamino groups.

In some embodiments of the method of inhibiting GSK-3 in a subject and/or the method of treating a biological condition mediated by GSK-3 activity in a subject, $R^2$ is a substituted and unsubstituted aryl group selected from phenyl, 2-chlorophenyl, 2-methylphenyl, 2-ethylphenyl, 2-hydroxyphenyl, 2-methoxyphenyl, 2-trifluoromethylphenyl, 3-methoxyphenyl, 3-nitrophenyl, 3-carboxyphenyl, 3-acetylphenyl, 3-aminophenyl, 3-hydroxyphenyl, 3-acetamidophenyl, 3-carbomethoxyphenyl, 3-trifluoromethylphenyl, 3-ureidophenyl, 4-chlorophenyl, 4-cyanophenyl, 4-hydroxyphenyl, 4-nitrophenyl, 4-ethylphenyl, 4-methylphenyl, 4-methoxyphenyl, 4-acetylphenyl, 4-acetamidophenyl, 4-carboxyphenyl, 4-formylphenyl,4-methylthiophenyl, 4-dimethylaminophenyl, 4-carbomethoxyphenyl, 4-carboethoxyphenyl, 4-carboxamidophenyl, 4-(methylsulfonyl)phenyl,4-trifluoromethylphenyl, 2,4-difluorophenyl, 2-fluoro-4-chlorophenyl, 2,4-dichlorophenyl, 2-amino-4-carbomethoxyphenyl, 2-amino-4-carboxyphenyl, 2,6-difluorophenyl, or 3,4-(methylenedioxy)phenyl.

In some embodiments of the method of inhibiting GSK-3 in a subject and/or the method of treating a biological condition mediated by GSK-3 activity in a subject, $R^2$ is selected from —H, —Cl, —F, or —CH$_3$. In some such embodiments $R^2$ is —F.

In some embodiments of the method of inhibiting GSK-3 in a subject and/or the method of treating a biological condition mediated by GSK-3 activity in a subject, $R^4$ is selected from —H or —CH$_3$. In some such embodiments, $R^4$ is —H.

In some embodiments of the method of inhibiting GSK-3 in a subject and/or the method of treating a biological condition mediated by GSK-3 activity in a subject, $R^5$ and $R^8$ are independently selected from —H, saturated heterocyclyl groups, or are absent. In some such embodiments, $R^5$ and $R^8$ are independently selected from —H, or saturated heterocyclyl groups.

In some embodiments of the method of inhibiting GSK-3 in a subject and/or the method of treating a biological condition mediated by GSK-3 activity in a subject, A and D are both carbon, $R^5$ is —H, and $R^8$ is —H.

In some embodiments of the method of inhibiting GSK-3 in a subject and/or the method of treating a biological condition mediated by GSK-3 activity in a subject, $R^6$ and $R^7$ are independently selected from —H, —F, —Cl, —OH, or substituted and unsubstituted heterocyclyl groups. In some such embodiments, $R^6$ is —H and $R^7$ is —H.

In some embodiments of the method of inhibiting GSK-3 in a subject and/or the method of treating a biological condition mediated by GSK-3 activity in a subject, A, B, C, and D are all carbon, and $R^5$, $R^6$, $R^7$, and $R^8$ are all —H.

In some embodiments of the method of inhibiting GSK-3 in a subject and/or the method of treating a biological condition mediated by GSK-3 activity in a subject, $R^3$ is selected from —H, —F, —Cl, —Br, —CH$_3$, —OH, —CN, substituted and unsubstituted aryl groups, substituted and unsubstituted heterocyclyl groups, substituted and unsubstituted alkoxy groups, substituted and unsubstituted alkylamino groups, substituted and unsubstituted dialkylamino groups, substituted and unsubstituted —C(=O)-heterocyclyl groups, substituted and unsubstituted —C(=O)—N(alkyl)$_2$ groups, or —C(=O)—NH$_2$ groups.

In some embodiments of the method of inhibiting GSK-3 in a subject and/or the method of treating a biological condition mediated by GSK-3 activity in a subject, $R^3$ is selected from —H, —F, —Cl, —Br, —CH$_3$, —CN, —OMe, hydroxyalkylamino groups, dialkylamino groups, dialkylaminoalkylamino groups, alkoxyalkylamino groups, substituted and unsubstituted heterocyclylalkylamino groups, acetamidoalkylamino groups, cyanoalkylamino groups, thioalkylamino groups, (methylsulfonyl)alkylamino groups, cycloalkylalkylamino groups, dialkylaminoalkoxy groups, heterocyclylalkoxy groups, substituted and unsubstituted piperidinyl groups, substituted and unsubstituted imidazolyl groups, substituted and unsubstituted morpholinyl groups, substituted and unsubstituted pyrrolyl groups, substituted and unsubstituted pyrrolidinyl groups, substituted and unsubstituted piperazinyl groups, substituted and unsubstituted aryl groups, substituted and unsubstituted —C(=O)-heterocyclyl groups, substituted and unsubstituted —C(=O)—N(alkyl)$_2$ groups, or —C(=O)—NH$_2$ groups.

In some embodiments of the method of inhibiting GSK-3 in a subject and/or the method of treating a biological condition mediated by GSK-3 activity in a subject, $R^3$ is selected from substituted and unsubstituted alkylamino groups or substituted and unsubstituted dialkylamino groups. In some such embodiments, $R^3$ is a dimethylamino group.

In some embodiments of the method of inhibiting GSK-3 in a subject and/or the method of treating a biological condition mediated by GSK-3 activity in a subject, A, B, C, and D are all carbon, and $R^4$, $R^5$, $R^6$, $R^7$, $R^8$, and $R^{10}$ are all —H.

In some embodiments of the method of inhibiting GSK-3 in a subject and/or the method of treating a biological condition mediated by GSK-3 activity in a subject, the IC$_{50}$ value of the compound is less than or equal to 10 µM with respect to GSK-3. In other such embodiments, the IC$_{50}$ value is less than or equal to 1 µM, is less than or equal to 0.1 µM, is less than or equal to 0.050 µM, is less than or equal to 0.030 µM, is less than or equal to 0.025 µM, or is less than or equal to 0.010 µM.

In some embodiments of the method of inhibiting GSK-3 in a subject and/or the method of treating a biological condition mediated by GSK-3 activity in a subject, the subject is a mammal and in some such embodiments is a human.

In some embodiments of the method of treating a biological condition mediated by GSK-3 activity in a subject, the biological condition is diabetes, and in some such embodiments the biological condition is noninsulin dependent diabetes mellitus (NIDDM). In other such embodiments, the biological condition is Alzheimer's disease or is bipolar disorder.

Methods Relating to Cyclin Dependent Kinase 2

In some embodiments of the method of inhibiting a serine/threonine kinase in a subject and/or the method of treating a biological condition mediated by serine/threonine kinase activity in a subject using a compound of Structure I, a tautomer of the compound, a pharmaceutically acceptable salt of the compound, a pharmaceutically acceptable salt of the tautomer, or mixtures thereof, the serine/threonine kinase is Cdk2. In some such methods, the Cdk2 is inhibited in the subject after administration. In methods of inhibiting Cdk2, Structure I has the following formula:

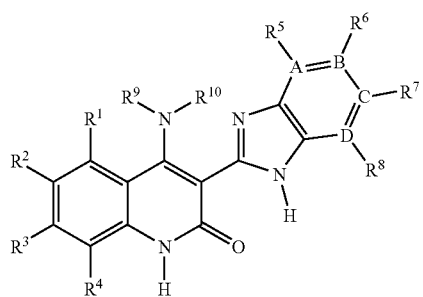

I where:
A, B, C, and D are independently selected from carbon or nitrogen;
$R^1$, $R^4$, $R^5$, and $R^8$ are independently selected from —H or substituted and unsubstituted straight and branched chain alkyl groups having from 1 to 8 carbon atoms; or $R^5$ may be absent if A is nitrogen; or $R^8$ may be absent if D is nitrogen;
$R^2$ and $R^3$ are independently selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, or substituted and unsubstituted heterocyclylalkyl groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, substituted and unsubstituted —N(aryl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups;
$R^6$ and $R^7$ are independently selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —OH, substituted and unsubstituted alkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(H)—C(=O)-heterocyclyl groups, or substituted and unsubstituted —N(H) =C(=O)-heterocyclylalkyl groups; or $R^6$ may be absent if B is nitrogen; or $R^7$ may be absent if C is nitrogen;
$R^9$ is selected from —H, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —OH, substituted and unsubstituted alkoxy groups, substituted and unsubstituted heterocyclyloxy groups, substituted and unsubstituted heterocyclylalkoxy groups, substituted and unsubstituted —C(=O)-alkyl groups, substituted and unsubstituted —C(=O)-heterocyclyl groups, substituted and unsubstituted —C(=O)-heterocyclylalkyl groups; and
$R^{10}$ is —H.

In some embodiments of the method of inhibiting Cdk2 in a subject and/or the method of treating a biological condition mediated by Cdk2 activity in a subject,
$R^2$ and $R^3$ are independently selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, or substituted and unsubstituted —N(aryl)$_2$ groups;
$R^6$ and $R^7$ are independently selected from —H, —F, —Cl, —Br, —I, substituted and unsubstituted alkyl groups having from 1 to 8 carbon atoms, substituted and unsubstituted heterocyclyl groups, —OH, substituted and unsubstituted alkoxy groups, substituted and unsubstituted heterocyclyloxy groups, substituted and unsubstituted heterocyclylalkoxy groups, substituted and unsubstituted —N(H)(heterocyclyl) groups, substituted and unsubstituted —N(alkyl)(heterocyclyl) groups, substituted and unsubstituted —N(heterocyclyl)$_2$ groups, or $R^6$ may be absent if B is nitrogen and $R^7$ may be absent if C is nitrogen.

In some embodiments of the method of inhibiting Cdk2 in a subject and/or the method of treating a biological condition mediated by Cdk2 activity in a subject, A, B, C, and D are all carbon.

In some embodiments of the method of inhibiting Cdk2 in a subject and/or the method of treating a biological condition mediated by Cdk2 activity in a subject, one of A or D is nitrogen, and B and C are both carbon.

In some embodiments of the method of inhibiting Cdk2 in a subject and/or the method of treating a biological condition mediated by Cdk2 activity in a subject, $R^9$ is selected from —H, substituted and unsubstituted chain alkyl groups having from 1-12 carbon atoms, substituted and unsubstituted aryl groups, substituted and unsubstituted aralkyl groups, substituted and unsubstituted heterocyclyl groups, substituted and unsubstituted heterocyclylalkyl groups, substituted and unsubstituted alkoxy groups, or substituted and unsubstituted heterocyclylalkoxy groups.

In some embodiments of the method of inhibiting Cdk2 in a subject and/or the method of treating a biological condition mediated by Cdk2 activity in a subject, $R^9$ is selected from —H, substituted and unsubstituted straight or branched chain alkyl groups having from 1-8 carbon atoms, substituted and unsubstituted saturated heterocyclyl groups, substituted and unsubstituted heterocyclylalkyl groups wherein the heterocyclyl moiety is saturated, substituted and unsubstituted alkoxy groups, or substituted and unsubstituted heterocyclylalkoxy groups wherein the heterocyclyl moiety is saturated.

In some embodiments of the method of inhibiting Cdk2 in a subject and/or the method of treating a biological condition mediated by Cdk2 activity in a subject, $R^9$ is selected from —H, unsubstituted straight or branched chain alkyl groups having from 1-8 carbon atoms, aminoalkyl groups, alkylaminoalkyl groups, dialkylaminoalkyl groups, substituted and unsubstituted saturated heterocyclyl groups, or substituted and unsubstituted heterocyclylalkyl groups wherein the heterocyclyl moiety is saturated.

In some embodiments of the method of inhibiting Cdk2 in a subject and/or the method of treating a biological condition mediated by Cdk2 activity in a subject, $R^9$ is selected from pyrrolidinyl, pyrrolidinylalkyl, piperidinyl, piperidinylalkyl, or quinuclidinyl.

In some embodiments of the method of inhibiting Cdk2 in a subject and/or the method of treating a biological condition mediated by Cdk2 activity in a subject, $R^1$ is —H.

In some embodiments of the method of inhibiting Cdk2 in a subject and/or the method of treating a biological condition mediated by Cdk2 activity in a subject, $R^2$ is selected from —H, —F, —Cl, —Br, —I, —NO$_2$, —CN, —NH$_2$, substituted and unsubstituted straight or branched chain alkyl groups having from 1 to 8 carbons, substituted and unsubstituted aryl groups, or substituted and unsubstituted pyridinyl groups. In some such embodiments, $R^2$ is selected from —H, —F, —Cl, —Br, —I, —CN, unsubstituted straight or branched chain alkyl groups having from 1 to 8 carbons, dihalophenyl, carboxyphenyl, aminophenyl, aminocarboxyphenyl, methylcarboxyphenyl, or hydroxyphenyl. In other such embodiments, $R^2$ is selected from —H, —F, —Cl, —Br, —I, —CN, —CH$_3$, 2,6-difluorophenyl, 4-carboxyphenyl, 3-aminophenyl, 2-amino-4-methylcarboxyphenyl, 3-methylcarboxyphenyl, or 3-hydroxyphenyl.

In some embodiments of the method of inhibiting Cdk2 in a subject and/or the method of treating a biological condition mediated by Cdk2 activity in a subject, $R^3$ is selected from the group consisting of —H, —F, —Cl, —Br, —I, substituted and unsubstituted straight or branched chain alkyl groups having from 1 to 8 carbon atoms, substituted and unsubstituted aryl groups, substituted and unsubstituted aralkyl groups. In some such embodiments, $R^3$ is selected from —H, —F, —Cl, —Br, —I, unsubstituted straight or branched chain alkyl groups having from 1 to 8 carbon atoms, aminoalkylamino groups, or substituted aryl groups. In other such embodiments, $R^3$ is selected from —H, —F, —Cl, —Br, —CH$_3$, 2-aminopropylamino groups, or 4-carboxamidophenyl, or $R^3$ is selected from —H, —F, —Cl, —Br, or —CH$_3$.

In some embodiments of the method of inhibiting Cdk2 in a subject and/or the method of treating a biological condition mediated by Cdk2 activity in a subject, $R^4$ is —H.

In some embodiments of the method of inhibiting Cdk2 in a subject and/or the method of treating a biological condition mediated by Cdk2 activity in a subject, $R^5$ or $R^8$ is —H, or are both —H.

In some embodiments of the method of inhibiting Cdk2 in a subject and/or the method of treating a biological condition mediated by Cdk2 activity in a subject, $R^6$ and $R^7$ are independently selected from —H, —F, —Cl, —Br, —I, —OH, substituted and unsubstituted —N(alkyl)(piperidinyl), substituted and unsubstituted piperidinyl groups, substituted and unsubstituted morpholinyl groups, or substituted and unsubstituted piperazinyl groups; or $R^6$ may be absent if B is nitrogen; or $R^7$ may be absent if C is nitrogen. In some such embodiments, $R^6$ and $R^7$ are independently selected from —H, —F, —Cl, —OH, substituted and unsubstituted —N(methyl)(4-(N-methylpiperidinyl)), N-morpholinyl groups, or 4-N-methylpiperazinyl groups; or $R^6$ may be absent if B is nitrogen; or $R^7$ may be absent if C is nitrogen. In other such embodiments, $R^6$ and $R^7$ are both —H, and B and C are both carbon.

In some embodiments of the method of inhibiting Cdk2 in a subject and/or the method of treating a biological condition mediated by Cdk2 activity in a subject, $R^5$ and $R^8$ are both —H, and A and D are both carbon.

In some embodiments of the method of inhibiting Cdk2 in a subject and/or the method of treating a biological condition mediated by Cdk2 activity in a subject, the IC$_{50}$ value of the compound is less than or equal to 10 µM with respect to Cdk2. In other such embodiments, the IC$_{50}$ value is less than or equal to 1 µM, is less than or equal to 0.1 µM, is less than or equal to 0.050 µM, is less than or equal to 0.030 µM, is less than or equal to 0.025 µM, or is less than or equal to 0.010 µM.

In some embodiments of the method of inhibiting Cdk2 in a subject and/or the method of treating a biological condition mediated by Cdk2 activity in a subject, the subject is a mammal or is a human.

In some embodiments of the method of treating a biological condition mediated by Cdk2 activity in a subject, the biological condition is cancer.

Methods Relating to Checkpoint Kinase 1

In some embodiments of the method of inhibiting a serine/threonine kinase in a subject and/or the method of treating a biological condition mediated by serine/threonine kinase activity in a subject using a compound of Structure I, a tautomer of the compound, a pharmaceutically acceptable salt of the compound, a pharmaceutically acceptable salt of the tautomer, or mixtures thereof, the serine/threonine kinase is CHK1. In some such methods, the CHK1 is inhibited in the subject after administration. In methods of inhibiting CHK1, Structure I has the following formula:

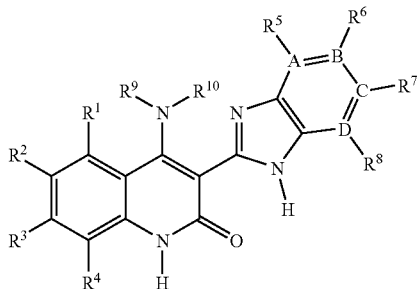

where,
- A, B, C, and D are independently selected from carbon or nitrogen;
- $R^1$ is selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted alkynyl groups having from 1 to 8 carbon atoms, substituted and unsubstituted heterocyclyl groups, —OH, substituted and unsubstituted alkoxy groups, substituted and unsubstituted aryloxy groups, substituted and unsubstituted arylalkoxy groups, substituted and unsubstituted heterocyclyloxy groups, substituted and unsubstituted heterocyclylalkoxy groups, —SH, substituted and unsubstituted —S-alkyl groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, or substituted and unsubstituted —N(heterocyclylalkyl)$_2$ groups;
- $R^2$ and $R^3$ are independently selected from —H, —F, —Cl, —Br, —I, —NO$_2$, —CN, substituted and unsubstituted alkyl groups having from 1 to 12 carbon atoms, substituted and unsubstituted alkenyl groups having from 1 to 12 carbon atoms, substituted and unsubstituted alkynyl groups having from 1 to 8 carbon atoms, substituted and unsubstituted aryl groups, substituted and unsubstituted aralkyl groups, substituted and unsubstituted heterocyclyl groups, substituted and unsubstituted heterocyclylalkyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)$_2$-heterocyclyl groups, substituted and unsubstituted —S(=O)-alkyl groups, substituted and unsubstituted —S(=O)-heterocyclyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, substituted and unsubstituted —S(=O)$_2$—N(H)(aryl) groups, substituted and unsubstituted —S(=O)$_2$—N(alkyl)(aryl) groups, substituted and unsubstituted —S(=O)$_2$—N(aryl)$_2$ groups, substituted and unsubstituted —S(=O)$_2$—N(H)(aralkyl) groups, substituted and unsubstituted —S(=O)$_2$—N(alkyl)(aralkyl) groups, substituted and unsubstituted —S(=O)$_2$—N(aralkyl)$_2$ groups, —OH, substituted and unsubstituted alkoxy groups, substituted and unsubstituted aryloxy groups, substituted and unsubstituted arylalkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, substituted and unsubstituted —N(aryl)$_2$ groups, substituted and unsubstituted —N(H)(aralkyl) groups, substituted and unsubstituted —N(alkyl)(aralkyl) groups, substituted and unsubstituted —N(aralkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—S(=O)$_2$-alkyl groups, substituted and unsubstituted —N(H)—S(=O)$_2$-aryl groups, substituted and unsubstituted —N(H)—S(=O)$_2$-aralkyl groups, substituted and unsubstituted —N(H)—S(=O)$_2$-heterocyclyl groups, substituted and unsubstituted —N(H)—S(=O)$_2$-heterocyclylalkyl groups, substituted and unsubstituted —N(H)—C(=O)-alkyl groups, substituted and unsubstituted —N(H)—C(=O)-aryl groups, substituted and unsubstituted —N(H)—C(=O)-aralkyl groups, substituted and unsubstituted —N(H)—C(=O)-heterocyclyl groups, substituted and unsubstituted —N(H)—C(=O)-heterocyclylalkyl groups, substituted and unsubstituted —N(alkyl)-C(=O)-alkyl groups, substituted and unsubstituted —N(alkyl)-C(=O)-aryl groups, substituted and unsubstituted —N(alkyl)-C(=O)-aralkyl groups, substituted and unsubstituted —N(alkyl)-C(=O)-heterocyclyl groups, substituted and unsubstituted —N(alkyl)-C(=O)-heterocyclylalkyl groups, substituted and unsubstituted —N(alkyl)-S(=O)-alkyl groups, substituted and unsubstituted —N(alkyl)-S(=O)-aryl groups, substituted and unsubstituted —N(alkyl)-S(=O)-aralkyl groups, substituted and unsubstituted —N(alkyl)-S(=O)-heterocyclyl groups, substituted and unsubstituted —N(alkyl)-S(=O)-heterocyclylalkyl groups, —N(H)—C(=O)—NH$_2$, substituted and unsubstituted —N(H)—C(=O)—N(H)(alkyl) groups, substituted and unsubstituted —N(H)—C(=O)—N(alkyl)$_2$ groups, substituted and unsubstituted —N(H)—C(=O)—N(H)(aryl) groups, substituted and unsubstituted —N(H)—C(=O)—N(alkyl)(aryl) groups, substituted and unsubstituted —N(H)—C(=O)—N(aryl)$_2$ groups, substituted and unsubstituted —N(H)—C(=O)—N(H)(aralkyl) groups, substituted and unsubstituted —N(H)—C(=O)—N(alkyl)(aralkyl) groups, substituted and unsubstituted —N(H)—C(=O)—N(aralkyl)$_2$ groups, substituted and unsubstituted —N(H)—C(=O)—N(H)(heterocyclyl) groups, substituted and unsubstituted —N(H)—C(=O)—N(alkyl)(heterocyclyl) groups, substituted and unsubstituted —N(H)—C(=O)—N(heterocyclyl)$_2$ groups, substituted and unsubstituted —N(H)—C(=O)—N(H)(heterocyclylalkyl) groups, substituted and unsubstituted —N(H)—C(=O)—N(alkyl)(heterocyclylalkyl) groups, substituted and unsubstituted —N(H)—C(=O)—N(heterocyclylalkyl)$_2$ groups, substituted and unsubstituted —N(alkyl)-C(=O)—NH$_2$ groups, substituted and unsubstituted —N(alkyl)-C(=O)—N(H)(alkyl) groups substituted and unsubstituted —N(alkyl)-C(=O)—N(alkyl)$_2$ groups, substituted and unsubstituted —N(alkyl)-C(=O)—N(H)(aryl) groups, substituted and unsubstituted —N(alkyl)-C(=O)—N(alkyl)(aryl) groups, substituted and unsubstituted —N(alkyl)-C(=O)—N(aryl)$_2$ groups, substituted and unsubstituted —N(alkyl)-C(=O)—N(H)(aralkyl) groups, substituted and unsubstituted —N(alkyl)-C(=O)—N(alkyl)(aralkyl) groups, substituted and unsubstituted —N(alkyl)-C(=O)—N(aralkyl)$_2$ groups, substituted and unsubstituted —N(alkyl)-C(=O)—N(H)(heterocyclyl) groups, substituted and unsubstituted —N(alkyl)-C(=O)—N(alkyl)(heterocyclyl) groups, substituted and unsubstituted —N(alkyl)-C(=O)—N(heterocyclyl)$_2$ groups, substituted and unsubstituted —N(alkyl)-C(=O)—N(H)(heterocyclylalkyl) groups, substituted and unsubstituted —N(alkyl)-C(=O)—N(alkyl)(heterocyclylalkyl) groups, substituted and unsubstituted —N(alkyl)-C(=O)—N(heterocyclylalkyl)$_2$ groups, substituted and unsubstituted —C(=O)-alkyl groups, substituted and unsubstituted —C(=O)-aryl groups, substituted and unsubstituted —C(=O)-aralkyl groups, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(aryl) groups, substituted and unsubstituted —C(=O)—N(alkyl)(aryl) groups, substituted and unsubstituted —C(=O)—N(aryl)$_2$ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)$_2$ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)$_2$ groups, —CO$_2$H, substituted and unsubstituted —C(=O)—O-alkyl groups, substituted and unsubstituted —C(=O)—O-aryl groups, substituted and unsubstituted —C(=O)—O-heterocyclyl groups, or substituted and unsubstituted —C(=O)—O-heterocyclylalkyl groups;

$R^4$ is selected from —H or substituted and unsubstituted alkyl groups having from 1 to 12 carbon atoms;

$R^5$ and $R^8$ are independently selected from —H, substituted and unsubstituted alkyl groups having from 1 to 12 carbon atoms, substituted and unsubstituted alkenyl groups having from 1 to 12 carbon atoms, substituted and unsubstituted heterocyclyl groups; or $R^5$ may be absent if A is nitrogen; or $R^8$ may be absent if D is nitrogen;

$R^6$ and $R^7$ are independently selected from —H, —F, —Cl, —Br, —I, —NO$_2$, —CN, substituted and unsubstituted alkyl groups having from 1 to 12 carbon atoms, substituted and unsubstituted alkenyl groups having from 1 to 12 carbon atoms, substituted and unsubstituted alkynyl groups having from 1 to 8 carbon atoms, substituted and unsubstituted heterocyclyl groups, substituted and unsubstituted heterocyclylalkyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)$_2$-heterocyclyl groups, substituted and unsubstituted —S(=O)-alkyl groups, substituted and unsubstituted —S(=O)-heterocyclyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, substituted and unsubstituted —S(=O)$_2$—N(H)(heterocyclyl) groups, substituted and unsubstituted —S(=O)$_2$—N(alkyl)(heterocyclyl) groups, substituted and unsubstituted —S(=O)$_2$—N(heterocyclyl)$_2$ groups, substituted and unsubstituted —S(=O)$_2$—N(H)(heterocyclylalkyl) groups, substituted and unsubstituted —S(=O)$_2$—N(alkyl)(heterocyclylalkyl) groups, substituted and unsubstituted —S(=O)$_2$—N(heterocyclylalkyl)$_2$ groups, —OH, substituted and unsubstituted alkoxy groups, substituted and unsubstituted aryloxy groups, substituted and unsubstituted arylalkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, substituted and unsubstituted —N(aryl)$_2$ groups, substituted and unsubstituted —N(H)(aralkyl) groups, substituted and unsubstituted —N(alkyl)(aralkyl) groups, substituted and unsubstituted —N(aralkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—S(=O)$_2$-alkyl groups, substituted and unsubstituted —N(H)—S(=O)$_2$-heterocyclyl groups, substituted and unsubstituted —N(H)—S(=O)$_2$-heterocyclylalkyl groups, substituted and unsubstituted —N(H)—C(=O)-alkyl groups, substituted and unsubstituted —N(H)—C(=O)-heterocyclyl groups, substituted and unsubstituted —N(H)—C(=O)-heterocyclylalkyl groups, substituted and unsubstituted —N(alkyl)-C(=O)-alkyl groups, substituted and unsubstituted —N(alkyl)-C(=O)-heterocyclyl groups, substituted and unsubstituted —N(alkyl)-C(=O)-heterocyclylalkyl groups, substituted and unsubstituted —N(alkyl)-S(=O)$_2$-alkyl groups, substituted and unsubstituted —N(alkyl)-S(=O)$_2$-heterocyclyl groups, substituted and unsubstituted —N(alkyl)-S(=O)$_2$-heterocyclylalkyl groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(aryl) groups, substituted and unsubstituted —C(=O)—N(alkyl)(aryl) groups, substituted and unsubstituted —C(=O)—N(aryl)$_2$ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)$_2$ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)$_2$ groups, —CO$_2$H, substituted and unsubstituted —C(=O)—O-alkyl groups, substituted and unsubstituted —C(=O)—O-heterocyclyl groups, or substituted and unsubstituted —C(=O)—O-heterocyclylalkyl groups; or R$^6$ may be absent if B is nitrogen; or R$^7$ may be absent if C is nitrogen;

R$^9$ is selected from —H, substituted and unsubstituted alkyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, substituted and unsubstituted heterocyclylaminoalkyl groups, substituted and unsubstituted alkoxy groups, or —NH$_2$, or R$^9$ and R$^{10}$ join together to form one or more rings, each having 5, 6, or 7 ring members; and R$^{10}$ is —H, or R$^9$ and R$^{10}$ join together to form one or more rings, each having 5, 6, or 7 ring members.

In some embodiments of the method of inhibiting CHK1 in a subject and/or the method of treating a biological condition mediated by CHK1 activity in a subject, R$^1$ is selected from —H, —F, —Cl, —Br, —I, —CN, —NO$_2$, substituted and unsubstituted straight and branched chain alkyl groups having from 1 to 8 carbon atoms, substituted and unsubstituted cycloalkyl groups, substituted and unsubstituted alkenyl groups having from 1 to 12 carbon atoms, substituted and unsubstituted heterocyclyl groups, —OH, substituted and unsubstituted alkoxy groups, substituted and unsubstituted aryloxy groups, substituted and unsubstituted arylalkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(H)(heterocyclylalkyl) groups, or substituted and unsubstituted —N(alkyl)(heterocyclylalkyl) groups;

R$^2$ and R$^3$ are independently selected from —H, —F, —Cl, —Br, —I, —NO$_2$, —CN, substituted and unsubstituted alkyl groups having from 1 to 12 carbon atoms, substituted and unsubstituted alkenyl groups having from 1 to 12 carbon atoms, substituted and unsubstituted alkynyl groups having from 1 to 8 carbon atoms, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted aryloxy groups, substituted and unsubstituted arylalkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, substituted and unsubstituted —N(aryl)$_2$ groups, substituted and unsubstituted —N(H)(aralkyl) groups, substituted and unsubstituted —N(alkyl)(aralkyl) groups, substituted and unsubstituted —N(aralkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(H)—C(=O)-aryl groups, substituted and unsubstituted —N(H)—C(=O)-aralkyl groups, substituted and unsubstituted —N(H)—C(=O)-heterocyclyl groups, substituted and unsubstituted —N(H)—C(=O)-heterocyclylalkyl groups, substituted and unsubstituted —N(alkyl)-C(=O)-alkyl groups, substituted and unsubstituted —N(alkyl)-C(=O)-aryl groups, substituted and unsubstituted —N(alkyl)-C(=O)-aralkyl groups, substituted and unsubstituted —N(alkyl)-C(=O)-heterocyclyl groups, substituted and unsubstituted —N(alkyl)-C(=O)-heterocyclylalkyl groups, —N(H)—C(=O)—NH$_2$, substituted and unsubstituted —N(H)—C(=O)—N(H)(alkyl) groups, substituted and unsubstituted —N(H)—C(=O)—N(alkyl)$_2$ groups, substituted and unsubstituted —N(H)—C(=O)—N(H)(aryl) groups, substituted and unsubstituted —N(H)—C(=O)—N(alkyl)(aryl) groups, substituted and unsubstituted —N(H)—C(=O)—N(aryl)$_2$ groups, substituted and unsubstituted —N(H)—C(=O)—N(H)(aralkyl) groups, substituted and unsubstituted —N(H)—C(=O)—N(alkyl)(aralkyl) groups, substituted and unsubstituted —N(H)—C(=O)—N(aralkyl)$_2$ groups, substituted and unsubstituted —N(H)—C(=O)—N(H)(heterocyclyl) groups, substituted and unsubstituted —N(H)—C(=O)—N(alkyl)(heterocyclyl) groups, substituted and unsubstituted —N(H)—C(=O)—N(heterocyclyl)$_2$ groups, substituted and unsubstituted —N(H)—C(=O)—N(H)(heterocyclylalkyl) groups, substituted and unsubstituted —N(H)—C(=O)—N(alkyl)(heterocyclylalkyl) groups, substituted and unsubstituted —N(H)—C(=O)—N(heterocyclylalkyl)$_2$ groups, substituted and unsubstituted —N(alkyl)-C(=O)—NH$_2$ groups, substituted and unsubstituted —N(alkyl)-C(=O)—N(H)(alkyl) groups, substituted and unsubstituted —N(alkyl)-C(=O)—N(H)(aryl) groups, substituted and unsubstituted —N(alkyl)-C(=O)—N(H)(aralkyl) groups, substituted and unsubstituted —N(alkyl)-C(=O)—N(H)(heterocyclyl) groups, substituted and unsubstituted —N(alkyl)-C(=O)—N(H)(heterocyclylalkyl) groups, substituted and unsubstituted —C(=O)-alkyl groups, substituted and unsubstituted —C(=O)-aryl groups, substituted and unsubstituted —C(=O)-aralkyl groups, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(aryl) groups, substituted and unsubstituted —C(=O)—N(alkyl)(aryl) groups, substituted and unsubstituted —C(=O)—N(aryl)$_2$ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)$_2$ groups, —CO₂H, substituted and unsubstituted —C(=O)—O-alkyl groups, substituted and unsubstituted —C(=O)—O-aryl groups, substituted and unsubstituted —C(=O)—O-heterocyclyl groups, or substituted and unsubstituted —C(=O)—O-heterocyclylalkyl groups;

$R^6$ and $R^7$ are independently selected from —H, —F, —Cl, —Br, —I, —NO₂, —CN, substituted and unsubstituted alkyl groups having from 1 to 12 carbon atoms, substituted and unsubstituted alkenyl groups having from 1 to 12 carbon atoms, substituted and unsubstituted alkynyl groups having from 1 to 8 carbon atoms, substituted and unsubstituted heterocyclyl groups, substituted and unsubstituted heterocyclylalkyl groups, —S(=O)₂—NH₂, substituted and unsubstituted —S(=O)₂—N(H)(alkyl) groups, substituted and unsubstituted —S(=O)₂—N(alkyl)₂ groups, —OH, substituted and unsubstituted alkoxy groups, substituted and unsubstituted aryloxy groups, substituted and unsubstituted arylalkoxy groups, substituted and unsubstituted heterocyclyloxy groups, substituted and unsubstituted heterocyclylalkoxy groups, —NH₂, substituted and unsubstituted —N(H)(alkyl) groups, substituted and unsubstituted —N(alkyl)₂ groups, substituted and unsubstituted —N(H)(heterocyclyl) groups, substituted and unsubstituted —N(alkyl)(heterocyclyl) groups, substituted and unsubstituted —N(heterocyclyl)₂ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)₂ groups, substituted and unsubstituted —N(H)—C(=O)-alkyl groups, substituted and unsubstituted —N(H)—C(=O)-heterocyclyl groups, substituted and unsubstituted —N(H)—C(=O)-heterocyclylalkyl groups, substituted and unsubstituted —N(alkyl)-C(=O)-alkyl groups, substituted and unsubstituted —N(alkyl)-C(=O)-heterocyclyl groups, substituted and unsubstituted —N(alkyl)-C(=O)-heterocyclylalkyl groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH₂, substituted and unsubstituted —C(=O)—N(H)(alkyl) groups, substituted and unsubstituted —C(=O)—N(alkyl)₂ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)₂ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)₂ groups, —CO₂H, substituted and unsubstituted —C(=O)—O-alkyl groups, substituted and unsubstituted —C(=O)—O-heterocyclyl groups, or substituted and unsubstituted —C(=O)—O-heterocyclylalkyl groups; or $R^6$ may be absent if B is nitrogen; or $R^7$ may be absent if C is nitrogen.

In some embodiments of the method of inhibiting CHK1 in a subject and/or the method of treating a biological condition mediated by CHK1 activity in a subject, A, B, C, and D are all carbon.

In some embodiments of the method of inhibiting CHK1 in a subject and/or the method of treating a biological condition mediated by CHK1 activity in a subject, one of A or D is nitrogen, and B and C are both carbon.

In some embodiments of the method of inhibiting CHK1 in a subject and/or the method of treating a biological condition mediated by CHK1 activity in a subject, $R^{10}$ is —H, and $R^9$ is selected from substituted and unsubstituted straight and branched chain alkyl groups having from 1 to 8 carbon atoms, substituted and unsubstituted cycloalkyl groups, substituted and unsubstituted aryl groups, substituted and unsubstituted aralkyl groups, substituted and unsubstituted heterocyclyl groups, substituted and unsubstituted heterocyclylalkyl groups, or substituted and unsubstituted heterocyclylaminoalkyl groups.

In some embodiments of the method of inhibiting CHK1 in a subject and/or the method of treating a biological condition mediated by CHK1 activity in a subject, $R^{10}$ is —H, and $R^9$ is selected from unsubstituted straight and branched chain alkyl groups having from 1 to 8 carbon atoms, substituted and unsubstituted cycloalkyl groups, substituted and unsubstituted hydroxyalkyl groups, substituted and unsubstituted dialkylaminoalkyl groups, substituted and unsubstituted alkylaminoalkyl groups, or substituted and unsubstituted aminoalkyl groups. In some such embodiments, $R^{10}$ is —H, and $R^9$ is selected from 2-amino-4-methyl-pentyl, 2-amino-3-methyl-butyl, 2-amino-butyl, 2,2-dimethyl-3-amino-propyl, 1-aminomethyl-propyl, 2-hydroxy-3-amino-propyl, 3-aminopropyl, 2-dimethylamino-ethyl, 2-methylamino-ethyl, 2-hydroxy-ethyl, or 2-amino-ethyl.

In some embodiments of the method of inhibiting CHK1 in a subject and/or the method of treating a biological condition mediated by CHK1 activity in a subject, $R^{10}$ is —H and $R^9$ is selected from substituted and unsubstituted cycloalkyl groups, substituted and unsubstituted aryl groups, substituted and unsubstituted aralkyl groups, substituted and unsubstituted heterocyclyl groups, substituted and unsubstituted heterocyclylalkyl groups, or substituted and unsubstituted heterocyclylaminoalkyl groups. In some such embodiments, $R^{10}$ is —H and $R^9$ is selected from substituted and unsubstituted phenylpropyl groups, substituted and unsubstituted phenylmethyl groups, or substituted and unsubstituted phenyl groups. In other such embodiments, $R^{10}$ is —H and $R^9$ is selected from phenyl, 4-aminomethyl-phenylmethyl, 2-(2-amino-ethyloxy)-phenylmethyl, 4-(2-amino-ethyloxy)-phenylmethyl, 4-sulfonamido-phenylmethyl, 1-benzyl-2-amino-ethyl, or 2-amino-3-phenyl-propyl.

In some embodiments of the method of inhibiting CHK1 in a subject and/or the method of treating a biological condition mediated by CHK1 activity in a subject, $R^{10}$ is —H and $R^9$ is selected from substituted and unsubstituted cyclohexyl groups, substituted and unsubstituted cyclohexylalkyl groups, substituted and unsubstituted pyrrolidinyl groups, substituted and unsubstituted pyrrolidinylalkyl groups, substituted and unsubstituted tetrahydrofuranylalkyl groups, substituted and unsubstituted piperidinyl groups, substituted and unsubstituted piperidinylalkyl groups, substituted and unsubstituted piperazinylalkyl groups, substituted and unsubstituted morpholinylalkyl groups, or substituted and unsubstituted quinuclidinyl groups. In some such embodiments, $R^9$ is selected from cyclohexyl, cyclohexylmethyl, 1-cyclohexylethyl, 2-amino-cyclohexyl, 4-amino-cyclohexyl, pyrrolidin-3-yl, 1-methyl-pyrrolidin-3-yl, 1-ethyl-pyrrolidin-2-yl, pyrrolidin-2-ylmethyl, 1-ethyl-pyrrolidin-2-ylmethyl, pyrrolidin-1-ylethyl, 1-methyl-pyrrolidin-2-ylethyl, pyrrolidin-1-ylpropyl, 2-oxo-pyrrolidin-1-ylpropyl, tetrahydrofuran-2-ylmethyl, piperidin-3-yl, 1-ethyl-piperidin-3-yl, piperidin-4-yl, 1-methyl-piperidin-4-yl, 1-benzyl-piperidin-4-yl, piperidin-2-ylmethyl, piperidin-3-ylmethyl, piperidin-4-ylmethyl, piperidin-1-ylethyl, piperidin-2-ylethyl, 4-methyl-piperazin-1-ylpropyl, morpholin-4-ylethyl, morpholin-4-ylpropyl, or quinuclidin-3-yl. In other such embodiments, $R^9$ is a quinuclidin-3-yl. In further such embodiments $R^9$ is a piperidin-3-ylmethyl. In other such embodiments, $R^9$ is selected from pyrrolidin-3-yl, 1-methyl-pyrrolidin-3-yl, or pyrrolidin-2-ylmethyl.

In some embodiments of the method of inhibiting CHK1 in a subject and/or the method of treating a biological condition mediated by CHK1 activity in a subject, $R^{10}$ is —H and $R^9$ is selected from substituted and unsubstituted imidazolylalkyl groups, substituted and unsubstituted pyridinyl groups, substituted and unsubstituted pyridinylalkyl groups, substituted and unsubstituted pyridinylaminoalkyl groups, substituted and unsubstituted pyrimidinylalkyl groups, substituted and unsubstituted pyrazinylalkyl groups, substituted and unsubstituted indolylalkyl groups, substituted and unsubstituted benzimidazolylalkyl groups. In some such embodiments, $R^{10}$ is —H and $R^9$ is selected from 3-(imidazol-1-yl)-propyl, 3-(imidazol-4-yl)-propyl, pyridin-2-yl, pyridin-4-yl, 2-methoxy-pyridin-5-yl, 2-(piperidin-4-yloxy)-pyridin-3-yl, 2-(piperidin-3-yloxy)-pyridin-5-yl, pyridin-3-ylmethyl, pyridin-4-ylmethyl, pyridin-2-ylethyl, pyridin-3-ylethyl, 2-(5-trifluromethyl-pyridin-2-ylamino)-ethyl, 2-(2-carboxamido-pyridin-5-ylamino)-ethyl, 2-(4-amino-5-nitro-pyridin-2-ylamino)-ethyl, pyridin-2-ylpropyl, pyrazin-2-yl, 2-methyl-4-amino-pyrazin-5-yl, 5-fluoro-indol-3-ylethyl, benzimidazol-2-ylmethyl, benzimidazol-5-ylmethyl, 2-piperidin-4-yl-benzimidazol-5-ylethyl, and benzimidazol-2-ylethyl.

In some embodiments of the method of inhibiting CHK1 in a subject and/or the method of treating a biological condition mediated by CHK1 activity in a subject, $R^9$ is selected from monocyclic, bicyclic, and polycyclic saturated heterocyclyl groups.

In some embodiments of the method of inhibiting CHK1 in a subject and/or the method of treating a biological condition mediated by CHK1 activity in a subject, $R^9$ and $R^{10}$ join together to form one or more rings, each having 5, 6, or 7 ring members.

In some embodiments of the method of inhibiting CHK1 in a subject and/or the method of treating a biological condition mediated by CHK1 activity in a subject, $R^1$ is selected from —H, —F, —Cl, —Br, —I, substituted and unsubstituted straight and branched chain alkyl groups having from 1 to 4 carbon atoms, substituted and unsubstituted heterocyclyl groups, —OH, substituted and unsubstituted alkoxy groups, substituted and unsubstituted aryloxy groups, substituted and unsubstituted heterocyclyloxy groups, substituted and unsubstituted heterocyclylalkoxy groups, or substituted and unsubstituted —N(H)(alkyl) groups. In some such embodiments, $R^1$ is selected from —H, —F, —Cl, —CH$_3$, substituted and unsubstituted piperazinyl groups, —OCH$_3$, substituted and unsubstituted phenyloxy groups, substituted and unsubstituted piperidinyloxy groups, substituted and unsubstituted quinuclidinyloxy groups, substituted and unsubstituted morpholinylalkoxy groups, or —NCH$_3$. In other such embodiments, $R^1$ is selected from 4-methyl-piperazin-1-yl, 4-ethyl-piperazin-1-yl, 4-amino-phenyloxy, 3-dimethylamino-phenyloxy, 3-acetamido-phenyloxy, 4-acetamido-phenyloxy, or 2-(morpholin-4-yl)-ethyloxy. In still other such embodiments, $R^1$ is —H.

In some embodiments of the method of inhibiting CHK1 in a subject and/or the method of treating a biological condition mediated by CHK1 activity in a subject, $R^2$ and $R^3$ are independently selected from —H, —F, —Cl, —Br, —I, —NO$_2$, —CN, substituted and unsubstituted straight or branched chain alkyl groups having from 1 to 8 carbon atoms, substituted and unsubstituted cycloalkyl groups, substituted and unsubstituted alkenyl groups having from 1 to 8 carbon atoms, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted aryloxy groups, substituted and unsubstituted arylalkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, substituted and unsubstituted —N(aryl)$_2$ groups, substituted and unsubstituted —N(H)(aralkyl) groups, substituted and unsubstituted —N(alkyl)(aralkyl) groups, substituted and unsubstituted —N(aralkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(H)—C(=O)-aryl groups, substituted and unsubstituted —N(H)—C(=O)-aralkyl groups, substituted and unsubstituted —N(H)—C(=O)-heterocyclyl groups, substituted and unsubstituted —N(H)—C(=O)-heterocyclylalkyl groups, substituted and unsubstituted —N(alkyl)-C(=O)-alkyl groups, substituted and unsubstituted —N(alkyl)-C(=O)-aryl groups, substituted and unsubstituted —N(alkyl)-C(=O)-aralkyl groups, substituted and unsubstituted —N(alkyl)-C(=O)-heterocyclyl groups, substituted and unsubstituted —N(alkyl)-C(=O)-heterocyclylalkyl groups, —N(H)—C(=O)—NH$_2$, substituted and unsubstituted —N(H)—C(=O)—N(H)(alkyl) groups, substituted and unsubstituted —N(H)—C(=O)—N(alkyl)$_2$ groups, substituted and unsubstituted —N(H)—C(=O)—N(H)(aryl) groups, substituted and unsubstituted —N(H)—C(=O)—N(alkyl)(aryl) groups, substituted and unsubstituted —N(H)—C(=O)—N(aryl)$_2$ groups, substituted and unsubstituted —N(H)—C(=O)—N(H)(aralkyl) groups, substituted and unsubstituted —N(H)—C(=O)—N(alkyl)(aralkyl) groups, substituted and unsubstituted —N(H)—C(=O)—N(aralkyl)$_2$ groups, substituted and unsubstituted —N(H)—C(=O)—N(H)(heterocyclyl) groups, substituted and unsubstituted —N(H)—C(=O)—N(alkyl)(heterocyclyl) groups, substituted and unsubstituted —N(H)—C(=O)—N(heterocyclyl)$_2$ groups, substituted and unsubstituted —N(H)—C(=O)—N(H)(heterocyclylalkyl) groups, substituted and unsubstituted —N(H)—C(=O)—N(alkyl)(heterocyclylalkyl) groups, substituted and unsubstituted —N(H)—C(=O)—N(heterocyclylalkyl)$_2$ groups, substituted and unsubstituted —C(=O)-alkyl groups, substituted and unsubstituted —C(=O)-aryl groups, substituted and unsubstituted —C(=O)-aralkyl groups, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(aryl) groups, substituted and unsubstituted —C(=O)—N(alkyl)(aryl) groups, substituted and unsubstituted —C(=O)—N(aryl)$_2$ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)$_2$ groups, —CO₂H, substituted and unsubstituted —C(=O)—O-alkyl groups, substituted and unsubstituted —C(=O)—O-aryl groups, substituted and unsubstituted —C(=O)—O-heterocyclyl groups, or substituted and unsubstituted —C(=O)—O-heterocyclylalkyl groups.

In some embodiments of the method of inhibiting CHK1 in a subject and/or the method of treating a biological condition mediated by CHK1 activity in a subject, $R^2$ is selected from —H, —F, —Cl, —Br, —I, —NO₂, —CN, substituted and unsubstituted straight or branched chain alkyl groups having from 1 to 8 carbon atoms, substituted and unsubstituted cycloalkyl groups, substituted and unsubstituted alkenyl groups having from 1 to 8 carbon atoms, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted aryloxy groups, substituted and unsubstituted arylalkoxy groups, —NH₂, substituted and unsubstituted —N(H)(alkyl) groups, substituted and unsubstituted —N(alkyl)₂ groups, substituted and unsubstituted —N(H)(aryl) groups, substituted and unsubstituted —N(alkyl)(aryl) groups, substituted and unsubstituted —N(aryl)₂ groups, substituted and unsubstituted —N(H)(aralkyl) groups, substituted and unsubstituted —N(alkyl)(aralkyl) groups, substituted and unsubstituted —N(aralkyl)₂ groups, substituted and unsubstituted —N(H)(heterocyclyl) groups, substituted and unsubstituted —N(alkyl)(heterocyclyl) groups, substituted and unsubstituted —N(heterocyclyl)₂ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)₂ groups, substituted and unsubstituted —N(H)—C(=O)-alkyl groups, substituted and unsubstituted —N(H)—C(=O)-aryl groups, substituted and unsubstituted —N(H)—C(=O)-aralkyl groups, substituted and unsubstituted —N(H)—C(=O)-heterocyclyl groups, substituted and unsubstituted —N(H)—C(=O)-heterocyclylalkyl groups, —N(H)—C(=O)—NH₂, substituted and unsubstituted —N(H)—C(=O)—N(H)(alkyl) groups, substituted and unsubstituted —N(H)—C(=O)—N(H)(aryl) groups, substituted and unsubstituted —N(H)—C(=O)—N(H)(aralkyl) groups, substituted and unsubstituted —N(H)—C(=O)—N(H)(heterocyclyl) groups, substituted and unsubstituted —N(H)—C(=O)—N(H)(heterocyclylalkyl) groups, substituted and unsubstituted —C(=O)-alkyl groups, substituted and unsubstituted —C(=O)-aryl groups, substituted and unsubstituted —C(=O)-aralkyl groups, substituted and unsubstituted —C(=O)-heterocyclyl groups, substituted and unsubstituted —C(=O)-heterocyclylalkyl groups, —C(=O)—NH₂, substituted and unsubstituted —C(=O)—N(H)(alkyl) groups, substituted and unsubstituted —C(=O)—N(alkyl)₂ groups, substituted and unsubstituted —C(=O)—N(H)(aryl) groups, substituted and unsubstituted —C(=O)—N(alkyl)(aryl) groups, substituted and unsubstituted —C(=O)—N(aryl)₂ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)₂ groups, —CO₂H, or substituted and unsubstituted —C(=O)—O-alkyl groups.

In some embodiments of the method of inhibiting CHK1 in a subject and/or the method of treating a biological condition mediated by CHK1 activity in a subject, $R^2$ is selected from 2-substituted phenyl groups, 3-substituted phenyl groups, 4-substituted phenyl groups, 2,4-disubstituted phenyl groups, 2,6-disubstituted phenyl groups, substituted or unsubstituted pyrrole groups, substituted and unsubstituted thiophene groups, substituted and unsubstituted tetrahydropyridine groups, or substituted and unsubstituted pyridine groups.

In some embodiments of the method of inhibiting CHK1 in a subject and/or the method of treating a biological condition mediated by CHK1 activity in a subject, $R^2$ is a substituted and unsubstituted aryl group selected from phenyl, 2-chlorophenyl, 2-ethylphenyl, 2-hydroxyphenyl, 2-methoxyphenyl, 2-methylphenyl, 2-trifluoromethylphenyl, 3-acetylphenyl, 3-acetamidophenyl, 3-aminophenyl, 3-methoxycarbonylphenyl, 3-carboxyphenyl, 3-hydroxyphenyl, 3-methoxyphenyl, 3-nitrophenyl, 3-trifluoromethylphenyl 4-acetylphenyl, 4-methoxycarbonylphenyl, 4-carboxamidophenyl, 4-carboxyphenyl, 4-chlorophenyl, 4-cyanophenyl, 4-dimethylaminophenyl, 4-ethylphenyl, 4-formylphenyl, 4-hydroxyphenyl, 4-methoxyphenyl, 4-methylthiophenyl, 4-nitrophenyl, 4-(methylsulfonyl)-phenyl, 2,4-difluorophenyl, 2-fluoro-4-chlorophenyl, 2,4-dichlorophenyl, 2-amino-4-methoxycarbonylphenyl, 2-amino-4-carboxyphenyl, or 2,6-difluorophenyl. In some such embodiments, $R^2$ is selected from 2-hydroxyphenyl, 2-methoxyphenyl, 3-hydroxyphenyl, 3-methoxyphenyl, 3-aminophenyl, 4-cyanophenyl, 4-hydroxyphenyl, and 4-methoxyphenyl.

In some embodiments of the method of inhibiting CHK1 in a subject and/or the method of treating a biological condition mediated by CHK1 activity in a subject, $R^2$ is a substituted and unsubstituted heterocyclyl or heterocyclylalkyl group selected from 1-tert-butyloxycarbonyl-pyrrol-2-yl, thiophen-2-yl, thiophen-3-yl, 1,2,5,6-tetrahydropyridin-4-yl, 4-(tert-butyloxycarbonyl)-1,2,5,6-tetrahydropyridin-4-yl, pyridin-2-yl, pyridin-3-yl, pyridin-4-yl, benzo[1,3]dioxol-5-yl, or benzo[b]thiophen-2-yl. In some such embodiments, $R^2$ is selected from thiophen-2-yl or thiophen-3-yl. In other such embodiments, $R^2$ is selected from pyridin-2-yl, pyridin-3-yl, or pyridin-4-yl.

In some embodiments of the method of inhibiting CHK1 in a subject and/or the method of treating a biological condition mediated by CHK1 activity in a subject, $R^2$ is selected from —H, —Cl, —F, —Br, —I, —NO₂, —CN, —CH₃, —OH, —OCH₃, —CO₂H, or —CO₂CH₃. In some such embodiments, $R^2$ is —Cl.

In some embodiments of the method of inhibiting CHK1 in a subject and/or the method of treating a biological condition mediated by CHK1 activity in a subject, $R^2$ is selected from —NH₂, substituted and unsubstituted —N(H)(alkyl) groups, substituted and unsubstituted —N(alkyl)₂ groups, substituted and unsubstituted —N(H)(aryl) groups, substituted and unsubstituted —N(alkyl)(aryl) groups, substituted and unsubstituted —N(aryl)₂ groups, substituted and unsubstituted —N(H)(aralkyl) groups, substituted and unsubstituted —N(alkyl)(aralkyl) groups, substituted and unsubstituted —N(aralkyl)₂ groups, substituted and unsubstituted —N(H)(heterocyclyl) groups, substituted and unsubstituted —N(alkyl)(heterocyclyl) groups, substituted and unsubstituted —N(heterocyclyl)₂ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)₂ groups, substituted and unsubstituted —N(H)—C(=O)-alkyl groups, substituted and unsubstituted —N(H)—C(=O)-aryl groups, substituted and unsubstituted —N(H)—C(=O)-aralkyl groups, substituted and unsubstituted —N(H)—C(=O)-heterocyclyl groups, substituted and unsubstituted —N(H)—C(=O)-heterocyclylalkyl groups, —N(H)—C(=O)—NH₂, substituted and unsubstituted —N(H)—C(=O)—N(H)(alkyl) groups, substituted and unsubstituted —N(H)—C (=O)—N(H)(aryl) groups, substituted and unsubstituted —N(H)—C(=O)—N(H)(aralkyl) groups, substituted and unsubstituted —N(H)—C(=O)—N(H)(heterocyclyl) groups, substituted and unsubstituted —N(H)—C(=O)—N (H)(heterocyclylalkyl) groups, substituted and unsubstituted —C(=O)—N(H)(alkyl) groups, substituted and unsubstituted —C(=O)—N(H)(aryl) groups, or substituted and unsubstituted —C(=O)—N(H)(aralkyl) groups.

In some embodiments of the method of inhibiting CHK1 in a subject and/or the method of treating a biological condition mediated by CHK1 activity in a subject, $R^2$ is selected from —$NH_2$, substituted and unsubstituted —N(H)(alkyl) groups, substituted and unsubstituted —$N(alkyl)_2$ groups, substituted and unsubstituted —N(H)(aralkyl) groups, substituted and unsubstituted —N(H)(heterocyclyl) groups, substituted and unsubstituted —N(alkyl)(heterocyclyl) groups, substituted and unsubstituted —N(H)(heterocyclylalkyl) groups, or substituted and unsubstituted —N(alkyl)(heterocyclylalkyl) groups. In some such embodiments, $R^2$ is selected from —$NH_2$, —N(H)(methyl), —$N(methyl)_2$, —N(H)(2-methyl-propyl), —N(H)(2,2-dimethyl-propyl), —N(H)(2-methyl-butyl), —N(H)(heptyl), —N(H)(cyclohexylmethyl), —N(methyl)(isobutyl), —N(methyl)(cyclohexylmethyl), —N(H)(benzyl), —N(H)(piperidin-4-yl), —N(H)(pyrrolidin-2-ylmethyl), —N(H)(2-dimethylaminomethyl-furan-5-ylmethyl), —N(H)(3-methyl-thiophen-2-ylmethyl), —N(H)(3-phenyloxy-thiophen-2-ylmethyl), —N(H)(2-ethyl-5-methyl-imidazol-4-ylmethyl), —N(H)(5-methyl-isoxazol-3-ylmethyl), —N(H)(thiazol-2-ylmethyl), —N(H)(pyrazin-2-ylmethyl), or —N(methyl)(1-methyl-piperidin-4-yl).

In some embodiments of the method of inhibiting CHK1 in a subject and/or the method of treating a biological condition mediated by CHK1 activity in a subject, $R^2$ is selected from substituted and unsubstituted —N(H)—C(=O)-alkyl groups, wherein the alkyl moiety is a straight or branched chain alkyl having from 1 to 8 carbon atoms, substituted and unsubstituted —N(H)—C(=O)-cycloalkyl groups, substituted and unsubstituted —N(H)—C(=O)-aryl groups, substituted and unsubstituted —N(H)—C(=O)-aralkyl groups, substituted and unsubstituted —N(H)—C(=O)-heterocyclyl groups, substituted and unsubstituted —N(H)—C(=O)-heterocyclylalkyl groups, or substituted and unsubstituted —C(=O)—N(H)(aralkyl) groups. In some such embodiments, $R^2$ is selected from substituted and unsubstituted —N(H)—C(=O)-methyl groups, substituted and unsubstituted —N(H)—C(=O)-cyclohexyl groups, substituted and unsubstituted —N(H)—C(=O)-phenyl groups, substituted and unsubstituted —N(H)—C(=O)-phenylalkyl groups, substituted and unsubstituted —N(H)—C(=O)-furan groups, substituted and unsubstituted —N(H)—C(=O)-thiophenylalkyl groups. In other such embodiments, $R^2$ is selected from —N(H)—C(=O)-methyl, —N(H)—C(=O)-propyl, —N(H)—C(=O)-isopropyl, —N(H)—C(=O)-benzyloxymethyl, N(H)—C(=O)-benzylaminomethyl, —N(H)—C(=O)-cyclohexyl groups, —N(H)—C(=O)-4-ethyl-phenyl, —N(H)—C(=O)-4-cyano-phenyl, —N(H)—C(=O)-2-phenyl-ethyl groups, —N(H)—C(=O)-furan-2-yl, —N(H)—C(=O)-thiophen-2-ylmethyl groups, or —N(H)—C(=O)-pyrazin-2-yl.

In some embodiments of the method of inhibiting CHK1 in a subject and/or the method of treating a biological condition mediated by CHK1 activity in a subject, $R^2$ is selected from —N(H)—C(=O)—$NH_2$, substituted and unsubstituted —N(H)—C(=O)—N(H)(alkyl) groups, substituted and unsubstituted —N(H)—C(=O)—N(H)(aryl) groups, substituted and unsubstituted —N(H)—C(=O)—N(H)(aralkyl) groups, substituted and unsubstituted —N(H)—C(=O)—N (H)(heterocyclyl) groups, substituted and unsubstituted —N(H)—C(=O)—N(H)(heterocyclylalkyl) groups. In some such embodiments, $R^2$ is selected from substituted and unsubstituted —N(H)—C(=O)—N(H)(alkyl) groups, wherein the alkyl moiety is a straight or branched chain alkyl group having from 1 to 12 carbons, substituted and unsubstituted —N(H)—C(=O)—N(H)(phenyl) groups, or substituted and unsubstituted —N(H)—C(=O)—N(H)(phenylalkyl) groups. In other such embodiments, $R^2$ is selected from —N(H)—C(=O)—N(H)(isopropyl), —N(H)—C(=O)—N (H)(heptyl), —N(H)—C(=O)—N(H)(phenyl), —N(H)—C(=O)—N(H)(2-ethoxyphenyl), —N(H)—C(=O)—N(H) (2-methylthiophenyl), —N(H)—C(=O)—N(H)(3-trifluoromethylphenyl), —N(H)—C(=O)—N(H)(3,5-dimethylphenyl), or —N(H)—C(=O)—N(H)(benzyl).

In some embodiments of the method of inhibiting CHK1 in a subject and/or the method of treating a biological condition mediated by CHK1 activity in a subject, $R^3$ is selected from —H, —F, —Cl, —Br, —I, —CN, —$NO_2$, substituted and unsubstituted straight or branched chain alkyl groups having from 1 to 8 carbon atoms, substituted and unsubstituted cycloalkyl groups, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted heterocyclyloxy groups, substituted and unsubstituted heterocyclylalkoxy groups, —$NH_2$, substituted and unsubstituted —N(H)(alkyl) groups, substituted and unsubstituted —$N(alkyl)_2$ groups, substituted and unsubstituted —N(H)(heterocyclyl) groups, substituted and unsubstituted —N(alkyl)(heterocyclyl) groups, substituted and unsubstituted —$N(heterocyclyl)_2$ groups, substituted and unsubstituted —N(H)(heterocyclylalkyl) groups, substituted and unsubstituted —N(alkyl)(heterocyclylalkyl) groups, substituted and unsubstituted —$N(heterocyclylalkyl)_2$ groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—$NH_2$, substituted and unsubstituted —C(=O)—N(H)(alkyl) groups, substituted and unsubstituted —C(=O)—$N(alkyl)_2$ groups, —$CO_2H$, or substituted and unsubstituted —C(=O)—O-alkyl groups.

In some embodiments of the method of inhibiting CHK1 in a subject and/or the method of treating a biological condition mediated by CHK1 activity in a subject, $R^3$ is selected from —H, —F, —Cl, —Br, —I, —CN, —$NO_2$, substituted and unsubstituted straight or branched chain alkyl groups having from 1 to 8 carbon atoms, —OH, substituted and unsubstituted alkoxy groups, substituted and unsubstituted heterocyclyloxy groups, or substituted and unsubstituted heterocyclylalkoxy groups. In some such embodiments, $R^3$ is selected from —H, —F, —Cl, —Br, —CN, —$CH_3$, —OH, —$OCH_3$, 2-dimethylamino-ethoxy, pyrrolidin-2-ylmethoxy, or 2-oxo-pyrrolidin-1-ylethoxy.

In some embodiments of the method of inhibiting CHK1 in a subject and/or the method of treating a biological condition mediated by CHK1 activity in a subject, $R^3$ is selected from substituted and unsubstituted aryl groups, substituted and unsubstituted aralkyl groups, substituted and unsubstituted heterocyclyl groups, or substituted and unsubstituted heterocyclylalkyl groups.

In some embodiments of the method of inhibiting CHK1 in a subject and/or the method of treating a biological condition mediated by CHK1 activity in a subject, $R^3$ is selected from 2-substituted phenyl groups, 3-substituted phenyl groups, 4-substituted phenyl groups, 2,4-disubstituted phenyl groups, substituted or unsubstituted pyrrole groups, substituted and unsubstituted thiophene groups, substituted and unsubstituted piperidine groups, substituted and unsubstituted piperazine groups, substituted and unsubstituted morpholine groups, substituted and unsubstituted azepane groups, substituted and unsubstituted pyrrole groups, substituted and unsubstituted imidazole groups, substituted and unsubstituted pyridine groups, or substituted and unsubstituted benzodioxole groups.

In some embodiments of the method of inhibiting CHK1 in a subject and/or the method of treating a biological condition mediated by CHK1 activity in a subject, $R^3$ is a substituted and unsubstituted aryl group selected from 2-methoxy-phenyl, 2-methylphenyl, 2-trifluoromethyl-phenyl, 3-acetylphenyl, 3-acetamidophenyl, 3-methoxycarbonyl-phenyl, 3-carboxyphenyl, 4-acetylphenyl, 4-carboxamidophenyl, 4-carboxyphenyl, 4-cyanophenyl, 4-formylphenyl, 4-methoxycarbonyl-phenyl, 4-methylsulfonyl-phenyl, 2,4-dichlorophenyl, 2-amino-4-methoxycarbonylphenyl, or 2-amino-4-methoxycarbonyl-phenyl.

In some embodiments of the method of inhibiting CHK1 in a subject and/or the method of treating a biological condition mediated by CHK1 activity in a subject, $R^3$ is a substituted and unsubstituted heterocyclyl group selected from pyrrolidin-1-yl, 3-dimethylamino-pyrrolidin-1-yl, 3-acetamidopyrrolidin-1-yl, 3-hydroxy-pyrrolidin-1-yl, 3-methylsulfonyl-pyrrolidin-1-yl, 3-trifluoroacetamido-pyrrolidin-1-yl, piperidin-1-yl, 2-hydroxy-piperidin-1-yl, 3-carboxamide-piperidin-1-yl, 3-carboxy-piperidin-1-yl, 3-methoxycarbonyl-piperidin-1-yl, 3-(pyridin-4-yl)-pyrrolidin-3-yl, 4-carboxamido-piperidin-1-yl, 4-carboxy-piperidin-1-yl, 4-ethoxycarbonyl-piperidin-1-yl, 4-methyl-piperazin-1-yl, 4-(pyridin-2-ylmethyl)-piperazin-1-yl, morpholin-4-yl, azepan-1-yl, pyrrol-1-yl, 3-acetyl-pyrrol-1-yl, 3-carboxy-pyrrol-1-yl, imidazol-1-yl, 2-methyl-imidazol-1-yl, 2-ethyl-imidazol-1-yl, 2-isopropyl-imidazol-1-yl, or benzo[1,3]dioxol-5-yl.

In some embodiments of the method of inhibiting CHK1 in a subject and/or the method of treating a biological condition mediated by CHK1 activity in a subject, $R^3$ is selected from —$NH_2$, substituted and unsubstituted —N(H)(alkyl) groups, substituted and unsubstituted —$N(alkyl)_2$ groups, substituted and unsubstituted —N(H)(heterocyclyl) groups, substituted and unsubstituted —N(alkyl)(heterocyclyl) groups, substituted and unsubstituted —$N(heterocyclyl)_2$ groups, substituted and unsubstituted —N(H)(heterocyclylalkyl) groups, substituted and unsubstituted —N(alkyl)(heterocyclylalkyl) groups, or substituted and unsubstituted —$N(heterocyclylalkyl)_2$ groups.

In some embodiments of the method of inhibiting CHK1 in a subject and/or the method of treating a biological condition mediated by CHK1 activity in a subject, $R^3$ is selected from —$NH_2$, —N(H)(methyl), —N(H)(2-methylpropyl), —N(H)(2-acetamidoethyl), —N(H)(2-aminoethyl), —N(H)(2-cyanoethyl), —N(H)(2-diethylamino-ethyl), —N(H)(2-dimethylamino-ethyl), —N(H)(2-hydroxyethyl), —N(H)(2-methoxyethyl), —N(H)(2-thioethyl), —N(H)(3-dimethylaminopropyl), —N(H)(3-hydroxypropyl), —N(H)(3-methoxypropyl), —N(H)(2-methylsulfonyl-ethyl), —N(H)(cyclopropyl), —N(H)(4-hydroxy-cyclohexyl), —N(H)(1-hydroxy-cyclohexylmethyl), —$N(methyl)_2$, —$N(ethyl)_2$, —N(methyl)(ethyl), —N(methyl)(2-dimethylamino-ethyl), —N(H)(morpholin-4-ylethyl), —N(H)(pyrrolidin-1-ylethyl), —N(H)(1-methyl-pyrrolidin-2-ylethyl), —N(H)(pyrrolidin-1-ylpropyl), —N(H)(2-oxo-pyrrolidin-1-ylpropyl), —N(H)(piperidin-3-ylmethyl), —N(H)(piperidin-1-ylethyl), —N(H)(pyridin-2-ylmethyl), —N(H)(pyridin-2-ylethyl), —N(H)(pyridin-3-ylethyl), or —N(H)(pyridin-4-ylethyl).

In some embodiments of the method of inhibiting CHK1 in a subject and/or the method of treating a biological condition mediated by CHK1 activity in a subject, $R^3$ is selected from substituted and unsubstituted —C(=O)-heterocyclyl groups, —C(=O)—$NH_2$, substituted and unsubstituted —C(=O)—$N(alkyl)_2$ groups, or —$CO_2H$. In some such embodiments, $R^3$ is selected from —C(=O)-morpholin-4-yl, —C(=O)—$NH_2$, —C(=O)—$N(methyl)_2$, or —$CO_2H$.

In some embodiments of the method of inhibiting CHK1 in a subject and/or the method of treating a biological condition mediated by CHK1 activity in a subject, $R^4$ is selected from —H or —$CH_3$. In some such embodiments, $R^4$ is —H.

In some embodiments of the method of inhibiting CHK1 in a subject and/or the method of treating a biological condition mediated by CHK1 activity in a subject, $R^5$ and $R^8$ are independently selected from —H or saturated heterocyclyl groups, or are absent. In some such embodiments, A and D are both carbon, $R^5$ is —H, and $R^8$ is —H.

In some embodiments of the method of inhibiting CHK1 in a subject and/or the method of treating a biological condition mediated by CHK1 activity in a subject, $R^6$ and $R^7$ are independently selected from —H, —F, —Cl, —Br, —I, substituted and unsubstituted alkyl groups having from 1 to 8 carbon atoms, substituted and unsubstituted heterocyclyl groups, substituted and unsubstituted heterocyclylalkyl groups, —$S(=O)_2$—$NH_2$, substituted and unsubstituted —$S(=O)_2$—N(H)(alkyl) groups, substituted and unsubstituted —$S(=O)_2$—$N(alkyl)_2$ groups, —OH, substituted and unsubstituted alkoxy groups, substituted and unsubstituted aryloxy groups, substituted and unsubstituted arylalkoxy groups, substituted and unsubstituted heterocyclyloxy groups, substituted and unsubstituted heterocyclylalkoxy groups, —$NH_2$, substituted and unsubstituted —N(H)(alkyl) groups, substituted and unsubstituted —$N(alkyl)_2$ groups, substituted and unsubstituted —N(H)(heterocyclyl) groups, substituted and unsubstituted —N(alkyl)(heterocyclyl) groups, substituted and unsubstituted —N(H)(heterocyclylalkyl) groups, substituted and unsubstituted —N(alkyl)(heterocyclylalkyl) groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—$NH_2$, substituted and unsubstituted —C(=O)—N(H)(alkyl) groups, substituted and unsubstituted —C(=O)—$N(alkyl)_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(H)(heterocyclylalkyl) groups, substituted and unsubstituted —C(=O)—N(alkyl)(heterocyclylalkyl) groups, —$CO_2H$, substituted and unsubstituted —C(=O)—O-alkyl groups, substituted and unsubstituted —C(=O)—O-heterocyclyl groups, or substituted and unsubstituted —C(=O)—O-heterocyclylalkyl groups; or $R^6$ may be absent if B is nitrogen; or $R^7$ may be absent if C is nitrogen. In some such embodiments, $R^6$ and $R^7$ are independently selected from —H, —F, —Cl, —Br, —I, or —$CH_3$.

In some embodiments of the method of inhibiting CHK1 in a subject and/or the method of treating a biological condition mediated by CHK1 activity in a subject, $R^6$ and $R^7$ are independently selected from substituted and unsubstituted heterocyclyl groups or substituted and unsubstituted heterocyclylalkyl groups; or $R^6$ may be absent if B is nitrogen; or $R^7$ may be absent if C is nitrogen.

In some embodiments of the method of inhibiting CHK1 in a subject and/or the method of treating a biological condition mediated by CHK1 activity in a subject, $R^6$ and $R^7$ are independently selected from substituted and unsubstituted pyrrolidinyl groups, substituted and unsubstituted piperidinylalkyl groups, substituted and unsubstituted piperazinyl groups, substituted and unsubstituted morpholinyl groups, substituted and unsubstituted thiomorpholinyl groups, substituted and unsubstituted dizaepanyl groups, substituted and unsubstituted oxazepanyl groups, or pyridinylalkyl groups.

In some embodiments of the method of inhibiting CHK1 in a subject and/or the method of treating a biological condition mediated by CHK1 activity in a subject, $R^6$ and $R^7$ are independently selected from 3-(acetyl-methyl-amino)-pyrrolidin-1-yl, 3-diethylamino-pyrrolidin-1-yl, 3-dimethylamino-pyrrolidin-1-yl, 3-(N-oxido-N,N-dimethylamino)-pyrrolidin-1-yl, 3-(pyrrolidin-1-yl)-pyrrolidin-1-yl, 2-(pyrrolidin-1-ylmethyl)-pyrrolidin-1-yl, 4-(piperidin-1-yl)piperidin-1-yl, 1-acetyl-piperazin-4-yl, 1-carboxymethyl-piperazin-4-yl, 1-methyl-piperazin-4-yl, 1-ethyl-piperazin-4-yl, 1-cyclohexyl-piperazin-4-yl, 1-isopropyl-piperazin-4-yl, morpholin-4-yl, 2-dimethylamino-morpholin-4-yl, 2,6-dimethyl-morpholin-4-yl, 2-dimethylamino-5-methyl-morpholin-4-yl, thiomorpholin-4-yl, thiomorpholin-4-yl 1-oxide 1-methyl-[1,4]dizaepan-1-yl, 2-dimethylaminomethyl-[1,4]oxazepan-4-yl, or pyridin-4-ylmethyl.

In some embodiments of the method of inhibiting CHK1 in a subject and/or the method of treating a biological condition mediated by CHK1 activity in a subject, $R^6$ and $R^7$ are independently selected from —OH, substituted and unsubstituted alkoxy groups, substituted and unsubstituted aryloxy groups, substituted and unsubstituted arylalkoxy groups, substituted and unsubstituted heterocyclyloxy groups, substituted and unsubstituted heterocyclylalkoxy groups, —NH₂, substituted and unsubstituted —N(H)(alkyl) groups, substituted and unsubstituted —N(alkyl)₂ groups, substituted and unsubstituted —N(H)(heterocyclyl) groups, substituted and unsubstituted —N(alkyl)(heterocyclyl) groups, substituted and unsubstituted —N(H)(heterocyclylalkyl) groups, or substituted and unsubstituted —N(alkyl)(heterocyclylalkyl) groups; or $R^6$ may be absent if B is nitrogen; or $R^7$ may be absent if C is nitrogen.

In some embodiments of the method of inhibiting CHK1 in a subject and/or the method of treating a biological condition mediated by CHK1 activity in a subject, $R^6$ and $R^7$ are independently selected from —OH, substituted and unsubstituted alkoxyalkoxy groups, substituted and unsubstituted pyrrolidinyloxy groups, substituted and unsubstituted tetrahydrofuranyloxy groups, substituted and unsubstituted pyrrolidinylalkoxy groups, substituted and unsubstituted morpholinylalkoxy groups, substituted and unsubstituted pyridinyloxy groups, —NH₂, substituted and unsubstituted —N(H)(pyrrolidinyl) groups, substituted and unsubstituted —N(H)(piperidinyl) groups, substituted and unsubstituted —N(H)(piperidinylalkyl) groups, substituted and unsubstituted —N(H)(pyridinylalkyl) groups, or substituted and unsubstituted —N(alkyl)(piperidinyl) groups.

In some embodiments of the method of inhibiting CHK1 in a subject and/or the method of treating a biological condition mediated by CHK1 activity in a subject, $R^6$ and $R^7$ are independently selected from —OH, methyloxy, 2-methyloxyethyloxy, 4-acetamido-phenyloxy, 1-methyl-pyrrolidin-3-yloxy, pyridin-3-yloxy, 3-(pyrrolidin-1-yl)-propyloxy, tetrahydrofuran-2-ylmethyloxy, 2-(morpholin-4-yl)-ethyloxy, 3-(morpholin-4-yl)-propyloxy, —NH₂, —N(H)(2-(methyloxymethyl)-pyrrolidin-4-yl), —N(H)(piperidin-3-yl), —N(H)(1,3-dimethyl-piperidin-4-yl), —N(H)(1-(ethoxycarbonyl)-piperidin-4-yl), —N(methyl)(1-methylpiperidin-1-yl), —N(H)(piperidin-1-ylethyl), or —N(H)(pyridin-2-ylmethyl). In some such embodiments, $R^6$ and $R^7$ are independently selected from —H or —N(methyl)(1-methylpiperidin-1-yl).

In some embodiments of the method of inhibiting CHK1 in a subject and/or the method of treating a biological condition mediated by CHK1 activity in a subject, $R^6$ and $R^7$ are independently selected from —S(=O)₂—NH₂, substituted and unsubstituted —S(=O)₂—N(H)(alkyl) groups, substituted and unsubstituted —S(=O)₂—N(alkyl)₂ groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH₂, substituted and unsubstituted —C(=O)—N(H)(alkyl) groups, substituted and unsubstituted —C(=O)—N(alkyl)₂ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(H)(heterocyclylalkyl) groups, substituted and unsubstituted —C(=O)—N(alkyl)(heterocyclylalkyl) groups, or —CO₂H; or $R^6$ may be absent if B is nitrogen; or $R^7$ may be absent if C is nitrogen.

In some embodiments of the method of inhibiting CHK1 in a subject and/or the method of treating a biological condition mediated by CHK1 activity in a subject, $R^6$ and $R^7$ are independently selected from substituted and unsubstituted —S(=O)₂—N(alkyl)₂ groups, substituted and unsubstituted —C(=O)-pyrrolidinyl groups, substituted and unsubstituted —C(=O)-piperidinyl groups, substituted and unsubstituted —C(=O)-pyrazinyl groups, substituted and unsubstituted —C(=O)-diazabicycloheptanyl groups, —C(=O)—NH₂, substituted and unsubstituted —C(=O)—N(H)(alkyl) groups, substituted and unsubstituted —C(=O)—N(alkyl)₂ groups, substituted and unsubstituted —C(=O)—N(H)(piperidinyl) groups, substituted and unsubstituted —C(=O)—N(H)(pyridinyl) groups, substituted and unsubstituted —C(=O)—N(H)(pyrrolidinylalkyl) groups, substituted and unsubstituted —C(=O)—N(H)(piperidinylalkyl) groups, or substituted and unsubstituted —C(=O)—N(alkyl)(piperidinyl).

In some embodiments of the method of inhibiting CHK1 in a subject and/or the method of treating a biological condition mediated by CHK1 activity in a subject, $R^6$ and $R^7$ are independently selected from —S(=O)₂—N(methyl)₂, —C(=O)-3-amino-pyrrolidin-1-yl, —C(=O)-3-(dimethylcarbamoyl)-pyrrolidin-1-yl, —C(=O)-3-hydroxy-pyrrolidin-1-yl, —C(=O)-4-dimethylamino-piperidin-1-yl, —C(=O)-3-hydroxy-piperidin-1-yl, —C(=O)-4-(piperidin-1-yl)-piperidin-1-yl, —C(=O)-pyridin-3-yl, —C(=O)-piperazin-1-yl, —C(=O)-1-acetyl-piperazin-4-yl, —C(=O)-1-cyclohexyl-piperazin-4-yl, —C(=O)-1-(ethoxycarbonylmethyl)-piperazin-4-yl, —C(=O)-1-hydroxyethyl-piperazin-4-yl, —C(=O)-1-isopropyl-piperazin-4-yl, —C(=O)-1-methyl-piperazin-4-yl, —C(=O)-2-methyl-piperazin-4-yl, —C(=O)-morpholin-4-yl, —C(=O)-2-methyl-2,5-diaza-bicyclo[2.2.1]heptan-5-yl, —C(=O)—N(methyl)(2-dimethylamino-ethyl), —C(=O)—N(ethyl)(2-dimethylamino-ethyl), —C(=O)—N(H)(piperidin-4-yl), —C(=O)—N(H)(piperidin-3-yl), —C(=O)—N(H)(1-ethoxycarbonyl-3-methoxy-piperidin-4-yl), —C(=O)—N(H)(1-aza-bicyclo[2.2.1]heptan-3-yl), —C(=O)—N(H)(2-(pyrrolidin-1-yl)-ethyl), —C(=O)—N(H)(2-(piperidin-1-yl)-ethyl), —C(=O)—N(methyl)(1-methyl-pyrrolidin-3-yl), or —C(=O)—N(methyl)(1-methylpiperidin-4-yl).

In some embodiments of the method of inhibiting CHK1 in a subject and/or the method of treating a biological condition mediated by CHK1 activity in a subject, B and C are both carbon and $R^6$ is —H and $R^7$ is —H.

In some embodiments of the method of inhibiting CHK1 in a subject and/or the method of treating a biological condition mediated by CHK1 activity in a subject, A, B, C, and D are all carbon, and $R^5$, $R^6$, $R^7$, and $R^8$ are all —H.

In some embodiments of the method of inhibiting CHK1 in a subject and/or the method of treating a biological condition mediated by CHK1 activity in a subject, A, B, C, and D are all carbon, and $R^4$, $R^5$, $R^6$, $R^7$, $R^8$, and $R^{10}$ are all —H.

In some embodiments of the method of inhibiting CHK1 in a subject and/or the method of treating a biological condition mediated by CHK1 activity in a subject, the $IC_{50}$ value of the compound is less than or equal to 10 µM with respect to CHK1. In other such embodiments, the $IC_{50}$ value is less than or equal to 1 µM, is less than or equal to 0.1 µM, is less than or equal to 0.050 µM, is less than or equal to 0.030 µM, is less than or equal to 0.025 µM, is less than or equal to 0.010 µM, or is less than or equal to 0.001 µM.

In some embodiments of the method of inhibiting CHK1 in a subject and/or the method of treating a biological condition mediated by CHK1 activity in a subject, the subject is a mammal or is a human.

In some embodiments of the method of treating a biological condition mediated by CHK1 activity in a subject, the biological condition is cancer.

Methods Relating to Ribosomal S6 Kinase 2

In some embodiments of the method of inhibiting a serine/threonine kinase in a subject and/or the method of treating a biological condition mediated by serine/threonine kinase activity in a subject using a compound of Structure I, a tautomer of the compound, a pharmaceutically acceptable salt of the compound, a pharmaceutically acceptable salt of the tautomer, or mixtures thereof, the serine/threonine kinase is Rsk2. In some such methods, the Rsk2 is inhibited in the subject after administration. In methods of inhibiting Rsk2, Structure I has the following formula:

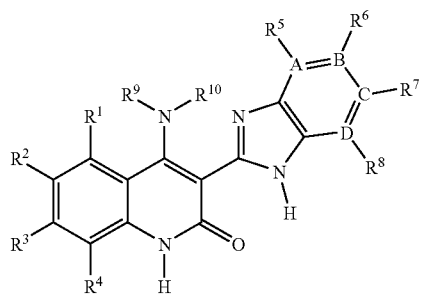

I where:
A, B, C, and D are independently selected from carbon or nitrogen;
$R^1$ is selected from —H, —F, —Cl, —Br, —I, —CN, —NO₂, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —OH, substituted and unsubstituted alkoxy groups, substituted and unsubstituted heterocyclyloxy groups, substituted and unsubstituted heterocyclylalkoxy groups, —NH₂, substituted and unsubstituted —N(H)(alkyl) groups, substituted and unsubstituted —N(H)(heterocyclyl) groups, substituted and unsubstituted —N(H)(heterocyclylalkyl) groups, substituted and unsubstituted —N(H)—C(═O)-alkyl groups, substituted and unsubstituted —N(H)—C(═O)-heterocyclyl groups, substituted and unsubstituted —N(H)—C(═O)-heterocyclylalkyl groups, substituted and unsubstituted —C(═O)-alkyl groups, substituted and unsubstituted —C(═O)-heterocyclyl groups, substituted and unsubstituted —C(═O)-heterocyclylalkyl groups, —C(═O)—NH₂, substituted and unsubstituted —C(═O)—N(H)(alkyl) groups, substituted and unsubstituted —C(═O)—N(alkyl)₂ groups, substituted and unsubstituted —C(═O)—N(H)(heterocyclyl) groups, —C(═O)—N(H)(heterocyclylalkyl) groups, —CO₂H, substituted and unsubstituted —C(═O)—O-alkyl groups, substituted and unsubstituted —C(═O)—O-heterocyclyl groups, or substituted and unsubstituted —C(═O)—O-heterocyclylalkyl groups;

$R^2$ and $R^3$ are independently selected from —H, —F, —Cl, —Br, —I, —CN, —NO₂, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —SH, substituted and unsubstituted —S-alkyl groups, substituted and unsubstituted —S-aryl groups, substituted and unsubstituted —S-aralkyl groups, —OH, substituted and unsubstituted alkoxy groups, substituted and unsubstituted heterocyclyloxy groups, substituted and unsubstituted heterocyclylalkoxy groups, —NH₂, substituted and unsubstituted —N(H)(alkyl) groups, substituted and unsubstituted —N(alkyl)₂ groups, substituted and unsubstituted —N(H)(aryl) groups, substituted and unsubstituted —N(H)(aralkyl) groups, substituted and unsubstituted —N(H)(heterocyclyl) groups, substituted and unsubstituted —N(H)(heterocyclylalkyl) groups, substituted and unsubstituted —N(H)—C(═O)-alkyl groups, substituted and unsubstituted —N(H)—C(═O)-aryl groups, substituted and unsubstituted —N(H)—C(═O)-aralkyl groups, substituted and unsubstituted —N(H)—C(═O)-heterocyclyl groups, substituted and unsubstituted —N(H)—C(═O)-heterocyclylalkyl groups, substituted and unsubstituted —C(═O)-alkyl groups, substituted and unsubstituted —C(═O)-aryl groups, substituted and unsubstituted —C(═O)-aralkyl groups, substituted and unsubstituted —C(═O)-heterocyclyl groups, substituted and unsubstituted —C(═O)-heterocyclylalkyl groups, —C(═O)—NH₂, substituted and unsubstituted —C(═O)—N(H)(alkyl) groups, substituted and unsubstituted —C(═O)—N(alkyl)₂ groups, substituted and unsubstituted —C(═O)—N(H)(aryl) groups, substituted and unsubstituted —C(═O)—N(H)(aralkyl) groups, substituted and unsubstituted —C(═O)—N(H)(heterocyclyl) groups, —C(═O)—N(H)(heterocyclylalkyl) groups, —CO₂H, substituted and unsubstituted —C(═O)—O-alkyl groups, substituted and unsubstituted —C(═O)—O-aryl groups, substituted and unsubstituted —C(═O)—O-aralkyl groups, substituted and unsubstituted —C(═O)—O-heterocyclyl groups, substituted and unsubstituted —C(=O)—O-heterocyclylalkyl groups; or $R^2$ and $R^3$ may join together to form a cyclic group, $R^4$, $R^5$, and $R^8$ are independently selected from —H or substituted and unsubstituted straight and branched chain alkyl groups having from 1 to 8 carbon atoms; or $R^5$ may be absent if A is nitrogen; or $R^8$ may be absent if D is nitrogen.

$R^6$ is selected from —H, —F, —Cl, —Br, —I, —CN, —$NO_2$, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —OH, substituted and unsubstituted alkoxy groups, substituted and unsubstituted heterocyclyloxy groups, substituted and unsubstituted heterocyclylalkoxy groups, —$CO_2H$, —C(=O)—$NH_2$, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, —C(=O)—N(H)(heterocyclylalkyl) groups, substituted and unsubstituted —C(=O)—O-alkyl groups, substituted and unsubstituted —C(=O)—O-heterocyclyl groups, substituted and unsubstituted —C(=O)—O-heterocyclylalkyl groups, substituted and unsubstituted —C(=O)-alkyl groups, substituted and unsubstituted —C(=O)-heterocyclyl groups, substituted and unsubstituted —C(=O)-heterocyclylalkyl groups, —$NH_2$, substituted and unsubstituted —N(H)(alkyl) groups, substituted and unsubstituted —N(H)(heterocyclyl) groups, substituted and unsubstituted —N(H)(heterocyclylalkyl) groups, substituted and unsubstituted —N(H)—C(=O)-alkyl groups, substituted and unsubstituted —N(H)—C(=O)-heterocyclyl groups, or substituted and unsubstituted —N(H)—C(=O)-heterocyclylalkyl groups;

$R^7$ is selected from —H, —F, —Cl, —Br, —I, —CN, —$NO_2$, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —OH, substituted and unsubstituted alkoxy groups, substituted and unsubstituted heterocyclyloxy groups, substituted and unsubstituted heterocyclylalkoxy groups, —SH, substituted and unsubstituted —S-alkyl groups, —$CO_2H$, —C(=O)—$NH_2$, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, —C(=O)—N(H)(heterocyclylalkyl) groups, substituted and unsubstituted —C(=O)—O-alkyl groups, substituted and unsubstituted —C(=O)—O-heterocyclyl groups, substituted and unsubstituted —C(=O)—O-heterocyclylalkyl groups, substituted and unsubstituted —C(=O)-alkyl groups, substituted and unsubstituted —C(=O)-heterocyclyl groups, substituted and unsubstituted —C(=O)-heterocyclylalkyl groups, —$NH_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(H)—C(=O)-heterocyclyl groups, or substituted and unsubstituted —N(H)—C(=O)-heterocyclylalkyl groups; or $R^7$ may be absent if C is nitrogen;

$R^9$ is selected from —H, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted aryloxy groups, substituted and unsubstituted arylalkoxy groups, substituted and unsubstituted heterocyclyloxy groups, substituted and unsubstituted heterocyclylalkoxy groups, substituted and unsubstituted —C(=O)-alkyl groups, substituted and unsubstituted —C(=O)-aryl groups, substituted and unsubstituted —C(=O)-aralkyl groups, substituted and unsubstituted —C(=O)-heterocyclyl groups, substituted and unsubstituted —C(=O)-heterocyclylalkyl groups; or $R^9$ and $R^{10}$ join together to form a ring having 5, 6, or 7 ring members; and $R^{10}$ is —H, or $R^9$ and $R^{10}$ join together to form a ring having 5, 6, or 7 ring members.

In some embodiments of the method of inhibiting Rsk2 in a subject and/or the method of treating a biological condition mediated by Rsk2 activity in a subject, $R^1$ is selected from —H, —F, —Cl, —Br, —I, substituted and unsubstituted alkyl groups having from 1 to 12 carbon atoms, substituted and unsubstituted heterocyclyl groups, substituted and unsubstituted heterocyclylalkyl groups, —OH, substituted and unsubstituted alkoxy groups, substituted and unsubstituted heterocyclyloxy groups, or substituted and unsubstituted heterocyclylalkoxy groups;

$R^2$ and $R^3$ are independently selected from —H, —F, —Cl, —Br, —I, —CN, —$NO_2$, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted heterocyclyloxy groups, substituted and unsubstituted heterocyclylalkoxy groups, or —$CO_2H$; or $R^2$ and $R^3$ may join together to form a cyclic group $R^6$ is selected from —H, —F, —Cl, —Br, —I, substituted and unsubstituted alkyl groups having from 1 to 8 carbon atoms, substituted and unsubstituted heterocyclyl groups, —OH, substituted and unsubstituted alkoxy groups, substituted and unsubstituted heterocyclyloxy groups, or substituted and unsubstituted heterocyclylalkoxy groups; or $R^6$ may be absent if B is nitrogen;

$R^7$ is selected from the group consisting —H, —F, —Cl, —Br, —I, substituted and unsubstituted alkyl groups having from 1 to 8 carbon atoms, substituted and unsubstituted heterocyclyl groups, —OH, substituted and unsubstituted alkoxy groups, substituted and unsubstituted heterocyclyloxy groups, or substituted and unsubstituted heterocyclylalkoxy groups; or $R^7$ may be absent if C is nitrogen.

In some embodiments of the method of inhibiting Rsk2 in a subject and/or the method of treating a biological condition mediated by Rsk2 activity in a subject, A, B, C, and D are all carbon.

In some embodiments of the method of inhibiting Rsk2 in a subject and/or the method of treating a biological condition mediated by Rsk2 activity in a subject, of A or D is nitrogen, and B and C are both carbon.

In some embodiments of the method of inhibiting Rsk2 in a subject and/or the method of treating a biological condition mediated by Rsk2 activity in a subject, $R^{10}$ is —H and $R^9$ is selected from —H, substituted and unsubstituted alkyl groups having from 1-12 carbon atoms, substituted and unsubstituted aryl groups, substituted and unsubstituted aralkyl groups, substituted and unsubstituted heterocyclyl groups, substituted and unsubstituted heterocyclylalkyl groups, substituted and unsubstituted alkoxy groups, or substituted and unsubstituted heterocyclylalkoxy groups.

In some embodiments of the method of inhibiting Rsk2 in a subject and/or the method of treating a biological condition mediated by Rsk2 activity in a subject, $R^9$ is selected from —H, substituted and unsubstituted straight or branched chain alkyl groups having from 1-12 carbon atoms, substituted and unsubstituted cycloalkyl groups, substituted and unsubstituted aryl groups, substituted and unsubstituted aralkyl groups, substituted and unsubstituted saturated heterocyclyl groups, substituted and unsubstituted heterocyclylalkyl groups wherein the heterocyclyl moiety is saturated, substituted and unsubstituted alkoxy groups, or substituted and unsubstituted heterocyclylalkoxy groups wherein the heterocyclyl moiety is saturated.

In some embodiments of the method of inhibiting Rsk2 in a subject and/or the method of treating a biological condition mediated by Rsk2 activity in a subject, $R^{10}$ is —H and $R^9$ is selected from —H, unsubstituted straight or branched chain alkyl groups having from 1-12 carbon atoms, unsubstituted cycloalkyl groups, alkoxyalkyl groups, aminoalkyl groups, alkylaminoalkyl groups, dialkylaminoalkyl groups, aminocyclohexyl groups, substituted and unsubstituted saturated heterocyclyl groups, substituted and unsubstituted heterocyclylalkoxy groups wherein the heterocyclyl moiety is saturated. In some such embodiments, $R^9$ is selected from pyrrolidinyl, pyrrolidinylalkyl, piperidinyl, piperidinylalkyl, quinuclidinyl, or aminocyclohexyl groups.

In some embodiments of the method of inhibiting Rsk2 in a subject and/or the method of treating a biological condition mediated by Rsk2 activity in a subject, $R^1$ is selected from —H, —F, —Cl, substituted and unsubstituted morpholinyl groups, substituted and unsubstituted morpholinylalkyl groups, or substituted and unsubstituted morpholinylalkoxy groups. In some such embodiments, $R^1$ is selected from —H or —F. In other such embodiments, $R^1$ is —H.

In some embodiments of the method of inhibiting Rsk2 in a subject and/or the method of treating a biological condition mediated by Rsk2 activity in a subject, $R^2$ is selected from —H, —F, —Cl, —Br, —I, —NO$_2$, —CH$_3$, —OCH$_3$, —CO$_2$H, substituted and unsubstituted aryl groups, or substituted and unsubstituted pyridinyl groups. In some such embodiments, $R^2$ is selected from —H, —Br, —I, —CH$_3$, —CO$_2$H, —NH$_2$, or 4-hydroxyphenyl.

In some embodiments of the method of inhibiting Rsk2 in a subject and/or the method of treating a biological condition mediated by Rsk2 activity in a subject, $R^3$ is selected from —H, —F, —Cl, —Br, —I, —CH$_3$, —OCH$_3$, substituted and unsubstituted imidazolyl, substituted and unsubstituted dialkylaminoalkoxy, or substituted and unsubstituted heterocyclylalkoxy. In some such embodiments, $R^3$ is selected from —H or —F.

In some embodiments of the method of inhibiting Rsk2 in a subject and/or the method of treating a biological condition mediated by Rsk2 activity in a subject, $R^4$ is —H.

In some embodiments of the method of inhibiting Rsk2 in a subject and/or the method of treating a biological condition mediated by Rsk2 activity in a subject, $R^5$ is —H; or may be absent.

In some embodiments of the method of inhibiting Rsk2 in a subject and/or the method of treating a biological condition mediated by Rsk2 activity in a subject, $R^6$ is selected from —H, —F, —Cl, —Me, substituted and unsubstituted morpholinyl groups, substituted and unsubstituted morpholinylalkoxy groups, substituted and unsubstituted piperidinyl groups, or substituted and unsubstituted piperazinyl groups; or may be absent.

In some embodiments of the method of inhibiting Rsk2 in a subject and/or the method of treating a biological condition mediated by Rsk2 activity in a subject, wherein $R^7$ is selected from —H, —F, -Me, substituted and unsubstituted morpholinyl groups, substituted and unsubstituted pyrrolidinyl groups, substituted and unsubstituted piperidinyl groups, or substituted and unsubstituted piperazinyl groups; or may be absent.

In some embodiments of the method of inhibiting Rsk2 in a subject and/or the method of treating a biological condition mediated by Rsk2 activity in a subject, $R^8$ is —H; or may be absent.

In some embodiments of the method of inhibiting Rsk2 in a subject and/or the method of treating a biological condition mediated by Rsk2 activity in a subject, the IC$_{50}$ value of the compound is less than or equal to 10 µM with respect to CHK1. In other such embodiments, the IC$_{50}$ value is less than or equal to 1 µM, is less than or equal to 0.1 µM, is less than or equal to 0.050 µM, is less than or equal to 0.030 µM, is less than or equal to 0.025 µM, is less than or equal to 0.010 µM, or is less than or equal to 0.001 µM.

In some embodiments of the method of inhibiting Rsk2 in a subject and/or the method of treating a biological condition mediated by Rsk2 activity in a subject, the subject is a mammal or is a human.

In some embodiments of the method of treating a biological condition mediated by Rsk2 activity in a subject, the biological condition is cancer.

Methods Relating to PAR-1

In some embodiments of the method of inhibiting a serine/threonine kinase in a subject and/or the method of treating a biological condition mediated by serine/threonine kinase activity in a subject using a compound of Structure I, a tautomer of the compound, a pharmaceutically acceptable salt of the compound, a pharmaceutically acceptable salt of the tautomer, or mixtures thereof, the serine/threonine kinase is PAR-1. In some such methods, the PAR-1 is inhibited in the subject after administration. In methods of inhibiting PAR-1, Structure I has the following formula:

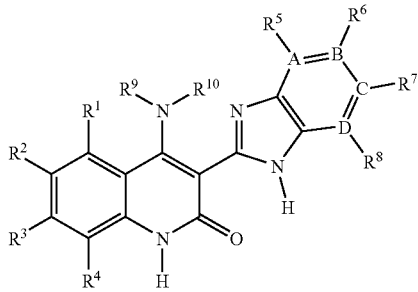

where,
- A, B, C, and D are independently selected from carbon or nitrogen;
- $R^1$ is selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted heterocyclyl groups, or substituted and unsubstituted heterocyclylalkyl groups;
- $R^2$ is selected from —H, —F, —Cl, —Br, —I, —NO$_2$, —CN, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, —OH, substituted and unsubstituted alkoxy, substituted and unsubstituted heterocyclyloxy, substituted and unsubstituted heterocyclylalkoxy, substituted and unsubstituted —C(═O)-alkyl groups, substituted and unsubstituted —C(═O)-aryl, substituted and unsubstituted —C(═O)-aralkyl, —CO$_2$H, substituted and unsubstituted —C(═O)—O-alkyl groups, substituted and unsubstituted —C(═O)—O-aryl groups, or substituted and unsubstituted —C(═O)—O-aralkyl groups;
- $R^3$ is selected from —H, —F, —Cl, —Br, —I, —NO$_2$, —CN, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —SH, substituted and unsubstituted —S-alkyl groups, substituted and unsubstituted —S(═O)$_2$—O-alkyl groups, substituted and unsubstituted —S(═O)$_2$-alkyl groups, substituted and unsubstituted —S(═O)$_2$-heterocyclyl groups, —S(═O)$_2$—NH$_2$, substituted and unsubstituted —S(═O)$_2$—N(H)(alkyl) groups, substituted and unsubstituted —S(═O)$_2$—N(alkyl)$_2$ groups, substituted and unsubstituted —S(═O)-alkyl groups, substituted and unsubstituted —S(═O)-aryl groups, substituted and unsubstituted —S(═O)-heterocyclyl groups, —OH, substituted and unsubstituted alkoxy groups, substituted and unsubstituted aryloxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, substituted and unsubstituted —N(aryl)$_2$ groups, substituted and unsubstituted —N(H)(aralkyl) groups, substituted and unsubstituted —N(alkyl)(aralkyl) groups, substituted and unsubstituted —N(aralkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(═O)-alkyl groups, substituted and unsubstituted —N(alkyl)-C(═O)-alkyl groups, substituted and unsubstituted —N(H)—C(═O)-aryl groups, substituted and unsubstituted —N(alkyl)-C(═O)-aryl groups, substituted and unsubstituted —N(H)—C(═O)-aralkyl groups, substituted and unsubstituted —N(alkyl)-C(═O)-aralkyl groups, substituted and unsubstituted —N(H)—C(═O)-heterocyclyl groups, substituted and unsubstituted —N(alkyl)-C(═O)-heterocyclyl groups, substituted and unsubstituted —N(H)—C(═O)-heterocyclylalkyl groups, substituted and unsubstituted —N(alkyl)-C(═O)-heterocyclylalkyl groups, substituted and unsubstituted —N(H)—S(═O)$_2$-alkyl groups, substituted and unsubstituted —N(H)—S(═O)$_2$-aryl, substituted and unsubstituted —N(H)—S(═O)$_2$-heterocyclyl groups, substituted and unsubstituted —C(═O)-alkyl groups, substituted and unsubstituted —C(═O)-aryl, substituted and unsubstituted —C(═O)-aralkyl, substituted and unsubstituted —C(═O)-heterocyclyl groups, substituted and unsubstituted —C(═O)-heterocyclylalkyl groups, —C(═O)—NH$_2$, substituted and unsubstituted —C(═O)—N(H)(alkyl) groups, substituted and unsubstituted —C(═O)—N(alkyl)$_2$ groups, substituted and unsubstituted —C(═O)—N(H)(aryl) groups, substituted and unsubstituted —C(═O)—N(alkyl)(aryl) groups, substituted and unsubstituted —C(═O)—N(aryl)$_2$ groups, substituted and unsubstituted —C(═O)—N(H)(aralkyl) groups, substituted and unsubstituted —C(═O)—N(alkyl)(aralkyl) groups, substituted and unsubstituted —C(═O)—N(aralkyl)$_2$ groups, substituted and unsubstituted —C(═O)—N(H)(heterocyclyl) groups, substituted and unsubstituted —C(═O)—N(alkyl)(heterocyclyl) groups, substituted and unsubstituted —C(═O)—N(heterocyclyl)$_2$ groups, substituted and unsubstituted —C(═O)—N(H)(heterocyclylalkyl) groups, substituted and unsubstituted —C(═O)—N(alkyl)(heterocyclylalkyl) groups, substituted and unsubstituted —C(═O)—N(heterocyclylalkyl)$_2$ groups, —CO$_2$H, substituted and unsubstituted —C(═O)—O-alkyl groups, substituted and unsubstituted —C(═O)—O-aryl groups, substituted and unsubstituted —C(═O)—O-aralkyl groups, substituted and unsubstituted —C(═O)—O-heterocyclyl groups, or substituted and unsubstituted —C(═O)—O-heterocyclylalkyl groups;
- $R^4$, $R^5$ and $R^8$ are independently selected from —H or substituted and unsubstituted alkyl groups having from 1 to 12 carbon atoms; or $R^5$ may be absent if A is nitrogen; or $R^8$ may be absent if D is nitrogen;
- $R^6$ and $R^7$ are independently selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —SH, substituted and unsubstituted —S-alkyl groups, substituted and unsubstituted —S-heterocyclyl groups, —OH, substituted and unsubstituted alkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, or substituted and unsubstituted —N(heterocyclylalkyl)$_2$ groups; or $R^6$ is absent if B is nitrogen; or $R^7$ is absent if C is nitrogen;

$R^9$ is selected from —H, substituted and unsubstituted alkyl groups having from 1 to 12 carbon atoms, substituted and unsubstituted alkenyl groups having from 1 to 12 carbons, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, or substituted and unsubstituted heterocyclylalkoxy groups; and $R^{10}$ is —H.

In some embodiments of the method of inhibiting PAR-1 in a subject and/or the method of treating a biological condition mediated by PAR-1 activity in a subject, $R^3$ is selected from —H, —F, —Cl, —Br, —I, —NO$_2$, —CN, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted aryloxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, substituted and unsubstituted —N(aryl)$_2$ groups, substituted and unsubstituted —N(H)(aralkyl) groups, substituted and unsubstituted —N(alkyl)(aralkyl) groups, substituted and unsubstituted —N(aralkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(aryl) groups, substituted and unsubstituted —C(=O)—N(alkyl)(aryl) groups, substituted and unsubstituted —C(=O)—N(aryl)$_2$ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)$_2$ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)$_2$ groups, —CO$_2$H, substituted and unsubstituted —C(=O)—O-alkyl groups, substituted and unsubstituted —C(=O)—O-heterocyclyl groups, or substituted and unsubstituted —C(=O)—O-heterocyclylalkyl groups;

$R^6$ and $R^7$ are independently selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —OH, substituted and unsubstituted alkoxy groups, substituted and unsubstituted heterocyclyloxy groups, or substituted and unsubstituted heterocyclylalkoxy groups; or $R^6$ is absent if B is nitrogen; or $R^7$ is absent if C is nitrogen.

In some embodiments of the method of inhibiting PAR-1 in a subject and/or the method of treating a biological condition mediated by PAR-1 activity in a subject, A, B, C, and D are all carbon.

In some embodiments of the method of inhibiting PAR-1 in a subject and/or the method of treating a biological condition mediated by PAR-1 activity in a subject, one of A or D is nitrogen, and B and C are both carbon.

In some embodiments of the method of inhibiting PAR-1 in a subject and/or the method of treating a biological condition mediated by PAR-1 activity in a subject, $R^9$ is selected from —H, substituted and unsubstituted straight and branched chain alkyl groups having from 1 to 8 carbon atoms, substituted and unsubstituted cycloalkyl groups, substituted and unsubstituted heterocyclyl groups, or substituted and unsubstituted heterocyclylalkyl groups.

In some embodiments of the method of inhibiting PAR-1 in a subject and/or the method of treating a biological condition mediated by PAR-1 activity in a subject, $R^9$ is selected from —H, unsubstituted straight and branched chain alkyl groups having from 1 to 8 carbon atoms, substituted and unsubstituted cycloalkyl groups, substituted and unsubstituted heterocyclyl groups, substituted and unsubstituted heterocyclylalkyl groups, substituted and unsubstituted dialkylaminoalkyl groups, substituted and unsubstituted alkylaminoalkyl groups, substituted and unsubstituted aminoalkyl groups, or substituted and unsubstituted alkylsulfonylalkyl groups.

In some embodiments of the method of inhibiting PAR-1 in a subject and/or the method of treating a biological condition mediated by PAR-1 activity in a subject, $R^9$ is selected from —H, unsubstituted straight or branched chain alkyl groups of 1-8 carbons, substituted and unsubstituted alkylaminoalkyl groups, substituted and unsubstituted dialkylaminoalkyl groups, substituted and unsubstituted alkylsulfonylalkyl groups, substituted and unsubstituted cycloalkyl groups, substituted and unsubstituted saturated heterocyclyl groups, or substituted and unsubstituted heterocyclylalkyl groups wherein the heterocyclyl moiety is saturated.

In some embodiments of the method of inhibiting PAR-1 in a subject and/or the method of treating a biological condition mediated by PAR-1 activity in a subject, $R^9$ is selected from substituted and unsubstituted methylaminoethyl groups, substituted and unsubstituted dimethylaminoethyl groups, substituted and unsubstituted methylsulfonylethyl groups, substituted and unsubstituted quinuclidinyl groups, substituted and unsubstituted piperazinylalkyl groups, substituted and unsubstituted piperidinyl groups, substituted and unsubstituted piperidinylalkyl groups, substituted and unsubstituted pyrrolidinyl groups, substituted and unsubstituted pyrrolidinylalkyl groups, substituted and unsubstituted imidazolylalkyl groups, or substituted and unsubstituted cyclohexyl groups.

In some embodiments of the method of inhibiting PAR-1 in a subject and/or the method of treating a biological condition mediated by PAR-1 activity in a subject, $R^9$ is selected from —H, methylaminoethyl, dimethylaminoethyl, methylsulfonylethyl, 1-aminocyclohexyl, quinuclidinyl, 4-methylpiperazin-1-ylpropyl, 1-benzylpiperidinyl, piperidin-3-yl, piperidin-4-yl, piperidin-3-ylethyl, piperidin-4-ylethyl, imidazol-5-ylethyl, pyrrolidin-1-ylethyl, 1-methylpyrrolidin-2-ylethyl, or pyrrolidin-3-yl. In some such embodiments, $R^9$ is a quinuclidinyl group. In other such embodiments, $R^9$ is a quinuclidin-3-yl group. In still other such embodiments, $R^9$ is —H.

In some embodiments of the method of inhibiting PAR-1 in a subject and/or the method of treating a biological condition mediated by PAR-1 activity in a subject, $R^9$ is selected from monocyclic, bicyclic, or polycyclic saturated heterocyclyl groups.

In some embodiments of the method of inhibiting PAR-1 in a subject and/or the method of treating a biological condition mediated by PAR-1 activity in a subject, $R^1$ is selected from —H, —F, —Cl, —Br, —I, substituted and unsubstituted straight and branched chain alkyl groups having from 1 to 8 carbon atoms, substituted and unsubstituted cycloalkyl groups, or substituted and unsubstituted heterocyclyl groups. In some such embodiments, $R^1$ is selected from —H, —F, —Cl, or substituted and unsubstituted piperazinyl. In other such embodiments, $R^1$ is selected from —H, —F, —Cl, or 4-ethylpiperazin-1-yl. In still other such embodiments, $R^1$ is —H.

In some embodiments of the method of inhibiting PAR-1 in a subject and/or the method of treating a biological condition mediated by PAR-1 activity in a subject, $R^2$ is selected from —H, —F, —Cl, —Br, —I, —NO$_2$, —CN, substituted and unsubstituted straight and branched chain alkyl groups having from 1 to 12 carbon atoms, substituted and unsubstituted cycloalkyl groups, substituted and unsubstituted aryl groups, or substituted and unsubstituted aralkyl groups.

In some embodiments of the method of inhibiting PAR-1 in a subject and/or the method of treating a biological condition mediated by PAR-1 activity in a subject, $R^2$ is selected from —H, —Cl, —F, —Br, —I, —CN, substituted and unsubstituted straight or branched chain alkyl having from 1 to 8 carbons, or substituted and unsubstituted phenyl groups.

In some embodiments of the method of inhibiting PAR-1 in a subject and/or the method of treating a biological condition mediated by PAR-1 activity in a subject, $R^2$ is a substituted and unsubstituted aryl group selected from 2-amino-4-carboxymethylphenyl, 2-methylphenyl, 2-ethylphenyl, 2-methoxyphenyl, 2,4-dichlorophenyl, 2-fluoro-4-chlorophenyl, 2,6-difluorophenyl, 3-methoxyphenyl, 3-carboxyphenyl, 3-acetylphenyl, 3-acetamidophenyl, 3-methylcarboxyphenyl, 4-acetylphenyl, 4-dimethylaminophenyl, 4-cyanophenyl, 4-carboxamidophenyl, 4-carboxyphenyl, 4-methylcarboxyphenyl, 4-methylsulfonylphenyl, or phenyl.

In some embodiments of the method of inhibiting PAR-1 in a subject and/or the method of treating a biological condition mediated by PAR-1 activity in a subject, $R^2$ is selected from —F, —Cl, —Br, —I, —CN, methyl, methoxy, or —CO$_2$H. In some such embodiments, $R^2$ is —Cl.

In some embodiments of the method of inhibiting PAR-1 in a subject and/or the method of treating a biological condition mediated by PAR-1 activity in a subject, $R^3$ is selected from —H, —F, —Cl, —Br, —I, —CN, substituted and unsubstituted straight or branched chain alkyl groups having from 1 to 8 carbon atoms, substituted and unsubstituted cycloalkyl groups, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted heterocyclyloxy groups, substituted and unsubstituted heterocyclylalkoxy groups, substituted and unsubstituted —N(H)(alkyl) groups, substituted and unsubstituted —N(alkyl)$_2$ groups, or substituted and unsubstituted —N(H)(heterocyclylalkyl) groups.

In some embodiments of the method of inhibiting PAR-1 in a subject and/or the method of treating a biological condition mediated by PAR-1 activity in a subject, $R^3$ is selected from —H, —F, —Cl, —Br, —I, —CN, substituted and unsubstituted straight or branched chain alkyl groups having from 1 to 8 carbon atoms, —OH, unsubstituted straight or branched chain alkoxy groups, dialkylaminoalkoxy groups, or substituted and unsubstituted pyrrolidinylalkoxy groups. In some such embodiments, $R^3$ is selected from —H, —Cl, methoxy, 2-(dimethylamino)ethyl-1-oxy, and pyrrolidin-2-ylmethyloxy.

In some embodiments of the method of inhibiting PAR-1 in a subject and/or the method of treating a biological condition mediated by PAR-1 activity in a subject, $R^3$ is selected from substituted and unsubstituted phenyl groups or substituted and unsubstituted unsaturated heterocyclyl groups. In some such embodiments, $R^3$ is selected from 2-amino-4-carboxyphenyl, 3-acetamidophenyl, 3-carboxyphenyl, 4-carboxyphenyl, 4-methylsulfonylphenyl, 2-ethyl-imidazol-1-yl, 2-methyl-imidazol-1-yl, imidazol-1-yl, and 3-acetylpyrrol-1-yl.

In some embodiments of the method of inhibiting PAR-1 in a subject and/or the method of treating a biological condition mediated by PAR-1 activity in a subject, $R^3$ is a saturated heterocyclyl group. In some such embodiments, $R^3$ a saturated heterocyclyl group selected from substituted and unsubstituted thiomorpholinyl groups, substituted and unsubstituted piperazinyl groups, substituted and unsubstituted piperidinyl groups, or substituted and unsubstituted pyrrolidinyl groups. In other such embodiments, $R^3$ is selected from 3-phenylthiomorpholin-4-yl groups, morpholin-4-yl, 4-methylpiperazin-1-yl groups, 4-methylcarboxypiperidin-1-yl, piperidin-1-yl, 3-dimethylaminopyrrolidin-1-yl, or 3-acetamidopyrrolidin-1-yl.

In some embodiments of the method of inhibiting PAR-1 in a subject and/or the method of treating a biological condition mediated by PAR-1 activity in a subject, $R^3$ is selected from substituted and unsubstituted —N(H)(alkyl) groups, substituted and unsubstituted —N(alkyl)$_2$ groups, or substituted and unsubstituted —N(H)(heterocyclylalkyl) groups, wherein the heterocyclyl moiety is saturated.

In some embodiments of the method of inhibiting PAR-1 in a subject and/or the method of treating a biological condition mediated by PAR-1 activity in a subject, $R^3$ is selected from substituted and unsubstituted —N(H)(hydroxyalkyl), substituted and unsubstituted —N(H)(aminoalkyl), substituted and unsubstituted —N(H)(dialkylaminoalkyl), substituted and unsubstituted —N(H)(alkylcarboxamidoalkyl), substituted and unsubstituted —N(H)(alkoxyalkyl), substituted and unsubstituted —N(H)(arylsulfonylalkyl), substituted and unsubstituted —N(H)(alkylsulfonylalkyl), substituted and unsubstituted —N(H)(cycloalkyl), substituted and unsubstituted —N(H)(morpholinylalkyl), substituted and unsubstituted —N(H)(piperidinylalkyl), or substituted and unsubstituted —N(H)(pyrrolidinonylalkyl).

In some embodiments of the method of inhibiting PAR-1 in a subject and/or the method of treating a biological condition mediated by PAR-1 activity in a subject, $R^3$ is selected from —N(H)(2-hydroxyethyl), —N(H)(2-aminoethyl), —N(H)(dimethylaminoethyl), —N(H)(2-diethylaminoethyl), —N(H)(3-dimethylaminopropyl), —N(H)(2-acetamidoethyl), —N(H)(2-methoxyethyl), —N(H)(2-(methylsulfonyl)ethyl), —N(H)(2-(phenylsulfonyl)ethyl), —N(H)(cyclopropyl), —N(methyl)(ethyl), —N(methyl)$_2$, —N(H)(2-morpholin-4-yl-2-phenylethyl), —N(H)(2-piperidin-1-ylethyl), or —N(H)(3-pyrrolidinon-1-ylpropyl).

In some embodiments of the method of inhibiting PAR-1 in a subject and/or the method of treating a biological condition mediated by PAR-1 activity in a subject, $R^4$ is —H.

In some embodiments of the method of inhibiting PAR-1 in a subject and/or the method of treating a biological condition mediated by PAR-1 activity in a subject, A and D are both carbon, $R^5$ is —H, and $R^8$ is —H.

In some embodiments of the method of inhibiting PAR-1 in a subject and/or the method of treating a biological condition mediated by PAR-1 activity in a subject, $R^6$ and $R^7$ are independently selected from —H, —F, —Cl, —Br, —I, —CN, —NO$_2$, substituted and unsubstituted straight or branched chain alkyl groups having from 1 to 8 carbon atoms, substituted and unsubstituted cycloalkyl groups, substituted and unsubstituted heterocyclyl groups, substituted and unsubstituted heterocyclylalkyl groups, —OH, substituted and unsubstituted alkoxy groups, substituted and unsubstituted heterocyclyloxy groups, or substituted and unsubstituted heterocyclylalkoxy groups; or $R^6$ is absent if B is nitrogen; or $R^7$ is absent if C is nitrogen.

In some embodiments of the method of inhibiting PAR-1 in a subject and/or the method of treating a biological condition mediated by PAR-1 activity in a subject, $R^6$ and $R^7$ are independently selected from —H, —F, —Cl, —Br, —I, substituted and unsubstituted straight or branched chain alkyl groups having from 1 to 8 carbon atoms, substituted and unsubstituted heterocyclyl groups, —OH, or substituted and unsubstituted heterocyclylalkoxy groups; or $R^6$ is absent if B is nitrogen; or $R^7$ is absent if C is nitrogen.

In some embodiments of the method of inhibiting PAR-1 in a subject and/or the method of treating a biological condition mediated by PAR-1 activity in a subject, $R^6$ and $R^7$ are independently selected from —H, —F, —Cl, —Br, —I, unsubstituted straight or branched chain alkyl groups having from 1 to 8 carbon atoms, substituted and unsubstituted morpholinyl groups, substituted and unsubstituted piperazinyl groups, substituted and unsubstituted pyrrolidinyl groups, —OH, or pyrrolidinylalkoxy; or $R^6$ is absent if B is nitrogen; or $R^7$ is absent if C is nitrogen. In some such embodiments, $R^6$ and $R^7$ are independently selected from —H, —F, methyl, morpholin-4-yl, 4-isopropyl-piperazin-1-yl, 4-methylpiperazin-1-yl, —OH; and 3-(pyrrolidin-1-yl)propyl-1-oxy; or $R^6$ is absent if B is nitrogen; or $R^7$ is absent if C is nitrogen. In other such embodiments, B and C are both carbon and $R^6$ and $R^7$ are both —H.

In some embodiments of the method of inhibiting PAR-1 in a subject and/or the method of treating a biological condition mediated by PAR-1 activity in a subject, A, B, C, and D are all carbon, and $R^5$, $R^6$, $R^7$, and $R^8$ are all —H.

In some embodiments of the method of inhibiting PAR-1 in a subject and/or the method of treating a biological condition mediated by PAR-1 activity in a subject, the IC$_{50}$ value of the compound is less than or equal to 10 µM with respect to PAR-1. In other such embodiments, the IC$_{50}$ value is less than or equal to 1 µM, is less than or equal to 0.1 µM, is less than or equal to 0.050 µM, is less than or equal to 0.030 µM, is less than or equal to 0.025 µM, or is less than or equal to 0.010 µM.

In some embodiments of the method of inhibiting PAR-1 in a subject and/or the method of treating a biological condition mediated by PAR-1 activity in a subject, the subject is a mammal or is a human.

In some embodiments of the method of treating a biological condition mediated by PAR-1 activity in a subject, the biological condition is controlled by the Wnt pathway and/or is controlled by the planar cell polarity pathway. In some cases, the biological condition is cancer which in some embodiments is caused by aberrant regulation of the Wnt pathway in a mammal such as a human. Thus, in some embodiments, the invention provides a method of regulating the Wnt pathway in a subject. In other embodiments, the invention provides a method of modulating the Wnt β-catenin signaling.

Methods Relating to Tyrosine Kinases

In another aspect, the present invention provides a method of inhibiting a tyrosine kinase in a subject and/or a method of treating a biological condition mediated by a tyrosine kinase in a subject. The tyrosine kinase is Cdc2 kinase, Fyn, Lck, c-Kit, c-ABL, p60src, VEGFR3, PDGFRα, PDGFRβ, FGFR3, FLT-3, or Tie-2. In some embodiments, the tyrosine kinase is Cdc2 kinase, Fyn, Lck, or Tie-2 and in some other embodiments, the tyrosine kinase is c-Kit, c-ABL, p60src, FGFR3, VEGFR3, PDGFRα, PDGFRβ, or FLT-3. The methods include administering to the subject a compound of Structure I, a tautomer of the compound, a pharmaceutically acceptable salt of the compound, a pharmaceutically acceptable salt of the tautomer, or mixtures thereof. In the method of inhibiting a tyrosine kinase, the tyrosine kinase is inhibited in the subject after administration. Structure I has the following formula:

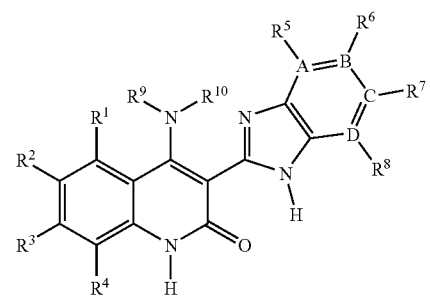

I where,
A, B, C, and D are independently selected from carbon or nitrogen;
$R^1$ is selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —SH, substituted and unsubstituted —S-alkyl groups, substituted and unsubstituted —S-heterocyclyl groups, —OH, substituted and unsubstituted alkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(═O)-alkyl groups, substituted and unsubstituted —N(H)—C(═O)-heterocyclyl groups, substituted and unsubstituted —N(H)—C(═O)-heterocyclylalkyl groups, substituted and unsubstituted —N(alkyl)-S(═O)$_2$-alkyl groups, substituted and unsubstituted —N(alkyl)-S(═O)$_2$-heterocyclyl groups, substituted and unsubstituted —N(alkyl)-S(═O)$_2$-heterocyclylalkyl groups, substituted and unsubstituted —C(═O)-alkyl groups, substituted and unsubstituted —C(═O)-heterocyclyl groups, substituted and unsubstituted —C(═O)-heterocyclylalkyl groups, —C(═O)—NH$_2$, substituted and unsubstituted —C(═O)—N(H)(alkyl) groups, substituted and unsubstituted —C(═O)—N(alkyl)$_2$ groups, substituted and unsubstituted —C(═O)—N(H)(heterocyclyl) groups, substituted and unsubstituted —C(═O)—N(alkyl)(heterocyclyl) groups, substituted and unsubstituted —C(═O)—N(heterocyclyl)$_2$ groups, substituted and unsubstituted —C(═O)—N(H)(heterocyclylalkyl) groups, substituted and unsubstituted —C(═O)—N(alkyl)(heterocyclylalkyl) groups, substituted and unsubstituted —C(═O)—N(heterocyclylalkyl)$_2$ groups, —CO$_2$H, substituted and unsubstituted —C(═O)—O-alkyl groups, substituted and unsubstituted —C(═O)—O-heterocyclyl groups, or substituted and unsubstituted —C(═O)—O-heterocyclylalkyl groups;

$R^2$ and $R^3$ are independently selected from —H, —F, —Cl, —Br, —I, —NO$_2$, —CN, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —SH, substituted and unsubstituted —S-alkyl groups, substituted and unsubstituted —S(═O)$_2$—O-alkyl groups, substituted and unsubstituted —S(═O)$_2$-alkyl groups, substituted and unsubstituted —S(═O)$_2$-heterocyclyl groups, —S(═O)$_2$—NH$_2$, substituted and unsubstituted —S(═O)$_2$—N(H)(alkyl) groups, substituted and unsubstituted —S(═O)$_2$—N(alkyl)$_2$ groups, substituted and unsubstituted —S(═O)-alkyl groups, substituted and unsubstituted —S(═O)-heterocyclyl groups, —OH, substituted and unsubstituted alkoxy groups, substituted and unsubstituted aryloxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, substituted and unsubstituted —N(aryl)$_2$ groups, substituted and unsubstituted —N(H)(aralkyl) groups, substituted and unsubstituted —N(alkyl)(aralkyl) groups, substituted and unsubstituted —N(aralkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(═O)-alkyl groups, substituted and unsubstituted —N(alkyl)-C(═O)-alkyl groups, substituted and unsubstituted —N(H)—C(═O)-aryl groups, substituted and unsubstituted —N(alkyl)-C(═O)-aryl groups, substituted and unsubstituted —N(H)—C(═O)-aralkyl groups, substituted and unsubstituted —N(alkyl)-C(═O)-aralkyl groups, substituted and unsubstituted —N(H)—C(═O)-heterocyclyl groups, substituted and unsubstituted —N(alkyl)-C(═O)-heterocyclyl groups, substituted and unsubstituted —N(H)—C(═O)-heterocyclylalkyl groups, substituted and unsubstituted —N(alkyl)-C(═O)-heterocyclylalkyl groups, substituted and unsubstituted —N(H)—S(═O)$_2$-alkyl groups, substituted and unsubstituted —N(H)—S(═O)$_2$-aryl, substituted and unsubstituted —N(H)—S(═O)$_2$-heterocyclyl groups, substituted and unsubstituted —C(═O)-alkyl groups, substituted and unsubstituted —C(═O)-aryl, substituted and unsubstituted —C(═O)-aralkyl, substituted and unsubstituted —C(═O)-heterocyclyl groups, substituted and unsubstituted —C(═O)-heterocyclylalkyl groups, —C(═O)—NH$_2$, substituted and unsubstituted —C(═O)—N(H)(alkyl) groups, substituted and unsubstituted —C(═O)—N(alkyl)$_2$ groups, substituted and unsubstituted —C(═O)—N(H)(aryl) groups, substituted and unsubstituted —C(═O)—N(alkyl)(aryl) groups, substituted and unsubstituted —C(═O)—N(aryl)$_2$ groups, substituted and unsubstituted —C(═O)—N(H)(aralkyl) groups, substituted and unsubstituted —C(═O)—N(alkyl)(aralkyl) groups, substituted and unsubstituted —C(═O)—N(aralkyl)$_2$ groups, substituted and unsubstituted —C(═O)—N(H)(heterocyclyl) groups, substituted and unsubstituted —C(═O)—N(alkyl)(heterocyclyl) groups, substituted and unsubstituted —C(═O)—N(heterocyclyl)$_2$ groups, substituted and unsubstituted —C(═O)—N(H)(heterocyclylalkyl) groups, substituted and unsubstituted —C(═O)—N(alkyl)(heterocyclylalkyl) groups, substituted and unsubstituted —C(═O)—N(heterocyclylalkyl)$_2$ groups, —CO$_2$H, substituted and unsubstituted —C(═O)—O-alkyl groups, C(═O)—O-aryl groups —C(═O)—O-aralkyl groups, substituted and unsubstituted —C(═O)—O-heterocyclyl groups, or substituted and unsubstituted —C(═O)—O-heterocyclylalkyl groups;

$R^4$ is selected from —H or substituted and unsubstituted alkyl groups having from 1 to 12 carbon atoms;

$R^5$ and $R^8$ are independently selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —OH, substituted and unsubstituted alkoxy groups, substituted and unsubstituted heterocyclyloxy groups, substituted and unsubstituted heterocyclylalkoxy groups; or $R^5$ may be absent if A is nitrogen; or $R^8$ may be absent if D is nitrogen;

$R^6$ and $R^7$ are independently selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted arylakyl groups, substituted and unsubstituted heterocyclyl groups, substituted and unsubstituted heterocyclylalkyl groups, —SH, substituted and unsubstituted —S-alkyl groups, substituted and unsubstituted —S-heterocyclyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, —OH, substituted and unsubstituted alkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(H)—C(=O)-heterocyclyl groups, substituted and unsubstituted —N(H)—C(=O)-heterocyclylalkyl groups, substituted and unsubstituted —N(alkyl)-C(=O)-alkyl groups, substituted and unsubstituted —N(alkyl)-C(=O)-heterocyclyl groups, substituted and unsubstituted —N(alkyl)-C(=O)-heterocyclylalkyl, substituted and unsubstituted —N(H)—S(=O)$_2$-alkyl groups, substituted and unsubstituted —N(H)—S(=O)$_2$-heterocyclyl groups, substituted and unsubstituted —N(H)—S(=O)$_2$-heterocyclylalkyl groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)$_2$ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)$_2$ groups, —CO$_2$H, substituted and unsubstituted —C(=O)—O-alkyl groups, substituted and unsubstituted —C(=O)—O-heterocyclyl groups, or substituted and unsubstituted —C(=O)—O-heterocyclylalkyl groups; or $R^6$ is absent if B is nitrogen; or $R^7$ is absent if C is nitrogen;

$R^9$ is selected from —H, substituted and unsubstituted alkyl groups having from 1 to 12 carbon atoms, substituted and unsubstituted alkenyl groups having from 1 to 12 carbons, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted heterocyclyloxy groups, —NH$_2$, or substituted and unsubstituted heterocyclylaminoalkyl; and $R^{10}$ is —H.

In some embodiments of the method of inhibiting a tyrosine kinase in a subject and/or the method of treating a biological condition mediated by tyrosine kinase activity in a subject using a compound of Structure I, a tautomer of the compound, a pharmaceutically acceptable salt of the compound, a pharmaceutically acceptable salt of the tautomer, or mixtures thereof, the tyrosine kinase is FLT-3. In other embodiments, the tyrosine kinase is c-Kit. In still other embodiments, the tyrosine kinase is c-ABL. In still other embodiments, the tyrosine kinase is FGFR3. In still other embodiments, the tyrosine kinase is p60src. In still other embodiments, the tyrosine kinase is VEGFR3. In still other embodiments, the tyrosine kinase is PDGFRα. In other embodiments, the tyrosine kinase is PDGFRβ.

In some embodiments of the method of inhibiting a tyrosine kinase in a subject and/or the method of treating a biological condition mediated by tyrosine kinase activity in a subject using a compound of Structure I, a tautomer of the compound, a pharmaceutically acceptable salt of the compound, a pharmaceutically acceptable salt of the tautomer, or mixtures thereof, the compound of Structure I has the following formula.

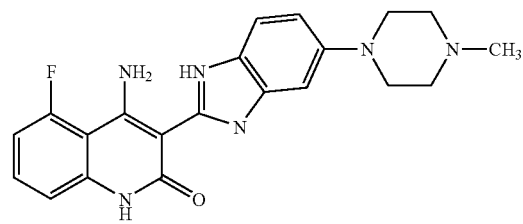

Methods Relating to Cell Division Cycle 2 Kinase

In some embodiments of the method of inhibiting a tyrosine kinase in a subject and/or the method of treating a biological condition mediated by tyrosine kinase activity in a subject using a compound of Structure I, a tautomer of the compound, a pharmaceutically acceptable salt of the compound, a pharmaceutically acceptable salt of the tautomer, or mixtures thereof, the tyrosine kinase is Cdc2, c-Kit, c-ABL, p60src, VEGFR3, PDGFRα, PDGFRβ, FGFR3, or FLT-3. In some such methods, the Cdc2 or other kinase is inhibited in the subject after administration. In methods of inhibiting Cdc2, Structure I has the following formula:

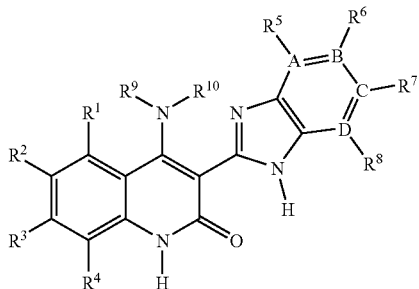

where,
A, B, C, and D are independently selected from carbon or nitrogen;
$R^1$ is selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —SH, substituted and unsubstituted —S-alkyl groups, substituted and unsubstituted —S-heterocyclyl groups, —OH, substituted and unsubstituted alkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(H)—C(=O)-heterocyclyl groups, substituted and unsubstituted —N(H)—C(=O)-heterocyclylalkyl groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)$_2$ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)$_2$ groups, —CO$_2$H, substituted and unsubstituted —C(=O)—O-alkyl groups, substituted and unsubstituted —C(=O)—O-heterocyclyl groups, or substituted and unsubstituted —C(=O)—O-heterocyclylalkyl groups;

$R^2$ and $R^3$ are independently selected from —H, —F, —Cl, —Br, —I, —NO$_2$, —CN, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)$_2$-heterocyclyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, substituted and unsubstituted —S(=O)-alkyl groups, substituted and unsubstituted —S(=O)-heterocyclyl groups, —OH, substituted and unsubstituted alkoxy groups, substituted and unsubstituted aryloxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, substituted and unsubstituted —N(aryl)$_2$ groups, substituted and unsubstituted —N(H)(aralkyl) groups, substituted and unsubstituted —N(alkyl)(aralkyl) groups, substituted and unsubstituted —N(aralkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(alkyl)-C(=O)-alkyl groups, substituted and unsubstituted —N(H)—C(=O)-aryl groups, substituted and unsubstituted —N(alkyl)-C(=O)-aryl groups, substituted and unsubstituted —N(H)—C(=O)-aralkyl groups, substituted and unsubstituted —N(alkyl)-C(=O)-aralkyl groups, substituted and unsubstituted —N(H)—C(=O)-heterocyclyl groups, substituted and unsubstituted —N(alkyl)-C(=O)-heterocyclyl groups, substituted and unsubstituted —N(H)—C(=O)-heterocyclylalkyl groups, substituted and unsubstituted —N(alkyl)-C(=O)-heterocyclylalkyl groups, substituted and unsubstituted —N(H)—S(=O)$_2$-alkyl groups, substituted and unsubstituted —N(H)—S(=O)$_2$-aryl, substituted and unsubstituted —N(H)—S(=O)$_2$-heterocyclyl groups, substituted and unsubstituted —C(=O)-alkyl groups, substituted and unsubstituted —C(=O)-aryl, substituted and unsubstituted —C(=O)-aralkyl, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(aryl) groups, substituted and unsubstituted —C(=O)—N(alkyl)(aryl) groups, substituted and unsubstituted —C(=O)—N(aryl)$_2$ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)$_2$ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)$_2$ groups, —CO$_2$H, substituted and unsubstituted —C(=O)—O-alkyl groups, C(=O)—O-aryl groups —C(=O)—O-aralkyl groups, substituted and unsubstituted —C(=O)—O-heterocyclyl groups, or substituted and unsubstituted —C(=O)—O-heterocyclylalkyl groups;

$R^4$ is selected from —H or substituted and unsubstituted alkyl groups having from 1 to 12 carbon atoms;

$R^5$ and $R^8$ are independently selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —OH, substituted and unsubstituted alkoxy groups, substituted and unsubstituted heterocyclyloxy groups, or substituted and unsubstituted heterocyclylalkoxy groups; or $R^5$ may be absent if A is nitrogen; or $R^8$ may be absent if D is nitrogen;

$R^6$ and $R^7$ are independently selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —SH, substituted and unsubstituted —S-alkyl groups, substituted and unsubstituted —S-heterocyclyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, —OH, substituted and unsubstituted alkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(H)—C(=O)-heterocyclyl groups, substituted and unsubstituted —N(H)—C(=O)-heterocyclylalkyl groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)$_2$ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)$_2$ groups, —CO$_2$H, substituted and unsubstituted —C(=O)—O-alkyl groups, substituted and unsubstituted —C(=O)—O-heterocyclyl groups, or substituted and unsubstituted —C(=O)—O-heterocyclylalkyl groups; or $R^6$ is absent if B is nitrogen; or $R^7$ is absent if C is nitrogen;

$R^9$ is selected from —H, substituted and unsubstituted alkyl groups having from 1 to 12 carbon atoms, substituted and unsubstituted alkenyl groups having from 1 to 12 carbons, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, or —NH$_2$; and $R^{10}$ is —H.

In some embodiments of the method of inhibiting Cdc2 kinase, c-Kit, c-ABL, p60src, VEGFR3, PDGFRα, PDGFRβ, FGFR3, or FLT-3 in a subject and/or the method of treating a biological condition mediated by Cdc2 kinase, c-Kit, p60src, c-ABL, VEGFR3, PDGFRα, PDGFRβ, FGFR3, or FLT-3 activity in a subject, $R^1$ is selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —OH, substituted and unsubstituted alkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, or substituted and unsubstituted —N(heterocyclylalkyl)$_2$ groups;

$R^2$ and $R^3$ are independently selected from —H, —F, —Cl, —Br, —I, —NO$_2$, —CN, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted aryloxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(aryl) groups, substituted and unsubstituted —N(alkyl)(aryl) groups, substituted and unsubstituted —N(aryl)$_2$ groups, substituted and unsubstituted —N(H)(aralkyl) groups, substituted and unsubstituted —N(alkyl)(aralkyl) groups, substituted and unsubstituted —N(aralkyl)$_2$ groups, substituted and unsubstituted —N(H)(heterocyclyl) groups and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH₂, substituted and unsubstituted —C(=O)—N(H)(alkyl) groups, substituted and unsubstituted —C(=O)—N(alkyl)₂ groups, substituted and unsubstituted —C(=O)—N(H)(aryl) groups, substituted and unsubstituted —C(=O)—N(alkyl)(aryl) groups, substituted and unsubstituted —C(=O)—N(aryl)₂ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)₂ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)₂ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)₂ groups, —CO₂H, substituted and unsubstituted —C(=O)—O-alkyl groups, substituted and unsubstituted —C(=O)—O-heterocyclyl groups, or substituted and unsubstituted —C(=O)—O-heterocyclylalkyl groups;

$R^6$ and $R^7$ are independently selected from —H, —F, —Cl, —Br, —I, —CN, —NO₂, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —S(=O)₂—NH₂, substituted and unsubstituted —S(=O)₂—N(H)(alkyl) groups, substituted and unsubstituted —S(=O)₂—N(alkyl)₂ groups, —OH, substituted and unsubstituted alkoxy groups, substituted and unsubstituted heterocyclyloxy groups, substituted and unsubstituted heterocyclylalkoxy groups, —NH₂, substituted and unsubstituted —N(H)(alkyl) groups, substituted and unsubstituted —N(alkyl)₂ groups, substituted and unsubstituted —N(H)(heterocyclyl) groups, substituted and unsubstituted —N(alkyl)(heterocyclyl) groups, substituted and unsubstituted —N(heterocyclyl)₂ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)₂ groups, substituted and unsubstituted —N(H)—C(=O)-alkyl groups, substituted and unsubstituted —N(H)—C(=O)-heterocyclyl groups, substituted and unsubstituted —N(H)—C(=O)-heterocyclylalkyl groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH₂, substituted and unsubstituted —C(=O)—N(H)(alkyl) groups, substituted and unsubstituted —C(=O)—N(alkyl)₂ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)₂ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)₂ groups, —CO₂H, substituted and unsubstituted —C(=O)—O-alkyl groups, substituted and unsubstituted —C(=O)—O-heterocyclyl groups, or substituted and unsubstituted —C(=O)—O-heterocyclylalkyl groups; or $R^6$ is absent if B is nitrogen; or $R^7$ is absent if C is nitrogen.

In some embodiments of the method of inhibiting Cdc2 kinase, c-Kit, c-ABL, p60src, VEGFR3, PDGFRα, PDGFRβ, FGFR3, or FLT-3 in a subject and/or the method of treating a biological condition mediated by Cdc2 kinase, c-Kit, c-ABL, p60src, VEGFR3, PDGFRα, PDGFRβ, FGFR3, or FLT-3 activity in a subject, A, B, C, and D are all carbon.

In some embodiments of the method of inhibiting Cdc2 kinase, c-Kit, c-ABL, p60src, VEGFR3, PDGFRα, PDGFRβ, FGFR3, or FLT-3 in a subject and/or the method of treating a biological condition mediated by Cdc2 kinase, c-Kit, c-ABL, p60src, VEGFR3, PDGFRα, PDGFRβ, FGFR3, or FLT-3 activity in a subject, one of A or D is nitrogen, and B and C are both carbon.

In some embodiments of the method of inhibiting Cdc2 kinase, c-Kit, c-ABL, p60src, VEGFR3, PDGFRα, PDGFRβ, FGFR3, or FLT-3 in a subject and/or the method of treating a biological condition mediated by Cdc2 kinase, c-Kit, c-ABL, p60src, VEGFR3, PDGFRα, PDGFRβ, FGFR3, or FLT-3 activity in a subject, $R^9$ is selected from —H, substituted and unsubstituted straight and branched chain alkyl groups having from 1 to 8 carbon atoms, substituted and unsubstituted cycloalkyl groups, substituted and unsubstituted aryl groups, substituted and unsubstituted aralkyl groups, substituted and unsubstituted heterocyclyl groups, substituted and unsubstituted heterocyclylalkyl groups, substituted and unsubstituted alkoxy groups, or —NH₂.

In some embodiments of the method of inhibiting Cdc2 kinase, c-Kit, c-ABL, p60src, VEGFR3, PDGFRα, PDGFRβ, FGFR3, or FLT-3 in a subject and/or the method of treating a biological condition mediated by Cdc2 kinase, c-Kit, c-ABL, p60src, VEGFR3, PDGFRα, PDGFRβ, FGFR3, or FLT-3 activity in a subject, $R^9$ is selected from —H, unsubstituted straight and branched chain alkyl groups having from 1 to 8 carbon atoms, substituted and unsubstituted cycloalkyl groups, substituted and unsubstituted aryl groups, substituted and unsubstituted aralkyl groups, substituted and unsubstituted heterocyclyl groups, substituted and unsubstituted heterocyclylalkyl groups, substituted and unsubstituted alkoxy groups, substituted and unsubstituted hydroxyalkyl groups, —NH₂, substituted and unsubstituted dialkylaminoalkyl groups, substituted and unsubstituted alkylaminoalkyl groups, or substituted and unsubstituted aminoalkyl groups.

In some embodiments of the method of inhibiting Cdc2 kinase, c-Kit, c-ABL, p60src, VEGFR3, PDGFRα, PDGFRβ, FGFR3, or FLT-3 in a subject and/or the method of treating a biological condition mediated by Cdc2 kinase, c-Kit, c-ABL, p60src, VEGFR3, PDGFRα, PDGFRβ, FGFR3, or FLT-3 activity in a subject, $R^9$ is selected from —H, substituted and unsubstituted cycloalkyl groups, substituted and unsubstituted aralkyl groups, substituted and unsubstituted saturated heterocyclyl groups, substituted and unsubstituted condensed unsaturated heterocyclyl groups, substituted and unsubstituted heterocyclylalkyl groups wherein the heterocyclyl moiety is saturated, or substituted and unsubstituted aminoalkyl groups.

In some embodiments of the method of inhibiting Cdc2 kinase, c-Kit, c-ABL, p60src, VEGFR3, PDGFRα, PDGFRβ, FGFR3, or FLT-3 in a subject and/or the method of treating a biological condition mediated by Cdc2 kinase, c-Kit, c-ABL, p60src, VEGFR3, PDGFRα, PDGFRβ, FGFR3, or FLT-3 activity in a subject, $R^9$ is selected from 4-aminomethylbenzyl groups, benzimidazolyl groups, quinuclidinyl groups, piperidinyl groups, piperidinylalkyl groups, pyrrolidinyl groups, pyrrolidinylalkyl groups, N-alkylpyrrolidinylalkyl groups, imidazolylalkyl groups, tetrahydrofuranylalkyl groups, aminocyclohexyl groups, hydroxycyclohexyl groups, or 2,2-dimethyl-3-aminopropyl groups. In some such embodiments, $R^9$ is a quinuclidinyl group. In other such embodiments, $R^9$ is a quinuclidin-3-yl group.

In some embodiments of the method of inhibiting Cdc2 kinase, c-Kit, c-ABL, p60src, VEGFR3, PDGFRα, PDGFRβ, FGFR3, or FLT-3 in a subject and/or the method of treating a biological condition mediated by Cdc2 kinase, c-Kit, c-ABL, p60src, VEGFR3, PDGFRα, PDGFRβ, FGFR3, or FLT-3 activity in a subject, $R^9$ is selected from monocyclic, bicyclic, and polycyclic saturated heterocyclyl groups.

In some embodiments of the method of inhibiting Cdc2 kinase, c-Kit, c-ABL, p60src, VEGFR3, PDGFRα, PDGFRβ, FGFR3, or FLT-3 in a subject and/or the method of treating a biological condition mediated by Cdc2 kinase, c-Kit, c-ABL, p60src, VEGFR3, PDGFRα, PDGFRβ, FGFR3, or FLT-3 activity in a subject, $R^9$ is —H.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, $R^1$ is selected from —H, —F, —Cl, —Br, —I, substituted and unsubstituted straight and branched chain alkyl groups having from 1 to 8 carbon atoms, substituted and unsubstituted cycloalkyl groups, substituted and unsubstituted heterocyclyl groups, substituted and unsubstituted heterocyclylalkyl groups, substituted and unsubstituted alkoxy groups, substituted and unsubstituted heterocyclyloxy groups, or substituted and unsubstituted heterocyclylalkoxy groups.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, $R^1$ is selected from —H, —F, —Cl, substituted and unsubstituted straight or branched chain alkoxy, substituted and unsubstituted piperidinyloxy, substituted and unsubstituted morpholinyl, or substituted and unsubstituted piperazinyl. In some such embodiments, $R^1$ is selected from —H, —F, —Cl. methoxy, N-methylpiperidin-3-yloxy, N-methylpiperidin-4-yloxy, morpholin-4-yl, N-methylpiperazin-4-yl, or N-ethylpiperazin-4-yl. In other such embodiments, $R^1$ is —H.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, $R^2$ is selected from —H, —F, —Cl, —Br, —I, —NO$_2$, —CN, substituted and unsubstituted straight and branched chain alkyl groups having from 1 to 12 carbon atoms, substituted and unsubstituted cycloalkyl groups, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted heterocyclylalkoxy groups, —NH$_2$, substituted and unsubstituted —N(H)(alkyl) groups, substituted and unsubstituted —N(alkyl)$_2$ groups, —C(=O)—NH$_2$, substituted and unsubstituted —C(=O)—N(H)(aryl) groups, substituted and unsubstituted —C(=O)—N(alkyl)(aryl) groups, substituted and unsubstituted —C(=O)—N(aryl)$_2$ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)$_2$ groups, or —CO$_2$H.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, $R^2$ is selected from —H, —Cl, —F, —Br, —I, —NO$_2$, —CN, substituted and unsubstituted straight or branched chain alkyl having from 1 to 8 carbons, substituted and unsubstituted phenyl groups, substituted and unsubstituted thiophene groups, substituted and unsubstituted 1,2,3,6-tetrahydropyridinyl groups, substituted and unsubstituted pyridinyl groups, substituted and unsubstituted straight or branched chain alkoxy groups, substituted and unsubstituted pyridinylalkoxy groups, substituted and unsubstituted dialkylamino groups, or —CO$_2$H.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, $R^2$ is a substituted and unsubstituted aryl group selected from phenyl, 2-hydroxyphenyl, 2-amino-4-carboxyphenyl, 2, 6-difluorophenyl, 3-methoxyphenyl, 3-carboxyphenyl, 3-acetylphenyl, 3-aminophenyl, 3-hydroxyphenyl, 3-acetamidophenyl, 3-carboxamidophenyl, 4-cyanophenyl, 4-hydroxyphenyl, 4-methoxyphenyl, or 4-carboxyphenyl.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, $R^2$ is selected from —H, —F, —Cl, —Br, —I, methyl, methoxy, or —CO$_2$H. In some such embodiments, $R^2$ is —CO$_2$H.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, $R^3$ is selected from —H, —F, —Cl, —Br, —I, —CN, substituted and unsubstituted straight or branched chain alkyl groups having from 1 to 8 carbon atoms, substituted and unsubstituted cycloalkyl groups, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted heterocyclyloxy groups, substituted and unsubstituted heterocyclylalkoxy groups, substituted and unsubstituted —N(H)(alkyl) groups, substituted and unsubstituted —N(alkyl)$_2$ groups, or substituted and unsubstituted —N(H)(heterocyclylalkyl) groups.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, or VEGFR3, PDGFRα, PDGFRβ, FLT-3 activity in a subject, $R^3$ is selected from —H, —F, —Cl, —Br, —I, —CN, substituted and unsubstituted straight or branched chain alkyl groups having from 1 to 8 carbon atoms, substituted and unsubstituted phenyl groups, substituted and unsubstituted heterocyclyl groups, substituted and unsubstituted heterocyclylalkyl groups, —OH, unsubstituted straight or branched chain alkoxy groups, dialkylaminoalkoxy groups, substituted and unsubstituted pyrrolidinylalkoxy groups, substituted and unsubstituted pyrrolidinonealkoxy, substituted and unsubstituted —N(H)(alkyl) groups, substituted and unsubstituted —N(alkyl)$_2$ groups, or substituted and unsubstituted —N(H)(pyrrolidinylalkyl) groups.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, $R^3$ is selected from methoxy, 3-acetamidophenyl groups, 4-carboxamidophenyl groups, 4-carboxyphenyl groups, 2-alkylimidazolyl groups, N-alkylpiperazinyl groups, 3-substituted pyrrolidinyl groups, 4-carboxyamidopiperidinyl groups, dimethylamino groups, or —N(H)(cyclohexylalkyl) groups wherein the cyclohexyl moiety is substituted with hydroxy.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, $R^3$ is selected from —H, —F, —Cl, —Br, methoxy, and dimethylamino groups.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, $R^4$ is selected from —H or —CH$_3$. In some such embodiments, $R^4$ is —H.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, $R^5$ and $R^8$ are independently selected from —H, —F, —OH, or saturated heterocyclyl groups; or $R^5$ is absent if A is nitrogen; or $R^8$ is absent if D is nitrogen. In some such embodiments, A and D are both carbon, $R^5$ is —H, and $R^8$ is —H.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, $R^6$ and $R^7$ are independently selected from —H, —F, —Cl, —Br, —I, —CN, substituted and unsubstituted straight and branched chain alkyl groups having from 1 to 8 carbon atoms, substituted and unsubstituted heterocyclyl groups, substituted and unsubstituted heterocyclylalkyl groups, substituted and unsubstituted —S(=O)$_2$—N(H)(alkyl) groups, substituted and unsubstituted —S(=O)$_2$—N(alkyl)$_2$ groups, —OH, substituted and unsubstituted alkoxy groups, substituted and unsubstituted heterocyclyloxy groups, substituted and unsubstituted heterocyclylalkoxy groups, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(H)(heterocyclylalkyl) groups, substituted and unsubstituted —N(alkyl)(heterocyclylalkyl) groups, substituted and unsubstituted —C(=O)-heterocyclyl groups, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, or substituted and unsubstituted —C(=O)—N(alkyl)(heterocyclyl) groups; or $R^6$ is absent if B is nitrogen; or $R^7$ is absent if C is nitrogen.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, $R^6$ and $R^7$ are independently selected from —H, —F, —Cl, —CN, substituted and unsubstituted straight and branched chain alkyl groups having from 1 to 8 carbon atoms, substituted and unsubstituted heterocyclyl groups, substituted and unsubstituted heterocyclylalkyl groups, substituted and unsubstituted —S(=O)$_2$—N(alkyl)$_2$ groups, —OH, substituted and unsubstituted straight and branched chain alkoxy groups, substituted and unsubstituted pyrrolidinyloxy groups, substituted and unsubstituted piperidinyloxy groups, substituted and unsubstituted pyrrolidinylalkoxy groups, substituted and unsubstituted tetrahydrofuranylalkoxy groups, substituted and unsubstituted morpholinylalkoxy groups, substituted and unsubstituted —N(alkyl)$_2$ groups, substituted and unsubstituted —N(H)(piperidinyl) groups, substituted and unsubstituted —N(alkyl)(piperidinyl) groups, substituted and unsubstituted —N(H)(piperidinylalkyl) groups, substituted and unsubstituted —C(=O)-heterocyclyl groups, substituted and unsubstituted —C(=O)—N(alkyl)$_2$ groups, or substituted and unsubstituted —C(=O)—N(alkyl)(heterocyclyl) groups; or $R^6$ is absent if B is nitrogen; or $R^7$ is absent if C is nitrogen.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, $R^6$ and $R^7$ are independently selected from —H, —F, —Cl, —CN, substituted and unsubstituted straight and branched chain alkyl groups having from 1 to 8 carbon atoms, substituted and unsubstituted pyrrolidinyl groups, substituted and unsubstituted morpholinyl groups, substituted and unsubstituted piperazinyl groups, substituted and unsubstituted diazepinyl groups, substituted and unsubstituted triazolyl groups, substituted and unsubstituted thiomorpholine 1-oxide groups, substituted and unsubstituted pyridinylalkyl groups, substituted and unsubstituted —S(=O)$_2$—N(alkyl)$_2$ groups, —OH, substituted and unsubstituted straight and branched chain alkoxy groups, substituted and unsubstituted heterocyclyloxy groups, substituted and unsubstituted heterocyclylalkoxy groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(H)(heterocyclylalkyl) groups, substituted and unsubstituted —C(=O)—N(alkyl)$_2$ groups, substituted and unsubstituted —C(=O)—N(alkyl)(piperidinyl) groups, substituted and unsubstituted —C(=O)-(morpholin-4-yl) groups, or substituted and unsubstituted —C(=O)-(piperazin-1-yl) groups; or $R^6$ is absent if B is nitrogen; or $R^7$ is absent if C is nitrogen. In some such embodiments, $R^6$ and $R^7$ are independently selected from —H, —F, —Cl, —CN, or —OH; or $R^6$ is absent if B is nitrogen; or $R^7$ is absent if C is nitrogen. In other such embodiments, B and C are both carbon and $R^6$ and $R^7$ are both —H.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, A, B, C, and D are all carbon, and $R^5$, $R^6$, $R^7$, and $R^8$ are all —H.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, the $IC_{50}$ value of the compound is less than or equal to 10 µM with respect to Cdc2 kinase, c-Kit, c-ABL, p60src, FGFR3, VEGFR3, PDGFRα, PDGFRβ, or FLT-3. In other such embodiments, the $IC_{50}$ value is less than or equal to 1 µM, is less than or equal to 0.1 µM, is less than or equal to 0.050 µM, is less than or equal to 0.030 µM, is less than or equal to 0.025 µM, or is less than or equal to 0.010 µM.

In some embodiments of the method of inhibiting Cdc2 kinase, c-Kit, c-ABL, p60src, FGFR3, VEGFR3, PDGFRα, PDGFRβ, or FLT-3 in a subject and/or the method of treating a biological condition mediated by Cdc2 kinase, c-Kit, c-ABL, p60src, FGFR3, VEGFR3, PDGFRα, PDGFRβ, or FLT-3 activity in a subject, the subject is a mammal or is a human.

In some embodiments of the method of treating a biological condition mediated by Cdc2 kinase, c-Kit, c-ABL, p60src, FGFR3, VEGFR3, PDGFRα, PDGFRβ, or FLT-3 activity in a subject, the biological condition is cancer.

Methods Relating to FYN Oncogene Kinase Related to SRC, FGR, YES

In some embodiments of the method of inhibiting a tyrosine kinase in a subject and/or the method of treating a biological condition mediated by tyrosine kinase activity in a subject using a compound of Structure I, a tautomer of the compound, a pharmaceutically acceptable salt of the compound, a pharmaceutically acceptable salt of the tautomer, or mixtures thereof, the tyrosine kinase is Fyn. In some such methods, the Fyn is inhibited in the subject after administration. In methods of inhibiting Fyn, Structure I has the following formula:

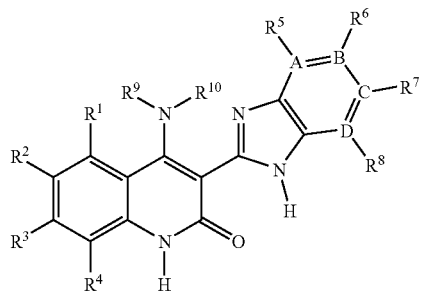

I where:
A, B, C, and D are independently selected from carbon or nitrogen;

$R^1$ and $R^3$ are independently selected from —H, —F, —Cl, —Br, —I, —CN, —NO₂, or substituted and unsubstituted straight and branched chain alkyl groups having from 1 to 8 carbon atoms;

$R^2$ is selected from —H, —F, —Cl, —Br, —I, —CN, —NO₂, substituted and unsubstituted alkyl groups having from 1 to 12 carbon atoms, substituted and unsubstituted aryl groups, or substituted and unsubstituted aralkyl groups;

$R^4$ is selected from —H or substituted and unsubstituted straight and branched chain alkyl groups having from 1 to 8 carbon atoms;

$R^5$ and $R^8$ are independently selected from —H or substituted and unsubstituted straight and branched chain alkyl groups having from 1 to 8 carbon atoms; or $R^5$ may be absent if A is nitrogen; or $R^8$ may be absent if D is nitrogen;

$R^6$ and $R^7$ are independently selected from —H, —F, —Cl, —Br, —I, —CN, —NO₂, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —SH, substituted and unsubstituted —S-alkyl groups, —OH, substituted and unsubstituted alkoxy groups, substituted and unsubstituted heterocyloxy groups, substituted and unsubstituted heterocyclylalkoxy groups, —NH₂, substituted and unsubstituted —N(H)(alkyl) groups, substituted and unsubstituted —N(alkyl)₂ groups, substituted and unsubstituted —N(H)(heterocyclyl) groups, substituted and unsubstituted —N(alkyl)(heterocyclyl) groups, substituted and unsubstituted —N(heterocyclyl)₂ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)₂ groups, substituted and unsubstituted —N(H)—C(═O)-alkyl groups, substituted and unsubstituted —N(H)—C(═O)-heterocyclyl groups, substituted and unsubstituted —N(H)—C(═O)-heterocyclylalkyl, substituted and unsubstituted —N(alkyl)-C(═O)-alkyl groups, substituted and unsubstituted —N(alkyl)-C(═O)-heterocyclyl groups, substituted and unsubstituted —N(alkyl)-C(═O)-heterocyclylalkyl, substituted and unsubstituted —N(H)—S(═O)₂-alkyl groups, substituted and unsubstituted —N(H)—S(═O)₂-heterocyclyl groups, substituted and unsubstituted —N(H)—S(═O)₂-heterocyclylalkyl groups, substituted and unsubstituted —C(═O)-alkyl groups, substituted and unsubstituted —C(═O)-heterocyclyl groups, substituted and unsubstituted —C(═O)-heterocyclylalkyl groups, —C(═O)—NH₂, substituted and unsubstituted —C(═O)—N(H)(alkyl) groups, substituted and unsubstituted —C(═O)—N(alkyl)₂ groups, substituted and unsubstituted —C(═O)—N(H)(heterocyclyl) groups, substituted and unsubstituted —C(═O)—N(alkyl)(heterocyclyl) groups, substituted and unsubstituted —C(═O)—N(H)(heterocyclylalkyl) groups, substituted and unsubstituted —C(═O)—N(alkyl)(heterocyclylalkyl) groups, —CO₂H, substituted and unsubstituted —C(═O)—O-alkyl groups, substituted and unsubstituted —C(═O)—O-heterocyclyl groups, or substituted and unsubstituted —C(═O)—O-heterocyclylalkyl groups; or $R^6$ may be absent if B is nitrogen; or $R^7$ may be absent if C is nitrogen;

$R^9$ is selected from —H, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, substituted and unsubstituted alkoxy groups, substituted and unsubstituted heterocyclyloxy groups, or substituted and unsubstituted heterocyclylalkoxy; and $R^{10}$ is —H.

In some embodiments of the method of inhibiting Fyn in a subject and/or the method of treating a biological condition mediated by Fyn activity in a subject, $R^6$ and $R^7$ are independently selected from —H, —F, —Cl, —Br, —I, substituted and unsubstituted alkyl groups having from 1 to 8 carbon atoms, substituted and unsubstituted heterocyclyl groups, substituted and unsubstituted heterocyclylalkyl groups, —OH, substituted and unsubstituted alkoxy groups, substituted and unsubstituted heterocyclyloxy, substituted and unsubstituted heterocyclylalkoxy, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(H)—C(=O)-heterocyclyl groups, substituted and unsubstituted —N(H)—C(=O)-heterocyclylalkyl, substituted and unsubstituted —N(alkyl)-C(=O)-alkyl groups, substituted and unsubstituted —N(alkyl)-C(=O)-heterocyclyl groups, substituted and unsubstituted —N(alkyl)-C(=O)-heterocyclylalkyl, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(H)(heterocyclylalkyl) groups, or substituted and unsubstituted —C(=O)—N(alkyl)(heterocyclylalkyl) groups; or $R^6$ may be absent if B is nitrogen; or $R^7$ may be absent if C is nitrogen.

In some embodiments of the method of inhibiting Fyn in a subject and/or the method of treating a biological condition mediated by Fyn activity in a subject, A, B, C, and D are all carbon.

In some embodiments of the method of inhibiting Fyn in a subject and/or the method of treating a biological condition mediated by Fyn activity in a subject, one of A or D is nitrogen, and B and C are both carbon.

In some embodiments of the method of inhibiting Fyn in a subject and/or the method of treating a biological condition mediated by Fyn activity in a subject, $R^9$ is selected from —H, substituted and unsubstituted straight or branched chain alkyl groups having from 1 to 8 carbons, substituted and unsubstituted cycloalkyl groups, substituted and unsubstituted heterocyclyl groups, substituted and unsubstituted heterocyclylalkyl groups, or substituted and unsubstituted heterocyclyloxy groups.

In some embodiments of the method of inhibiting Fyn in a subject and/or the method of treating a biological condition mediated by Fyn activity in a subject, $R^9$ is selected from —H, alkylaminoalkyl groups, substituted and unsubstituted saturated heterocyclyl groups, or substituted and unsubstituted heterocyclylalkyl groups wherein the heterocyclyl moiety is saturated.

In some embodiments of the method of inhibiting Fyn in a subject and/or the method of treating a biological condition mediated by Fyn activity in a subject, $R^9$ is selected from —H, substituted and unsubstituted quinuclidinyl groups, substituted and unsubstituted piperidinyl groups, substituted and unsubstituted N-alkylpiperidinyl groups, substituted and unsubstituted piperidinylalkyl groups, substituted and unsubstituted pyrrolidinyl groups, substituted and unsubstituted N-alkyl-pyrrolidinyl, or substituted and unsubstituted pyrrolidinylalkyl groups. In some such embodiments, $R^9$ is —H.

In some embodiments of the method of inhibiting Fyn in a subject and/or the method of treating a biological condition mediated by Fyn activity in a subject, $R^9$ is selected from quinuclidin-3-yl, piperidin-3-yl, piperidin-4-yl, N-methylpiperidin-4-yl, 3-piperidinylmethyl, or pyrrolidin-3-yl.

In some embodiments of the method of inhibiting Fyn in a subject and/or the method of treating a biological condition mediated by Fyn activity in a subject, $R^1$ and $R^3$ are independently selected from —H or —F. In some such embodiments, $R^1$ is —H.

In some embodiments of the method of inhibiting Fyn in a subject and/or the method of treating a biological condition mediated by Fyn activity in a subject, $R^2$ is selected from —H, —F, —Cl, —Br, —I, substituted and unsubstituted straight or branched chain alkyl groups having from 1 to 8 carbons, or substituted and unsubstituted aryl groups. In some such embodiments, $R^2$ is selected from —H, —F, —Cl, —Br, —I, substituted straight or branched chain alkyl groups having from 1 to 4 carbons, or substituted aryl groups. In other such embodiments, $R^2$ is selected from —H, —Cl, —Br, and —I. In still other such embodiments, $R^2$ is —H.

In some embodiments of the method of inhibiting Fyn in a subject and/or the method of treating a biological condition mediated by Fyn activity in a subject, $R^3$ is —H.

In some embodiments of the method of inhibiting Fyn in a subject and/or the method of treating a biological condition mediated by Fyn activity in a subject, $R^3$ is —F.

In some embodiments of the method of inhibiting Fyn in a subject and/or the method of treating a biological condition mediated by Fyn activity in a subject, $R^4$ is —H.

In some embodiments of the method of inhibiting Fyn in a subject and/or the method of treating a biological condition mediated by Fyn activity in a subject, $R^5$ is —H; or where B is nitrogen and $R^5$ is absent.

In some embodiments of the method of inhibiting Fyn in a subject and/or the method of treating a biological condition mediated by Fyn activity in a subject, $R^6$ and $R^7$ are independently selected from —H, —F, —Cl, —Br, —I, substituted and unsubstituted alkyl groups having from 1 to 8 carbon atoms, substituted and unsubstituted heterocyclyl groups, substituted and unsubstituted heterocyclylalkyl groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(H)(heterocyclylalkyl) groups, substituted and unsubstituted —N(alkyl)(heterocyclylalkyl) groups, substituted and unsubstituted —N(H)—C(=O)-alkyl groups, substituted and unsubstituted —N(H)—C(=O)-heterocyclyl groups, substituted and unsubstituted —N(alkyl)-C(=O)-heterocyclylalkyl, substituted and unsubstituted —N(alkyl)-C(=O)-alkyl groups, substituted and unsubstituted —N(alkyl)-C(=O)-heterocyclyl groups, or substituted and unsubstituted —N(alkyl)-C(=O)-heterocyclylalkyl; or $R^6$ may be absent if B is nitrogen; or $R^7$ may be absent if C is nitrogen.

In some embodiments of the method of inhibiting Fyn in a subject and/or the method of treating a biological condition mediated by Fyn activity in a subject, $R^6$ and $R^7$ are independently selected from —H, —F, —Cl, —Br, —I, substituted and unsubstituted alkyl groups having from 1 to 8 carbon atoms, substituted and unsubstituted heterocyclyl groups, substituted and unsubstituted heterocyclylalkyl groups, substituted and unsubstituted —N(alkyl)(heterocyclyl) groups, or substituted and unsubstituted —N(alkyl)-C(=O)-alkyl groups; or $R^6$ may be absent if B is nitrogen; or $R^7$ may be absent if C is nitrogen.

In some embodiments of the method of inhibiting Fyn in a subject and/or the method of treating a biological condition mediated by Fyn activity in a subject, $R^6$ and $R^7$ are independently selected from —H, —F, —Cl, —Br, —I, substituted and unsubstituted alkyl groups having from 1 to 8 carbon atoms, substituted and unsubstituted saturated heterocyclyl groups, substituted and unsubstituted —N(alkyl)(heterocyclyl) groups, wherein the heterocyclyl moiety is saturated, or substituted and unsubstituted —N(alkyl)-C(=O)-alkyl groups; or $R^6$ may be absent if B is nitrogen; or $R^7$ may be absent if C is nitrogen. In other such embodiments, $R^6$ and $R^7$ are independently selected from —H, —F, or —Cl; or $R^6$ may be absent if B is nitrogen; or $R^7$ may be absent if C is nitrogen. In other such embodiments, B is carbon and $R^6$ is —H; or C is carbon and $R^7$ is —H.

In some embodiments of the method of inhibiting Fyn in a subject and/or the method of treating a biological condition mediated by Fyn activity in a subject, $R^6$ and $R^7$ are independently selected from substituted and unsubstituted piperazinyl groups, substituted and unsubstituted morpholinyl groups, substituted and unsubstituted pyrrolidinyl groups, substituted and unsubstituted —N(alkyl)(piperidinyl) groups, or substituted and unsubstituted —N(alkyl)-C(=O)-alkyl groups; or $R^6$ may be absent if B is nitrogen; or $R^7$ may be absent if C is nitrogen.

In some embodiments of the method of inhibiting Fyn in a subject and/or the method of treating a biological condition mediated by Fyn activity in a subject, $R^6$ and $R^7$ are independently selected from 4-alkylpiperazin-1-yl groups, 4-alkyl-2-alkyl-piperazin-1-yl groups, 4-alkyl-3-alkylpiperazin-1-yl groups, morpholin-4-yl groups, 2-dialkylaminoalkyl-5-alkylmorpholin-4-yl groups, 3-dialkylaminopyrrolidin-1-yl groups, 3-dialkylaminoalkylpyrrolidin-1-yl groups, —N(alkyl)(1-alkylpiperidinyl) groups, or —N(alkyl)-C(=O)-alkyl groups; or $R^6$ may be absent if B is nitrogen; or $R^7$ may be absent if C is nitrogen.

In some embodiments of the method of inhibiting Fyn in a subject and/or the method of treating a biological condition mediated by Fyn activity in a subject, $R^6$ and $R^7$ are independently selected from 4-methylpiperazin-1-yl groups, 4-ethylpiperazin-1-yl groups, 4-isopropylpiperazin-1-yl groups, 4-methyl-2-methylpiperazin-1-yl groups, 4-ethyl-2-methylpiperazin-1-yl groups, 4-isopropyl-2-methylpiperazin-1-yl groups, 4-cyclobutyl-2-methylpiperazin-1-yl groups, 4-methyl-3-methylpiperazin-1-yl groups, morpholin-4-yl groups, 2-dimethylaminomethyl-5-methylmorpholin-4-yl groups, 3-dimethylaminopyrrolidin-1-yl groups, 3-dimethylaminomethylpyrrolidin-1-yl groups, —N(methyl)(1-methylpiperidin-4-yl) groups, or —N(methyl)-C(=O)-methyl groups; or $R^6$ may be absent if B is nitrogen; or $R^7$ may be absent if C is nitrogen.

In some embodiments of the method of inhibiting Fyn in a subject and/or the method of treating a biological condition mediated by Fyn activity in a subject, the $IC_{50}$ value of the compound is less than or equal to 10 μM with respect to Fyn. In other such embodiments, the $IC_{50}$ value is less than or equal to 1 μM, is less than or equal to 0.1 μM, is less than or equal to 0.050 μM, is less than or equal to 0.030 μM, is less than or equal to 0.025 μM, or is less than or equal to 0.010 μM.

In some embodiments of the method of inhibiting Fyn in a subject and/or the method of treating a biological condition mediated by Fyn activity in a subject, the subject is a mammal or is a human.

In some embodiments of the method of treating a biological condition mediated by Fyn activity in a subject, the biological condition is an autoimmune disease, and in some such embodiments the biological condition is rheumatoid arthritis or systemic lupus erythematosus. In other such embodiments, the biological condition is organ transplant rejection.

Methods Relating to Lymphocyte-Specific Protein Tyrosine Kinase

In some embodiments of the method of inhibiting a tyrosine kinase in a subject and/or the method of treating a biological condition mediated by tyrosine kinase activity in a subject using a compound of Structure I, a tautomer of the compound, a pharmaceutically acceptable salt of the compound, a pharmaceutically acceptable salt of the tautomer, or mixtures thereof, the tyrosine kinase is Lck. In some such methods, the Lck is inhibited in the subject after administration. In methods of inhibiting Lck, Structure I has the following formula:

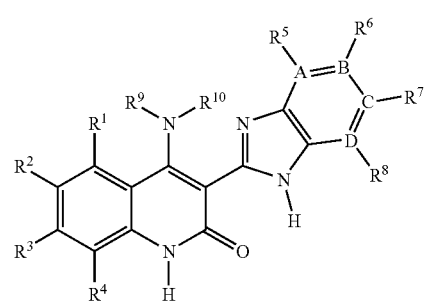

where,
A, B, C, and D are independently selected from carbon or nitrogen;
$R^1$, $R^2$, and $R^3$ are independently selected from —H, —F, —Cl, —Br, —I, —CN, —NO$_2$, or substituted and unsubstituted straight and branched chain alkyl groups having from 1 to 8 carbon atoms;
$R^4$ is selected from —H or substituted and unsubstituted straight and branched chain alkyl groups having from 1 to 8 carbon atoms;
$R^5$ and $R^8$ are independently selected from —H or substituted and unsubstituted straight and branched chain alkyl groups having from 1 to 8 carbon atoms; or $R^5$ may be absent if A is nitrogen; or $R^8$ may be absent if D is nitrogen;
$R^6$ and $R^7$ are independently selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, —SH, substituted and unsubstituted —S-alkyl groups, —OH, substituted and unsubstituted alkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(H)—C(=O)-heterocyclyl groups, substituted and unsubstituted —N(H)—C(=O)-heterocyclylalkyl, substituted and unsubstituted —N(alkyl)-C(=O)-alkyl groups, substituted and unsubstituted —N(alkyl)-C(=O)-heterocyclyl groups, substituted and unsubstituted —N(alkyl)-C(=O)-heterocyclylalkyl, substituted and unsubstituted —N(H)—S(=O)$_2$-alkyl groups, substituted and unsubstituted —N(H)—S(=O)$_2$-heterocyclyl groups, substituted and unsubstituted —N(H)—S(=O)$_2$-heterocyclylalkyl groups, substituted and unsubstituted —N(alkyl)-S(=O)$_2$-alkyl groups, substituted and unsubstituted —N(alkyl)-S(=O)$_2$-heterocyclyl groups, substituted and unsubstituted —N(alkyl)-S(=O)$_2$-heterocyclylalkyl groups, substituted and unsubstituted —C(=O)-alkyl groups, substituted and unsubstituted —C(=O)-heterocyclyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(H)(heterocyclylalkyl) groups, substituted and unsubstituted —C(=O)—N(alkyl)(heterocyclylalkyl) groups, —CO$_2$H, substituted and unsubstituted —C(=O)—O-alkyl groups, substituted and unsubstituted —C(=O)—O-heterocyclyl groups, or substituted and unsubstituted —C(=O)—O-heterocyclylalkyl groups; or R$^6$ may be absent if B is nitrogen; or R$^7$ may be absent if C is nitrogen;

R$^9$ is selected from —H, substituted and unsubstituted alkyl groups having from 1 to 12 carbon atoms, substituted and unsubstituted alkenyl groups having from 1 to 12 carbon atoms, substituted and unsubstituted heterocyclyl groups, substituted and unsubstituted heterocyclylalkyl groups, substituted and unsubstituted alkoxy groups, or substituted and unsubstituted heterocyclyloxy groups; and R$^{10}$ is —H.

In some embodiments of the method of inhibiting Lck in a subject and/or the method of treating a biological condition mediated by Lck activity in a subject, R$^6$ and R$^7$ are independently selected from —H, —F, —Cl, —Br, —I, substituted and unsubstituted alkyl groups having from 1 to 8 carbon atoms, substituted and unsubstituted heterocyclyl groups, substituted and unsubstituted heterocyclylalkyl groups, —OH, substituted and unsubstituted alkoxy groups, substituted and unsubstituted heterocyclyloxy, substituted and unsubstituted heterocyclylalkoxy, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(heterocyclyl)$_2$ groups, substituted and unsubstituted —N(H)(heterocyclylalkyl) groups, substituted and unsubstituted —N(alkyl)(heterocyclylalkyl) groups, substituted and unsubstituted —N(heterocyclylalkyl)$_2$ groups, substituted and unsubstituted —N(H)—C(=O)-alkyl groups, substituted and unsubstituted —N(H)—C(=O)-heterocyclyl groups, substituted and unsubstituted —N(H)—C(=O)-heterocyclylalkyl, substituted and unsubstituted —N(alkyl)-C(=O)-alkyl groups, substituted and unsubstituted —N(alkyl)-C(=O)-heterocyclyl groups, substituted and unsubstituted —N(alkyl)-C(=O)-heterocyclylalkyl, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(H)(heterocyclylalkyl) groups, or substituted and unsubstituted —C(=O)—N(alkyl)(heterocyclylalkyl) groups; or R$^6$ may be absent if B is nitrogen; or R$^7$ may be absent if C is nitrogen.

In some embodiments of the method of inhibiting Lck in a subject and/or the method of treating a biological condition mediated by Lck activity in a subject, A, B, C, and D are all carbon.

In some embodiments of the method of inhibiting Lck in a subject and/or the method of treating a biological condition mediated by Lck activity in a subject, one of A or D is nitrogen, and B and C are both carbon.

In some embodiments of the method of inhibiting Lck in a subject and/or the method of treating a biological condition mediated by Lck activity in a subject, R$^9$ is selected from —H, substituted and unsubstituted straight or branched chain alkyl groups having from 1 to 8 carbons, substituted and unsubstituted cycloalkyl groups, substituted and unsubstituted heterocyclyl groups, substituted and unsubstituted heterocyclylalkyl groups, or substituted and unsubstituted heterocyclyloxy groups.

In some embodiments of the method of inhibiting Lck in a subject and/or the method of treating a biological condition mediated by Lck activity in a subject, R$^9$ is selected from —H, aminoalkyl groups, alkylaminoalkyl groups, dialkylaminoalkyl groups, substituted and unsubstituted saturated heterocyclyl groups, or substituted and unsubstituted heterocyclylalkyl groups wherein the heterocyclyl moiety is saturated. In some such embodiments, R$^9$ is selected from quinuclidinyl groups, piperidinyl groups, N-alkylpiperidinyl groups, piperidinylalkyl groups, pyrrolidinyl groups, or pyrrolidinylalkyl groups. In other such embodiments, R$^9$ —H.

In some embodiments of the method of inhibiting Lck in a subject and/or the method of treating a biological condition mediated by Lck activity in a subject, R$^1$ and R$^3$ are independently selected from —H or —F. In some such embodiments, R$^1$ is —H.

In some embodiments of the method of inhibiting Lck in a subject and/or the method of treating a biological condition mediated by Lck activity in a subject, R$^2$ is selected from —H, —F, —Cl, —Br, —I, or substituted and unsubstituted straight or branched chain alkyl groups having from 1 to 4 carbons. In some such embodiments, R$^2$ is selected from —H, —F, —Cl, —Br, and methyl. In other such embodiments, R$^2$ is selected from —H, —Cl, and —Br. In still other such embodiments, R$^2$ is —H.

In some embodiments of the method of inhibiting Lck in a subject and/or the method of treating a biological condition mediated by Lck activity in a subject, $R^3$ is —H.

In some embodiments of the method of inhibiting Lck in a subject and/or the method of treating a biological condition mediated by Lck activity in a subject, $R^4$ is —H.

In some embodiments of the method of inhibiting Lck in a subject and/or the method of treating a biological condition mediated by Lck activity in a subject, A is carbon and $R^5$ is —H; or D is carbon and $R^8$ is —H. In some such embodiments, both A and D are carbon and both $R^5$ and $R^8$ are —H.

In some embodiments of the method of inhibiting Lck in a subject and/or the method of treating a biological condition mediated by Lck activity in a subject, $R^6$ and $R^7$ are independently selected from —H, —F, —Cl, —Br, —I, substituted and unsubstituted alkyl groups having from 1 to 8 carbon atoms, substituted and unsubstituted heterocyclyl groups, substituted and unsubstituted heterocyclylalkyl groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(H)(heterocyclylalkyl) groups, substituted and unsubstituted —N(alkyl)(heterocyclylalkyl) groups, substituted and unsubstituted —N(H)—C(=O)-alkyl groups, substituted and unsubstituted —N(H)—C(=O)-heterocyclyl groups, substituted and unsubstituted —N(alkyl)-C(=O)-heterocyclylalkyl, substituted and unsubstituted —N(alkyl)-C(=O)-alkyl groups, substituted and unsubstituted —N(alkyl)-C(=O)-heterocyclyl groups, or substituted and unsubstituted —N(alkyl)-C(=O)-heterocyclylalkyl; or $R^6$ may be absent if B is nitrogen; or $R^7$ may be absent if C is nitrogen.

In some embodiments of the method of inhibiting Lck in a subject and/or the method of treating a biological condition mediated by Lck activity in a subject, $R^6$ and $R^7$ are independently selected from —H, —F, —Cl, —Br, —I, substituted and unsubstituted alkyl groups having from 1 to 8 carbon atoms, substituted and unsubstituted heterocyclyl groups, substituted and unsubstituted heterocyclylalkyl groups, substituted and unsubstituted —N(alkyl)(heterocyclyl) groups, or substituted and unsubstituted —N(alkyl)-C(=O)-alkyl groups; or $R^6$ may be absent if B is nitrogen; or $R^7$ may be absent if C is nitrogen.

In some embodiments of the method of inhibiting Lck in a subject and/or the method of treating a biological condition mediated by Lck activity in a subject, $R^6$ and $R^7$ are independently selected from —H, —F, —Cl, —Br, —I, substituted and unsubstituted alkyl groups having from 1 to 8 carbon atoms, substituted and unsubstituted saturated heterocyclyl groups, substituted and unsubstituted —N(alkyl)(heterocyclyl) groups, wherein the heterocyclyl moiety is saturated, substituted and unsubstituted —N(alkyl)-C(=O)-alkyl groups; or $R^6$ may be absent if B is nitrogen; or $R^7$ may be absent if C is nitrogen. In some such embodiments, $R^6$ and $R^7$ are independently selected from —H, —F, or —Cl; or $R^6$ may be absent if B is nitrogen; or $R^7$ may be absent if C is nitrogen. In other such embodiments, B is carbon and $R^6$ is —H; or C is carbon and $R^7$ is —H.

In some embodiments of the method of inhibiting Lck in a subject and/or the method of treating a biological condition mediated by Lck activity in a subject, $R^6$ and $R^7$ are independently selected from substituted and unsubstituted piperazinyl groups, substituted and unsubstituted morpholinyl groups, substituted and unsubstituted pyrrolidinyl groups, substituted and unsubstituted —N(alkyl)(piperidinyl) groups, or substituted and unsubstituted —N(alkyl)-C(=O)-alkyl groups; or $R^6$ may be absent if B is nitrogen; or $R^7$ may be absent if C is nitrogen.

In some embodiments of the method of inhibiting Lck in a subject and/or the method of treating a biological condition mediated by Lck activity in a subject, $R^6$ and $R^7$ are independently selected from 4-alkylpiperazin-1-yl groups, 4-alkyl-2-alkyl-piperazin-1-yl groups, 4-alkyl-3-alkylpiperazin-1-yl groups, morpholin-4-yl groups, 2-dialkylaminoalkyl-5-alkylmorpholin-4-yl groups, 3-dialkylaminopyrrolidin-1-yl groups, 3-dialkylaminoalkylpyrrolidin-1-yl groups, —N(alkyl)(1-alkylpiperidinyl) groups, or —N(alkyl)-C(=O)-alkyl groups; or $R^6$ may be absent if B is nitrogen; or $R^7$ may be absent if C is nitrogen.

In some embodiments of the method of inhibiting Lck in a subject and/or the method of treating a biological condition mediated by Lck activity in a subject, $R^6$ and $R^7$ are independently selected from 4-methylpiperazin-1-yl groups, 4-ethylpiperazin-1-yl groups, 4-isopropylpiperazin-1-yl groups, 4-methyl-2-methylpiperazin-1-yl groups, 4-ethyl-2-methylpiperazin-1-yl groups, 4-isopropyl-2-methylpiperazin-1-yl groups, 4-cyclobutyl-2-methylpiperazin-1-yl groups, 4-methyl-3-methylpiperazin-1-yl groups, morpholin-4-yl groups, 2-dimethylaminomethyl-5-methylmorpholin-4-yl groups, 3-dimethylaminopyrrolidin-1-yl groups, 3-dimethylaminomethylpyrrolidin-1-yl groups, —N(methyl)(1-methylpiperidin-4-yl) groups, or —N(methyl)-C(=O)-methyl groups; or $R^6$ may be absent if B is nitrogen; or $R^7$ may be absent if C is nitrogen.

In some embodiments of the method of inhibiting Lck in a subject and/or the method of treating a biological condition mediated by Lck activity in a subject, the IC$_{50}$ value of the compound is less than or equal to 10 µM with respect to Lck. In other such embodiments, the IC$_{50}$ value is less than or equal to 1 µM, is less than or equal to 0.1 µM, is less than or equal to 0.050 µM, is less than or equal to 0.030 µM, is less than or equal to 0.025 µM, or is less than or equal to 0.010 µM.

In some embodiments of the method of inhibiting Lck in a subject and/or the method of treating a biological condition mediated by Lck activity in a subject, the subject is a mammal or is a human.

In some embodiments of the method of treating a biological condition mediated by Lck activity in a subject, the biological condition is an autoimmune disease, and in some such embodiments the biological condition is rheumatoid arthritis or systemic lupus erythematosus. In other such embodiments, the biological condition is organ transplant rejection.

Methods Relating to Tie-2

In some embodiments of the method of inhibiting a tyrosine kinase in a subject and/or the method of treating a biological condition mediated by tyrosine kinase activity in a subject using a compound of Structure I, a tautomer of the compound, a pharmaceutically acceptable salt of the compound, a pharmaceutically acceptable salt of the tautomer, or mixtures thereof, the tyrosine kinase is Tie-2. In some such methods, the Tie-2 is inhibited in the subject after administration. In methods of inhibiting Tie-2, Structure I has the following formula:

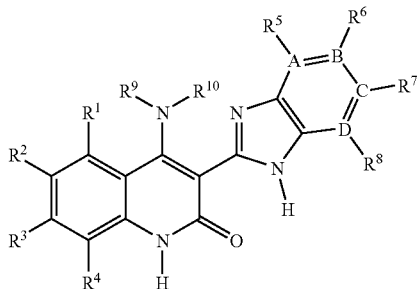

where,
A, B, C, and D are independently selected from carbon or nitrogen;

$R^1$ is selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —SH, substituted and unsubstituted —S-alkyl groups, —OH, substituted and unsubstituted alkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(alkyl)(heterocyclylalkyl) groups, substituted and unsubstituted —N(heterocyclyl)$_2$ groups, substituted and unsubstituted —N(H)—C(=O)-alkyl groups, substituted and unsubstituted —N(H)—S(=O)$_2$-alkyl groups, substituted and unsubstituted —C(=O)-alkyl groups, substituted and unsubstituted —C(=O)-heterocyclylalkyl groups, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, substituted and unsubstituted —C(=O)—N(alkyl)(heterocyclyl) groups, substituted and unsubstituted —C(=O)—N(heterocyclyl)$_2$ groups, substituted and unsubstituted —C(=O)—N(H)(heterocyclylalkyl) groups, substituted and unsubstituted —C(=O)—N(alkyl)(heterocyclylalkyl) groups, substituted and unsubstituted —C(=O)—N(heterocyclylalkyl)$_2$ groups, —CO$_2$H, substituted and unsubstituted —C(=O)—O-alkyl groups, substituted and unsubstituted —C(=O)—O-heterocyclyl groups, or substituted and unsubstituted —C(=O)—O-heterocyclylalkyl groups;

$R^2$ is selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted heterocyclyloxy groups, substituted and unsubstituted heterocyclylalkoxy groups, —SH, substituted and unsubstituted —S-alkyl groups, —CO$_2$H, —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, substituted and unsubstituted —C(=O)—N(H)(heterocyclylalkyl) groups, substituted and unsubstituted —C(=O)—O-alkyl groups, substituted and unsubstituted —C(=O)—O-heterocyclyl groups, substituted and unsubstituted —C(=O)—O-heterocyclylalkyl groups, substituted and unsubstituted —C(=O)-alkyl groups, substituted and unsubstituted —C(=O)-heterocyclylalkyl groups, —NH$_2$, substituted and unsubstituted —N(H)(alkyl) groups, substituted and unsubstituted —N(H)(aryl) groups, substituted and unsubstituted —N(H)(heterocyclyl) groups, substituted and unsubstituted —N(alkyl)(heterocyclyl) groups, substituted and unsubstituted —N(alkyl)(heterocyclylalkyl) groups, substituted and unsubstituted —N(alkyl)$_2$ groups, substituted and unsubstituted —N(heterocyclyl)$_2$ groups, substituted and unsubstituted —N(H)—C(=O)-alkyl groups, or substituted and unsubstituted —N(H)—S(=O)-alkyl groups; or $R^2$ and $R^3$ may join together to form a cyclic group;

$R^3$ and $R^4$ are independently selected from —H or substituted and unsubstituted straight and branched chain alkyl groups having from 1 to 8 carbon atoms;

$R^5$ is selected from —H, —F, —Cl, —Br, —I, or substituted and unsubstituted straight and branched chain alkyl groups having from 1 to 8 carbon atoms; or $R^5$ may be absent if A is nitrogen;

$R^6$ is selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —SH, substituted and unsubstituted —S-alkyl groups, substituted and unsubstituted —S(=O)$_2$—O-alkyl groups, substituted and unsubstituted —S(=O)$_2$-alkyl groups, substituted and unsubstituted —S(=O)$_2$-heterocyclyl groups, substituted and unsubstituted —S(=O)-alkyl groups, substituted and unsubstituted —S(=O)-heterocyclyl groups, —S(=O)$_2$—NH$_2$, substituted and unsubstituted —S(=O)$_2$—N(H)(alkyl) groups, substituted and unsubstituted —S(=O)$_2$—N(alkyl)$_2$ groups, —OH, substituted and unsubstituted alkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(H)(aryl) groups, substituted and unsubstituted —N(H)(heterocyclyl) groups, substituted and unsubstituted —N(alkyl)(heterocyclyl) groups, substituted and unsubstituted —N(alkyl)(heterocyclylalkyl) groups, substituted and unsubstituted —N(alkyl)$_2$ groups, substituted and unsubstituted —N(heterocyclyl)$_2$ groups, substituted and unsubstituted —N(H)—C(=O)-alkyl groups, substituted and unsubstituted —N(H)—C(=O)-heterocyclyl groups, substituted and unsubstituted —N(alkyl)-C(=O)-alkyl groups, substituted and unsubstituted —N(alkyl)-C(=O)-heterocyclyl groups, substituted and unsubstituted —N(H)—S(=O)-alkyl groups, substituted and unsubstituted —N(H)—S(=O)-heterocyclyl groups, substituted and unsubstituted —N(alkyl)-S(=O)-alkyl groups, substituted and unsubstituted —N(alkyl)-S(=O)-heterocyclyl groups, substituted and unsubstituted —C(=O)-alkyl groups, substituted and unsubstituted —C(=O)-heterocyclylalkyl groups —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, —C(=O)—N(H)(heterocyclylalkyl) groups, —CO$_2$H, substituted and unsubstituted —C(=O)—O-alkyl groups, substituted and unsubstituted —C(=O)—O-heterocyclyl groups, or substituted and unsubstituted —C(=O)—O-heterocyclylalkyl groups; or $R^6$ may be absent if B is nitrogen;

$R^7$ is selected from —H, —F, —Cl, —Br, —I, —CN, —NO$_2$, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, —SH, substituted and unsubstituted —S-alkyl groups, —OH, substituted and unsubstituted alkoxy groups, substituted and unsubstituted heterocyclyloxy groups, substituted and unsubstituted heterocyclylalkoxy groups, —NH$_2$, substituted and unsubstituted —N(H)(alkyl) groups, substituted and unsubstituted —N(H)(aryl) groups, substituted and unsubstituted —N(H)(heterocyclyl) groups, substituted and unsubstituted —N(alkyl)(heterocyclyl) groups, substituted and unsubstituted —N(alkyl)(heterocyclylalkyl) groups, substituted and unsubstituted —N(alkyl)$_2$ groups, substituted and unsubstituted —N(heterocyclyl)$_2$ groups, substituted and unsubstituted —N(H)—C(=O)-alkyl groups, substituted and unsubstituted —N(H)—S(=O)$_2$-alkyl groups, substituted and unsubstituted —C(=O)-alkyl groups, substituted and unsubstituted —C(=O)-heterocyclylalkyl groups —C(=O)—NH$_2$, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, —C(=O)—N(H)(heterocyclylalkyl) groups, —CO$_2$H, substituted and unsubstituted —C(=O)—O-alkyl groups, substituted and unsubstituted —C(=O)—O-heterocyclyl groups, or substituted and unsubstituted —C(=O)—O-heterocyclylalkyl groups; or $R^7$ may be absent if C is nitrogen;

$R^8$ is selected from —H, substituted and unsubstituted alkyl groups having from 1 to 12 carbon atoms; or $R^8$ may be absent if D is nitrogen;

$R^9$ is selected from —H, substituted and unsubstituted alkyl groups having from 1 to 12 carbon atoms, substituted and unsubstituted alkenyl groups having from 1 to 12 carbon atoms, substituted and unsubstituted aryl groups, substituted and unsubstituted aralkyl groups, substituted and unsubstituted heterocyclyl groups, substituted and unsubstituted heterocyclylalkyl groups, substituted and unsubstituted alkoxy groups, substituted and unsubstituted heterocyclyloxy groups, —NH$_2$, or substituted and unsubstituted heterocyclylaminoalkyl; or $R^9$ and $R^{10}$ join together to form a ring having 5, 6, or 7 ring members; and $R^{10}$ is —H.

In some embodiments of the method of inhibiting Tie-2 in a subject and/or the method of treating a biological condition mediated by Tie-2 activity in a subject, $R^1$ is selected from —H, —F, —Cl, —Br, —I, substituted and unsubstituted alkyl groups having from 1 to 12 carbon atoms, substituted and unsubstituted heterocyclyl groups, substituted and unsubstituted heterocyclylalkyl groups, —OH, substituted and unsubstituted alkoxy groups, substituted and unsubstituted heterocyclyloxy groups, or substituted and unsubstituted heterocyclylalkoxy groups;

$R^2$ is selected from —H, —F, —Cl, —Br, —I, substituted and unsubstituted alkyl groups having from 1 to 12 carbon atoms, substituted and unsubstituted cycloalkenyl groups, substituted and unsubstituted aryl groups, substituted and unsubstituted heterocyclyl groups, —OH, substituted and unsubstituted alkoxy groups, substituted and unsubstituted heterocyclyloxy groups, substituted and unsubstituted heterocyclylalkoxy groups;

$R^6$ is selected from —H, substituted and unsubstituted alkyl groups having from 1 to 8 carbon atoms, substituted and unsubstituted heterocyclyl groups, —OH, substituted and unsubstituted alkoxy groups, substituted and unsubstituted heterocyclyloxy, substituted and unsubstituted heterocyclylalkoxy, substituted and unsubstituted —N(H)(alkyl) groups, substituted and unsubstituted —N(H)(heterocyclyl) groups, or substituted and unsubstituted —N(alkyl)(heterocyclyl) groups; or $R^6$ may be absent if B is nitrogen;

$R^7$ is selected from —H, —Cl, —F, —Br, substituted and unsubstituted alkyl groups having from 1 to 8 carbon atoms, —OH, substituted and unsubstituted alkoxy groups, substituted and unsubstituted heterocyclyl groups, substituted and unsubstituted —N(H)(alkyl) groups, substituted and unsubstituted —N(H)(heterocyclyl) groups, or substituted and unsubstituted —N(alkyl)(heterocyclyl) groups,; or $R^7$ may be absent if C is nitrogen.

In some embodiments of the method of inhibiting Tie-2 in a subject and/or the method of treating a biological condition mediated by Tie-2 activity in a subject, A, B, C, and D are all carbon.

In some embodiments of the method of inhibiting Tie-2 in a subject and/or the method of treating a biological condition mediated by Tie-2 activity in a subject, one of A or D is nitrogen, and B and C are both carbon.

In some embodiments of the method of inhibiting Tie-2 in a subject and/or the method of treating a biological condition mediated by Tie-2 activity in a subject, $R^9$ is selected from —H, substituted and unsubstituted cycloalkyl groups, substituted and unsubstituted alkoxy groups, substituted and unsubstituted heterocyclyl groups, substituted and unsubstituted heterocyclylalkyl groups, substituted and unsubstituted heterocyclylalkoxy, —NH$_2$, or substituted and unsubstituted heterocyclylaminoalkyl groups.

In some embodiments of the method of inhibiting Tie-2 in a subject and/or the method of treating a biological condition mediated by Tie-2 activity in a subject, $R^9$ is selected from —H, substituted and unsubstituted saturated heterocyclyl groups, substituted and unsubstituted heterocyclylalkyl groups wherein the heterocyclyl moiety is saturated, substituted and unsubstituted alkoxy groups, substituted and unsubstituted heterocyclylalkoxy groups wherein the heterocyclyl moiety is saturated, or substituted and unsubstituted heterocyclylaminoalkyl groups wherein the heterocyclyl moiety is saturated.

In some embodiments of the method of inhibiting Tie-2 in a subject and/or the method of treating a biological condition mediated by Tie-2 activity in a subject, $R^9$ is selected from —H, substituted and unsubstituted cycloalkyl groups, substituted and unsubstituted saturated heterocyclyl groups, or substituted and unsubstituted alkoxy groups. In some such embodiments, $R^9$ is selected from —H or quinuclidinyl. In other such embodiments, $R^9$ is —H.

In some embodiments of the method of inhibiting Tie-2 in a subject and/or the method of treating a biological condition mediated by Tie-2 activity in a subject, $R^1$ is selected from —H, —F, —Cl, —OCH$_3$ substituted and unsubstituted piperidinyloxy groups, substituted and unsubstituted piperidinylalkoxy groups, substituted and unsubstituted morpholinyloxy groups, or substituted and unsubstituted morpholinylalkoxy groups. In some such embodiments, $R^1$ is selected from —H or —Cl. In other such embodiments, $R^1$ is —H.

In some embodiments of the method of inhibiting Tie-2 in a subject and/or the method of treating a biological condition mediated by Tie-2 activity in a subject, $R^2$ is selected from —H, —F, —Cl, —Br, —I, —CH$_3$, substituted and unsubstituted pyridinylalkoxy groups.

In some embodiments of the method of inhibiting Tie-2 in a subject and/or the method of treating a biological condition mediated by Tie-2 activity in a subject, $R^2$ is —H.

In some embodiments of the method of inhibiting Tie-2 in a subject and/or the method of treating a biological condition mediated by Tie-2 activity in a subject, $R^3$ is —H.

In some embodiments of the method of inhibiting Tie-2 in a subject and/or the method of treating a biological condition mediated by Tie-2 activity in a subject, $R^4$ is —H.

In some embodiments of the method of inhibiting Tie-2 in a subject and/or the method of treating a biological condition mediated by Tie-2 activity in a subject, $R^5$ is —H or is absent if A is nitrogen.

In some embodiments of the method of inhibiting Tie-2 in a subject and/or the method of treating a biological condition mediated by Tie-2 activity in a subject, $R^6$ is selected from —H, substituted and unsubstituted morpholinyl groups, substituted and unsubstituted morpholinylalkoxy groups, substituted and unsubstituted pyrrolidinyl groups, substituted and unsubstituted pyrrolidinylalkoxy groups, substituted and unsubstituted piperidinyl groups, substituted and unsubstituted piperidinyloxy groups, substituted and unsubstituted piperazinyl groups, or substituted and unsubstituted —S(=O)$_2$—N(alkyl)$_2$ groups; or may be absent if B is nitrogen.

In some embodiments of the method of inhibiting Tie-2 in a subject and/or the method of treating a biological condition mediated by Tie-2 activity in a subject, $R^7$ is selected from —H, —F, —Cl, substituted and unsubstituted morpholinyl groups, substituted and unsubstituted pyridinylalkyl groups, or substituted and unsubstituted piperazinyl groups; or may be absent if C is nitrogen.

In some embodiments of the method of inhibiting Tie-2 in a subject and/or the method of treating a biological condition mediated by Tie-2 activity in a subject, $R^8$ is —H or is absent if D is nitrogen.

In some embodiments of the method of inhibiting Tie-2 in a subject and/or the method of treating a biological condition mediated by Tie-2 activity in a subject, the IC$_{50}$ value of the compound is less than or equal to 10 µM with respect to Tie-2. In other such embodiments, the IC$_{50}$ value is less than or equal to 1 µM, is less than or equal to 0.1 µM, is less than or equal to 0.050 µM, is less than or equal to 0.030 µM, is less than or equal to 0.025 µM, or is less than or equal to 0.010 µM.

In some embodiments of the method of inhibiting Tie-2 in a subject and/or the method of treating a biological condition mediated by Tie-2 activity in a subject, the subject is a mammal or is a human.

In some embodiments of the method of treating a biological condition mediated by Tie-2 activity in a subject, the biological condition is cancer.

In some embodiments of the method of treating a biological condition mediated by serine/threonine kinase or tyrosine kinase activity in a subject, the compound, the tautomer, the pharmaceutically acceptable salt of the compound, the pharmaceutically acceptable salt of the tautomer, or mixtures thereof, is a component of a pharmaceutical formulation or a medicament that includes a pharmaceutically acceptable carrier. In some such embodiments the serine/threonine kinase or tyrosine kinase activity is selected from FLT-1, VEGFR2, VEGFR3, FGFR1, GSK-3, Cdk2, NEK-2, CHK1, Rsk2, PAR-1, Cdc2, c-Kit, c-ABL, p60src, FGFR3, FLT-3, Fyn, Lck, Tie-2, PDGFRα, or PDGFRβ activity. In other such embodiments, the serine/threonine kinase or tyrosine kinase activity is selected from GSK-3, Cdk2, CHK1, Rsk2, PAR-1, Cdc2, c-Kit, c-ABL, p60src, FGFR3, VEGFR3, PDGFRα, PDGFRβ, FLT-3, Fyn, Lck, or Tie-2 activity. In another such embodiment the serine/threonine kinase activity is CHK1 activity.

In other aspects, the invention provides compounds of Structure I, tautomers of the compounds, pharmaceutically acceptable salts of the compounds, pharmaceutically acceptable salts of the tautomers, and mixtures thereof. The invention also provides compounds having any of the $R^1$ through $R^{10}$ values described in the various embodiments described above.

The invention further provides the use of the compounds of Structure I, tautomers of the compounds, pharmaceutically acceptable salts of the compounds, pharmaceutically acceptable salts of the tautomers, and mixtures thereof in the preparation of medicaments, and in treatment of biological conditions mediated by FLT-1, VEGFR2, VEGFR3, FGFR1, GSK-3, Cdk2, NEK-2, CHK1, Rsk2, PAR-1, Cdc2, c-Kit, c-ABL, p60src, FGFR3, FLT-3, Fyn, Lck, Tie-2, PDGFRα, or PDGFRβ activity.

The present invention further provides methods of inhibiting GSK-3 and treating biological conditions mediated by GSK-3 in a subject using a compound of Structure IB. The invention also provides the use of a compound of Structure IB in preparing a medicament for use in inhibiting GSK-3 in a subject and/or for use in treating a biological condition mediated by GSK-3. In one aspect, a method of inhibiting GSK-3 or treating a biological condition mediated by GSK-3 includes administering to the subject a compound of Structure IB, a tautomer of the compound, a pharmaceutically acceptable salt of the compound, a pharmaceutically acceptable salt of the tautomer, or mixtures thereof. The invention further provides methods of inhibiting any of the other kinases described herein and methods of treating any of the biological conditions mediated by such kinases using the compounds of Structure IB. In some embodiments, GSK-3 is inhibited in the subject after administration. Structure IB has the following formula:

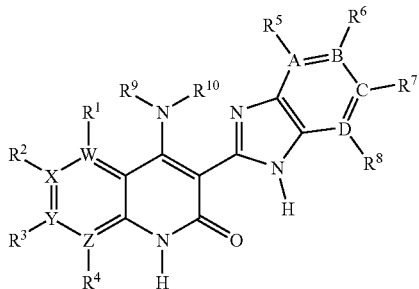

IB where:
- A, B, C, and D are independently selected from carbon or nitrogen;
- W, X, Y, and Z are independently selected from the group consisting of carbon and nitrogen and at least one of W, X, Y, and Z is a nitrogen;
- $R^1$ is selected from —H, —F, —Cl, —Br, —I, substituted or unsubstituted straight or branched chain alkyl groups having from 1 to 8 carbon atoms, substituted or unsubstituted alkenyl groups having from 1 to 8 carbon atoms, substituted or unsubstituted alkynyl groups having from 1 to 8 carbon atoms, —CN, —NO$_2$, —OH, —SH, substituted or unsubstituted alkoxy groups, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)-alkyl groups, —S(=O)—NH$_2$, substituted or unsubstituted —S(=O)—N(H)(alkyl) groups, substituted or unsubstituted —S(=O)—N(alkyl)$_2$ groups, —C(=O)—NH$_2$, substituted or unsubstituted —C(=O)—N(H)(alkyl) groups, substituted or unsubstituted —C(=O)—N(alkyl)$_2$ groups, substituted or unsubstituted —C(=O)—O-alkyl groups, —NH$_2$, substituted or unsubstituted —N(H)(alkyl) groups, substituted or unsubstituted —N(alkyl)$_2$ groups, substituted or unsubstituted —N(H)—C(=O)-alkyl groups, or substituted or unsubstituted —N(H)—S(=O)-alkyl groups; or $R^1$ may be absent if W is nitrogen;
- $R^2$ is selected —H, —F, —Cl, —Br, —I, —NO$_2$, —CN, —NH$_2$, —CO$_2$H, —OH, substituted or unsubstituted straight or branched chain alkyl groups having from 1 to 8 carbon atoms, substituted or unsubstituted cycloalkenyl groups, substituted or unsubstituted cycloalkyl groups, substituted or unsubstituted alkoxy groups, substituted or unsubstituted —N(H)(alkyl) groups, substituted or unsubstituted —N(alkyl)$_2$ groups, substituted or unsubstituted heterocyclyl groups, substituted or unsubstituted aryl groups, substituted or unsubstituted alkenyl groups having from 1 to 8 carbon atoms, substituted or unsubstituted alkynyl groups having from 1 to 8 carbon atoms, —SH, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)$_2$-heterocyclyl groups, substituted or unsubstituted —S(=O)-alkyl groups, substituted or unsubstituted —S(=O)-heterocyclyl groups, —S(=O)—NH$_2$, substituted or unsubstituted —S(=O)—N(H)(alkyl) groups, substituted or unsubstituted —S(=O)—N(alkyl)$_2$ groups, —C(=O)—NH$_2$, substituted or unsubstituted —C(=O)—N(H)(alkyl) groups, substituted or unsubstituted —C(=O)—N(alkyl)$_2$ groups, substituted or unsubstituted —C(=O)-alkyl groups, substituted or unsubstituted —C(=O)-heterocyclyl groups, substituted or unsubstituted —C(=O)—O-alkyl groups, substituted or unsubstituted —N(H)—C(=O)-alkyl groups, substituted or unsubstituted —N(H)—C(=O)-heterocyclyl groups, substituted or unsubstituted —N(H)—S(=O)-alkyl groups, substituted or unsubstituted —N(H)—S(=O)-heterocyclyl groups, —N(alkyl)-C(=O)-alkyl groups, substituted or unsubstituted —N(alkyl)-C(=O)-heterocyclyl groups, substituted or unsubstituted —N(alkyl)-S(=O)-alkyl groups, substituted or unsubstituted —N(alkyl)-S(=O)-heterocyclyl groups, —N(H)—C(=O)—NH$_2$, substituted or unsubstituted —N(H)—C(=O)—N(H)(alkyl) groups, substituted or unsubstituted —N(H)—C(=O)—N(alkyl)$_2$ groups, —N(alkyl)-C(=O)—NH$_2$, substituted or unsubstituted —N(alkyl)-C(=O)—N(H)(alkyl) groups, or substituted or unsubstituted —N(alkyl)-C(=O)—N(alkyl)$_2$ groups; or $R^2$ and $R^3$ may join together to form a cyclic group when X and Y are both carbon; or $R^2$ may be absent if X is nitrogen;
- $R^3$ is selected from —H, —F, —Cl, —Br, —I, —OH, substituted or unsubstituted straight or branched chain alkyl groups having from 1 to 8 carbon atoms, substituted or unsubstituted alkoxy groups, —CO$_2$H, —CN, substituted or unsubstituted —N(H)(alkyl) groups, substituted or unsubstituted —N(H)(cycloalkyl) groups, substituted or unsubstituted —N(alkyl)$_2$ groups, substituted or unsubstituted heterocyclyl groups, substituted or unsubstituted aryl groups, substituted or unsubstituted —C(=O)-heterocyclyl groups, substituted or unsubstituted —C(=O)-alkyl groups, substituted or unsubstituted —C(=O)—N(H)(alkyl) groups, substituted or unsubstituted —C(=O)—N(alkyl)$_2$ groups, —C(=O)—NH$_2$ groups, substituted or unsubstituted —C(=O)—N(H)(heterocyclyl) groups, substituted or unsubstituted —C(=O)—N(H)(aryl) groups, substituted or unsubstituted alkenyl groups having from 1 to 8 carbon atoms, substituted or unsubstituted alkynyl groups having from 1 to 8 carbon atoms, —NO$_2$, —SH, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)$_2$-heterocyclyl groups, substituted or unsubstituted —S(=O)-alkyl groups, substituted or unsubstituted —S(=O)-heterocyclyl groups, —S(=O)—NH$_2$, substituted or unsubstituted —S(=O)—N(H)(alkyl) groups, substituted or unsubstituted —S(=O)—N(alkyl)$_2$ groups, substituted or unsubstituted —C(=O)—O-alkyl groups, —NH$_2$, substituted or unsubstituted —N(H)—C(=O)-alkyl groups, substituted or unsubstituted —N(H)—C(=O)-heterocyclyl groups, substituted or unsubstituted —N(H)—S(=O)-alkyl groups, substituted or unsubstituted —N(H)—S(=O)-heterocyclyl groups, substituted or unsubstituted —N(alkyl)-C(=O)-alkyl groups, substituted or unsubstituted —N(alkyl)-C(=O)-heterocyclyl groups, substituted or unsubstituted —N(alkyl)-S(=O)-alkyl groups, substituted or unsubstituted —N(alkyl)-S(=O)-heterocyclyl groups, —N(H)—C(=O)—NH$_2$, substituted or unsubstituted —N(H)—C(=O)—N(H)(alkyl) groups, substituted or unsubstituted —N(H)—C(=O)—N(alkyl)$_2$ groups, —N(alkyl)-C(=O)—NH$_2$, substituted or unsubstituted —N(alkyl)-C(=O)—N(H)(alkyl) groups, or substituted or unsubstituted —N(alkyl)-C(=O)—N(alkyl)$_2$ groups; or $R^2$ and $R^3$ may join together to form a cyclic group when X and Y are both carbon; or $R^3$ may be absent if Y is nitrogen;

$R^4$ is selected from of —H, —F, —Cl, —Br, —I, substituted or unsubstituted straight or branched chain alkyl groups having from 1 to 8 carbon atoms, substituted or unsubstituted alkenyl groups having from 1 to 8 carbon atoms, substituted or unsubstituted alkynyl groups having from 1 to 8 carbon atoms, —CN, —NO$_2$, —OH, —SH, substituted or unsubstituted alkoxy groups, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)-alkyl groups, —S(=O)—NH$_2$, substituted or unsubstituted —S(=O)—N(H)(alkyl) groups, substituted or unsubstituted —S(=O)—N(alkyl)$_2$ groups, —C(=O)—NH$_2$, substituted or unsubstituted —C(=O)—N(H)(alkyl) groups, substituted or unsubstituted —C(=O)—N(alkyl)$_2$ groups, substituted or unsubstituted —C(=O)—O-alkyl groups, —NH$_2$, substituted or unsubstituted —N(H)(alkyl) groups, substituted or unsubstituted —N(alkyl)$_2$ groups, substituted or unsubstituted —N(H)—C(=O)-alkyl groups, or substituted or unsubstituted —N(H)—S(=O)-alkyl groups; or $R^4$ may be absent if Z is nitrogen;

$R^5$ is selected from —H, —F, —Cl, —Br, —I, substituted or unsubstituted straight or branched chain alkyl groups having from 1 to 8 carbon atoms, substituted or unsubstituted heterocyclyl groups, substituted or unsubstituted alkenyl groups having from 1 to 8 carbon atoms, substituted or unsubstituted alkynyl groups having from 1 to 8 carbon atoms, —CN, —NO$_2$, —OH, —SH, substituted or unsubstituted alkoxy groups, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)-alkyl groups, —S(=O)—NH$_2$, substituted or unsubstituted —S(=O)—N(H)(alkyl) groups, substituted or unsubstituted —S(=O)—N(alkyl)$_2$ groups, —C(=O)—NH$_2$, substituted or unsubstituted —C(=O)—N(H)(alkyl) groups, substituted or unsubstituted —C(=O)—N(alkyl)$_2$ groups, substituted or unsubstituted —C(=O)—O-alkyl groups, —NH$_2$, substituted or unsubstituted —N(H)(alkyl) groups, substituted or unsubstituted —N(alkyl)$_2$ groups, substituted or unsubstituted —N(H)—C(=O)-alkyl groups, or substituted or unsubstituted —N(H)—S(=O)-alkyl groups; or $R^5$ may be absent if A is nitrogen;

$R^6$ is selected from —H, —Cl, —F, —Br, —OH, substituted or unsubstituted heterocyclyl groups, substituted or unsubstituted —N(H)(alkyl) groups, substituted or unsubstituted —N(H)(heterocyclyl) groups, substituted or unsubstituted —N(alkyl)(heterocyclyl) groups, substituted or unsubstituted alkoxy groups, substituted or unsubstituted alkyl groups having from 1 to 8 carbon atoms, substituted or unsubstituted alkenyl groups having from 1 to 8 carbon atoms, substituted or unsubstituted alkynyl groups having from 1 to 8 carbon atoms, —CN, —NO$_2$, —OH, —SH, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)$_2$-heterocyclyl groups, substituted or unsubstituted —S(=O)-alkyl groups, substituted or unsubstituted —S(=O)-heterocyclyl groups, —S(=O)—NH$_2$, substituted or unsubstituted —S(=O)—N(H)(alkyl) groups, substituted or unsubstituted —S(=O)—N(alkyl)$_2$ groups, —C(=O)—NH$_2$, substituted or unsubstituted —C(=O)—N(H)(alkyl) groups, substituted or unsubstituted —C(=O)—N(alkyl)$_2$ groups, substituted or unsubstituted —C(=O)-alkyl groups, substituted or unsubstituted —C(=O)-heterocyclyl groups, substituted or unsubstituted —C(=O)—O-alkyl groups, —NH$_2$, substituted or unsubstituted —N(alkyl)$_2$ groups, substituted or unsubstituted —N(H)—C(=O)-alkyl groups, substituted or unsubstituted —N(H)—C(=O)-heterocyclyl groups, substituted or unsubstituted —N(alkyl)-C(=O)-alkyl groups, substituted or unsubstituted —N(alkyl)-C(=O)-heterocyclyl groups, substituted or unsubstituted —N(H)—S(=O)-alkyl groups, substituted or unsubstituted —N(H)—S(=O)-heterocyclyl groups, substituted or unsubstituted —N(alkyl)-S(=O)-alkyl groups, or substituted or unsubstituted —N(alkyl)-S(=O)-heterocyclyl groups; or $R^6$ may be absent if B is nitrogen;

$R^7$ is selected from —H, —Cl, —F, —Br, —OH, substituted or unsubstituted heterocyclyl groups, substituted or unsubstituted —N(H)(alkyl) groups, substituted or unsubstituted —N(H)(heterocyclyl) groups, substituted or unsubstituted —N(alkyl)(heterocyclyl) groups, substituted or unsubstituted alkoxy groups, substituted or unsubstituted alkyl groups having from 1 to 8 carbon atoms, substituted or unsubstituted alkenyl groups having from 1 to 8 carbon atoms, substituted or unsubstituted alkynyl groups having from 1 to 8 carbon atoms, —CN, —NO$_2$, —OH, —SH, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)$_2$-heterocyclyl groups, substituted or unsubstituted —S(=O)-alkyl groups, substituted or unsubstituted —S(=O)-heterocyclyl groups, —S(=O)—NH$_2$, substituted or unsubstituted —S(=O)—N(H)(alkyl) groups, substituted or unsubstituted —S(=O)—N(alkyl)$_2$ groups, —C(=O)—NH$_2$, substituted or unsubstituted —C(=O)—N(H)(alkyl) groups, substituted or unsubstituted —C(=O)—N(alkyl)$_2$ groups, substituted or unsubstituted —C(=O)-alkyl groups, substituted or unsubstituted —C(=O)-heterocyclyl groups, substituted or unsubstituted —C(=O)—O-alkyl groups, —NH$_2$, substituted or unsubstituted —N(alkyl)$_2$ groups, substituted or unsubstituted —N(H)—C(=O)-alkyl groups, substituted or unsubstituted —N(H)—C(=O)-heterocyclyl groups, substituted or unsubstituted —N(alkyl)-C(=O)-alkyl groups, substituted or unsubstituted —N(alkyl)-C(=O)-heterocyclyl groups, substituted or unsubstituted —N(H)—S(=O)-alkyl groups, substituted or unsubstituted —N(H)—S(=O)-heterocyclyl groups, substituted or unsubstituted —N(alkyl)-S(=O)-alkyl groups, or substituted or unsubstituted —N(alkyl)-S(=O)-heterocyclyl groups; or $R^7$ may be absent if C is nitrogen;

$R^8$ is selected from —H, —F, —Cl, —Br, —I, substituted or unsubstituted straight or branched chain alkyl groups having from 1 to 8 carbon atoms, substituted or unsubstituted heterocyclyl groups, substituted or unsubstituted alkenyl groups having from 1 to 8 carbon atoms, substituted or unsubstituted alkynyl groups having from 1 to 8 carbon atoms, —CN, —NO$_2$, —OH, —SH, substituted or unsubstituted alkoxy groups, substituted or unsubstituted —S-alkyl groups, substituted or unsubstituted —S(=O)$_2$—O-alkyl groups, substituted or unsubstituted —S(=O)$_2$-alkyl groups, substituted or unsubstituted —S(=O)-alkyl groups, —S(=O)—NH$_2$, substituted or unsubstituted —S(=O)—N(H)(alkyl) groups, substituted or unsubstituted —S(=O)—N(alkyl)$_2$ groups, —C(=O)—NH$_2$, substituted or unsubstituted —C(=O)—N(H)(alkyl) groups, substituted or unsubstituted —C(=O)—N(alkyl)$_2$ groups, substituted or unsubstituted —C(=O)—O-alkyl groups, —NH$_2$, substituted or unsubstituted —N(H)(alkyl) groups, substituted or unsubstituted —N(alkyl)$_2$ groups, substituted or unsubstituted —N(H)—C(=O)-alkyl groups, or substituted or unsubstituted —N(H)—S(=O)-alkyl groups; or $R^8$ may be absent if D is nitrogen;

$R^9$ is selected from of substituted or unsubstituted heterocyclyl groups, substituted or unsubstituted aryl groups, substituted or unsubstituted alkoxy groups, —NH$_2$, substituted or unsubstituted cycloalkyl groups, or substituted or unsubstituted straight or branched chain alkyl groups having from 1 to 8 carbon atoms, or $R^9$ and $R^{10}$ join together to form a ring having 5, 6, or 7 ring members; or $R^{10}$ is —H, or $R^9$ and $R^{10}$ join together to form a ring having 5, 6, or 7 ring members.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^1$ is selected from —H, —F, —Cl, —Br, —I, or straight or branched chain alkyl groups having from 1 to 8 carbon atoms; or $R^1$ may be absent if W is nitrogen $R^2$ is selected from —H, —F, —Cl, —Br, —I, —NO$_2$, —CN, —NH$_2$, —CO$_2$H, —OH, straight or branched chain alkyl groups having from 1 to 8 carbon atoms, substituted or unsubstituted cycloalkenyl groups, substituted or unsubstituted cycloalkyl groups, substituted or unsubstituted alkoxy groups, substituted or unsubstituted —N(H)(alkyl) groups, substituted or unsubstituted —N(alkyl)$_2$ groups, substituted or unsubstituted heterocyclyl groups, or substituted or unsubstituted aryl groups; or $R^2$ may be absent if X is nitrogen;

$R^3$ is selected from —H, —F, —Cl, —Br, —I, —OH, straight or branched chain alkyl groups having from 1 to 8 carbon atoms, substituted or unsubstituted alkoxy groups, —CO$_2$H, —CN, substituted or unsubstituted —N(H)(alkyl) groups, substituted or unsubstituted —N(H)(cycloalkyl) groups, substituted or unsubstituted —N(alkyl)$_2$ groups, substituted or unsubstituted heterocyclyl groups, substituted or unsubstituted aryl groups, substituted or unsubstituted —C(=O)-heterocyclyl groups, substituted or unsubstituted —C(=O)-alkyl groups, substituted or unsubstituted —C(=O)—N(H)(alkyl) groups, substituted or unsubstituted —C(=O)—N(alkyl)$_2$ groups, —C(=O)—NH$_2$ groups, substituted or unsubstituted —C(=O)—N(H)(heterocyclyl) groups, or substituted or unsubstituted —C(=O)—N(H)(aryl) groups; or $R^3$ may be absent if Y is nitrogen;

$R^4$ is selected from —H, —F, —Cl, —Br, —I, or straight or branched chain alkyl groups having from 1 to 8 carbon atoms; or $R^4$ may be absent if Z is nitrogen;

$R^5$ is selected from —H, —F, —Cl, —Br, —I, straight or branched chain alkyl groups having from 1 to 8 carbon atoms, or substituted or unsubstituted heterocyclyl groups; or $R^5$ may be absent if A is nitrogen;

$R^6$ is selected from —H, —Cl, —F, —Br, —OH, substituted or unsubstituted heterocyclyl groups, substituted or unsubstituted —N(H)(alkyl) groups, substituted or unsubstituted —N(H)(heterocyclyl) groups, substituted or unsubstituted —N(alkyl)(heterocyclyl) groups, substituted or unsubstituted alkoxy groups, or substituted or unsubstituted alkyl groups having from 1 to 8 carbon atoms; or $R^6$ may be absent if B is nitrogen;

$R^7$ is selected from —H, —Cl, —F, —Br, —OH, substituted or unsubstituted heterocyclyl groups, substituted or unsubstituted —N(H)(alkyl) groups, substituted or unsubstituted —N(H)(heterocyclyl) groups, substituted or unsubstituted —N(alkyl)(heterocyclyl) groups, substituted or unsubstituted alkoxy groups, or substituted or unsubstituted alkyl groups having from 1 to 8 carbon atoms; or $R^7$ may be absent if C is nitrogen; and $R^8$ is selected from —H, —F, —Cl, —Br, —I, straight or branched chain alkyl groups having from 1 to 8 carbon atoms, or substituted or unsubstituted heterocyclyl groups; or $R^8$ may be absent if D is nitrogen.

In some embodiments of the method of inhibiting GSK-3 using a compound of Structure IB, a tautomer of the compound, a pharmaceutically acceptable salt of the compound, a pharmaceutically acceptable salt of the tautomer, or mixtures thereof, A, B, C, and D are all carbon. In some such embodiments, $R^5$ is —H, $R^6$ is —H, $R^7$ is —H, and $R^8$ is —H In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, one of A or D is nitrogen, and B and C are both carbon.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, W is nitrogen. In some such embodiments, X, Y, and Z are all carbon.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, X is nitrogen. In some such embodiments, W, Y, and Z are all carbon.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, Y is nitrogen. In some such embodiments, W, X, and Z are all carbon.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, Z is nitrogen. In some such embodiments, W, X, and Y are all carbon.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, two of W, X, Y, and Z are nitrogen atoms. In some such embodiments, X and Z are nitrogen atoms and W and Y are carbon atoms.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^{10}$ is —H and $R^9$ is selected from substituted or unsubstituted heterocyclyl groups, substituted or unsubstituted aryl groups, substituted or unsubstituted alkoxy groups, —NH$_2$, substituted or unsubstituted cycloalkyl groups, or substituted or unsubstituted straight or branched chain alkyl groups having from 1 to 8 carbon atoms.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^9$ is selected from substituted or unsubstituted heterocyclyl groups, substituted or unsubstituted aryl groups, unsubstituted alkoxy groups, —NH$_2$, substituted or unsubstituted cycloalkyl groups, unsubstituted straight or branched chain alkyl groups having from 1 to 8 carbon atoms, substituted or unsubstituted heterocyclylalkyl groups wherein the heterocyclyl group is saturated, substituted or unsubstituted heterocyclylalkyl groups wherein the heterocyclyl group is unsaturated, substituted or unsubstituted aralkyl groups, substituted or unsubstituted alkoxyalkyl groups, substituted or unsubstituted hydroxyalkyl groups, substituted or unsubstituted dialkylaminoalkyl groups, substituted or unsubstituted alkylaminoalkyl groups, substituted or unsubstituted aminoalkyl groups, substituted or unsubstituted heterocyclylaminoalkyl groups, substituted or unsubstituted (heterocyclyl)(alkyl)aminoalkyl groups, or substituted or unsubstituted alkyl-(SO$_2$)-alkyl groups.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^{10}$ is —H and $R^9$ is selected from substituted or unsubstituted saturated heterocyclyl groups, substituted or unsubstituted aminoalkyl groups, substituted or unsubstituted cycloalkyl groups, or substituted or unsubstituted heterocyclylalkyl groups.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^9$ is selected from quinuclidinyl groups, piperidinyl groups, pyrrolidinyl groups, and aminocyclohexyl groups. In some such embodiments, $R^9$ is a quinuclidinyl group and in some such embodiments, $R^9$ is a quinuclidin-3-yl group.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^9$ is selected from monocyclic, bicyclic, or polycyclic saturated heterocyclyl groups.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^1$ is selected from —H, —F, —Cl, or —CH$_3$ groups. In some such embodiments, $R^1$ is —H or —F. In other such embodiments, $R^1$ is —H.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^2$ is selected from —H, —Cl, —F, —Br, —I, —CH$_3$, —NO$_2$, —OMe, —CN, —CO$_2$H, substituted or unsubstituted 1,2,3,6-tetrahydropyridine groups, substituted or unsubstituted thiophene groups, substituted or unsubstituted imidazole groups, substituted or unsubstituted 3-pyridyl groups, substituted or unsubstituted 4-pyridyl groups, 2-substituted phenyl groups, 2,4-disubstituted phenyl groups, 4-substituted phenyl groups, 3-substituted phenyl groups, 2,6-disubstituted phenyl groups, phenyl, substituted or unsubstituted dialkylamino groups, or substituted or unsubstituted alkylamino groups. In some such embodiments, $R^2$ is selected from —H, —Cl, —F, or —CH$_3$. In other such embodiments, $R^2$ is —F.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^2$ is a substituted or unsubstituted aryl group selected from phenyl, 2-chlorophenyl, 2-methylphenyl, 2-ethylphenyl, 2-hydroxyphenyl, 2-methoxyphenyl, 2-trifluoromethylphenyl, 3-methoxyphenyl, 3-nitrophenyl, 3-carboxyphenyl, 3-acetylphenyl, 3-aminophenyl, 3-hydroxyphenyl, 3-acetamidophenyl, 3-carbomethoxyphenyl, 3-trifluoromethylphenyl, 3-ureidophenyl, 4-chlorophenyl, 4-cyanophenyl, 4-hydroxyphenyl, 4-nitrophenyl, 4-ethylphenyl, 4-methylphenyl, 4-methoxyphenyl, 4-acetylphenyl, 4-acetamidophenyl, 4-carboxyphenyl, 4-formylphenyl, 4-methylthiophenyl, 4-dimethylaminophenyl, 4-carbomethoxyphenyl, 4-carboethoxyphenyl, 4-carboxamidophenyl, 4-(methylsulfonyl)phenyl, 4-trifluoromethylphenyl, 2,4-difluorophenyl, 2-fluoro-4-chlorophenyl, 2,4-dichlorophenyl, 2-amino-4-carbomethoxyphenyl, 2-amino-4-carboxyphenyl, 2,6-difluorophenyl, or 3,4-(methylenedioxy)phenyl.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^4$ is —H or —CH$_3$. In some such embodiments, $R^4$ is —H.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^5$ and $R^8$ are independently selected from —H, or saturated heterocyclyl groups, or are absent. In some such embodiments, $R^5$ and $R^8$ are independently selected from —H or saturated heterocyclyl groups. In some such embodiments $R^5$ is —H and $R^8$ is —H.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^6$ and $R^7$ are independently selected from —H, —F, —Cl, —OH, or substituted or unsubstituted heterocyclyl groups. In some such embodiments, $R^6$ is —H and $R^7$ is —H.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^5$ is —H, $R^6$ is —H, $R^7$ is —H, and $R^8$ is —H.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^3$ is selected from —H, —F, —Cl, —Br, —CH$_3$, —OH, —CN, substituted or unsubstituted alkoxy groups, substituted or unsubstituted alkylamino groups, substituted or unsubstituted dialkylamino groups, substituted or unsubstituted heterocyclyl groups, substituted or unsubstituted aryl groups, substituted or unsubstituted —C(=O)-heterocyclyl groups, substituted or unsubstituted —C(=O)—N(alkyl)$_2$ groups, or —C(=O)—NH$_2$ groups.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^3$ is selected from —H, —F, —Cl, —Br, —CH$_3$, —CN, —OMe, hydroxyalkylamino groups, dialkylamino groups, dialkylaminoalkylamino groups, alkoxyalkylamino groups, substituted or unsubstituted heterocyclylalkylamino groups, acetamidoalkylamino groups, cyanoalkylamino groups, alkoxyalkylamino groups, thioalkylamino groups, (methylsulfonyl)alkylamino groups, cycloalkylalkylamino groups, dialkylaminoalkoxy groups, heterocyclylalkoxy groups, substituted or unsubstituted piperidinyl groups, substituted or unsubstituted imidazolyl groups, substituted or unsubstituted morpholinyl groups, substituted or unsubstituted pyrrolyl groups, substituted or unsubstituted pyrrolidinyl groups, substituted or unsubstituted piperazinyl groups, substituted or unsubstituted aryl groups, substituted or unsubstituted —C(=O)-heterocyclyl groups, substituted or unsubstituted —C(=O)—N(alkyl)$_2$ groups, or —C(=O)—NH$_2$ groups. In some embodiments, $R^3$ is selected from —H, —F, —Cl, —Br, —CH$_3$, —OH, —CN, substituted and unsubstituted alkoxy groups, substituted and unsubstituted alkylamino groups, substituted and unsubstituted dialkylamino groups, substituted and unsubstituted heterocyclyl groups, substituted and unsubstituted aryl groups, substituted and unsubstituted —C(=O)-heterocyclyl groups, substituted and unsubstituted —C(=O)—N(alkyl)$_2$ groups, and —C(=O)—NH$_2$ groups.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^3$ is selected from substituted or unsubstituted alkylamino groups or substituted or unsubstituted dialkylamino groups. In some such embodiments, $R^3$ is a dimethylamino group.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, $R^4$, $R^5$, $R^6$, $R^7$, $R^8$, and $R^{10}$ are all —H.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, the IC$_{50}$ value of the compound is less than or equal to 10 µM with respect to GSK-3. In other such embodiments, the IC$_{50}$ value is less than or equal to 1 µM, is less than or equal to 0.1 µM, is less than or equal to 0.050 µM, is less than or equal to 0.030 µM, is less than or equal to 0.025 µM, or is less than or equal to 0.010 µM.

In some embodiments of the method of inhibiting GSK-3 in a subject and/or the method of treating a biological condition mediated by GSK-3 activity in a subject using a compound of Structure IB, a tautomer of the compound, a pharmaceutically acceptable salt of the compound, a pharmaceutically acceptable salt of the tautomer, or mixtures thereof, the subject is a mammal, and in some embodiments is a human.

In some embodiments of the method of inhibiting GSK-3 in a subject and/or the method of treating a biological condition mediated by GSK-3 activity in a subject using a compound of Structure IB, the biological condition is diabetes, and in some such embodiments the biological condition is noninsulin dependent diabetes mellitus (NIDDM). In other such embodiments, the biological condition is Alzheimer's disease or is bipolar disorder.

In groups including heterocyclyl groups, the heterocyclyl group may be attached in various ways. For example, in a heterocycylakoxy group, the heterocyclyl group may be bonded to a methylene carbon of the alkoxy group of the heterocyclylalkoxy group through various ring members. By way of non-limiting example, where the heterocyclyl group of the heterocyclylalkoxy group is tetrahydrofuran, the group could be represented by the formula —OCH$_2$CH$_2$(tetrahydrofuranyl) which corresponds to the following two structures:

II

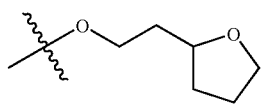

-continued

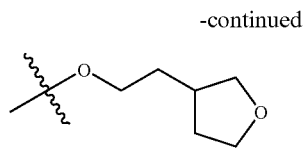
III where Structure II represents the group that can be referred to as the —OCH$_2$CH$_2$(2-tetrahydrofuranyl) or —OCH$_2$CH$_2$(tetrahydrofuran-2-yl) group and Structure III represents the group that can be referred to as the —OCH$_2$CH$_2$(3-tetrahydrofuranyl) or —OCH$_2$CH$_2$(tetrahydrofuran-3-yl)group. When the heterocyclyl group is a N-containing heterocycle, such as, but not limited to piperidine, piperazine, morpholine, or pyrrolidine, the heterocycle can be bonded to the methylene carbon through a ring carbon atom or through a nitrogen atom in the ring of the N-containing heterocycle. Both of these are preferred. Where the heterocyclyl group is a piperidine for a —OCH$_2$CH$_2$CH$_2$(heterocyclyl) group, the following structures are possible and preferred:

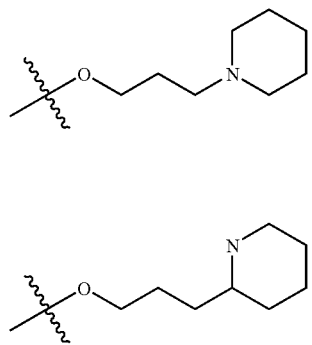
IV

V

VI

VII

Structure IV is an example of a —O(CH$_2$)$_3$(N-piperidinyl) or —O(CH$_2$)$_3$(1-piperidinyl) or —O(CH$_2$)$_3$(piperidin-1-yl) group. Structure V is an example of a —O(CH$_2$)$_3$-(2-piperidinyl) or —O(CH$_2$)$_3$(piperidin-2-yl) group. Structure VI is an example of a —O(CH$_2$)$_3$(3-piperidinyl) or —O(CH$_2$)$_3$(piperidin-3-yl) group. Structure VII is an example of a —O(CH$_2$)$_3$(4-piperidinyl) or —O(CH$_2$)$_3$(piperidin-4-yl) group. Where the heterocyclyl group is a piperazine for an —OCH$_2$CH$_2$(heterocyclyl) group, the following structures are possible and preferred:

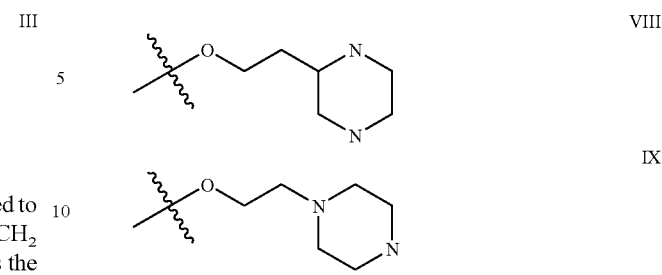
VIII

IX

Structure VIII is an example of a —O(CH$_2$)$_2$(2-piperazinyl) or —O(CH$_2$)$_2$(piperazin-2-yl) group, and Structure IX is an example of a —O(CH$_2$)$_2$(1-piperazinyl) or —O(CH$_2$)$_2$(N-piperazinyl) or —O(CH$_2$)$_2$(piperazin-1-yl) group. Where the heterocyclyl group is a morpholine for a —OCH$_2$CH$_2$(heterocyclyl) group, the following structures are possible and preferred:

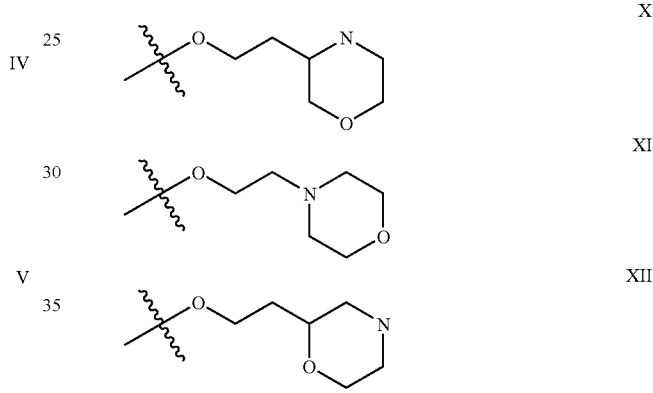
X

XI

XII

Structure X is an example of a —O(CH$_2$)$_2$(3-morpholinyl) or —O(CH$_2$)$_2$(morpholin-3-yl) group, Structure XI is an example of a —O(CH$_2$)$_2$(4-morpholinyl) or —O(CH$_2$)$_2$(N-morpholinyl) or —O(CH$_2$)$_2$(morpholin-4-yl)group, and Structure XII is an example of a —O(CH$_2$)$_2$(2-morpholinyl) or —O(CH$_2$)$_2$(morpholin-2-yl) group. It will be observed that where the heterocyclyl group is a pyrrolidine in a —OCH$_2$CH$_2$(heterocyclyl) group, the structures available include —O(CH$_2$)$_2$(1-pyrrolidinyl) or —O(CH$_2$)$_2$(N-pyrrolidinyl) or —O(CH$_2$)$_2$(pyrrolidin-1-yl), —O(CH$_2$)$_2$(2-pyrrolidinyl) or —O(CH$_2$)$_2$(pyrrolidin-2-yl), and —O(CH$_2$)$_2$(3-pyrrolidinyl) or —O(CH$_2$)$_2$(pyrrolidin-3-yl).

Compounds of Structure I and IB may be synthesized from simple starting molecules as shown in Schemes 1-6 and the Examples. As shown in Scheme 1, hydroxy derivatives of compounds of Structure I may generally be prepared using aromatic compounds substituted with amines and carboxylic acid groups. These compounds may then be converted to compounds of Structure I using the methods described in Schemes 3 and 5 and the Examples. Hydroxy derivatives of heterocyclic analogs of Structure I such as compounds of Structure IB may be similarly prepared using the appropriate heteroaromatic analogs of the compounds as shown in Scheme 2. These may then be converted to heterocyclic analogs of Structure I such as compounds of Structure IB using the methods described in Schemes 4 and 5.

Scheme 1.

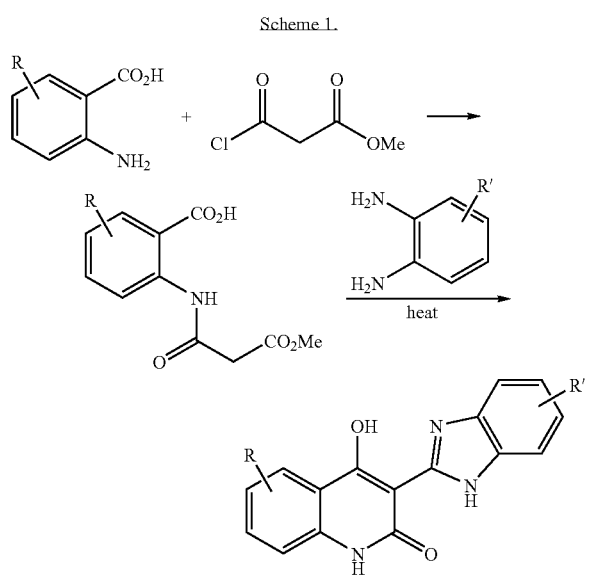

As shown in Scheme 1, a substituted aromatic compound such as a substituted or unsubstituted 2-aminobenzoic acid may be reacted with an acyl halide such as methyl 2-(chlorocarbonyl)acetate to produce an amide that will react with a substituted or unsubstituted 1,2-diaminobenzene. The resulting product is a 4-hydroxy-substituted analog of a compound of Structure I.

Scheme 2.

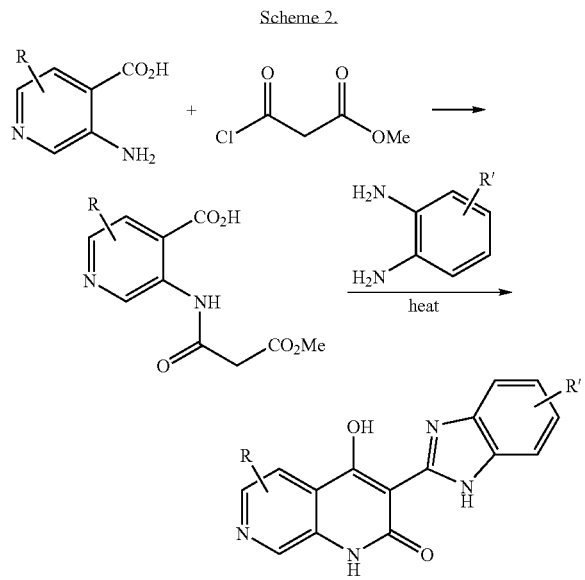

As shown in Scheme 2, a substituted pyridine such as a substituted or unsubstituted 3-amino-pyridine-4-carboxylic acid may be reacted with an acyl halide such as methyl 2-(chlorocarbonyl)acetate to produce an amide that will react with a substituted or unsubstituted 1,2-diaminobenzene or a pyridine analog. The resulting product is a 4-hydroxy-substituted heterocyclic analog of a compound of Structure I or IB. The use of starting pyridines with different substitution patterns such as 2-aminonicotinic acid (2-aminopyridine-4-carboxylic acid) provides compounds where the nitrogen is in a different position in the pyridine ring of the final compound. One skilled in the art will recognize that the procedure set forth in Scheme 2 may be modified to produce various 4-hydroxy heterocyclic analogs of compounds of Structure I and IB.

Scheme 3 illustrates a general synthetic route that allows for the synthesis of various compounds of Structure I. An inspection of Scheme 3 shows that 4-hydroxy substituted analogs of compounds of Structure I may be converted into the 4-chloro derivative by reaction with phosphorus oxychloride or thionyl chloride. The 4-chloro derivative may then be reacted with an appropriate amine such as an alkylamine, a dialkylamine, a heterocyclylamine, a cycloalkylamine, an aromatic amine, and the like to produce the corresponding protected compound of Structure I. Deprotection affords the final desired compounds of Structure I.

The various 2-aminobenzoic acid starting materials used to synthesize isatoic anhydrides may be obtained from commercial sources or prepared by methods known to one of skill in the art. General isatoic anhydride synthesis methods are described in *J. Med. Chem.* 1981, 24 (6), 735 and *J. Heterocyl. Chem.* 1975, 12(3), 565 which are both hereby incorporated by reference in their entirety for all purposes as if fully set forth herein.

Scheme 3.

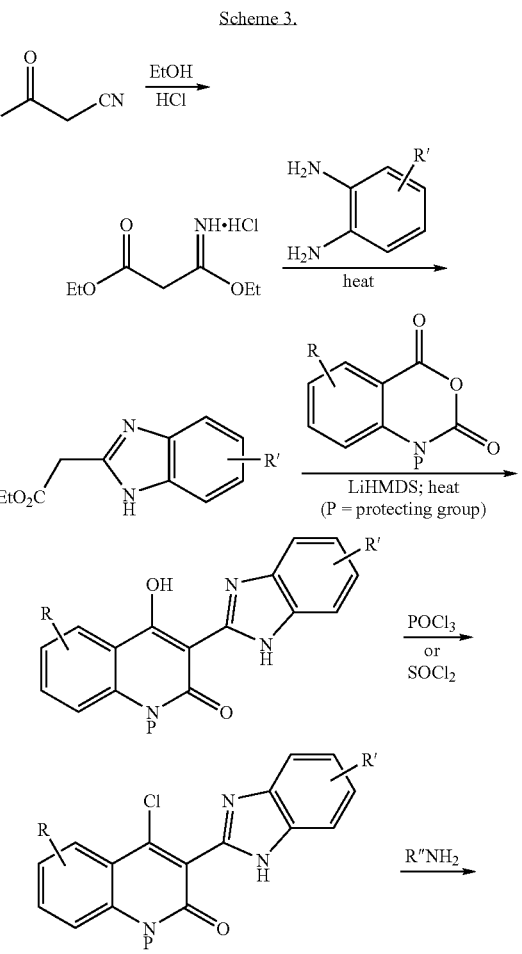

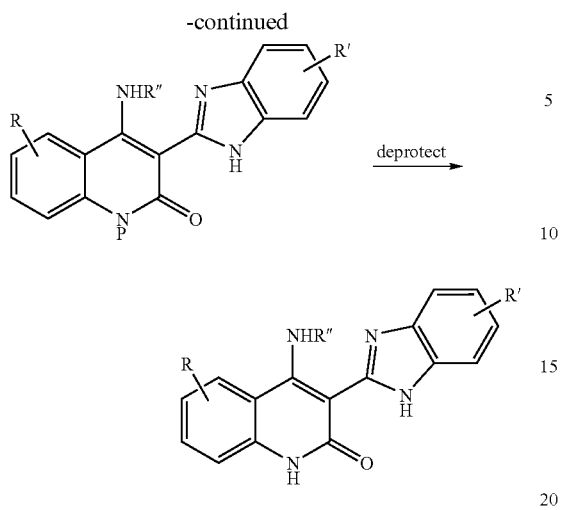

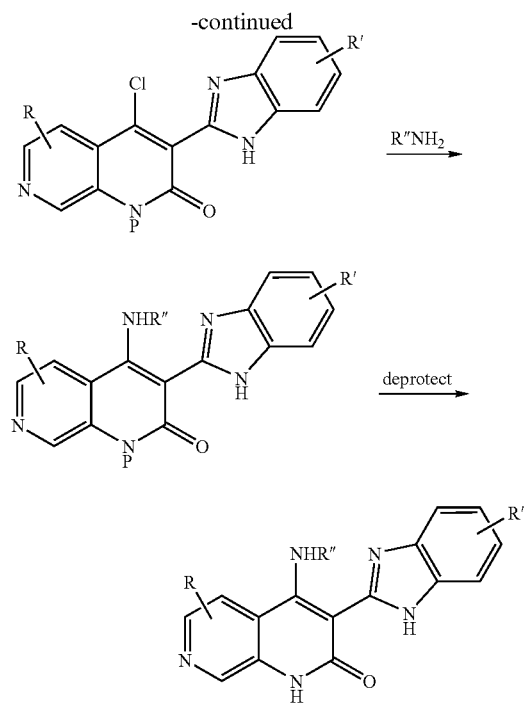

Scheme 4 illustrates a general synthetic route that allows for the synthesis of various heterocyclic compounds of Structure IB. An inspection of Scheme 4 shows that 4-hydroxy substituted analogs of Structure IB may be converted into the 4-chloro derivative by reaction with phosphorous oxychloride or thionyl chloride. The 4-chloro derivative may then be reacted with an appropriate amine such as an alkylamine, a dialkylamine, a heterocyclylamine, a cycloalkylamine, an aromatic amine, and the like to produce the corresponding protected compounds of Structure IB. Deprotection affords the final desired heterocyclic analogs of compounds of Structure I.

Scheme 5 depicts a general synthetic route that allows for the synthesis of various compounds of Structure I. An inspection of Scheme 5 shows that the hydroxy group of 4-hydroxy substituted analogs of compounds of Structure I may be converted to a leaving group by triflation with triflating agents such as triflic anhydride. The resulting triflates may then be reacted with a wide variety of nitrogen nucleophiles such as 3-aminoquinuclidine and other amines to produce protected analogs of compound of Structure I. Deprotection of the resulting products affords the desired compounds of Structure I. An analogous procedure may be used to prepare heterocyclic compounds of Structure I.

Scheme 4.

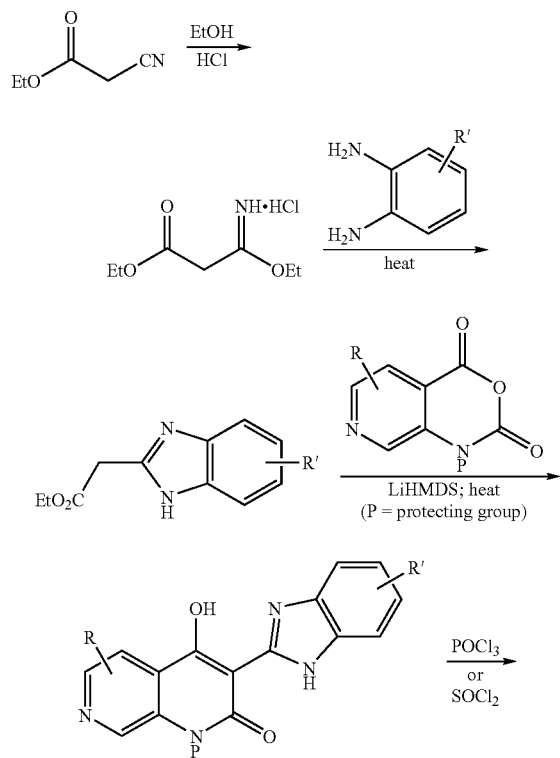

Scheme 5.

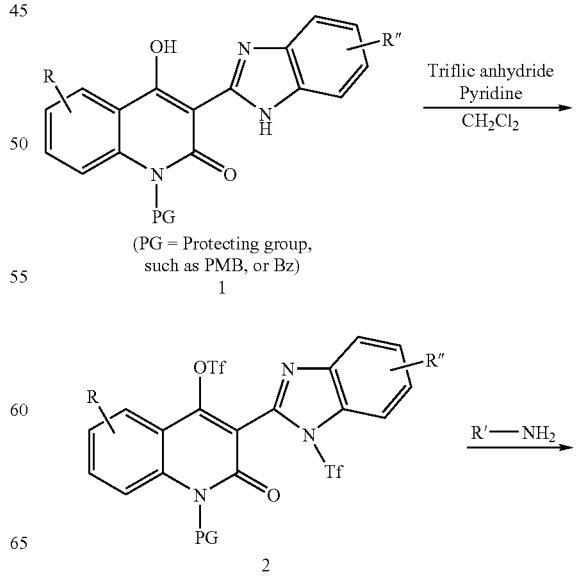

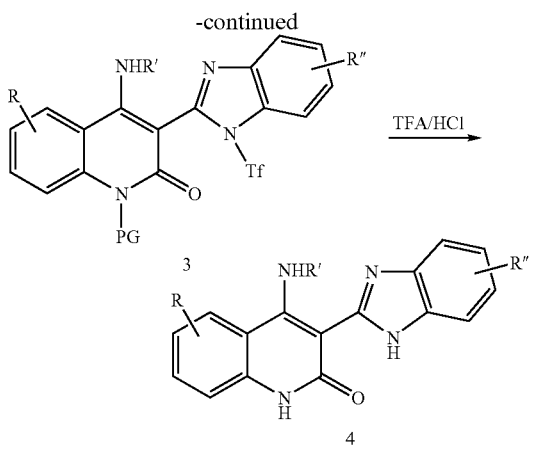

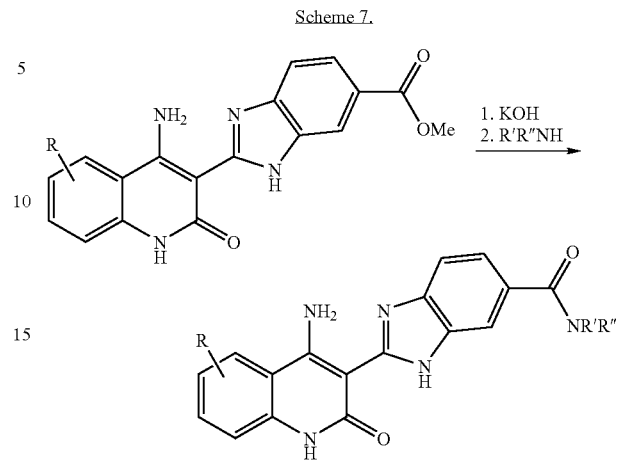

Heteroaromatic diamines may be simply prepared and used as precursors of compounds of Structure I and IB and heterocyclic analogs of compounds of Structure I and IB where one or more of A, B, C, or D is a nitrogen as shown in Scheme 6.

Introduction of substituents on the benzimidazole ring need not be limited to the early stages of the synthesis and may be accomplished after formation of the quinolinone ring.

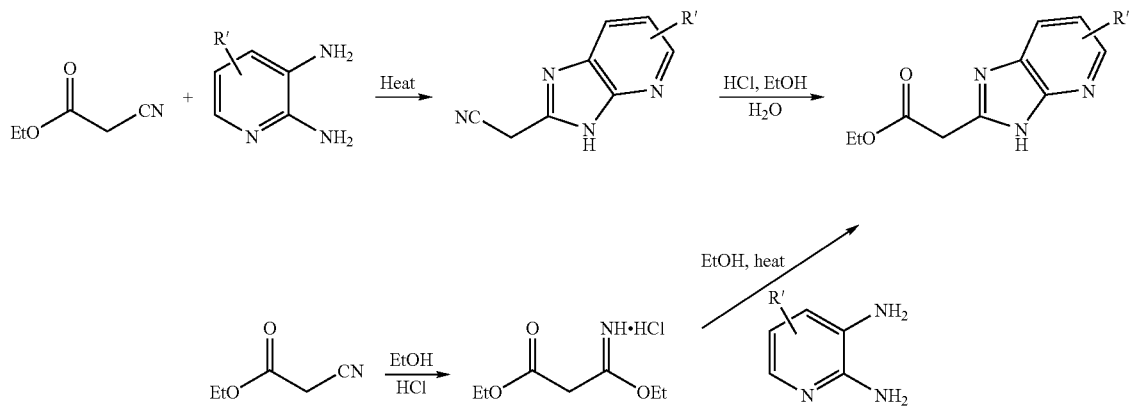

As shown in Scheme 6, a compound such as ethyl cyanoacetate may be condensed with a substituted or unsubstituted heterocycle containing two ortho amino groups such as substituted or unsubstituted 1,2-diaminopyridine to obtain a substituted or unsubstituted 2-imidazolo[5,4-b]pyridin-2-ylethanenitrile, which may subsequently be hydrolyzed in acidic medium to provide a substituted or unsubstituted ethyl 2-imidazolo[5,4-b]pyridin-2-ylacetate. As an alternate route, a substituted or unsubstituted ethyl 2-imidazolo[5,4-b]pyridin-2-ylacetate may be obtained from a compound such as the hydrochloride salt of 3-ethoxy-3-iminopropanoate and a substituted or unsubstituted 1,2-diaminopyridine. Reaction of a substituted or unsubstituted ethyl 2-imidazolo[5,4-b]pyridin-2-ylacetates with an appropriate aromatic compound provides compounds of Structure I and heterocyclic analogs of compounds of Structure I where one or more of A, B, C, or D is a nitrogen atom.

For example, amides can be obtained by coupling the advanced acid intermediate shown in Scheme 7 with a variety of amine.

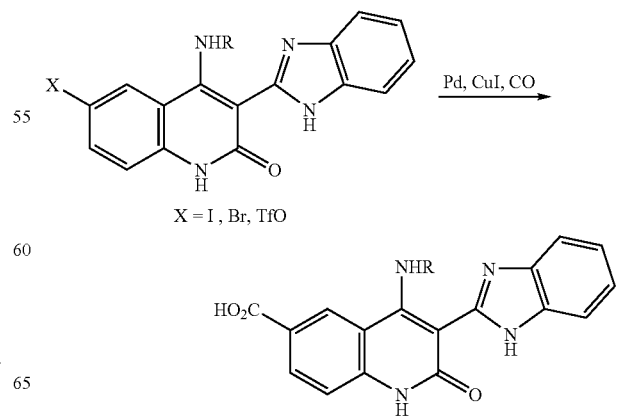

Conversion of the C-6 or C-7 halides to an acid group was accomplished using procedures in the following references which are herein incorporated by reference in their entirety for all purposes as if fully set forth herein: Koga, H.; et al., *Tet. Let.*, 1995, 36, 1, 87-90; and Fukuyama, T.; et al., *J. Am. Chem. Soc.*, 1994, 116, 3125-3126.

Scheme 9.

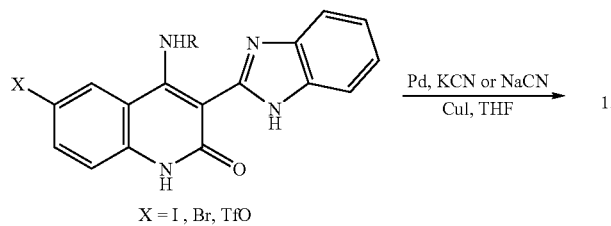

X = I, Br, TfO

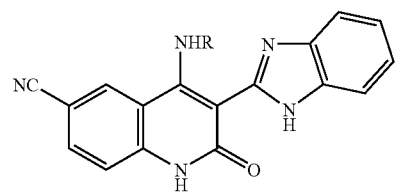

Conversion of the C-6 or C-7 halides to a cyano group was accomplished using procedures in the following reference which is herein incorporated by reference in its entirety for all purposes as if fully set forth herein: Anderson, B. A.; et al., *J. Org. Chem.*, 1998, 63, 8224-828. Preferred reaction conditions for Scheme 9 are described in Method 26 below.

Scheme 10.

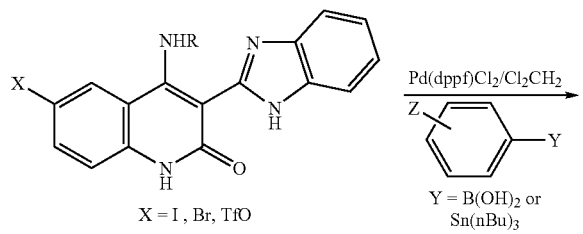

X = I, Br, TfO

Y = B(OH)$_2$ or Sn(nBu)$_3$

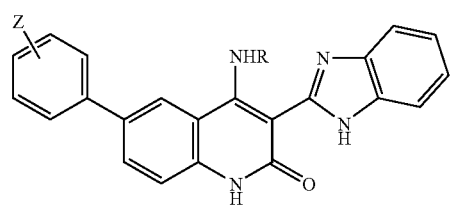

Conversion of the C-6 or C-7 halides to an aryl group was accomplished using standard Suzuki or Stille procedures such as described below.

Scheme 11.

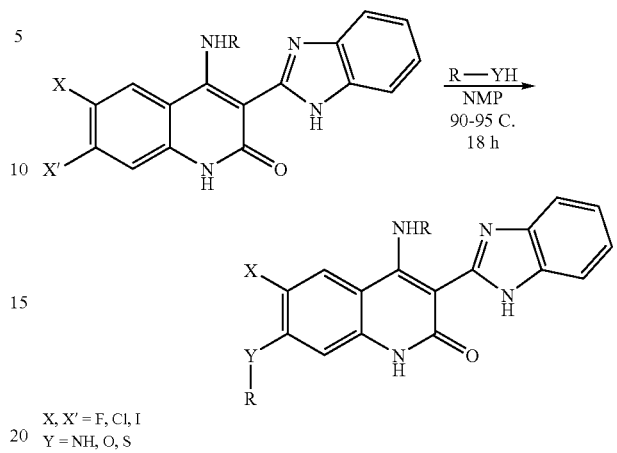

X, X' = F, Cl, I
Y = NH, O, S

Additional functionalization using a dihaloquinolone was accomplished as depicted in Scheme 11 by reaction of the dihaloquinolone with nucleophiles such as amines, alcohols and thiols.

The compounds of Structure I and IB, tautomers of the compounds, pharmaceutically acceptable salts of the compounds, pharmaceutically acceptable salts of the tautomers, and mixtures thereof may be used to prepare medicaments, that may be used for the purposes described herein, and may be used to treat various biological conditions as described herein.

Pharmaceutical formulations may include any of the compounds of any of the embodiments described above in combination with a pharmaceutically acceptable carrier such as those described herein.

The instant invention also provides for compositions which may be prepared by mixing one or more compounds of the instant invention, or pharmaceutically acceptable salts tautomers thereof, or mixtures thereof with pharmaceutically acceptable carriers, excipients, binders, diluents or the like to treat or ameliorate a variety of disorders related to the activity of VEGF-RTK, more particularly angiogenesis associated with cancer or related to the activity of FLT-1, VEGFR2, VEGFR3, FGFR1, GSK-3, Cdk2, Cdk4, MEK1, NEK-2, CHK2, CK1ε, Raf, NEK-2, CHK1, Rsk2, PAR-1, Cdc2, c-Kit, c-ABL, p60src, FGFR3, FLT-3, Fyn, Lck, Tie-2, PDGFRα, and PDGFRβ. The compositions of the inventions may be used to create formulations such as medicaments and pharmaceutical formulations that inhibit tyrosine kinases and/or serine/threonine kinases and may be used to treat biological conditions mediated by such kinases. Such compositions can be in the form of, for example, granules, powders, tablets, capsules, syrup, suppositories, injections, emulsions, elixirs, suspensions or solutions. The instant compositions can be formulated for various routes of administration, for example, by oral administration, by nasal administration, by rectal administration, subcutaneous injection, intravenous injection, intramuscular injections, or intraperitoneal injection. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, pharmaceutically acceptable salts, tautomers, or mixtures thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oil include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remington Pharmaceutical Sciences" Mack Pub. Co., New Jersey (1991), which is incorporated herein by reference in its entirety for all purposes as if fully set forth herein.

The formulations of the invention may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. The preferred compound or compounds of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

"Treating" within the context of the instant invention, means an alleviation of symptoms associated with a disorder or disease, or halt of further progression or worsening of those symptoms, or prevention or prophylaxis of the disease or disorder. For example, within the context of treating patients in need of an inhibitor of VEGF-RTK, successful treatment may include a reduction in the proliferation of capillaries feeding a tumor or diseased tissue, an alleviation of symptoms related to a cancerous growth or tumor, proliferation of capillaries, or diseased tissue, a halting in capillary proliferation, or a halting in the progression of a disease such as cancer or in the growth of cancerous cells. Treatment may also include administering the pharmaceutical formulations of the present invention in combination with other therapies. For example, the compounds and pharmaceutical formulations of the present invention may be administered before, during, or after surgical procedure and/or radiation therapy. The compounds of the invention can also be administered in conjunction with other anti-cancer drugs including those used in antisense and gene therapy. Appropriate combinations can be determined by those of skill in the oncology and medicine arts.

Pharmaceutical formulations and medicaments according to the invention include any of the compounds described above in combination with a pharmaceutically acceptable carrier. Thus, the compounds of the invention may be used to prepare medicaments and pharmaceutical formulations. In some such embodiments, the medicaments and pharmaceutical formulations comprise any of the compounds of any of the embodiments of compounds of Structure I or Structure IB or pharmaceutically acceptable salts thereof. The invention also provides for the use of any of the compounds of any of the embodiments of compounds of Structure I or IB or pharmaceutically acceptable salts thereof for the inhibition of an enzyme such as FLT-1, VEGFR2, VEGFR3, FGFR1, GSK-3, Cdk2, Cdk4, MEK1, NEK-2, CHK2, CK1ε, Raf, NEK-2, CHK1, Rsk2, PAR-1, c-Kit, c-ABL, p60src, FGFR3, FLT-3, Cdc2, Fyn, Lck, Tie-2, PDGFRα, and PDGFRβ, or for the treatment of a disease or condition associated with any of these enzymes as described in greater detail below. The invention also provides the use of any of the compounds of any of the embodiments of compounds of Structure I or IB or pharmaceutically acceptable salts thereof for the manufacture of enzyme inhibition agent such as a tyrosine kinase inhibitor or a serine/threonine kinase inhibitor, a pharmaceutical formulation, or a medicament that inhibits enzymes such as FLT-1, VEGFR2, VEGFR3, FGFR1, GSK-3, Cdk2, Cdk4, MEK1, NEK-2, CHK2, CK1ε, Raf, NEK-2, CHK1, Rsk2, PAR-1, c-Kit, c-ABL, p60src, FGFR3, FLT-3, Cdc2, Fyn, Lck, Tie-2, PDGFRα, and PDGFRβ or treats a disease or condition associated with any of these enzymes as described in greater detail below.

A method of treating a patient in need of an inhibitor of vascular endothelial growth factor receptor tyrosine kinase includes administering an effective amount of a pharmaceutical formulation, a medicament according to the invention or any of the compounds of any of the embodiments of compounds of Structure I or IB to a patient in need thereof.

A method for inhibiting tumor growth in a patient includes administering an effective amount of the compound, a pharmaceutically acceptable salt thereof of any of the compounds of Structure I or IB, or a medicament to a patient having a tumor.

A method for inhibiting angiogenesis and tumor growth in a patient includes administering an effective amount of the compound or a pharmaceutically acceptable salt thereof according to a patient in need.

The invention provides a method of treating a subject with various tumor types. The method includes administering to the subject, such as a human subject, a compound according to any of the embodiments of compounds or a pharmaceutically acceptable salt thereof of Structure I or IB to the subject. In some such embodiments, the method includes a method of treating a cancer patient.

The invention provides a method of inhibiting an enzyme such as a tyrosine kinase. The method includes administering to a subject, such as a human subject, a mammalian subject, or a cell subject, a compound according to any of the embodiments of compounds or a pharmaceutically acceptable salt thereof of Structure I or IB to the subject. In some such embodiments, the tyrosine kinase is VEGF.

The invention provides a method of treating a subject with type II diabetes. The method includes administering to the subject, such as a human subject, a compound according to any of the embodiments of compounds or a pharmaceutically acceptable salt thereof of Structure I or IB to the subject. In some such embodiments, the method includes a method of treating a prediabetic or diabetic patient.

The invention provides a method of stimulating insulin-dependent processes in a patient. The method includes administering to the patient, such as a human patient, a compound according to any of the embodiments of compounds of Structure I or IB, or a pharmaceutically acceptable salt thereof, to the subject. In some such embodiments, the method includes a method of reducing plasma glucose levels, increasing glycogen uptake, potentiating insulin, upregulating glucose synthase activity, and stimulating glycogen synthesis such as in skin, muscle, and fat cells.

The invention provides a method of treating a subject with Alzheimer's disease. The method includes administering to the subject, such as a human subject, a compound according to any of the embodiments of compounds of Structure I or IB, or a pharmaceutically acceptable salt thereof, to the subject. In some such embodiments, the method includes reducing tau phosphorylation, reducing the generation of neurofibrillary tangles, and slowing the progression of Alzheimer's disease.

The invention provides a method of treating a subject with a central nervous system disorder. The method includes administering to the subject, such as a human subject, a compound according to any of the embodiments of compounds of Structure I or IB, or a pharmaceutically acceptable salt thereof, to the subject. In some such embodiments, the method includes a method of treating bipolar disorder; increasing the survival of neurons subjected to aberrantly high levels of excitation induced by glutamate; reducing neurodegeneration associated with acute damage such as in cerebral ischemia, traumatic brain injury, and bacterial injury; and reducing chronic neuronal damage associated with Alzheimer's disease, Huntington's disease, Parkinson's disease, AIDS associated dementia, amyotrophic lateral sclerosis (ALS) and multiple sclerosis.

The invention provides a method of prolonging an immune response in a subject. The method includes administering to the subject, such as a human subject, a compound according to any of the embodiments of compounds of Structure I or IB, or a pharmaceutically acceptable salt thereof, to the subject. In some such embodiments, the method includes prolonging and/or potentiating immunostimulatory effects of cytokines, and enhancing the potential of cytokines for immunotherapy such as tumor immunotherapy.

The invention provides a method of reducing the splitting of centrosomes in the cells of a subject. The method includes administering to the subject, such as a human subject, a compound according to any of the embodiments of compounds of Structure I or IB, or a pharmaceutically acceptable salt thereof, to the subject. In some such embodiments, the subject is a cancer patient.

The invention provides a method of blocking DNA repair in a cancer cell of a cancer patient. The method includes administering to the patient, such as a human patient, a compound according to any of the embodiments of compounds of Structure I or IB, or a pharmaceutically acceptable salt thereof, to the patient.

The invention provides a method of promoting phosphorylation of Cdc25 and Wee1 in a patient. The method includes administering to the patient, such as a human patient, a compound according to any of the embodiments of compounds of Structure I or IB, or a pharmaceutically acceptable salt thereof, to the patient.

The invention provides a method of modulating and/or preventing cell cycle arrest in a cell. The method includes contacting the cell with a compound according to any of the embodiments of compounds of Structure I or IB, or a pharmaceutically acceptable salt thereof. In one method, the cells are defective in the p53 gene and/or have p53 mutations and/or are deficient in p53. In some embodiments, the cells are cancer cells such as those deficient in p53. In some embodiments, arrest at the G2/M checkpoint is prevented or inhibited. In some embodiments, the method includes treating a patient, such as a human patient with any of the compounds of the invention, and in some such further embodiments, the method further includes treating the patient with another therapeutic agent such as a chemotherapeutic agent or with radiation or heat.

A method of preparing pharmaceutical formulations and medicaments includes mixing any of the above-described compounds with a pharmaceutically acceptable carrier.

As noted above, compounds of Structure I and IB, tautomers of compounds of Structure I and IB, pharmaceutically acceptable salts of the compounds, pharmaceutically acceptable salts of the tautomers, and mixtures thereof are useful inhibitors of CHK1. One of the advantages of many of these compounds is that they exhibit selectivity for CHK1 over other enzymes such as CHK2 and FLT-1, VEGFR2, and FGFR1. In some embodiments the $IC_{50}$ values with respect to CHK1 show that the inhibitors of the invention are 1,000 times, 100 times, or 10 times more selective towards CHK1 compared to CHK2. CHK1 inhibitors of the invention may be administered to cancer patients alone or in combination with other anti-cancer drugs or therapies. The present CHK1 inhibitors are particularly useful against p53 cancers. In some embodiments, the cancers that the CHK1 inhibitors of the invention are useful in treating include breast cancer, particularly human breast cancer, and colon cancer.

The CHK1 inhibitors of the present invention are particularly suitable for use in combination therapy as they have been shown to exhibit synergistic effect when used in combination with anti-cancer drugs such as camptothecin, doxorubicin, cisplatin, irinotecan (CPT-11), alkylating agents, topoisomerase I and II inhibitors, and radiation treatment. When an inhibitor of CHK1 of the present invention is used in combination therapy along with an anti-cancer drug such as camptothecin, cisplatin, irinotecan, or doxorubicin, isobolograms show that the amount of the anti-cancer drug may be reduced due to the synergistic interaction (supraadditivity) between the CHK1 inhibitor and the conventional anti-cancer drug. Therefore, the invention provides pharmaceutical formulations that include the compounds of Structure I and IB in combination with an anticancer drug, the use of the compounds in creating such formulations and medicaments.

The compounds of the invention may be used to inhibit kinases and used to treat biological conditions mediated by kinases in a variety of subjects. Suitable subjects include animals such as mammals and humans. Suitable mammals include, but are not limited to, primates such as, but not limited to lemurs, apes, and monkeys; rodents such as rats, mice, and guinea pigs; rabbits and hares; cows; horses; pigs; goats; sheep; marsupials; and carnivores such as felines, canines, and ursines. In some embodiments, the subject or patient is a human. In other embodiments, the subject or patient is a rodent such as a mouse or a rat. In some embodiments, the subject or patient is an animal other than a human and in some such embodiments, the subject or patient is a mammal other than a human.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure. For example, Structure I is shown below with one tautomer, Tautomer Ia:

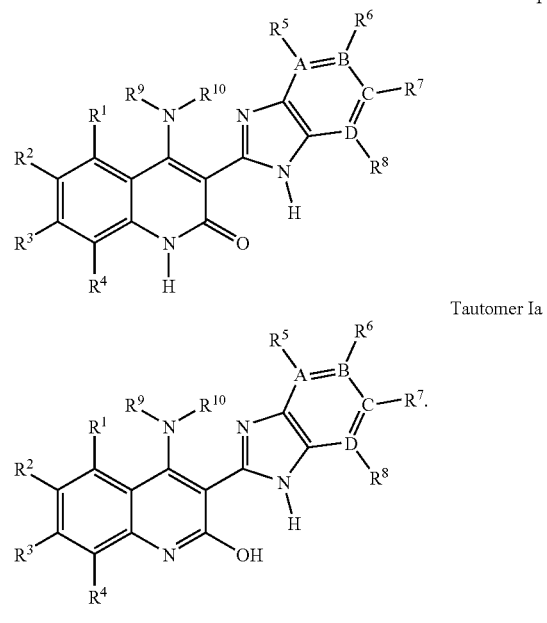

Other tautomers of Structure I, Tautomer Ib and Tautomer Ic, are shown below:

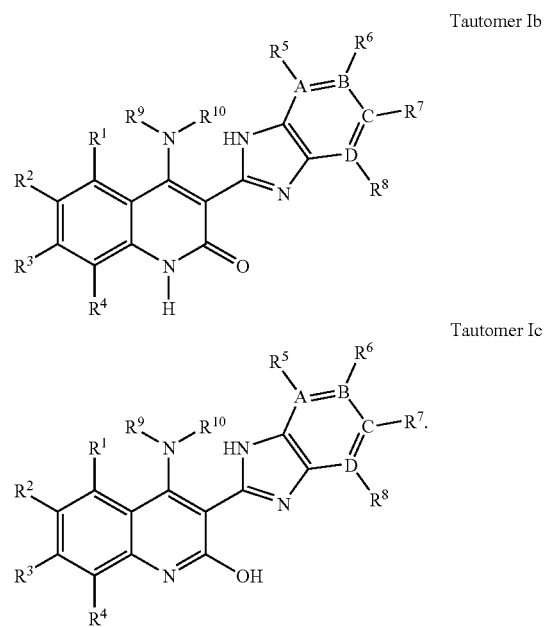

Notably, the same types of tautomers occur with respect to compounds of Structure IB.

The present invention, thus generally described, will be understood more readily by reference to the following examples, which are provided by way of illustration and are not intended to be limiting of the present invention.

EXAMPLES

Nomenclature for the Example compounds was provided using ACD Name version 5.07 software (Nov. 14, 2001) available from Advanced Chemistry Development, Inc., Cheminnovation NamExpert+Nomenclator™ brand software available from Cheminnovation Software, Inc., and AutoNom version 2.2 available in the ChemOffice® Ultra software package version 7.0 available from CambridgeSoft Corporation (Cambridge, Mass.). Some of the compounds and starting materials were named using standard IUPAC nomenclature.

The following abbreviations are used throughout the application with respect to chemical terminology:

| | |
|---|---|
| AcOH: | Acetic acid |
| ATP: | Adenosine triphosphate |
| BINAP: | 2,2'-Bis(diphenylphosphino)-1,1'-binaphthyl |
| Boc: | N-tert-Butoxycarbonyl |
| Bn: | Benzyl |
| BSA: | Bovine Serum Albumin |
| Cbz: | Carbobenzyloxy |
| DEAD: | Diethyl azodicarboxylate |
| DIEA: | Diisopropylethylamine |
| DMA: | N,N-Dimethylacetamide |
| DMAP: | 4-Dimethylaminopyridine |
| DMF: | N,N-Dimethylformamide |
| DMSO: | Dimethylsulfoxide |
| dppf: | 1,1'(diphenylphosphino)ferrocene |
| DTT: | DL-Dithiothreitol |
| $ED_{50}$: | Dose therapeutically effective in 50% of the population |
| EDC or EDCl: | 1-(3-Dimethylaminopropyl)-3-ethylcarbodiimide hydrochloride |
| EDTA: | Ethylene diamine tetraacetic acid |
| EtOAc: | Ethyl acetate |
| EtOH: | Ethanol |
| Fmoc: | 9-fluorenylmethyl |
| HBTU: | O-Benzotriazol-1-yl-N,N,N',N'-tetramethyluronium hexafluorophosphate |
| HPLC: | High Pressure Liquid Chromatography |
| $IC_{50}$ value: | The concentration of an inhibitor that causes a 50% reduction in a measured activity. |
| KHMDS: | Potassium bis(trimethylsilyl)amide |
| LC/MS: | Liquid Chromatography/Mass Spectroscopy |
| LiHMDS: | Lithium bis(trimethylsilyl)amide |
| MeOH: | Methanol |
| NMP: | N-methylpyrrolidone |
| Pd(dba)2: | Bis(dibenzylideneacetone)Palladium |
| PPTS: | Pyridinium p-toluenesulfonate |
| Pyr: | Pyridine |
| SEMCl: | 2-(Trimethylsilyl)ethoxymethyl chloride |
| TBAF: | Tetrabutylammonium fluoride |
| TEA: | Triethylamine |
| TES: | Triethylsilyl |
| TFAA: | Trifluoroacetic anhydride |
| THF: | Tetrahydrofuran |
| TMS: | Trimethylsilyl |

Purification and Characterization of Compounds

Compounds of the present invention were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburg, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; Solvent system: 5-95% acetonitrile in water with 0.05% TFA; Flow rate 0.8 mL/minute; Molecular weight range 150-850; Cone Voltage 20 V; Column temperature 40° C.) or a Hewlett Packard System (Series 1100 HPLC; Column: Eclipse XDB-C18, 2.1×50 mm; Solvent system: 1-95% acetonitrile in water with 0.05% TFA; Flow rate 0.4 mL/minute; Molecular weight range 150-850; Cone Voltage 50 V; Column temperature 30° C.). All masses are reported as those of the protonated parent ions.

GCMS analysis was performed on a Hewlet Packard instrument (HP6890 Series gas chromatograph with a Mass Selective Detector 5973; Injector volume: 1 μL; Initial column temperature: 50° C.; Final column temperature: 250° C.; Ramp time: 20 minutes; Gas flow rate: 1 mL/minute; Column: 5% Phenyl Methyl Siloxane, Model #HP 190915-443, Dimensions: 30.0 m×25 μm×0.25 μm).

Preparative separations were carried out using either a Flash 40 chromatography system and KP-Sil, 60A (Biotage, Charlottesville, Va.), or by HPLC using a C-18 reversed phase column. Typical solvents employed for the Flash 40 Biotage system were dichloromethane, methanol, ethyl acetate, hexane and triethyl amine. Typical solvents employed for the reverse phase HPLC were varying concentrations of acetonitrile and water with 0.1% trifluoroacetic acid.

Various functionalized aryl diamines were obtained from commercial sources, prepared by methods know to those of skilled in the art, or were prepared by the following general methods. Some of the aryl diamines and Examples were prepared by the methods set forth in U.S. Provisional Application No. 60/405,729. Therefore, U.S. Provisional Application No. 60/405,729 in hereby incorporated by reference in its entirety for all purposes as if fully set forth herein including the methods and Examples set forth.

Method 1

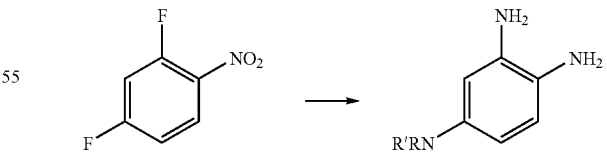

2,4-Difluoronitrobenzene (1.0 equivalent) was placed in a dry round-bottomed flask equipped with a dry ice condenser charged with acetone and dry ice. Ammonia was condensed into the flask, and the resulting solution was stirred at reflux for 7 hours. A yellow precipitate formed within 1 hour. After 7 hours, the condenser was removed and the liquid ammonia was allowed to evaporate over several hours. The crude product was purified by flash chromatography on silica gel (85:15 hexanes:ethyl acetate, product at $R_f$=0.32, contaminant at $R_f$=0.51); GC/MS m/z 156.1 (M+), $R_t$ 11.16 minutes.

The resulting 5-fluoro-2-nitrophenylamine (1.0 equivalents) and an amine (1.1 equivalents) e.g. N-methyl piperazine, were dissolved in NMP and triethylamine (2.0 equivalents) was added. The reaction mixture was heated at 100° C. for 3 hours. The solution was then cooled to room temperature and diluted with water. The resulting precipitate was filtered and dried under vacuum to provide the 2-nitro-diamino product. Alternatively, the same product may be obtained from commercially available 5-chloro-2-nitrophenylamine under identical conditions except heating at 130° C. for 1-2 days. In some examples, the displacement on either 5-fluoro-2-nitrophenylamine or 5-chloro-2-nitrophenylamine can be conducted in neat amine (5 equivalents) at 100° C. or 130° C., respectively. The product is isolated in an identical manner. LC/MS m/z 237.1 (MH+), $R_t$ 1.304 minutes.

The nitroamine (1.0 equivalent) and 10% Pd/C (0.1 equivalents) was suspended in anhydrous ethanol at room temperature. The reaction flask was evacuated and subsequently filled with $H_2$. The resulting mixture was then stirred under a hydrogen atmosphere overnight. The resulting solution was filtered through Celite and concentrated under vacuum to provide the crude product which was used without further purification.

Method 2

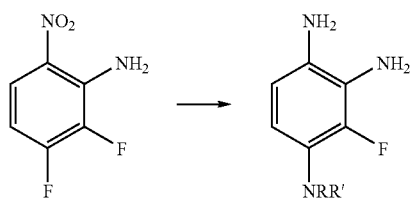

A round-bottom flask was charged with 2,3-difluoro-6-nitrophenylamine (1 equivalent) and enough NMP to make a viscous slurry. An amine (5 equivalents), e.g., N-methyl piperazine, was added and the solution was heated at 100° C. After 2 hours, the solution was cooled and poured into water. A bright yellow solid formed which was filtered and dried. The nitroamine was reduced as in Method 1 to provide the crude product which was used without further purification. LC/MS m/z 225.1 (MH+), $R_t$ 0.335 minutes.

Method 3

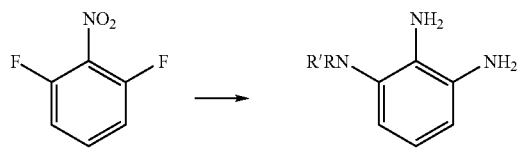

To a 0.1 M DMF solution of 1,3-difluoro-2-nitrobenzene was added $Et_3N$ (2 equivalents) followed by an amine (1 equivalent), e.g. morpholine. The mixture was stirred for 18 hours and then diluted with water and extracted with ethyl acetate. LC/MS m/z 227.2 (MH+), $R_t$ 2.522 minutes. The combined organic layers were dried over $MgSO_4$, filtered, and concentrated. Ammonia was condensed into a pressure vessel containing the crude product. The pressure vessel was sealed and heated to 100° C. (over 400 psi). After 72 hours, the pressure vessel was allowed to cool and the ammonia was evaporated to provide a reddish solid. The nitroamine was reduced as in Method 1 to provide the crude product which was used without further purification. LC/MS m/z 194.1 (MH+), $R_t$ 1.199 minutes.

Method 4

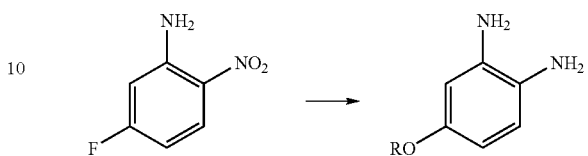

To a stirred NMP solution containing NaH (1.3 equivalents) was added an alcohol (1.0 equivalent), e.g. 2-methyloxyethanol. The resulting mixture was then stirred for 30 minutes. A slurry of 5-fluoro-2-nitrophenylamine in NMP was then added slowly. The mixture was then heated to 100° C. After 2 hours, the reaction mixture was cooled and water was added. The mixture was then filtered and the captured solid was washed with water and purified by silica gel chromatography (1:1 ethyl acetate:hexane). LC/MS m/z 213.2 (MH+), $R_t$ 2.24 minutes. The nitroamine was reduced as in Method 1 to provide the crude product which was used without further purification. LC/MS m/z 183.1 (MH+), $R_t$ 0.984 minutes.

Method 5

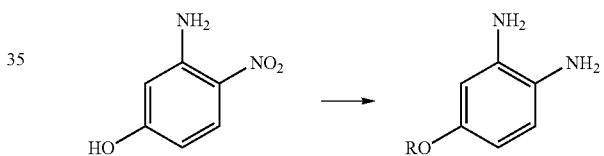

Diisopropyl azodicarboxylate (1.1 equivalents) was added dropwise to a stirred solution of 3-amino-4-nitrophenol (1.0 equivalent), triphenylphosphine (1.1 equivalents), and an alcohol, e.g. N-(2-hydroxyethyl)morpholine (1.0 equivalent), in tetrahydrofuran at 0° C. The mixture was allowed to warm to room temperature and stirred for 18 hours. The solvent was evaporated, and the product was purified by silica gel chromatography (98:2 $CH_2Cl_2$:methanol) to yield 4-(2-morpholin-4-ylethoxy)-2-nitrophenylamine as a dark reddish-brown oil. LC/MS m/z 268.0 (MH+), $R_t$ 1.01 minutes. The nitroamine was reduced as in Method 1 to give the crude product which was used without further purification. LC/MS m/z 238.3 (MH+), $R_t$ 0.295 minutes.

Method 6

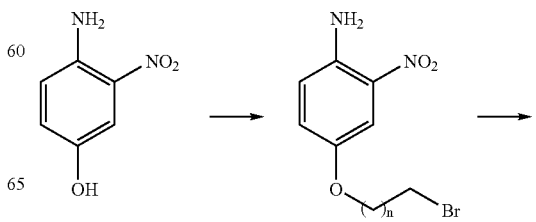

-continued

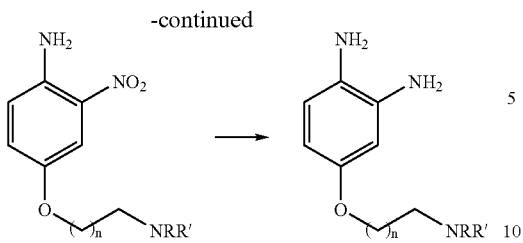

To a flask charged with 4-amino-3-nitrophenol (1 equivalent), $K_2CO_3$ (2 equivalents), and 2-butanone, was added an alkyl dibromide, e.g. 1,3-dibromopropane (1.5 equivalents). The resulting mixture was then heated at 80° C. for 18 hours. After cooling, the mixture was filtered, concentrated, and diluted with water. The solution was then extracted with $CH_2Cl_2$ (3×) and the combined organic layers were concentrated to give a solid that was then washed with pentane. LCMS m/z 275.1 (MH+), $R_t$ 2.74 minutes.

An acetonitrile solution of the bromide prepared above, an amine, e.g., pyrrolidine (5 equivalents), $Cs_2CO_3$ (2 equivalents) and $Bu_4NI$ (0.1 equivalents) was heated at 70° C. for 48 hours. The reaction mixture was cooled, filtered, and concentrated. The residue was dissolved in $CH_2Cl_2$, washed with water, and concentrated to give the desired nitroamine, 2-nitro-4-(3-pyrrolidin-1-ylpropoxy)phenylamine. LCMS m/z 266.2 (MH+), $R_t$ 1.51 minutes. The nitroamine was reduced as in Method 1 to provide the crude product which was used without further purification.

Method 7

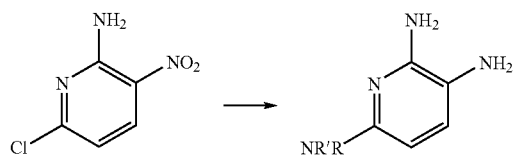

To a suspension of 6-chloro-3-nitropyridin-2-amine (1 equivalent) in acetonitrile was added an amine, e.g. morpholine (4 equivalents). The resulting reaction mixture was stirred at 70° C. for 5 hours. The solvent was evaporated under reduced pressure, and the residue triturated with ether to provide the desired compound as a bright yellow powder. LC/MS m/z 225.0 (MH+), $R_t$ 1.79 minutes. The nitroamine was reduced as in Method 1 to provide the crude product which was used without further purification.

Method 8

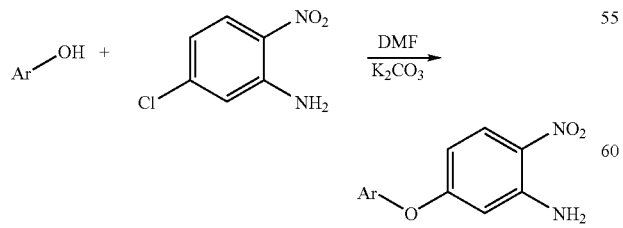

A phenol (1 equivalent) and 5-chloro-2-nitro aniline (1 equivalent) were dissolved in DMF, and solid $K_2CO_3$ (2 equivalents) was added in one portion. The reaction mixture was heated at 120° C. overnight. The reaction mixture was cooled to room temperature, most of the DMF was distilled off, and water was added to the residue to obtain a precipitate. The solid was dried and purified by chromatography on silicagel (2-10% $MeOH/CH_2Cl_2$) to afford the desired product. The nitroamine was reduced as in method 1 to give the crude product that was used without further purification.

Method 9:

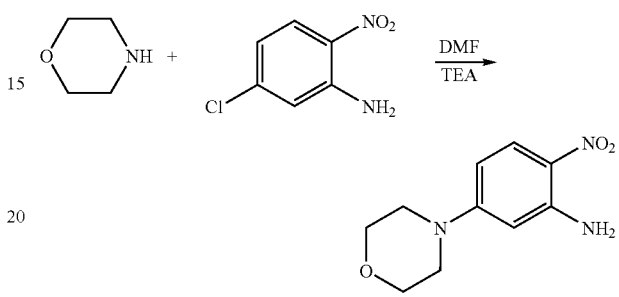

Morpholine (1 equivalent) and 5-chloro-2-nitroaniline (1 equivalent) were dissolved in DMF, and TEA (2 equivalents) was added. The reaction mixture was heated at 120° C. overnight. The reaction mixture was then cooled to room temperature, most of the DMF was distilled off, and water was added to the residue to obtain the crude product as a precipitate. The solid was dried and purified by chromatography on silica gel (2-10% $MeOH/CH_2Cl_2$) to afford the desired product, 5-morpholin-4-yl-2-nitro-phenylamine.

The various 2-amino benzoic acid starting materials used to synthesize isatoic anhydrides may be obtained from commercial sources, prepared by methods known to one of skill in the art, or prepared by the following general methods. General isatoic anhydride synthesis methods are described in *J. Med. Chem.* 1981, 24 (6), 735 and *J. Heterocycl. Chem.* 1975, 12(3), 565.

Method 10:

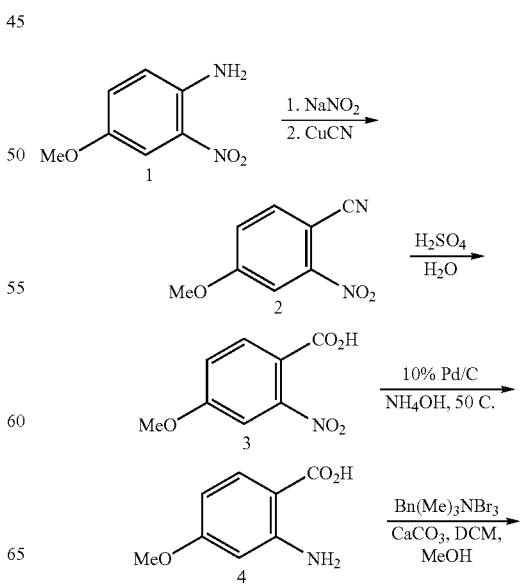

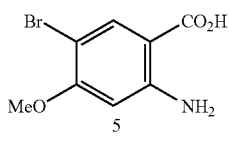

Compounds 1-3 were made using similar procedures to those in U.S. Pat. No. 4,287,341 which is herein incorporated by reference in its entirety for all purposes as if fully set forth herein. Compound 3 was reduced using standard hydrogenation conditions of 10% Pd/C in NH₄OH at 50° C. over 48 hours. The product was precipitated by neutralizing with glacial acetic acid, filtering, and washing with water and ether. Yields were about 50%. Compound 5 was prepared in a manner similar to that disclosed in U.S. Pat. No. 5,716,993 herein incorporated by reference in its entirety for all purposes as if fully set forth herein.

Method 11:

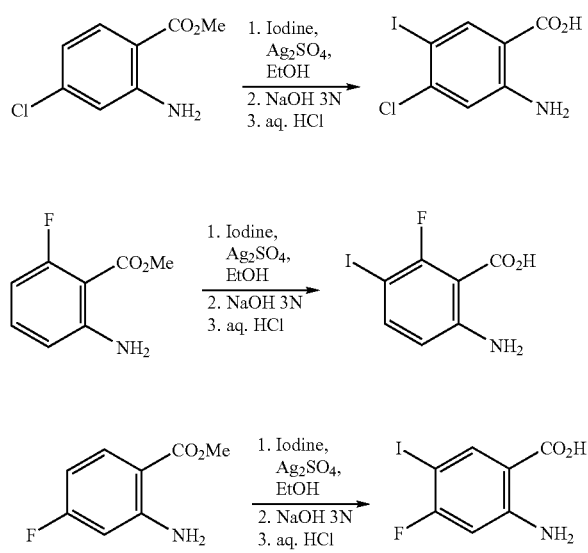

Iodination of aniline containing compounds: Iodination was accomplished using a procedure similar to that set forth in the following reference which is herein incorporated by reference in its entirety for all purposes as if fully set forth herein: *J. Med. Chem.* 2001, 44, 6, 917-922. The anthranilic ester in EtOH was added to a mixture of silver sulfate (1 equivalent) and I₂ (1 equivalent). The reaction was typically done after 3 hours at room temperature. The reaction was filtered through Celite and concentrated. The residue was taken up in EtOAc and washed with aqueous saturated NaHCO₃ (3×), water (3×), brine (1×), dried (MgSO₄), filtered, and concentrated. The crude product (~5 g) was dissolved in MeOH (60-100 mL), NaOH 6 N (25 mL), and water (250 mL). The reactions were typically done after heating at 70-80° C. for 4 hours. The reaction mixture was extracted with EtOAc (2×), neutralized with aqueous HCl, filtered to collect the solids, and the solid products were washed with water. The products were dried in vacuo.

Method 12:

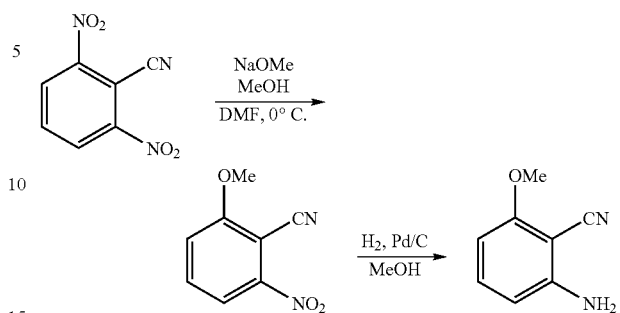

2-Amino-6-methoxy-benzonitrile

The title compound was prepared from 2,6-dinitrobenzonitrile following literature procedures set forth in the following references which are herein incorporated by reference in their entirety for all purposes as if fully set forth herein: Harris, V. N.: Smith, C; Bowden, K.; *J. Med. Chem.* 1990, 33, 434; and Sellstedt, J. H. et al. *J. Med. Chem.* 1975, 18, 926. LC/MS m/z 405.4 (MH+), $R_t$ 1.71 minutes.

Method 13:

2-Amino-4-fluorobenzenecarbonitrile

The title compound was obtained from commercially available 2-nitro-4-fluorobenzenecarbonitrile via reduction with SnCl₂ in concentrated HCl as previously described in the following reference which is herein incorporated by reference in its entirety for all purposes as if fully set forth herein: Hunziker, F. et Al. *Eur. J. Med. Chem., Chim. Ther.* 1981, 16(5), 391. GC/MS m/z: 136.1 (M+, 100%), $R_t$ 9.26 minutes.

Method 14:

2-Amino-5-fluorobenzenecarbonitrile

The title compound was synthesized from commercially available 2-nitro-5-fluorobenzenecarbonitrile via reduction with SnCl₂ in concentrated HCl as previously described in the following reference which is herein incorporated by reference in its entirety for all purposes as if fully set forth herein: Hunziker, F. et al. *Eur. J. Med. Chem., Chim. Ther.* 1981, 16(5), 391. GC/MS m/z: 136.1 (M+, 100%), $R_t$ 8.87 minutes.

Method 15:

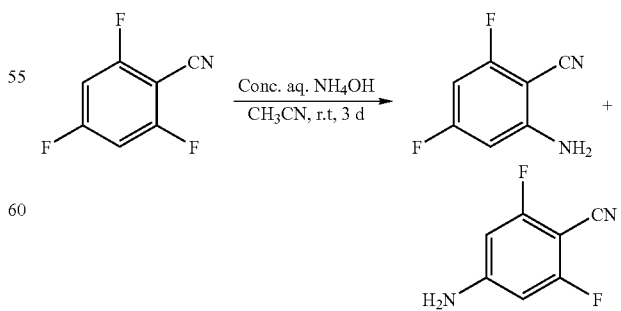

The depicted compounds were synthesized following a procedure in WO 97/14686 which is herein incorporated by reference in its entirety for all purposes as if fully set forth herein. 2,4,6-Trifluorobenzonitrile was dissolved in a mixture of CH₃CN and concentrated aqueous NH₄OH (1:2) and stirred at room temperature for two days. The reaction mixture was concentrated and extracted with CH₂Cl₂. The organic extracts were collected, dried (Na₂SO₄), and evaporated to afford an approximately 1:1 mixture of 2-amino-4,6-difluoro benzonitrile and 4-amino-2,6-difluorobenzonitrile. The desired 2-amino-4,6-difluoro benzonitrile was isolated by column chromatography on silicagel (EtOAc/Hexanes 1:2) as the compound with higher $R_f$; LC/MS m/z 155.1 (MH+), $R_t$ 2.08 minutes; GC/MS m/z 154.1 (M+), $R_t$ 9.35 minutes.

Method 16:

2-Amino-6-trifluoromethylbenzenecarbonitrile

2-Fluoro-6-trifluoromethylbenzenecarbonitrile was heated at 100° C. in a saturated solution of NH₃ in EtOH overnight. The reaction mixture was concentrated and the residue was purified by column chromatography on silicagel (EtOAc/Hexanes 1:5), to obtain the title compound as a white solid. GC/MS m/z 186.1 (M+), $R_t$ 10.1 minutes.

Method 17:

5-Acetyl-2-aminobenzenecarbonitrile

The title compound was obtained from commercially available precursors as described in Goidl, J. O. and Claus, T. H., U.S. Pat. No. 4,814,350 which is herein incorporated by reference in its entirety for all purposes as if fully set forth herein. GC/MS m/z: 160 (M+, 45%), $R_t$ 15.04 minutes; LC/MS m/z: 161.2 (MH+), $R_t$ 1.75 minutes.

Method 18:

Dimethyl(1,4-oxazaperhydroepin-2-ylmethyl)amine

The title compound was obtained from 3-aminopropan-1-ol according to the synthetic route outlined above for (2S, 5R)-2-[dimethylamino(methyl)]-5-methylmorpholine (see also: Harada H. et al *Chem. Pharm. Bull.*, 1995, 43(8), 1364 and Freifelder. M. et al, *J. Am. Chem. Soc.*, 1958, 80, 4320 which are both hereby incorporated by reference in their entirety for all purposes as if fully set forth herein). LC/MS m/z 159.1 (MH+), $R_t$ 0.39 minutes.

Method 19:

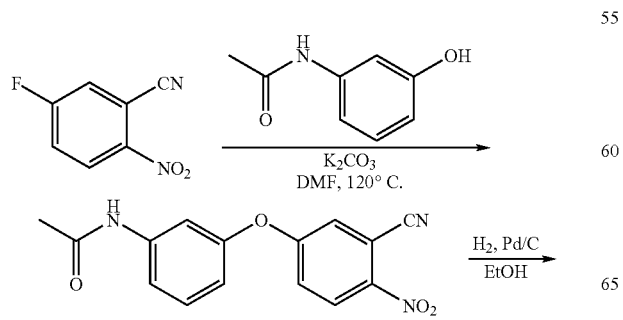

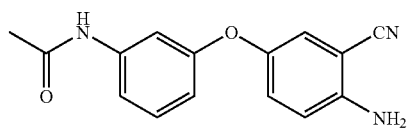

Step 1: 2-Nitro-5-(3-acetamido)phenoxybenzene carbonitrile

5-Fluoro-2-nitrobenzenecarbonitrile and 3-acetamidophenol were dissolved in DMF, and solid K₂CO₃ (2 equivalents) was added in one portion. The reaction mixture was heated at 120° C. overnight. The reaction mixture was cooled to room temperature, most of the DMF was distilled off and water was added to the residue. The solid thus obtained was filtered off and dried to afford the desired product. LC/MS m/z: 298.1 (MH+), $R_t$ 2.55 minutes.

Step 2: 2-Amino-5-(3-acetamido)phenoxybenzene carbonitrile

2-Nitro-5-(3-acetamido)phenoxybenzene carbonitrile was dissolved in EtOH, and 10% Pd/C was added. The reaction flask was evacuated and purged with H₂ three times. The reaction mixture was stirred under 1 atm of H₂ overnight, then filtered and concentrated. The residue was purified by chromatography on silicagel (2-5% MeOH/CH₂Cl₂) to afford the desired product. LC/MS m/z: 268.2 (MH+), $R_t$ 2.28 minutes Method 20:

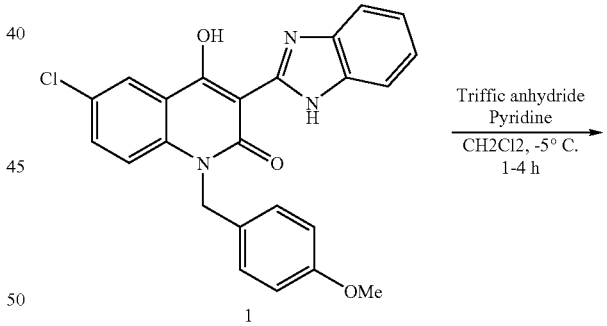

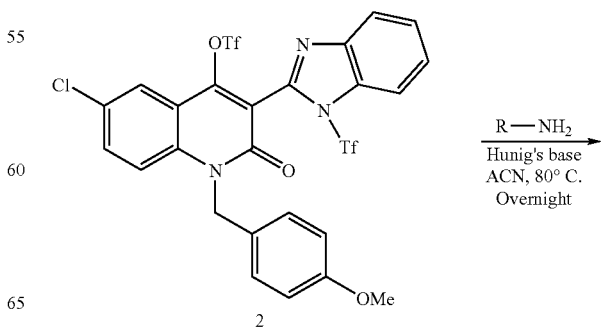

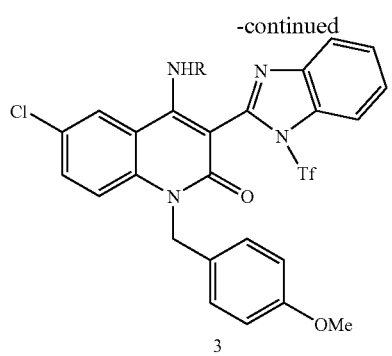

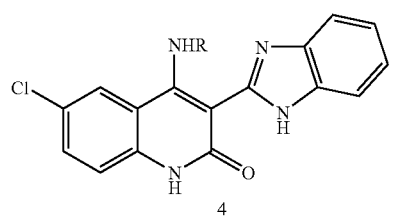

3-(1H-Benzoimidazol-2-yl)-6-chloro-4-hydroxy-1-(4-methoxy-benzyl)-1H-quinolin-2-one (1) (1 equivalent) was suspended in methylene chloride or chloroform (0.01 M) in the presence of pyridine (20 equivalents). The mixture was warmed to ensure maximum solubilization. The mixture was then cooled to −5° C. and triflic anhydride (8 equivalents) was added dropwise. The reaction mixture was stirred at −5° C. until the reaction was complete (1 to 4 hours), and saturated aqueous NaHCO$_3$ was added. The aqueous phase was extracted with CH$_2$Cl$_2$, and the organic extracts were collected, washed with 1 M citric acid solution (×1), 1 M NaHCO$_3$ solution, water (×1), and dried over Na$_2$SO$_4$. The solvent was evaporated under reduced pressure to afford the title compound, 6-chloro-1-[(4-methoxyphenyl)methyl]-2-oxo-3-{1-[(trifluoromethyl)sulfonyl]-benzimidazol-2-yl}-4-hydroquinolyl (trifluoromethyl)sulfonate (2), as a solid.

A solution of 6-chloro-1-[(4-methoxyphenyl)methyl]-2-oxo-3-{1-[(trifluoromethyl)sulfonyl]-benzimidazol-2-yl}-4-hydroquinolyl (trifluoromethyl)sulfonate (2) (1 equivalent), an appropriate amine (1.2 equivalents), and Hunig's base (4 equivalents) in acetonitrile (0.15 M), was heated at 80° C. for 20 hours. The reaction mixture was cooled to room temperature, diluted with EtOAc, washed with saturated aqueous NaHCO$_3$, water, and brine, and dried over Na$_2$SO$_4$. The organic solution was concentrated and the product thus obtained (3) was directly used in the next step. Compound 3 was dissolved in a mixture of trifluoroacetic acid and concentrated HCl (7:1) and heated at 90° C. overnight. The reaction mixture was cooled to room temperature, and then water was added. The aqueous solution was washed with EtOAc and then made basic by addition of saturated NaHCO$_3$. The precipitate thus formed was collected by filtration, washed with water, and dried to afford the desired product, (4).

Method 21:

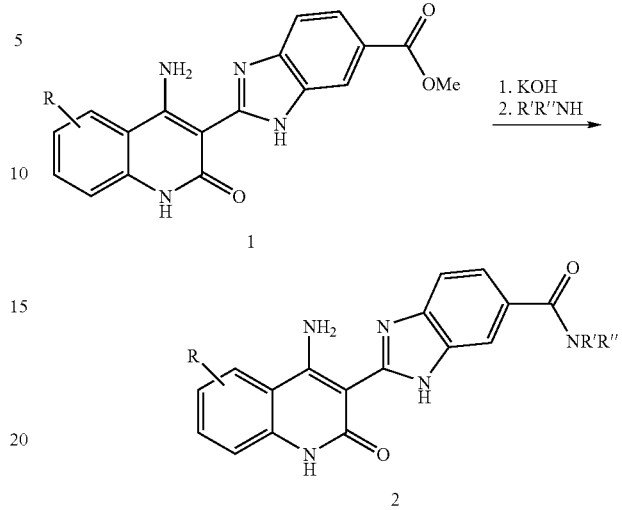

The crude methyl ester (1) was dissolved in a 1:1 mixture of EtOH and 30% aqueous KOH and stirred overnight at 70° C. The reaction mixture was then cooled and acidified with 1 N HCl to give a precipitate. The solid was filtered, washed with water and dried to obtain 2-(4-amino-2-oxo-1,2-dihydroquinolin-3-yl)-1H-benzimidazole-6-carboxylic acid as a brown solid. LC/MS m/z: 321.1 (MH+), R$_t$ 2.26 minutes.

A mixture of 2-(4-amino-2-oxo-1,2-dihydroquinolin-3-yl)-1H-benzimidazole-6-carboxylic acid (1 equivalent) the amine (1 equivalent), EDC (1-(3-dimethylaminopropyl)-3-ethylcarbodiimide hydrochloride, 1.2 equivalents), HOAT (1-hydroxy-7-azabenzotriazole, 1.2 equivalents) and triethylamine (2.5 equivalents) in DMF, was stirred at 23° C. for 20 hours. The reaction mixture was partitioned between water and ethyl acetate. The combined organic layers were dried (Na$_2$SO$_4$) and concentrated. Water was added and the precipitate thus formed was filtered off and dried to afford the desired amide product (2).

Method 22:

A 7-Fluoroquinolinone derivative in a 8 M solution of MeNH$_2$ in EtOH:NMP (1:1), was submitted to microwave irradiation 4 times for 5 minutes at 220° C. After cooling, water was added, and the mixture was extracted with EtOAc. The organic extracts were collected and dried over Na$_2$SO$_4$. Evaporation of the solvent under reduced pressure and purification of the residue by reverse phase preparative HPLC afforded the desired product. Other primary and secondary amines were used neat, 1:1 with NMP.

Method 23:

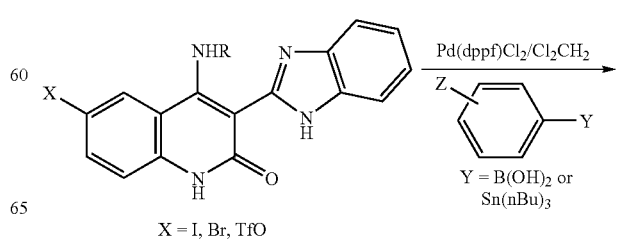

-continued

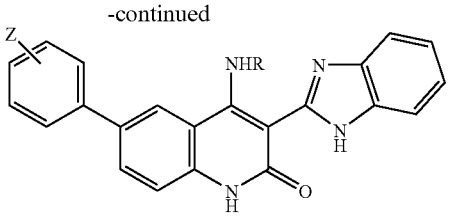

Conversion of the C-6 or C-7 halides to an aryl group was accomplished using standard Suzuki or Stille procedures such as described below.

Suzuki Method: To a 1 dram (4 mL) vial was added sequentially the quinolone (1 equivalent), boronic acid (1.2-1.5 equivalents), Pd(dppf)Cl$_2$, Cl$_2$CH$_2$ (0.2 equivalents), DMF (0.5-1 mL), and TEA (4 equivalents). The reaction was flushed with argon, capped, and heated at 85° C. for 12 hours. Once complete, the reaction was cooled to room temperature, and filtered with a syringe filter disk. The clear solution was then neutralized with TFA (a couple of drops) and injected directly onto a preparative HPLC. The products were lyophilized to dryness.

Stille Method: To a 1 dram (4 mL) vial was added sequentially the quinolone (1 equivalent), tin reagent (1.8 equivalent), Pd(dppf)Cl$_2$. Cl$_2$CH$_2$ (0.2 equivalents), and DMF (0.5-1 mL). The reaction was flushed with argon, capped, and heated at 60-85° C. for 4 hours. Once complete, the reaction was cooled to room temperature, and filtered with a syringe filter disk. The clear solution was then neutralized with TFA (a couple of drops) and injected directly onto a preparative HPLC. The products were lyophilized to dryness.

Method 24:

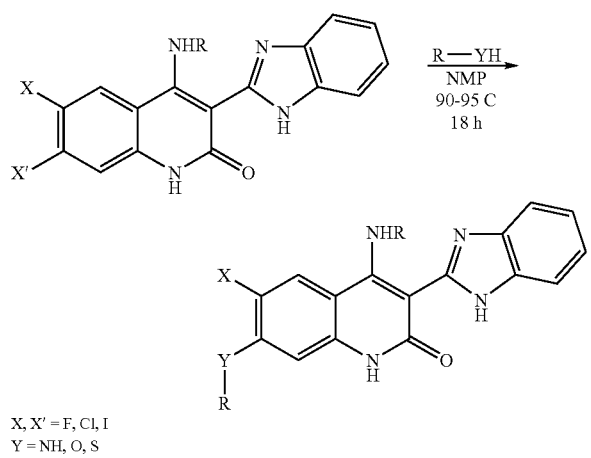

X, X' = F, Cl, I
Y = NH, O, S

A dihaloquinolone such as a difluoroquinolone (12-15 mg) was placed in a 1 dram (2 mL) vial. NMP (dry and pre-purged with argon for 5 minutes) was added to the vial (0.5 mL). A selected amine reagent (40-50 mg) was added next. If the amine was an HCl salt, the reaction was neutralized with TEA (~1.2-1.5 equivalents). The reaction was purged again with argon for about 5 seconds, and immediately capped. The reaction was typically heated in a heating block at 90-95° C. for 18 hours. The reaction was followed by HPLC or LCMS. After taking samples for HPLC, the vial was purged with argon again and capped. Some coupling partners took 24 or 48 hours to reach completion. Less nucleophilic amines like pyrrole required the addition of a strong base to reach completion. In these cases, cesium carbonate (2 equivalents based on the amine used) was added to the reaction. Once complete, the reaction was cooled to room temperature, and filtered with a syringe filter disk. The clear solution was then neutralized with TFA (a couple of drops) and injected directly onto a preparative HPLC. The products were lyophilized to dryness.

Example 1

Synthesis of 4-Amino-3-benzimidazol-2-yl-6-(4-methylpiperazinyl)hydroquinolin-2-one Step 1: Ethyl 2-benzimidazol-2-ylacetate A solution of 1,2-phenylenediamine (1.0 equivalent) and ethyl 3-ethoxy-3-iminopropanoate hydrochloride (1.3 equivalents) in ethanol was stirred at 90° C. overnight. The reaction was cooled to room temperature and the solvent was removed in vacuo. Water and CH$_2$Cl$_2$ were added to the residue. The organic layer was separated, dried over Na$_2$SO$_4$ and the solvent removed. The solid recovered was used without purification. LC/MS m/z 205.2 (MH+), R$_t$ 1.44 minutes.

Step 2:
5-(4-Methylpiperazinyl)-2-nitrobenzenecarbonitrile

5-Fluoro-2-nitrobenzenecarbonitrile (1.02 equivalents) and N-methylpiperazine (1.0 equivalents) were dissolved in NMP. Triethylamine (2.1 equivalents) was added, and the resulting solution heated at 100° C. for 1 hour. The solution was cooled to room temperature and poured into H$_2$O. A precipitate formed which was filtered to yield the desired product as a green solid. LC/MS m/z 247.3 (MH+), R$_t$ 1.46 minutes.

Step 3:
2-Amino-5-(4-methylpiperazinyl)benzenecarbonitrile 5-(4-Methylpiperazinyl)-2-nitrobenzenecarbonitrile (1.0 equivalent) was dissolved in EtOAc. The flask was purged with nitrogen, and 10% Pd/C (0.1 equivalents) was added. The flask was evacuated and purged with H$_2$ three times. The resulting mixture was stirred for three days at room temperature. The mixture was filtered through Celite and the filter pad was washed with EtOAc. The solvent was removed in vacuo to give a yellow solid which was purified by silica gel chromatography (5:1:95 MeOH:Et$_3$N:EtOAc) to give the desired product as a yellow solid. LC/MS m/z 217.3 (MH+), R$_t$ 0.95 minutes.

Step 4: 4-Amino-3-benzimidazol-2-yl-6-(4-methylpiperazinyl)hydroquinolin-2-one

Ethyl 2-benzimidazol-2-ylacetate (1.1 equivalents) and 2-amino-5-(4-methylpiperazinyl)benzenecarbonitrile (1.0 equivalent) were dissolved in 1,2-dichloroethane, and then SnCl$_4$ (11 equivalents) was added. The mixture was heated at reflux overnight. Upon cooling, the mixture was concentrated in vacuo. NaOH (3 M) was added to the solid, and the mixture heated at 80° C. for 0.5 hours. The solid was filtered and washed sequentially with H$_2$O, CH$_2$Cl$_2$, and acetone. LC/MS indicated that the product was present in the acetone layer and the solid. These fractions were combined and purified by silica gel chromatography (5-10% MeOH in CH$_2$Cl$_2$ with 1% Et$_3$N) to give the desired product. LC/MS m/z 375.4 (MH+), R$_t$ 1.65 minutes.

Example 2

Synthesis of 4-Amino-3-benzimidazol-2-yl-5-(2-morpholin-4-ylethoxy)hydroquinolin-2-on

Step 1: 6-Amino-2-(2-morpholin-4-ylethoxy)benzenecarbonitrile 4-(Hydroxyethyl)morpholine (1.02 equivalents) was added to NaH (1.2 equivalents) in NMP. After 10 minutes, 6-amino-2-fluorobenzenecarbonitrile (1.0 equivalent) was added in NMP. The resulting mixture was heated at 100° C. for 1 hour. The mixture was then cooled and poured into $H_2O$. The aqueous layer was extracted with EtOAc. The combined organic layers were washed with brine, dried over $Na_2SO_4$, filtered, and concentrated in vacuo to a yield a brown gum. The crude material was purified by silica gel chromatography (5:1:95 MeOH:$Et_3$N:EtOAc) to give the desired product. LC/MS m/z 248.3 (MH+), $R_t$ 1.26 minutes.

Step 2: 4-Amino-3-benzimidazol-2-yl-5-(2-morpholin-4-ylethoxy)hydroquinolin-2-one The title compound was synthesized as described in Example 1 (Step 4), using 6-amino-2-(2-morpholin-4-ylethoxy)benzenecarbonitrile. LC/MS m/z 406.4 (MH+), $R_t$ 1.67 minutes.

Example 3

Synthesis of 4-Amino-3-[5-(2-morpholin-4-ylethoxy)benzimidazol-2-yl]-6-nitrohydroquinolin-2-one

Step 1: 4-(2-Morpholin-4-ylethoxy)-2-nitrophenylamine

Diisopropyl azodicarboxylate (1.1 equivalents) was added dropwise to a stirred solution of 4-amino-3-nitrophenol (1.0 equivalent), triphenylphosphine (1.1 equivalents), and N-(2-hydroxyethyl)morpholine (1.0 equivalent), in THF at 0° C. The mixture was allowed to warm to room temperature and left to stir for 18 hours. The solvent was evaporated and the product was purified by silica gel chromatography (98:2 $CH_2Cl_2$:MeOH) to yield a dark reddish-brown oil. LC/MS m/z 268.0 (MH+), $R_t$ 1.01 minutes.

Step 2: 4-(2-Morpholin-4-ylethoxy)benzene-1,2-diamine

To a solution 4-(2-morpholin-4-ylethoxy)-2-nitrophenylamine (1.0 equivalent) in EtOH was added Pd/C (0.1 equivalents). The reaction vessel was repeatedly purged with hydrogen, then stirred under a hydrogen atmosphere (1 atm) for 18 hours. The product was filtered through a Celite plug, and the plug washed with EtOH. The diamine was used without purification. LC/MS m/z 238.3 (MH+), $R_t$ 0.295 minutes.

Step 3: Ethyl 2-[5-(2-morpholin-4-ylethoxy)benzimidazol-2-yl]acetate

The title compound was synthesized as described in Example 1 using 4-(2-morpholin-4-ylethoxy)benzene-1,2-diamine. The organic layer was concentrated and the residue was purified by silica gel chromatography (10:1:2 $CH_2Cl_2$:MeOH:EtOAc) to yield a dark reddish brown oil. LC/MS m/z 334.4 (MH+) $R_t$ 1.08 minutes.

Step 4: 4-Amino-3-[5-(2-morpholin-4-ylethoxy)benzimidazol-2-yl]-6-nitrohydroquinolin-2-one The title compound was synthesized as described in Example 1 (Step 4), using ethyl 2-[5-(2-morpholin-4-ylethoxy)benzimidazol-2-yl]acetate and 5-nitroanthranilonitrile. The crude product was purified by silica gel chromatography (5-10% MeOH in $CH_2Cl_2$ with 1% $Et_3$N) to give the desired product. LC/MS m/z 451.2 (MH+), $R_t$ 1.89 minutes.

Example 4

Synthesis of 4-Amino-5-(2-morpholin-4-ylethoxy)-3-[5-(2-morpholin-4-ylethoxy)-benzimidazol-2-yl]hydroquinolin-2-one The title compound was synthesized as described in Example 1 (Step 1), using ethyl 2-[5-(2-morpholin-4-ylethoxy)benzimidazol-2-yl]acetate and 6-amino-2-(2-morpholin-4-ylethoxy)benzenecarbonitrile. LC/MS m/z 535.4 (MH+), $R_t$ 1.44 minutes.

Example 5

Synthesis of [2-(4-amino-2-oxo(3-hydroquinolyl))benzimidazol-5-yl]-N,N-dimethylcarboxamide

Step 1: 2-[(Ethoxycarbonyl)methyl]benzimidazole-5-carboxylic acid

The title compound was synthesized as described in Example 1 using 3,4-diaminobenzoic acid. The crude material was purified by silica gel chromatography (5:95 MeOH:$CH_2Cl_2$) to afford the desired product as a white to off-white solid. LC/MS m/z 249.1 (MH+), $R_t$ 1.35 minutes.

Step 2: Ethyl 2-[5-(N,N-dimethylcarbamoyl)benzimidazol-2-yl]acetate

2-[(Ethoxycarbonyl)methyl]benzimidazole-5-carboxylic acid (1.0 equivalent) was dissolved in THF. HBTU (1.1 equivalents) and diisopropylethylamine (2.0 equivalents) were added, followed by dimethylamine (2.0 M in THF, 1.1 equivalents). The reaction was stirred at room temperature overnight then concentrated and the resulting residue was purified by silica gel chromatography (5:95 MeOH:$CH_2Cl_2$) to afford the desired compound. LC/MS m/z 276.2 (MH+), $R_t$ 1.18 minutes.

Step 3: [2-(4-amino-2-oxo(3-hydroquinolyl))benzimidazol-5-yl]-N,N-dimethylcarboxamide The title compound was synthesized as described in Example 1 (Step 4), using ethyl 2-[5-(N,N-dimethylcarbamoyl)benzimidazol-2-yl]acetate and anthranilonitrile. The resulting solid was collected by filtration and washed with water followed by acetone to afford the desired product as a white solid. LC/MS m/z 348.3 (MH+), $R_t$ 1.87 minutes.

Example 6

Synthesis of 4-Amino-3-[5-(morpholin-4-ylcarbonyl)benzimidazol-2-yl]hydroquinolin-2-one 2-[(Ethoxycarbonyl)methyl]benzimidazole-5-carboxylic acid (1.0 equivalent) was dissolved in THF. HBTU (1.1 equivalents) and diisopropylethylamine (2.0 equivalents)

were added, followed by morpholine (1.1 equivalents). The reaction was stirred at room temperature for 3 days then concentrated and purified by silica gel chromatography (5-10% methanol/dichloromethane). The product-containing fractions were concentrated and dissolved in anhydrous 1,2-dichloroethane. Anthranilonitrile (1.0 equivalent) was added followed by $SnCl_4$ (5.0 equivalents) and the reaction was heated at 90° C. overnight. The reaction mixture was concentrated and the resulting residue was re-dissolved in NaOH (2 M) and heated at 90° C. for 4 hours. After cooling to room temperature, the resulting solid was collected and washed with water followed by acetone to afford the desired product. LC/MS m/z 390.2 (MH+), $R_t$ 1.95 minutes.

Example 7

Synthesis of 4-Amino-3-[5-(2-thienyl)benzimidazol-2-yl]hydroquinolin-2-one

Step 1: 4-Bromobenzene-1,2-diamine

A solution of 4-bromo-2-nitroaniline (1.0 equivalent) and $SnCl_2$ (2.2 equivalents) in EtOH was heated at reflux for 3 hours. After this time, the solution was poured onto ice, brought to pH 10 with 2 M NaOH and extracted with $Et_2O$. The combined organic layers were dried over $MgSO_4$ and concentrated. The resulting brown oil was purified by silica gel chromatography (0-50% EtOAc:hexanes) to provide a light yellow solid. LC/MS m/z 187.1 (MH+), $R_t$ 1.33 minutes.

Step 2: 2-Nitro-4-(2-thienyl)phenylamine

4-Bromobenzene-1,2-diamine (1.0 equivalent) and $Na_2CO_3$ (2.0 equivalents) were dissolved in $DMF/H_2O$ (5:1) at room temperature. Nitrogen was bubbled through the reaction mixture for 5 minutes and $PdCl_2(dppf)_2$ (0.1 equivalents) was added. After stirring at 23° C. for approximately 10 minutes, 2-thiopheneboronic acid (1.1 equivalents) in DMF was added and the reaction was heated at 90° C. for 12 hours. After this time, the solution was concentrated and partitioned between EtOAc and $H_2O$. The layers were separated and the aqueous layer was extracted with EtOAc. The combined organic layers were dried over $MgSO_4$ and concentrated under reduced pressure. The resulting black residue was purified by silica gel chromatography (0-20% EtOAc:hexanes) to yield an orange solid. LC/MS m/z 221.1 (MH+), $R_t$ 2.67 minutes.

Step 3: Ethyl 2-[5-(2-thienyl)benzimidazol-2-yl]acetate

2-Nitro-4-(2-thienyl)phenylamine (1.0 equivalent) and 10% Pd/C (0.1 equivalents) were suspended in anhydrous EtOH at room temperature. The reaction flask was evacuated and subsequently filled with $H_2$. The resulting mixture was allowed to stir under a hydrogen atmosphere for 3 hours. Ethyl 3-ethoxy-3-iminopropanoate hydrochloride (2.0 equivalents) was then added and the resulting mixture was heated at reflux for 12 hours. After this time, the solution was filtered through a plug of Celite, concentrated, dissolved in 50 mL of 2 N HCl and washed with $CH_2Cl_2$. The aqueous layer was brought to pH 12 with concentrated $NH_4OH(aq)$ and extracted with $CH_2Cl_2$. The combined organic layers were dried with $MgSO_4$ and concentrated to yield a brown oil which was purified by silica gel chromatography (5:95 $MeOH:CH_2Cl_2$) to provide a yellow solid. LC/MS m/z 287.1 (MH+), $R_t$ 1.98 minutes.

Step 4: 4-Amino-3-[5-(2-thienyl)benzimidazol-2-yl]hydroquinolin-2-one

The title compound was synthesized as described in Example 1 (Step 4), using ethyl 2-[5-(2-thienyl)benzimidazol-2-yl]acetate and anthranilonitrile. LC/MS m/z 359.2 (MH+), $R_t$ 2.68 minutes.

Example 8

Synthesis of 4-Amino-3-{5-[1-(1,2,4-triazolyl)]benzimidazol-2-yl}hydroquinolin-2-one Step 1: 5-Fluoro-2-nitrophenylamine The synthesis was performed according to Method 1. The crude product was purified by flash chromatography on silica gel (85:15 hexanes:EtOAc, product at $R_f$=0.32, contaminant at $R_f$=0.51). GC/MS m/z 156.1 (M+), $R_t$ 11.16 minutes.

Step 2: 2-Nitro-5-[1-(1,2,4-triazolyl)]phenylamine

5-Fluoro-2-nitrophenylamine (1.0 equivalent), 1H-1,2,4-triazole (3.0 equivalents) and NaH (3.0 equivalents) in NMP were heated at 100° C. for 1 hour. The solution was cooled to room temperature and slowly poured onto ice water. The resulting precipitate was filtered and dried under vacuum to yield the desired product. The resulting solid was recrystallized from EtOH to afford pure product as a bright yellow solid. LC/MS m/z 206.2 (MH+), $R_t$ 1.88 minutes.

Step 3: Ethyl 2-{5-[1-(1,2,4-triazolyl)]benzimidazol-2-yl}acetate

The title compound was synthesized as described in Example 7 using 2-nitro-5-[1-(1,2,4-triazolyl)]phenylamine. LC/MS m/z 272.1 (MH+), $R_t$ 1.19 minutes.

Step 4: 4-Amino-3-{5-[1-(1,2,4-triazolyl)]benzimidazol-2-yl}hydroquinolin-2-one

The title compound was synthesized as described in Example 1 (Step 4), using ethyl 2-{5-[1-(1,2,4-triazolyl)]benzimidazol-2-yl}acetate and anthranilonitrile. The crude solid was collected and purified by silica gel chromatography (92:7:1 $CH_2Cl_2$:MeOH:$Et_3N$). LC/MS m/z 344.3 (MH+), $R_t$ 2.01 minutes.

Example 9

Synthesis of 4-Amino-6-chloro-3-(5-morpholin-4-ylbenzimidazol-2-yl)hydroquinolin-2-one N-(4-Chloro-2-cyanophenyl)-2-(5-morpholin-4-yl-benzimidazol-2-yl)acetamide LiHMDS (2.5 equivalents) was added to ethyl 2-[5-(2-morpholin-4-ylethoxy)benzimidazol-2-yl]acetate (1.0 equivalent) in THF at −78° C. After 1 hour, 2-amino-5-chlorobenzenecarbonitrile (0.82 equivalents) in THF was added. The reaction was allowed to warm to 23° C. and stirred overnight. The resulting mixture was quenched with $NH_4Cl$ (aqueous saturated solution) and extracted with EtOAc. The combined organic layers were washed with $H_2O$ and brine, dried over $Na_2SO_4$, filtered and concentrated in vacuo to yield a brown solid. The crude material was purified by silica gel chromatography (5:1 EtOAc:hexane) to give the desired product. LC/MS m/z 396.1 (MH+), $R_t$ 1.79 minutes. N-(4-chloro-2-cyanophenyl)-2-(5-morpholin-4-ylbenzimidazol-2-yl)acetamide (1.0 equivalent) was heated in NaOMe (0.5 M in MeOH, 18 equivalents) at 70° C. for 2 hours. The resulting mixture was cooled, and the resulting solid was filtered and washed with water to give the desired product. LC/MS m/z 396.4 (MH+), $R_t$ 2.13 minutes.

Example 10

Synthesis of 4-amino-3-(5-piperidylbenzimidazol-2-yl)hydroquinolin-2-one

Step 1: 2-Nitro-5-piperidylphenylamine

The title compound was synthesized as described in Method 1 using piperidine (3.0 equivalents). The desired product was obtained as a yellow, crystalline solid. LC/MS m/z 222.2 (MH+), $R_t$ 2.53 minutes.

Step 2: Ethyl 2-(5-piperidylbenzimidazol-2-yl)acetate

The title compound was synthesized as described in Example 7 using 2-nitro-5-piperidylphenylamine. The desired product was obtained as a yellow oil. LC/MS m/z 288.3 (MH+), $R_t$ 1.31 minutes.

Step 3: 4-amino-3-(5-piperidylbenzimidazol-2-yl)hydroquinolin-2-one

The title compound was synthesized as described in Example 9 using ethyl 2-(5-piperidylbenzimidazol-2-yl)acetate and anthranilonitrile. The acyclic amide was used crude in the NaOMe cyclization step. The desired product was obtained following purification by silica gel chromatography (96.5:3.0:0.5 $CH_2Cl_2$:MeOH:$Et_3N$, $R_f$ 0.2). LC/MS m/z 360.4 (MH+), $R_t$ 1.83 minutes.

Example 11

Synthesis of 4-Amino-3-{5-[3-(dimethylamino)pyrrolidinyl]benzimidazol-2-yl}-6-chlorohydroquinolin-2-one Step 1: [1-(3-Amino-4-nitrophenyl)pyrrolidin-3-yl]dimethylamine The title compound was synthesized as described in Method 1 using 3-(dimethylamino)pyrrolidine (3.0 equivalents). LC/MS m/z 251.3 (MH+), $R_t$ 1.25 minutes.

Step 2: Ethyl 2-{5-[3-(dimethylamino)pyrrolidinyl]benzimidazol-2-yl}acetate

The title compound was synthesized as described in Example 7 using [1-(3-amino-4-nitrophenyl)pyrrolidin-3-yl]dimethylamine. The desired product was obtained as a yellow oil. LC/MS m/z 317.4 (MH+), $R_t$ 1.36 minutes.

Step 3: 4-Amino-3-{5-[3-(dimethylamino)pyrrolidinyl]benzimidazol-2-yl}-6-chlorohydroquinolin-2-one The title compound was synthesized as described in Example 9 using 2-{5-[3-(dimethylamino)pyrrolidinyl]benzimidazol-2-yl}-N-(4-chloro-2-cyanophenyl)acetamide. LC/MS m/z 423.4 (MH+), $R_t$ 1.71 minutes.

Example 12

Synthesis of 4-Amino-3-[5-(dimethylamino)benzimidazol-2-yl]hydroquinolin-2-one

Step 1: Ethyl 2-[5-(dimethylamino)benzimidazol-2-yl]acetate

The title compound was synthesized as described in Example 7 using (3-amino4-nitrophenyl)dimethylamine. The resulting tan film was purified by silica gel chromatography (5:1:94 MeOH:$Et_3N$:$CH_2Cl_2$) to give the desired product. LC/MS 248.3 m/z (MH+), $R_t$ 1.24 minutes.

Step 2: 4-Amino-3-[5-(dimethylamino)benzimidazol-2-yl]hydroquinolin-2-one

The title compound was synthesized as described in Example 9 using 2-[5-(dimethylamino)benzimidazol-2-yl]-N-(2-cyanophenyl)acetamide. LC/MS m/z 320.2 (MH+), $R_t$ 1.72 minutes.

Example 13

Synthesis of 2-(4-Amino-2-oxo-3-hydroquinolyl)benzimidazole-5-carbonitrile

Step 1: Ethyl 2-(5-cyanobenzimidazol-2-yl)acetate

The title compound was synthesized as described in Example 7 using 4-amino-3-nitro-benzonitrile. LC/MS m/z 230.2 (MH+), $R_t$ 1.29 minutes.

Step 2: 2-(4-Amino-2-oxo-3-hydroquinolyl)benzimidazole-5-carbonitrile

The title compound was synthesized as described in Example 9 using ethyl 2-(5-cyanobenzimidazol-2-yl)acetate and anthranilonitrile (no acyclic amide was observed so the NaOMe step was not needed). LC/MS m/z 302.3 (MH+), $R_t$ 2.62 minutes.

Example 14

Synthesis of 2-(4-Amino-2-oxo-3-hydroquinolyl)benzimidazole-5-carboxamidine 2-(4-Amino-2-oxo-3-hydroquinolyl)benzimidazole-5-carbonitrile (Example 13) (1.0 equivalent) in EtOH was placed into a glass pressure vessel, cooled to 0° C. and HCl (g) was bubbled through for 15 minutes. The pressure vessel was then sealed, brought to room temperature and stirred overnight. The solvent was removed in vacuo. The residue was dissolved in EtOH in a glass pressure vessel and cooled to 0° C. $NH_3$ (g) was bubbled through for 15 minutes and the pressure vessel was sealed and heated to 80° C. for 5 hours. The solvent was removed in vacuo and the crude product was purified by reversed-phase HPLC. LC/MS m/z 319.2 (MH+), $R_t$ 1.70 minutes.

Example 15

Synthesis of 4-Amino-3-[5-(2-morpholin-4-ylethoxy)-benzimidazol-2-yl]hydroquinolin-2-one The title compound was synthesized as described in Example 9 (Step 1), using anthranilonitrile. The crude acyclic amide was used without purification in the NaOMe cyclization step. The crude final product was purified by reversed-phase HPLC (DMSO/5% TFA). LC/MS m/z 406.4 (MH+), $R_t$ 1.56 minutes.

Example 16

Synthesis of 4-Hydroxy-3-(5-morpholin-4-ylbenzimidazol-2-yl)hydroquinolin-2-one

Step 1: 5-Morpholin-4-yl-2-nitrophenylamine

The title compound was synthesized as described in Method 9 using morpholine LC/MS m/z 224.1 (MH+), $R_t$ 1.89 minutes.

Step 2: Ethyl 2-(5-morpholin-4-ylbenzimidazol-2-yl)acetat 5-morpholin-4-yl-2-nitrophenylamine (1.0 equivalent), prepared as described in Method 9, and 10% Pd/C (0.1 equivalents) were suspended in anhydrous EtOH at room temperature. The reaction flask was evacuated and subsequently filled with $H_2$. The resulting mixture was stirred under a hydrogen atmosphere overnight. Ethyl 3-ethoxy-3-iminopropanoate hydrochloride (2.0 equivalents) was then added, and the resulting mixture was heated at reflux overnight. The resulting solution was filtered through Celite and evaporated under reduced pressure. The residue was suspended in $CH_2Cl_2$, and concentrated $NH_4OH$ was added until a pH of 11 was achieved. The $NH_4Cl$ thus formed was filtered off. The two phases were separated, and the organic phase was dried over $Na_2SO_4$. Evaporation of the solvent and trituration of the residue with ether afforded the title compound as a light green powder. LC/MS m/z 290.3 (MH+), $R_t$ 1.31 minutes.

Step 3: 4-Hydroxy-3-(5-morpholin-4-ylbenzimidazol-2-yl)hydroquinolin-2-one

To a solution of ethyl 2-(5-morpholin-4-ylbenzimidazol-2yl)acetate (1.0 equivalent) in anhydrous THF at −78° C. under an atmosphere of nitrogen was added LiHMDS (1 M in THF, 3.1 equivalents) and the solution was stirred for 1 hour. A solution of 1-benzylbenzo[d]1,3-oxazaperhydroine-2,4-dione (1.05 equivalents) in anhydrous THF was then added dropwise and the resulting solution was allowed to warm to 0° C. over 1 hour. The resulting mixture was quenched with a saturated aqueous solution of ammonium chloride and the organic layer was separated. The aqueous layer was extracted with $CH_2Cl_2$ (4 times). The combined organic layers were dried over $Na_2SO_4$, concentrated in vacuo, and the crude material was dissolved in toluene and heated at reflux for 16 hours. The toluene was removed in vacuo and the crude material was used without further purification. The product was obtained as a white solid. LC/MS m/z 453.1 (MH+), $R_t$ 2.91 minutes. Crude 4-hydroxy-3-(5-morpholin-4-ylbenzimidazol-2-yl)-1-benzylhydroquinolin-2-one (1.0 equivalent) was dissolved in trifluoromethanesulfonic acid and heated at 40° C. for 16 hours. The resulting solution was diluted with water and neutralized with 6 N NaOH (aq), whereupon a yellow precipitate formed. The crude solid was isolated by centrifugation and purified by reversed-phase HPLC to produce the desired product as a bright yellow solid. LC/MS m/z 363.3 (MH+), $R_t$ 1.77 minutes.

Example 17

Synthesis of 3-[5-(3-aminopyrrolidinyl)benzimidazol-2-yl]-4-hydroxyhydroquinolin-2-one

Step 1: N-[1-(3-Amino-4-nitrophenyl)pyrrolidin-3-yl](tert-butoxy)carboxamide The title compound was synthesized as described in Method 1 using 3-(tert-butoxycarbonylamino)pyrrolidine (1.01 equivalents) with diisopropylethylamine (2.0 equivalents). The product was obtained as an orange, crystalline solid. LC/MS m/z 323.3 (MH+), $R_t$ 2.53 minutes.

Step 2: Ethyl 2-(5-{3-[(tert-butoxy)carbonylamino]pyrrolidinyl}benzimidazol-2-yl)acetate The title compound was synthesized as described in Example 7 using N-[1-(3-amino-4-nitrophenyl)pyrrolidin-3-yl](tert-butoxy)carboxamide. The product was obtained as a yellow oil. LC/MS m/z 323.3 (MH+), $R_t$ 2.53 minutes.

Step 3: 3-[5-(3-aminopyrrolidinyl)benzimidazol-2-yl]-4-hydroxyhydroquinolin-2-one The title compound was synthesized following the procedure described in Example 16, using ethyl 2-(5-{3-[(tert-butoxy)carbonylamino]-pyrrolidinyl}benzimidazol-2-yl)acetate. The product was obtained as a yellow solid following cleavage of the benzyl group (see procedure in Example 15). LC/MS m/e 362.3 (MH+), $R_t$ 1.55 minutes.

Example 18

Synthesis of 3-(5-{[2-(Dimethylamino)ethyl]methylamino}benzimidazol-2-yl)-4-hydroxyhydroquinolin-2-one

Step 1: (3-Amino-4-nitrophenyl)[2-(dimethylamino)ethyl]methylamine

The title compound was synthesized as described in Example 8 using 1,1,4-trimethylethylenediamine (1.01 equivalents) with diisopropylethylamine (2.0 equivalents). The product was obtained as a bright yellow, crystalline solid. LC/MS m/z 239.3 (MH+), $R_t$ 1.29 minutes.

Step 2: Ethyl 2-(5-{[2-(dimethylamino)ethyl]methylamino}benzimidazol-2-yl)acetate The title compound was synthesized as described in Example 7 using (3-amino-4-nitrophenyl)[2-(dimethylamino)ethyl]methylamine. The desired product was obtained as a yellow oil. LC/MS m/z 305.2 (MH+), $R_t$ 1.17 minutes.

Step 3: 3-(5-{[2-(Dimethylamino)ethyl] methylamino}benzimidazol-2-yl)-4-hydroxy-1-benzylhydroquinolin-2-one The title compound was synthesized as described in Example 16, using ethyl 2-(5-{[2-(dimethylamino)ethyl] methylamino}benzimidazol-2-yl)acetate. The product was obtained as a pale yellow solid. LC/MS m/z 468.4 (MH+), $R_t$ 2.26 minutes.

Step 4: 3-(5-{[2-(Dimethylamino)ethyl] methylamin}benzimidazol-2-yl)-4-hydroxyhydroquinolin-2-one The title compound was synthesized as described in Example 16, using 3-(5-{[2-(dimethylamino)ethyl] methylamino}benzimidazol-2-yl)-4-hydroxy-1-benzylhydroquinolin-2-one. The crude material was purified by reversed-phase HPLC to yield the product as a yellow solid. LC/MS m/z 378.4 (MH+), $R_t$ 1.99 minutes.

Example 19

Synthesis of 4-[(2-methoxyethyl)amino]-3-(5-morpholin-4-ylbenzimidazol-2-yl)hydroquinolin-2-one

Step 1: 4-Chloro-3-(5-morpholin-4-ylbenzimidazol-2-yl)-1-benzylhydroquinolin-2-one A solution of 4-hydroxy-3-(5-morpholin-4-ylbenzimidazol-2-yl)-1-benzylhydroquinolin-2-one (1.0 equivalent) and POCl$_3$ in a dry, round-bottomed flask was heated at 80° C. for 2 hours. The excess POCl$_3$ was removed in vacuo, and the crude material was quenched with water. The crude product was collected by filtration and purified by silica gel chromatography (1:9 MeOH:CH$_2$Cl$_2$). 4-Chloro-3-(5-morpholin-4-ylbenzimidazol-2-yl)-1-benzylhydroquinolin-2-one was isolated as a red solid. LC/MS m/z 471.4 (MH+), $R_t$ 2.35 minutes.

Step 2: 4-[(2-Methoxyethyl)amino]-3-(5-morpholin-4-ylbenzimidazol-2-yl)-1-benzylhydroquinolin-2-one A solution of 4-chloro-3-(5-morpholin-4-ylbenzimidazol-2-yl)-1-benzylhydroquinolin-2-one (1.0 equivalent) and EtOH was treated with 2methoxyethyl-amine (10 equivalents) at room temperature. The resulting solution was heated at reflux for 16 hours and then the solvent was removed in vacuo. The crude solid was sonicated in water, filtered, sonicated in hexanes, and filtered again. The crude product was used without further purification. LC/MS m/z 510.4 (MH+), $R_t$ 2.20 minutes.

Step 3: 4-[(2-Methoxy thyl)amino]-3-(5-morpholin-4-ylbenzimidazol-2-yl)hydroquinolin-2-one 4-[(2-methoxyethyl)amino]-3-(5-morpholin-4-ylbenzimidazol-2yl)-1-benzylhydroquinolin-2-one was debenzylated using the procedure described in Example 16 to produce the title compound. LC/MS m/z 420.2 (MH+), $R_t$ 1.57 minutes.

4-[(2-hydroxyethyl)amino]-3-(5-morpholin-4-ylbenzimidazol-2-yl)hydroquinolin-2-one was produced as a side product (see below).

Example 20

Synthesis of 4-[(2-hydroxyethyl)amino]-3-(5-morpholin-4-ylbenzimidazol-2-yl)hydroquinolin-2-one The title compound was obtained as a side-product of the debenzylation of 4-[(2-methoxyethyl)amino]-3-(5-morpholin-4-ylbenzimidazol-2-yl)-1-benzylhydroquinolin-2-one using the procedure described in Example 16 and was isolated by reversed-phase HPLC as a yellow solid. LC/MS m/z 406.2 (MH+), $R_t$ 1.39 minutes.

Example 21

Synthesis of 4-(Methoxyamino)-3-(5-morpholin-4-ylbenzimidazol-2-yl)hydroquinolin-2-one

Step 1: 4-(Methoxyamino)-3-(5-morpholin-4-ylbenzimidazol-2-yl)-1-benzylhydroquinolin-2-one The title compound was synthesized as described in Example 19, using O-methylhydroxylamine. The product was used without purification.

Step 2: 4-(Methoxyamino)-3-(5-morpholin-4-ylbenzimidazol-2-yl)hydroquinolin-2-one The title compound was obtained as a yellow solid after debenzylation of 4-(methoxyamino)-3-(5-morpholin-4-ylbenzimidazol-2-yl)-1-benzylhydroquinolin-2-one using the procedure described in Example 16. LC/MS m/z 392.2 (MH+), $R_t$ 1.82 minutes.

Example 22

Synthesis of 3-(5-Morpholin-4-ylbenzimidazol-2-yl)-4-(3-piperidylamino)hydroquinolin-2-one

Step 1: tert-Butyl-3-{[3-(5-morpholin-4-ylbenzimidazol-2-yl)-2-oxo-1-benzyl-4-hydroquinolyl] amino}piperidinecarboxylate The title compound was synthesized as described in Example 19 using 1-tert-butoxycarbonyl-3-aminopiperidine. The product was used without purification.

Step 2: 3-(5-Morpholin-4-ylbenzimidazol-2-yl)-4-(3-piperidylamino)hydroquinolin-2-one The product was obtained as a yellow solid after debenzylation of tert-butyl-3-{[3-(5-morpholin-4-ylbenzimidazol-2-yl)-2-oxo-1-benzyl-4-hydroquinolyl] amino}piperidinecarboxylate using the procedure described in Example 16. The t-butoxycarbonyl group is removed under the reaction conditions. LC/MS m/z 445.4 (MH+), $R_t$ 1.73 minutes.

Example 23

Synthesis of 3-(5-Morpholin-4-ylbenzimidazol-2-yl)-4-[(3-piperidylmethyl)amino]-hydroquinolin-2-one Step 1: tert-Butyl-3-({[3-(5-morpholin-4-ylbenzimidazol-2-yl)-2-oxo-1benzyl4-hydroquinolyl]amino}methyl)piperidinecarboxylate The title compound was synthesized as described in Example 19, using 1-tert-butoxycarbonyl-3-aminomethylpiperidine. The product was used without purification.

Step 2: 3-(5-Morpholin-4-ylbenzimidazol-2-yl)-4-[(3-piperidylmethyl)amino]-hydroquinolin-2-one The title compound was obtained as a yellow solid after debenzylation of tert-butyl-3-({[3-(5-morpholin-4-ylbenzimidazol-2-yl)-2-oxo-1-benzyl4-hydroquinolyl]amino}methyl)piperidinecarboxylate using the procedure described in Example 16. LC/MS m/z 459.6 (MH+), $R_t$ 1.71 minutes.

Example 24

Synthesis of 4-{[2-(Dimethylamino)ethyl]amino}-3-(5-morpholin-4-ylbenzimidazol-2-yl)hydroquinolin-2-one Step 1: 4-{[2-(Dimethylamino)ethyl]amino}-3-(5-morpholin-4-ylbenzimidazol-2-yl)-1-benzylhydroquinolin-2-one The title compound was synthesized as described in Example 19 using 1,1-dimethylethylenediamine. The product was used without purification.

Step 2: 4-{[2-(Dimethylamino)ethyl]amino}-3-(5-morpholin-4-ylbenzimidazol-2-yl)hydroquinolin-2-one The title compound was obtained as a yellow solid after debenzylation of 4-{[2-(dimethylamino)ethyl]amino}-3-(5-morpholin-4-ylbenzimidazol-2-yl)-1-benzylhydroquinolin-2-one using the procedure described in Example 16. LC/MS m/z 433.4 (MH+), $R_t$ 1.55 minutes.

Example 25

Synthesis of 3-(5-Morpholin-4-ylbenzimidazol-2-yl)-4-[(oxolan-2-ylmethyl)amino]-hydroquinolin-2-one Step 1: 3-(5-Morpholin-4-ylbenzimidazol-2-yl)-4-[(oxolan-2-ylmethyl)amino]-1-benzylhydroquinolin-2-one The title compound was synthesized as described in Example 19 using 2-aminomethyltetrahydrofuran. The product was used without purification.

Step 2: 3-(5-Morpholin-4-ylbenzimidazol-2-yl)-4-[(oxolan-2-ylmethyl)amino]-hydroquinolin-2-one The title compound was obtained as a yellow solid after debenzylation of 3-(5-morpholin-4-ylbenzimidazol-2-yl)-4-[(oxolan-2-ylmethyl)amino]-1-benzylhydroquinolin-2-one using the procedure described in Example 16. LC/MS m/z 446.5 (MH+), $R_t$ 2.19 minutes.

Example 26

Synthesis of 4-{[2-(Methylamino)ethyl]amino}-3-(5-morpholin-4-ylbenzimidazol-2-yl)hydroquinolin-2-one Step 1: 4-{[2-(Methylamino)ethyl]amino}-3-(5-morpholin-4-ylbenzimidazol-2-yl)-1-benzylhydroquinolin-2-one The title compound was synthesized as described in Example 19 using 1-tert-butoxycarbonyl-1-methylethylenediamine. The product was used without purification.

Step 2: 4-{[2-(Methylamino)ethyl]amino}-3-(5-morpholin-4-ylbenzimidazol-2-yl)hydroquinolin-2-one The title compound was obtained as a yellow solid after debenzylation of 4-{[2-(methylamino)ethyl]amino}-3-(5-morpholin-4-ylbenzimidazol-2-yl)-1-benzylhydroquinolin-2-one using the procedure described in Example 16. The t-butoxycarbonyl group is removed under the reaction conditions. LC/MS m/z 419.4 (MH+), $R_t$ 1.50 minutes.

Example 27

Synthesis of 3-(5-Morpholin-4-ylbenzimidazol-2-yl)-4-(pyrrolidin-3-ylamino)hydroquinolin-2-one Step 1: tert-Butyl-3-{[3-(5-morpholin-4-ylbenzimidazol-2-yl)-2-oxo-1-benzyl-4-hydroquinolyl]amino}pyrrolidinecarboxylate The title compound was synthesized as described in Example 19 using 1-tert-butoxycarbonyl-3-aminopyrrolidine. The product was used without purification.

Step 2: 3-(5-Morpholin-4-ylbenzimidazol-2-yl)-4-(pyrrolidin-3-ylamino)hydroquinolin-2-one The title compound was obtained as a yellow solid after debenzylation of tert-butyl-3-{[3-(5-morpholin-4-ylbenzimidazol-2-yl)-2-oxo-1-benzyl-4-hydroquinolyl]amino}pyrrolidinecarboxylate using the procedure described in Example 16. LC/MS m/z 431.4 (MH+), $R_t$ 1.50 minutes.

Example 28

Synthesis of 4-[((2S)-2-Amino-4-methylpentyl)amino]-3-(5-morpholin-4-ylbenzimidazol-2-yl)hydroquinolin-2-one Step 1: 4-[((2S)-2-Amino-4-methylpentyl)amino]-3-(5-morpholin-4-ylbenzimidazol-2-yl)-1-benzylhydroquinolin-2-one The title compound was synthesized as described in Example 19 using (2S)-2-tert-butoxycarbonylamino-4-methylpentylamine. The product was used without purification.

Step 2: 4-[((2S)-2-Amino-4-methylpentyl)amino]-3-(5-morpholin-4-ylbenzimidazol-2-yl)hydroquinolin-2-one The title compound was obtained as a yellow solid after debenzylation of 4-[((2S)-2-amino-4-methylpentyl)amino]-3-(5-morpholin-4-ylbenzimidazol-2-yl)-1-benzylhydroquinolin-2-one using the procedure described in Example 16. LC/MS m/z 461.4 (MH+), $R_t$ 1.78 minutes.

Example 29

Synthesis of 4-[((2S)-2-Amino-3-methylbutyl)amino]-3-(5-morpholin-4-ylbenzimidazol-2-yl)hydroquinolin-2-one

Step 1: t-Butoxycarbonyl protected 4-[((2S)-2-amino-3-methylbutyl)amino]-3-(5-morpholin-4-yl-benzimidazol-2-yl)-1-benzylhydroquinolin-2-one The title compound was synthesized as described in Example 19, using (2S)-2-tert-butoxycarbonylamino-3-methylbutylamine. The product was used without purification.

Step 2: 4-[((2S)-2-Amino-3-methylbutyl)amino]-3-(5-morpholin-4-ylbenzimidazol-2-yl)hydroquinolin-2-one The title compound was obtained as a yellow solid after debenzylation of 4-[((2S)-2-amino-3-methylbutyl)amino]-3-(5-morpholin-4-ylbenzimidazol-2-yl)-1-benzylhydroquinolin-2-one using the procedure described in Example 16. The t-butoxycarbonyl group is removed under the reaction conditions. LC/MS m/z 447.5 (MH+), $R_t$ 2.96 minutes.

Example 30

Synthesis of 4-Amino-3-(5-morpholin-4-ylbenzimidazol-2-yl)hydroquinolin-2-one

Step 1: 4-Amino-3-(5-morpholin-4-ylbenzimidazol-2-yl)-1-benzylhydroquinolin-2-one The title compound was synthesized as described in Example 19, using ammonia in a sealed glass tube. The product was used without purification.

Step 2: 4-Amino-3-(5-morpholin-4-ylbenzimidazol-2-yl)hydroquinolin-2-one

The title compound was obtained as a bright yellow solid after debenzylation of 4-amino-3-(5-morpholin-4-ylbenzimidazol-2-yl)-1-benzylhydroquinolin-2-one using the procedure described in Example 16 and purification by reversed-phase HPLC. LC/MS m/z 362.3 (MH+), $R_t$ 1.61 minutes.

Example 31

Synthesis of 3-(Benzimidazol-2-yl)-4-chloro-1-benzylhydroquinolin-2-one

Step 1: 3-Benzimidazol-2-yl-4-hydroxy-1-benzylhydroquinolin-2-one

The title compound was synthesized as described in Example 16, using ethyl 2-benzimidazol-2-ylacetate. The product was obtained as a white solid and used without further purification. LC/MS m/z 368.4 (MH+), $R_t$ 2.99 minutes.

Step 2: 3-(Benzimidazol-2-yl)-4-chloro-1-benzylhydroquinolin-2-one

The title compound was synthesized as described in Example 19, using 3-benzimidazol-2-yl-4-hydroxy-1-benzylhydroquinolin-2-one. The crude product was used without purification.

Example 32

Synthesis of 3-Benzimidazol-2-yl-4-(methylamino)hydroquinolin-2-one

The benzylated title compound was synthesized as described in Example 19, using methylamine and 3-(benzimidazol-2-yl)-4-chloro-1benzylhydroquinolin-2-one. The product was obtained after debenzylation as a yellow solid using the procedure described in Example 16. LC/MS m/z 291.3 (MH+), $R_t$ 1.64 minutes.

Example 33

Synthesis of 3-Benzimidazol-2-yl-4-(ethylamino)hydroquinolin-2-one

The benzylated title compound was synthesized as described in Example 19, using ethylamine and 3-(benzimidazol-2-yl)4-chloro-1-benzylhydroquinolin-2-one. The title compound was obtained after debenzylation as a yellow solid using the procedure described in Example 16. LC/MS m/z 305.3 (MH+), $R_t$ 2.01 minutes.

Example 34

Synthesis of 3-Benzimidazol-2-yl-4-[(oxolan-2-ylmethyl)amino]hydroquinolin-2-one The benzylated title compound was synthesized as described in Example 19, using 2-aminomethyltetrahydrofuran and 3-(benzimidazol-2-yl)-4-chloro-1-benzylhydroquinolin-2-one. The title compound was obtained after debenzylation as a yellow solid using the procedure described in Example 16. LC/MS m/z 361.2 (MH+), $R_t$ 1.74 minutes.

Example 35

Synthesis of 3-Benzimidazol-2-yl-4-[(4-piperidylmethyl)amino]hydroquinolin-2-one The protected title compound was synthesized as described in Example 19, using 1-tert-butoxycarbonyl-4-aminomethylpiperidine and 3-(benzimidazol-2-yl)-4-chloro-1-benzylhydroquinolin-2-one. The title compound was obtained after deprotection and debenzylation as a yellow solid using the procedure described in Example 16. LC/MS m/z 374.3 (MH+), $R_t$ 1.29 minutes.

Example 36

Synthesis of 3-Benzimidazol-2-yl-4-[(4-fluorophenyl)amino]hydroquinolin-2-one

The benzylated title compound was synthesized as described in Example 19, using 4-fluoroaniline and 3-(benzimidazol-2-yl)-4-chloro-1-benzylhydroquinolin-2-one. The title compound was obtained after debenzylation as a yellow solid using the procedure described in Example 16. LC/MS m/z 371.2 (MH+), $R_t$ 1.92 minutes.

Example 37

Synthesis of 3-Benzimidazol-2-yl-4-(methoxyamino)hydroquinolin-2-one

3-Benzimidazol-2-yl-4-(methoxyamino)hydroquinolin-2-one

The benzylated title compound was synthesized as described in Example 19, using O-methylhydroxylamine and 3-(benzimidazol-2-yl)-4-chloro-1-benzylhydroquinolin-2-one. The title compound was obtained after debenzylation as a yellow solid using the procedure described in Example 16. LC/MS m/z 307.3 (MH+), $R_t$ 1.77 minutes.

Example 38

Synthesis of 3-Benzimidazol-2-yl-4-(benzimidazol-6-ylamino)hydroquinolin-2-one

3-Benzimidazol-2-yl-4-(benzimidazol-6-ylamino)hydroquinolin-2-one

The benzylated title compound was synthesized as described in Example 19, using 5-aminobenzimidazole and 3-(benzimidazol-2-yl)-4-chloro-1-benzylhydroquinolin-2-one. The title compound was obtained after debenzylation as a yellow solid using the procedure described in Example 16. LC/MS m/z 393.4 (MH+), $R_t$ 1.41 minutes.

Example 39

Synthesis of 3-Benzimidazol-2-yl-4-(phenylamino)hydroquinolin-2-one

3-Benzimidazol-2-yl-4-(phenylamino)hydroquinolin-2-one

The benzylated title compound was synthesized as described in Example 19, using aniline and 3-(benzimidazol-2-yl)-4-chloro-1-benzylhydroquinolin-2-one. The title compound was obtained after debenzylation as a yellow solid using the procedure described in Example 16. LC/MS m/z 353.4 (MH+), $R_t$ 2.38 minutes.

Example 40

Synthesis of 3-Benzimidazol-2-yl-4-(quinuclidin-3-ylamino)hydroquinolin-2-one

The benzylated title compound was synthesized as described in Example 19, using 3-aminoquinuclidine and 3-(benzimidazol-2-yl)-4-chloro-1-benzylhydroquinolin-2-one. The title compound was obtained after debenzylation as a yellow solid using the procedure described in Example 16. LC/MS m/z 386.4 (MH+), $R_t$ 1.82 minutes.

Example 41

Synthesis of 3-Benzimidazol-2-yl-4-[(imidazol-5-ylmethyl)amino]hydroquinolin-2-one 3-Benzimidazol-2-yl-4-[(imidazol-5-ylmethyl)amino]hydroquinolin-2-one The benzylated title compound was synthesized as described in Example 19, using 4-aminomethyl-1H-imidazole and 3-(benzimidazol-2-yl)-4-chloro-1-benzylhydroquinolin-2-one. The title compound was obtained after debenzylation as a yellow solid using the procedure described in Example 16. LC/MS m/z 357.4 (MH+), $R_t$ 1.34 minutes.

Example 42

Synthesis of 3-Benzimidazol-2-yl-4-(morpholin-4-ylamino)hydroquinolin-2-one

The benzylated title compound was synthesized as described in Example 19, using 4-aminomorpholine and 3-(benzimidazol-2-yl)-4-chloro-1-benzylhydroquinolin-2-one. The title compound was obtained after debenzylation as a yellow solid using the procedure described in Example 16. LC/MS m/z 362.4 (MH+), $R_t$ 1.42 minutes.

Example 43

Synthesis of 3-Benzimidazol-2-yl-4-hydrazinohydroquinolin-2-one

The benzylated title compound was synthesized as described in Example 19, using hydrazine and 3-(benzimidazol-2-yl)-4-chloro-1-benzylhydroquinolin-2-one. The title compound was obtained as a yellow solid after debenzylation using the procedure described in Example 16. LC/MS m/z 292.3 (MH+), $R_t$ 1.19 minutes.

Example 44

Synthesis of 3-Benzimidazol-2-yl-2-oxohydroquinoline-4-carbonitrile

3-Benzimidazol-2-yl-4-chloro-1-benzylhydroquinolin-2-one (1 equivalent) was dissolved in DMA, and CuCN (10 equivalents) was added in one portion. The reaction mixture was stirred at 90° C. overnight. The resulting mixture was allowed to cool to room temperature, water was added, and the orange precipitate was removed by filtration. The solid was treated with a solution of hydrated $FeCl_3$ at 70° C. for 1 hour. The suspension was centrifuged and the solution removed. The remaining solid was washed with 6 N HCl (2 times), saturated $Na_2CO_3$ (2 times), water (2 times) and lyophilized. The resulting powder was dissolved in 1 mL of triflic acid and heated at 60° C. overnight. The resulting mixture was cooled to 0° C. and water was slowly added. Saturated LiOH was added dropwise to the suspension to a pH of 8, then the solid was filtered and washed with water (3 times). Purification by reversed-phase HPLC afforded the desired product. LC/MS m/z 287.1 (MH+), $R_t$ 1.89 minutes.

Example 45

Synthesis of 3-(5,6-Dimethylbenzimidazol-2-yl)-4-(3-piperidylamino)hydroquinolin-2-one

Step 1: Ethyl 2-(5,6-dimethylbenzimidazol-2-yl)acetate

The title compound was synthesized as described in Example 1 using 4,5-dimethylbenzene-1,2-diamine. The crude yellow oil was purified first by silica gel chromatography (96.5:3.0:0.5, $CH_2Cl_2$:MeOH:$Et_3N$), and then by recrystallization from toluene to yield the title compound as a pale, yellow solid. LC/MS m/z 233.1 (MH+), $R_t$ 1.73 minutes.

Step 2: 3-(5,6-Dimethylbenzimidazol-2-yl)-4-hydroxy-1-benzylhydroquinolin-2-one The title compound was synthesized as described in Example 16, using ethyl 2-(5,6-dimethylbenzimidazol-2-yl) acetate. The crude material was purified by silica gel chromatography (98.5:1.5, $CH_2Cl_2$:MeOH) to yield the title compound as a yellow solid. LC/MS m/z 396.2 (MH+), $R_t$ 3.60 minutes.

Step 3: 3-(5,6-Dimethylbenzimidazol-2-yl)-4-chloro-1-benzylhydroquinolin-2-one The title compound was synthesized as described in Example 19, using 3-(5,6-dimethylbenzimidazol-2-yl)-4-hydroxy-1-benzylhydroquinolin-2-one. The title compound was obtained as an orange-yellow solid. LC/MS m/z 414.2 (MH+), $R_t$ 2.47 minutes.

Step 4: tert-Butyl 3-{[3-(5,6-dimethylbenzimidazol-2-yl)-2-oxo-1-benzyl-4-hydroquinolyl]amino}piperidinecarboxylate The title compound was synthesized as described in Example 19, using 1-tert-butoxycarbonyl-3-aminopiperidine. The crude material was purified by silica gel chromatography (99:1 $CH_2Cl_2$:MeOH) to yield the title compound as a yellow solid. LC/MS m/z 578.5 (MH+), $R_t$ 3.05 minutes.

Step 5: 3-(5,6-Dimethylbenzimidazol-2-yl)-4-(3-piperidylamino)hydroquinolin-2-one tert-Butyl 3-{[3-(5,6-dimethylbenzimidazol-2-yl)-2-oxo-1-benzyl-4-hydroquinolyl]amino}piperidine-carboxylate was debenzylated as described in Example 16. The crude material was purified by reversed-phase HPLC to yield the title compound as a light yellow solid. LC/MS m/z 388.4 (MH+), $R_t$ 1.61 minutes.

Example 46

Synthesis of 4-Amino-3-(3H-imidazo[4,5-b]pyridin-2-yl)quinolin-2(1H)-one

Step 1: 3H-Imidazo[4,5-b]pyridin-2-ylacetonitrile

Ethyl cyanoacetate (1.5 equivalents) and 2,3-diaminopyridine (1 equivalent) were heated at 185° C. for 30 minutes. The reaction mixture was cooled to room temperature and the black solid was triturated with ether. The desired product was thus obtained as a dark brown powder. LC/MS m/z 159.1 (MH+), $R_t$ 0.44 minutes.

Step 2: Ethyl 3H-imidazo[4,5-b]pyridin-2-ylacetate

3H-Imidazo[4,5-b]pyridin-2-ylacetonitrile was suspended in EtOH, and gaseous HCl was bubbled through for 3 hours. The suspension initially seemed to dissolve, but a precipitate started forming almost immediately. The reaction mixture was cooled to 0° C. and a cold saturated $NaHCO_3$ solution was carefully added. Solid $NaHCO_3$ was also added to bring the pH to a value of 7.6. The aqueous phase was then extracted with EtOAc, and the organic extracts were dried ($Na_2SO_4$). After evaporation of the solvent under reduced pressure, the residue was purified by chromatography on silicagel (10% MeOH in $CH_2Cl_2$ with 1% $Et_3N$) providing the desired product as a light brown solid. LC/MS m/z 206.1 (MH+), $R_t$ 0.97 minutes.

Step 3: 4-Amino-3-(3H-imidazo[4,5-b]pyridin-2-yl)quinolin-2(1H)-one

LiHMDS (3.0 equivalents) was added to ethyl 3H-imidazo[4,5-b]pyridin-2-ylacetate (1.0 equivalent) in THF at −78° C. After 20 minutes, a solution of 2-aminobenzenecarbonitrile (1.1 equivalents) in THF was added. The resulting mixture was allowed to warm to room temperature, stirred for 3 hours, and then refluxed overnight. The mixture was cooled to 0° C. and quenched with an aqueous saturated $NH_4Cl$ solution. A precipitate formed, was filtered off, and was washed repeatedly with ether to yield the desired compound as a light brown solid. LC/MS m/z 278.2 (MH+), $R_t$ 1.82 minutes.

Example 47

Synthesis of 4-Amino-3-(5-morpholin-4-yl-3H-imidazo[4,5-b]pyridin-2-yl)quinolin-2(1H)-one

Step 1: 6-Morpholin-4-yl-3-nitropyridin-2-amine

Morpholine (4 equivalents) was added to a suspension of 6-chloro-3-nitropyridin-2-amine (1 equivalent) in $CH_3CN$, and the reaction mixture was stirred at 70° C. for 5 hours. The solvent was evaporated under reduced pressure, and the residue was triturated with ether to afford the desired compound as a bright yellow powder. LC/MS m/z 225.0 (MH+), $R_t$ 1.79 minutes.

Step 2: Ethyl (5-mrpholin-4-yl-3H-imidazo[4,5-b]pyridin-2-yl)acetate

To a solution 6-chloro-3-nitropyridin-2-amine (1.0 equivalent) in EtOH was added Pd/C (0.1 equivalents). The reaction vessel was repeatedly purged with hydrogen and then stirred under a hydrogen atmosphere (1 atm) for 18 hours. Ethyl 3-ethoxy-3-iminopropanoate hydrochloride (2.0 equivalents) was added in one portion, and the reaction mixture was refluxed overnight. The reaction mixture was cooled to room temperature, filtered through a Celite plug, and the plug was washed with EtOH. After evaporation of the solvent under reduced pressure, the residue was purified by silica gel chromatography (5% MeOH in $CH_2Cl_2$ with 1% $Et_3N$) providing the desired product as a brown solid. LC/MS m/z 291.3 (MH+), $R_t$ 1.71 minutes.

Step 3: 4-Amino-3-(5-morpholin-4-yl-3H-imidazo[4,5-b]pyridin-2-yl)quinolin-2(1H)-one The title compound was synthesized as described in Example 46, using ethyl 2-(5-morpholin-4-ylimidazolo[5,4- b]pyridin-2-yl)acetate and 2-aminobenzenecarbonitrile, with a modified workup procedure. After quenching with a saturated aqueous ammonium chloride solution, the two phases were separated and the aqueous phase extracted with EtOAc. Upon standing, a solid formed and precipitated out of the organic extracts. The precipitate, a dark brown solid, was filtered off and dried. Purification by reverse phase chromatography afforded the desired product as a reddish solid. LC/MS m/z 363.2 (MH+), $R_t$ 2.20 minutes.

Example 48

Synthesis of 4-Amino-5-[(2R,6S)-2,6-dimethylmorpholin-4-yl]-3-(3H-imidazo[4,5-b]pyridin-2-yl)quinolin-2(1H)-one LiHMDS (3.0 equivalents) was added to ethyl 3H-imidazo[4,5-b]pyridin-2-ylacetate (1.0 equivalent) in THF at –78° C. After 20 minutes, a solution of 2-amino-6-[(2R,6S)-2,6-dimethylmorpholin-4-yl]benzonitrile (1.1 equivalents) in THF was added. The resulting mixture was allowed to warm to room temperature, stirred for 2 hours, and then it was heated to 60° C. overnight. The mixture was cooled to 0° C. and quenched with an aqueous saturated NH$_4$Cl solution. The aqueous phase was extracted with CH$_2$Cl$_2$ (5 times) and the organic extracts were collected, dried (Na$_2$SO$_4$), and concentrated. The crude product was purified by HPLC. LC/MS m/z 391.2 (MH+), $R_t$ 2.35 minutes.

Example 49

Synthesis of 4-Amino-3-{5-[3-(dimethylamino)pyrrolidin-1-yl]-3H-imidazo[4,5-b]pyridin-2-yl}quinolin-2(1H)-one Step 1: Ethyl {5-[3-(dimethylamino)pyrrolidin-1-yl]-3H-imidazo[4,5-b]pyridin-2-yl}acetate 6-chloro-3-nitro-2-aminopyridine (1.0 equivalent) and 3-(dimethylamino)pyrrolidine (1.1 equivalents) were dissolved in CH$_3$CN and diisopropylethylamine(2.0 equivalents) was added. The reaction mixture was heated at 70° C. overnight. The solution was cooled to room temperature, and the solvent was evaporated. The residue was triturated with ether and water and dried under vacuum (LC/MS m/z 252.2 (MH+), $R_t$ 1.09 minutes). The isolated product (1.0 equivalent) and 10% Pd/C (0.1 equivalents) were suspended in anhydrous EtOH at room temperature. The reaction flask was evacuated and subsequently filled with H$_2$. The resulting mixture was allowed to stir under a hydrogen atmosphere overnight. Ethyl 3-ethoxy-3-iminopropanoate hydrochloride (2.0 equivalents) was then added and the resulting mixture was heated at reflux overnight. The solution was then filtered through Celite and evaporated under reduced pressure. The residue was suspended in CH$_2$Cl$_2$ and concentrated NH$_4$OH was added until a pH of 11 was achieved. The NH$_4$Cl thus formed was filtered off. The two phases were separated, and the organic phase was dried (Na$_2$SO$_4$). Evaporation of the solvent and trituration of the residue with ether gave a light green powder. LC/MS m/z 318.1 (MH+), $R_t$ 1.11 minutes.

Step 2: 4-Amino-3-{5-[3-(dimethylamino)pyrrolidin-1-yl]-3H-imidazo[4,5-b]pyridin-2-yl}quinolin-2(1H)-one LiHMDS (3.5 equivalents) was added to ethyl {5-[3-(dimethylamino)pyrrolidin-1-yl]-3H-imidazo[4,5-b]pyridin-2-yl}acetate (1.0 equivalent) in THF at –40° C. After 10 minutes, a solution of 2-aminobenzenecarbonitrile (1.1 equivalents) in THF was added. The resulting mixture was allowed to warm to room temperature, stirred for 1 hour, and then heated to 60° C. overnight. The mixture was cooled to room temperature and quenched with NH$_4$Cl (aqueous saturated). The aqueous phase was extracted with CH$_2$Cl$_2$ (5 times). The product crashed out of the organic solution during the extractions. Evaporation of the solvent under reduced pressure afforded a brown solid that was triturated repeatedly with MeOH and acetone to obtain a yellow greenish powder. LC/MS m/z 390.2 (MH+), $R_t$ 1.48 minutes.

Example 50

Synthesis of 4-Amino-3-(1H-benzimidazol-2-yl)-5-(4-ethylpiperazin-1-yl)quinolin-2(1H)-one Step 1: 2-(4-Ethylpiperazinyl)-6-nitrobenzenecarbonitrile 2,6-Dinitrobenzenecarbonitrile (1.0 equivalent) and ethylpiperazine (3.6 equivalents) were dissolved in DMF. The resulting solution was heated at 90° C. for 2 hours. The solution was cooled to room temperature and poured into H$_2$O. A precipitate formed which was filtered to yield the desired product as a brown solid. LC/MS m/z 260.1 (MH+), $R_t$ 1.69 minutes.

Step 2: 6-Amino-2-(4-ethylpiperazinyl)benzenecarbonitrile 2-(4-Ethylpiperazinyl)-6-nitrobenzenecarbonitrile (1.0 equivalent) was dissolved in EtOH and EtOAc. The flask was purged with N$_2$, and 10% Pd/C (0.1 equivalents) was added. The flask was evacuated and purged with H$_2$ three times. The resulting mixture was stirred overnight at room temperature. The mixture was filtered through Celite, and the filter pad was washed with EtOAc. The solvent was removed in vacuo to provide the desired product as a yellow solid. LC/MS m/z 231.2 (MH+), $R_t$ 1.42 minutes.

Step 3: 4-Amino-3-(1H-benzimidazol-2-yl)-5-(4-ethylpiperazin-1-yl)quinolin-2(1H)-one t-BuLi (3.1 equivalents) was added to ethyl 2-benzimidazol-2-ylacetate (1.0 equivalent) and 6-amino-2-(4-ethylpiperazinyl) benzenecarbonitrile (1.0 equivalent) in THF at 0° C. The reaction was stirred overnight. The resulting mixture was quenched with NH$_4$Cl (aqueous saturated) and extracted with EtOAc. The combined organic layers were washed with H$_2$O and brine, dried over Na$_2$SO$_4$, filtered, and concentrated in vacuo to yield a brown solid. The crude material was triturated with CH$_2$Cl$_2$ and MeOH to provide a tan solid. LC/MS m/z 389.1 (MH+), $R_t$ 1.80 minutes.

Example 51

Synthesis of 3-(1H-Benzoimidazol-2-yl)-4-hydroxy-1H-[1,7]naphthyridin-2-one

Step 1: 3-[2-(Methoxycarbonyl)acetylamino]pyridine-4-carboxylic acid

A solution of 3-aminopyridine-4-carboxylic acid (1.0 equivalent), methyl 2-(chlorocarbonyl)acetate (1.1 equivalents), and triethylamine (2.0 equivalents) in acetone was stirred overnight at room temperature. The solvent was removed in vacuo. The product was used without further purification. LC/MS m/z 239.2 (MH+), $R_t$ 1.40 minutes.

Step 2: 3-(1H-Benzoimidazol-2-yl)-4-hydroxy-1H-[1,7]naphthyridin-2-one

3-[2-(Methoxycarbonyl)acetylamino]pyridine-4-carboxylic acid (1.1 equivalents) was combined with 1,2-phenylenediamine (1.0 equivalent) and heated at 150° C. for 3 hours. The crude product was purified by reversed-phase HPLC (DMSO/5% TFA). LC/MS m/z 279.3 (MH+), $R_t$ 1.73 minutes.

Example 52

Synthesis of 4-Hydroxy-3-(6-methyl-1H-benzoimidazol-2-yl)-1H-[1,7]naphthyridin-2-one The title compound was synthesized as described in Example 50 using 3-[2-(methoxycarbonyl)acetylamino]-pyridine-4-carboxylic acid and 4-methyl-1,2-phenylenediamine. The crude product was purified by reversed-phase HPLC (DMSO/5% TFA). LC/MS m/z 293.3 (MH+), $R_t$ 1.99 minutes.

Example 53

Synthesis of 4-[(2-Hydroxyethyl)amino]-3-(5-morpholin-4-ylbenzimidazol-2-yl)hydroquinolin-2-one The title compound was obtained as a side-product of the debenzylation of 4-[(2-methoxyethyl)amino]-3-(5-morpholin-4-ylbenzimidazol-2-yl)-1-benzylhydroquinolin-2-one (Example 52) using the procedure described in Example 16 and was isolated by reverse-phase HPLC as a yellow solid. LC/MS m/z 406.2 (MH+), $R_t$ 1.39 minutes.

Example 54

Synthesis of 4-(Methoxyamino)-3-(5-morpholin-4-ylbenzimidazol-2-yl)hydroquinolin-2-one

Step 1: 4-(Methoxyamino)-3-(5-morpholin-4-ylbenzimidazol-2-yl)-1-benzylhydroquinolin-2-one The title compound was synthesized as described in Example 19 using O-methylhydroxylamine as the nucleophile. The product was used without purification.

Step 2: 4-(Methoxyamino)-3-(5-morpholin-4-ylbenzimidazol-2-yl)hydroquinolin-2-one The title compound was obtained as a yellow solid after debenzylation of 4-(methoxyamino)-3-(5-morpholin-4-ylbenzimidazol-2-yl)-1-benzylhydroquinolin-2-one using the procedure described in Example 16. LC/MS m/z 392.2 (MH+), $R_t$ 1.82 minutes.

Example 55

Synthesis of 3-(5-Morpholin-4-ylbenzimidazol-2-yl)-4-(3-piperidylamino)hydroquinolin-2-one

Step 1: tert-Butyl-3-{[3-(5-morpholin-4-ylbenzimidazol-2-yl)-2-oxo-1-benzyl-4-hydroquinolyl]amino}piperidinecarboxylate The title compound was synthesized as described in Example 19 using 1-tert-butoxycarbonyl-3-aminopiperidine as the amine. The product was used without purification.

Step 2: 3-(5-Morpholin-4-ylbenzimidazol-2-yl)-4-(3-piperidylamino) hydroquinolin-2-one The product was obtained as a yellow solid after debenzylation of tert-butyl-3-{[3-(5-morpholin-4-ylbenzimidazol-2-yl)-2-oxo-1-benzyl-4-hydroquinolyl]amino}piperidinecarboxylate using the procedure described in Example 16. The t-butoxycarbonyl group was removed under the reaction conditions. LC/MS m/z 445.4 (MH+), $R_t$ 1.73 minutes.

Example 56

Synthesis of 3-(5-Morpholin-4-ylbenzimidazol-2-yl)-4-[(3-piperidylmethyl)amino]-hydroquinolin-2-one

Step 1: tert-Butyl-3-({[3-(5-morpholin-4-ylbenzimidazol-2-yl)-2-oxo-1-benzyl-4-hydroquinolyl]amino}methyl)piperidinecarboxylate The title compound was synthesized as described in Example 19 using 1-tert-butoxycarbonyl-3-aminomethylpiperidine as the amine. The product was used without purification.

Step 2: 3-(5-Morpholin-4-ylbenzimidazol-2-yl)-4-[(3-piperidylmethyl)amino]-hydroquinolin-2-one The title compound was obtained as a yellow solid after debenzylation of tert-butyl-3-({[3-(5-morpholin-4-ylbenzimidazol-2-yl)-2-oxo-1benzyl-4-hydroquinolyl]amino}methyl)piperidinecarboxylate using the procedure described in Example 16. LC/MS m/z 459.6 (MH+), $R_t$ 1.71 minutes.

Example 57

Synthesis of 3-(5-Morpholin-4-ylbenzimidazol-2-yl)-4-[(oxolan-2-ylmethyl)amino]-hydroquinolyl-2-one

Step 1: 3-(5-Morpholin-4-ylbenzimidazol-2-yl)-4-[(oxolan-2-ylmethyl)amino]-1-benzylhydroquinolin-2-one The title compound was synthesized as described in Example 19 using 2-aminomethyltetrahydrofuran as the amine. The product was used without purification.

Step 2: 3-(5-Morpholin-4-ylbenzimidaz-2-yl)-4-[(oxolan-2-ylmethyl)amino]-hydroquinolin-2-one The title compound was obtained as a yellow solid after debenzylation of 3-(5-morpholin-4-ylbenzimidazol-2-yl)-4-[(oxolan-2-ylmethyl)amino]-1-benzylhydroquinolin-2-one using the procedure described in Example 16. LC/MS m/z 446.5 (MH+), $R_t$ 2.19 minutes.

Example 58

Synthesis of 3-(5-Morpholin-4-ylbenzimidazol-2-yl)-4-(pyrrolidin-3-ylamino)hydroquinolin-2-one Step 1: tert-Butyl-3-{[3-(5-morpholin-4-ylbenzimidazol-2-yl)-2-oxo-1-benzyl-4-hydroquinolyl]amino}pyrrolidinecarboxylate The title compound was synthesized as described in Example 19 using 1-tert-butoxycarbonyl-3-aminopyrrolidine as the amine. The product was used without purification.

Step 2: 3-(5-Morpholin-4-ylbenzimidazol-2-yl)-4-(pyrrolidin-3-ylamino)hydroquinolin-2-one The title compound was obtained as a yellow solid after debenzylation of tert-butyl-3-{[3-(5-morpholin-4-ylbenzimidazol-2-yl)-2-oxo-1-benzyl-4-hydroquinolyl]amino}pyrrolidinecarboxylate using the procedure described in Example 16. LC/MS m/z 431.4 (MH+), $R_t$ 1.50 minutes.

Example 59

Synthesis of 3-Benzimidazol-2-yl-4-(ethylamino)hydroquinolin-2-one

The benzylated title compound was synthesized as described in Example 19 using ethylamine as the amine and 3-(benzimidazol-2-yl)-4-chloro-1-benzylhydroquinolin-2-one. The title compound was obtained after debenzylation as a yellow solid using the procedure described in Example 16. LC/MS m/z 305.3 (MH+), $R_t$ 2.01 minutes.

Example 60

Synthesis of 3-Benzimidazol-2-yl-4-[(oxolan-2-ylmethyl)amino]hydroquinolin-2-one The benzylated title compound was synthesized as described in Example 19 using 2-aminomethyltetrahydrofuran as the amine and 3-(benzimidazol-2-yl)-4-chloro-1-benzylhydroquinolin-2-one. The title compound was obtained after debenzylation as a yellow solid using the procedure described in Example 16. LC/MS m/z 361.2 (MH+), $R_t$ 1.74 minutes.

Example 61

Synthesis of 3-Benzimidazol-2-yl-4-[(4-piperidylmethyl)amino]hydroquinolin-2-one The protected title compound was synthesized as described in Scheme 11 using 1-tert-butoxycarbonyl-4-aminomethylpiperidine as the amine and 3-(benzimidazol-2-yl)-4-chloro-1-benzylhydroquinolin-2-one. The title compound was obtained after deprotection and debenzylation as a yellow solid using the procedure described in Example 16. LC/MS m/z 374.3 (MH+), $R_t$ 1.29 minutes.

Example 62

Synthesis of 3-Benzimidazol-2-yl-4-[(4-fluorophenyl)amino]hydroquinolin-2-one

The benzylated title compound was synthesized as described in Example 19 using 4-fluoroaniline as the amine and 3-(benzimidazol-2-yl)-4-chloro-1-benzylhydroquinolin-2-one. The title compound was obtained after debenzylation as a yellow solid using the procedure described in Example 16. LC/MS m/z 371.2 (MH+), $R_t$ 1.92 minutes.

Example 63

Synthesis of 3-Benzimidazol-2-yl-4-(methoxyamino)hydroquinolin-2-one

The benzylated title compound was synthesized as described in Example 19 using O-methylhydroxylamine as the amine and 3-(benzimidazol-2-yl)-4-chloro-1-benzylhydroquinolin-2-one. The title compound was obtained after debenzylation as a yellow solid using the procedure described in Example 16. LC/MS m/z 307.3 (MH+), $R_t$ 1.77 minutes.

Example 64

Synthesis of 3-Benzimidazol-2-yl-4-(benzimidazol-6-ylamino)hydroquinolin-2-one

The benzylated title compound was synthesized as described in Example 19 using 5-aminobenzimidazole as the amine and 3-(benzimidazol-2-yl)-4-chloro-1-benzylhydroquinolin-2-one. The title compound was obtained after debenzylation as a yellow solid using the procedure described in Example 16. LC/MS m/z 393.4 (MH+), $R_t$ 1.41 minutes.

Example 65

Synthesis of 3-Benzimidazol-2-yl-4-(phenylamino)hydroquinolin-2-one

The benzylated title compound was synthesized as described in Example 19 using aniline as the amine and 3-(benzimidazol-2-yl)-4-chloro-1-benzylhydroquinolin-2-one. The title compound was obtained after debenzylation as a yellow solid using the procedure described in Example 16. LC/MS m/z 353.4 (MH+), $R_t$ 2.38 minutes.

Example 66

Synthesis of 3-Benzimidazol-2-yl-4-(quinuclidin-3-ylamino)hydroquinolin-2-one

The benzylated title compound was synthesized as described in Example 19 using 3-aminoquinuclidine as the amine and 3-(benzimidazol-2-yl)-4-chloro-1-benzylhydroquinolin-2-one. The title compound was obtained after debenzylation as a yellow solid using the procedure described in Example 16. LC/MS m/z 386.4 (MH+), $R_t$ 1.82 minutes.

Example 67

Synthesis of 3-Benzimidazol-2-yl-4-[(imidazol-5-ylmethyl)amino]hydroquinolin-2-one The benzylated title compound was synthesized as described in Example 19 using 4-aminomethyl-1H-imidazole as the amine and 3-(benzimidazol-2-yl)-4-chloro-1-benzylhydroquinolin-2-one. The title compound was obtained after debenzylation as a yellow solid using the procedure described in Example 16. LC/MS m/z 357.4 (MH+), $R_t$ 1.34 minutes.

Example 68

3-Benzimidazol-2-yl-4-(morpholin-4-ylamino)hydroquinolin-2-one

The benzylated title compound was synthesized as described in Example 19 using 4-aminomorpholine as the amine and 3-(benzimidazol-2-yl)-4-chloro-1-benzylhydroquinolin-2-one. The title compound was obtained after debenzylation as a yellow solid using the procedure described in Example 16. LC/MS m/z 362.4 (MH+), $R_t$ 1.42 minutes.

Example 69

Synthesis of 3-Benzimidazol-2-yl-4-hydrazinohydroquinolin-2-one

The benzylated title compound was synthesized as described in Example 19 using hydrazine as the nucleophile and 3-(benzimidazol-2-yl)-4-chloro-1-benzylhydroquinolin-2-one. The title compound was obtained as a yellow solid after debenzylation using the procedure described in Example 16. LC/MS m/z 292.3 (MH+), $R_t$ 1.19 minutes.

Example 70

Synthesis of 3-(5,6-Dimethylbenzimidazol-2-yl)-4-(3-piperidylamino)hydroquinolin-2-one

Step 1: Ethyl 2-(5,6-dimethylbenzimidazol-2-yl)acetate

The title compound was synthesized as described in Example 16 using 4,5-dimethylbenzene-1,2-diamine as the diamine. The crude yellow oil was purified by silica gel chromatography (96.5:3.0:0.5, $CH_2Cl_2$:MeOH:TEA), and then by recrystallization from toluene to yield the title compound as a pale, yellow solid. LC/MS m/z 233.1 (MH+), $R_t$ 1.73 minutes.

Step 2: 3-(5,6-Dimethylbenzimidazol-2-yl)-4-hydroxy-1-benzylhydroquinolin-2-one The title compound was synthesized as described in Example 16 using ethyl 2-(5,6-dimethylbenzimidazol-2-yl) acetate. The crude material was purified by silica gel chromatography (98.5:1.5, $CH_2Cl_2$:MeOH) to yield the title compound as a yellow solid. LC/MS m/z 396.2 (MH+), $R_t$ 3.60 minutes.

Step 3: 3-(5,6-Dimethylbenzimidazol-2-yl)-4-chloro-1-benzylhydroquinolin-2-one The title compound was synthesized as described in Example 19, using 3-(5,6-dimethylbenzimidazol-2-yl)-4-hydroxy-1-benzylhydroquinolin-2-one. The title compound was obtained as an orange-yellow solid. LC/MS m/z 414.2 (MH+), $R_t$ 2.47 minutes.

Step 4: tert-Butyl 3-{[3-(5,6-dimethylbenzimidazol-2-yl)-2-oxo-1-benzyl-4-hydroquinolyl]amino}piperidinecarboxylate The title compound was synthesized as described in Example 19, using 1-tert-butoxycarbonyl-3-aminopiperidine as the amine and 3-(5,6-dimethylbenzimidazol-2-yl)-4-chloro-1-benzylhydroquinolin-2-one. The crude material was purified by silica gel chromatography (99:1 $CH_2Cl_2$:MeOH) to yield the title compound as a yellow solid. LC/MS m/z 578.5 (MH+), $R_t$ 3.05 minutes.

Step 5: 3-(5,6-Dimethylbenzimidazol-2-yl)-4-(3-piperidylamino)hydroquinolin-2-one tert-Butyl 3-{[3-(5,6-dimethylbenzimidazol-2-yl)-2-oxo-1-benzyl-4-hydroquinolyl]amino}piperidine-carboxylate was debenzylated as described in Example 16. The crude material was purified by reversed-phase HPLC to yield the title compound as a light yellow solid. LC/MS m/z 388.4 (MH+), $R_t$ 1.61 minutes.

Example 71

Synthesis of 4-[(3S)-1-Azabicyclo[2.2.2]oct-3-ylamino]-3-(1H-benzimidazol-2-yl)-6-(4-methoxyphenyl)quinolin-2(1H)-one A vial was charged with the hydrochloride salt of 4-[(3S)-1-azabicyclo[2.2.2]oct-3-ylamino]-3-(1H-benzimidazol-2-yl)-6-bromoquinolin-2(1H)-one (1.0 equivalent) and 4-methoxyphenyl boronic acid (1.3 equivalents). To this solution was added DME and 2 M aqueous $Na_2CO_3$ (10%). The mixture was degassed by bubbling argon through the solution for 5 minutes. $Pd(dppf)_2Cl_2 \cdot CH_2Cl_2$ (0.2 equivalents) was then added to the degassed solution. The mixture was heated at 90° C. for 16 hours, and the top organic layer was separated and filtered. The solvent was removed, and the residue was purified by reverse phase HPLC affording the desired product. MS m/z 492.6 (M+H).

Example 72

Synthesis of 4-[(3S)-1-Azabicyclo[2.2.2]oct-3-ylamino]-3-(1H-benzimidazol-2-yl)-6-(4-hydroxyphenyl)quinolin-2(1H)-one 4-[(3S)-1-azabicyclo[2.2.2]oct-3-ylamino]-3-(1H-benzimidazol-2-yl)-6-(4methoxyphenyl)quinolin-2(1H)-one (Example 70) was dissolved in 30% HBr/AcOH and heated at 60° C. until the reaction was complete. The resulting mixture was allowed to cool, and it was then neutralized with 2 M NaOH. The resulting mixture was extracted with EtOAc, and the organic layers were dried over $Na_2SO_4$, filtered, and evaporated under reduced pressure. The residue was purified by reverse phase HPLC to give the desired product. MS m/z 478.6 (M+H).

Example 73

Synthesis of 4-[((3S)-Quinuclidin-3-yl)amino]-3-benzimidazol-2-yl-6-chloro-hydropyridino[3,4-b]pyridin-2-one

Step 1: Methyl 5-[(tert-butoxy)carbonylamino]-2-chloropyridine-4-carboxylate 5-[(tert-butoxy)carbonylamino]-2-chloropyridine-4-carboxylic acid (1 equivalent) was dissolved in THF and MeOH. The mixture was heated to 50° C. to completely dissolve the starting material. The solution was then cooled to 0° C., and TMSCHN$_2$ (2 M in THF, 2 equivalents) was added. The reaction was allowed to warm to room temperature and stirred overnight. The reaction was the concentrated to yield the methyl ester (100%) as a brown solid.

Step 2: Methyl 5-{(tert-butoxy)-N-[(4-methoxyphenyl)methyl]carbonylamino}-2-chloropyridine-4-carboxylate NaH (60% in oil, 1.5 equivalents) in a round bottom flask was washed with hexanes to remove mineral oil. DMF was then added to the washed NaH. A solution of methyl 5-[(tert-butoxy)carbonylamino]-2-chloropyridine-4-carboxylate (1 equivalent) in DMF, in an addition funnel, was added to the mixture of NaH in DMF followed by stirring at room temperature for 15 minutes. The mixture was heated at 50° C. for 1.5 hours. The reaction was then cooled to room temperature, and 4-methoxybenzyl chloride (1.3 equivalents) dissolved in DMF was added through an addition funnel. The reaction was stirred overnight at 50° C. Upon cooling, water was added to the reaction mixture. Ethyl acetate was then added, and the mixture was stirred for 15 minutes. The aqueous layer was extracted with ethyl acetate. The organic layers were combined, washed with water and brine, dried over MgSO$_4$, filtered, and concentrated to yield methyl 5-{(tert-butoxy)-N-[(4-methoxyphenyl)-methyl]-carbonylamino}-2-chloropyridine-4-carboxylate (81%) as a brown oil.

Step 3: Methyl 2-chloro-5-{(4-methoxyphenyl)methyl]amino}pyridine-4-carboxylate To a solution of crude methyl 5-{(tert-butoxy)-N-[(4-methoxyphenyl)methyl]carbonylamino}-2-chloropyridine-4-carboxylate (1 equivalent) in CH$_2$Cl$_2$, was added 1 M HCl (2 equivalents). The reaction was stirred overnight and then concentrated to yield crude methyl 2-chloro-5-{(4-methoxyphenyl)methyl]-amino}pyridine-4-carboxylate (80%).

Step 4: 2-Chloro-5-{[(4-methoxyphenyl)methyl]amino}pyridine-4-carboxylic acid To a solution of methyl 5-{(tert-butoxy)-N-[(4-methoxyphenyl)-methyl]carbonylamino}-2-chloropyridine-4-carboxilate (1 equivalent) in MeOH, was added an aqueous solution of NaOH (3 equivalents). A precipitate formed immediately. The reaction was heated until the solution was clear and was then stirred for 1 hour at room temperature. Aqueous citric acid (1 M) was then added causing the product to crash out of solution. The product was then collected to afford the title compound in 77% yield.

Step 5: 6-Chloro-1-[(4-methoxyphenyl)methyl]pyridino[3,4-d]-1,3-oxazaperhydroine-2,4-dione To a solution of 2-chloro-5-{[(4-methoxyphenyl)methyl]-amino}pyridine-4-carboxylic acid (1 equivalent) in dioxane, was added phosgene/toluene (excess). The reaction was stirred overnight and then evaporated to yield the desired product (63%).

Step 6: 3-Benzimidazol-2-yl-6-chloro-4-hydroxy-1-[(4-methoxyphenyl)-methyl]hydropyridino[3,4-b]pyridin-2-one To a solution of ethyl 2-benzimidazol-2-ylacetate (1 equivalent) in DMF and THF (2:1) at −78° C., was added LiHMDS (3 equivalents) dropwise. After being stirred for 1 hour, a solution of 6-chloro-1-[(4-methoxyphenyl)methyl]pyridino-[3,4-d]-1,3-oxazaperhydroine-2,4-dione in DMF and THF (1:2) was added dropwise, and the reaction was stirred for 1.5 hours. The reaction was quenched with aqueous NH$_4$Cl and allowed to warm to room temperature. The aqueous phase was extracted with EtOAc, and the organic layers were combined, washed with H$_2$O and brine, dried over MgSO$_4$, and concentrated. Toluene was added to the residue, and the reaction was refluxed overnight. The mixture was then cooled allowing the product to crash out. The reaction was filtered, and the product was washed with toluene and EtOH to give the product (45%).

Step 7: 6-Chloro-1-[(4-methoxyphenyl)methyl]-2-oxo-3-{1-[(trifluoromethyl)sulfonyl]-benzimidazol-2-yl}hydropyridino[3,4-b]pyridin-4-yl (trifluoromethyl)sulfonate A solution of 3-benzimidazol-2-yl-6-chloro-4-hydroxy-1-[(4-methoxyphenyl)methyl]hydropyridino[3,4-b]pyridin-2-one (1 equivalent) in CH$_2$Cl$_2$ was cooled to −10° C., and pyridine (16 equivalents) was added. Trifluoromethane-sulfonic anhydride (8 equivalents) was then slowly added dropwise, using a syringe, so that the temperature did not exceed −4° C. The reaction was stirred for 2 hours at 4° C. The reaction was allowed to warm to room temperature and stirred until clear (4 hours). The reaction was then quenched with saturated NaHCO$_3$. The organic layer was washed with saturated aqueous NaHCO$_3$, 1.0 M citric acid, H$_2$O, saturated aqueous NaHCO$_3$, H$_2$O, and brine. The organic layer was dried over MgSO$_4$, filtered, and concentrated to yield the product (96%) as a yellow solid.

Step 8: 4-[((3S)-Quinuclidin-3-yl)amino]-6-chloro-1-[(4-methoxyphenyl)methyl]-3-{1-[(trifluoromethyl)sulfonyl]benzimidazol-2-yl}hydropyridino[3,4-b]pyridin-2-one To a solution of 6-chloro-1-[(4-methoxyphenyl)methyl]-2-oxo-3-{1-[(trifluoromethyl)sulfonyl]benzimidazol-2-yl}hydropyridino[3,4-b]pyridin-4-yl (trifluoromethyl)sulfonate (1 equivalent) in CH$_3$CN was added triethylamine (4 equivalents), followed by the (3S)-aminoquinuclidine (3 equivalents). The reaction was then stirred at 80° C. for 2 hours. The reaction was cooled to room temperature and evaporated. The crude material was carried on to the next step.

189

Step 9: 4-[((3S)-Quinuclidin-3-yl)amino]-3-benzimidazol-2-yl-6-chloro-hydropyridino[3,4-b]pyridin-2-one Crude 4-[((3S)quinuclidin-3-yl)amino]-6-chloro-1-[(4-methoxyphenyl)methyl]-3-{1-[(trifluoromethyl)sulfonyl]benzimidazol-2-yl}hydropyridino[3,4-b]pyridin-2-one was dissolved in a mixture of TFA and HCl (8:1 ratio, premixed). The reaction was stirred overnight at 80° C. The reaction was then cooled to room temperature, and the solvent was evaporated. The crude product was neutralized and subsequently purified using prep HPLC. The combined fractions from the prep. LC were made basic with NaOH first and then with NaHCO$_3$(sat) causing the free base to precipitate. After 30 minutes, the precipitate was collected and washed several times with water. The precipitate was placed in a flask, and a solution of H$_2$O/CH$_3$CN (1:1) was added. To this solution was added HCl (1 M), and the solution was lyophilized to yield the product salt (17% over 2 steps). MS m/z 421.9 (M+H).

Example 74

Synthesis of 4-(R)-(1-Aza-bicyclo[2.2.2]oct-3-ylamino)-3-(1H-benzoimidazol-2-yl)-6-(1,2,3,6-tetrahydro-pyridin-4-yl)-1H-quinolin-2-one Step 1: 4(R)-[4-(1-Aza-bicyclo[2.2.2]oct-3-ylamino)-3-(1H-benzoimidazol-2-yl)-2-oxo-1,2-dihydro-quinolin-6-yl]-3,6-dihydro-2H-pyridine-1-carboxylic acid tert-butyl ester (3).

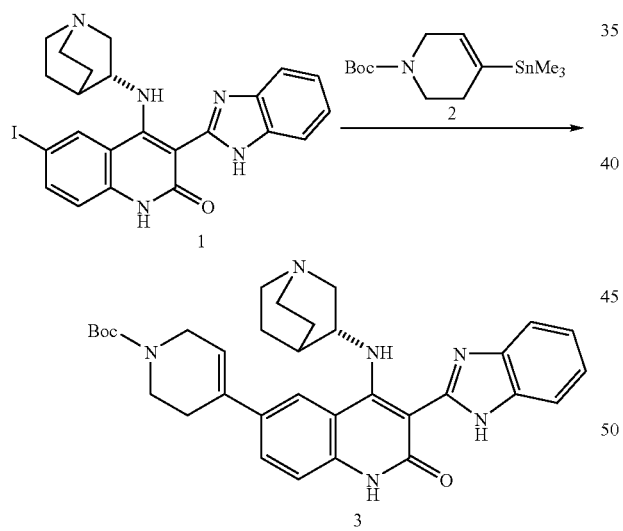

For similar procedures see the following reference, herein incorporated by reference in its entirety for all purposes as if fully set forth herein, and references therein: Eastwood, P. R. *Tetrahedron Letters* 2000, 41, 3705-3708. The palladium catalyst, Pd(dppf)$_2$Cl$_2$.CH$_2$Cl$_2$ (6 mg, 0.007 mmol) was added in one portion to a stirred and argon sparged (1 minute) solution of 6-iodoquinolinone (1) (25 mg, 0.049 mmol) and 4-trimethylstannyl-3,6-dihydro-2H-pyridine-1-carboxylic acid tert-butyl ester (2) (24 mg, 0.069 mmol) in DMF at room temperature. The reaction heated to 85° C. under argon for 2 hours. The product was purified by prep. HPLC using a reverse phase Ultro 120 C18 column running a 2% gradient (AcCN/water, 0.1% TFA). The purified fractions were lyophilized to dryness to give 6 mg of white powder in 21% yield and >97% purity.

Step 2: 4-(R)-(1-Aza-bicyclo[2.2.2]oct-3-ylamino)-3-(1H-benzoimidazol-2-yl)-6-(1,2,3,6-tetrahydro-pyridin-4-yl)-1H-quinolin-2-one

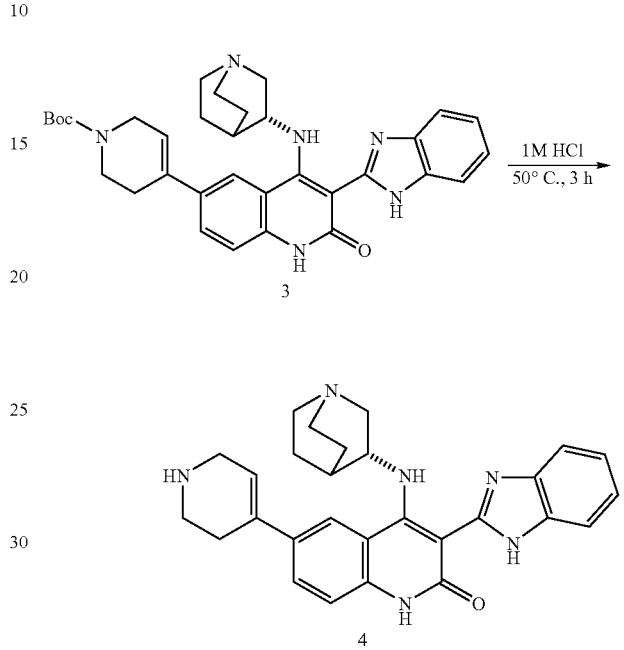

1 M aqueous HCl (1 mL) was added to lyophilized Boc-piperidine quinolone (3) powder (5 mg, 0.009 mmol). The resulting solution was stirred for 3 hours at 50° C. The product was purified by prep. HPLC using a reverse phase Ultro 120 C18 column running a 2% gradient (AcCN/water, 0.1% TFA). The purified fractions were lyophilized to dryness affording 4 mg of white powder in 78% yield and >98% purity.

Example 75

Synthesis of 4-(R)-(1-Aza-bicycl[2.2.2]oct-3-ylamino)-3-(1H-benzoimidazol-2-yl)-6,7-dihydroxy-1H-quinolin-2-one

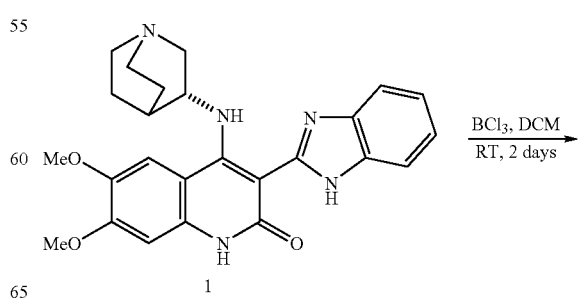

-continued

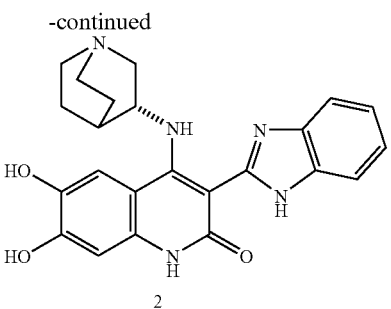

BCl$_3$ (1 M in CH$_2$Cl$_2$) (5 mL) was added to 6,7-Dimethoxyquinolone (1) powder (20 mg, 0.045 mmol) in an 8 mL vial. The vial was capped, and the resulting solution was stirred for 2 days at 40° C. The progress of the reaction was monitored by HPLC and LCMS. More BCl$_3$ was added if needed. The reaction was concentrated to dryness, and the residue was dissolved in DMSO (1 mL). The product was purified by prep. HPLC using a reverse phase Ultro 120 C18 column running a 2% gradient (AcCN/water, 0.1% TFA). The purified fractions were lyophilized to dryness to give 6 mg of white powder in 32% yield and >98% purity.

Example 76

Synthesis of 4-(R)-(1-Aza-bicyclo[2.2.2]oct-3-ylamino)-3-(1H-benzoimidazol-2-yl)-7-(morpholine-4-carbonyl)-1H-quinolin-2-one

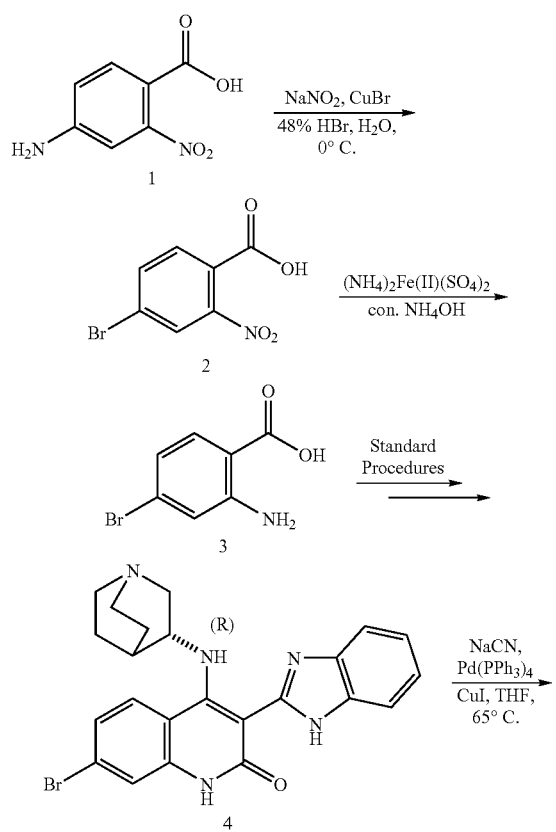

-continued

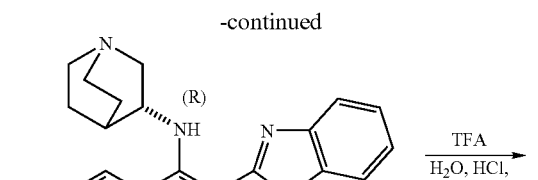

Step 1: 4-Bromo-2-nitro-benzoic acid

A modification of a procedure in the following reference which is herein incorporated by reference in its entirety, for all purposes as if fully set forth herein, was used: Boojamra, C. G.; Burow, K. M.; Thompson, L. A.; Ellman, J. A. *J. Org. Chem.*, 1997, 62,1240-1256. A solution of NaNO$_2$ (1.9 g, 27.4 mmol) in water (65 mL) was added to a stirred solution of 4-amino-2-nitro-benzoic acid (1) (5 g, 27.4 mmol) in aqueous 48% HBr (40 mL) and water (82 mL) at 0° C. The cloudy reaction mixture turned into a clear orange-yellow solution after about 15 minutes. After stirring for 25 minutes, the solution was added dropwise to a solution of CuBr (5.2 g, 36.3 mmol) in aqueous 48% HBr (90 mL) at 0° C. A yellow foam developed and gas was evolved from the purple-brown mixture. After stirring at 0° C. for 1 hour, the mixture was concentrated under reduced pressure. The aqueous layer was extracted with EtOAc (4×300 mL) which was dried with Na$_2$SO$_4$ and concentrated to dryness giving a dark solid. The crude product was filtered through a plug of florisil (~20 g) eluting with EtOAc. The combined organic fractions were evaporated to approx. 200 mL and washed with 1 M HCl (2×50 mL), brine (50 mL), dried with Na$_2$SO$_4$, filtered and concentrated to dryness giving 6.1 g of a light yellow solid product (2) in 91% yield and >90% purity by HPLC.

Step 2: 2-Amino-4-bromo-benzoic acid

A modification of a procedure in the following reference herein incorporated by reference in its entirety, for all purposes as if fully set forth herein, was used: Boojamra, C. G.; Burow, K. M.; Thompson, L. A.; Ellman, J. A. *J. Org. Chem.*, 1997, 62, 1240-1256. A solution of $(NH_4)_2Fe^{(II)}(SO_4)_2 \cdot 6 H_2O$ (24.4 g, 63 mmol) in water (60 mL) was added to a stirred solution of 4-bromo-2-nitro-benzoic acid (2) (3.05 g, 12.45 mmol) in concentrated aqueous $NH_4OH$ (40 mL) at room temperature. The iron sulfate solution flask was washed with an additional portion of water (20 mL) which was added to the reaction. After 16 hours, the reaction had changed from a dark green solution to a rusty-brown mixture which was filtered through a plug of Celite and washed with concentrated aqueous $NH_4OH$ (80 mL) and water (4×80 mL). The combined aqueous fractions were acidified to pH 1-2 with aqueous concentrated HCl and extracted with EtOAc (4×500 mL). The organic fractions were evaporated under reduced pressure to a brown solid. The crude product was dissolved in EtOAc (300 mL), washed with water (40 mL), brine (40 mL), dried with $Na_2SO_4$, filtered, and concentrated to dryness giving 2.47 g of product (3) as a brown solid in 91% yield and >90% purity by HPLC.

Step 3: 4-(R)-(1-Aza-bicyclo[2.2.2]oct-3-ylamino)-3-(1H-benzoimidazol-2-yl)-7-bromo-1H-quinolin-2-one The (R)-quinolone 4 was prepared using the standard methods described in the other Examples set forth herein.

Step 4: 4-(R)-(1-Aza-bicyclo[2.2.2]oct-3-ylamino)-3-(1H-benzoimidazol-2yl)-2-oxo-1,2-dihydro-quinoline-7-carbonitrile A modification of a procedure described in the following reference incorporated herein in its entirety, for all purposes as if fully set forth herein, was used: Anderson, B. A.; Bell, E. C.; Ginah, F. O.; Harn, N. K.; Pagh, L. M.; Wepsiec, J. P. *J. Org. Chem.*, 1998, 63, 8224-8228. A mixture of 6-bromo-(R)-quinolone (4) (99 mg, 0.21 mmol), KCN (85 mg, 1.3 mmol), CuI (70 mg, 0.37 mmol), $Pd(PPh_3)_4$ (207 mg, 0.18 mmol) in THF (20 mL) and $CH_3CH_2CN$ (5 mL) was sparged with dry argon (1 minute) and sonicated until a homogeneous cloudy yellow suspension was formed. The reaction was stirred under argon at 85° C. for 4 days until complete as determined using HPLC and LCMS. The milky greenish-yellow mixture was filtered, and the filter was washed with AcCN (100 mL). The filtrate was evaporated under reduced pressure to give a yellow solid. The crude product was dissolved in DMSO (1 mL). The product was purified by prep. HPLC using a reverse phase Ultro 120 C18 column running a 1% gradient (AcCN/water, 0.1% TFA). The purified fractions were then lyophilized to dryness to give 60 mg of 5 as a white solid in 70% yield and 98% purity.

Step 5a: 4-(S)-(1-Aza-bicyclo[2.2.2]oct-3-ylamino)-3-(1H-benzoimidazol-2-yl)-2-oxo-1,2-dihydro-quinoline-7-carboxylic acid A solution of 6-cyano-quinolone (5 (S)) (12 mg, 0.029 mmol) in TFA (3.75 mL), aqueous concentrated HCl (1.25 mL) and water (2.5 mL) was stirred at 75° C. for 20 hours. LCMS analysis showed the formation of the product acid (6) and the primary amide. The yellow solution was stirred at 75° C. for an additional 20 hours until most of the primary amide was hydrolyzed. The reaction was evaporated under reduced pressure to give a yellow glass. The crude product was dissolved in DMSO (1 mL). The product was purified by prep. HPLC using a reverse phase BDX C18 (20×50 mm) column running a 3% gradient (AcCN/water, 0.1% TFA). The purified fractions were lyophilized to dryness to give 2.5 mg of yellow solid 6 (S) in 16% yield and >95% purity.

Step 5b: 4-(R)-(1-Aza-bicyclo[2.2.2]oct-3-ylamino)-3-(1H-benzoimidazol-2-yl)-2-oxo-1,2-dihydro-quinoline-7-carboxylic acid A solution of 6-cyano-quinolone (5 (R)) (56 mg, 0.136 mmol) in TFA (7.5 mL), aqueous concentrated HCl (5.0 mL), and water (2.5 mL) was stirred at 85° C. for 40 hours. HPLC and LCMS analysis showed the formation of the product acid (6 (R)) 85% and the primary amide about 15%. The yellow solution was evaporated under reduced pressure to give a yellow solid. The crude product was lyophilized from AcCN/water (1:1) twice to give 51 mg of yellow solid as the TFA salt in 69% yield and 85% purity.

Step 6: 4-(R)-(1-Aza-bicyclo[2.2.2]oct-3-ylamino)-3-(1H-benzoimidazol-2yl)-7-(morpholine-4-carbonyl)-1H-quinolin-2-one Morpholine (30 µL, 0.34 mmol) was added to a pre-mixed (20 minutes of stirring) solution of 6-carboxy-(R)-quinolone (6) (15 mg, 0.035 mmol), HBTU (19 mg, 0.05 mmol), and DIEA (18 µL, 0.1 mmol) in NMP (0.5 mL). After stirring 12 hours, the crude product was purified by prep. HPLC using a reverse phase BDX C18 column running a 1.5% gradient (AcCN/water, 0.1% TFA). The purified fractions were lyophilized to dryness affording 4 mg of product 7 as a white solid TFA salt in 19% yield and 97% purity.

Example 77

Synthesis of 4-(R)-(1-Aza-bicyclo[2.2.2]oct-3-ylamino)-3-(1H-benzoimidazol-2-yl)-6,7-dichloro-1H-quinolin-2-one

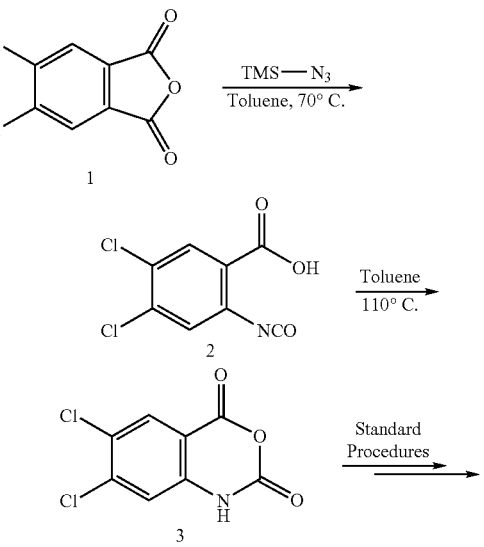

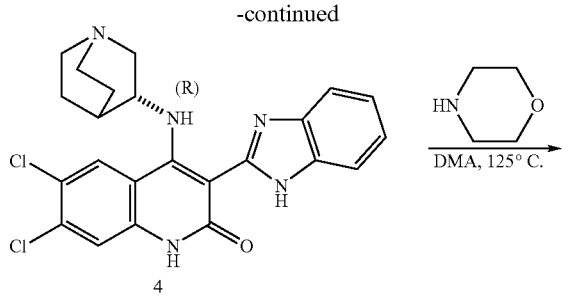

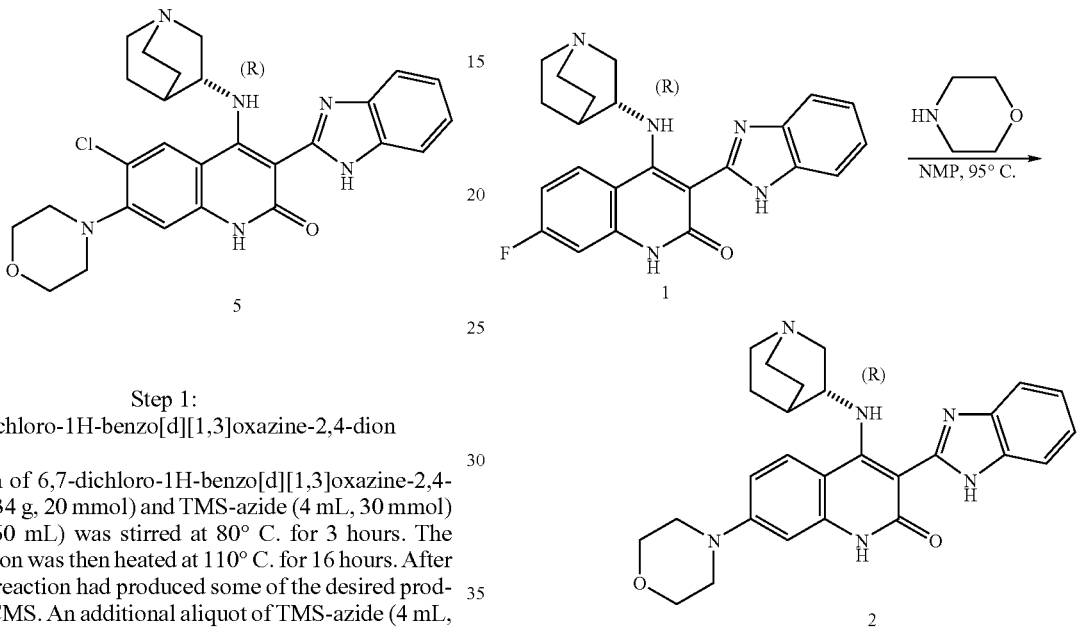

Step 1: 6,7-Dichloro-1H-benzo[d][1,3]oxazine-2,4-dion

A solution of 6,7-dichloro-1H-benzo[d][1,3]oxazine-2,4-dione (1) (4.34 g, 20 mmol) and TMS-azide (4 mL, 30 mmol) in toluene (60 mL) was stirred at 80° C. for 3 hours. The cloudy solution was then heated at 110° C. for 16 hours. After cooling, the reaction had produced some of the desired product (3) by LCMS. An additional aliquot of TMS-azide (4 mL, 30 mmol) was added to the reaction which was again heated with stirring under nitrogen to 80° C. for 2 hours and 110° C. for 16 hours. HPLC and LCMS showed that the reaction had proceeded to near completion. The reaction was concentrated under reduced pressure to give a yellow slurry which was diluted with absolute EtOH (8 mL). An ivory-colored solid formed and was collected by suction filtration. The solid was washed with absolute EtOH (50 mL) and dried in vacuo to give 2.9 g of pure product 3 in 63% yield.

Step 2: 4-(R)-(1-Aza-bicyclo[2.2.2]oct-3-ylamino)-3-(1H-benzoimidazol-2-yl)-6,7-dichloro-1H-quinolin-2-one 4-(R)-(1-Aza-bicyclo[2.2.2]oct-3-ylamino)-3-(1H-benzoimidazol-2-yl)-6,7-dichloro-1H-quinolin-2-one (4) was prepared using the standard methods described in previous Examples.

Step 3: 4-(R)-(1-Aza-bicyclo[2.2.2]oct-3-ylamino)-3-(1H-benzoimidazol-2yl)-6,7-dichloro-1H-quinolin-2-one An argon sparged (1 minute) solution of 6,7-Dichloroquinolone (4) (20 mg, 0.044 mmol) and morpholine (1 mL) in DMA (2 mL) was stirred at 120° C. for 48 hours. HPLC and LCMS showed that the reaction had proceeded to approximately 60% completion. Heating at 120° C. seemed to cause some loss of chlorine. The reaction was again sparged with argon, capped and heated to 100° C. for 3 days until complete as determined by LCMS. The crude product was purified by prep. HPLC using a reverse phase BDX C18 column running a 4% gradient (AcCN/water, 0.1% TFA). The purified fractions were lyophilized to dryness to give 7 mg of product 5 as white solid TFA salt in 25% yield and 97% purity.

Example 78

4-(R)-(1-Aza-bicyclo[2.2.2]oct-3-ylamino)-3-(1H-benzoimidazol-2-yl)-6,7-dichloro-1H-quinolin-2-one An argon sparged (1 minute) solution of 6,7-Dichloroquinolone (4) (20 mg, 0.044 mmol) and morpholine (100 µL) in NMP (800 µL) was stirred at 95° C. for 48 hours. HPLC and LCMS showed that the reaction had proceeded to completion. The crude product was purified by prep. HPLC using a reverse phase BDX C18 column running a 3% gradient (AcCN/water, 0.1% TFA). The purified fractions were lyophilized to dryness to give 9 mg of product 2 as white solid TFA salt in 35% yield and 97% purity.

Example 79

Synthesis of 4-(R)-(1-Aza-bicyclo[2.2.2]oct-3-ylamino)-3-(1H-benzoimidazol-2-yl)-1H-[1,7]naphthyridin-2-one

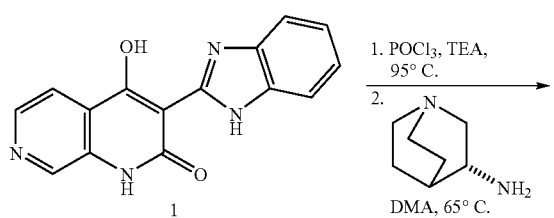

-continued

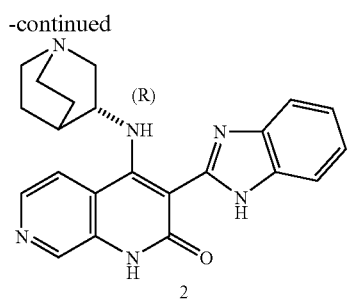

2

POCl$_3$ (1.5 mL, 5.94 mmol) was added to the 3-(1H-benzoimidazol-2-yl)-4-hydroxy-1H-[1,7]naphthyridin-2-one (1) (200 mg, 0.72 mmol) with stirring. TEA (153 μL, 1.1 mmol) was added to the reaction, and the reaction was heated to 60° C. for 1.5 hours. The brown solution was concentrated under reduced pressure to provide a brown solid. The solid was dissolved in EtOAc (100 mL) and washed with saturated NaHCO$_3$ (50 mL). The organic layer was evaporated under reduced pressure to a light yellow solid which was dissolved in DMA (5 mL). After adding 3-(R)-Aminoquinuclidine dihydrochloride salt (200 mg, 1.0 mmol) and DIEA (430 μL), the solution was stirred at 65° C. for 10 hours. LCMS showed that product had formed. The crude product was purified by prep. HPLC using a reverse phase BDX C18 column running a 3% gradient (AcCN/water, 0.1% TFA). The purified fractions were lyophilized to dryness to give product 2 as a yellow solid TFA salt.

Example 80

Synthesis of 4-amino-3-{6-[(2,4-dimethylmorpholin-2-yl)methylamino]benzimidazol-2-yl}hydroquinolin-2-one Step 1: 2-(methylamino)methyl-4-benzyl morpholine Commercially available 2-chloromethyl-4-benzyl morpholine was dissolved in an 8 M solution of NH$_2$Me in EtOH and heated in a glass pressure vessel at 110° C. overnight. The solvent was removed in vacuo, and the compound was used in the next step without further purification. LC/MS m/z: 221.2 (MH+), R$_t$ 0.55 minutes.

Step 2: 2-[(3-amino-4-nitrophenyl)methylamino]-2-methylmorpholin-4-yl phenyl ketone The title compound was synthesized using the procedure set forth in Example 46) LC/MS m/z: 357.3 (MH+), R$_t$ 1.98 minutes.

Step 3: ethyl 2-(6-{methyl[2-methyl-4-(phenylcarbonyl)morpholin-2-yl]amino}benzimidazol-2-yl)acetate The synthesis of the title compound was conducted using the procedure set forth in Example 46. LC/MS m/z: 317.3 (MH+), R$_t$ 2.45 minutes.

Step 4: 4-amino-3-(6-{methyl[2-methyl-4-(phenylcarbonyl)morpholin-2-yl]amino}benzimidazol-2-yl)hydroquinolin-2-one The synthesis of 4-amino-3-(6-{methyl[2-methyl-4-(phenylcarbonyl)morpholin-2-yl]amino}benzimidazol-2-yl)hydroquinolin-2-one was performed according to the general synthesis procedure described in Example 19.

Step 5: 4-amino-3-{6-[(2,4-dimethylmorpholin-2-yl)methylamino]benzimidazol-2-yl}hydroquinolin-2-one a) Debenzylation of the compound of Step 4 above was accomplished using the following procedure. The benzylated compound (1.0 equivalent) and 10% Pd/C (0.1 equivalents) were suspended in 1:1 ethanol and 1 N aqueous HCl at room temperature. The reaction flask was evacuated and subsequently filled with H$_2$. The resulting mixture was stirred under a hydrogen atmosphere overnight. The resulting solution was filtered through Celite and concentrated under vacuum. The water was then made basic with 30% aqueous KOH, and the product was extracted with EtOAc. The combined organic layers were concentrated. The resulting residue was dissolved in CH$_2$Cl$_2$:MeOH:AcOH (2:2:1).

b) Methylation was accomplished using the following procedure. Paraformaldehyde (1.2 equivalents) and BH$_3$pyridine (3 equivalents, 8 M solution) were added, and the mixture was stirred overnight at room temperature. The solvent was removed in vacuo, and water was added. The product was extracted with EtOAc (3×). The combined organic layers were concentrated. The residue was purified by chromatography on silicagel (10% MeOH/CH$_2$Cl$_2$) to afford the desired product.

Example 81

Synthesis of 2-(4-Amino-5-fluoro-2-oxo-3-hydroquinolyl)benzimidazole-6-carboxylic acid Step 1: 2-[5-(methoxycarbonyl)benzimidazol-2-yl]acetate Methyl 3,4-diaminobenzoate (1 equivalent), was stirred with ethyl-3-ethoxy-3-iminopropanoate hydrochloride (2 equivalents) in EtOH at 70° C. overnight. The reaction mixture was cooled to room temperature, and the EtOH was removed under reduced pressure. The residue was taken up in water and extracted with CH$_2$Cl$_2$ (3×). The organic extracts were dried over Na$_2$SO$_4$, and the solvent was removed. The solid was triturated with Et$_2$O to yield the desired ethyl 2-[5-(methoxycarbonyl)-benzimidazol-2-yl]acetate as an off-white solid. LC/MS m/z: 263.2 (MH+), R$_t$ 1.80 minutes.

Step 2: Methyl 2-(4-amino-5-fluoro-2-oxo-3-hydroquinolyl) benzimidazole-6-carboxylate In a procedure similar to that described in Example 9, LiHMDS (1.0 N solution in THF, 4.0 equivalents) was added to a solution of 2-[5-(methoxycarbonyl)benzimidazol-2-yl]acetate (1.0 equivalent) and 2-amino-6-fluorobenzene carbonitrile (1.1 equivalents) in anhydrous THF in a flame dried round bottom flask at 0° C. The resulting mixture was allowed to warm to room temperature, was stirred overnight, and was then heated at 55° C. for 8 hours. The mixture was cooled to 0° C. and quenched with saturated NH$_4$Cl. The aqueous phase was extracted with EtOAc (3×), and the organic extracts were collected and dried (Na$_2$SO$_4$). The solvent was removed under reduced pressure, and the residue was triturated with MeOH to obtain a white solid containing 50% of methyl 2-(4-amino-5-fluoro-2-oxo-3-hydroquinolyl) benzimidazole-6-carboxylate and 50% of its uncyclized isomer. LC/MS m/z 353.2 (MH+), R$_t$ 2.14 minutes.

Step 3: 2-(4-Amino-5-fluoro-2-oxo-3-hydroquinolyl)benzimidazole-6-carboxylic acid The crude product obtained in Step 2 was dissolved in a 1:1 mixture of EtOH and 30% aqueous KOH and stirred overnight at 70° C. The reaction mixture was cooled and acidified with 1 N HCl. A crash out formed. The solid was filtered, washed with water and dried providing 190 mg (40%) of 2-(4-amino-5-fluoro-2-oxo-3-hydroquinolyl)benzimidazole-6-carboxylic acid as a brown solid. LC/MS m/z: 339.1 (MH+), R$_t$ 2.41 minutes.

Step 4: Amide Functionalization of 2-(4-amino-2-oxo-3-hydroquinolyl)benzimidazole-4-carboxylic acid A mixture of 2-(4-amino-2-oxo-3-hydroquinolyl)benzimidazole-6-carboxylic acid (1 equivalent), primary or secondary amine (1 equivalent), EDC (1-(3-dimethylaminopropyl)-3-ethylcarbodiimide hydrochloride, 1.2 equivalents), HOAT (1-hydroxy-7-azabenzotriazole, 1.2 equivalents), and triethylamine (2.5 equivalents) in DMF, was stirred at 23° C. for 20 hours. The reaction mixture was partitioned between water and ethyl acetate. The combined organic layers were dried (Na$_2$SO$_4$), and concentrated. Water was added, and the precipitate thus formed was filtered and dried. The crude was purified by reverse phase prep. HPLC to afford the desired carboxamide.

Examples 82 and 83

Synthesis of 3-(6-{(2R,5R)-2-[(dimethylamino)methyl]-5-methylmorpholin-4-yl}benzimidazol-2-yl)-4-aminohydroquinolin-2-one (7a) and 3-(6-{(2S,5R)-2-[(dimethylamino)methyl]-5-methylmorpholin-4-yl}benzimidazol-2-yl)-4-aminohydroquinolin-2-one

Step 1: (2R)-2-[Benzylamino]propan-1-ol

A mixture of (2R)-2-amino propanol (1.2 equivalents), benzaldehyde (1 equivalent), NaHCO$_3$ (1.5 equivalents), and MeOH, (~1 M) was heated at reflux for 4 hours and then cooled to 0° C. Sodium borohydride (4.8 equivalents) was added portionwise to the stirred reaction mixture during a period of 2 hours at ca. 10° C. The whole was stirred at room temperature for 4 hours. The insoluble materials were filtered off and then the filtrate was concentrated to dryness. The residue was dissolved in CH$_2$Cl$_2$, and the solution was washed successively with water (2×) and brine (1×). The organic extracts were collected and dried (Na$_2$SO$_4$). The solvent was evaporated to give the desired product as a colorless oil, which solidified on standing and was used in the next step without further purification. GC/MS: 134 (100%, M+−CH$_2$OH), R$_t$ 11.57 minutes.

Step 2a and 2b: (2S,5R)-2-(chloromethyl)-5-methyl-4-benzylmorpholine and (2R,5R)-2-(chloromethyl)-5-methyl-4-benzylmorpholine

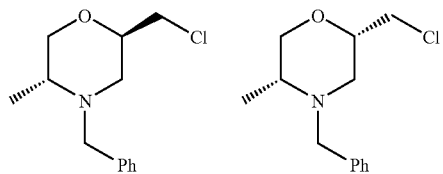

A mixture of (2R)-2-[benzylamino]propan-1-ol (1 equivalent) and epichlorohydrin (2 equivalents) was stirred at 40° C. for 2.5 hours and concentrated at reduced pressure. The residue was cooled to 0° C. and cold trifluoromethanesulfonic acid (3 equivalents) was added very slowly. The flask was equipped with a reflux condenser and the mixture was stirred at 160° C. overnight. The reaction mixture was cooled to room temperature, and the black tar thus formed was dissolved in CH$_2$Cl$_2$ and transferred to an Erlenmeyer flask equipped with a magnetic stir bar. The solution was then cooled to 0° C., and ice water was slowly added. The dark biphasic mixture was made basic (pH=12) with 30% NaOH solution. The two phases were separated, and the aqueous phase was further extracted with CH$_2$Cl$_2$. The organic layer was washed with water, treated with brine, dried (Na$_2$SO$_4$), and concentrated to afford a dark brown oil. The crude product mixture contained a mixture of (2S,5R)-2-(chloromethyl)-5-methyl-4-benzylmorpholine and (2R,5R)-2-(chloromethyl)-5-methyl-4-benzylmorpholine which were separated by chromatography on silicagel (EtOAc/Hexanes 1:20 to 1:8). (2S,5R) isomer: TLC (EtOAc/Hexanes 1:8): R$_f$=0.75; GC/MS: 239 (10%, M+), R$_t$ 15.17 minutes; LC/MS m/z 240.0 (MH+), R$_t$ 1.60 minutes. (2R,5R) isomer: TLC (EtOAc/Hexanes 1:8): R$_f$ 0.60; GC/MS: 239 (15%, M+), R$_t$ 15.08 minutes; LC/MS m/z 240.0 (MH+), R$_t$ 1.56 minutes.

Step 3a: (2S,5R)-2-[dimethylamino(methyl)]-5-methyl-4-benzylmorpholine

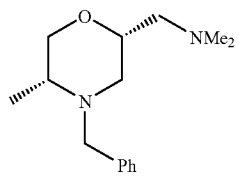

A mixture of (2S,5R)-2-(chloromethyl)-5-methyl-4-benzylmorpholine (1 equivalent) and dimethylamine in ethanol (33%, approx. 5.6 M, 5 equivalents) was heated at 150° C. over 2 days in a glass pressure vessel. The reaction mixture was cooled to room temperature and concentrated under reduced pressure. The residue was dissolved in 1 N HCl, and the solution was washed with CH$_2$Cl$_2$. The water phase was made basic with 30% NaOH solution (to pH=12) and extracted with CH$_2$Cl$_2$. The organic extracts were collected and dried (Na$_2$SO$_4$). Evaporation of the solvent under reduced pressure afforded (2S,5R)-2-[dimethylamino(methyl)]-5-methyl-4-benzylmorpholine as a brown oil which was used in the next step without purification. GC/MS: 247 (2%, M−H), 204 (55%, M−NMe$_2$), R$_t$ 15.5 minutes; LC/MS m/z 249.2 (MH+), R$_t$ 0.72 minutes.

Step 4a: (2S,5R)-2-[dimethylamino(methyl)]-5-methylmorpholine

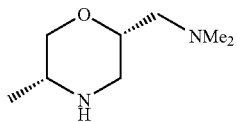

(2S,5R)-2-[Dimethylamino(methyl)]-5-methyl-4-benzylmorpholine (28 g, 113 mmol, 1 equivalent), was dissolved in EtOH (1 M), and the solution was transferred to a stainless steel high pressure vessel equipped with a pressure gauge. 10% Pd/C was added (2.8 g, 10 wt. %), and the vessel charged with $H_2$. The reaction mixture was stirred at 130° C. and 200 psi of $H_2$ overnight. The reaction mixture was cooled to room temperature, filtered and evaporated. The desired amine was obtained in quantitative yield as a yellow oil. GC/MS: 128 (10%, M+−2×$CH_3$), 58 (100%, $NHCH_2CHO$), $R_t$ 8.16 minutes.

Step 3b: (2R,5R)-2-[dimethylamino(methyl)]-5-methyl-4-benzylmorpholine

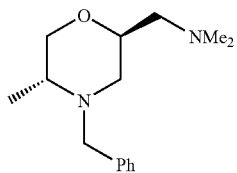

The title compound was obtained by treating (2R,5R)-2-(chloromethyl)-5-methyl-4-benzylmorpholine with dimethylamine in EtOH, as described above (Step 3a) diastereomer. GC/MS: 247 (2%, M−H), 204 (55%, M−$NMe_2$), $R_t$ 15.40 minutes; LC/MS m/z 249.2 (MH+), $R_t$ 0.79 minutes.

Step 4b: (2R,5R)-2-[dimethylamino(methyl)]-5-methylmorpholine

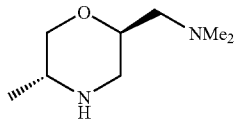

The title product was obtained by debenzylating (2R,5R)-2-[dimethylamino(methyl)]-5-methyl-4-benzylmorpholine as described earlier (Step 4a). GC/MS: 158 (1%, M+), 128 (3%, M+−2×$CH_3$), 58 (100%, $NHCH_2CHO$), $R_t$ 7.64 minutes.

The same procedure can be employed to prepare (2S,5S)-2-[dimethylamino(methyl)]-5-methylmorpholine and (2R,5S)-2-[dimethylamino(methyl)]-5-methylmorpholine provided that (2S)-2-aminopropanol is used as starting material.

Step 5a: {[(2S,5R)-4-(3-amino-4-nitrophenyl)-5-methylmorpholin-2-yl]methyl}dimethylamine

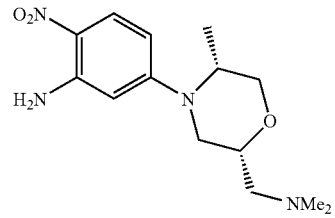

A mixture of 5-fluoro-2-nitroaniline (1.1 equivalents), [((2S,5R)-5-methylmorpholin-2-yl)methyl]dimethylamine (1 equivalent), triethylamine (3 equivalents), and NMP was heated at 140° C. for 48 hours in a sealed high pressure vessel. The reaction mixture was cooled to 25° C. and dissolved in $CH_2Cl_2$. The solution was washed with water (2×) and dried ($Na_2SO_4$). Purification via chromatography on silicagel (10% MeOH in dichloromethane), afforded the desired product as a dark yellow foam. LC/MS m/z 295.2 (MH+) $R_t$ 1.86 minutes.

Step 6a: Ethyl 2-(6-{(2R,5R)-2-[(dimethylamino)methyl]-5-methylmorpholin-4-yl}benzimidazol-2-yl)acetate

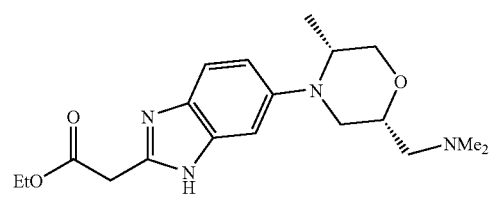

The title compound was synthesized using the general procedure for synthesis of benzimidazoles, but at room temperature for two days. Purification by column chromatography on silicagel afforded the purified product. LC/MS m/z 361.2 (MH+) $R_t$ 1.27 minutes.

Step 5b: {[(2R,5R)-4-(3-amino-4-nitrophenyl)-5-methylmorpholin-2-yl]methyl}dimethylamine

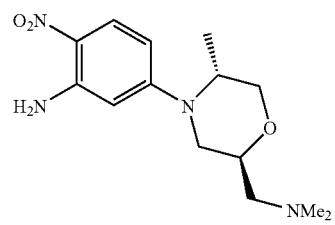

A mixture of 5-fluoro-2-nitroaniline (1.1 equivalents), [((2R,5R)-5-methylmorpholin-2-yl)methyl]dimethylamine (1 equivalent), triethylamine (3 equivalents), and NMP was heated at 140° C. for 48 hours in a sealed high pressure vessel. The reaction mixture was cooled to 25° C. and dissolved in $CH_2Cl_2$. The solution was washed with water (2×) and dried ($Na_2SO_4$). Purification via chromatography on silicagel (10%

MeOH in dichloromethane), afforded the desired product as a dark yellow foam. LC/MS m/z 295.1 (MH+) R$_t$ 1.85 minutes.

Step 6b: Ethyl 2-(6-{(2R,5R)-2-[(dimethylamino)methyl]-5-methylmorpholin-4-yl}benzimidazol-2-yl)acetate

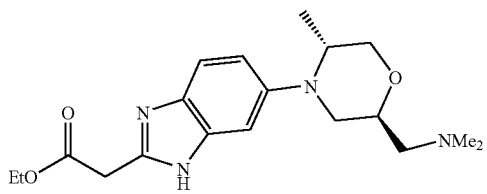

The title compound was prepared using the general procedure for synthesis of benzimidazoles, but at room temperature for two days. Purification by column chromatography on silicagel afforded the purified product. LC/MS m/z 361.2 (MH+) R$_t$ 1.20 minutes.

Step 7a; 3-(6-{(2R,5R)-2-[(dimethylamino)methyl]-5-methylmorpholin-4-yl}benzimidazol-2-yl)-4-aminohydroquinolin-2-one

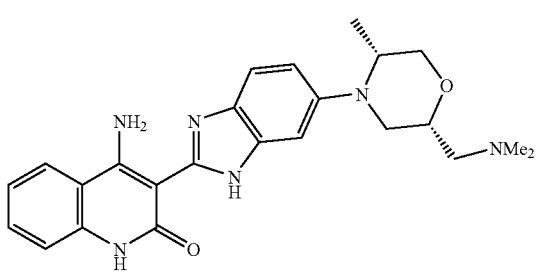

The title compound was synthesized according to Example 46 (LC/MS m/z 433.1 (MH+) R$_t$ 1.58 minutes).

Step 7b: 3-(6-{(2S,5R)-2-[(dimethylamino)methyl]-5-methylmorpholin-4-yl}benzimidazol-2-yl)-4-aminohydroquinolin-2-one

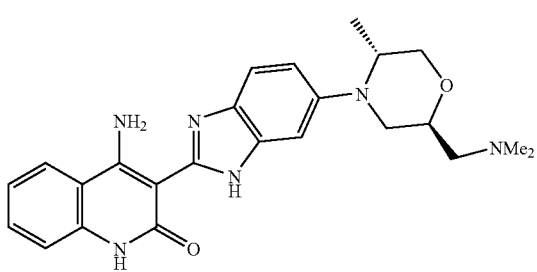

The title compound was synthesized according to Example 46 (LC/MS m/z 433.1 (MH+) R$_t$ 1.58 minutes).

Example 84

Synthesis of 4-amino-3-[5-(4-methylpiperazinyl)benzimidazol-2-yl]-2-oxohydroquinoline-6-carbonitrile

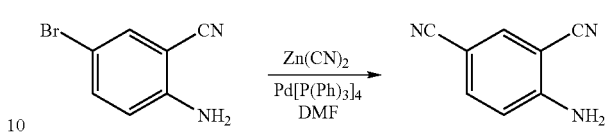

Using a literature procedure described in the following literature reference which is herein incorporated by reference in its entirety for all purposes as if fully set forth herein, a dry round bottom flask was charged with 2-amino-5-bromo benzonitrile (1 equivalent) and zinc cyanide (2 equivalents), and DMF was added: *J. Med. Chem.* 2000, 43, 4063. Nitrogen was bubbled through the solution for 5 minutes, and Pd[P(Ph)$_3$]$_4$ was added in one portion. The reaction mixture was stirred at 90° C. overnight. After cooling to room temperature, saturated NaHCO$_3$ was added, and the mixture was extracted with EtOAc. The organic extracts were collected and dried (Na$_2$SO$_4$). Evaporation of the solvent under reduced pressure and purification by column chromatography on silicagel (2% methanol in methylene chloride) afforded the desired 4-aminobenzene-1,3-dicarbonitrile as a white solid. GC/MS m/z: 143 (M+, 100%), R$_t$ 14.7 minutes 4-amino-3-[5-(4-methylpiperazinyl)benzimidazol-2-yl]-2-oxohydroquinoline-6-carbonitrile

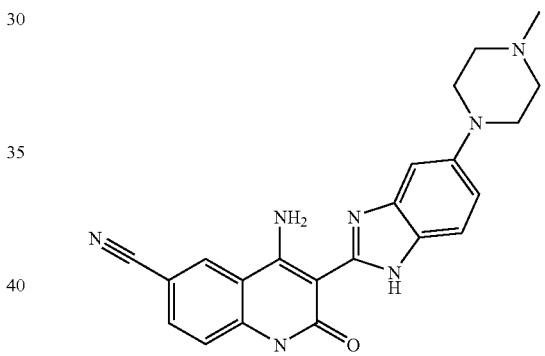

4-Amino-isophthalonitrile and ethyl 2-[5-(4-methylpiperazinyl) benzimidazol-2-yl]acetate were reacted according to Example 46. LC/MS m/z 400.1 (MH+), R$_t$ 1.54 minutes.

Example 85

Synthesis of 4-amino-3-[5-(4-methylpiperazinyl)benzimidazol-2-yl]-2-oxohydroquinoline-6-carboxylic acid

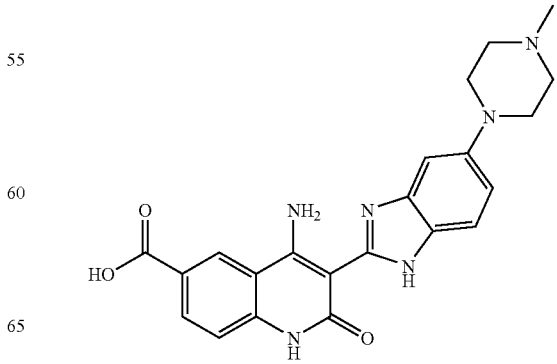

4-amino-3-[5-(4-methylpiperazinyl)benzimidazol-2-yl]-2-oxohydroquinoline-6-carbonitrile (Example 84) derivative was dissolved in a 1:1 mixture of EtOH and 30% aqueous NaOH. The solution was heated to 100° C. for 2 hours. The mixture was cooled to room temperature, concentrated, and neutralized with 1 N HCl until the product precipitated from solution. The solid was washed with water twice and dried to afford the desired product. The HCl salt was then obtained by lyophilization from a 1:1 mixture of CH$_3$CN and 1 N HCl (LC/MS m/z 331.3 (MH+) R$_t$ 1.60 minutes).

Example 86

Synthesis of {4-amino-3-[5-(4-methylpiperazinyl)benzimidazol-2-yl]-2-oxo(6-hydroquinolyl)}-N-benzylcarboxamide

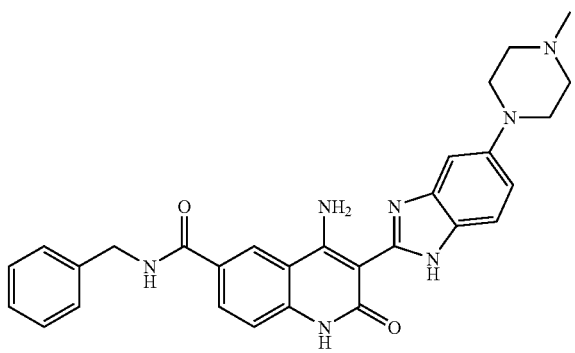

4-amino-3-[5-(4-methylpiperazinyl)benzimidazol-2-yl]-2-oxohydroquinoline-6-carboxylic acid (Example 85), as the HCl salt (1 equivalent), was suspended in DMF. Et$_3$N (2 equivalents) and a primary or secondary amine (1.2 equivalents) were added, followed by EDC (1.2 equivalents) and HOAT (1.2 equivalents). The reaction mixture was stirred at room temperature for 2 days. Water was added, and the mixture was extracted with EtOAc. The residue was purified by prep. HPLC obtaining the desired product.

Example 87

Synthesis of 4-amino-3-(6-{3-[(dimethylamino)methyl]pyrrolidinyl}benzimidazol-2-yl)hydroquinolin-2-one

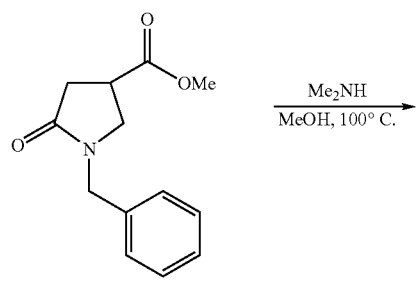

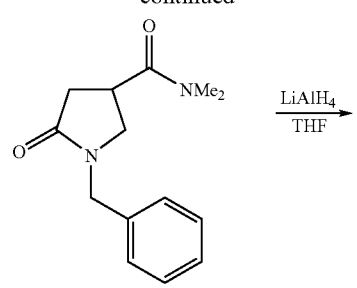

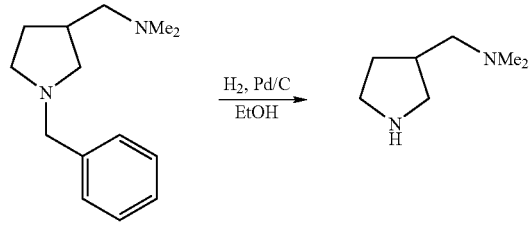

Dimethyl(pyrrolidin-3-ylmethyl)amine was synthesized from commercially available methyl-5-oxo-1-(phenylmethyl)pyrrolidine carboxylate following a procedure previously described in the literature (Domagala, J. M. U.S. Pat. No. 5,281,612, hereby incorporated by reference in its entirety for all purposes as if fully set forth herein). LC/MS m/z 265.1 (MH+), 1.62 minutes. Conversion to the concomitant 4-amino-3-(6-{3-[(dimethylamino)methyl]pyrrolidinyl}benzimidazol-2-yl)hydroquinolin-2-one was performed according to the procedure in Example 8 (LC/MS m/z 403.2 (MH+), R$_t$ 1.64 minutes).

Example 88

Synthesis of 3-[6-((1S)-3,6-diazabicyclo[4.3.0]non-3-yl)benzimidazol-2-yl]-4-amino-5-fluorohydroquinolin-2-one

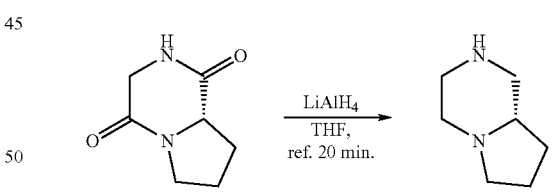

(6S)-1,4-diazabicyclo[4.3.0]nonane was synthesized as shown above by LAH (lithium aluminum hydride) reduction of commercially available Cyclo-Gly-Pro, employing the literature procedure set forth in the following reference which is herein incorporated by reference in its entirety for all purposes as if fully set forth herein: de Costa B. R. et al. *J. Med. Chem.*, 1993, 36, 2311. Conversion to the concomitant 3-[6-((1S)-3,6-diazabicyclo[4.3.0]non-3-yl)benzimidazol-2-yl]-4-amino-5-fluorohydroquinolin-2-one was performed according to the procedure in Example 8 (LC/MS m/z 419.1 (MH+), R$_t$ 1.96 minutes).

Example 89

Synthesis of 4-amino-3-[6-(2,4-dimethylpiperazinyl) benzimidazol-2-yl]-5-fluorohydroquinolin-2-one To a stirred solution of 2-methylpiperazine (2 equivalents) in dichloromethane at −10° C., was added di-tert-butyl dicarbonate (1 equivalent). The mixture was stirred for 10 minutes at −10° C. and was then quenched with saturated aqueous NaHCO$_3$. The two phases were separated, and the organic layer was extracted with methylene chloride. The organic extracts were collected, dried (Na$_2$SO$_4$), and concentrated to give the desired tert-butyl 3-methylpiperazine-carboxylate (LC/MS m/z 201.0 (MH+), R$_t$ 1.67 minutes). Conversion to tert-butyl 4-[2-(4-amino-5-fluoro-2-oxo(3-hydroquinolyl)) benzimidazol-6-yl]-3-methylpiperazinecarboxylate was performed according to the procedure in Example 8 (LC/MS m/z 493.3 (MH+), R$_t$ 2.45 minutes). Subsequent removal of the Boc group was preformed by bubbling HCl gas into a MeOH solution until saturated (LC/MS m/z 393.2 (MH+), R$_t$ 1.95 minutes). The free amine was subsequently reacted with paraformaldehyde (5 equivalents) in MeOH:AcOH (5:1) and NaCNBH$_4$ (4 equivalents) over molecular sieves at 80° C. After 10 hours, the mixture was cooled, filtered, and concentrated. The residue was dissolved in CH$_2$Cl$_2$, washed with saturated NaHCO$_3$, and dried with Na$_2$SO$_4$ to give the desired 4-amino-3-[6-(2,4-dimethylpiperazinyl)benzimidazol-2-yl]-5-fluorohydroquinolin-2-one (LC/MS m/z 407.3 (MH+), R$_t$ 2.03 minutes). Further purification was performed via reverse phase prep. HPLC.

Example 90

4-amino-3-[6-(3,4-dimethylpiperazinyl)benzimidazol-2-yl]hydroquinolin-2-one tert-Butyl-3-methylpiperazine carboxylate (see Example 89; 1 equivalent) and paraformaldehyde (5 equivalents) were dissolved in a mixture of MeOH and AcOH (5:1) on molecular sieves. NaCNBH$_3$ (4 equivalents) was added to the suspension at 25° C. The slurry was subsequently heated to 80° C. After 10 hours, the mixture was cooled, filtered, and concentrated. The residue was dissolved in dichloromethane and washed with saturated aqueous NaHCO$_3$. The organic solution was dried (Na$_2$SO$_4$), and concentrated. The tert-butoxycarbonyl group was removed by treating the crude amine with saturated HCl in MeOH, at room temperature for 30 minutes. The mixture was then concentrated and excess HCl was removed in-vacuo. The desired 1,2-dimethylpiperazine was obtained as the bis HCl salt (LC/MS m/z 115.0 (MH+), R$_t$ 0.33 minutes). Concomitant conversion to tert-butyl 4-[2-(4-amino-2-oxo(3-hydroquinolyl))benzimidazol-6-yl]-3-methylpiperazinecarboxylate was performed according to the procedure in Example 8 (LC/MS m/z 389.2 (MH+), R$_t$ 1.84 minutes).

Example 91

General Synthesis of 4-amino-5-fluoro-3-(6-aminomethyl-1H-benzimidazol-2-yl)quinolin-2(1H)-ones

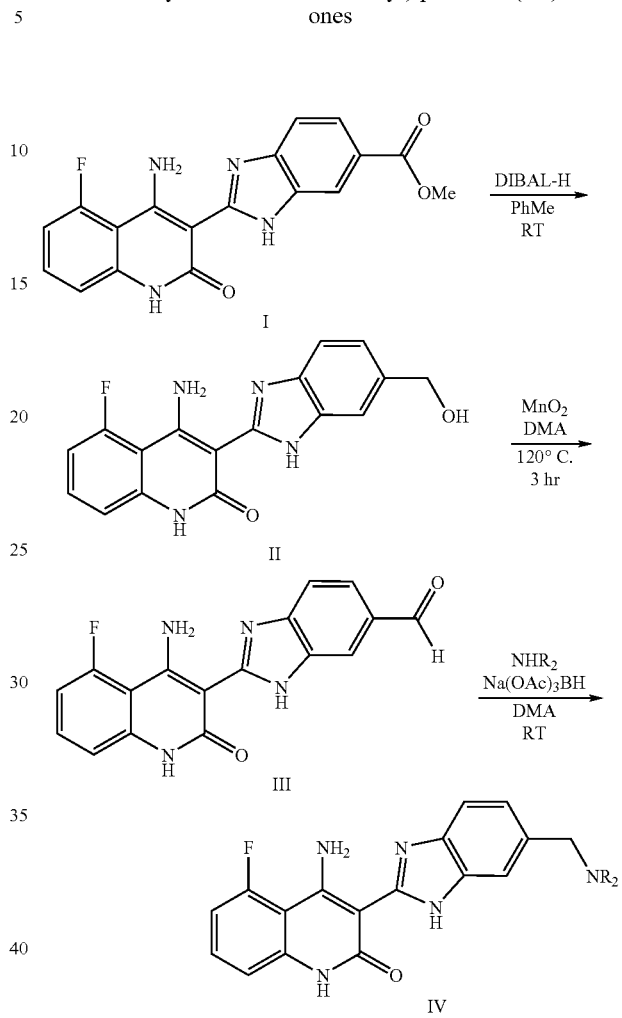

Methyl ester I was suspended as a fine powder in Toluene. To this room temperature suspension was added DIBAL-H (10 equivalents, 1 M in toluene) via an addition funnel at a rate in which gas evolution was steady and controllable. After complete addition, the homogeneous solution was allowed to stir for 10 hours. After this time, NaF (40 equivalents) and water (10 equivalents) were added. The resulting mixture was stirred at room temperature for 4 hours during which time a solid precipitate formed. This solid was collected and heated in dimethyl acetamide (DMA) at 120° C. for 2 hours after which time the remaining solid was filtered away and resulting solution concentrated to a thick oil. The resulting oil was treated with water and the resulting solid collected and dried to provide compound II as a yellow solid. MH+=325.1.

Alcohol II was dissolved in DMA at room temperature and treated with MnO$_2$ (15 equivalents). The reaction was heated at 120° C. for 3 hours and the mixture was filtered hot through a pad of Celite. The resulting solution was concentrated in vacuo to provide a yellow solid identified as aldehyde III MH+=323.1.

Aldehyde III was dissolved in DMA and treated with an appropriate amine (2.0 equivalent) followed by sodium triacetoxyborohydride (2.5 equivalents). The reaction stirred at room temperature for 12 hours and was concentrated to provide a thick oil. This oil was purified by reverse phase HPLC to yield the desired compounds.

Example 92

General Synthesis of 4-amino-5-fluoro-3-(6-amido-1H-benzimidazol-2-yl)quinolin-2(1H)-ones

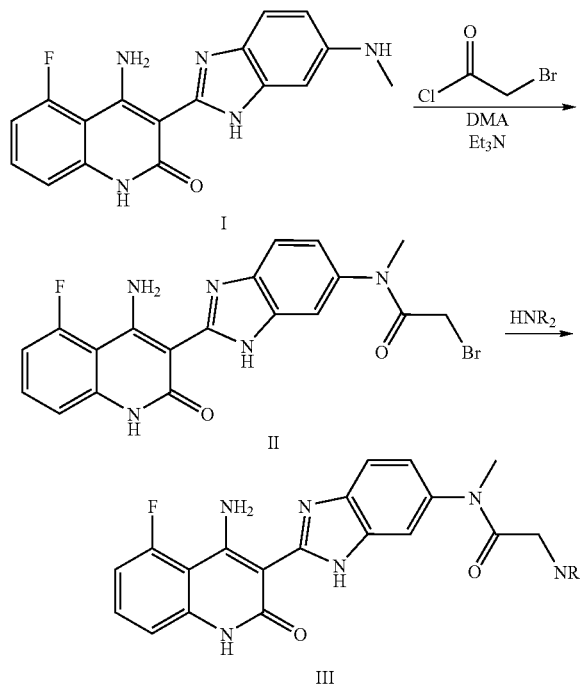

Amine I was dissolved in DMA and treated sequentially with bromoacetyl chloride (1.5 equivalents) and triethylamine (5 equivalents) at room temperature. The reaction was stirred for 2 hours and was then poured into water. The resulting solid was collected and dried to give the desired bromide II. MH+=444.

Bromide II was dissolved in DMA and the appropriate amine (10 equivalents) was added at room temperature. The reaction was stirred for 12 hours and was then concentrated to a dark oil which was purified by reverse phase HPLC to provide the desired product.

Example 93

Synthesis of 4-{[2-(4-amino-5-fluoro-2-oxo-1,2-dihydroquinolin-3-yl)-1H-benzimidazol-6-yl]oxy}-N-methylpyridine-2-carboxamide

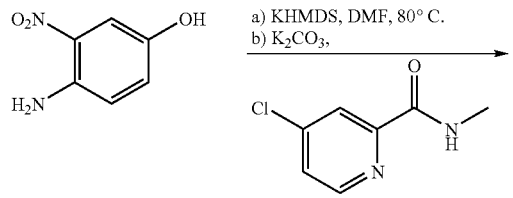

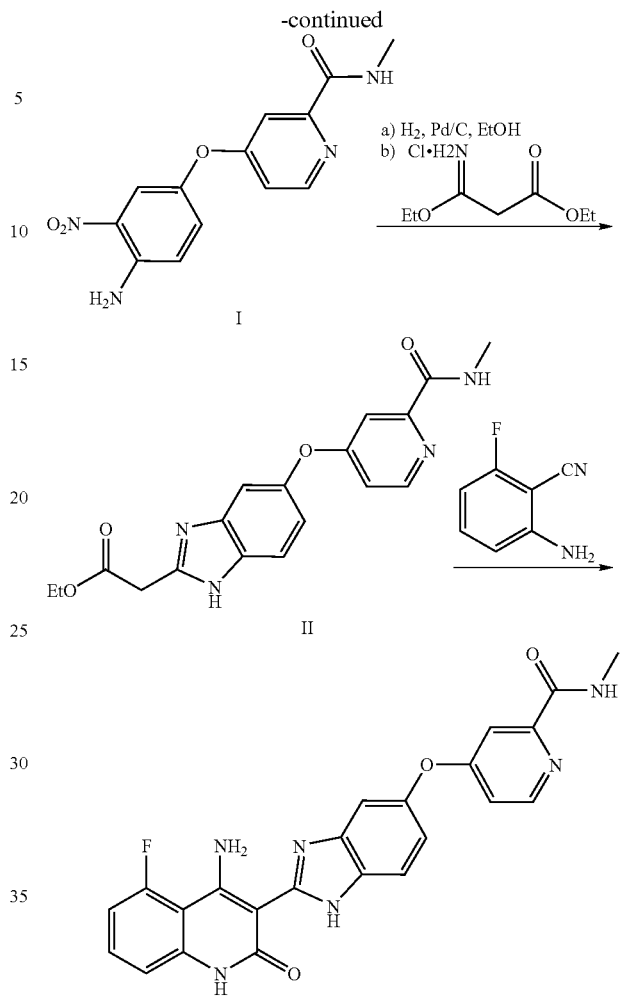

4-Amino-3-nitrophenol (1.0 equivalent) and potassium bis(trimethylsilyl)amide (2.0 equivalents) were stirred in DMF for 2 hours. To this mixture was added (4-chloro(2-pyridyl))-N-methoxycarboxamide (1.0 equivalent) and $K_2CO_3$ (1.2 equivalents). The mixture was heated at 90° C. overnight. The solvent was then removed and the mixture was diluted with $H_2O$. The aqueous layer was extracted with EtOAc. The organic layer was washed with and brine (2×), dried over $Na_2SO_4$, filtered and concentrated to give a brown solid. The crude material was purified by column chromatography (50% EtOAc/hexane with 2% $Et_3N$ to give compound I. MH+=289.2.

Compound I (1.0 equivalent) and 10% Pd/C (0.1 equivalents) were suspended in anhydrous EtOH at room temperature. The reaction flask was evacuated and subsequently filled with $H_2$. The resulting mixture was allowed to stir under a hydrogen atmosphere for 2 days. Ethyl 3-ethoxy-3-iminopropanoate hydrochloride (2.0 equivalents) was then added and the resulting mixture was heated at reflux overnight. After this time, the solution was filtered through a plug of Celite, concentrated and dissolved in $CH_2Cl_2$. The organic layer was washed with $NH_4OH$(aq, conc.), $H_2O$ (3×) and brine and then dried over $Na_2SO_4$, filtered and concentrated to yield a brown gum which was purified by silica gel chromatography (EtOAc to 10% MeOH in $CH_2Cl_2$ with 2% $Et_3N$) to provide the product II as a tan solid. MH+=287.1.

KHMDS (4.2 equivalents) was added to compound II (1.4 equivalents) and 2-amino-6-fluorobenzenecarbonitrile (1.0 equivalent) in DMF at room temperature. The reaction was heated at 50° C. overnight. The resulting mixture was poured into EtOAc and extracted with H₂O (3×). The organic layer was washed brine, dried over Na₂SO₄, filtered and concentrated in vacuo to yield a brown solid. The crude material was sonicated in 5% acetone/94.5% Et2O/0.5% MeOH to give the desired product as a tan solid. The solid was further purified by reverse phase HPLC. MH+=445.2.

Example 94

Synthesis of 4-amino-3-[5-(4-ethyl-4-oxidopiperazin-1-yl)-1H-benzimidazol-2-yl]-5-fluoroquinolin-2(1H)-one

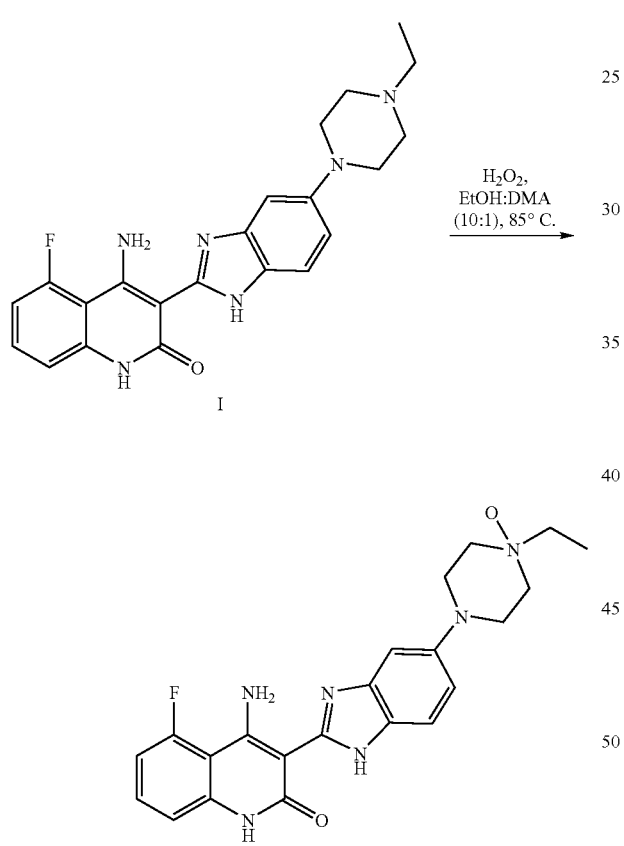

Piperazine I was suspended in EtOH:DMA (10:1). Hydrogen peroxide (10 equivalents) was added, and the reaction was heated to 85° C. during which time a homogeneous solution formed. After 1 hour, the reaction was complete by LC/MS. The reaction was stirred at room temperature overnight during which a precipitate formed. The solid was filtered and washed with EtOH and then Et₂O to give 4-amino-3-[5-(4-ethyl-4-oxidopiperazin-1-yl)-1H-benzimidazol-2-yl]-5-fluoroquinolin-2(1H)-one. MH+=423.3.

Example 95

Synthesis of 4-amino-6-chloro-1-methyl-3-(5-morpholin-4-yl-1H-benzimidazol-2-yl)quinolin-2(1H)-one

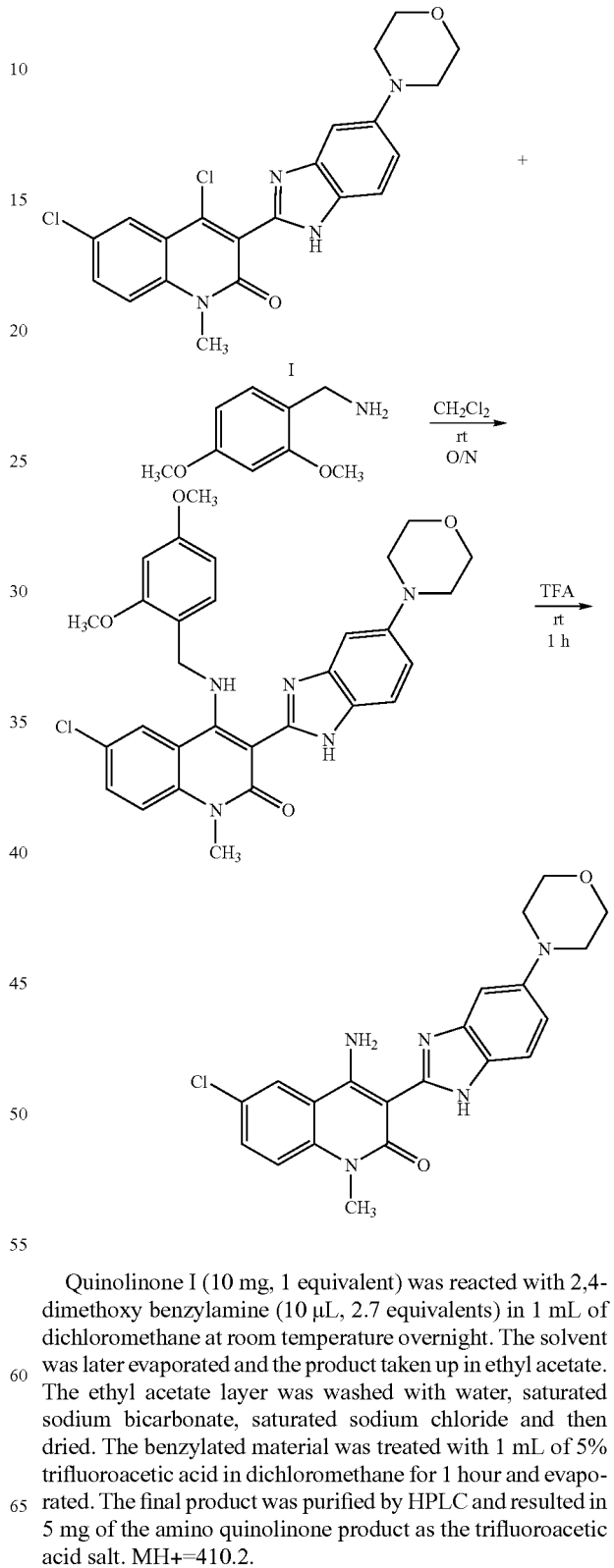

Quinolinone I (10 mg, 1 equivalent) was reacted with 2,4-dimethoxy benzylamine (10 µL, 2.7 equivalents) in 1 mL of dichloromethane at room temperature overnight. The solvent was later evaporated and the product taken up in ethyl acetate. The ethyl acetate layer was washed with water, saturated sodium bicarbonate, saturated sodium chloride and then dried. The benzylated material was treated with 1 mL of 5% trifluoroacetic acid in dichloromethane for 1 hour and evaporated. The final product was purified by HPLC and resulted in 5 mg of the amino quinolinone product as the trifluoroacetic acid salt. MH+=410.2.

Example 96

Synthesis of 4-amino-3-(1H-benzimidazol-2-yl)-6-chloro-1-methylquinolin-2(1H)-one

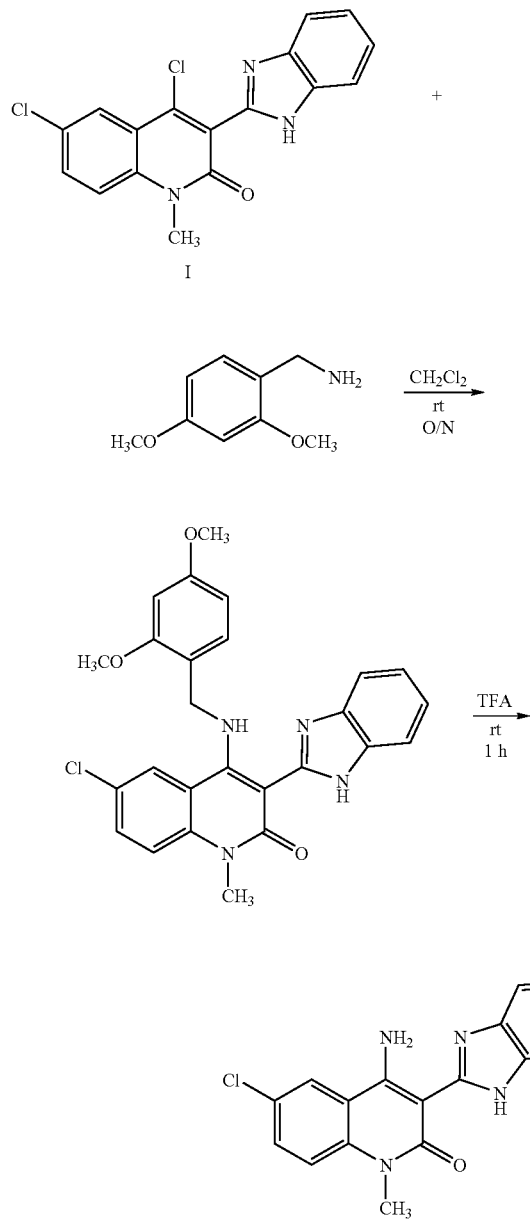

Quinolinone I (20 mg, 1 equivalent) was reacted with 2,4-dimethoxy benzylamine (20 μL, 2 equivalents) in 1 mL of dichloromethane at room temperature overnight. The solvent was later evaporated and the product taken up in ethyl acetate. The ethyl acetate layer was washed with water, saturated sodium bicarbonate, saturated sodium chloride and then dried. The benzylated material was treated with 1 mL of 5% trifluoroacetic acid in dichloromethane for 1 hour and evaporated. The final product was purified by HPLC and resulted in 17.2 mg of the amino quinolinone as the trifluoroacetic acid salt. MH+=325.1.

Example 97

Synthesis of 4-amino-6-chloro-1-methyl-3-[5-(4-methylpiperazin-1-yl)-1H-benzimidazol-2-yl]quinolin-2(1H)-one

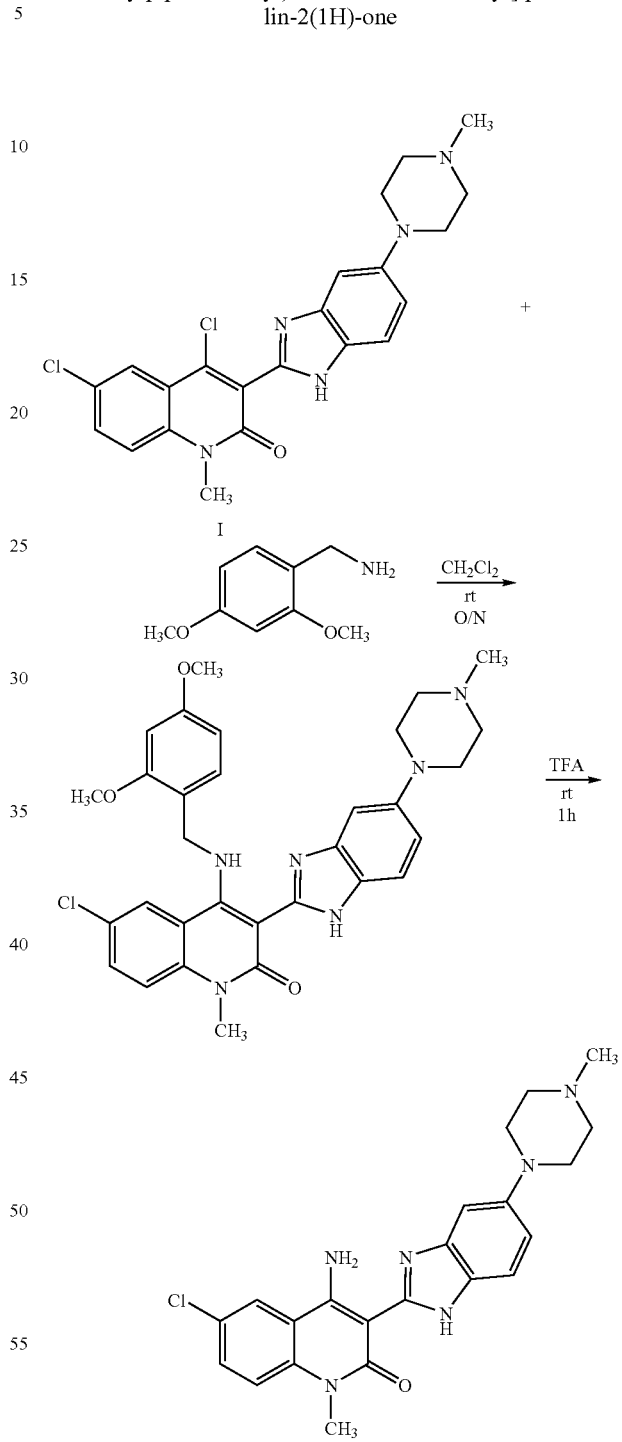

Quinolinone I (20 mg, 1 equivalent) was reacted with 2,4-dimethoxy benzylamine (20 μL, 2 equivalents) in 1 mL of dichloromethane at room temperature overnight. The solvent was later evaporated and the product taken up in ethyl acetate. The ethyl acetate layer was washed with water, saturated sodium bicarbonate, saturated sodium chloride and then dried. The benzylated material was treated with 1 mL of 5% trifluoroacetic acid in dichloromethane for 1 hour and evaporated. The final product was purified by HPLC and resulted in 11.5 mg of the amino quinolinone as the trifluoroacetic acid salt. MH+=423.1.

Example 98

Synthesis of 4-amino-1-methyl-3-(5-morpholin-4-yl-1H-benzimidazol-2-yl)quinolin-1H)-one

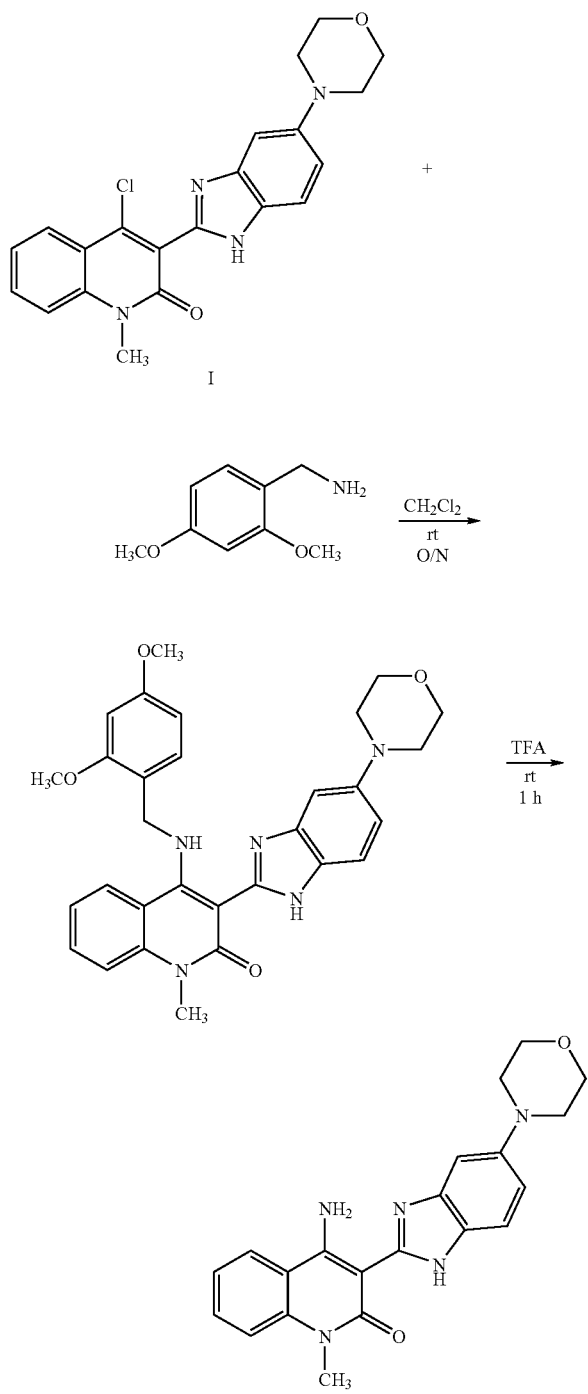

The quinolinone starting material I (20 mg, 1 equivalent) was reacted with 2,4-dimethoxy benzylamine (20 μL, 2 equivalents) in 1 mL of dichloromethane at room temperature overnight. The solvent was later evaporated and the product taken up in ethyl acetate. The ethyl acetate layer was washed with water, saturated sodium bicarbonate, saturated sodium chloride and then dried. The benzylated material was treated with 1 mL of 5% trifluoroacetic acid in dichloromethane for 1 hour and evaporated. The final product was purified by HPLC and resulted in 16.6 mg of the amino quinolinone as the trifluoroacetic acid salt. MH+=376.3.

Example 99

Synthesis of 4-amino-5-fluoro-3-{5-[4-(2,2,2-trifluoroethyl)piperazin-1-yl]-1H-benzimidazol-2-yl}quinolin-2(1H)-one

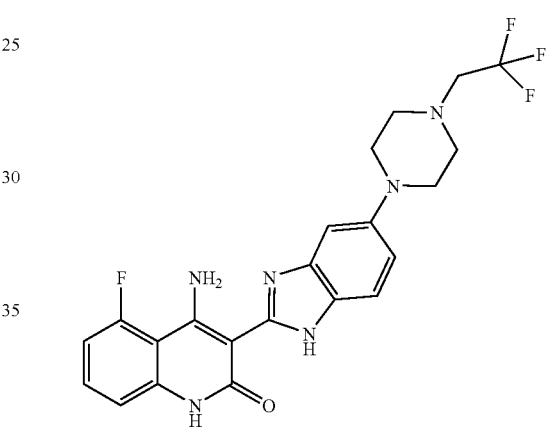

4-Amino-5-fluoro-3-(6-piperazin-1-yl-1H-benzoimidazol-2-yl)-1H-quinolin-2-one was taken up in ethyl trifluoroacetate and N,N-dimethylacetamide (DMA). The resulting solution was heated at 130° C. in a sealed tube for 30 minutes. The reaction was cooled to room temperature and quenched by addition of saturated aqueous sodium bicarbonate followed by pouring the mixture into water. The resulting solid was collected by filtration and washed with diethyl ether to afford 4-amino-5-fluoro-3-{6-[4-(2,2,2-trifluoro-acetyl)-piperazin-1-yl]-1H-benzoimidazol-2-yl}-1H-quinolin-2-one ($R_t$ 2.63 minutes, MH+=457.1), which was immediately taken up in THF. Borane-THF complex (3.3 equivalents) was added and the reaction was stirred at room temperature overnight. After quenching the excess borane with water, the mixture was extracted into ethyl acetate, dried over magnesium sulfate, filtered and concentrated to a brown solid which was purified by reverse phase HPLC to yield the desired compound. MH+=461.1.

Example 100

Synthesis of 4-amino-5-fluoro-3-(6-{methyl[(4-methylmorpholin-3-yl)methyl]amino}-1H-benzimidazol-2-yl)quinolin-2(1H)-one

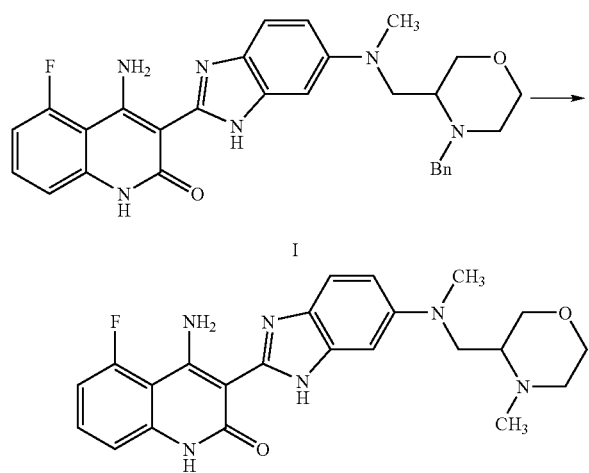

Quinolinone I was synthesized from commercially available 2-chloromethyl-4-benzyl morpholine, methylamine, 4-chloro-2-nitroaniline, and 2-amino-6-fluorobenzonitrile following the general procedure of Example 49. (2-(methylamino)methyl-4-benzyl morpholine was dissolved in an 8 M solution of NH$_2$Me in EtOH and heated in a glass bomb at 110° C. overnight to form the product 2-(methylamino)methyl-4-benzyl morpholine following removal of the solvent). Compound I (1.0 equivalent) and 10% Pd/C (0.1 equivalents) were suspended in 1:1 ethanol and 1 N aqueous HCl at room temperature. The reaction flask was evacuated and subsequently filled with H$_2$. The resulting mixture was stirred under a hydrogen atmosphere overnight, filtered through Celite, and concentrated under vacuum. The solution was made basic with 30% aq. KOH and the product was extracted with EtOAc. The combined organic layers were concentrated and resuspended in CH$_2$Cl$_2$:MeOH:AcOH (2:2:1). Paraformaldehyde (1.2 equivalents) and BH$_3$ pyridine (3 equivalents, 8 M) was then added and the mixture was stirred overnight at room temperature. The solvent was removed in vacuo and washed with water. The aqueous layer was extracted with EtOAc (3×), and the combined organic layers were concentrated and purified by silica gel chromatography (10% MeOH/CH$_2$Cl$_2$) to afford the desired product. MH+=437.4.

Example 101

General synthesis of 4-amino-3-1H-benzimidazol-2-yl-5-fluoroquinolin-2(1H)-one propionamides

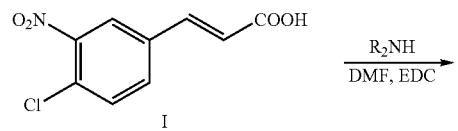

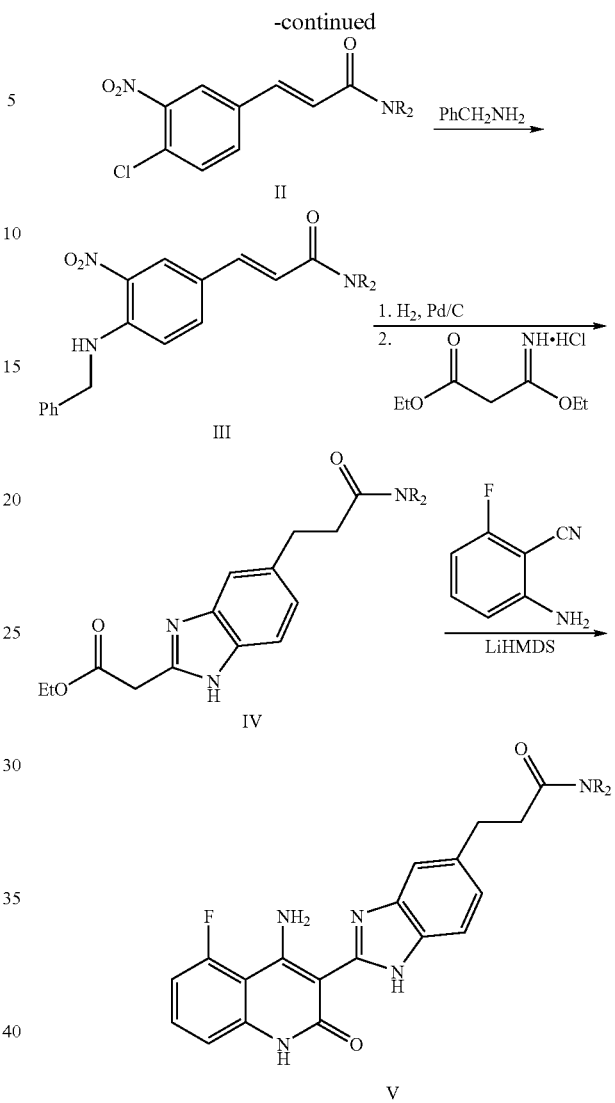

To a DMF solution of compound I (1 equivalent) in DMF was added an amine (1.1 equivalents) and EDC (1.1 equivalents). The solution was left to stir for 2 hours at room temperature. The reaction mixture was quenched with water and filtered to give the desired product II.

In a microwave tube, compound II (1 equivalent) was suspended in benzyl amine and heated in a microwave at 150° C. for five minutes. The resulting crude product III was sonicated in ether and filtered.

To a high pressure stainless steel vessel charged with compound III (1 equivalent) in a solution of EtOH was added 10% Pd/C followed by 120 psi H$_2$. The mixture was left at 100° C. for one day followed by addition of ethyl 3-ethoxy-3-iminopropanoate hydrochloride (2.5 equivalents). The reaction was left at 80° C. under nitrogen for one additional day. The palladium was then filtered off through a pad of Celite, and the resulting EtOH mixture was evaporated in vacuo. The product was then taken up in a generous amount of CH$_2$Cl$_2$, made basic, filtered over a pad of sodium sulfate, and concentrated in vacuo. Purification by silica gel chromatography (10% MeOH:CH$_2$Cl$_2$) gave compound IV, which was coupled with 2-amino-6-fluorobenzenecarbonitrile following the general procedure of Example 49 to give propionamide V.

Example 102

Synthesis of 4-amino-3-[5-(1-ethylpiperidin-4-yl)-1H-benzimidazol-2-yl]-5-fluoroquinolin-1H)-one

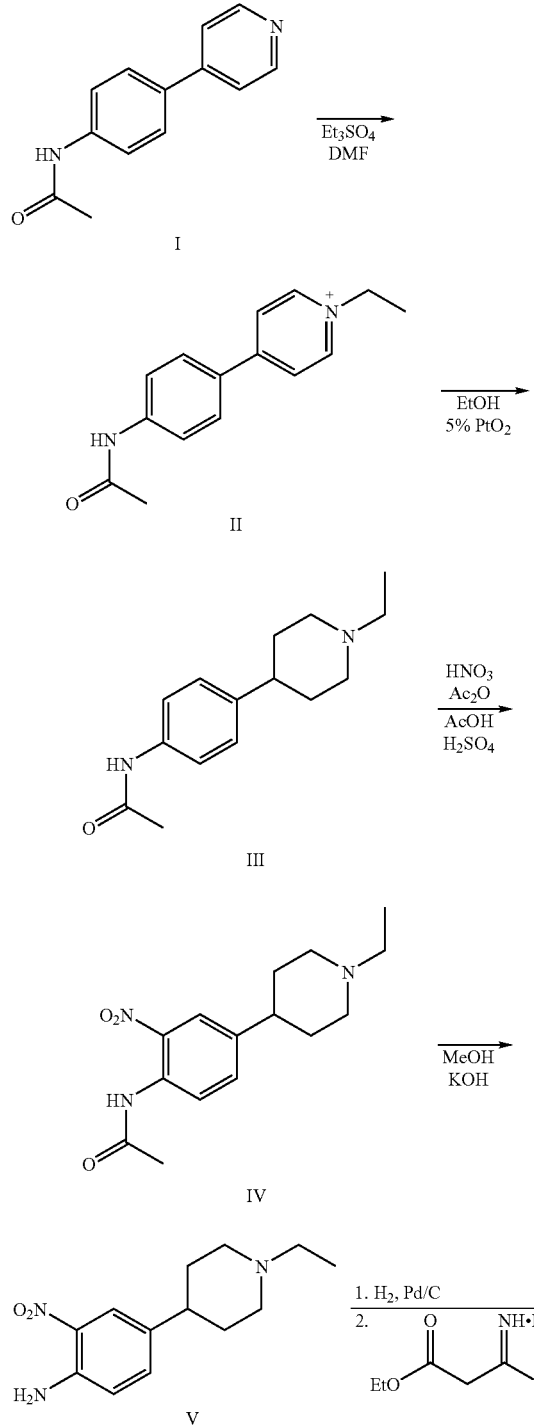

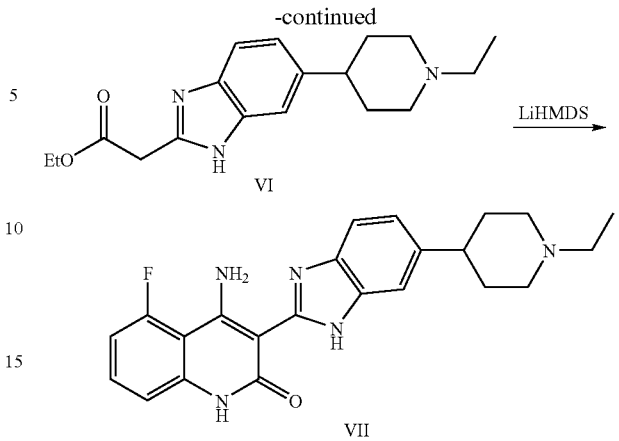

Compound I (1 equivalent) was dissolved in DMF and $Et_3SO_4$ (4 equivalents) was added slowly at 0° C. The solution was left to stir overnight at room temperature. The resulting mixture was poured into $Et_2O$ while stirring. The solid, compound II, was filtered off, washed once with EtOH, and resuspended in EtOH. To this mixture was added 5% $PtO_2$, and the resulting mixture was left under 1 atmosphere of $H_2$ overnight. The $PtO_2$ was filtered off using a pad of Celite to afford the desired product as an orange solid III that was used without further purification. Compound III was nitrated and used in the next step without further purification. To a MeOH solution of compound IV was added excess 30% KOH to give a bright yellow solution that was allowed to stir overnight. MeOH was removed in vacuo and the residue was taken up in $CH_2Cl_2$ and extracted with water to give compound V that was then converted to desired product VII following the procedure described in Example 49. The product was purified by sonicating in ether:acetone:ethanol (10:1:1) and then refluxing in acetonitrile overnight. MH+=406.3.

Example 103

Synthesis of 4-(1-methylpiperidin-4-yl)-2-nitroaniline

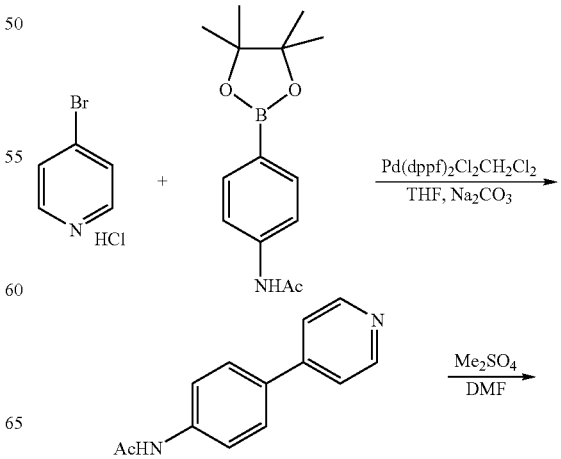

Step 1: N-(4-(4-pyridyl)phenyl)acetamide

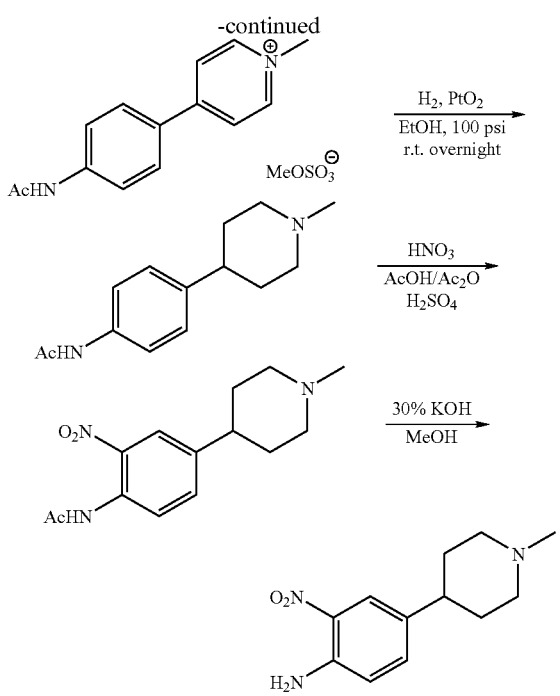

A round bottom flask was charged with a 2 N $Na_2CO_3$ solution (4 equivalents) and THF and the mixture was sparged with $N_2$ through a dispersion tube. 4-Bromopyridine hydrochloride (1 equivalent) and N-[4-(4,4,5,5-tetramethyl-1,3,2-dioxaborolan-2-yl)phenyl]acetamide (1.2 equivalents) were subsequently added, followed by Pd(dppf)$_2$Cl$_2$ (2.5 mol %). The reaction mixture was refluxed overnight, cooled to room temperature and diluted with EtOAc. The two phases were separated and the organic phase was washed with a 2 N $Na_2CO_3$ solution, brine, and dried ($Na_2SO_4$). Evaporation of the solvent under reduced pressure and purification by silica gel chromatography afforded the desired product as a white solid. MH+=213.1.

Step 2: N-[4-(1-methyl-4-piperidyl)phenyl]acetamide

N-(4-(4-pyridyl)phenyl)acetamide (1.0 equivalent) was dissolved in DMF and dimethyl sulfate (1.5 equivalent) was added dropwise. After an initial induction period a solid crashed out. The reaction mixture was stirred for 6 hour at room temperature and then poured into diethyl ether. After a sticky solid crashed out, the ether was decanted and the residue was triturated with EtOH, filtered, and washed with EtOH to give a light yellow solid. The pyridinium salt thus obtained (MH+=227.3) was suspended in EtOH and PtO$_2$ (5 mol %) was added, and the mixture was hydrogenated at atmospheric pressure for 3 days. After the catalyst was filtered off over a pad of Celite, the filter cake was washed repeatedly with water and the resulting EtOH/water mixture was concentrated under reduced pressure. The solution was made basic with 30% NaOH and extracted with CH$_2$Cl$_2$. The organic extracts were collected and dried (Na$_2$SO$_4$). Evaporation of the solvent under reduced pressure afforded the desired product as a white solid. MH+=233.1.

Step 3: N-[4-(1-methyl(4-piperidyl))-2-nitrophenyl]acetamide

A round bottom flask was charged with acetic anhydride and acetic acid, and the mixture was cooled down to −10° C. with and ice/salt bath. HNO$_3$ (2 equivalents) was added, followed by 2 drops of H$_2$SO$_4$. N-[4-(1-Methyl-4-piperidyl) phenyl]acetamide (1 equivalent) in acetic acid (in such an amount as to obtain a final 1:1 ratio between AcO$_2$ and AcOH) was added dropwise to the cold solution. The reaction mixture was allowed to warm to room temperature and stirred for 6 hours. The reaction was then poured into diethyl ether. A sticky solid crashed out, the ether was decanted, and the residue was dissolved in water. The water solution was made basic with 30% NaOH and an orange solid precipitated. The solid was filtered off and dried to afford the desired product. MH+=278.3.

Step 4: 4-(1-methylpiperidin-4-yl)-2-nitroaniline

N-[4-(1-methyl(4-piperidyl))-2-nitrophenyl]acetamide (1 equivalent) was dissolved in methanol and 30% KOH (2.5 equivalents) was added dropwise with vigorous stirring. The reaction mixture was stirred at room temperature for 3 hours and then concentrated under reduced pressure. The residue was dissolved in CH$_2$Cl$_2$ and washed with water (2×) and brine (1×). The organic solution was dried (Na$_2$SO$_4$) and evaporated to obtain the desired product as an orange brown solid. MH+=236.2.

Example 104

General synthesis of 5-aminopropyl benzimidazoles

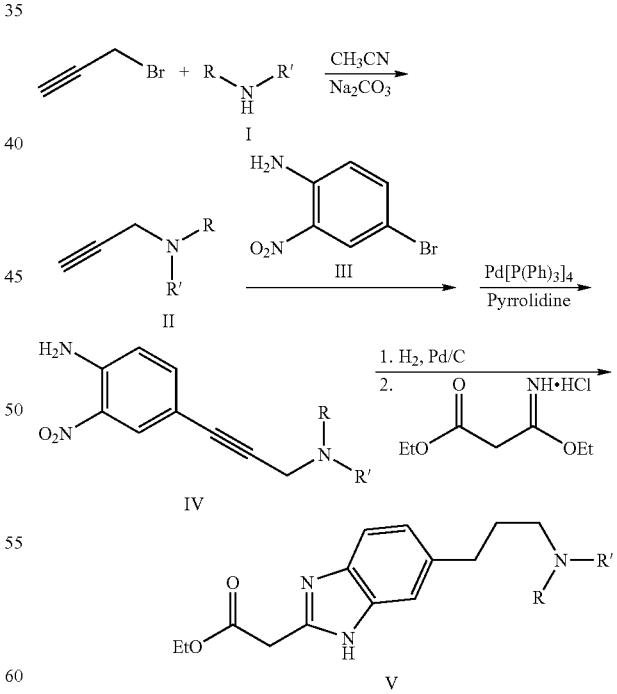

Propargyl amines may be obtained commercially or generally prepared as shown (see Banholzer, R. et. al. U.S. Pat. No. 4,699,910 which is herein incorporated in its entirety and for all purposes as is fully set forth herein). A mixture of propargyl bromide (70% in toluene, 1.1 equivalents), the amine 1 (1 equivalents), Na₂CO₃ (2.5 equivalents) in acetonitrile, (about 0.2 M) was refluxed overnight. The reaction mixture was cooled to room temperature and the solid was filtered off. The solution was evaporated under reduced pressure, and the residue was dissolved in EtOAc (or CH₂Cl₂) and washed with water. The organic solution was dried (Na₂SO₄). The solvent was evaporated under reduced pressure to give the desired propargyl amine II as a brown oil which was used in the next step without further purification.

Aryl alkynes may be made by following a modified procedure (Jon L. Wright et al. J. Med. Chem. 2000, 43, 3408-3419 which is hereby incorporated by reference in its entirety and for all purposes as if fully set forth herein). A round bottom flask was charged with THF and the solvent was sparged with nitrogen for 10 minutes using a dispersion tube. The propargylamine II (1 equivalent), pyrrolidine (2 equivalents) and 2-nitro-4-bromoaniline III (1 equivalent) were added, while still bubbling nitrogen through the solution. Pd[P(Ph)₃]₄ (2.5 mol %) was added last, and the sparging was then discontinued. The flask was equipped with a reflux condenser, and the reaction mixture was refluxed overnight under nitrogen and then cooled down room temperature. The THF was evaporated and the desired product IV was obtained by silica gel chromatography of the crude mixture (usually EtOAc/hexane 1:1).

Exposure of IV to catalytic hydrogenation conditions typically gave the fully reduced alkane, which was then converted to ester V as described in Example 49.

Example 105

Synthesis of 4-amino-5-fluoro-3-{5-[3-(methylamino)propyl]-1H-benzimidazol-2-yl}quinolin-2(1H)-one

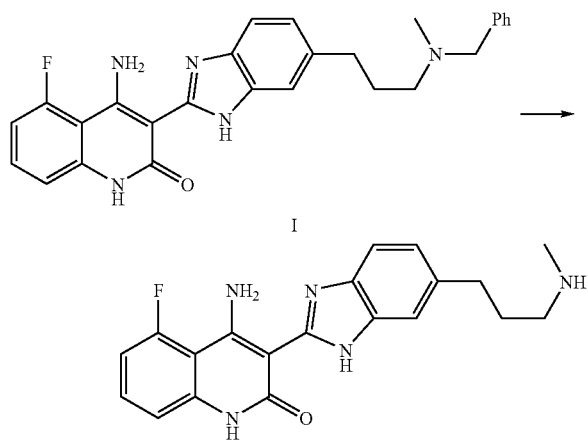

Benzyl quninolinone I (1.0 equivalent) was suspended in EtOH and 1 N HCl (1.1 equivalent) was added providing a clear solution. 10% Pd/C (12 wt %) was added, and the reaction mixture was hydrogenated in a steel bomb at 200 psi of H₂ and 60° C. for two days. The reaction mixture was cooled to room temperature, filtered, and the solvent was evaporated under reduced pressure. The residue was purified by reverse phase preparative HPLC to give the desired product. MH+=366.1.

Example 106

Synthesis of 4-amino-5-fluoro-3-(5-{3-[methyl(1-methylpiperidin-4-yl)amino]propyl}-1H-benzimidazol-2-yl)quinolin-2(1H)-one

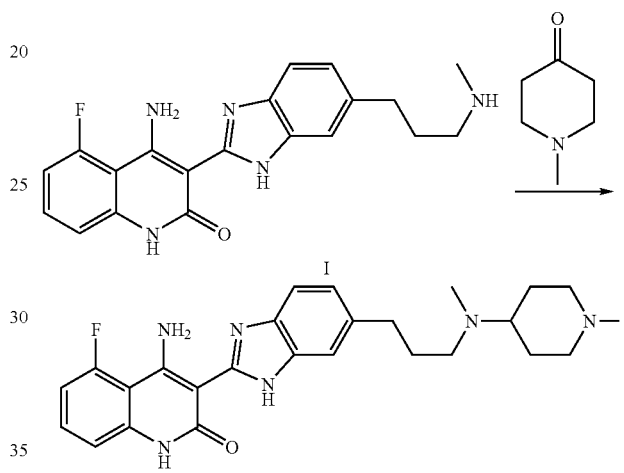

To a MeOH solution of quinolinone I (1.0 equivalent) was added 1-methyl-4-piperidinone (1.5 equivalents) followed by NaCNBH₃ (3 equivalents). The reaction mixture was then refluxed overnight and cooled to room temperature. 15% NaOH was added, and the reaction mixture was stirred for 1 hour at room temperature. The solvent was concentrated under reduced pressure and the residue was dissolved in DMSO and purified by reverse phase preparative HPLC to give the desired product. MH+=463.2.

Examples 107-211

Each of the compounds in the following table was synthesized following procedures described in the Examples and Methods described above. Starting materials used to synthesize the following compounds are readily recognizable by one skilled in the art in light of the previous disclosure.

TABLE 1

Table of Examples 107-211.

| Example | Name | LC/MS m/z (MH+) |
|---|---|---|
| 107 | 4-amino-3-{5-[(3S)-3-(dimethylamino)pyrrolidin-1-yl]-1H-benzimidazol-2-yl}quinolin-2(1H)-one | 389.4 |
| 123 | 4-amino-6-chloro-3-{5-[(3R)-3-(dimethylamino)pyrrolidin-1-yl]-1H-benzimidazol-2-yl}quinolin-2(1H)-one | 423 |

TABLE 1-continued

Table of Examples 107-211.

| Example | Name | LC/MS m/z (MH+) |
|---|---|---|
| 124 | ethyl {4-[2-(4-amino-2-oxo-1,2-dihydroquinolin-3-yl)-1H-benzimidazol-6-yl]piperazin-1-yl}acetate | 447.2 |
| 125 | 4-amino-3-{6-[methyl(1-methylpiperidin-4-yl)amino]-1H-benzimidazol-2-yl}quinolin-2(1H)-one | 403.1 |
| 126 | 3-[6-(4-acetylpiperazin-1-yl)-1H-benzimidazol-2-yl]-4-aminoquinolin-2(1H)-one | 403.3 |
| 127 | 4-amino-3-[6-(1,4'-bipiperidin-1'-yl)-1H-benzimidazol-2-yl]quinolin-2(1H)-one | 443.3 |
| 128 | 2-(4-amino-2-oxo-1,2-dihydroquinolin-3-yl)-1H-benzimidazole-6-carboxylic acid | 321.2 |
| 129 | 4-amino-5-(methyloxy)-3-[6-(4-methylpiperazin-1-yl)-1H-benzimidazol-2-yl]quinolin-2(1H)-one | 405.3 |
| 130 | 4-amino-3-{6-[4-(1-methylethyl)piperazin-1-yl]-1H-benzimidazol-2-yl}quinolin-2(1H)-one | 403.3 |
| 131 | {4-[2-(4-amino-2-oxo-1,2-dihydroquinolin-3-yl)-1H-benzimidazol-6-yl]piperazin-1-yl}acetic acid | 419.2 |
| 132 | 4-[(3S)-1-azabicyclo[2.2.2]oct-3-ylamino]-3-(1H-benzimidazol-2-yl)quinolin-2(1H)-one | 386.1 |
| 133 | 4-[(3R)-1-azabicyclo[2.2.2]oct-3-ylamino]-3-(1H-benzimidazol-2-yl)quinolin-2(1H)-one | 386.1 |
| 134 | 4-amino-3-[5-(4-ethylpiperazin-1-yl)-1H-benzimidazol-2-yl]quinolin-2(1H)-one | 389.1 |
| 135 | 4-amino-3-(5-{(2S,5S)-2-[(dimethylamino)methyl]-5-methylmorpholin-4-yl}-1H-benzimidazol-2-yl)quinolin-2(1H)-one | 433.3 |
| 136 | 4-amino-6-chloro-3-[5-(4-methylpiperazin-1-yl)-1H-benzimidazol-2-yl]quinolin-2(1H)-one | 409.2 |
| 137 | 4-amino-6-chloro-3-{5-[(3S)-3-(dimethylamino)pyrrolidin-1-yl]-1H-benzimidazol-2-yl}quinolin-2(1H)-one | 423.1 |
| 138 | 4-amino-5,6-dichloro-3-{5-[(3S)-3-(dimethylamino)pyrrolidin-1-yl]-1H-benzimidazol-2-yl}quinolin-2(1H)-one | 457.2 |
| 139 | 4-amino-5,6-dichloro-3-[5-(4-methylpiperazin-1-yl)-1H-benzimidazol-2-yl]quinolin-2(1H)-one | 443.2 |
| 140 | 4-amino-3-(1H-benzimidazol-2-yl)-6-[(pyridin-2-ylmethyl)oxy]quinolin-2(1H)-one | 384.2 |
| 141 | 4-amino-3-(1H-benzimidazol-2-yl)-6-[(2R,6S)-2,6-dimethylmorpholin-4-yl]quinolin-2(1H)-one | 390.1 |
| 142 | 4-amino-3-(1H-benzimidazol-2-yl)-6-morpholin-4-ylquinolin-2(1H)-one | 362.2 |
| 143 | 4-amino-3-(1H-benzimidazol-2-yl)-5-[(1-methylpiperidin-3-yl)oxy]quinolin-2(1H)-one | 390.2 |
| 144 | 4-amino-3-(1H-benzimidazol-2-yl)-5-[(pyridin-2-ylmethyl)oxy]quinolin-2(1H)-one | 384.1 |
| 145 | 4-amino-3-(5-morpholin-4-yl-1H-benzimidazol-2-yl)-5-[(pyridin-4-ylmethyl)oxy]quinolin-2(1H)-one | 469.2 |
| 146 | 4-amino-3-(1H-benzimidazol-2-yl)-5-(methyloxy)quinolin-2(1H)-one | 307.1 |
| 147 | 4-amino-3-(5-methyl-1H-benzimidazol-2-yl)-5-(methyloxy)quinolin-2(1H)-one | 321.1 |
| 148 | 4-amino-3-{5-[(2R,6S)-2,6-dimethylmorpholin-4-yl]-1H-benzimidazol-2-yl}-5-(methyloxy)quinolin-2(1H)-one | 420.2 |
| 149 | 4-amino-3-(1H-benzimidazol-2-yl)-5-morpholin-4-ylquinolin-2(1H)-one | 362.2 |
| 150 | 4-amino-3-(1H-benzimidazol-2-yl)-5-[(2R,6S)-2,6-dimethylmorpholin-4-yl]quinolin-2(1H)-one | 390.2 |
| 151 | 4-amino-3-(1H-benzimidazol-2-yl)-5-(4-methylpiperazin-1-yl)quinolin-2(1H)-one | 375.1 |
| 152 | 4-amino-5,6-dichloro-3-(5-morpholin-4-yl-1H-benzimidazol-2-yl)quinolin-2(1H)-one | 430 |
| 153 | 3-{5-[(2-morpholin-4-ylethyl)oxy]-1H-benzimidazol-2-yl}quinolin-2(1H)-one | 391.3 |
| 154 | 4-amino-3-{5-[(3-pyrrolidin-1-ylpropyl)oxy]-1H-benzimidazol-2-yl}quinolin-2(1H)-one | 404 |
| 155 | 4-amino-3-{5-[(3-morpholin-4-ylpropyl)oxy]-1H-benzimidazol-2-yl}quinolin-2(1H)-one | 420.4 |
| 156 | 4-amino-6-fluoro-3-(5-morpholin-4-yl-1H-benzimidazol-2-yl)quinolin-2(1H)-one | 380 |
| 157 | 4-amino-3-{5-[3-(dimethylamino)pyrrolidin-1-yl]-1H-benzimidazol-2-yl}-6-fluoroquinolin-2(1H)-one | 407 |
| 158 | 4-amino-3-(1H-benzimidazol-2-yl)-6-fluoroquinolin-2(1H)-one | 295 |

TABLE 1-continued

Table of Examples 107-211.

| Example | Name | LC/MS m/z (MH+) |
|---|---|---|
| 159 | 4-amino-3-(6-fluoro-5-morpholin-4-yl-1H-benzimidazol-2-yl)quinolin-2(1H)-one | 380 |
| 160 | 4-amino-3-{5-[(tetrahydrofuran-2-ylmethyl)oxy]-1H-benzimidazol-2-yl}quinolin-2(1H)-one | 377 |
| 161 | 4-amino-6-fluoro-3-(6-fluoro-5-morpholin-4-yl-1H-benzimidazol-2-yl)quinolin-2(1H)-one | 398 |
| 162 | 4-amino-3-[6-fluoro-5-(4-methylpiperazin-1-yl)-1H-benzimidazol-2-yl]quinolin-2(1H)-one | 393 |
| 163 | 4-amino-3-(5-{[2-(methyloxy)ethyl]oxy}-1H-benzimidazol-2-yl)quinolin-2(1H)-one | 351 |
| 164 | 4-amino-3-[4,6-difluoro-5-(4-methylpiperazin-1-yl)-1H-benzimidazol-2-yl]quinolin-2(1H)-one | 411 |
| 165 | 4-amino-3-{5-[3-(dimethylamino)pyrrolidin-1-yl]-1H-benzimidazol-2-yl}-5-fluoroquinolin-2(1H)-one | 407.1 |
| 166 | 4-amino-5-fluoro-3-[5-(4-methylpiperazin-1-yl)-1H-benzimidazol-2-yl]quinolin-2(1H)-one | 393.1 |
| 167 | 4-amino-5-chloro-3-[5-(4-methylpiperazin-1-yl)-1H-benzimidazol-2-yl]quinolin-2(1H)-one | 409.1 |
| 168 | 4-amino-3-{5-[3-(dimethylamino)pyrrolidin-1-yl]-6-fluoro-1H-benzimidazol-2-yl}quinolin-2(1H)-one | 407.1 |
| 169 | 4-amino-5-chloro-3-{5-[3-(dimethylamino)pyrrolidin-1-yl]-1H-benzimidazol-2-yl}quinolin-2(1H)-one | 423.1 |
| 170 | 4-amino-6-chloro-3-{5-[3-(dimethylamino)pyrrolidin-1-yl]-6-fluoro-1H-benzimidazol-2-yl}quinolin-2(1H)-one | 441 |
| 171 | 4-amino-5-[(2R,6S)-2,6-dimethylmorpholin-4-yl]-3-(3H-imidazo[4,5-b]pyridin-2-yl)quinolin-2(1H)-one | 391.2 |
| 172 | 4-amino-3-(6-thiomorpholin-4-yl-1H-benzimidazol-2-yl)quinolin-2(1H)-one | 378.4 |
| 173 | 4-amino-3-[5-(4-cyclohexylpiperazin-1-yl)-1H-benzimidazol-2-yl]quinolin-2(1H)-one | 443.1 |
| 174 | 4-amino-3-{6-[3-(diethylamino)pyrrolidin-1-yl]-1H-benzimidazol-2-yl}quinolin-2(1H)-one | 417.1 |
| 175 | 4-amino-3-[6-(4-pyridin-2-ylpiperazin-1-yl)-1H-benzimidazol-2-yl]quinolin-2(1H)-one | 438.3 |
| 176 | 4-amino-3-[5-(4-methylpiperazin-1-yl)-3H-imidazo[4,5-b]pyridin-2-yl]quinolin-2(1H)-one | 376.3 |
| 177 | 4-amino-6-chloro-3-[5-(4-methylpiperazin-1-yl)-1H-imidazo[4,5-b]pyridin-2-yl]quinolin-2(1H)-one | 410.2 |
| 178 | 2-(4-amino-2-oxo-1,2-dihydroquinolin-3-yl)-N-methyl-N-(1-methylpiperidin-4-yl)-1H-benzimidazole-5-carboxamide | 431.3 |
| 179 | 4-amino-3-(5-{[4-(1-methylethyl)piperazin-1-yl]carbonyl}-1H-benzimidazol-2-yl)quinolin-2(1H)-one | 431.3 |
| 180 | 4-amino-3-[5-(4-methylpiperazin-1-yl)-1H-benzimidazol-2-yl]-6-nitroquinolin-2(1H)-one | 420.2 |
| 181 | 4-amino-3-[5-(1,4'-bipiperidin-1'-ylcarbonyl)-1H-benzimidazol-2-yl]quinolin-2(1H)-one | 471.1 |
| 182 | 4-amino-3-{5-[(4-methylpiperazin-1-yl)carbonyl]-1H-benzimidazol-2-yl}quinolin-2(1H)-one | 403.3 |
| 183 | 4-amino-3-[5-(1-oxidothiomorpholin-4-yl)-1H-benzimidazol-2-yl]quinolin-2(1H)-one | 394.5 |
| 184 | 3-{5-[(4-acetylpiperazin-1-yl)carbonyl]-1H-benzimidazol-2-yl}-4-aminoquinolin-2(1H)-one | 431.3 |
| 185 | 4-amino-3-(5-{[(3R)-3-(dimethylamino)pyrrolidin-1-yl]carbonyl}-1H-benzimidazol-2-yl)quinolin-2(1H)-one | 417.4 |
| 186 | 4-amino-3-(5-{[(3S)-3-(dimethylamino)pyrrolidin-1-yl]carbonyl}-1H-benzimidazol-2-yl)quinolin-2(1H)-one | 417.4 |
| 187 | 4-amino-3-(5-{[4-(dimethylamino)piperidin-1-yl]carbonyl}-1H-benzimidazol-2-yl)quinolin-2(1H)-one | 431.4 |
| 188 | methyl 2-(4-amino-5-fluoro-2-oxo-1,2-dihydroquinolin-3-yl)-1H-benzimidazole-6-carboxylate | 353.2 |
| 189 | 4-amino-3-[5-(1,3'-bipyrrolidin-1'-yl)-1H-benzimidazol-2-yl]quinolin-2(1H)-one | 415.5 |
| 190 | 4-amino-3-[5-(pyridin-3-yloxy)-1H-benzimidazol-2-yl]quinolin-2(1H)-one | 370.2 |
| 191 | 4-amino-5,6-bis(methyloxy)-3-[5-(4-methylpiperazin-1-yl)-1H-benzimidazol-2-yl]quinolin-2(1H)-one | 435.5 |
| 192 | 2-(4-amino-2-oxo-1,2-dihydroquinolin-3-yl)-N-[2-(dimethylamino)ethyl]-N-methyl-1H-benzimidazole-5-carboxamide | 405.3 |
| 193 | 2-(4-amino-2-oxo-1,2-dihydroquinolin-3-yl)-N-methyl-N-(1-methylpyrrolidin-3-yl)-1H-benzimidazole-5-carboxamide | 417.2 |
| 194 | 4-amino-3-{5-[(5-methyl-2,5-diazabicyclo[2.2.1]hept-2-yl)carbonyl]-1H-benzimidazol-2-yl}quinolin-2(1H)-one | 415.2 |

TABLE 1-continued

Table of Examples 107-211.

| Example | Name | LC/MS m/z (MH+) |
|---|---|---|
| 195 | 4-amino-3-{5-[(4-cyclohexylpiperazin-1-yl)carbonyl]-1H-benzimidazol-2-yl}quinolin-2(1H)-one | 471.6 |
| 196 | 4-amino-3-{5-[(2-piperidin-1-ylethyl)amino]-1H-benzimidazol-2-yl}quinolin-2(1H)-one | 403.2 |
| 197 | ethyl 4-{(2-(4-amino-2-oxo-1,2-dihydroquinolin-3-yl)-1H-benzimidazol-5-yl]amino}piperidine-1-carboxylate | 447.3 |
| 198 | 4-amino-3-[5-({(5R)-5-[(methyloxy)methyl]pyrrolidin-3-yl}amino)-1H-benzimidazol-2-yl]quinolin-2(1H)-one | 405.2 |
| 199 | 4-amino-3-{5-[(pyridin-2-ylmethyl)amino]-1H-benzimidazol-2-yl}quinolin-2(1H)-one | 383.3 |
| 200 | 4-amino-3-[5-(piperidin-3-ylamino)-1H-benzimidazol-2-yl]quinolin-2(1H)-one | 375.2 |
| 201 | 4-amino-5-fluoro-3-{5-[(pyridin-2-ylmethyl)amino]-1H-benzimidazol-2-yl}quinolin-2(1H)-one | 401.3 |
| 202 | ethyl 4-{[2-(4-amino-5-fluoro-2-oxo-1,2-dihydroquinolin-3-yl)-1H-benzimidazol-5-yl]amino}piperidine-1-carboxylate | 465.5 |
| 203 | 4-amino-5-fluoro-3-[5-(piperidin-3-ylamino)-1H-benzimidazol-2-yl]quinolin-2(1H)-one | 393.3 |
| 204 | 4-amino-3-(1H-benzimidazol-2-yl)-6-bromoquinolin-2(1H)-one | 357.1 |
| 205 | 4-amino-3-(1H-benzimidazol-2-yl)-7-bromoquinolin-2(1H)-one | 357.1 |
| 206 | 4-amino-3-(5-bromo-1H-benzimidazol-2-yl)quinolin-2(1H)-one | 357.1 |
| 207 | N,N-dimethyl-2-(2-oxo-1,2-dihydroquinolin-3-yl)-1H-benzimidazole-5-carboxamide | 333.1 |
| 208 | 4-amino-3-(5-thien-2-yl-1H-benzimidazol-2-yl)quinolin-2(1H)-one | 359.2 |
| 209 | 2-(4-amino-2-oxo-1,2-dihydroquinolin-3-yl)-N,N-dimethyl-1H-benzimidazole-5-sulfonamide | 384.1 |
| 210 | 4-amino-6-iodo-3-[5-(4-methylpiperazin-1-yl)-1H-benzimidazol-2-yl]quinolin-2(1H)-one | 501.1 |
| 211 | 4-amino-3-(5-{2-[(dimethylamino)methyl]-morpholin-4-yl}-1H-benzimidazol-2-yl)quinolin-2(1H)-one | 419.2 |

Examples 212-338

Example 212 to 338 listed in Table 2 were synthesized using the methods described above such as Methods 1-24 and those set forth in the Schemes and other Examples or modified as apparent to one of reasonable skill in the art using commercially available materials.

TABLE 2

Table of Examples 212-338.

| Example | Name | LC/MS m/z (MH+) |
|---|---|---|
| 212 | 4-[(3R)-1-azabicyclo[2.2.2]oct-3-ylamino]-3-(1H-benzimidazol-2-yl)-7-chloro-6-iodoquinolin-2(1H)-one | 547 |
| 213 | 4-[(3R)-1-azabicyclo[2.2.2]oct-3-ylamino]-3-(1H-benzimidazol-2-yl)-6-nitroquinolin-2(1H)-one | 431 |
| 214 | 4-[(3R)-1-azabicyclo[2.2.2]oct-3-ylamino]-3-(1H-benzimidazol-2-yl)-6-methylquinolin-2(1H)-one | 401 |
| 215 | 4-[(3R)-1-azabicyclo[2.2.2]oct-3-ylamino]-3-(1H-benzimidazol-2-yl)-6,7-difluoroquinolin-2(1H)-one | 422 |
| 216 | 4-[(3S)-1-azabicyclo[2.2.2]oct-3-ylamino]-3-(1H-benzimidazol-2-yl)-7-chloroquinolin-2(1H)-one | 421 |
| 217 | 4-[(3R)-1-azabicyclo[2.2.2]oct-3-ylamino]-3-(1H-benzimidazol-2-yl)-6-bromoquinolin-2(1H)-one | 465 |
| 218 | 4-[(3R)-1-azabicyclo[2.2.2]oct-3-ylamino]-3-(1H-benzimidazol-2-yl)-2-oxo-1,2-dihydroquinoline-6-carbonitrile | 411 |
| 219 | 4-[(3R)-1-azabicyclo[2.2.2]oct-3-ylamino]-3-(1H-benzimidazol-2-yl)-6-fluoroquinolin-2(1H)-one | 404 |
| 220 | 4-[(3S)-1-azabicyclo[2.2.2]oct-3-ylamino]-3-(1H-benzimidazol-2-yl)-6,7-bis(methyloxy)quinolin-2(1H)-one | 447 |
| 221 | 4-[(3R)-1-azabicyclo[2.2.2]oct-3-ylamino]-3-(1H-benzimidazol-2-yl)-6,7-dichloroquinolin-2(1H)-one | 455 |

TABLE 2-continued

Table of Examples 212-338.

| Example | Name | LC/MS m/z (MH+) |
|---|---|---|
| 222 | 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-4-carboxamide | 531 |
| 223 | 4-[(3S)-1-azabicyclo[2.2.2]oct-3-ylamino]-3-(1H-benzimidazol-2-yl)-6-fluoro-7-[(3-hydroxypropyl)amino]quinolin-2(1H)-one | 478 |
| 224 | 4-[(3S)-1-azabicyclo[2.2.2]oct-3-ylamino]-3-(1H-benzimidazol-2-yl)-7-(dimethylamino)-6-fluoroquinolin-2(1H)-one | 448 |
| 225 | 4-[(3R)-1-azabicyclo[2.2.2]oct-3-ylamino]-3-(1H-benzimidazol-2-yl)-5-fluoroquinolin-2(1H)-one | 404 |
| 226 | 4-[(3R)-1-azabicyclo[2.2.2]oct-3-ylamino]-3-(1H-benzimidazol-2-yl)-6-(4-nitrophenyl)quinolin-2(1H)-one | 508 |
| 227 | 4-[(3S)-1-azabicyclo[2.2.2]oct-3-ylamino]-3-(1H-benzimidazol-2-yl)-7-{[2-(dimethylamino)ethyl]amino}-6-fluoroquinolin-2(1H)-one | 491 |
| 228 | 4-[(3S)-1-azabicyclo[2.2.2]oct-3-ylamino]-3-(1H-benzimidazol-2-yl)-6-fluoro-7-(1H-imidazol-1-yl)quinolin-2(1H)-one | 471 |
| 229 | 4-[(3R)-1-azabicyclo[2.2.2]oct-3-ylamino]-3-(1H-benzimidazol-2-yl)-6-[4-(methyloxy)phenyl]quinolin-2(1H)-one | 493 |
| 230 | 4-[(3S)-1-azabicyclo[2.2.2]oct-3-ylamino]-3-(1H-benzimidazol-2-yl)-6-fluoro-7-morpholin-4-ylquinolin-2(1H)-one | 490 |
| 231 | 4-[(3R)-1-azabicyclo[2.2.2]oct-3-ylamino]-6,7-difluoro-3-(3H-imidazo[4,5-b]pyridin-2-yl)quinolin-2(1H)-one | 423 |
| 232 | 4-[(3R)-1-azabicyclo[2.2.2]oct-3-ylamino]-3-(1H-benzimidazol-2-yl)-6-(3-nitrophenyl)quinolin-2(1H)-one | 508 |
| 233 | 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-3-carboxamide | 531 |
| 234 | 4-[(3S)-1-azabicyclo[2.2.2]oct-3-ylamino]-3-(1H-benzimidazol-2-yl)-5-methylquinolin-2(1H)-one | 401 |
| 235 | 6-(3-acetylphenyl)-4-[(3R)-1-azabicyclo[2.2.2]oct-3-ylamino]-3-(3H-imidazo[4,5-b]pyridin-2-yl)quinolin-2(1H)-one | 506 |
| 236 | 4-[(3S)-1-azabicyclo[2.2.2]oct-3-ylamino]-3-(1H-benzimidazol-2-yl)-5-chloroquinolin-2(1H)-one | 421 |
| 237 | 4-[(3R)-1-azabicyclo[2.2.2]oct-3-ylamino]-6-fluoro-3-(3H-imidazo[4,5-b]pyridin-2-yl)-7-morpholin-4-ylquinolin-2(1H)-one | 491 |
| 238 | 4-[(3S)-1-azabicyclo[2.2.2]oct-3-ylamino]-3-(1H-benzimidazol-2-yl)-7-(cyclopropylamino)-6-fluoroquinolin-2(1H)-one | 460 |
| 239 | N-{3-[4-[(3R)-1-azabicyclo[2.2.2]oct-3-ylamino)-3-(3H-imidazo[4,5-b]pyridin-2-yl)-2-oxo-1,2-dihydroquinolin-6-yl]phenyl}acetamide | 521 |
| 240 | 4-[(3S)-1-azabicyclo[2.2.2]oct-3-ylamino]-3-(1H-benzimidazol-2-yl)-6-fluoro-7-(4-methylpiperazin-1-yl)quinolin-2(1H)-one | 503 |
| 241 | 4-[(3R)-1-azabicyclo[2.2.2]oct-3-ylamino]-6-fluoro-7-(1H-imidazol-1-yl)-3-(3H-imidazo[4,5-b]pyridin-2-yl)quinolin-2(1H)-one | 472 |
| 242 | 4-[(3S)-1-azabicyclo[2.2.2]oct-3-ylamino]-3-(1H-benzimidazol-2-yl)-6-fluoro-7-[(2-pyridin-2-ylethyl)amino]quinolin-2(1H)-one | 525 |
| 243 | 4-[(3S)-1-azabicyclo[2.2.2]oct-3-ylamino]-3-(1H-benzimidazol-2-yl)-6-fluoro-7-piperidin-1-ylquinolin-2(1H)-one | 488 |
| 244 | 6-chloro-3-(3H-imidazo[4,5-b]pyridin-2-yl)quinolin-2(1H)-one | 298 |
| 245 | ethyl 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-4-carboxylate | 560 |
| 246 | 4-[(3R)-1-azabicyclo[2.2.2]oct-3-ylamino]-3-(1H-benzimidazol-2-yl)-6-(1-benzothien-2-yl)quinolin-2(1H)-one | 519 |
| 247 | 4-[(3S)-1-azabicyclo[2.2.2]oct-3-ylamino]-3-(1H-benzimidazol-2-yl)-6-fluoro-7-pyrrolidin-1-ylquinolin-2(1H)-one | 474 |
| 248 | 4-[(3R)-1-azabicyclo[2.2.2]oct-3-ylamino]-3-(3H-imidazo[4,5-b]pyridin-2-yl)-6-[2-(trifluoromethyl)phenyl]quinolin-2(1H)-one | 532 |

TABLE 2-continued

Table of Examples 212-338.

| Example | Name | LC/MS m/z (MH+) |
|---|---|---|
| 249 | 4-[(3R)-1-azabicyclo[2.2.2]oct-3-ylamino]-3-(3H-imidazo[4,5-b]pyridin-2-yl)-6-[2-(methyloxy)phenyl]quinolin-2(1H)-one | 494 |
| 250 | ethyl 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-3-carboxylate | 560 |
| 251 | 4-[(3R)-1-azabicyclo[2.2.2]oct-3-ylamino]-3-(1H-benzimidazol-2-yl)-6-(4-ethylphenyl)quinolin-2(1H)-one | 491 |
| 252 | 4-[(3S)-1-azabicyclo[2.2.2]oct-3-ylamino]-3-(1H-benzimidazol-2-yl)-6-fluoro-7-[(2-methylpropyl)amino]quinolin-2(1H)-one | 476 |
| 253 | 4-[(3R)-1-azabicyclo[2.2.2]oct-3-ylamino]-3-(1H-benzimidazol-2-yl)-5-methylquinolin-2(1H)-one | 401 |
| 254 | 4-[(3R)-1-azabicyclo[2.2.2]oct-3-ylamino]-6-(2,4-dichlorophenyl)-3-(3H-imidazo[4,5-b]pyridin-2-yl)quinolin-2(1H)-one | 532 |
| 255 | 4-[(3R)-1-azabicyclo[2.2.2]oct-3-ylamino]-3-(1H-benzimidazol-2-yl)-6-[3-(trifluoromethyl)phenyl]quinolin-2(1H)-one | 531 |
| 256 | 3-(1H-benzimidazol-2-yl)-4-(dimethylamino)quinolin-2(1H)-one | 305 |
| 257 | 4-hydroxy-3-(1H-imidazo[4,5-f]quinolin-2-yl)quinolin-2(1H)-one | 329 |
| 258 | 4-hydroxy-3-(1H-imidazo[4,5-b]pyridin-2-yl)quinolin-2(1H)-one | 279 |
| 259 | 4-[4-[(3R)-1-azabicyclo[2.2.2]oct-3-ylamino]-3-(1H-benzimidazol-2-yl)-5-fluoro-2-oxo-1,2-dihydroquinolin-6-yl]benzoic acid | 525 |
| 260 | 4-[4-[(3R)-1-azabicyclo[2.2.2]oct-3-ylamino]-3-(1H-benzimidazol-2-yl)-5-fluoro-2-oxo-1,2-dihydroquinolin-6-yl]benzamide | 524 |
| 261 | N-{3-[4-[(3R)-1-azabicyclo[2.2.2]oct-3-ylamino]-3-(1H-benzimidazol-2-yl)-5-fluoro-2-oxo-1,2-dihydroquinolin-6-yl]phenyl}acetamide | 538 |
| 262 | 3-[4-[(3R)-1-azabicyclo[2.2.2]oct-3-ylamino]-3-(1H-benzimidazol-2-yl)-5-fluoro-2-oxo-1,2-dihydroquinolin-6-yl]benzoic acid | 525 |
| 263 | 4-[4-[(3R)-1-azabicyclo[2.2.2]oct-3-ylamino]-3-(1H-benzimidazol-2-yl)-7-fluoro-2-oxo-1,2-dihydroquinolin-6-yl]benzoic acid | 525 |
| 264 | N-{3-[4-[(3R)-1-azabicyclo[2.2.2]oct-3-ylamino]-3-(1H-benzimidazol-2-yl)-7-fluoro-2-oxo-1,2-dihydroquinolin-6-yl]phenyl}acetamide | 538 |
| 265 | 4-[(3R)-1-azabicyclo[2.2.2]oct-3-ylamino]-3-(1H-benzimidazol-2-yl)-7-chloro-6-(2-methylphenyl)quinolin-2(1H)-one | 511 |
| 266 | 4-[(3R)-1-azabicyclo[2.2.2]oct-3-ylamino]-3-(1H-benzimidazol-2-yl)-2-oxo-1,2-dihydroquinoline-7-carbonitrile | 411 |
| 267 | 4-[(3R)-1-azabicyclo[2.2.2]oct-3-ylamino]-3-(1H-benzimidazol-2-yl)-7-(methyloxy)quinolin-2(1H)-one | 417 |
| 268 | 4-[4-[(3R)-1-azabicyclo[2.2.2]oct-3-ylamino]-3-(1H-benzimidazol-2-yl)-2-oxo-1,2-dihydroquinolin-7-yl]benzamide | 506 |
| 269 | 4-[(3R)-1-azabicyclo[2.2.2]oct-3-ylamino)-3-(1H-benzimidazol-2-yl)-6-fluoro-7-(methyloxy)quinolin-2(1H)-one | 434 |
| 270 | 4-[(3R)-1-azabicyclo[2.2.2]oct-3-ylamino]-3-(1H-benzimidazol-2-yl)-6-chloro-7-(dimethylamino)quinolin-2(1H)-one | 464 |
| 271 | 4-[(3R)-1-azabicyclo[2.2.2]oct-3-ylamino]-3-(1H-benzimidazol-2-yl)-7-(dimethylamino)-6-iodoquinolin-2(1H)-one | 555 |
| 272 | 3-[4-[(3R)-1-azabicyclo[2.2.2]oct-3-ylamino]-3-(1H-benzimidazol-2-yl)-7-(1H-imidazol-1-yl)-2-oxo-1,2-dihydroquinolin-6-yl]benzoic acid | 573 |
| 273 | 4-[4-[(3R)-1-azabicyclo[2.2.2]oct-3-ylamino]-3-(1H-benzimidazol-2-yl)-2-oxo-7-piperidin-1-yl-1,2-dihydroquinolin-6-yl]benzoic acid | 590 |
| 274 | 4-[(3R)-1-azabicyclo[2.2.2]oct-3-ylamino]-3-(1H-benzimidazol-2-yl)-7-(methyloxy)-6-[4-(methylsulfonyl)phenyl]quinolin-2(1H)-one | 571 |
| 275 | 4-[(3R)-1-azabicyclo[2.2.2]oct-3-ylamino]-3-(1H-benzimidazol-2-yl)-8-methylquinolin-2(1H)-one | 401 |

TABLE 2-continued

Table of Examples 212-338.

| Example | Name | LC/MS m/z (MH+) |
|---|---|---|
| 276 | 4-[(3S)-1-azabicyclo[2.2.2]oct-3-ylamino]-3-(1H-benzimidazol-2-yl)-6,7-difluoroquinolin-2(1H)-one | 422 |
| 277 | 3-(1H-benzimidazol-2-yl)-6-methyl-4-(piperidin-3-ylamino)quinolin-2(1H)-one | 374 |
| 278 | 4-[(3S)-1-azabicyclo[2.2.2]oct-3-ylamino]-3-(1H-benzimidazol-2-yl)-6-[2-(methyloxy)phenyl]quinolin-2(1H)-one | 493 |
| 279 | 4-[(3S)-1-azabicyclo[2.2.2]oct-3-ylamino]-3-(1H-benzimidazol-2-yl)-6-[3-(methyloxy)phenyl]quinolin-2(1H)-one | 493 |
| 280 | 3-(1H-benzimidazol-2-yl)-6,7-difluoro-4-(piperidin-4-ylamino)quinolin-2(1H)-one | 396 |
| 281 | 3-(1H-benzimidazol-2-yl)-6,7-difluoro-4-(pyrrolidin-3-ylamino)quinolin-2(1H)-one | 382 |
| 282 | 3-(1H-benzimidazol-2-yl)-6-chloro-4-[(3-morpholin-4-ylpropyl)amino]quinolin-2(1H)-one | 439 |
| 283 | 6-chloro-3-(5-morpholin-4-yl-1H-benzimidazol-2-yl)-4-(piperidin-4-ylamino)quinolin-2(1H)-one | 480 |
| 284 | 6-chloro-3-(5-morpholin-4-yl-1H-benzimidazol-2-yl)-4-[(piperidin-2-ylmethyl)amino]quinolin-2(1H)-one | 494 |
| 285 | 4-[(3S)-1-azabicyclo[2.2.2]oct-3-ylamino]-6-chloro-3-(5-morpholin-4-yl-1H-benzimidazol-2-yl)quinolin-2(1H)-one | 506 |
| 286 | 6-chloro-3-(5-morpholin-4-yl-1H-benzimidazol-2-yl)-4-(piperidin-3-ylamino)quinolin-2(1H)-one | 480 |
| 287 | 6-chloro-4-{[2-(dimethylamino)ethyl]amino}-3-(5-morpholin-4-yl-1H-benzimidazol-2-yl)quinolin-2(1H)-one | 468 |
| 288 | 4-[(3R)-1-azabicyclo[2.2.2]oct-3-ylamino]-6-chloro-3-(5-morpholin-4-yl-1H-benzimidazol-2-yl)quinolin-2(1H)-one | 506 |
| 289 | 6-chloro-3-(5-morpholin-4-yl-1H-benzimidazol-2-yl)-4-[(piperidin-3-ylmethyl)amino]quinolin-2(1H)-one | 494 |
| 290 | 6-chloro-3-(5-morpholin-4-yl-1H-benzimidazol-2-yl)-4-[(piperidin-4-ylmethyl)amino]quinolin-2(1H)-one | 494 |
| 291 | 4-{[(1R,2R)-2-aminocyclohexyl]amino}-6-chloro-3-(5-morpholin-4-yl-1H-benzimidazol-2-yl)quinolin-2(1H)-one | 494 |
| 292 | 4-[(4-aminocyclohexyl)amino]-6-chloro-3-(5-morpholin-4-yl-1H-benzimidazol-2-yl)quinolin-2(1H)-one | 494 |
| 293 | 4-{[(2S)-2-amino-3-methylbutyl]amino}-6-chloro-3-(5-morpholin-4-yl-1H-benzimidazol-2-yl)quinolin-2(1H)-one | 482 |
| 294 | 4-({[4-(aminomethyl)phenyl]methyl}amino)-6-chloro-3-(5-morpholin-4-yl-1H-benzimidazol-2-yl)quinolin-2(1H)-one | 516 |
| 295 | 6-chloro-3-(5-morpholin-4-yl-1H-benzimidazol-2-yl)-4-[(pyrrolidin-2-ylmethyl)amino]quinolin-2(1H)-one | 480 |
| 296 | 4-{[(1R)-1-(aminomethyl)propyl]amino}-6-chloro-3-(5-morpholin-4-yl-1H-benzimidazol-2-yl)quinolin-2(1H)-one | 468 |
| 297 | 4-{[(1S)-2-amino-1-(phenylmethyl)ethyl]amino}-6-chloro-3-(5-morpholin-4-yl-1H-benzimidazol-2-yl)quinolin-2(1H)-one | 530 |
| 298 | 6-chloro-4-{[3-(4-methylpiperazin-1-yl)propyl]amino}-3-(5-morpholin-4-yl-1H-benzimidazol-2-yl)quinolin-2(1H)-one | 537 |
| 299 | 6-chloro-3-(5-morpholin-4-yl-1H-benzimidazol-2-yl)-4-{[1-(phenylmethyl)piperidin-4-yl]amino}quinolin-2(1H)-one | 570 |
| 300 | 6-chloro-3-(5-morpholin-4-yl-1H-benzimidazol-2-yl)-4-[(3-morpholin-4-ylpropyl)amino]quinolin-2(1H)-one | 524 |
| 301 | 6-chloro-3-(5-morpholin-4-yl-1H-benzimidazol-2-yl)-4-[(2-piperidin-1-ylethyl)amino]quinolin-2(1H)-one | 508 |
| 302 | 6-chloro-3-(5-morpholin-4-yl-1H-benzimidazol-2-yl)-4-[(pyridin-3-ylmethyl)amino]quinolin-2(1H)-one | 488 |
| 303 | 6-chloro-4-{[3-(1H-imidazol-1-yl)propyl]amino}-3-(5-morpholin-4-yl-1H-benzimidazol-2-yl)quinolin-2(1H)-one | 505 |
| 304 | 6-chloro-3-(5-morpholin-4-yl-1H-benzimidazol-2-yl)-4-[(pyridin-4-ylmethyl)amino]quinolin-2(1H)-one | 488 |
| 305 | 6-chloro-4-{[2-(methylamino)ethyl]amino}-3-(5-morpholin-4-yl-1H-benzimidazol-2-yl)quinolin-2(1H)-one | 454 |
| 306 | 6-chloro-4-{[(2-methyl-1-piperidin-4-yl-1H-benzimidazol-5-yl)methyl]amino}-3-(5-morpholin-4-yl-1H-benzimidazol-2-yl)quinolin-2(1H)-one | 624 |
| 307 | 6-chloro-3-(5-morpholin-4-yl-1H-benzimidazol-2-yl)-4-[(2-pyrrolidin-1-ylethyl)amino]quinolin-2(1H)-one | 494 |
| 308 | 6-chloro-3-(5-morpholin-4-yl-1H-benzimidazol-2-yl)-4-(pyrrolidin-3-ylamino)quinolin-2(1H)-one | 466 |

TABLE 2-continued

Table of Examples 212-338.

| Example | Name | LC/MS m/z (MH+) |
|---|---|---|
| 309 | 4-{[(1R,2R)-2-aminocyclohexyl]amino}-6-chloro-3-[5-(4-methylpiperazin-1-yl)-1H-benzimidazol-2-yl]quinolin-2(1H)-one | 507 |
| 310 | 4-[(4-aminocyclohexyl)amino]-6-chloro-3-[5-(4-methylpiperazin-1-yl)-1H-benzimidazol-2-yl]quinolin-2(1H)-one | 507 |
| 311 | 4-({[4-(aminomethyl)phenyl]methyl}amino)-6-chloro-3-[5-(4-methylpiperazin-1-yl)-1H-benzimidazol-2-yl]quinolin-2(1H)-one | 529 |
| 312 | 6-chloro-4-{[2-(methylamino)ethyl]amino}-3-[5-(4-methylpiperazin-1-yl)-1H-benzimidazol-2-yl]quinolin-2(1H)-one | 467 |
| 313 | 6-chloro-3-[5-(4-methylpiperazin-1-yl)-1H-benzimidazol-2-yl]-4-{[3-(4-methylpiperazin-1-yl)propyl]amino}quinolin-2(1H)-one | 550 |
| 314 | 6-chloro-3-[5-(4-methylpiperazin-1-yl)-1H-benzimidazol-2-yl]-4-{[1-(phenylmethyl)piperidin-4-yl]amino}quinolin-2(1H)-one | 583 |
| 315 | 6-chloro-3-[5-(4-methylpiperazin-1-yl)-1H-benzimidazol-2-yl]-4-[(2-pyrrolidin-1-ylethyl)amino]quinolin-2(1H)-one | 507 |
| 316 | 6-chloro-3-[5-(4-methylpiperazin-1-yl)-1H-benzimidazol-2-yl]-4-(pyrrolidin-3-ylamino)quinolin-2(1H)-one | 479 |
| 317 | 6-chloro-3-[5-(4-methylpiperazin-1-yl)-1H-benzimidazol-2-yl]-4-(piperidin-4-ylamino)quinolin-2(1H)-one | 493 |
| 318 | 6-chloro-3-(5-morpholin-4-yl-1H-benzimidazol-2-yl)-4-[(2-piperidin-2-ylethyl)amino]quinolin-2(1H)-one | 508 |
| 319 | 4-[(3S)-1-azabicyclo[2.2.2]oct-3-ylamino]-7-chloro-3-(5-morpholin-4-yl-1H-benzimidazol-2-yl)quinolin-2(1H)-one | 506 |
| 320 | 7-chloro-3-(5-morpholin-4-yl-1H-benzimidazol-2-yl)-4-(piperidin-3-ylamino)quinolin-2(1H)-one | 480 |
| 321 | 6-chloro-3-[5-(4-methylpiperazin-1-yl)-1H-benzimidazol-2-yl]-4-[(piperidin-2-ylmethyl)amino]quinolin-2(1H)-one | 507 |
| 322 | 6-chloro-3-[5-(4-methylpiperazin-1-yl)-1H-benzimidazol-2-yl]-4-{[(2S)-pyrrolidin-2-ylmethyl]amino}quinolin-2(1H)-one | 493 |
| 323 | 6-chloro-3-[5-(4-methylpiperazin-1-yl)-1H-benzimidazol-2-yl]-4-{[(2R)-pyrrolidin-2-ylmethyl]amino}quinolin-2(1H)-one | 493 |
| 324 | 6-chloro-4-({[(2S)-1-ethylpyrrolidin-2-yl]methyl}amino)-3-[5-(4-methylpiperazin-1-yl)-1H-benzimidazol-2-yl]quinolin-2(1H)-one | 521 |
| 325 | 6-chloro-4-({[(2R)-1-ethylpyrrolidin-2-yl]methyl}amino)-3-[5-(4-methylpiperazin-1-yl)-1H-benzimidazol-2-yl]quinolin-2(1H)-one | 521 |
| 326 | 4-[(3S)-1-azabicyclo[2.2.2]oct-3-ylamino]-3-(1H-benzimidazol-2-yl)-6-[4-(methyloxy)phenyl]quinolin-2(1H)-one | 493 |
| 327 | 6-(3-aminophenyl)-4-[(3S)-1-azabicyclo[2.2.2]oct-3-ylamino]-3-(1H-benzimidazol-2-yl)quinolin-2(1H)-one | 478 |
| 328 | 4-amino-3-(1H-benzimidazol-2-yl)-1,7-naphthyridin-2(1H)-one | 278.3 |
| 329 | 4-amino-3-(5-methyl-1H-benzimidazol-2-yl)-1,7-naphthyridin-2(1H)-one | 292.4 |
| 330 | 4-amino-3-[5-(2-morpholin-4-ylethoxy)-1H-benzimidazol-2-yl]-1,7-naphthyridin-2(1H)-one | 407.4 |
| 331 | 2-(4-amino-2-oxo-1,2-dihydro-1,7-naphthyridin-3-yl)-N,N-dimethyl-1H-benzimidazole-5-carboxamide | 349.3 |
| 332 | 4-amino-3-(5-morpholin-4-yl-1H-benzimidazol-2-yl)-1,7-naphthyridin-2(1H)-one | 363.2 |
| 333 | 4-amino-3-{5-[3-(dimethylamino)pyrrolidin-1-yl]-1H-benzimidazol-2-yl}-1,7-naphthyridin-2(1H)-one | 390.2 |
| 334 | 4-amino-3-(3H-imidazo[4,5-b]pyridin-2-yl)-1,7-naphthyridin-2(1H)-one | 279.0 |
| 335 | 4-amino-3-[5-(4-methylpiperazin-1-yl)-1H-benzimidazol-2-yl]-1,7-naphthyridin-2(1H)-one | 376.3 |
| 336 | 4-amino-3-(5-morpholin-4-yl-1H-benzimidazol-2-yl)-1,6-naphthyridin-2(1H)-one | 363.2 |
| 337 | 4-amino-3-{5-[3-(dimethylamino)pyrrolidin-1-yl]-1H-benzimidazol-2-yl}-1,5-naphthyridin-2(1H)-one | 390.2 |
| 338 | 4-amino-3-[5-(4-methylpiperazin-1-yl)-1H-benzimidazol-2-yl]-1,5-naphthyridin-2(1H)-one | 376.1 |

Examples 339-1273

Examples 339 to 1273 listed in Table 3 were synthesized using the methods described above such as Methods 1-24 and those set forth in the Schemes and other Examples or modified as apparent to one of reasonable skill in the art using commercially available materials.

TABLE 3

Table of Examples 339-1273.

| Example | Name | LC/MS m/z (MH⁺) |
|---|---|---|
| 339 | 4-amino-3-(1H-benzimidazol-2-yl)quinolin-2(1H)-one | 277.3 |
| 340 | 4-amino-3-(1H-benzimidazol-2-yl)-6,7-dimethoxyquinolin-2(1H)-one | 337.3 |
| 341 | 3-(1H-benzimidazol-2-yl)-4-(dimethylamino)-1-methylquinolin-2(1H)-one | 319.4 |
| 342 | 3-(1H-benzimidazol-2-yl)-4-{[2-(dimethylamino)ethyl]amino}-1-methylquinolin-2(1H)-one | 362.4 |
| 343 | 4-amino-3-(1H-benzimidazol-2-yl)-1-methylquinolin-2(1H)-one | 291.3 |
| 344 | 4-amino-3-(6-methyl-1H-benzimidazol-2-yl)quinolin-2(1H)-one | 291.3 |
| 345 | 3-(1H-benzimidazol-2-yl)-4-{[3-(1H-imidazol-1-yl)propyl]amino}quinolin-2(1H)-one | 385.4 |
| 346 | 3-(1H-benzimidazol-2-yl)-4-[(pyridin-3-ylmethyl)amino]quinolin-2(1H)-one | 368.4 |
| 347 | 4-amino-3-(1H-benzimidazol-2-yl)-5-fluoroquinolin-2(1H)-one | 295.3 |
| 348 | 3-(1H-benzimidazol-2-yl)-4-pyrrolidin-1-ylquinolin-2(1H)-one | 331.4 |
| 349 | 3-(1H-benzimidazol-2-yl)-4-[(pyridin-4-ylmethyl)amino]quinolin-2(1H)-one | 368.4 |
| 350 | 3-(1H-benzimidazol-2-yl)-4-{[2-(1-methylpyrrolidin-2-yl)ethyl]amino}quinolin-2(1H)-one | 388.5 |
| 351 | 4-amino-3-(1H-benzimidazol-2-yl)-7-methylquinolin-2(1H)-one | 291.3 |
| 352 | 4-amino-3-(1H-benzimidazol-2-yl)-7-chloroquinolin-2(1H)-one | 311.7 |
| 353 | 4-amino-3-(1H-benzimidazol-2-yl)-6-chloroquinolin-2(1H)-one | 311.7 |
| 354 | 4-amino-3-[6-(3-aminopyrrolidin-1-yl)-1H-benzimidazol-2-yl]quinolin-2(1H)-one | 361.4 |
| 355 | 3-(1H-benzimidazol-2-yl)-4-(diethylamino)quinolin-2(1H)-one | 333.4 |
| 356 | 3-(1H-benzimidazol-2-yl)-4-(1,2-dimethylhydrazino)quinolin-2(1H)-one | 320.4 |
| 357 | 4-amino-3-[5-(trifluoromethyl)-1H-benzimidazol-2-yl]quinolin-2(1H)-one | 345.3 |
| 358 | 4-amino-3-(5,6-dichloro-1H-benzimidazol-2-yl)quinolin-2(1H)-one | 346.2 |
| 359 | 4-(3-aminopyrrolidin-1-yl)-3-(5-morpholin-4-yl-1H-benzimidazol-2-yl)quinolin-2(1H)-one | 431.5 |
| 360 | 4-amino-5-fluoro-3-(5-methyl-1H-benzimidazol-2-yl)quinolin-2(1H)-one | 309.3 |
| 361 | 4-amino-3-(1H-benzimidazol-2-yl)-6-nitroquinolin-2(1H)-one | 322.3 |
| 362 | 4-amino-3-(4-methyl-1H-benzimidazol-2-yl)quinolin-2(1H)-one | 291.3 |
| 363 | 4-amino-3-(6-ethoxy-1H-benzimidazol-2-yl)quinolin-2(1H)-one | 321.4 |
| 364 | 4-amino-3-(7-hydroxy-1H-benzimidazol-2-yl)quinolin-2(1H)-one | 293.3 |
| 365 | 4-amino-3-(6-tert-butyl-1H-benzimidazol-2-yl)quinolin-2(1H)-one | 333.4 |
| 366 | 2-(4-amino-2-oxo-1,2-dihydroquinolin-3-yl)-1H-benzimidazole-5-carbonitrile | 302.3 |
| 367 | 4-amino-3-(5,6-dimethyl-1H-benzimidazol-2-yl)quinolin-2(1H)-one | 305.4 |
| 368 | 4-amino-3-(4,5-dimethyl-1H-benzimidazol-2-yl)quinolin-2(1H)-one | 305.4 |
| 369 | 4-amino-6-chloro-3-(5-methyl-1H-benzimidazol-2-yl)quinolin-2(1H)-one | 325.8 |
| 370 | 4-amino-3-(1H-benzimidazol-2-yl)-6,8-dichloroquinolin-2(1H)-one | 346.2 |
| 371 | 4-amino-3-(1H-benzimidazol-2-yl)-5-chloroquinolin-2(1H)-one | 311.7 |
| 372 | 2-(4-amino-2-oxo-1,2-dihydroquinolin-3-yl)-N,N-dimethyl-1H-benzimidazole-5-carboxamide | 348.4 |

TABLE 3-continued

Table of Examples 339-1273.

| Example | Name | LC/MS m/z (MH+) |
|---|---|---|
| 373 | 4-amino-3-{5-[3-(dimethylamino)pyrrolidin-1-yl]-1H-benzimidazol-2-yl}quinolin-2(1H)-one | 389.5 |
| 374 | 4-amino-3-(6-methoxy-5-methyl-1H-benzimidazol-2-yl)quinolin-2(1H)-one | 321.4 |
| 375 | 2-(4-amino-2-oxo-1,2-dihydroquinolin-3-yl)-1H-benzimidazole-6-carboximidamide | 319.3 |
| 376 | 4-amino-7-(3-aminophenyl)-3-(1H-benzimidazol-2-yl)quinolin-2(1H)-one | 368.4 |
| 377 | 4-amino-3-(1H-benzimidazol-2-yl)-7-thien-2-ylquinolin-2(1H)-one | 359.4 |
| 378 | 4-amino-3-(5-thien-3-yl-1H-benzimidazol-2-yl)quinolin-2(1H)-one | 359.4 |
| 379 | 4-amino-3-(1H-benzimidazol-2-yl)-7-thien-3-ylquinolin-2(1H)-one | 359.4 |
| 380 | 4-{[(1S,2R)-2-aminocyclohexyl]amino}-3-(5-morpholin-4-yl-1H-benzimidazol-2-yl)quinolin-2(1H)-one | 459.6 |
| 381 | 4-{[(1R,2R)-2-aminocyclohexyl]amino}-3-(5-morpholin-4-yl-1H-benzimidazol-2-yl)quinolin-2(1H)-one | 459.6 |
| 382 | 4-{[(1S,2S)-2-aminocyclohexyl]amino}-3-(5-morpholin-4-yl-1H-benzimidazol-2-yl)quinolin-2(1H)-one | 459.6 |
| 383 | 4-amino-3-{5-[(2R,6S)-2,6-dimethylmorpholin-4-yl]-1H-benzimidazol-2-yl}quinolin-2(1H)-one | 390.5 |
| 384 | 3-(1H-benzimidazol-2-yl)-4-morpholin-4-ylquinolin-2(1H)-one | 347.4 |
| 385 | 3-(1H-benzimidazol-2-yl)-4-(piperidin-3-ylamino)quinolin-2(1H)-one | 360.4 |
| 386 | 4-(1-azabicyclo[2.2.2]oct-3-ylamino)-3-(5-chloro-1H-benzimidazol-2-yl)quinolin-2(1H)-one | 420.9 |
| 387 | 4-[(3R)-1-azabicyclo[2.2.2]oct-3-ylamino]-6-chloro-3-(5-methyl-1H-benzimidazol-2-yl)quinolin-2(1H)-one | 434.9 |
| 388 | 6-chloro-3-(5-methyl-1H-benzimidazol-2-yl)-4-(piperidin-3-ylamino)quinolin-2(1H)-one | 408.9 |
| 389 | 3-(1H-benzimidazol-2-yl)-4-[(2-hydroxyethyl)amino]quinolin-2(1H)-one | 321.4 |
| 390 | 3-(1H-benzimidazol-2-yl)-6-chloro-4-(piperidin-3-ylamino)quinolin-2(1H)-one | 394.9 |
| 391 | 3-(1H-benzimidazol-2-yl)-6-chloro-4-{[(1S)-1-cyclohexylethyl]amino}quinolin-2(1H)-one | 421.9 |
| 392 | 3-(1H-benzimidazol-2-yl)-6-chloro-4-[(piperidin-3-ylmethyl)amino]quinolin-2(1H)-one | 408.9 |
| 393 | 3-(1H-benzimidazol-2-yl)-6-chloro-4-(pyridin-4-ylamino)quinolin-2(1H)-one | 388.8 |
| 394 | 3-(1H-benzimidazol-2-yl)-6-chloro-4-[(piperidin-4-ylmethyl)amino]quinolin-2(1H)-one | 408.9 |
| 395 | 3-(1H-benzimidazol-2-yl)-6-chloro-4-[(2-morpholin-4-ylethyl)amino]quinolin-2(1H)-one | 424.9 |
| 396 | 3-(1H-benzimidazol-2-yl)-6-chloro-4-(cyclohexylamino)quinolin-2(1H)-one | 393.9 |
| 397 | 3-(1H-benzimidazol-2-yl)-6-chloro-4-{[3-(1H-imidazol-1-yl)propyl]amino}quinolin-2(1H)-one | 419.9 |
| 398 | 3-(1H-benzimidazol-2-yl)-6-chloro-4-{[2-(dimethylamino)ethyl]amino}quinolin-2(1H)-one | 382.9 |
| 399 | 3-(1H-benzimidazol-2-yl)-6-chloro-4-[(cyclohexylmethyl)amino]quinolin-2(1H)-one | 407.9 |
| 400 | 3-(1H-benzimidazol-2-yl)-6-chloro-4-[(tetrahydrofuran-2-ylmethyl)amino]quinolin-2(1H)-one | 395.9 |
| 401 | 3-(1H-benzimidazol-2-yl)-6-chloro-4-[(pyridin-4-ylmethyl)amino]quinolin-2(1H)-one | 402.9 |
| 402 | 3-(1H-benzimidazol-2-yl)-6,7-difluoro-4-(piperidin-3-ylamino)quinolin-2(1H)-one | 396.4 |
| 403 | 4-[(3S)-1-azabicyclo[2.2.2]oct-3-ylamino]-3-(1H-benzimidazol-2-yl)-6-bromoquinolin-2(1H)-one | 465.4 |
| 404 | 3-(1H-benzimidazol-2-yl)-6-fluoro-4-(piperidin-3-ylamino)quinolin-2(1H)-one | 378.4 |
| 405 | 4-[(3S)-1-azabicyclo[2.2.2]oct-3-ylamino]-3-(1H-benzimidazol-2-yl)-6-methylquinolin-2(1H)-one | 400.5 |
| 406 | 4-[(3S)-1-azabicyclo[2.2.2]oct-3-ylamino]-3-(1H-benzimidazol-2-yl)-6-fluoroquinolin-2(1H)-one | 404.5 |
| 407 | 4-amino-3-[6-(4-methylpiperazin-1-yl)-1H-benzimidazol-2-yl]-1-propylquinolin-2(1H)-one | 417.5 |
| 408 | 3-(1H-benzimidazol-2-yl)-6-chloro-4-{[(1-ethylpyrrolidin-2-yl)methyl]amino}quinolin-2(1H)-one | 422.9 |

TABLE 3-continued

Table of Examples 339-1273.

| Example | Name | LC/MS m/z (MH+) |
|---|---|---|
| 409 | 3-(1H-benzimidazol-2-yl)-6-chloro-4-{[3-(2-oxopyrrolidin-1-yl)propyl]amino}quinolin-2(1H)-one | 436.9 |
| 410 | 3-(1H-benzimidazol-2-yl)-6-chloro-4-[(piperidin-2-ylmethyl)amino]quinolin-2(1H)-one | 408.9 |
| 411 | 3-(1H-benzimidazol-2-yl)-6-chloro-4-(4-methyl-1,4-diazepan-1-yl)quinolin-2-(1H)-one | 408.9 |
| 412 | 3-(1H-benzimidazol-2-yl)-6-chloro-4-[(pyridin-3-ylmethyl)amino]quinolin-2(1H)-one | 402.9 |
| 413 | 4-anilino-3-(1H-benzimidazol-2-yl)-6-chloroquinolin-2(1H)-one | 387.8 |
| 414 | 3-(1H-benzimidazol-2-yl)-6-chloro-4-{[(5-methylpyrazin-2-yl)methyl]amino}quinolin-2(1H)-one | 417.9 |
| 415 | 3-(1H-benzimidazol-2-yl)-6-chloro-4-(piperidin-4-ylamino)quinolin-2(1H)-one | 402.9 |
| 416 | 3-(1H-benzimidazol-2-yl)-6-chloro-4-{[2-(1-methylpyrrolidin-2-yl)ethyl]amino}quinolin-2(1H)-one | 422.9 |
| 417 | 3-(1H-benzimidazol-2-yl)-4-[(1H-benzimidazol-5-ylmethyl)amino]-6-chloroquinolin-2(1H)-one | 441.9 |
| 418 | 3-(1H-benzimidazol-2-yl)-6-chloro-4-(piperidin-4-ylamino)quinolin-2(1H)-one | 394.9 |
| 419 | 3-(1H-benzimidazol-2-yl)-6-chloro-4-[(4-hydroxycyclohexyl)amino]quinolin-2(1H)-one | 409.9 |
| 420 | 4-[(3S)-1-azabicyclo[2.2.2]oct-3-ylamino]-3-(1H-benzimidazol-2-yl)-5-fluoroquinolin-2(1H)-one | 404.5 |
| 421 | 3-(1H-benzimidazol-2-yl)-6,8-dimethyl-4-(piperidin-3-ylamino)quinolin-2(1H)-one | 388.5 |
| 422 | 3-(1H-benzimidazol-2-yl)-5-fluoro-4-(piperidin-3-ylamino)quinolin-2(1H)-one | 378.4 |
| 423 | 4-[(3R)-1-azabicyclo[2.2.2]oct-3-ylamino]-3-(1H-benzimidazol-2-yl)-6,8-dimethylquinolin-2(1H)-one | 414.5 |
| 424 | 4-[(3S)-1-azabicyclo[2.2.2]oct-3-ylamino]-3-(1H-benzimidazol-2-yl)-6,8-dimethylquinolin-2(1H)-one | 414.5 |
| 425 | 4-[(3R)-1-azabicyclo[2.2.2]oct-3-ylamino]-3-(1H-benzimidazol-2-yl)-7-chloroquinolin-2(1H)-one | 420.9 |
| 426 | 3-(1H-benzimidazol-2-yl)-6-chloro-4-[(2-piperidin-1-ylethyl)amino]quinolin-2(1H)-one | 422.9 |
| 427 | 4-({2-[(4-amino-5-nitropyridin-2-yl)amino]ethyl}amino)-3-(1H-benzimidazol-2-yl)-6-chloroquinolin-2(1H)-one | 491.9 |
| 428 | 3-(1H-benzimidazol-2-yl)-6-chloro-4-({2-[(5-nitropyridin-2-yl)amino]ethyl}amino)quinolin-2(1H)-one | 476.9 |
| 429 | 3-(1H-benzimidazol-2-yl)-4-[(1H-benzimidazol-2-ylmethyl)amino]-6-chloroquinolin-2(1H)-one | 441.9 |
| 430 | 3-(1H-benzimidazol-2-yl)-6-chloro-4-(2,5-diazabicyclo[2.2.1]hept-2-yl)quinolin-2(1H)-one | 392.9 |
| 431 | 3-(1H-benzimidazol-2-yl)-6-chloro-4-[(2-{[5-(trifluoromethyl)pyridin-2-yl]amino}ethyl)amino]quinolin-2(1H)-one | 499.9 |
| 432 | 4-[(3S)-1-azabicyclo[2.2.2]oct-3-ylamino]-3-(1H-benzimidazol-2-yl)-7-methylquinolin-2(1H)-one | 400.5 |
| 433 | 4-[(3R)-1-azabicyclo[2.2.2]oct-3-ylamino]-3-(1H-benzimidazol-2-yl)-7-methylquinolin-2(1H)-one | 400.5 |
| 434 | 3-(1H-benzimidazol-2-yl)-7-chloro-4-{[(2R)-pyrrolidin-2-ylmethyl]amino}quinolin-2(1H)-one | 394.9 |
| 435 | 3-(1H-benzimidazol-2-yl)-6-chloro-4-[(pyrrolidin-2-ylmethyl)amino]quinolin-2(1H)-one | 394.9 |
| 436 | 6-[(2-{[3-(1H-benzimidazol-2-yl)-6-chloro-2-oxo-1,2-dihydroquinolin-4-yl]amino}ethyl)amino]nicotinamide | 474.9 |
| 437 | 3-(1H-benzimidazol-2-yl)-6-chloro-4-(pyrrolidin-3-ylamino)quinolin-2(1H)-one | 380.8 |
| 438 | 4-{[(2R)-2-aminobutyl]amino}-3-(1H-benzimidazol-2-yl)-6-chloroquinolin-2(1H)-one | 382.9 |
| 439 | 4-{[(2S)-2-amino-3-phenylpropyl]amino}-3-(1H-benzimidazol-2-yl)-6-chloroquinolin-2(1H)-one | 444.9 |
| 440 | 4-[(4-aminocyclohexyl)amino]-3-(1H-benzimidazol-2-yl)-6-chloroquinolin-2(1H)-one | 408.9 |
| 441 | 4-[(3R)-1-azabicyclo[2.2.2]oct-3-ylamino]-3-(1H-benzimidazol-2-yl)-6-iodoquinolin-2(1H)-one | 512.4 |
| 442 | 4-[(3S)-1-azabicyclo[2.2.2]oct-3-ylamino]-3-(1H-benzimidazol-2-yl)-6-iodoquinolin-2(1H)-one | 512.4 |
| 443 | 3-(1H-benzimidazol-2-yl)-6,7-dimethoxy-4-(piperidin-3-ylamino)quinolin-2(1H)-one | 420.5 |
| 444 | 4-[(3R)-1-azabicyclo[2.2.2]oct-3-ylamino]-3-(1H-benzimidazol-2-yl)-6,7-dimethoxyquinolin-2(1H)-one | 446.5 |

TABLE 3-continued

Table of Examples 339-1273.

| Example | Name | LC/MS m/z (MH+) |
|---|---|---|
| 445 | 4-[(3S)-1-azabicyclo[2.2.2]oct-3-ylamino]-3-(1H-benzimidazol-2-yl)-6-nitroquinolin-2(1H)-one | 431.5 |
| 446 | 3-(1H-benzimidazol-2-yl)-6-iodo-4-(piperidin-3-ylamino)quinolin-2(1H)-one | 486.3 |
| 447 | 4-[(3R)-1-azabicyclo[2.2.2]oct-3-ylamino]-3-(1H-benzimidazol-2-yl)-5-chloroquinolin-2(1H)-one | 420.9 |
| 448 | 3-(1H-benzimidazol-2-yl)-6-chloro-4-{[(1-piperidin-4-yl-1H-benzimidazol-6-yl)methyl]amino}quinolin-2(1H)-one | 525.0 |
| 449 | 3-(1H-benzimidazol-2-yl)-6-methyl-4-[(piperidin-3-ylmethyl)amino]quinolin-2(1H)-one | 388.5 |
| 450 | 3-(1H-benzimidazol-2-yl)-6-methyl-4-(piperidin-4-ylamino)quinolin-2(1H)-one | 374.5 |
| 451 | 3-(1H-benzimidazol-2-yl)-6-methyl-4-[(piperidin-4-ylmethyl)amino]quinolin-2(1H)-one | 388.5 |
| 452 | 3-(1H-benzimidazol-2-yl)-6-methyl-4-[(piperidin-2-ylmethyl)amino]quinolin-2(1H)-one | 388.5 |
| 453 | 4-{[4-(2-aminoethoxy)benzyl]amino}-3-(1H-benzimidazol-2-yl)-6-chloroquinolin-2(1H)-one | 460.9 |
| 454 | 4-{[2-(2-aminoethoxy)benzyl]amino}-3-(1H-benzimidazol-2-yl)-6-chloroquinolin-2(1H)-one | 460.9 |
| 455 | 4-(1-azabicyclo[2.2.2]oct-3-ylamino)-3-(5-hydroxy-1H-benzimidazol-2-yl)quinolin-2(1H)-one | 402.5 |
| 456 | 4-[(3S)-1-azabicyclo[2.2.2]oct-3-ylamino]-3-(1H-benzimidazol-2-yl)-2-oxo-1,2-dihydroquinoline-6-carbonitrile | 411.5 |
| 457 | 4-[(3R)-1-azabicyclo[2.2.2]oct-3-ylamino]-3-(1H-benzimidazol-2-yl)-6,7-dihydroxyquinolin-2(1H)-one | 418.5 |
| 458 | 4-[(3S)-1-azabicyclo[2.2.2]oct-3-ylamino]-3-(1H-benzimidazol-2-yl)-6,7-dihydroxyquinolin-2(1H)-one | 418.5 |
| 459 | 4-[(3R)-1-azabicyclo[2.2.2]oct-3-ylamino]-3-(1H-benzimidazol-2-yl)-2-oxo-1,2-dihydroquinoline-6-carboxylic acid | 430.5 |
| 460 | 4-[(3R)-1-azabicyclo[2.2.2]oct-3-ylamino]-3-(1H-benzimidazol-2-yl)-7-fluoroquinolin-2(1H)-one | 404.5 |
| 461 | 4-[(3S)-1-azabicyclo[2.2.2]oct-3-ylamino]-3-(1H-benzimidazol-2-yl)-7-fluoroquinolin-2(1H)-one | 404.5 |
| 462 | 2-(4-amino-2-oxo-1-propyl-1,2-dihydroquinolin-3-yl)-1H-benzimidazole-6-carbonitrile | 344.4 |
| 463 | tert-butyl 4-[4-[(3R)-1-azabicyclo[2.2.2]oct-3-ylamino]-3-(1H-benzimidazol-2-yl)-2-oxo-1,2-dihydroquinolin-6-yl]-3,6-dihydropyridine-1(2H)-carboxylate | 567.7 |
| 464 | tert-butyl 4-[4-[(3S)-1-azabicyclo[2.2.2]oct-3-ylamino]-3-(1H-benzimidazol-2-yl)-2-oxo-1,2-dihydroquinolin-6-yl]-3,6-dihydropyridine-1(2H)-carboxylate | 567.7 |
| 465 | 4-[(3R)-1-azabicyclo[2.2.2]oct-3-ylamino]-3-(1H-benzimidazol-2-yl)-6-(1,2,3,6-tetrahydropyridin-4-yl)quinolin-2(1H)-one | 467.6 |
| 466 | 4-[(3S)-1-azabicyclo[2.2.2]oct-3-ylamino]-3-(1H-benzimidazol-2-yl)-6-thien-2-ylquinolin-2(1H)-one | 468.6 |
| 467 | 4-[(3S)-1-azabicyclo[2.2.2]oct-3-ylamino]-3-(1H-benzimidazol-2-yl)-6-(1,2,3,6-tetrahydropyridin-4-yl)quinolin-2(1H)-one | 467.6 |
| 468 | 4-[(3S)-1-azabicyclo[2.2.2]oct-3-ylamino]-3-(1H-benzimidazol-2-yl)-6-(2,4-difluorophenyl)quinolin-2(1H)-one | 498.5 |
| 469 | tert-butyl 2-[4-[(3S)-1-azabicyclo[2.2.2]oct-3-ylamino]-3-(1H-benzimidazol-2-yl)-2-oxo-1,2-dihydroquinolin-6-yl]-1H-pyrrole-1-carboxylate | 551.7 |
| 470 | tert-butyl 2-[4-[(3R)-1-azabicyclo[2.2.2]oct-3-ylamino]-3-(1H-benzimidazol-2-yl)-2-oxo-1,2-dihydroquinolin-6-yl]-1H-pyrrole-1-carboxylate | 551.7 |
| 471 | 4-[(3S)-1-azabicyclo[2.2.2]oct-3-ylamino]-3-(1H-benzimidazol-2-yl)-6-pyridin-2-ylquinolin-2(1H)-one | 463.6 |
| 472 | 4-[(3R)-1-azabicyclo[2.2.2]oct-3-ylamino]-3-(1H-benzimidazol-2-yl)-6-thien-2-ylquinolin-2(1H)-one | 468.6 |
| 473 | 4-[(3R)-1-azabicyclo[2.2.2]oct-3-ylamino]-3-(1H-benzimidazol-2-yl)-6-(2,4-difluorophenyl)quinolin-2(1H)-one | 498.5 |
| 474 | 4-[(3R)-1-azabicyclo[2.2.2]oct-3-ylamino]-3-(1H-benzimidazol-2-yl)-6-thien-3-ylquinolin-2(1H)-one | 468.6 |
| 475 | 4-[4-[(3S)-1-azabicyclo[2.2.2]oct-3-ylamino]-3-(1H-benzimidazol-2-yl)-2-oxo-1,2-dihydroquinolin-6-yl]benzonitrile | 487.6 |

TABLE 3-continued

Table of Examples 339-1273.

| Example | Name | LC/MS m/z (MH+) |
|---|---|---|
| 476 | 4-[(3R)-1-azabicyclo[2.2.2]oct-3-ylamino]-3-(1H-benzimidazol-2-yl)-6-(2-chlorophenyl)quinolin-2(1H)-one | 497.0 |
| 477 | 4-[(3R)-1-azabicyclo[2.2.2]oct-3-ylamino]-3-(1H-benzimidazol-2-yl)-6-[2-(trifluoromethyl)phenyl]quinolin-2(1H)-one | 530.6 |
| 478 | 4-[(3R)-1-azabicyclo[2.2.2]oct-3-ylamino]-3-(1H-benzimidazol-2-yl)-6-(3-methoxyphenyl)quinolin-2(1H)-one | 492.6 |
| 479 | 4-[(3S)-1-azabicyclo[2.2.2]oct-3-ylamino]-3-(1H-benzimidazol-2-yl)-6-pyridin-3-ylquinolin-2(1H)-one | 463.6 |
| 480 | 4-[(3S)-1-azabicyclo[2.2.2]oct-3-ylamino]-3-(1H-benzimidazol-2-yl)-6-pyridin-4-ylquinolin-2(1H)-one | 463.6 |
| 481 | 4-[(3S)-1-azabicyclo[2.2.2]oct-3-ylamino]-3-(1H-benzimidazol-2-yl)-2-oxo-1,2-dihydroquinoline-6-carboxylic acid | 430.5 |
| 482 | 3-(5-hydroxy-1H-benzimidazol-2-yl)-4-(piperidin-3-ylamino)quinolin-2(1H)-one | 376.4 |
| 483 | 4-[(3S)-1-azabicyclo[2.2.2]oct-3-ylamino]-3-(1H-benzimidazol-2-yl)-8-methylquinolin-2(1H)-one | 400.5 |
| 484 | 4-[(3S)-1-azabicyclo[2.2.2]oct-3-ylamino]-3-(1H-benzimidazol-2-yl)-6-(2-chlorophenyl)quinolin-2(1H)-one | 497.0 |
| 485 | 4-[(3S)-1-azabicyclo[2.2.2]oct-3-ylamino]-3-(1H-benzimidazol-2-yl)-6-[2-(trifluoromethyl)phenyl]quinolin-2(1H)-one | 530.6 |
| 486 | 4-[4-[(3S)-1-azabicyclo[2.2.2]oct-3-ylamino]-3-(1H-benzimidazol-2-yl)-2-oxo-1,2-dihydroquinolin-6-yl]benzonitrile | 487.6 |
| 487 | 4-[(3S)-1-azabicyclo[2.2.2]oct-3-ylamino]-3-(1H-benzimidazol-2-yl)-6-thien-3-ylquinolin-2(1H)-one | 468.6 |
| 488 | 4-[(3R)-1-azabicyclo[2.2.2]oct-3-ylamino]-3-(1H-benzimidazol-2-yl)-6-pyridin-4-ylquinolin-2(1H)-one | 463.6 |
| 489 | 4-[(3R)-1-azabicyclo[2.2.2]oct-3-ylamino]-3-(1H-benzimidazol-2-yl)-6-(2-methoxyphenyl)quinolin-2(1H)-one | 492.6 |
| 490 | 4-[(3R)-1-azabicyclo[2.2.2]oct-3-ylamino]-3-(1H-benzimidazol-2-yl)-6-(2-methylphenyl)quinolin-2(1H)-one | 476.6 |
| 491 | 6-(3-acetylphenyl)-4-[(3R)-1-azabicyclo[2.2.2]oct-3-ylamino]-3-(1H-benzimidazol-2-yl)quinolin-2(1H)-one | 504.6 |
| 492 | 6-(4-acetylphenyl)-4-[(3R)-1-azabicyclo[2.2.2]oct-3-ylamino]-3-(1H-benzimidazol-2-yl)quinolin-2(1H)-one | 504.6 |
| 493 | 4-[4-[(3R)-1-azabicyclo[2.2.2]oct-3-ylamino]-3-(1H-benzimidazol-2-yl)-2-oxo-1,2-dihydroquinolin-6-yl]benzoic acid | 506.6 |
| 494 | N-{3-[4-[(3R)-1-azabicyclo[2.2.2]oct-3-ylamino]-3-(1H-benzimidazol-2-yl)-2-oxo-1,2-dihydroquinolin-6-yl]phenyl}acetamide | 519.6 |
| 495 | 4-[(3R)-1-azabicyclo[2.2.2]oct-3-ylamino]-3-(1H-benzimidazol-2-yl)-6-(2,6-difluorophenyl)quinolin-2(1H)-one | 498.5 |
| 496 | 4-[(3R)-1-azabicyclo[2.2.2]oct-3-ylamino]-3-(1H-benzimidazol-2-yl)-6-(1,3-benzodioxol-5-yl)quinolin-2(1H)-one | 506.6 |
| 497 | 4-[(3R)-1-azabicyclo[2.2.2]oct-3-ylamino]-3-(1H-benzimidazol-2-yl)-6-(4-chlorophenyl)quinolin-2(1H)-one | 497.0 |
| 498 | 4-[4-[(3R)-1-azabicyclo[2.2.2]oct-3-ylamino]-3-(1H-benzimidazol-2-yl)-2-oxo-1,2-dihydroquinolin-6-yl]benzaldehyde | 490.6 |
| 499 | 4-[(3R)-1-azabicyclo[2.2.2]oct-3-ylamino]-3-(1H-benzimidazol-2-yl)-6-[4-(methylthio)phenyl]quinolin-2(1H)-one | 508.7 |
| 500 | 4-[(3R)-1-azabicyclo[2.2.2]oct-3-ylamino]-3-(1H-benzimidazol-2-yl)-6-[4-(dimethylamino)phenyl]quinolin-2(1H)-one | 505.6 |
| 501 | 4-[(3R)-1-azabicyclo[2.2.2]oct-3-ylamino]-3-(1H-benzimidazol-2-yl)-6-(4-chloro-2-fluorophenyl)quinolin-2(1H)-one | 515.0 |
| 502 | 4-[(3R)-1-azabicyclo[2.2.2]oct-3-ylamino]-3-(1H-benzimidazol-2-yl)-6-(2,4-dichlorophenyl)quinolin-2(1H)-one | 531.5 |
| 503 | 4-[(3R)-1-azabicyclo[2.2.2]oct-3-ylamino]-3-(1H-benzimidazol-2-yl)-6-phenylquinolin-2(1H)-one | 462.6 |
| 504 | 3-(1H-benzimidazol-2-yl)-6-chloro-4-[(1-ethylpiperidin-3-yl)amino]quinolin-2(1H)-one | 422.9 |

TABLE 3-continued

Table of Examples 339-1273.

| Example | Name | LC/MS m/z (MH+) |
|---|---|---|
| 505 | 1-[4-[(3R)-1-azabicyclo[2.2.2]oct-3-ylamino]-3-(1H-benzimidazol-2-yl)-6-fluoro-2-oxo-1,2-dihydroquinolin-7-yl]piperidine-4-carboxamide | 530.6 |
| 506 | ethyl 1-[4-[(3R)-1-azabicyclo[2.2.2]oct-3-ylamino]-3-(1H-benzimidazol-2-yl)-6-fluoro-2-oxo-1,2-dihydroquinolin-7-yl]piperidine-4-carboxylate | 559.7 |
| 507 | 1-[4-[(3R)-1-azabicyclo[2.2.2]oct-3-ylamino]-3-(1H-benzimidazol-2-yl)-6-fluoro-2-oxo-1,2-dihydroquinolin-7-yl]piperidine-3-carboxamide | 530.6 |
| 508 | ethyl 1-[4-[(3R)-1-azabicyclo[2.2.2]oct-3-ylamino]-3-(1H-benzimidazol-2-yl)-6-fluoro-2-oxo-1,2-dihydroquinolin-7-yl]piperidine-3-carboxylate | 559.7 |
| 509 | 4-[(3R)-1-azabicyclo[2.2.2]oct-3-ylamino]-3-(1H-benzimidazol-2-yl)-6-fluoro-7-(1H-imidazol-1-yl)quinolin-2(1H)-one | 470.5 |
| 510 | 4-[(3R)-1-azabicyclo[2.2.2]oct-3-ylamino]-3-(1H-benzimidazol-2-yl)-7-{[2-(dimethylamino)ethyl]amino}-6-fluoroquinolin-2(1H)-one | 490.6 |
| 511 | 4-[(3R)-1-azabicyclo[2.2.2]oct-3-ylamino]-3-(1H-benzimidazol-2-yl)-6-fluoro-7-morpholin-4-ylquinolin-2(1H)-one | 489.6 |
| 512 | 4-[(3R)-1-azabicyclo[2.2.2]oct-3-ylamino]-3-(1H-benzimidazol-2-yl)-7-(dimethylamino)-6-fluoroquinolin-2(1H)-one | 447.5 |
| 513 | 4-[(3R)-1-azabicyclo[2.2.2]oct-3-ylamino]-3-(1H-benzimidazol-2-yl)-7-bromoquinolin-2(1H)-one | 465.4 |
| 514 | 1-[4-[(3R)-1-azabicyclo[2.2.2]oct-3-ylamino]-3-(1H-benzimidazol-2-yl)-6-fluoro-2-oxo-1,2-dihydroquinolin-7-yl]piperidine-4-carboxylic acid | 531.6 |
| 515 | 1-[4-[(3R)-1-azabicyclo[2.2.2]oct-3-ylamino]-3-(1H-benzimidazol-2-yl)-6-fluoro-2-oxo-1,2-dihydroquinolin-7-yl]piperidine-3-carboxylic acid | 531.6 |
| 516 | methyl 4-[4-[(3R)-1-azabicyclo[2.2.2]oct-3-ylamino]-3-(1H-benzimidazol-2-yl)-2-oxo-1,2-dihydroquinolin-6-yl]benzoate | 520.6 |
| 517 | 4-[4-[(3R)-1-azabicyclo[2.2.2]oct-3-ylamino]-3-(1H-benzimidazol-2-yl)-7-chloro-2-oxo-1,2-dihydroquinolin-6-yl]benzamide | 505.6 |
| 518 | 4-[(3R)-1-azabicyclo[2.2.2]oct-3-ylamino]-3-(1H-benzimidazol-2-yl)-6-[4-(methylsulfonyl)phenyl]quinolin-2(1H)-one | 540.7 |
| 519 | methyl 3-amino-4-[4-[(3R)-1-azabicyclo[2.2.2]oct-3-ylamino]-3-(1H-benzimidazol-2-yl)-2-oxo-1,2-dihydroquinolin-6-yl]benzoate | 535.6 |
| 520 | 4-[4-[(3R)-1-azabicyclo[2.2.2]oct-3-ylamino)-3-(1H-benzimidazol-2-yl)-7-chloro-2-oxo-1,2-dihydroquinolin-6-yl]benzoic acid | 541.0 |
| 521 | N-{3-[4-[(3R)-1-azabicyclo[2.2.2]oct-3-ylamino]-3-(1H-benzimidazol-2-yl)-7-chloro-2-oxo-1,2-dihydroquinolin-6-yl]phenyl}acetamide | 554.1 |
| 522 | 6-(3-acetylphenyl)-4-[(3R)-1-azabicyclo[2.2.2]oct-3-ylamino]-3-(1H-benzimidazol-2-yl)-7-chloroquinolin-2(1H)-one | 539.0 |
| 523 | 4-[(3R)-1-azabicyclo[2.2.2]oct-3-ylamino]-3-(1H-benzimidazol-2-yl)-7-chloro-6-(2-methoxyphenyl)quinolin-2(1H)-one | 527.0 |
| 524 | 4-[(3R)-1-azabicyclo[2.2.2]oct-3-ylamino]-3-(1H-benzimidazol-2-yl)-7-chloro-6-(2,4-dichlorophenyl)quinolin-2(1H)-one | 565.9 |
| 525 | 6-(4-acetylphenyl)-4-[(3R)-1-azabicyclo[2.2.2]oct-3-ylamino]-3-(1H-benzimidazol-2-yl)-7-chloroquinolin-2(1H)-one | 539.0 |
| 526 | 4-[4-[(3R)-1-azabicyclo[2.2.2]oct-3-ylamino]-3-(1H-benzimidazol-2-yl)-7-chloro-2-oxo-1,2-dihydroquinolin-6-yl]benzamide | 540.0 |
| 527 | methyl 4-[4-[(3R)-1-azabicyclo[2.2.2]oct-3-ylamino]-3-(1H-benzimidazol-2-yl)-7-chloro-2-oxo-1,2-dihydroquinolin-6-yl]benzoate | 555.0 |
| 528 | 4-[(3R)-1-azabicyclo[2.2.2]oct-3-ylamino]-3-(1H-benzimidazol-2-yl)-7-[[2-(dimethylamino)ethyl](methyl)amino]-6-fluoroquinolin-2(1H)-one | 504.6 |

TABLE 3-continued

Table of Examples 339-1273.

| Example | Name | LC/MS m/z (MH+) |
|---|---|---|
| 529 | 4-[(3R)-1-azabicyclo[2.2.2]oct-3-ylamino]-3-(1H-benzimidazol-2-yl)-6-fluoro-7-[(3-methoxypropyl)amino]quinolin-2(1H)-one | 491.6 |
| 530 | N-{(3R)-1-[4-[(3R)-1-azabicyclo[2.2.2]oct-3-ylamino]-3-(1H-benzimidazol-2-yl)-6-fluoro-2-oxo-1,2-dihydroquinolin-7-yl]pyrrolidin-3-yl}acetamide | 530.6 |
| 531 | 4-[(3R)-1-azabicyclo[2.2.2]oct-3-ylamino]-3-(1H-benzimidazol-2-yl)-6-fluoro-7-{[3-(2-oxopyrrolidin-1-yl)propyl]amino}quinolin-2(1H)-one | 544.6 |
| 532 | 4-[(3R)-1-azabicyclo[2.2.2]oct-3-ylamino]-7-azepan-1-yl-3-(1H-benzimidazol-2-yl)-6-fluoroquinolin-2(1H)-one | 501.6 |
| 533 | 4-[(3R)-1-azabicyclo[2.2.2]oct-3-ylamino]-3-(1H-benzimidazol-2-yl)-6-fluoro-7-(1H-pyrrol-1-yl)quinolin-2(1H)-one | 469.5 |
| 534 | 4-[(3R)-1-azabicyclo[2.2.2]oct-3-ylamino]-3-(1H-benzimidazol-2-yl)-6-fluoro-7-(2-methyl-1H-imidazol-1-yl)quinolin-2(1H)-one | 484.5 |
| 535 | 4-[(3R)-1-azabicyclo[2.2.2]oct-3-ylamino]-3-(1H-benzimidazol-2-yl)-6-fluoro-7-pyrrolidin-1-ylquinolin-2(1H)-one | 473.6 |
| 536 | 4-[(3R)-1-azabicyclo[2.2.2]oct-3-ylamino]-3-(1H-benzimidazol-2-yl)-6-fluoro-7-piperidin-1-ylquinolin-2(1H)-one | 487.6 |
| 537 | 4-[(3R)-1-azabicyclo[2.2.2]oct-3-ylamino]-3-(1H-benzimidazol-2-yl)-6-fluoro-7-(4-methylpiperazin-1-yl)quinolin-2(1H)-one | 502.6 |
| 538 | 4-[(3R)-1-azabicyclo[2.2.2]oct-3-ylamino]-3-(1H-benzimidazol-2-yl)-6-fluoro-7-[(3-hydroxypropyl)amino]quinolin-2(1H)-one | 477.6 |
| 539 | 4-[(3R)-1-azabicyclo[2.2.2]oct-3-ylamino]-3-(1H-benzimidazol-2-yl)-6-chloro-7-morpholin-4-ylquinolin-2(1H)-one | 506.0 |
| 540 | 4-[(3R)-1-azabicyclo[2.2.2]oct-3-ylamino]-3-(1H-benzimidazol-2-yl)-6-chloro-7-(4-methylpiperazin-1-yl)quinolin-2(1H)-one | 519.1 |
| 541 | 4-[(3R)-1-azabicyclo[2.2.2]oct-3-ylamino]-3-(1H-benzimidazol-2-yl)-6-chloro-7-piperidin-1-ylquinolin-2(1H)-one | 504.0 |
| 542 | 4-[4-[(3R)-1-azabicyclo[2.2.2]oct-3-ylamino]-3-(1H-benzimidazol-2-yl)-2-oxo-1,2-dihydroquinolin-7-yl]benzoic acid | 506.6 |
| 543 | 4-[(3R)-1-azabicyclo[2.2.2]oct-3-ylamino)-3-(1H-benzimidazol-2-yl)-7-(2,4-dichlorophenyl)quinolin-2(1H)-one | 531.5 |
| 544 | 4-[(3R)-1-azabicyclo[2.2.2]oct-3-ylamino)-3-(1H-benzimidazol-2-yl)-7-(dimethylamino)quinolin-2(1H)-one | 429.5 |
| 545 | 7-(4-acetylphenyl)-4-[(3R)-1-azabicyclo[2.2.2]oct-3-ylamino]-3-(1H-benzimidazol-2-yl)quinolin-2(1H)-one | 504.6 |
| 546 | 4-[(3R)-1-azabicyclo[2.2.2]oct-3-ylamino]-3-(1H-benzimidazol-2-yl)-7-(2-methylphenyl)quinolin-2(1H)-one | 476.6 |
| 547 | 7-(3-acetylphenyl)-4-[(3R)-1-azabicyclo[2.2.2]oct-3-ylamino]-3-(1H-benzimidazol-2-yl)quinolin-2(1H)-one | 504.6 |
| 548 | 4-[(3R)-1-azabicyclo[2.2.2]oct-3-ylamino]-3-(1H-benzimidazol-2-yl)-7-(2-methoxyphenyl)quinolin-2(1H)-one | 492.6 |
| 549 | 3-(1H-benzimidazol-2-yl)-6,7-difluoro-4-[(piperidin-2-ylmethyl)amino]quinolin-2(1H)-one | 410.4 |
| 550 | N-[3-(1H-benzimidazol-2-yl)-6,7-difluoro-2-oxo-1,2-dihydroquinolin-4-yl]glycine | 371.3 |
| 551 | N-[3-(1H-benzimidazol-2-yl)-6,7-difluoro-2-oxo-1,2-dihydroquinolin-4-yl]-beta-alanine | 385.3 |
| 552 | 4-[(3S)-1-azabicyclo[2.2.2]oct-3-ylamino]-3-(6-fluoro-1H-benzimidazol-2-yl)-6,7-dimethoxyquinolin-2(1H)-one | 464.5 |
| 553 | 3-(6-fluoro-1H-benzimidazol-2-yl)-6,7-dimethoxy-4-(piperidin-3-ylamino)quinolin-2(1H)-one | 438.5 |
| 554 | 3-(6-fluoro-1H-benzimidazol-2-yl)-6,7-dimethoxy-4-(pyrrolidin-3-ylamino)quinolin-2(1H)-one | 424.4 |
| 555 | 4-[(4-aminocyclohexyl)amino]-3-(6-fluoro-1H-benzimidazol-2-yl)-6,7-dimethoxyquinolin-2(1H)-one | 452.5 |
| 556 | 4-[(3R)-1-azabicyclo[2.2.2]oct-3-ylamino]-3-(6-fluoro-1H-benzimidazol-2-yl)-6,7-dimethoxyquinolin-2(1H)-one | 464.5 |

TABLE 3-continued

Table of Examples 339-1273.

| Example | Name | LC/MS m/z (MH+) |
|---|---|---|
| 557 | 4-[(3R)-1-azabicyclo[2.2.2]oct-3-ylamino]-3-(1H-benzimidazol-2-yl)-7-[ethyl(methyl)amino]-6-fluoroquinolin-2(1H)-one | 461.6 |
| 558 | 4-[(3R)-1-azabicyclo[2.2.2]oct-3-ylamino]-3-(1H-benzimidazol-2-yl)-7-(diethylamino)-6-fluoroquinolin-2(1H)-one | 475.6 |
| 559 | 4-[(3R)-1-azabicyclo[2.2.2]oct-3-ylamino]-3-(1H-benzimidazol-2-yl)-7-[(3R)-3-(dimethylamino)pyrrolidin-1-yl]-6-fluoroquinolin-2(1H)-one | 516.6 |
| 560 | 7-(3-acetyl-1H-pyrrol-1-yl)-4-[(3R)-1-azabicyclo[2.2.2]oct-3-ylamino]-3-(1H-benzimidazol-2-yl)-6-fluoroquinolin-2(1H)-one | 511.6 |
| 561 | ethyl 4-[4-[(3R)-1-azabicyclo[2.2.2]oct-3-ylamino]-3-(1H-benzimidazol-2-yl)-2-oxo-1,2-dihydroquinolin-6-yl]benzoate | 534.6 |
| 562 | methyl 3-[4-[(3R)-1-azabicyclo[2.2.2]oct-3-ylamino]-3-(1H-benzimidazol-2-yl)-2-oxo-1,2-dihydroquinolin-6-yl]benzoate | 520.6 |
| 563 | 4-[(3R)-1-azabicyclo[2.2.2]oct-3-ylamino]-3-(1H-benzimidazol-2-yl)-7-{[2-(diethylamino)ethyl]amino}-6-fluoroquinolin-2(1H)-one | 518.6 |
| 564 | 4-[(3R)-1-azabicyclo[2.2.2]oct-3-ylamino]-3-(1H-benzimidazol-2-yl)-6-fluoro-7-[(2-pyrrolidin-1-ylethyl)amino]quinolin-2(1H)-one | 516.6 |
| 565 | 4-[(3R)-1-azabicyclo[2.2.2]oct-3-ylamino]-3-(1H-benzimidazol-2-yl)-6-fluoro-7-[(2-piperidin-1-ylethyl)amino]quinolin-2(1H)-one | 530.7 |
| 566 | 4-[(3R)-1-azabicyclo[2.2.2]oct-3-ylamino]-3-(1H-benzimidazol-2-yl)-7-{[3-(dimethylamino)propyl]amino}-6-fluoroquinolin-2(1H)-one | 504.6 |
| 567 | N-(2-{[4-[(3R)-1-azabicyclo[2.2.2]oct-3-ylamino]-3-(1H-benzimidazol-2-yl)-6-fluoro-2-oxo-1,2-dihydroquinolin-7-yl]amino}ethyl)acetamide | 504.6 |
| 568 | N-{1-[4-[(3R)-1-azabicyclo[2.2.2]oct-3-ylamino]-3-(1H-benzimidazol-2-yl)-6-fluoro-2-oxo-1,2-dihydroquinolin-7-yl]pyrrolidin-3-yl}-2,2,2-trifluoroacetamide | 584.6 |
| 569 | 3-{[4-[(3R)-1-azabicyclo[2.2.2]oct-3-ylamino]-3-(1H-benzimidazol-2-yl)-6-fluoro-2-oxo-1,2-dihydroquinolin-7-yl]amino}propanenitrile | 472.5 |
| 570 | 4-[(3R)-1-azabicyclo[2.2.2]oct-3-ylamino]-3-(1H-benzimidazol-2-yl)-6-fluoro-7-[(2-hydroxyethyl)amino]quinolin-2(1H)-one | 463.5 |
| 571 | 4-[(3R)-1-azabicyclo[2.2.2]oct-3-ylamino]-3-(1H-benzimidazol-2-yl)-6-fluoro-7-[(2-methoxyethyl)amino]quinolin-2(1H)-one | 477.6 |
| 572 | 4-[(3R)-1-azabicyclo[2.2.2]oct-3-ylamino]-3-(1H-benzimidazol-2-yl)-6-fluoro-7-(3-hydroxypiperidin-1-yl)quinolin-2(1H)-one | 503.6 |
| 573 | 4-[(3S)-1-azabicyclo[2.2.2]oct-3-ylamino]-3-(1H-benzimidazol-2-yl)-7-[[2-(dimethylamino)ethyl](methyl)amino]-6-fluoroquinolin-2(1H)-one | 504.6 |
| 574 | 4-[(3S)-1-azabicyclo[2.2.2]oct-3-ylamino]-3-(1H-benzimidazol-2-yl)-7-{[3-(dimethylamino)propyl]amino}-6-fluoroquinolin-2(1H)-one | 504.6 |
| 575 | 4-[(3S)-1-azabicyclo[2.2.2]oct-3-ylamino]-3-(1H-benzimidazol-2-yl)-7-{[2-(diethylamino)ethyl]amino}-6-fluoroquinolin-2(1H)-one | 518.6 |
| 576 | 4-[(3S)-1-azabicyclo[2.2.2]oct-3-ylamino]-3-(1H-benzimidazol-2-yl)-6-fluoro-7-[(2-pyrrolidin-1-ylethyl)amino]quinolin-2(1H)-one | 516.6 |
| 577 | 4-[(3S)-1-azabicyclo[2.2.2]oct-3-ylamino]-3-(1H-benzimidazol-2-yl)-6-fluoro-7-(3-hydroxypiperidin-1-yl)quinolin-2(1H)-one | 530.7 |
| 578 | 4-[(3S)-1-azabicyclo[2.2.2]oct-3-ylamino]-3-(1H-benzimidazol-2-yl)-6-fluoro-7-{[3-(2-oxopyrrolidin-1-yl)propyl]amino}quinolin-2(1H)-one | 544.6 |
| 579 | N-(2-{[4-[(3S)-1-azabicyclo[2.2.2]oct-3-ylamino]-3-(1H-benzimidazol-2-yl)-6-fluoro-2-oxo-1,2-dihydroquinolin-7-yl]amino}ethyl)acetamide | 504.6 |
| 580 | 4-[(3S)-1-azabicyclo[2.2.2]oct-3-ylamino]-3-(1H-benzimidazol-2-yl)-6-fluoro-7-[(3-methoxypropyl)amino]quinolin-2(1H)-one | 491.6 |

TABLE 3-continued

Table of Examples 339-1273.

| Example | Name | LC/MS m/z (MH+) |
|---|---|---|
| 581 | 4-[(3S)-1-azabicyclo[2.2.2]oct-3-ylamino]-3-(1H-benzimidazol-2-yl)-6-fluoro-7-[(2-methoxyethyl)amino]quinolin-2(1H)-one | 477.6 |
| 582 | 4-[(3S)-1-azabicyclo[2.2.2]oct-3-ylamino]-3-(1H-benzimidazol-2-yl)-6-fluoro-7-[(2-hydroxyethyl)amino]quinolin-2(1H)-one | 463.5 |
| 583 | 4-[(3S)-1-azabicyclo[2.2.2]oct-3-ylamino]-3-(1H-benzimidazol-2-yl)-7-[ethyl(methyl)amino]-6-fluoroquinolin-2(1H)-one | 461.6 |
| 584 | 4-[(3S)-1-azabicyclo[2.2.2]oct-3-ylamino]-3-(1H-benzimidazol-2-yl)-7-(diethylamino)-6-fluoroquinolin-2(1H)-one | 475.6 |
| 585 | N-{(3R)-1-[4-[(3S)-1-azabicyclo[2.2.2]oct-3-ylamino]-3-(1H-benzimidazol-2-yl)-6-fluoro-2-oxo-1,2-dihydroquinolin-7-yl]pyrrolidin-3-yl}acetamide | 530.6 |
| 586 | N-{(3S)-1-[4-[(3S)-1-azabicyclo[2.2.2]oct-3-ylamino]-3-(1H-benzimidazol-2-yl)-6-fluoro-2-oxo-1,2-dihydroquinolin-7-yl]pyrrolidin-3-yl}acetamide | 530.6 |
| 587 | 4-[(3S)-1-azabicyclo[2.2.2]oct-3-ylamino]-3-(1H-benzimidazol-2-yl)-7-[(3R)-3-(dimethylamino)pyrrolidin-1-yl]-6-fluoroquinolin-2(1H)-one | 516.6 |
| 588 | N-{1-[4-[(3S)-1-azabicyclo[2.2.2]oct-3-ylamino]-3-(1H-benzimidazol-2-yl)-6-fluoro-2-oxo-1,2-dihydroquinolin-7-yl]pyrrolidin-3-yl}-2,2,2-trifluoroacetamide | 584.6 |
| 589 | 4-[(3S)-1-azabicyclo[2.2.2]oct-3-ylamino]-7-azepan-1-yl-3-(1H-benzimidazol-2-yl)-6-fluoroquinolin-2(1H)-one | 501.6 |
| 590 | 4-[(3S)-1-azabicyclo[2.2.2]oct-3-ylamino]-3-(1H-benzimidazol-2-yl)-6-fluoro-7-(3-hydroxypiperidin-1-yl)quinolin-2(1H)-one | 503.6 |
| 591 | 3-{[4-[(3S)-1-azabicyclo[2.2.2]oct-3-ylamino]-3-(1H-benzimidazol-2-yl)-6-fluoro-2-oxo-1,2-dihydroquinolin-7-yl]amino}propanenitrile | 472.5 |
| 592 | 4-[(3S)-1-azabicyclo[2.2.2]oct-3-ylamino]-3-(1H-benzimidazol-2-yl)-6-fluoro-7-(1H-pyrrol-1-yl)quinolin-2(1H)-one | 469.5 |
| 593 | 7-(3-acetyl-1H-pyrrol-1-yl)-4-[(3S)-1-azabicyclo[2.2.2]oct-3-ylamino]-3-(1H-benzimidazol-2-yl)-6-fluoroquinolin-2(1H)-one | 511.6 |
| 594 | 4-[(3S)-1-azabicyclo[2.2.2]oct-3-ylamino]-3-(1H-benzimidazol-2-yl)-6-fluoro-7-(2-methyl-1H-imidazol-1-yl)quinolin-2(1H)-one | 484.5 |
| 595 | 4-[(3S)-1-azabicyclo[2.2.2]oct-3-ylamino]-3-(1H-benzimidazol-2-yl)-7-[(3S)-3-(dimethylamino)pyrrolidin-1-yl]-6-fluoroquinolin-2(1H)-one | 516.6 |
| 596 | 4-[(3S)-1-azabicyclo[2.2.2]oct-3-ylamino]-3-(1H-benzimidazol-2-yl)-6-fluoro-7-methoxyquinolin-2(1H)-one | 434.5 |
| 597 | 4-[(3R)-1-azabicyclo[2.2.2]oct-3-ylamino]-3-(1H-benzimidazol-2-yl)-7-[(3S)-3-(dimethylamino)pyrrolidin-1-yl]-6-fluoroquinolin-2(1H)-one | 516.6 |
| 598 | N-{(3S)-1-[4-[(3R)-1-azabicyclo[2.2.2]oct-3-ylamino]-3-(1H-benzimidazol-2-yl)-6-fluoro-2-oxo-1,2-dihydroquinolin-7-yl]pyrrolidin-3-yl}acetamide | 530.6 |
| 599 | 4-[(3R)-1-azabicyclo[2.2.2]oct-3-ylamino]-3-(1H-benzimidazol-2-yl)-6-fluoro-7-[(2-pyridin-2-ylethyl)amino]quinolin-2(1H)-one | 524.6 |
| 600 | 4-[(3R)-1-azabicyclo[2.2.2]oct-3-ylamino]-3-(1H-benzimidazol-2-yl)-6-fluoro-7-(isobutylamino)quinolin-2(1H)-one | 475.6 |
| 601 | methyl 3-amino-4-[4-[(3R)-1-azabicyclo[2.2.2]oct-3-ylamino]-3-(1H-benzimidazol-2-yl)-7-chloro-2-oxo-1,2-dihydroquinolin-6-yl]benzoate | 570.1 |
| 602 | 4-[(3R)-1-azabicyclo[2.2.2]oct-3-ylamino]-3-(1H-benzimidazol-2-yl)-7-chloro-6-[4-(methylsulfonyl)phenyl]quinolin-2(1H)-one | 575.1 |
| 603 | methyl 3-(4-[(3R)-1-azabicyclo[2.2.2]oct-3-ylamino]-3-(1H-benzimidazol-2-yl)-7-chloro-2-oxo-1,2-dihydroquinolin-6-yl)benzoate | 555.0 |
| 604 | 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-4-carboxylic acid | 531.6 |
| 605 | 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-3-carboxylic acid | 531.6 |

TABLE 3-continued

Table of Examples 339-1273.

| Example | Name | LC/MS m/z (MH+) |
|---|---|---|
| 606 | 4-[(4-aminobenzyl)amino]-3-(1H-benzimidazol-2-yl)-6,7-dimethoxyquinolin-2(1H)-one | 442.5 |
| 607 | 4-(2-{[3-(1H-benzimidazol-2-yl)-6,7-dimethoxy-2-oxo-1,2-dihydroquinolin-4-yl]amino}ethyl)benzenesulfonamide | 520.6 |
| 608 | 4-[(3-aminopropyl)amino]-3-(1H-benzimidazol-2-yl)-6,7-dimethoxyquinolin-2(1H)-one | 394.4 |
| 609 | 4-[(2-aminoethyl)amino]-3-(1H-benzimidazol-2-yl)-6,7-dimethoxyquinolin-2(1H)-one | 380.4 |
| 610 | 3-(1H-benzimidazol-2-yl)-4-{[2-(1H-imidazol-5-yl)ethyl]amino}-6,7-dimethoxyquinolin-2(1H)-one | 431.5 |
| 611 | 3-(1H-benzimidazol-2-yl)-4-{[2-(1H-benzimidazol-2-yl)ethyl]amino}-6,7-dimethoxyquinolin-2(1H)-one | 481.5 |
| 612 | 4-{[(4-amino-2-methylpyrimidin-5-yl)methyl]amino}-3-(1H-benzimidazol-2-yl)-6,7-dimethoxyquinolin-2(1H)-one | 458.5 |
| 613 | 3-(1H-benzimidazol-2-yl)-4-{[2-(5-fluoro-1H-indol-3-yl)ethyl]amino}-6,7-dimethoxyquinolin-2(1H)-one | 498.5 |
| 614 | 4-{[2-(4-aminophenyl)ethyl]amino}-3-(1H-benzimidazol-2-yl)-6,7-dimethoxyquinolin-2(1H)-one | 456.5 |
| 615 | 4-[(3R)-1-azabicyclo[2.2.2]oct-3-ylamino]-3-(1H-benzimidazol-2-yl)-7-morpholin-4-ylquinolin-2(1H)-one | 471.6 |
| 616 | 4-[(3R)-1-azabicyclo[2.2.2]oct-3-ylamino]-3-(5,6-difluoro-1H-benzimidazol-2-yl)-6,7-dimethoxyquinolin-2(1H)-one | 430.5 |
| 617 | methyl 3-amino-4-[4-[(3R)-1-azabicyclo[2.2.2]oct-3-ylamino]-3-(1H-benzimidazol-2-yl)-2-oxo-1,2-dihydroquinolin-7-yl]benzoate | 535.6 |
| 618 | 4-[(3R)-1-azabicyclo[2.2.2]oct-3-ylamino]-3-(1H-benzimidazol-2-yl)-7-[4-(methylsulfonyl)phenyl]quinolin-2(1H)-one | 540.7 |
| 619 | methyl 4-[4-[(3R)-1-azabicyclo[2.2.2]oct-3-ylamino]-3-(1H-benzimidazol-2-yl)-2-oxo-1,2-dihydroquinolin-7-yl]benzoate | 520.6 |
| 620 | methyl 3-[4-[(3R)-1-azabicyclo[2.2.2]oct-3-ylamino]-3-(1H-benzimidazol-2-yl)-2-oxo-1,2-dihydroquinolin-7-yl]benzoate | 520.6 |
| 621 | N-{3-[4-[(3R)-1-azabicyclo[2.2.2]oct-3-ylamino]-3-(1H-benzimidazol-2-yl)-2-oxo-1,2-dihydroquinolin-7-yl]phenyl}acetamide | 519.6 |
| 622 | 4-[(3R)-1-azabicyclo[2.2.2]oct-3-ylamino]-3-(5,6-difluoro-1H-benzimidazol-2-yl)-6,7-dimethoxyquinolin-2(1H)-one | 482.5 |
| 623 | 3-(5,6-difluoro-1H-benzimidazol-2-yl)-6,7-dimethoxy-4-(piperidin-3-ylamino)quinolin-2(1H)-one | 456.5 |
| 624 | 4-[(4-aminocyclohexyl)amino]-3-(5,6-difluoro-1H-benzimidazol-2-yl)-6,7-dimethoxyquinolin-2(1H)-one | 470.5 |
| 625 | 3-(5,6-difluoro-1H-benzimidazol-2-yl)-6,7-dimethoxy-4-(pyrrolidin-3-ylamino)quinolin-2(1H)-one | 442.4 |
| 626 | 4-[(3R)-1-azabicyclo[2.2.2]oct-3-ylamino]-3-(1H-benzimidazol-2-yl)-6-chloro-7-(1H-imidazol-1-yl)quinolin-2(1H)-one | 487.0 |
| 627 | 4-[(3R)-1-azabicyclo[2.2.2]oct-3-ylamino]-3-(1H-benzimidazol-2-yl)-7-[(3-hydroxypropyl)amino]quinolin-2(1H)-one | 459.6 |
| 628 | 4-[(3R)-1-azabicyclo[2.2.2]oct-3-ylamino]-3-(1H-benzimidazol-2-yl)-7-{[3-(2-oxopyrrolidin-1-yl)propyl]amino}quinolin-2(1H)-one | 526.7 |
| 629 | 4-[(3R)-1-azabicyclo[2.2.2]oct-3-ylamino]-3-(1H-benzimidazol-2-yl)-7-(4-methylpiperazin-1-yl)quinolin-2(1H)-one | 484.6 |
| 630 | 4-[4-[(3R)-1-azabicyclo[2.2.2]oct-3-ylamino]-3-(1H-benzimidazol-2-yl)-2-oxo-1,2-dihydroquinolin-7-yl]benzonitrile | 487.6 |
| 631 | 4-[(3R)-1-azabicyclo[2.2.2]oct-3-ylamino]-3-(1H-benzimidazol-2-yl)-7-[2-(trifluoromethyl)phenyl]quinolin-2(1H)-one | 530.6 |
| 632 | 4-[(3R)-1-azabicyclo[2.2.2]oct-3-ylamino]-3-(1H-benzimidazol-2-yl)-7-(1,3-benzodioxol-5-yl)quinolin-2(1H)-one | 506.6 |
| 633 | 4-[(3R)-1-azabicyclo[2.2.2]oct-3-ylamino]-3-(1H-benzimidazol-2-yl)-7-(morpholin-4-ylcarbonyl)quinolin-2(1H)-one | 499.6 |
| 634 | 4-[(3R)-1-azabicyclo[2.2.2]oct-3-ylamino]-3-(1H-benzimidazol-2-yl)-N,N-dimethyl-2-oxo-1,2-dihydroquinoline-7-carboxamide | 457.5 |

TABLE 3-continued

Table of Examples 339-1273.

| Example | Name | LC/MS m/z (MH+) |
|---|---|---|
| 635 | 4-[(3R)-1-azabicyclo[2.2.2]oct-3-ylamino]-3-(1H-benzimidazol-2-yl)-2-oxo-1,2-dihydroquinoline-7-carboxamide | 429.5 |
| 636 | 3-[4-[(3R)-1-azabicyclo[2.2.2]oct-3-ylamino]-3-(1H-benzimidazol-2-yl)-2-oxo-1,2-dihydroquinolin-7-yl]benzoic acid | 506.6 |
| 637 | 4-[(3S)-1-azabicyclo[2.2.2]oct-3-ylamino]-3-(1H-benzimidazol-2-yl)-7-bromoquinolin-2(1H)-one | 465.4 |
| 638 | 4-{4-[(3R)-1-azabicyclo[2.2.2]oct-3-ylamino]-3-(1H-benzimidazol-2-yl)-7-[4-(ethoxycarbonyl)piperidin-1-yl]-2-oxo-1,2-dihydroquinolin-6-yl}benzoic acid | 661.8 |
| 639 | 4-[7-(3-acetyl-1H-pyrrol-1-yl)-4-[(3R)-1-azabicyclo[2.2.2]oct-3-ylamino]-3-(1H-benzimidazol-2-yl)-2-oxo-1,2-dihydroquinolin-6-yl]benzoic acid | 613.7 |
| 640 | 4-[4-[(3R)-1-azabicyclo[2.2.2]oct-3-ylamino]-3-(1H-benzimidazol-2-yl)-7-(dimethylamino)-2-oxo-1,2-dihydroquinolin-6-yl]benzoic acid | 549.6 |
| 641 | 4-[4-[(3R)-1-azabicyclo[2.2.2]oct-3-ylamino]-3-(1H-benzimidazol-2-yl)-7-(1H-imidazol-1-yl)-2-oxo-1,2-dihydroquinolin-6-yl]benzoic acid | 572.6 |
| 642 | 4-[(3R)-1-azabicyclo[2.2.2]oct-3-ylamino]-3-(1H-benzimidazol-2-yl)-7-fluoro-6-iodoquinolin-2(1H)-one | 530.4 |
| 643 | 4-[(3R)-1-azabicyclo[2.2.2]oct-3-ylamino]-3-(1H-benzimidazol-2-yl)-7-fluoro-6-[4-(methylsulfonyl)phenyl]quinolin-2(1H)-one | 558.6 |
| 644 | 4-[4-[(3R)-1-azabicyclo[2.2.2]oct-3-ylamino]-3-(1H-benzimidazol-2-yl)-7-fluoro-2-oxo-1,2-dihydroquinolin-6-yl]benzamide | 523.6 |
| 645 | 6-(4-acetylphenyl)-4-[(3R)-1-azabicyclo[2.2.2]oct-3-ylamino]-3-(1H-benzimidazol-2-yl)-7-fluoroquinolin-2(1H)-one | 522.6 |
| 646 | methyl 4-[4-[(3R)-1-azabicyclo[2.2.2]oct-3-ylamino]-3-(1H-benzimidazol-2-yl)-7-fluoro-2-oxo-1,2-dihydroquinolin-6-yl]benzoate | 538.6 |
| 647 | methyl 3-amino-4-[4-[(3R)-1-azabicyclo[2.2.2]oct-3-ylamino]-3-(1H-benzimidazol-2-yl)-7-fluoro-2-oxo-1,2-dihydroquinolin-6-yl]benzoate | 553.6 |
| 648 | 6-(3-acetylphenyl)-4-[(3R)-1-azabicyclo[2.2.2]oct-3-ylamino]-3-(1H-benzimidazol-2-yl)-7-fluoroquinolin-2(1H)-one | 522.6 |
| 649 | methyl 3-[4-[(3R)-1-azabicyclo[2.2.2]oct-3-ylamino]-3-(1H-benzimidazol-2-yl)-7-fluoro-2-oxo-1,2-dihydroquinolin-6-yl]benzoate | 538.6 |
| 650 | 4-[(3R)-1-azabicyclo[2.2.2]oct-3-ylamino]-3-(1H-benzimidazol-2-yl)-7-fluoro-6-(2-methylphenyl)quinolin-2(1H)-one | 494.6 |
| 651 | 4-[(3R)-1-azabicyclo[2.2.2]oct-3-ylamino]-3-(1H-benzimidazol-2-yl)-7-fluoro-6-(2-methoxyphenyl)quinolin-2(1H)-one | 510.6 |
| 652 | 4-[(3R)-1-azabicyclo[2.2.2]oct-3-ylamino]-3-(1H-benzimidazol-2-yl)-6-(2,4-dichlorophenyl)-7-fluoroquinolin-2(1H)-one | 549.4 |
| 653 | ethyl 1-[4-[(3R)-1-azabicyclo[2.2.2]oct-3-ylamino]-3-(1H-benzimidazol-2-yl)-6-iodo-2-oxo-1,2-dihydroquinolin-7-yl]piperidine-4-carboxylate | 667.6 |
| 654 | 4-[(3R)-1-azabicyclo[2.2.2]oct-3-ylamino]-3-(1H-benzimidazol-2-yl)-7-(1H-imidazol-1-yl)-6-iodoquinolin-2(1H)-one | 578.4 |
| 655 | 4-[(3R)-1-azabicyclo[2.2.2]oct-3-ylamino]-3-(1H-benzimidazol-2-yl)-6-(2-ethylphenyl)-7-(1H-imidazol-1-yl)quinolin-2(1H)-one | 556.7 |
| 656 | 4-[4-[(3R)-1-azabicyclo[2.2.2]oct-3-ylamino]-3-(1H-benzimidazol-2-yl)-7-(1H-imidazol-1-yl)-2-oxo-1,2-dihydroquinolin-6-yl]benzamide | 571.7 |
| 657 | 6-(4-acetylphenyl)-4-[(3R)-1-azabicyclo[2.2.2]oct-3-ylamino]-3-(1H-benzimidazol-2-yl)-7-(1H-imidazol-1-yl)quinolin-2(1H)-one | 570.7 |
| 658 | 6-(3-acetylphenyl)-4-[(3R)-1-azabicyclo[2.2.2]oct-3-ylamino]-3-(1H-benzimidazol-2-yl)-7-(1H-imidazol-1-yl)quinolin-2(1H)-one | 587.7 |
| 659 | N-{3-[4-[(3R)-1-azabicyclo[2.2.2]oct-3-ylamino]-3-(1H-benzimidazol-2-yl)-7-(1H-imidazol-1-yl)-2-oxo-1,2-dihydroquinolin-6-yl]phenyl}acetamide | 585.7 |

TABLE 3-continued

Table of Examples 339-1273.

| Example | Name | LC/MS m/z (MH+) |
|---|---|---|
| 660 | 6-(3-acetylphenyl)-4-[(3R)-1-azabicyclo[2.2.2]oct-3-ylamino]-3-(1H-benzimidazol-2-yl)-7-(1H-imidazol-1-yl)quinolin-2(1H)-one | 570.7 |
| 661 | 4-[(3R)-1-azabicyclo[2.2.2]oct-3-ylamino]-3-(1H-benzimidazol-2-yl)-7-(1H-imidazol-1-yl)-6-(2-methylphenyl)quinolin-2(1H)-one | 542.7 |
| 662 | 4-[(3R)-1-azabicyclo[2.2.2]oct-3-ylamino]-3-(1H-benzimidazol-2-yl)-7-(1H-imidazol-1-yl)-6-(2-methoxyphenyl)quinolin-2(1H)-one | 558.7 |
| 663 | 4-[(3R)-1-azabicyclo[2.2.2]oct-3-ylamino]-3-(1H-benzimidazol-2-yl)-6-(2,4-dichlorophenyl)-7-(1H-imidazol-1-yl)quinolin-2(1H)-one | 597.5 |
| 664 | 4-[(3R)-1-azabicyclo[2.2.2]oct-3-ylamino]-3-(1H-benzimidazol-2-yl)-6-(2-ethylphenyl)quinolin-2(1H)-one | 490.6 |
| 665 | 4-[(3R)-1-azabicyclo[2.2.2]oct-3-ylamino]-3-(1H-benzimidazol-2-yl)-6-(2-ethylphenyl)-7-fluoroquinolin-2(1H)-one | 508.6 |
| 666 | 3-[4-[(3R)-1-azabicyclo[2.2.2]oct-3-ylamino]-3-(1H-benzimidazol-2-yl)-2-oxo-1,2-dihydroquinolin-6-yl]benzoic acid | 506.6 |
| 667 | 3-amino-4-[4-[(3R)-1-azabicyclo[2.2.2]oct-3-ylamino]-3-(1H-benzimidazol-2-yl)-7-chloro-2-oxo-1,2-dihydroquinolin-6-yl]benzoic acid | 556.0 |
| 668 | 3-[4-[(3R)-1-azabicyclo[2.2.2]oct-3-ylamino]-3-(1H-benzimidazol-2-yl)-7-chloro-2-oxo-1,2-dihydroquinolin-6-yl]benzoic acid | 541.0 |
| 669 | 4-[(3R)-1-azabicyclo[2.2.2]oct-3-ylamino]-3-(1H-benzimidazol-2-yl)-6-fluoro-7-[(pyridin-2-ylmethyl)amino]quinolin-2(1H)-one | 510.6 |
| 670 | 4-[(3R)-1-azabicyclo[2.2.2]oct-3-ylamino]-3-(1H-benzimidazol-2-yl)-6-fluoro-7-[(3-pyrrolidin-1-ylpropyl)amino]quinolin-2(1H)-one | 527.6 |
| 671 | 4-[(3R)-1-azabicyclo[2.2.2]oct-3-ylamino]-3-(1H-benzimidazol-2-yl)-6-fluoro-7-[(pyridin-3-ylmethyl)amino]quinolin-2(1H)-one | 510.6 |
| 672 | 4-[(3R)-1-azabicyclo[2.2.2]oct-3-ylamino]-3-(1H-benzimidazol-2-yl)-6-fluoro-7-[(3-pyrrolidin-1-ylpropyl)amino]quinolin-2(1H)-one | 530.7 |
| 673 | 4-[(3R)-1-azabicyclo[2.2.2]oct-3-ylamino]-3-(1H-benzimidazol-2-yl)-6-fluoro-7-[(3R)-3-hydroxypyrrolidin-1-yl]quinolin-2(1H)-one | 489.6 |
| 674 | 4-[(3R)-1-azabicyclo[2.2.2]oct-3-ylamino]-3-(1H-benzimidazol-2-yl)-6-fluoro-7-{[2-(1-methylpyrrolidin-2-yl)ethyl]amino}quinolin-2(1H)-one | 530.7 |
| 675 | 4-[(3R)-1-azabicyclo[2.2.2]oct-3-ylamino]-3-(1H-benzimidazol-2-yl)-6-fluoro-7-[(pyridin-4-ylmethyl)amino]quinolin-2(1H)-one | 510.6 |
| 676 | 4-[(3R)-1-azabicyclo[2.2.2]oct-3-ylamino]-3-(1H-benzimidazol-2-yl)-6-fluoro-7-[3-(methylsulfonyl)pyrrolidin-1-yl]quinolin-2(1H)-one | 551.7 |
| 677 | 4-[(3R)-1-azabicyclo[2.2.2]oct-3-ylamino]-3-(1H-benzimidazol-2-yl)-6-fluoro-7-(3-pyridin-4-ylpyrrolidin-1-yl)quinolin-2(1H)-one | 550.7 |
| 678 | 4-[(3R)-1-azabicyclo[2.2.2]oct-3-ylamino]-3-(1H-benzimidazol-2-yl)-6-fluoro-7-[(2-morpholin-4-ylethyl)amino]quinolin-2(1H)-one | 532.6 |
| 679 | 4-[(3R)-1-azabicyclo[2.2.2]oct-3-ylamino]-3-(1H-benzimidazol-2-yl)-6-fluoro-7-[4-(pyridin-4-ylmethyl)piperazin-1-yl]quinolin-2(1H)-one | 579.7 |
| 680 | 4-[(3R)-1-azabicyclo[2.2.2]oct-3-ylamino]-3-(1H-benzimidazol-2-yl)-7-(benzylamino)-6-fluoroquinolin-2(1H)-one | 509.6 |
| 681 | 4-[(3R)-1-azabicyclo[2.2.2]oct-3-ylamino]-3-(1H-benzimidazol-2-yl)-6-fluoro-7-(2-pyridin-3-ylpyrrolidin-1-yl)quinolin-2(1H)-one | 550.7 |
| 682 | 4-[(3R)-1-azabicyclo[2.2.2]oct-3-ylamino]-3-(1H-benzimidazol-2-yl)-6-fluoro-7-[(2-pyridin-4-ylethyl)amino]quinolin-2(1H)-one | 524.6 |
| 683 | 4-[(3R)-1-azabicyclo[2.2.2]oct-3-ylamino]-3-(1H-benzimidazol-2-yl)-6-fluoro-7-[(3-morpholin-4-ylpropyl)amino]quinolin-2(1H)-one | 546.7 |

TABLE 3-continued

Table of Examples 339-1273.

| Example | Name | LC/MS m/z (MH+) |
|---|---|---|
| 684 | 4-[(3R)-1-azabicyclo[2.2.2]oct-3-ylamino]-3-(1H-benzimidazol-2-yl)-6-fluoro-7-[(4-hydroxycyclohexyl)amino]quinolin-2(1H)-one | 524.6 |
| 685 | 7-{[2-(4-aminophenyl)ethyl]amino}-4-[(3R)-1-azabicyclo[2.2.2]oct-3-ylamino]-3-(1H-benzimidazol-2-yl)-6-fluoroquinolin-2(1H)-one | 538.6 |
| 686 | 4-[(3R)-1-azabicyclo[2.2.2]oct-3-ylamino]-3-(1H-benzimidazol-2-yl)-6-fluoro-7-[(4-hydroxycyclohexyl)amino]quinolin-2(1H)-one | 517.6 |
| 687 | 4-(1-azabicyclo[2.2.2]oct-3-ylamino)-3-(1H-benzimidazol-2-yl)-6-fluoro-7-[(piperidin-3-ylmethyl)amino]quinolin-2(1H)-one | 516.6 |
| 688 | 4-(1-azabicyclo[2.2.2]oct-3-ylamino)-3-(1H-benzimidazol-2-yl)-6-fluoro-7-(pyrrolidin-3-ylamino)quinolin-2(1H)-one | 488.6 |
| 689 | 4-[4-[(3R)-1-azabicyclo[2.2.2]oct-3-ylamino]-3-(1H-benzimidazol-2-yl)-7-(2-methyl-1H-imidazol-1-yl)-2-oxo-1,2-dihydroquinolin-6-yl]benzoic acid | 586.7 |
| 690 | 1-[4-[(3R)-1-azabicyclo[2.2.2]oct-3-ylamino]-3-(1H-benzimidazol-2-yl)-6-chloro-2-oxo-1,2-dihydroquinolin-7-yl]piperidine-4-carboxamide | 547.1 |
| 691 | ethyl 1-[4-[(3R)-1-azabicyclo[2.2.2]oct-3-ylamino]-3-(1H-benzimidazol-2-yl)-6-chloro-2-oxo-1,2-dihydroquinolin-7-yl]piperidine-4-carboxylate | 576.1 |
| 692 | 4-[(3R)-1-azabicyclo[2.2.2]oct-3-ylamino]-3-(1H-benzimidazol-2-yl)-7-(1H-imidazol-1-yl)quinolin-2(1H)-one | 452.5 |
| 693 | 4-[(3R)-1-azabicyclo[2.2.2]oct-3-ylamino]-3-(1H-benzimidazol-2-yl)-7-(2-methyl-1H-imidazol-1-yl)quinolin-2(1H)-one | 466.6 |
| 694 | ethyl 1-[4-[(3R)-1-azabicyclo[2.2.2]oct-3-ylamino]-3-(1H-benzimidazol-2-yl)-2-oxo-1,2-dihydroquinolin-7-yl]piperidine-4-carboxylate | 541.7 |
| 695 | 1-[4-[(3R)-1-azabicyclo[2.2.2]oct-3-ylamino]-3-(1H-benzimidazol-2-yl)-2-oxo-1,2-dihydroquinolin-7-yl]piperidine-4-carboxamide | 512.6 |
| 696 | 4-[(3R)-1-azabicyclo[2.2.2]oct-3-ylamino]-3-(1H-benzimidazol-2-yl)-6-fluoro-7-[(2-mercaptoethyl)amino]quinolin-2(1H)-one | 479.6 |
| 697 | 4-[(3R)-1-azabicyclo[2.2.2]oct-3-ylamino]-3-(1H-benzimidazol-2-yl)-6-fluoro-7-[4-(pyridin-3-ylmethyl)piperazin-1-yl]quinolin-2(1H)-one | 579.7 |
| 698 | 3-(1H-benzimidazol-2-yl)-4-[(2-hydroxyethyl)amino]-6,7-dimethoxyquinolin-2(1H)-one | 381.4 |
| 699 | 3-(1H-benzimidazol-2-yl)-4-[(3-hydroxypropyl)amino]-6,7-dimethoxyquinolin-2(1H)-one | 395.4 |
| 700 | 4-[(3R)-1-azabicyclo[2.2.2]oct-3-ylamino]-3-(1H-benzimidazol-2-yl)-6-fluoro-7-{[(1-hydroxycyclohexyl)methyl]amino}quinolin-2(1H)-one | 531.6 |
| 701 | 3-(1H-benzimidazol-2-yl)-6,7-dimethoxy-4-[(3-pyrrolidin-1-ylpropyl)amino]quinolin-2(1H)-one | 448.5 |
| 702 | 4-[(3S)-1-azabicyclo[2.2.2]oct-3-ylamino]-3-(1H-benzimidazol-2-yl)-2-oxo-1,2-dihydroquinoline-7-carbonitrile | 411.5 |
| 703 | 3-(1H-benzimidazol-2-yl)-6-chloro-4-(pyridin-3-ylamino)quinolin-2(1H)-one | 388.8 |
| 704 | 3-(1H-benzimidazol-2-yl)-4-[(1-benzylpiperidin-4-yl)amino]-6-chloroquinolin-2(1H)-one | 485.0 |
| 705 | 4-[(3S)-1-azabicyclo[2.2.2]oct-3-ylamino]-3-(1H-benzimidazol-2-yl)-7-methoxyquinolin-2(1H)-one | 416.5 |
| 706 | 4-[(3R)-1-azabicyclo[2.2.2]oct-3-ylamino]-3-(1H-benzimidazol-2-yl)-6-bromo-7-methoxyquinolin-2(1H)-one | 495.4 |
| 707 | 3-(1H-benzimidazol-2-yl)-6,7-dimethoxy-4-{[(5-methylpyrazin-2-yl)methyl]amino}quinolin-2(1H)-one | 443.5 |
| 708 | 4-[(3-amino-2-hydroxypropyl)amino]-3-(1H-benzimidazol-2-yl)-6,7-dimethoxyquinolin-2(1H)-one | 410.4 |
| 709 | 3-(1H-benzimidazol-2-yl)-6,7-dimethoxy-4-[(2-methoxyethyl)amino]quinolin-2(1H)-one | 395.4 |
| 710 | {[3-(1H-benzimidazol-2-yl)-6,7-dimethoxy-2-oxo-1,2-dihydroquinolin-4-yl]amino}acetonitrile | 376.4 |
| 711 | 3-(1H-benzimidazol-2-yl)-4-{[2-(2-hydroxyethoxy)ethyl]amino}-6,7-dimethoxyquinolin-2(1H)-one | 425.5 |
| 712 | 3-(1H-benzimidazol-2-yl)-4-[(3R)-3-hydroxypyrrolidin-1-yl]-6,7-dimethoxyquinolin-2(1H)-one | 407.4 |

TABLE 3-continued

Table of Examples 339-1273.

| Example | Name | LC/MS m/z (MH+) |
|---|---|---|
| 713 | 4-[4-[(3S)-1-azabicyclo[2.2.2]oct-3-ylamino]-3-(1H-benzimidazol-2-yl)-2-oxo-1,2-dihydroquinolin-7-yl]benzonitrile | 487.6 |
| 714 | 4-[4-[(3S)-1-azabicyclo[2.2.2]oct-3-ylamino]-3-(1H-benzimidazol-2-yl)-2-oxo-1,2-dihydroquinolin-7-yl]benzoic acid | 506.6 |
| 715 | 4-[4-[(3S)-1-azabicyclo[2.2.2]oct-3-ylamino]-3-(1H-benzimidazol-2-yl)-2-oxo-1,2-dihydroquinolin-7-yl]benzamide | 505.6 |
| 716 | methyl 3-[4-[(3S)-1-azabicyclo[2.2.2]oct-3-ylamino]-3-(1H-benzimidazol-2-yl)-2-oxo-1,2-dihydroquinolin-7-yl]benzoate | 520.6 |
| 717 | 6-chloro-3-(5-morpholin-4-yl-1H-benzimidazol-2-yl)-4-({[6-(piperidin-3-yloxy)pyridin-3-yl]methyl}amino)quinolin-2(1H)-one | 587.1 |
| 718 | 6-chloro-3-(5-morpholin-4-yl-1H-benzimidazol-2-yl)-4-{[3-(2-oxopyrrolidin-1-yl)propyl]amino}quinolin-2(1H)-one | 488.0 |
| 719 | 6-chloro-3-(5-morpholin-4-yl-1H-benzimidazol-2-yl)-4-[(2-pyridin-2-ylethyl)amino]quinolin-2(1H)-one | 502.0 |
| 720 | 6-chloro-3-(5-morpholin-4-yl-1H-benzimidazol-2-yl)-4-{[3-(2-oxopyrrolidin-1-yl)propyl]amino}quinolin-2(1H)-one | 522.0 |
| 721 | 6-chloro-4-[(6-methoxypyridin-3-yl)amino]-3-(5-morpholin-4-yl-1H-benzimidazol-2-yl)quinolin-2(1H)-one | 504.0 |
| 722 | 6-chloro-3-(5-morpholin-4-yl-1H-benzimidazol-2-yl)-4-[(3-pyridin-2-ylpropyl)amino]quinolin-2(1H)-one | 516.0 |
| 723 | 6-chloro-3-(5-morpholin-4-yl-1H-benzimidazol-2-yl)-4-(pyridin-4-ylamino)quinolin-2(1H)-one | 473.9 |
| 724 | 6-chloro-3-(5-morpholin-4-yl-1H-benzimidazol-2-yl)-4-({[6-(piperidin-3-ylmethoxy)pyridin-3-yl]methyl}amino)quinolin-2(1H)-one | 601.1 |
| 725 | 6-chloro-3-(5-morpholin-4-yl-1H-benzimidazol-2-yl)-4-(pyridin-2-ylamino)quinolin-2(1H)-one | 473.9 |
| 726 | 1-[4-[(3R)-1-azabicyclo[2.2.2]oct-3-ylamino]-3-(1H-benzimidazol-2-yl)-6-chloro-2-oxo-1,2-dihydroquinolin-7-yl]piperidine-4-carboxylic acid | 548.1 |
| 727 | 1-[4-[(3R)-1-azabicyclo[2.2.2]oct-3-ylamino]-3-(1H-benzimidazol-2-yl)-2-oxo-1,2-dihydroquinolin-7-yl]piperidine-4-carboxylic acid | 513.6 |
| 728 | 3-[4-[(3S)-1-azabicyclo[2.2.2]oct-3-ylamino]-3-(1H-benzimidazol-2-yl)-2-oxo-1,2-dihydroquinolin-7-yl]benzoic acid | 506.6 |
| 729 | 6-chloro-3-(5-morpholin-4-yl-1H-benzimidazol-2-yl)-4-({[2-(piperidin-4-yloxy)pyridin-3-yl]methyl}amino)quinolin-2(1H)-one | 430.5 |
| 730 | 4-[(3S)-1-azabicyclo[2.2.2]oct-3-ylamino]-3-(1H-benzimidazol-2-yl)-6,7-dichloroquinolin-2(1H)-one | 455.4 |
| 731 | 6-chloro-3-(5-morpholin-4-yl-1H-benzimidazol-2-yl)-4-({[2-(piperidin-4-yloxy)pyridin-3-yl]methyl}amino)quinolin-2(1H)-one | 587.1 |
| 732 | 6-chloro-3-(5-morpholin-4-yl-1H-benzimidazol-2-yl)-4-(pyrazin-2-ylamino)quinolin-2(1H)-one | 474.9 |
| 733 | 4-amino-3-(6-thiomorpholin-4-yl-1H-benzimidazol-2-yl)quinolin-2(1H)-one | 378.5 |
| 734 | 4-[(3R)-1-azabicyclo[2.2.2]oct-3-ylamino]-3-(1H-benzimidazol-2-yl)-6-fluoro-7-(3-pyridin-3-ylpyrrolidin-1-yl)quinolin-2(1H)-one | 550.7 |
| 735 | 4-[(3R)-1-azabicyclo[2.2.2]oct-3-ylamino]-3-(1H-benzimidazol-2-yl)-5-fluoro-6-[4-(methylsulfonyl)phenyl]quinolin-2(1H)-one | 558.6 |
| 736 | 6-(4-acetylphenyl)-4-[(3R)-1-azabicyclo[2.2.2]oct-3-ylamino]-3-(1H-benzimidazol-2-yl)-5-fluoroquinolin-2(1H)-one | 522.6 |
| 737 | methyl 4-[4-[(3R)-1-azabicyclo[2.2.2]oct-3-ylamino]-3-(1H-benzimidazol-2-yl)-5-fluoro-2-oxo-1,2-dihydroquinolin-6-yl]benzoate | 538.6 |
| 738 | methyl 3-amino-4-[4-[(3R)-1-azabicyclo[2.2.2]oct-3-ylamino]-3-(1H-benzimidazol-2-yl)-5-fluoro-2-oxo-1,2-dihydroquinolin-6-yl]benzoate | 553.6 |
| 739 | methyl 3-[4-[(3R)-1-azabicyclo[2.2.2]oct-3-ylamino]-3-(1H-benzimidazol-2-yl)-5-fluoro-2-oxo-1,2-dihydroquinolin-6-yl]benzoate | 538.6 |
| 740 | 4-[(3R)-1-azabicyclo[2.2.2]oct-3-ylamino]-3-(1H-benzimidazol-2-yl)-5-fluoro-6-(2-methylphenyl)quinolin-2(1H)-one | 494.6 |

TABLE 3-continued

Table of Examples 339-1273.

| Example | Name | LC/MS m/z (MH+) |
|---|---|---|
| 741 | 4-[(3R)-1-azabicyclo[2.2.2]oct-3-ylamino]-3-(1H-benzimidazol-2-yl)-6-(2-ethylphenyl)-5-fluoroquinolin-2(1H)-one | 508.6 |
| 742 | 4-[(3R)-1-azabicyclo[2.2.2]oct-3-ylamino]-3-(1H-benzimidazol-2-yl)-5-fluoro-6-(2-methoxyphenyl)quinolin-2(1H)-one | 510.6 |
| 743 | 4-[(3R)-1-azabicyclo[2.2.2]oct-3-ylamino]-3-(1H-benzimidazol-2-yl)-6-(2,4-dichlorophenyl)-5-fluoroquinolin-2(1H)-one | 549.4 |
| 744 | 4-[4-[(3S)-1-azabicyclo[2.2.2]oct-3-ylamino]-3-(1H-benzimidazol-2-yl)-7-fluoro-2-oxo-1,2-dihydroquinolin-6-yl]benzoic acid | 524.6 |
| 745 | 4-[4-[(3S)-1-azabicyclo[2.2.2]oct-3-ylamino]-3-(1H-benzimidazol-2-yl)-7-fluoro-2-oxo-1,2-dihydroquinolin-6-yl]benzamide | 523.6 |
| 746 | N-{3-[4-[(3S)-1-azabicyclo[2.2.2]oct-3-ylamino]-3-(1H-benzimidazol-2-yl)-7-fluoro-2-oxo-1,2-dihydroquinolin-6-yl]phenyl}acetamide | 537.6 |
| 747 | 3-[4-[(3S)-1-azabicyclo[2.2.2]oct-3-ylamino]-3-(1H-benzimidazol-2-yl)-7-fluoro-2-oxo-1,2-dihydroquinolin-6-yl]benzoic acid | 524.6 |
| 748 | 4-[(3S)-1-azabicyclo[2.2.2]oct-3-ylamino]-3-(1H-benzimidazol-2-yl)-7-fluoro-6-(2-methylphenyl)quinolin-2(1H)-one | 494.6 |
| 749 | 4-[(3R)-1-azabicyclo[2.2.2]oct-3-ylamino]-3-(1H-benzimidazol-2-yl)-7-(2-methyl-1H-imidazol-1-yl)-6-[4-(methylsulfonyl)phenyl]quinolin-2(1H)-one | 620.7 |
| 750 | N-{3-[4-[(3R)-1-azabicyclo[2.2.2]oct-3-ylamino]-3-(1H-benzimidazol-2-yl)-7-(2-methyl-1H-imidazol-1-yl)-2-oxo-1,2-dihydroquinolin-6-yl]phenyl}acetamide | 599.7 |
| 751 | N-{3-[4-[(3R)-1-azabicyclo[2.2.2]oct-3-ylamino]-3-(1H-benzimidazol-2-yl)-2-oxo-7-piperidin-1-yl-1,2-dihydroquinolin-6-yl]phenyl}acetamide | 602.8 |
| 752 | N-{3-[7-(3-acetyl-1H-pyrrol-1-yl)-4-[(3R)-1-azabicyclo[2.2.2]oct-3-ylamino]-3-(1H-benzimidazol-2-yl)-2-oxo-1,2-dihydroquinolin-6-yl]phenyl}acetamide | 626.7 |
| 753 | N-{3-[4-[(3R)-1-azabicyclo[2.2.2]oct-3-ylamino]-3-(1H-benzimidazol-2-yl)-7-(dimethylamino)-2-oxo-1,2-dihydroquinolin-6-yl]phenyl}acetamide | 562.7 |
| 754 | N-{3-[4-[(3R)-1-azabicyclo[2.2.2]oct-3-ylamino]-3-(1H-benzimidazol-2-yl)-7-(2-ethyl-1H-imidazol-1-yl)-2-oxo-1,2-dihydroquinolin-6-yl]phenyl}acetamide | 613.7 |
| 755 | 4-[(3R)-1-azabicyclo[2.2.2]oct-3-ylamino]-3-(1H-benzimidazol-2-yl)-7-(2-ethyl-1H-imidazol-1-yl)-6-fluoroquinolin-2(1H)-one | 498.6 |
| 756 | 4-[(3R)-1-azabicyclo[2.2.2]oct-3-ylamino]-3-(1H-benzimidazol-2-yl)-6-fluoro-7-(2-isopropyl-1H-imidazol-1-yl)quinolin-2(1H)-one | 512.6 |
| 757 | 1-[4-[(3R)-1-azabicyclo[2.2.2]oct-3-ylamino]-3-(1H-benzimidazol-2-yl)-6-fluoro-2-oxo-1,2-dihydroquinolin-7-yl]-1H-pyrrole-3-carboxylic acid | 513.5 |
| 758 | 4-[(3S)-1-azabicyclo[2.2.2]oct-3-ylamino]-3-(1H-benzimidazol-2-yl)-7-chloro-6-iodoquinolin-2(1H)-one | 546.8 |
| 759 | 4-[(3R)-1-azabicyclo[2.2.2]oct-3-ylamino]-3-(1H-benzimidazol-2-yl)-5-fluoro-6-iodoquinolin-2(1H)-one | 530.4 |
| 760 | 4-[(3S)-1-azabicyclo[2.2.2]oct-3-ylamino]-3-(1H-benzimidazol-2-yl)-7-fluoro-6-iodoquinolin-2(1H)-one | 530.4 |
| 761 | 6-chloro-3-(5-morpholin-4-yl-1H-benzimidazol-2-yl)-4-[(2-pyridin-3-ylethyl)amino]quinolin-2(1H)-one | 502.0 |
| 762 | 4-{[4-(aminomethyl)benzyl]amino}-3-(1H-benzimidazol-2-yl)-7-chloroquinolin-2(1H)-one | 430.9 |
| 763 | 3-(1H-benzimidazol-2-yl)-7-chloro-4-{[2-(dimethylamino)ethyl]amino}quinolin-2(1H)-one | 382.9 |
| 764 | 3-(1H-benzimidazol-2-yl)-4-(1,4'-bipiperidin-1'-yl)-7-chloroquinolin-2(1H)-one | 463.0 |
| 765 | 3-(1H-benzimidazol-2-yl)-7-chloro-4-{[3-(4-methylpiperazin-1-yl)propyl]amino}quinolin-2(1H)-one | 452.0 |
| 766 | 3-(1H-benzimidazol-2-yl)-7-chloro-4-[(2-piperidin-1-ylethyl)amino]quinolin-2(1H)-one | 422.9 |
| 767 | 3-(1H-benzimidazol-2-yl)-7-chloro-4-{[3-(1H-imidazol-1-yl)propyl]amino}quinolin-2(1H)-one | 419.9 |
| 768 | 3-(1H-benzimidazol-2-yl)-7-chloro-4-(pyridin-3-ylamino)quinolin-2(1H)-one | 388.8 |

TABLE 3-continued

Table of Examples 339-1273.

| Example | Name | LC/MS m/z (MH+) |
|---|---|---|
| 769 | 3-(1H-benzimidazol-2-yl)-7-chloro-4-(pyridin-4-ylamino)quinolin-2(1H)-one | 388.8 |
| 770 | 3-(1H-benzimidazol-2-yl)-7-chloro-4-({[6-(piperidin-3-yloxy)pyridin-3-yl]methyl}amino)quinolin-2(1H)-one | 502.0 |
| 771 | 3-(1H-benzimidazol-2-yl)-7-chloro-4-{[3-(2-oxopyrrolidin-1-yl)propyl]amino}quinolin-2(1H)-one | 436.9 |
| 772 | 4-[4-[(3R)-1-azabicyclo[2.2.2]oct-3-ylamino]-3-(1H-benzimidazol-2-yl)-7-methoxy-2-oxo-1,2-dihydroquinolin-6-yl]benzoic acid | 536.6 |
| 773 | 4-[4-[(3R)-1-azabicyclo[2.2.2]oct-3-ylamino]-3-(1H-benzimidazol-2-yl)-7-methoxy-2-oxo-1,2-dihydroquinolin-6-yl]benzamide | 535.6 |
| 774 | 6-(4-acetylphenyl)-4-[(3R)-1-azabicyclo[2.2.2]oct-3-ylamino]-3-(1H-benzimidazol-2-yl)-7-methoxyquinolin-2(1H)-one | 534.6 |
| 775 | methyl 4-[4-[(3R)-1-azabicyclo[2.2.2]oct-3-ylamino]-3-(1H-benzimidazol-2-yl)-7-methoxy-2-oxo-1,2-dihydroquinolin-6-yl]benzoate | 550.6 |
| 776 | methyl 3-amino-4-[4-[(3R)-1-azabicyclo[2.2.2]oct-3-ylamino]-3-(1H-benzimidazol-2-yl)-7-methoxy-2-oxo-1,2-dihydroquinolin-6-yl]benzoate | 565.6 |
| 777 | N-{3-[4-[(3R)-1-azabicyclo[2.2.2]oct-3-ylamino]-3-(1H-benzimidazol-2-yl)-7-methoxy-2-oxo-1,2-dihydroquinolin-6-yl]phenyl}acetamide | 549.6 |
| 778 | 6-(3-acetylphenyl)-4-[(3R)-1-azabicyclo[2.2.2]oct-3-ylamino]-3-(1H-benzimidazol-2-yl)-7-methoxyquinolin-2(1H)-one | 534.6 |
| 779 | methyl 3-[4-[(3R)-1-azabicyclo[2.2.2]oct-3-ylamino]-3-(1H-benzimidazol-2-yl)-7-methoxy-2-oxo-1,2-dihydroquinolin-6-yl]benzoate | 550.6 |
| 780 | 3-[4-[(3R)-1-azabicyclo[2.2.2]oct-3-ylamino]-3-(1H-benzimidazol-2-yl)-7-methoxy-2-oxo-1,2-dihydroquinolin-6-yl]benzoic acid | 536.6 |
| 781 | 4-[(3R)-1-azabicyclo[2.2.2]oct-3-ylamino]-3-(1H-benzimidazol-2-yl)-7-methoxy-6-(2-methylphenyl)quinolin-2(1H)-one | 506.6 |
| 782 | 4-[(3R)-1-azabicyclo[2.2.2]oct-3-ylamino]-3-(1H-benzimidazol-2-yl)-6-(2-ethylphenyl)-7-methoxyquinolin-2(1H)-one | 520.6 |
| 783 | 4-[(3R)-1-azabicyclo[2.2.2]oct-3-ylamino]-3-(1H-benzimidazol-2-yl)-7-methoxy-6-(2-methoxyphenyl)quinolin-2(1H)-one | 522.6 |
| 784 | 4-[(3R)-1-azabicyclo[2.2.2]oct-3-ylamino]-3-(1H-benzimidazol-2-yl)-6-(2,4-dichlorophenyl)-7-methoxyquinolin-2(1H)-one | 561.5 |
| 785 | 4-[(3R)-1-azabicyclo[2.2.2]oct-3-ylamino]-3-(1H-benzimidazol-2-yl)-7-[2-(dimethylamino)ethoxy]-6-fluoroquinolin-2(1H)-one | 491.6 |
| 786 | 4-[(3R)-1-azabicyclo[2.2.2]oct-3-ylamino]-3-(1H-benzimidazol-2-yl)-6-fluoro-7-[(2S)-pyrrolidin-2-ylmethoxy]quinolin-2(1H)-one | 503.6 |
| 787 | 4-[(3R)-1-azabicyclo[2.2.2]oct-3-ylamino]-3-(1H-benzimidazol-2-yl)-6-fluoro-7-[2-(2-oxopyrrolidin-1-yl)ethoxy]quinolin-2(1H)-one | 531.6 |
| 788 | 4-[(3R)-1-azabicyclo[2.2.2]oct-3-ylamino]-3-(1H-benzimidazol-2-yl)-6-fluoro-7-{[(2S)-1-(4-nitrophenyl)pyrrolidin-2-yl]methoxy}quinolin-2(1H)-one | 624.7 |
| 789 | 4-[(3R)-1-azabicyclo[2.2.2]oct-3-ylamino]-3-(1H-benzimidazol-2-yl)-6-fluoro-7-[(1-methylpiperidin-2-yl)methoxy]quinolin-2(1H)-one | 531.6 |
| 790 | 3-(1H-benzimidazol-2-yl)-6,7-dimethoxy-4-{[2-(1-methylpyrrolidin-2-yl)ethyl]amino}quinolin-2(1H)-one | 448.5 |
| 791 | 3-(1H-benzimidazol-2-yl)-6,7-dimethoxy-4-{[2-(methylsulfonyl)ethyl]amino}quinolin-2(1H)-one | 443.5 |
| 792 | 3-(1H-benzimidazol-2-yl)-6,7-dimethoxy-4-[(2-morpholin-4-yl-2-pyridin-3-ylethyl)amino]quinolin-2(1H)-one | 527.6 |
| 793 | 7-[(2-aminoethyl)amino]-4-[(3R)-1-azabicyclo[2.2.2]oct-3-ylamino]-3-(1H-benzimidazol-2-yl)-6-fluoroquinolin-2(1H)-one | 462.5 |
| 794 | 4-[(3R)-1-azabicyclo[2.2.2]oct-3-ylamino]-3-(1H-benzimidazol-2-yl)-6-fluoro-7-(3-phenylthiomorpholin-4-yl)quinolin-2(1H)-one | 581.7 |

TABLE 3-continued

Table of Examples 339-1273.

| Example | Name | LC/MS m/z (MH+) |
|---|---|---|
| 795 | 4-[(3R)-1-azabicyclo[2.2.2]oct-3-ylamino]-3-(1H-benzimidazol-2-yl)-6-fluoro-7-(2-phenylthiomorpholin-4-yl)quinolin-2(1H)-one | 581.7 |
| 796 | 4-[(3R)-1-azabicyclo[2.2.2]oct-3-ylamino]-3-(1H-benzimidazol-2-yl)-6-fluoro-7-{[2-(phenylsulfonyl)ethyl]amino}quinolin-2(1H)-one | 587.7 |
| 797 | 4-[(3R)-1-azabicyclo[2.2.2]oct-3-ylamino]-3-(1H-benzimidazol-2-yl)-6-fluoro-7-{[2-(methylsulfonyl)ethyl]amino}quinolin-2(1H)-one | 525.6 |
| 798 | 7-{[(2R)-2-aminopropyl]amino}-4-[(3R)-1-azabicyclo[2.2.2]oct-3-ylamino]-3-(1H-benzimidazol-2-yl)-6-fluoroquinolin-2(1H)-one | 476.6 |
| 799 | 4-[(3R)-1-azabicyclo[2.2.2]oct-3-ylamino]-3-(1H-benzimidazol-2-yl)-6-fluoro-7-[(2-morpholin-4-yl-2-pyridin-3-ylethyl)amino]quinolin-2(1H)-one | 609.7 |
| 800 | 3-[4-[(3R)-1-azabicyclo[2.2.2]oct-3-ylamino]-3-(1H-benzimidazol-2-yl)-7-fluoro-2-oxo-1,2-dihydroquinolin-6-yl]benzoic acid | 524.6 |
| 801 | 4-[4-[(3S)-1-azabicyclo[2.2.2]oct-3-ylamino]-3-(1H-benzimidazol-2-yl)-7-(1H-imidazol-1-yl)-2-oxo-1,2-dihydroquinolin-6-yl]benzoic acid | 572.6 |
| 802 | 4-[4-[(3S)-1-azabicyclo[2.2.2]oct-3-ylamino]-3-(1H-benzimidazol-2-yl)-7-(2-methyl-1H-imidazol-1-yl)-2-oxo-1,2-dihydroquinolin-6-yl]benzoic acid | 586.7 |
| 803 | 4-[4-[(3S)-1-azabicyclo[2.2.2]oct-3-ylamino]-3-(1H-benzimidazol-2-yl)-2-oxo-7-piperidin-1-yl-1,2-dihydroquinolin-6-yl]benzoic acid | 589.7 |
| 804 | 4-[4-[(3R)-1-azabicyclo[2.2.2]oct-3-ylamino]-3-(1H-benzimidazol-2-yl)-7-(2-ethyl-1H-imidazol-1-yl)-2-oxo-1,2-dihydroquinolin-6-yl]benzoic acid | 600.7 |
| 805 | 3-[4-[(3R)-1-azabicyclo[2.2.2]oct-3-ylamino]-3-(1H-benzimidazol-2-yl)-7-(2-methyl-1H-imidazol-1-yl)-2-oxo-1,2-dihydroquinolin-6-yl]benzoic acid | 586.7 |
| 806 | 3-[4-[(3R)-1-azabicyclo[2.2.2]oct-3-ylamino]-3-(1H-benzimidazol-2-yl)-2-oxo-7-piperidin-1-yl-1,2-dihydroquinolin-6-yl]benzoic acid | 589.7 |
| 807 | 6-chloro-3-[5-(4-methylpiperazin-1-yl)-1H-benzimidazol-2-yl]-4-[(piperidin-3-ylmethyl)amino]quinolin-2(1H)-one | 507.1 |
| 808 | 3-[4-[(3S)-1-azabicyclo[2.2.2]oct-3-ylamino]-3-(1H-benzimidazol-2-yl)-7-(1H-imidazol-1-yl)-2-oxo-1,2-dihydroquinolin-6-yl]benzoic acid | 572.6 |
| 809 | 6-chloro-3-[5-(4-methylpiperazin-1-yl)-1H-benzimidazol-2-yl]-4-[(piperidin-4-ylmethyl)amino]quinolin-2(1H)-one | 507.1 |
| 810 | 3-[4-[(3S)-1-azabicyclo[2.2.2]oct-3-ylamino]-3-(1H-benzimidazol-2-yl)-7-(2-methyl-1H-imidazol-1-yl)-2-oxo-1,2-dihydroquinolin-6-yl]benzoic acid | 586.7 |
| 811 | 6-chloro-3-[5-(4-methylpiperazin-1-yl)-1H-benzimidazol-2-yl]-4-[(pyrrolidin-2-ylmethyl)amino]quinolin-2(1H)-one | 493.0 |
| 812 | 3-[4-[(3S)-1-azabicyclo[2.2.2]oct-3-ylamino]-3-(1H-benzimidazol-2-yl)-2-oxo-7-piperidin-1-yl-1,2-dihydroquinolin-6-yl]benzoic acid | 589.7 |
| 813 | 4-{[(2R)-2-aminobutyl]amino}-6-chloro-3-[5-(4-methylpiperazin-1-yl)-1H-benzimidazol-2-yl]quinolin-2(1H)-one | 481.0 |
| 814 | 4-{[(2S)-2-amino-3-methylbutyl]amino}-6-chloro-3-[5-(4-methylpiperazin-1-yl)-1H-benzimidazol-2-yl]quinolin-2(1H)-one | 495.0 |
| 815 | 4-{[(1S)-2-amino-1-benzylethyl]amino}-6-chloro-3-[5-(4-methylpiperazin-1-yl)-1H-benzimidazol-2-yl]quinolin-2(1H)-one | 543.1 |
| 816 | 4-[(3S)-1-azabicyclo[2.2.2]oct-3-ylamino]-6-chloro-3-[5-(4-methylpiperazin-1-yl)-1H-benzimidazol-2-yl]quinolin-2(1H)-one | 519.1 |
| 817 | 6-chloro-3-[5-(4-methylpiperazin-1-yl)-1H-benzimidazol-2-yl]-4-(piperidin-3-ylamino)quinolin-2(1H)-one | 493.0 |
| 818 | 6-chloro-4-{[2-(dimethylamino)ethyl]amino}-3-[5-(4-methylpiperazin-1-yl)-1H-benzimidazol-2-yl]quinolin-2(1H)-one | 481.0 |
| 819 | 7-chloro-3-(5-morpholin-4-yl-1H-benzimidazol-2-yl)-4-(piperidin-4-ylamino)quinolin-2(1H)-one | 480.0 |
| 820 | 4-{[(1R,2R)-2-aminocyclohexyl]amino}-3-(1H-benzimidazol-2-yl)-7-chloroquinolin-2(1H)-one | 408.9 |

TABLE 3-continued

Table of Examples 339-1273.

| Example | Name | LC/MS m/z (MH+) |
|---|---|---|
| 821 | 3-(1H-benzimidazol-2-yl)-7-chloro-4-[(3-morpholin-4-ylpropyl)amino]quinolin-2(1H)-one | 438.9 |
| 822 | 3-(1H-benzimidazol-2-yl)-7-chloro-4-[(pyridin-3-ylmethyl)amino]quinolin-2(1H)-one | 402.9 |
| 823 | 3-(1H-benzimidazol-2-yl)-7-chloro-4-[(2-pyridin-3-ylethyl)amino]quinolin-2(1H)-one | 416.9 |
| 824 | 4-{[(1R,2R)-2-aminocyclohexyl]amino}-7-chloro-3-(5-morpholin-4-yl-1H-benzimidazol-2-yl)quinolin-2(1H)-one | 494.0 |
| 825 | 4-[(4-aminocyclohexyl)amino]-7-chloro-3-(5-morpholin-4-yl-1H-benzimidazol-2-yl)quinolin-2(1H)-one | 494.0 |
| 826 | 7-chloro-4-{[2-(methylamino)ethyl]amino}-3-(5-morpholin-4-4-yl-1H-benzimidazol-2-yl)quinolin-2(1H)-one | 453.9 |
| 827 | 7-chloro-3-(5-morpholin-4-yl-1H-benzimidazol-2-yl)-4-[(pyrrolidin-2-ylmethyl)amino]quinolin-2(1H)-one | 480.0 |
| 828 | 4-{[(1S)-2-amino-1-benzylethyl]amino}-7-chloro-3-(5-morpholin-4-yl-1H-benzimidazol-2-yl)quinolin-2(1H)-one | 530.0 |
| 829 | 7-chloro-3-(5-morpholin-4-yl-1H-benzimidazol-2-yl)-4-(pyrrolidin-3-ylamino)quinolin-2(1H)-one | 466.0 |
| 830 | 3-(1H-benzimidazol-2-yl)-7-chloro-4-[(2-pyrrolidin-1-ylethyl)amino]quinolin-2(1H)-one | 408.9 |
| 831 | 3-(1H-benzimidazol-2-yl)-7-chloro-4-[(2-piperidin-2-ylethyl)amino]quinolin-2(1H)-one | 422.9 |
| 832 | 3-(1H-benzimidazol-2-yl)-7-chloro-4-[(piperidin-3-ylmethyl)amino]quinolin-2(1H)-one | 408.9 |
| 833 | 3-(1H-benzimidazol-2-yl)-7-chloro-4-[(piperidin-4-ylmethyl)amino]quinolin-2(1H)-one | 408.9 |
| 834 | 3-(1H-benzimidazol-2-yl)-7-chloro-4-{[(2-methyl-1-piperidin-4-yl-1H-benzimidazol-5-yl)methyl]amino}quinolin-2(1H)-one | 539.1 |
| 835 | 4-[(4-aminocyclohexyl)amino]-3-(1H-benzimidazol-2-yl)-7-chloroquinolin-2(1H)-one | 408.9 |
| 836 | 3-(1H-benzimidazol-2-yl)-7-chloro-4-(pyrrolidin-3-ylamino)quinolin-2(1H)-one | 380.8 |
| 837 | 4-[(3S)-1-azabicyclo[2.2.2]oct-3-ylamino]-3-(1H-benzimidazol-2-yl)-6-[4-(trifluoromethyl)phenyl]quinolin-2(1H)-one | 530.6 |
| 838 | 4-[(3S)-1-azabicyclo[2.2.2]oct-3-ylamino]-3-(1H-benzimidazol-2-yl)-6-[3-(trifluoromethyl)phenyl]quinolin-2(1H)-one | 530.6 |
| 839 | 4-amino-5-fluoro-3-[6-(4-isopropylpiperazin-1-yl)-1H-benzimidazol-2-yl]quinolin-2(1H)-one | 421.5 |
| 840 | 7-chloro-3-(5-morpholin-4-yl-1H-benzimidazol-2-yl)-4-{[(2S)-pyrrolidin-2-ylmethyl]amino}quinolin-2(1H)-one | 480.0 |
| 841 | 7-chloro-3-(5-morpholin-4-yl-1H-benzimidazol-2-yl)-4-{[(2R)-pyrrolidin-2-ylmethyl]amino}quinolin-2(1H)-one | 480.0 |
| 842 | 7-chloro-4-({[(2S)-1-ethylpyrrolidin-2-yl]methyl}amino)-3-(5-morpholin-4-yl-1H-benzimidazol-2-yl)quinolin-2(1H)-one | 508.0 |
| 843 | 7-chloro-4-({[(2R)-1-ethylpyrrolidin-2-yl]methyl}amino)-3-(5-morpholin-4-yl-1H-benzimidazol-2-yl)quinolin-2(1H)-one | 508.0 |
| 844 | 4-[(3R)-1-azabicyclo[2.2.2]oct-3-ylamino]-7-chloro-3-(5-morpholin-4-yl-1H-benzimidazol-2-yl)quinolin-2(1H)-one | 506.0 |
| 845 | 7-chloro-3-(5-morpholin-4-yl-1H-benzimidazol-2-yl)-4-[(piperidin-3-ylmethyl)amino]quinolin-2(1H)-one | 494.0 |
| 846 | 7-chloro-3-(5-morpholin-4-yl-1H-benzimidazol-2-yl)-4-[(piperidin-4-ylmethyl)amino]quinolin-2(1H)-one | 494.0 |
| 847 | 4-{[(2S)-2-amino-3-methylbutyl]amino}-7-chloro-3-(5-morpholin-4-yl-1H-benzimidazol-2-yl)quinolin-2(1H)-one | 482.0 |
| 848 | 4-{[4-(aminomethyl)benzyl]amino}-7-chloro-3-(5-morpholin-4-yl-1H-benzimidazol-2-yl)quinolin-2(1H)-one | 516.0 |
| 849 | 4-{[(1R)-1-(aminomethyl)propyl]amino}-7-chloro-3-(5-morpholin-4-yl-1H-benzimidazol-2-yl)quinolin-2(1H)-one | 468.0 |
| 850 | 7-chloro-4-{[3-(4-methylpiperazin-1-yl)propyl]amino}-3-(5-morpholin-4-yl-1H-benzimidazol-2-yl)quinolin-2(1H)-one | 537.1 |
| 851 | 7-chloro-4-{[3-(1H-imidazol-1-yl)propyl]amino}-3-(5-morpholin-4-yl-1H-benzimidazol-2-yl)quinolin-2(1H)-one | 505.0 |
| 852 | 7-chloro-3-(5-morpholin-4-yl-1H-benzimidazol-2-yl)-4-[(2-pyrrolidin-1-ylethyl)amino]quinolin-2(1H)-one | 494.0 |
| 853 | 7-chloro-3-(5-morpholin-4-yl-1H-benzimidazol-2-yl)-4-[(piperidin-2-ylmethyl)amino]quinolin-2(1H)-one | 494.0 |
| 854 | 7-chloro-4-{[2-(dimethylamino)ethyl]amino}-3-(5-morpholin-4-yl-1H-benzimidazol-2-yl)quinolin-2(1H)-one | 468.0 |

TABLE 3-continued

Table of Examples 339-1273.

| Example | Name | LC/MS m/z (MH+) |
|---|---|---|
| 855 | 7-chloro-3-(5-morpholin-4-yl-1H-benzimidazol-2-yl)-4-[(3S)-pyrrolidin-3-ylamino]quinolin-2(1H)-one | 466.0 |
| 856 | 4-[(3S)-1-azabicyclo[2.2.2]oct-3-ylamino]-3-(1H-benzimidazol-2-yl)-6-(4-hydroxyphenyl)quinolin-2(1H)-one | 478.6 |
| 857 | 4-[(3S)-1-azabicyclo[2.2.2]oct-3-ylamino]-3-(1H-benzimidazol-2-yl)-6-(3-hydroxyphenyl)quinolin-2(1H)-one | 478.6 |
| 858 | 4-[(3S)-1-azabicyclo[2.2.2]oct-3-ylamino]-3-(1H-benzimidazol-2-yl)-6-(2-hydroxyphenyl)quinolin-2(1H)-one | 478.6 |
| 859 | 3-(1H-benzimidazol-2-yl)-7-chloro-4-{[(2S)-pyrrolidin-2-ylmethyl]amino}quinolin-2(1H)-one | 394.9 |
| 860 | 3-(1H-benzimidazol-2-yl)-7-chloro-4-({[(2S)-1-ethylpyrrolidin-2-yl]methyl}amino)quinolin-2(1H)-one | 422.9 |
| 861 | 3-(1H-benzimidazol-2-yl)-7-chloro-4-({[(2R)-1-ethylpyrrolidin-2-yl]methyl}amino)quinolin-2(1H)-one | 422.9 |
| 862 | 3-(1H-benzimidazol-2-yl)-7-chloro-4-[(3S)-pyrrolidin-3-ylamino]quinolin-2(1H)-one | 380.8 |
| 863 | 3-(1H-benzimidazol-2-yl)-6-chloro-4-{[(2S)-pyrrolidin-2-ylmethyl]amino}quinolin-2(1H)-one | 394.9 |
| 864 | 3-(1H-benzimidazol-2-yl)-6-chloro-4-{[(2R)-pyrrolidin-2-ylmethyl]amino}quinolin-2(1H)-one | 394.9 |
| 865 | 3-(1H-benzimidazol-2-yl)-6-chloro-4-({[(2S)-1-ethylpyrrolidin-2-yl]methyl}amino)quinolin-2(1H)-one | 422.9 |
| 866 | 3-(1H-benzimidazol-2-yl)-6-chloro-4-({[(2R)-1-ethylpyrrolidin-2-yl]methyl}amino)quinolin-2(1H)-one | 422.9 |
| 867 | 4-amino-3-[5-(1,4'-bipiperidin-1'-ylcarbonyl)-1H-benzimidazol-2-yl]quinolin-2(1H)-one | 380.8 |
| 868 | 4-[(3R)-1-azabicyclo[2.2.2]oct-3-ylamino]-7-bromo-3-(5-morpholin-4-yl-1H-benzimidazol-2-yl)quinolin-2(1H)-one | 550.5 |
| 869 | 4-[(3R)-1-azabicyclo[2.2.2]oct-3-ylamino]-7-bromo-3-(6-methoxy-1H-benzimidazol-2-yl)quinolin-2(1H)-one | 495.4 |
| 870 | 3-{[3-(1H-benzimidazol-2-yl)-6,7-dimethoxy-2-oxo-1,2-dihydroquinolin-4-yl]amino}bicyclo[2.2.1]heptane-2-carboxamide | 474.5 |
| 871 | 4-[(3-amino-2,2-dimethylpropyl)amino]-3-(1H-benzimidazol-2-yl)-6,7-dimethoxyquinolin-2(1H)-one | 422.5 |
| 872 | 3-(1H-benzimidazol-2-yl)-4-{[3-(dimethylamino)-2,2-dimethylpropyl]amino}-6,7-dimethoxyquinolin-2(1H)-one | 450.6 |
| 873 | 3-(1H-benzimidazol-2-yl)-7-chloro-4-[(pyridin-2-ylmethyl)amino]quinolin-2(1H)-one | 402.9 |
| 874 | 3-(1H-benzimidazol-2-yl)-7-chloro-4-[(2-pyridin-2-ylethyl)amino]quinolin-2(1H)-one | 416.9 |
| 875 | 3-(1H-benzimidazol-2-yl)-7-chloro-4-{[2-(methylamino)ethyl]amino}quinolin-2(1H)-one | 368.8 |
| 876 | 3-(1H-benzimidazol-2-yl)-7-chloro-4-[(piperidin-2-ylmethyl)amino]quinolin-2(1H)-one | 408.9 |
| 877 | 3-(1H-benzimidazol-2-yl)-7-chloro-4-(piperidin-4-ylamino)quinolin-2(1H)-one | 394.9 |
| 878 | 4-amino-3-[5-(1,4'-bipiperidin-1'-ylcarbonyl)-1H-benzimidazol-2-yl]quinolin-2(1H)-one | 471.6 |
| 879 | 4-amino-3-{5-[(3S)-3-(dimethylnitroryl)pyrrolidin-1-yl]-1H-benzimidazol-2-yl}quinolin-2(1H)-one | 405.5 |
| 880 | 4-amino-3-(5-{2-[(dimethylamino)methyl]morpholin-4-yl}-1H-benzimidazol-2-yl)quinolin-2(1H)-one | 419.5 |
| 881 | methyl 4-[4-[(3R)-1-azabicyclo[2.2.2]oct-3-ylamino]-3-(1H-benzimidazol-2-yl)-5-methyl-2-oxo-1,2-dihydroquinolin-6-yl]benzoate | 534.6 |
| 882 | 3-[4-[(3R)-1-azabicyclo[2.2.2]oct-3-ylamino]-3-(1H-benzimidazol-2-yl)-5-methyl-2-oxo-1,2-dihydroquinolin-6-yl]benzoic acid | 520.6 |
| 883 | 4-[4-[(3R)-1-azabicyclo[2.2.2]oct-3-ylamino]-3-(1H-benzimidazol-2-yl)-5-methyl-2-oxo-1,2-dihydroquinolin-6-yl]benzamide | 519.6 |
| 884 | 4-[4-[(3R)-1-azabicyclo[2.2.2]oct-3-ylamino]-3-(1H-benzimidazol-2-yl)-5-methyl-2-oxo-1,2-dihydroquinolin-6-yl]benzoic acid | 520.6 |
| 885 | 4-amino-3-{5-[(2S)-2-(pyrrolidin-1-ylmethyl)pyrrolidin-1-yl]-1H-benzimidazol-2-yl}quinolin-2(1H)-one | 429.5 |
| 886 | 2-(4-amino-5-fluoro-2-oxo-1,2-dihydroquinolin-3-yl)-N-methyl-N-(1-methylpiperidin-4-yl)-1H-benzimidazole-6-carboxamide | 449.5 |
| 887 | 4-amino-3-(1H-benzimidazol-2-yl)-5-[(1-methylpiperidin-4-yl)oxy]quinolin-2(1H)-one | 390.5 |

TABLE 3-continued

Table of Examples 339-1273.

| Example | Name | LC/MS m/z (MH+) |
|---|---|---|
| 888 | 4-amino-5-(1-azabicyclo[2.2.2]oct-3-yloxy)-3-(1H-benzimidazol-2-yl)quinolin-2(1H)-one | 402.5 |
| 889 | 4-amino-5-fluoro-3-{6-[(2-piperidin-1-ylethyl)amino]-1H-benzimidazol-2-yl}quinolin-2(1H)-one | 421.5 |
| 890 | 4,6-diamino-3-[6-(4-methylpiperazin-1-yl)-1H-benzimidazol-2-yl]quinolin-2(1H)-one | 390.5 |
| 891 | 2-(4-amino-5-fluoro-2-oxo-1,2-dihydroquinolin-3-yl)-1H-benzimidazole-5-carboxylic acid | 339.3 |
| 892 | 2-(4-amino-2-oxo-1,2-dihydroquinolin-3-yl)-N-pyridin-3-yl-1H-benzimidazole-5-carboxamide | 397.4 |
| 893 | 4-amino-3-(5-{[(3R)-3-hydroxypyrrolidin-1-yl]carbonyl}-1H-benzimidazol-2-yl)quinolin-2(1H)-one | 390.4 |
| 894 | N-{4-amino-3-[6-(4-methylpiperazin-1-yl)-1H-benzimidazol-2-yl]-2-oxo-1,2-dihydroquinolin-6-yl}acetamide | 432.5 |
| 895 | 4-amino-5-fluoro-3-(6-morpholin-4-yl-1H-benzimidazol-2-yl)quinolin-2(1H)-one | 380.4 |
| 896 | 3-(5-chloro-1H-benzimidazol-2-yl)-4-{[2-(dimethylamino)ethyl]amino}-6-methylquinolin-2(1H)-one | 396.9 |
| 897 | 4-{[(1R,2R)-2-aminocyclohexyl]amino}-3-(5-chloro-1H-benzimidazol-2-yl)-6-methylquinolin-2(1H)-one | 422.9 |
| 898 | 3-(5-chloro-1H-benzimidazol-2-yl)-6-methyl-4-[(piperidin-3-ylmethyl)amino]quinolin-2(1H)-one | 422.9 |
| 899 | 3-(5-chloro-1H-benzimidazol-2-yl)-6-methyl-4-[(piperidin-4-ylmethyl)amino]quinolin-2(1H)-one | 422.9 |
| 900 | 4-[(4-aminocyclohexyl)amino]-3-(5-chloro-1H-benzimidazol-2-yl)-6-methylquinolin-2(1H)-one | 422.9 |
| 901 | 3-(5-chloro-1H-benzimidazol-2-yl)-6-methyl-4-{[2-(methylamino)ethyl]amino}quinolin-2(1H)-one | 382.9 |
| 902 | 3-(5-chloro-1H-benzimidazol-2-yl)-6-methyl-4-(pyrrolidin-3-ylamino)quinolin-2(1H)-one | 394.9 |
| 903 | 3-(5-chloro-1H-benzimidazol-2-yl)-6-methyl-4-[(piperidin-2-ylmethyl)amino]quinolin-2(1H)-one | 422.9 |
| 904 | 4-[(3S)-1-azabicyclo[2.2.2]oct-3-ylamino]-3-(5-chloro-1H-benzimidazol-2-yl)-6-methylquinolin-2(1H)-one | 434.9 |
| 905 | 4-[(3R)-1-azabicyclo[2.2.2]oct-3-ylamino]-3-(5-chloro-1H-benzimidazol-2-yl)-6-methylquinolin-2(1H)-one | 434.9 |
| 906 | 4-amino-3-(6-{(2R,5R)-2-[(dimethylamino)methyl]-5-methylmorpholin-4-yl}-1H-benzimidazol-2-yl)quinolin-2(1H)-one | 433.5 |
| 907 | 4-amino-3-(5-{[(3R)-3-hydroxypiperidin-1-yl]carbonyl}-1H-benzimidazol-2-yl)quinolin-2(1H)-one | 404.4 |
| 908 | 2-(4-amino-2-oxo-1,2-dihydroquinolin-3-yl)-N-(2-piperidin-1-ylethyl)-1H-benzimidazole-5-carboxamide | 431.5 |
| 909 | 4-amino-3-[5-(piperazin-1-ylcarbonyl)-1H-benzimidazol-2-yl]quinolin-2(1H)-one | 389.4 |
| 910 | N-{4-amino-3-[6-(4-methylpiperazin-1-yl)-1H-benzimidazol-2-yl]-2-oxo-1,2-dihydroquinolin-6-yl}-2,2-dimethylpropanamide | 474.6 |
| 911 | N-{4-amino-3-[6-(4-methylpiperazin-1-yl)-1H-benzimidazol-2-yl]-2-oxo-1,2-dihydroquinolin-6-yl}-3-phenylpropanamide | 522.6 |
| 912 | N-{4-amino-3-[6-(4-methylpiperazin-1-yl)-1H-benzimidazol-2-yl]-2-oxo-1,2-dihydroquinolin-6-yl}-2-(benzyloxy)acetamide | 538.6 |
| 913 | N-{4-amino-3-[6-(4-methylpiperazin-1-yl)-1H-benzimidazol-2-yl]-2-oxo-1,2-dihydroquinolin-6-yl}-2-thien-2-ylacetamide | 514.6 |
| 914 | N-{4-amino-3-[6-(4-methylpiperazin-1-yl)-1H-benzimidazol-2-yl]-2-oxo-1,2-dihydroquinolin-6-yl}-2-furamide | 484.5 |
| 915 | 2-(4-amino-2-oxo-1,2-dihydroquinolin-3-yl)-N-(2-pyrrolidin-1-ylethyl)-1H-benzimidazole-5-carboxamide | 417.5 |
| 916 | ethyl (4-{[2-(4-amino-2-oxo-1,2-dihydroquinolin-3-yl)-1H-benzimidazol-5-yl]carbonyl}piperazin-1-yl)acetate | 475.5 |
| 917 | N-{4-amino-3-[6-(4-methylpiperazin-1-yl)-1H-benzimidazol-2-yl]-2-oxo-1,2-dihydroquinolin-6-yl}-N'-phenylurea | 509.6 |
| 918 | N-{4-amino-3-[6-(4-methylpiperazin-1-yl)-1H-benzimidazol-2-yl]-2-oxo-1,2-dihydroquinolin-6-yl}-N'-benzylurea | 523.6 |

TABLE 3-continued

Table of Examples 339-1273.

| Example | Name | LC/MS m/z (MH+) |
|---|---|---|
| 919 | N-{4-amino-3-[6-(4-methylpiperazin-1-yl)-1H-benzimidazol-2-yl]-2-oxo-1,2-dihydroquinolin-6-yl}-N'-(2-phenylethyl)urea | 537.6 |
| 920 | N-{4-amino-3-[6-(4-methylpiperazin-1-yl)-1H-benzimidazol-2-yl]-2-oxo-1,2-dihydroquinolin-6-yl}benzamide | 494.6 |
| 921 | 2-(4-amino-2-oxo-1,2-dihydroquinolin-3-yl)-N-piperidin-3-yl-1H-benzimidazole-5-carboxamide | 403.5 |
| 922 | 2-(4-amino-2-oxo-1,2-dihydroquinolin-3-yl)-N-[(3R)-1-azabicyclo[2.2.2]oct-3-yl]-1H-benzimidazole-6-carboxamide | 429.5 |
| 923 | 2-(4-amino-2-oxo-1,2-dihydroquinolin-3-yl)-N-[2-(diethylamino)ethyl]-N-ethyl-1H-benzimidazole-5-carboxamide | 447.6 |
| 924 | 4-amino-3-[6-(pyridin-4-yloxy)-1H-benzimidazol-2-yl]quinolin-2(1H)-one | 370.4 |
| 925 | 4-amino-5-fluoro-3-{6-[(4-methylpiperazin-1-yl)carbonyl]-1H-benzimidazol-2-yl}quinolin-2(1H)-one | 421.4 |
| 926 | 4-amino-5-fluoro-3-{6-[(4-isopropylpiperazin-1-yl)carbonyl]-1H-benzimidazol-2-yl}quinolin-2(1H)-one | 449.5 |
| 927 | 4-amino-3-{6-[(4-cyclohexylpiperazin-1-yl)carbonyl]-1H-benzimidazol-2-yl}-5-fluoroquinolin-2(1H)-one | 489.6 |
| 928 | 4-amino-6-(isobutylamino)-3-[6-(4-methylpiperazin-1-yl)-1H-benzimidazol-2-yl]quinolin-2(1H)-one | 446.6 |
| 929 | 2-(4-amino-5-fluoro-2-oxo-1,2-dihydroquinolin-3-yl)-N-methyl-N-(1-methylpyrrolidin-3-yl)-1H-benzimidazole-6-carboxamide | 488.6 |
| 930 | 4-amino-6-[(2-methylbutyl)amino]-3-[6-(4-methylpiperazin-1-yl)-1H-benzimidazol-2-yl]quinolin-2(1H)-one | 460.6 |
| 931 | 4-amino-6-[(cyclohexylmethyl)amino]-3-[6-(4-methylpiperazin-1-yl)-1H-benzimidazol-2-yl]quinolin-2(1H)-one | 486.6 |
| 932 | 4-amino-3-(6-{[(3S)-3-methylpiperazin-1-yl]carbonyl}-1H-benzimidazol-2-yl)quinolin-2(1H)-one | 403.5 |
| 933 | 2-(4-amino-2-oxo-1,2-dihydroquinolin-3-yl)-N-[(3S)-1-azabicyclo[2.2.2]oct-3-yl]-1H-benzimidazole-6-carboxamide | 429.5 |
| 934 | 4-amino-3-[6-(1,4'-bipiperidin-1'-ylcarbonyl)-1H-benzimidazol-2-yl]-5-fluoroquinolin-2(1H)-one | 489.6 |
| 935 | 2-(4-amino-5-fluoro-2-oxo-1,2-dihydroquinolin-3-yl)-N-methyl-N-(1-methylpyrrolidin-3-yl)-1H-benzimidazole-6-carboxamide | 435.5 |
| 936 | 4-amino-3-(1H-benzimidazol-2-yl)-5-[(4-methoxyphenyl)thio]quinolin-2(1H)-one | 415.5 |
| 937 | 4-amino-3-(1H-benzimidazol-2-yl)-5-[(4-methoxyphenyl)sulfonyl]quinolin-2(1H)-one | 447.5 |
| 938 | 4-amino-3-(1H-benzimidazol-2-yl)-5-[(2-methoxyphenyl)thio]quinolin-2(1H)-one | 415.5 |
| 939 | N-(4-{[2-(4-amino-2-oxo-1,2-dihydroquinolin-3-yl)-1H-benzimidazol-5-yl]oxy}phenyl)acetamide | 426.4 |
| 940 | 4-amino-6-(benzylamino)-3-[6-(4-methylpiperazin-1-yl)-1H-benzimidazol-2-yl]quinolin-2(1H)-one | 480.6 |
| 941 | 4-amino-3-[6-(4-methylpiperazin-1-yl)-1H-benzimidazol-2-yl]-6-{[(3-phenoxythien-2-yl)methyl]amino}quinolin-2(1H)-one | 578.7 |
| 942 | 4-amino-3-[6-(4-methylpiperazin-1-yl)-1H-benzimidazol-2-yl]-6-{[(3-methylthien-2-yl)methyl]amino}quinolin-2(1H)-one | 500.6 |
| 943 | 4-amino-3-[6-(4-methylpiperazin-1-yl)-1H-benzimidazol-2-yl]-6-[(1,3-thiazol-2-ylmethyl)amino]quinolin-2(1H)-one | 487.6 |
| 944 | 4-amino-3-[6-(4-methylpiperazin-1-yl)-1H-benzimidazol-2-yl]-6-[(pyrazin-2-ylmethyl)amino]quinolin-2(1H)-one | 482.6 |
| 945 | 4-amino-3-(5-{2-[(dimethylamino)methyl]-1,4-oxazepan-4-yl}-1H-benzimidazol-2-yl)-5-fluoroquinolin-2(1H)-one | 433.5 |
| 946 | 4-amino-3-(5-{2-[(dimethylamino)methyl]-1,4-oxazepan-4-yl}-1H-benzimidazol-2-yl)-5-fluoroquinolin-2(1H)-one | 451.5 |
| 947 | 6-chloro-4-{[2-(dimethylamino)-2-pyridin-3-ylethyl]amino}-3-(5-morpholin-4-yl-1H-benzimidazol-2-yl)quinolin-2(1H)-one | 545.1 |
| 948 | 6-amino-4-[(3S)-1-azabicyclo[2.2.2]oct-3-ylamino]-3-(1H-benzimidazol-2-yl)quinolin-2(1H)-one | 401.5 |
| 949 | 6-chloro-3-(5-chloro-1H-benzimidazol-2-yl)-4-{[2-(dimethylamino)ethyl]amino}quinolin-2(1H)-one | 417.3 |

TABLE 3-continued

Table of Examples 339-1273.

| Example | Name | LC/MS m/z (MH+) |
|---|---|---|
| 950 | 4-{[(1R,2R)-2-aminocyclohexyl]amino}-6-chloro-3-(5-chloro-1H-benzimidazol-2-yl)quinolin-2(1H)-one | 443.3 |
| 951 | 6-chloro-3-(5-chloro-1H-benzimidazol-2-yl)-4-[(piperidin-3-ylmethyl)amino]quinolin-2(1H)-one | 443.3 |
| 952 | 6-chloro-3-(5-chloro-1H-benzimidazol-2-yl)-4-[(piperidin-4-ylmethyl)amino]quinolin-2(1H)-one | 443.3 |
| 953 | 4-[(4-aminocyclohexyl)amino]-6-chloro-3-(5-chloro-1H-benzimidazol-2-yl)quinolin-2(1H)-one | 443.3 |
| 954 | 6-chloro-3-(5-chloro-1H-benzimidazol-2-yl)-4-{[2-(methylamino)ethyl]amino}quinolin-2(1H)-one | 403.3 |
| 955 | 6-chloro-3-(5-chloro-1H-benzimidazol-2-yl)-4-(pyrrolidin-3-ylamino)quinolin-2(1H)-one | 415.3 |
| 956 | 6-chloro-3-(5-chloro-1H-benzimidazol-2-yl)-4-[(piperidin-2-ylmethyl)amino]quinolin-2(1H)-one | 443.3 |
| 957 | 4-[(3S)-1-azabicyclo[2.2.2]oct-3-ylamino]-6-chloro-3-(5-chloro-1H-benzimidazol-2-yl)quinolin-2(1H)-one | 455.4 |
| 958 | 4-[(3R)-1-azabicyclo[2.2.2]oct-3-ylamino]-6-chloro-3-(5-chloro-1H-benzimidazol-2-yl)quinolin-2(1H)-one | 455.4 |
| 959 | 4-amino-3-[6-(4-methylpiperazin-1-yl)-1H-benzimidazol-2-yl]-6-{[(2S)-pyrrolidin-2-ylmethyl]amino}quinolin-2(1H)-one | 473.6 |
| 960 | 4-amino-6-{[(5-methylisoxazol-3-yl)methyl]amino}-3-[6-(4-methylpiperazin-1-yl)-1H-benzimidazol-2-yl]quinolin-2(1H)-one | 485.6 |
| 961 | 4-amino-3-(5-{(2S,5R)-2-[(dimethylamino)methyl]-5-methylmorpholin-4-yl}-1H-benzimidazol-2-yl)quinolin-2(1H)-one | 433.5 |
| 962 | 3-(5-chloro-1H-benzimidazol-2-yl)-4-{[2-(dimethylamino)ethyl]amino}-6,7-difluoroquinolin-2(1H)-one | 418.8 |
| 963 | 4-{[(1R,2R)-2-aminocyclohexyl]amino}-3-(5-chloro-1H-benzimidazol-2-yl)-6,7-difluoroquinolin-2(1H)-one | 444.9 |
| 964 | 3-(5-chloro-1H-benzimidazol-2-yl)-6,7-difluoro-4-[(piperidin-3-ylmethyl)amino]quinolin-2(1H)-one | 444.9 |
| 965 | 3-(5-chloro-1H-benzimidazol-2-yl)-6,7-difluoro-4-[(piperidin-4-ylmethyl)amino]quinolin-2(1H)-one | 444.9 |
| 966 | 4-[(4-aminocyclohexyl)amino]-3-(5-chloro-1H-benzimidazol-2-yl)-6,7-difluoroquinolin-2(1H)-one | 444.9 |
| 967 | 3-(5-chloro-1H-benzimidazol-2-yl)-6,7-difluoro-4-{[2-(methylamino)ethyl]amino}quinolin-2(1H)-one | 404.8 |
| 968 | 3-(5-chloro-1H-benzimidazol-2-yl)-6,7-difluoro-4-(pyrrolidin-3-ylamino)quinolin-2(1H)-one | 416.8 |
| 969 | 3-(5-chloro-1H-benzimidazol-2-yl)-6,7-difluoro-4-[(piperidin-2-ylmethyl)amino]quinolin-2(1H)-one | 444.9 |
| 970 | 4-[(3S)-1-azabicyclo[2.2.2]oct-3-ylamino]-3-(5-chloro-1H-benzimidazol-2-yl)-6,7-difluoroquinolin-2(1H)-one | 456.9 |
| 971 | 4-[(3R)-1-azabicyclo[2.2.2]oct-3-ylamino]-3-(5-chloro-1H-benzimidazol-2-yl)-6,7-difluoroquinolin-2(1H)-one | 456.9 |
| 972 | 4-amino-3-(6-{[(3R)-3-methylpiperazin-1-yl]carbonyl}-1H-benzimidazol-2-yl)quinolin-2(1H)-one | 403.5 |
| 973 | 4-amino-3-(5-{[(3S)-3-hydroxypyrrolidin-1-yl]carbonyl}-1H-benzimidazol-2-yl)quinolin-2(1H)-one | 390.4 |
| 974 | 4-amino-3-(5-{[4-(2-hydroxyethyl)piperazin-1-yl]carbonyl}-1H-benzimidazol-2-yl)quinolin-2(1H)-one | 433.5 |
| 975 | 4-amino-3-[6-(4-isopropylpiperazin-1-yl)-1H-benzimidazol-2-yl]-5-methoxyquinolin-2(1H)-one | 433.5 |
| 976 | 4-amino-3-(5-{3-[(dimethylamino)methyl]pyrrolidin-1-yl}-1H-benzimidazol-2-yl)quinolin-2(1H)-one | 403.5 |
| 977 | 4-amino-3-(5-{3-[(dimethylamino)methyl]pyrrolidin-1-yl}-1H-benzimidazol-2-yl)-5-fluoroquinolin-2(1H)-one | 421.5 |
| 978 | 4-amino-3-(6-{(2R,5S)-2-[(dimethylamino)methyl]-5-methylmorpholin-4-yl}-1H-benzimidazol-2-yl)quinolin-2(1H)-one | 433.5 |
| 979 | 4-amino-3-[6-(4-methylpiperazin-1-yl)-1H-benzimidazol-2-yl]-6-(piperidin-4-ylamino)quinolin-2(1H)-one | 473.6 |
| 980 | 6-chloro-3-[5-(4-methylpiperazin-1-yl)-1H-benzimidazol-2-yl]-4-[(3S)-pyrrolidin-3-ylamino]quinolin-2(1H)-one | 479.0 |
| 981 | 4-amino-3-{5-[(3R)-3-(dimethylamino)pyrrolidin-1-yl]-1H-benzimidazol-2-yl}-5-fluoroquinolin-2(1H)-one | 407.5 |
| 982 | 4-amino-3-{5-[(3S)-3-(dimethylamino)pyrrolidin-1-yl]-1H-benzimidazol-2-yl}-5-fluoroquinolin-2(1H)-one | 407.5 |
| 983 | 4-amino-3-[6-(2,6-dimethylmorpholin-4-yl)-1H-benzimidazol-2-yl]-5-fluoroquinolin-2(1H)-one | 408.4 |
| 984 | 4-amino-3-{6-[(3-aminopyrrolidin-1-yl)carbonyl]-1H-benzimidazol-2-yl}quinolin-2(1H)-one | 389.4 |

TABLE 3-continued

Table of Examples 339-1273.

| Example | Name | LC/MS m/z (MH+) |
|---|---|---|
| 985 | ethyl(3S,4R)-4-({[2-(4-amino-2-oxo-1,2-dihydroquinolin-3-yl)-1H-benzimidazol-6-yl]carbonyl}amino)-3-methoxypiperidine-1-carboxylate | 505.5 |
| 986 | 6-amino-3-(1H-benzimidazol-2-yl)-4-[(3S)-pyrrolidin-3-ylamino]quinolin-2(1H)-one | 361.4 |
| 987 | 4-amino-3-(6-{(2R,5S)-2-[(dimethylamino)methyl]-5-methylmorpholin-4-yl}-1H-benzimidazol-2-yl)-5-fluoroquinolin-2(1H)-one | 451.5 |
| 988 | N-{(3S)-1-[2-(4-amino-2-oxo-1,2-dihydroquinolin-3-yl)-1H-benzimidazol-6-yl]pyrrolidin-3-yl}-N-methylacetamide | 417.5 |
| 989 | 2-(4-amino-2-oxo-1,2-dihydroquinolin-3-yl)-N-piperidin-4-yl-1H-benzimidazole-6-carboxamide | 403.5 |
| 990 | 2-(4-amino-2-oxo-1,2-dihydroquinolin-3-yl)-N-[2-(1-methylpyrrolidin-2-yl)ethyl]-1H-benzimidazole-6-carboxamide | 431.5 |
| 991 | N-{4-amino-3-[6-(4-methylpiperazin-1-yl)-1H-benzimidazol-2-yl]-2-oxo-1,2-dihydroquinolin-6-yl}-N'-isopropylurea | 475.6 |
| 992 | N-{4-amino-3-[6-(4-methylpiperazin-1-yl)-1H-benzimidazol-2-yl]-2-oxo-1,2-dihydroquinolin-6-yl}-N'-(3,5-dimethylphenyl)urea | 537.6 |
| 993 | N-allyl-N'-{4-amino-3-[6-(4-methylpiperazin-1-yl)-1H-benzimidazol-2-yl]-2-oxo-1,2-dihydroquinolin-6-yl}urea | 473.6 |
| 994 | N-{4-amino-3-[6-(4-methylpiperazin-1-yl)-1H-benzimidazol-2-yl]-2-oxo-1,2-dihydroquinolin-6-yl}-N'-(tert-butyl)urea | 489.6 |
| 995 | N-{4-amino-3-[6-(4-methylpiperazin-1-yl)-1H-benzimidazol-2-yl]-2-oxo-1,2-dihydroquinolin-6-yl}-N'-[2-(methylthio)phenyl]urea | 555.7 |
| 996 | N-{4-amino-3-[6-(4-methylpiperazin-1-yl)-1H-benzimidazol-2-yl]-2-oxo-1,2-dihydroquinolin-6-yl}heptanamide | 502.6 |
| 997 | 4-amino-3-[6-(4-methylpiperazin-1-yl)-1H-benzimidazol-2-yl]-6-(neopentylamino)quinolin-2(1H)-one | 460.6 |
| 998 | N-{4-amino-3-[6-(4-methylpiperazin-1-yl)-1H-benzimidazol-2-yl]-2-oxo-1,2-dihydroquinolin-6-yl}-N'-(3,4-dichlorophenyl)urea | 578.5 |
| 999 | N-{4-amino-3-[6-(4-methylpiperazin-1-yl)-1H-benzimidazol-2-yl]-2-oxo-1,2-dihydroquinolin-6-yl}-N'-[3-(trifluoromethyl)phenyl]urea | 577.6 |
| 1000 | N-{4-amino-3-[6-(4-methylpiperazin-1-yl)-1H-benzimidazol-2-yl]-2-oxo-1,2-dihydroquinolin-6-yl}-N'-heptylurea | 531.7 |
| 1001 | N-{4-amino-3-[6-(4-methylpiperazin-1-yl)-1H-benzimidazol-2-yl]-2-oxo-1,2-dihydroquinolin-6-yl}-N'-(2-ethoxyphenyl)urea | 553.6 |
| 1002 | N-{4-amino-3-[6-(4-methylpiperazin-1-yl)-1H-benzimidazol-2-yl]-2-oxo-1,2-dihydroquinolin-6-yl}-2-methylpropanamide | 460.6 |
| 1003 | N-{4-amino-3-[6-(4-methylpiperazin-1-yl)-1H-benzimidazol-2-yl]-2-oxo-1,2-dihydroquinolin-6-yl}-4-ethylbenzamide | 522.6 |
| 1004 | N-{4-amino-3-[6-(4-methylpiperazin-1-yl)-1H-benzimidazol-2-yl]-2-oxo-1,2-dihydroquinolin-6-yl}-4-cyanobenzamide | 519.6 |
| 1005 | N-{4-amino-3-[6-(4-methylpiperazin-1-yl)-1H-benzimidazol-2-yl]-2-oxo-1,2-dihydroquinolin-6-yl}cyclohexanecarboxamide | 500.6 |
| 1006 | N-{4-amino-3-[6-(4-methylpiperazin-1-yl)-1H-benzimidazol-2-yl]-2-oxo-1,2-dihydroquinolin-6-yl}pyrazine-2-carboxamide | 496.5 |
| 1007 | N-{4-amino-3-[6-(4-methylpiperazinyl)benzimidazol-2-yl]-2-oxo(6-hydroquinolyl)}-2-[benzylamino]acetamide | 537.6 |
| 1008 | 4-amino-6-[methyl(1-methylpiperidin-4-yl)amino]-3-[6-(4-methylpiperazin-1-yl)-1H-benzimidazol-2-yl]quinolin-2(1H)-one | 501.6 |
| 1009 | 4-amino-6-[({5-[(dimethylamino)methyl]-2-furyl}methyl)amino]-3-[6-(4-methylpiperazin-1-yl)-1H-benzimidazol-2-yl]quinolin-2(1H)-one | 527.6 |
| 1010 | 4-amino-6-{[(2-ethyl-5-methyl-4H-imidazol-4-yl)methyl]amino}-3-[6-(4-methylpiperazin-1-yl)-1H-benzimidazol-2-yl]quinolin-2(1H)-one | 512.6 |

TABLE 3-continued

Table of Examples 339-1273.

| Example | Name | LC/MS m/z (MH+) |
|---|---|---|
| 1011 | N-{4-amino-3-[6-(4-methylpiperazin-1-yl)-1H-benzimidazol-2-yl]-2-oxo-1,2-dihydroquinolin-6-yl}butanamide | 460.6 |
| 1012 | 4-amino-3-(5-{[(2R)-2-(pyrrolidin-1-ylmethyl)pyrrolidin-1-yl]carbonyl}-1H-benzimidazol-2-yl)quinolin-2(1H)-one | 457.5 |
| 1013 | 4-amino-3-[5-({(2R,5R)-2-[(dimethylamino)methyl]-5-methylmorpholin-4-yl}carbonyl)-1H-benzimidazol-2-yl]quinolin-2(1H)-one | 461.5 |
| 1014 | 4-amino-3-[5-({(2S,5R)-2-[(dimethylamino)methyl]-5-methylmorpholin-4-yl}carbonyl)-1H-benzimidazol-2-yl]quinolin-2(1H)-one | 461.5 |
| 1015 | 4-amino-5-fluoro-3-(6-{[(3S)-3-methylpiperazin-1-yl]carbonyl}-1H-benzimidazol-2-yl)quinolin-2(1H)-one | 421.4 |
| 1016 | 4-amino-5-fluoro-3-(6-{[(3R)-3-methylpiperazin-1-yl]carbonyl}-1H-benzimidazol-2-yl)quinolin-2(1H)-one | 421.4 |
| 1017 | 4-amino-5-fluoro-3-(5-{[(2R)-2-(pyrrolidin-1-ylmethyl)pyrrolidin-1-yl]carbonyl}-1H-benzimidazol-2-yl)quinolin-2(1H)-one | 475.5 |
| 1018 | 4-amino-6-(dimethylamino)-3-[5-(4-methylpiperazin-1-yl)-1H-benzimidazol-2-yl]quinolin-2(1H)-one | 418.5 |
| 1019 | 4-amino-6-(methylamino)-3-[5-(4-methylpiperazin-1-yl)-1H-benzimidazol-2-yl]quinolin-2(1H)-one | 404.5 |
| 1020 | 4-amino-5-fluoro-3-[5-fluoro-6-(4-methylpiperazin-1-yl)-1H-benzimidazol-2-yl]quinolin-2(1H)-one | 411.4 |
| 1021 | 4-amino-3-[6-({(2R,5S)-2-[(dimethylamino)methyl]-5-methylmorpholin-4-yl}carbonyl)-1H-benzimidazol-2-yl]quinolin-2(1H)-one | 461.5 |
| 1022 | 4-amino-3-[6-({(2S,5S)-2-[(dimethylamino)methyl]-5-methylmorpholin-4-yl}carbonyl)-1H-benzimidazol-2-yl]quinolin-2(1H)-one | 461.5 |
| 1023 | 4-amino-3-{6-[(3,5-dimethylpiperazin-1-yl)carbonyl]-1H-benzimidazol-2-yl}quinolin-2(1H)-one | 417.5 |
| 1024 | 4-amino-3-[5-(4-ethylpiperazin-1-yl)-1H-benzimidazol-2-yl]-5-fluoroquinolin-2(1H)-one | 407.5 |
| 1025 | 4-amino-3-[6-({(2R,5S)-2-[(dimethylamino)methyl]-5-methylmorpholin-4-yl}carbonyl)-1H-benzimidazol-2-yl]-5-fluoroquinolin-2(1H)-one | 479.5 |
| 1026 | 4-amino-3-[6-({(2S,5S)-2-[(dimethylamino)methyl]-5-methylmorpholin-4-yl}carbonyl)-1H-benzimidazol-2-yl]-5-fluoroquinolin-2(1H)-one | 479.5 |
| 1027 | 4-amino-3-[5-({(2R,5R)-2-[(dimethylamino)methyl]-5-methylmorpholin-4-yl}carbonyl)-1H-benzimidazol-2-yl]-5-fluoroquinolin-2(1H)-one | 479.5 |
| 1028 | 4-amino-3-[5-({(2S,5R)-2-[(dimethylamino)methyl]-5-methylmorpholin-4-yl}carbonyl)-1H-benzimidazol-2-yl]-5-fluoroquinolin-2(1H)-one | 479.5 |
| 1029 | N-[3-({4-amino-3-[6-(4-methylpiperazin-1-yl)-1H-benzimidazol-2-yl]-2-oxo-1,2-dihydroquinolin-5-yl}oxy)phenyl]acetamide | 524.6 |
| 1030 | 4-amino-3-{6-[(4-ethylpiperazin-1-yl)carbonyl]-1H-benzimidazol-2-yl}quinolin-2(1H)-one | 417.5 |
| 1031 | 2-(4-amino-2-oxo-1,2-dihydroquinolin-3-yl)-N,N'-dimethyl-1H-benzimidazole-6-carbohydrazide | 363.4 |
| 1032 | 2-(4-amino-2-oxo-1,2-dihydroquinolin-3-yl)-N-(tetrahydrofuran-2-ylmethyl)-1H-benzimidazole-6-carboxamide | 404.4 |
| 1033 | 4-amino-5-[3-(dimethylamino)phenoxy]-3-[6-(4-methylpiperazin-1-yl)-1H-benzimidazol-2-yl]quinolin-2(1H)-one | 510.6 |
| 1034 | 4-amino-5-(4-aminophenoxy)-3-[6-(4-methylpiperazin-1-yl)-1H-benzimidazol-2-yl]quinolin-2(1H)-one | 482.6 |
| 1035 | 6-chloro-4-{[2-(dimethylamino)ethyl]amino}-3-(6-fluoro-1H-benzimidazol-2-yl)quinolin-2(1H)-one | 400.9 |
| 1036 | 4-{[(1R,2R)-2-aminocyclohexyl]amino}-6-chloro-3-(6-fluoro-1H-benzimidazol-2-yl)quinolin-2(1H)-one | 426.9 |
| 1037 | 6-chloro-3-(6-fluoro-1H-benzimidazol-2-yl)-4-[(piperidin-3-ylmethyl)amino]quinolin-2(1H)-one | 426.9 |
| 1038 | 6-chloro-3-(6-fluoro-1H-benzimidazol-2-yl)-4-[(piperidin-4-ylmethyl)amino]quinolin-2(1H)-one | 426.9 |
| 1039 | 4-[(4-aminocyclohexyl)amino]-6-chloro-3-(6-fluoro-1H-benzimidazol-2-yl)quinolin-2(1H)-one | 426.9 |
| 1040 | 6-chloro-3-(6-fluoro-1H-benzimidazol-2-yl)-4-{[2-(methylamino)ethyl]amino}quinolin-2(1H)-one | 386.8 |

TABLE 3-continued

Table of Examples 339-1273.

| Example | Name | LC/MS m/z (MH+) |
|---|---|---|
| 1041 | 6-chloro-3-(6-fluoro-1H-benzimidazol-2-yl)-4-[(3S)-pyrrolidin-3-ylamino]quinolin-2(1H)-one | 398.8 |
| 1042 | 6-chloro-3-(6-fluoro-1H-benzimidazol-2-yl)-4-[(3R)-pyrrolidin-3-ylamino]quinolin-2(1H)-one | 398.8 |
| 1043 | 6-chloro-3-(6-fluoro-1H-benzimidazol-2-yl)-4-[(piperidin-2-ylmethyl)amino]quinolin-2(1H)-one | 426.9 |
| 1044 | 4-[(3S)-1-azabicyclo[2.2.2]oct-3-ylamino]-6-chloro-3-(6-fluoro-1H-benzimidazol-2-yl)quinolin-2(1H)-one | 438.9 |
| 1045 | 6-bromo-4-{[2-(dimethylamino)ethyl]amino}-3-(6-fluoro-1H-benzimidazol-2-yl)quinolin-2(1H)-one | 445.3 |
| 1046 | 4-{[(1R,2R)-2-aminocyclohexyl]amino}-6-bromo-3-(6-fluoro-1H-benzimidazol-2-yl)quinolin-2(1H)-one | 471.3 |
| 1047 | 6-bromo-3-(6-fluoro-1H-benzimidazol-2-yl)-4-[(piperidin-3-ylmethyl)amino]quinolin-2(1H)-one | 471.3 |
| 1048 | 6-bromo-3-(6-fluoro-1H-benzimidazol-2-yl)-4-[(piperidin-4-ylmethyl)amino]quinolin-2(1H)-one | 471.3 |
| 1049 | 4-[(4-aminocyclohexyl)amino]-6-bromo-3-(6-fluoro-1H-benzimidazol-2-yl)quinolin-2(1H)-one | 471.3 |
| 1050 | 6-bromo-3-(6-fluoro-1H-benzimidazol-2-yl)-4-{[2-(methylamino)ethyl]amino}quinolin-2(1H)-one | 431.3 |
| 1051 | 6-bromo-3-(6-fluoro-1H-benzimidazol-2-yl)-4-[(3S)-pyrrolidin-3-ylamino]quinolin-2(1H)-one | 443.3 |
| 1052 | 6-bromo-3-(6-fluoro-1H-benzimidazol-2-yl)-4-[(piperidin-2-ylmethyl)amino]quinolin-2(1H)-one | 471.3 |
| 1053 | 4-[(3S)-1-azabicyclo[2.2.2]oct-3-ylamino]-6-bromo-3-(6-fluoro-1H-benzimidazol-2-yl)quinolin-2(1H)-one | 483.4 |
| 1054 | 6-bromo-3-(6-fluoro-1H-benzimidazol-2-yl)-4-[(3R)-pyrrolidin-3-ylamino]quinolin-2(1H)-one | 443.3 |
| 1055 | N-[4-({4-amino-3-[6-(4-methylpiperazin-1-yl)-1H-benzimidazol-2-yl]-2-oxo-1,2-dihydroquinolin-5-yl}oxy)phenyl]acetamide | 524.6 |
| 1056 | 4-amino-3-{6-[(4-ethylpiperazin-1-yl)carbonyl]-1H-benzimidazol-2-yl}-5-fluoroquinolin-2(1H)-one | 435.5 |
| 1057 | ethyl(3S,4R)-4-({[2-(4-amino-5-fluoro-2-oxo-1,2-dihydroquinolin-3-yl)-1H-benzimidazol-6-yl]carbonyl}amino)-3-methoxypiperidine-1-carboxylate | 523.5 |
| 1058 | 2-(4-amino-5-fluoro-2-oxo-1,2-dihydroquinolin-3-yl)-N-[(3R)-1-azabicyclo[2.2.2]oct-3-yl]-1H-benzimidazole-6-carboxamide | 447.5 |
| 1059 | 2-(4-amino-5-fluoro-2-oxo-1,2-dihydroquinolin-3-yl)-N-[(3S)-1-azabicyclo[2.2.2]oct-3-yl]-1H-benzimidazole-6-carboxamide | 447.5 |
| 1060 | 4-amino-5-fluoro-3-{5-[(5-methyl-2,5-diazabicyclo[2.2.1]hept-2-yl)carbonyl]-1H-benzimidazol-2-yl}quinolin-2(1H)-one | 433.5 |
| 1061 | 4-amino-3-[5-(1,4'-bipiperidin-1'-yl)-1H-benzimidazol-2-yl]-5-fluoroquinolin-2(1H)-one | 461.6 |
| 1062 | 4-[(3S)-1-azabicyclo[2.2.2]oct-3-ylamino]-6-chloro-3-(7-morpholin-4-yl-1H-benzimidazol-2-yl)quinolin-2(1H)-one | 506.0 |
| 1063 | 6-chloro-3-(7-morpholin-4-yl-1H-benzimidazol-2-yl)-4-(piperidin-4-ylamino)quinolin-2(1H)-one | 480.0 |
| 1064 | 6-chloro-3-(7-morpholin-4-yl-1H-benzimidazol-2-yl)-4-[(3S)-pyrrolidin-3-ylamino]quinolin-2(1H)-one | 466.0 |
| 1065 | 4-amino-7-fluoro-3-[5-(4-methylpiperazin-1-yl)-1H-benzimidazol-2-yl]quinolin-2(1H)-one | 393.4 |
| 1066 | 4-amino-3-{6-[(2,6-dimethylpiperazin-1-yl)carbonyl]-1H-benzimidazol-2-yl}quinolin-2(1H)-one | 417.5 |
| 1067 | 4-amino-3-(5-{(2S,5R)-2-[(dimethylamino)methyl]-5-methylmorpholin-4-yl}-1H-benzimidazol-2-yl)-5-fluoroquinolin-2(1H)-one | 451.5 |
| 1068 | 6-chloro-3-(5-morpholin-4-yl-1H-benzimidazol-2-yl)-4-[(3S)-pyrrolidin-3-ylamino]quinolin-2(1H)-one | 466.0 |
| 1069 | 4-amino-3-(5-{(2S,5S)-2-[(dimethylamino)methyl]-5-methylmorpholin-4-yl}-1H-benzimidazol-2-yl)-5-fluoroquinolin-2(1H)-one | 451.5 |
| 1070 | 4-amino-3-(1H-benzimidazol-2-yl)-6-[methyl(1-methylpiperidin-4-yl)amino]quinolin-2(1H)-one | 403.5 |
| 1071 | 4-amino-6-[isobutyl(methyl)amino]-3-[6-(4-methylpiperazin-1-yl)-1H-benzimidazol-2-yl]quinolin-2(1H)-one | 460.6 |
| 1072 | 4-amino-6-[(cyclohexylmethyl)(methyl)amino]-3-[6-(4-methylpiperazin-1-yl)-1H-benzimidazol-2-yl]quinolin-2(1H)-one | 500.7 |

TABLE 3-continued

Table of Examples 339-1273.

| Example | Name | LC/MS m/z (MH$^+$) |
|---|---|---|
| 1073 | 4,6-diamino-3-(6,7-dimethyl-1H-benzimidazol-2-yl)quinolin-2(1H)-one | 320.4 |
| 1074 | 4-amino-3-(6,7-dimethyl-1H-benzimidazol-2-yl)-6-(methylamino)quinolin-2(1H)-one | 334.4 |
| 1075 | 4-amino-3-(5,6-dimethyl-1H-benzimidazol-2-yl)-6-(methylamino)quinolin-2(1H)-one | 334.4 |
| 1076 | 4,6-diamino-3-(1H-benzimidazol-2-yl)quinolin-2(1H)-one | 292.3 |
| 1077 | 4-amino-3-(6,7-dimethyl-1H-benzimidazol-2-yl)-6-(isobutylamino)quinolin-2(1H)-one | 376.5 |
| 1078 | 4-amino-3-(5,6-dimethyl-1H-benzimidazol-2-yl)-6-(isobutylamino)quinolin-2(1H)-one | 376.5 |
| 1079 | N-(3-{[2-(4-amino-2-oxo-1,2-dihydroquinolin-3-yl)-1H-benzimidazol-6-yl]oxy}phenyl)acetamide | 426.4 |
| 1080 | 4-amino-3-[6-(3,4-dimethylpiperazin-1-yl)-1H-benzimidazol-2-yl]quinolin-2(1H)-one | 389.5 |
| 1081 | N-[3-({4-amino-3-[6-(4-methylpiperazin-1-yl)-1H-benzimidazol-2-yl]-2-oxo-1,2-dihydroquinolin-6-yl}oxy)phenyl]acetamide | 524.6 |
| 1082 | 4-amino-3-(6-{(2R,5R)-2-[(dimethylamino)methyl]-5-methylmorpholin-4-yl}-1H-benzimidazol-2-yl)-5-fluoroquinolin-2(1H)-one | 451.5 |
| 1083 | 4-{[(1R,2R)-2-aminocyclohexyl]amino}-6-bromo-3-(6-chloro-5-fluoro-1H-benzimidazol-2-yl)quinolin-2(1H)-one | 505.8 |
| 1084 | 6-bromo-3-(6-chloro-5-fluoro-1H-benzimidazol-2-yl)-4-[(piperidin-4-ylmethyl)amino]quinolin-2(1H)-one | 505.8 |
| 1085 | 4-[(4-aminocyclohexyl)amino]-6-bromo-3-(6-chloro-5-fluoro-1H-benzimidazol-2-yl)quinolin-2(1H)-one | 505.8 |
| 1086 | 6-bromo-3-(6-chloro-5-fluoro-1H-benzimidazol-2-yl)-4-{[2-(methylamino)ethyl]amino}quinolin-2(1H)-one | 465.7 |
| 1087 | 6-bromo-3-(6-chloro-5-fluoro-1H-benzimidazol-2-yl)-4-(pyrrolidin-3-ylamino)quinolin-2(1H)-one | 477.7 |
| 1088 | 6-bromo-3-(6-chloro-5-fluoro-1H-benzimidazol-2-yl)-4-[(3R)-pyrrolidin-3-ylamino]quinolin-2(1H)-one | 477.7 |
| 1089 | 6-bromo-3-(6-chloro-5-fluoro-1H-benzimidazol-2-yl)-4-[(piperidin-2-ylmethyl)amino]quinolin-2(1H)-one | 505.8 |
| 1090 | 4-[(3S)-1-azabicyclo[2.2.2]oct-3-ylamino]-6-bromo-3-(6-chloro-5-fluoro-1H-benzimidazol-2-yl)quinolin-2(1H)-one | 517.8 |
| 1091 | 4-[(3R)-1-azabicyclo[2.2.2]oct-3-ylamino]-6-bromo-3-(6-chloro-5-fluoro-1H-benzimidazol-2-yl)quinolin-2(1H)-one | 517.8 |
| 1092 | 4-[(3R)-1-azabicyclo[2.2.2]oct-3-ylamino]-6-bromo-3-(6-fluoro-1H-benzimidazol-2-yl)quinolin-2(1H)-one | 483.4 |
| 1093 | 4-[(3R)-1-azabicyclo[2.2.2]oct-3-ylamino]-6-chloro-3-(6-fluoro-1H-benzimidazol-2-yl)quinolin-2(1H)-one | 438.9 |
| 1094 | 4-amino-6-[bis(cyclohexylmethyl)amino]-3-(6,7-dimethyl-1H-benzimidazol-2-yl)quinolin-2(1H)-one | 512.7 |
| 1095 | 4-amino-6-[bis(cyclohexylmethyl)amino]-3-(5,6-dimethyl-1H-benzimidazol-2-yl)quinolin-2(1H)-one | 512.7 |
| 1096 | 4-amino-5-(methylamino)-3-[6-(4-methylpiperazin-1-yl)-1H-benzimidazol-2-yl]quinolin-2(1H)-one | 404.5 |
| 1097 | 4-amino-6-[(cyclohexylmethyl)amino]-3-(6,7-dimethyl-1H-benzimidazol-2-yl)quinolin-2(1H)-one | 416.5 |
| 1098 | 4-amino-6-[(cyclohexylmethyl)amino]-3-(5,6-dimethyl-1H-benzimidazol-2-yl)quinolin-2(1H)-one | 416.5 |
| 1099 | 4-amino-6,7-difluoro-3-[5-(4-methylpiperazin-1-yl)-1H-benzimidazol-2-yl]quinolin-2(1H)-one | 411.4 |
| 1100 | 4-amino-5-fluoro-3-[6-(2-methylpiperazin-1-yl)-1H-benzimidazol-2-yl]quinolin-2(1H)-one | 393.4 |
| 1101 | 4-amino-7-fluoro-3-{6-[(4-isopropylpiperazin-1-yl)carbonyl]-1H-benzimidazol-2-yl}quinolin-2(1H)-one | 449.5 |
| 1102 | 4-amino-3-[6-(2,4-dimethylpiperazin-1-yl)-1H-benzimidazol-2-yl]-5-fluoroquinolin-2(1H)-one | 407.5 |
| 1103 | 2-(4-amino-7-fluoro-2-oxo-1,2-dihydroquinolin-3-yl)-N-methyl-N-(1-methylpiperidin-4-yl)-1H-benzimidazole-5-carboxamide | 449.5 |
| 1104 | 6-chloro-3-(5-chloro-1H-benzimidazol-2-yl)-4-[(3S)-pyrrolidin-3-ylamino]quinolin-2(1H)-one | 415.3 |
| 1105 | 4-amino-7-fluoro-3-(5-{[(2R)-2-(pyrrolidin-1-ylmethyl)pyrrolidin-1-yl]carbonyl}-1H-benzimidazol-2-yl)quinolin-2(1H)-one | 475.5 |
| 1106 | 4-amino-3-{6-[4-(2-methoxyethyl)piperazin-1-yl]-1H-benzimidazol-2-yl}quinolin-2(1H)-one | 419.5 |
| 1107 | 4-amino-3-[5-(methylamino)-1H-benzimidazol-2-yl]quinolin-2(1H)-one | 306.3 |

TABLE 3-continued

Table of Examples 339-1273.

| Example | Name | LC/MS m/z (MH+) |
|---|---|---|
| 1108 | 6-chloro-3-[5-(4-methylpiperazin-1-yl)-1H-benzimidazol-2-yl]-4-{[(3S)-1-methylpyrrolidin-3-yl]amino}quinolin-2(1H)-one | 493.0 |
| 1109 | 6-chloro-3-(5-chloro-1H-benzimidazol-2-yl)-4-{[(3S)-1-methylpyrrolidin-3-yl]amino}quinolin-2(1H)-one | 429.3 |
| 1110 | 3-(1H-benzimidazol-2-yl)-6-chloro-4-{[(3S)-1-methylpyrrolidin-3-yl]amino}quinolin-2(1H)-one | 394.9 |
| 1111 | 3-(1H-benzimidazol-2-yl)-6-chloro-4-[(1-methylpiperidin-4-yl)amino]quinolin-2(1H)-one | 408.9 |
| 1112 | 6-chloro-3-(5-chloro-1H-benzimidazol-2-yl)-4-[(1-methylpiperidin-4-yl)amino]quinolin-2(1H)-one | 443.3 |
| 1113 | 6-chloro-3-[5-(4-methylpiperazin-1-yl)-1H-benzimidazol-2-yl]-4-[(1-methylpiperidin-4-yl)amino]quinolin-2(1H)-one | 507.1 |
| 1114 | 6-chloro-3-[5-(4-methylpiperazin-1-yl)-1H-benzimidazol-2-yl]-4-{[(1-methylpiperidin-2-yl)methyl]amino}quinolin-2(1H)-one | 521.1 |
| 1115 | 4-[(3S)-1-azabicyclo[2.2.2]oct-3-ylamino]-6-chloro-3-{5-[methyl(1-methylpiperidin-4-yl)amino]-1H-benzimidazol-2-yl}quinolin-2(1H)-one | 547.1 |
| 1116 | 6-chloro-3-{5-[methyl(1-methylpiperidin-4-yl)amino]-1H-benzimidazol-2-yl}-4-(piperidin-4-ylamino)quinolin-2(1H)-one | 521.1 |
| 1117 | 6-chloro-3-{5-[methyl(1-methylpiperidin-4-yl)amino]-1H-benzimidazol-2-yl}-4-[(3S)-pyrrolidin-3-ylamino]quinolin-2(1H)-one | 507.1 |
| 1118 | 4-{[(2R)-2-aminobutyl]amino}-6-chloro-3-{5-[methyl(1-methylpiperidin-4-yl)amino]-1H-benzimidazol-2-yl}quinolin-2(1H)-one | 509.1 |
| 1119 | 4-amino-3-{6-[(3S)-3,4-dimethylpiperazin-1-yl]-1H-benzimidazol-2-yl}quinolin-2(1H)-one | 389.5 |
| 1120 | 4-amino-3-[5-(4-methylpiperazin-1-yl)-1H-benzimidazol-2-yl]-2-oxo-1,2-dihydroquinoline-6-carbonitrile | 400.5 |
| 1121 | 4-amino-3-[5-(4-methylpiperazin-1-yl)-1H-benzimidazol-2-yl]-2-oxo-1,2-dihydroquinoline-6-carboxylic acid | 419.5 |
| 1122 | 4-amino-5-fluoro-3-{5-[(8aS)-hexahydropyrrolo[1,2-a]pyrazin-2(1H)-yl]-1H-benzimidazol-2-yl}quinolin-2(1H)-one | 419.5 |
| 1123 | 4-amino-3-{6-[(3S)-3,4-dimethylpiperazin-1-yl]-1H-benzimidazol-2-yl}-5-fluoroquinolin-2(1H)-one | 407.5 |
| 1124 | 4-[(3S)-1-azabicyclo[2.2.2]oct-3-ylamino]-6-chloro-3-{6-[(3R)-3-(dimethylamino)pyrrolidin-1-yl]-1H-benzimidazol-2-yl}quinolin-2(1H)-one | 533.1 |
| 1125 | 6-chloro-3-{6-[(3R)-3-(dimethylamino)pyrrolidin-1-yl]-1H-benzimidazol-2-yl}-4-(piperidin-4-ylamino)quinolin-2(1H)-one | 507.1 |
| 1126 | 6-chloro-3-{6-[(3R)-3-(dimethylamino)pyrrolidin-1-yl]-1H-benzimidazol-2-yl}-4-[(3S)-pyrrolidin-3-ylamino]quinolin-2(1H)-one | 493.0 |
| 1127 | 4-{[(2R)-2-aminobutyl]amino}-6-chloro-3-{6-[(3R)-3-(dimethylamino)pyrrolidin-1-yl]-1H-benzimidazol-2-yl}quinolin-2(1H)-one | 495.0 |
| 1128 | 6-chloro-3-{6-[(3R)-3-(dimethylamino)pyrrolidin-1-yl]-1H-benzimidazol-2-yl}-4-{[(3S)-1-methylpyrrolidin-3-yl]amino}quinolin-2(1H)-one | 507.1 |
| 1129 | 6-chloro-3-{6-[(3R)-3-(dimethylamino)pyrrolidin-1-yl]-1H-benzimidazol-2-yl}-4-[(1-methylpiperidin-4-yl)amino]quinolin-2(1H)-one | 521.1 |
| 1130 | 4-amino-7-(methylamino)-3-[6-(4-methylpiperazin-1-yl)-1H-benzimidazol-2-yl]quinolin-2(1H)-one | 404.5 |
| 1131 | 3-(1H-benzimidazol-2-yl)-6-chloro-4-[(2-morpholin-4-yl-2-pyridin-3-ylethyl)amino]quinolin-2(1H)-one | 502.0 |
| 1132 | 3-(1H-benzimidazol-2-yl)-6-chloro-4-{[2-(dimethylamino)-2-pyridin-3-ylethyl]amino}quinolin-2(1H)-one | 460.0 |
| 1133 | 4-[(3S)-1-azabicyclo[2.2.2]oct-3-ylamino]-6-chloro-3-(6-{3-[(dimethylamino)methyl]pyrrolidin-1-yl}-1H-benzimidazol-2-yl)quinolin-2(1H)-one | 547.1 |
| 1134 | 6-chloro-3-(6-{3-[(dimethylamino)methyl]pyrrolidin-1-yl}-1H-benzimidazol-2-yl)-4-(piperidin-4-ylamino)quinolin-2(1H)-one | 521.1 |
| 1135 | 6-chloro-3-(6-{3-[(dimethylamino)methyl]pyrrolidin-1-yl}-1H-benzimidazol-2-yl)-4-[(3S)-pyrrolidin-3-ylamino]quinolin-2(1H)-one | 507.1 |
| 1136 | 4-{[(2R)-2-aminobutyl]amino}-6-chloro-3-(6-{3-[(dimethylamino)methyl]pyrrolidin-1-yl}-1H-benzimidazol-2-yl)quinolin-2(1H)-one | 509.1 |

TABLE 3-continued

Table of Examples 339-1273.

| Example | Name | LC/MS m/z (MH+) |
|---|---|---|
| 1137 | 6-chloro-3-(6-{3-[(dimethylamino)methyl]pyrrolidin-1-yl}-1H-benzimidazol-2-yl)-4-{[(3S)-1-methylpyrrolidin-3-yl]amino}quinolin-2(1H)-one | 521.1 |
| 1138 | 6-chloro-3-(6-{3-[(dimethylamino)methyl]pyrrolidin-1-yl}-1H-benzimidazol-2-yl)-4-[(1-methylpiperidin-4-yl)amino]quinolin-2(1H)-one | 535.1 |
| 1139 | 3-(1H-benzimidazol-2-yl)-6-chloro-4-{[(3S)-piperidin-3-ylmethyl]amino}quinolin-2(1H)-one | 408.9 |
| 1140 | 3-(1H-benzimidazol-2-yl)-6-chloro-4-{[(3R)-piperidin-3-ylmethyl]amino}quinolin-2(1H)-one | 408.9 |
| 1141 | N-(3-{[4-amino-3-(1H-benzimidazol-2-yl)-2-oxo-1,2-dihydroquinolin-5-yl]oxy}phenyl)acetamide | 426.4 |
| 1142 | 4-[(3S)-1-azabicyclo[2.2.2]oct-3-ylamino]-6-chloro-3-{6-[3-(dimethylamino)pyrrolidin-1-yl]-1H-benzimidazol-2-yl}quinolin-2(1H)-one | 533.1 |
| 1143 | 6-chloro-3-{6-[3-(dimethylamino)pyrrolidin-1-yl]-1H-benzimidazol-2-yl}-4-(piperidin-4-ylamino)quinolin-2(1H)-one | 507.1 |
| 1144 | 4-{[(2R)-2-aminobutyl]amino}-6-chloro-3-{6-[3-(dimethylamino)pyrrolidin-1-yl]-1H-benzimidazol-2-yl}quinolin-2(1H)-one | 495.0 |
| 1145 | 6-chloro-3-{6-[3-(dimethylamino)pyrrolidin-1-yl]-1H-benzimidazol-2-yl}-4-[(1-methylpiperidin-4-yl)amino]quinolin-2(1H)-one | 521.1 |
| 1146 | 4-amino-7-[[2-(dimethylamino)ethyl](methyl)amino]-3-[6-(4-methylpiperazin-1-yl)-1H-benzimidazol-2-yl]quinolin-2(1H)-one | 475.6 |
| 1147 | 4-amino-5-fluoro-3-[6-(1,4-oxazepan-4-ylcarbonyl)-1H-benzimidazol-2-yl]quinolin-2(1H)-one | 422.4 |
| 1148 | methyl 4-amino-3-[5-(4-methylpiperazin-1-yl)-1H-benzimidazol-2-yl]-2-oxo-1,2-dihydroquinoline-6-carboxylate | 433.5 |
| 1149 | 4-amino-N-benzyl-3-[5-(4-methylpiperazin-1-yl)-1H-benzimidazol-2-yl]-2-oxo-1,2-dihydroquinoline-6-carboxamide | 508.6 |
| 1150 | 4-amino-3-{6-[4-(2-morpholin-4-ylethyl)piperazin-1-yl]-1H-benzimidazol-2-yl}quinolin-2(1H)-one | 474.6 |
| 1151 | 4-amino-7-fluoro-3-[6-(4-isopropylpiperazin-1-yl)-1H-benzimidazol-2-yl]quinolin-2(1H)-one | 421.5 |
| 1152 | 4-amino-3-[5-(4-ethylpiperazin-1-yl)-1H-benzimidazol-2-yl]-7-fluoroquinolin-2(1H)-one | 407.5 |
| 1153 | 4-amino-3-{6-[(2-aminoethyl)(methyl)amino]-1H-benzimidazol-2-yl}quinolin-2(1H)-one | 349.4 |
| 1154 | 4-amino-3-{6-[[(2-ethyl-4-methyl-1H-imidazol-5-yl)methyl](methyl)amino]-1H-benzimidazol-2-yl}quinolin-2(1H)-one | 428.5 |
| 1155 | 4-amino-3-[6-(hydroxymethyl)-1H-benzimidazol-2-yl]quinolin-2(1H)-one | 307.3 |
| 1156 | 4-amino-3-(6-{methyl[(2R)-pyrrolidin-2-ylmethyl]amino}-1H-benzimidazol-2-yl)quinolin-2(1H)-one | 389.5 |
| 1157 | 4-amino-3-{6-[(1H-imidazol-2-ylmethyl)(methyl)amino]-1H-benzimidazol-2-yl}quinolin-2(1H)-one | 386.4 |
| 1158 | 4-amino-3-{6-[(2-furylmethyl)(methyl)amino]-1H-benzimidazol-2-yl}quinolin-2(1H)-one | 386.4 |
| 1159 | 4-amino-3-{6-[methyl(piperidin-4-ylmethyl)amino]-1H-benzimidazol-2-yl}quinolin-2(1H)-one | 403.5 |
| 1160 | 4-amino-3-{6-[methyl(piperidin-3-ylmethyl)amino]-1H-benzimidazol-2-yl}quinolin-2(1H)-one | 403.5 |
| 1161 | 4-amino-3-(6-{methyl[2-(methylamino)ethyl]amino}-1H-benzimidazol-2-yl)quinolin-2(1H)-one | 363.4 |
| 1162 | 6-acetyl-4-amino-3-[6-(4-methylpiperazin-1-yl)-1H-benzimidazol-2-yl]quinolin-2(1H)-one | 417.5 |
| 1163 | 4-amino-5-[2-(methylamino)phenoxyl]-3-[6-(4-methylpiperazin-1-yl)-1H-benzimidazol-2-yl]quinolin-2(1H)-one | 496.6 |
| 1164 | 3-(1H-benzimidazol-2-yl)-6-chloro-4-{[(2S)-piperidin-2-ylmethyl]amino}quinolin-2(1H)-one | 408.9 |
| 1165 | 4-amino-3-[6-(1,4-oxazepan-4-yl)-1H-benzimidazol-2-yl]quinolin-2(1H)-one | 376.4 |
| 1166 | 4-amino-3-[5-(4-ethylpiperazin-1-yl)-1H-benzimidazol-2-yl]-6-fluoroquinolin-2(1H)-one | 407.5 |
| 1167 | 6-chloro-3-(5-chloro-1H-benzimidazol-2-yl)-4-[(3R)-pyrrolidin-3-ylamino]quinolin-2(1H)-one | 415.3 |

TABLE 3-continued

Table of Examples 339-1273.

| Example | Name | LC/MS m/z (MH+) |
|---|---|---|
| 1168 | 4-amino-6-fluoro-3-[5-(4-methylpiperazin-1-yl)-1H-benzimidazol-2-yl]-7-morpholin-4-ylquinolin-2(1H)-one | 478.5 |
| 1169 | 4-amino-6-fluoro-3-[5-(4-methylpiperazin-1-yl)-1H-benzimidazol-2-yl]-7-pyrrolidin-1-ylquinolin-2(1H)-one | 462.5 |
| 1170 | 4-amino-7-(dimethylamino)-6-fluoro-3-[5-(4-methylpiperazin-1-yl)-1H-benzimidazol-2-yl]quinolin-2(1H)-one | 436.5 |
| 1171 | 4-amino-6-fluoro-7-(4-methylpiperazin-1-yl)-3-[5-(4-methylpiperazin-1-yl)-1H-benzimidazol-2-yl]quinolin-2(1H)-one | 491.6 |
| 1172 | 4-amino-6-fluoro-7-[4-methoxybenzyl)amino]-3-[5-(4-methylpiperazin-1-yl)-1H-benzimidazol-2-yl]quinolin-2(1H)-one | 528.6 |
| 1173 | 4-amino-6-fluoro-3-[5-(4-methylpiperazin-1-yl)-1H-benzimidazol-2-yl]-7-[(pyridin-4-ylmethyl)amino]quinolin-2(1H)-one | 499.6 |
| 1174 | 4-amino-7-[[2-(dimethylamino)ethyl](methyl)amino]-6-fluoro-3-[5-(4-methylpiperazin-1-yl)-1H-benzimidazol-2-yl]quinolin-2(1H)-one | 493.6 |
| 1175 | 4-amino-3-[6-(4-cyclopentylpiperazin-1-yl)-1H-benzimidazol-2-yl]-5-fluoroquinolin-2(1H)-one | 447.5 |
| 1176 | 4-amino-6-[1-(methylamino)ethyl]-3-[6-(4-methylpiperazin-1-yl)-1H-benzimidazol-2-yl]quinolin-2(1H)-one | 432.5 |
| 1177 | 4-amino-5-fluoro-3-[6-(1,4-oxazepan-4-yl)-1H-benzimidazol-2-yl]quinolin-2(1H)-one | 394.4 |
| 1178 | 4-amino-3-{6-[methyl(pyridin-3-ylmethyl)amino]-1H-benzimidazol-2-yl}quinolin-2(1H)-one | 397.5 |
| 1179 | 4-amino-3-{6-[({5-[(dimethylamino)methyl]-2-furyl}methyl)(methyl)amino]-1H-benzimidazol-2-yl}quinolin-2(1H)-one | 443.5 |
| 1180 | 4-amino-3-[6-(4-oxopiperidin-1-yl)-1H-benzimidazol-2-yl]quinolin-2(1H)-one | 374.4 |
| 1181 | 4-amino-3-{6-[4-(4-methylpiperazin-1-yl)piperidin-1-yl]-1H-benzimidazol-2-yl}quinolin-2(1H)-one | 458.6 |
| 1182 | 4-amino-3-[6-(4-{[(4-benzylmorpholin-2-yl)methyl]amino}piperidin-1-yl)-1H-benzimidazol-2-yl]quinolin-2(1H)-one | 564.7 |
| 1183 | 3-(1H-benzimidazol-2-yl)-6-bromo-4-{[2-(dimethylamino)ethyl]amino}quinolin-2(1H)-one | 427.3 |
| 1184 | 4-{[(1R,2R)-2-aminocyclohexyl]amino}-3-(1H-benzimidazol-2-yl)-6-bromoquinolin-2(1H)-one | 453.4 |
| 1185 | 3-(1H-benzimidazol-2-yl)-6-bromo-4-[(piperidin-4-ylmethyl)amino]quinolin-2(1H)-one | 453.4 |
| 1186 | 4-[(4-aminocyclohexyl)amino]-3-(1H-benzimidazol-2-yl)-6-bromoquinolin-2(1H)-one | 453.4 |
| 1187 | 3-(1H-benzimidazol-2-yl)-6-bromo-4-{[2-(methylamino)ethyl]amino}quinolin-2(1H)-one | 413.3 |
| 1188 | 3-(1H-benzimidazol-2-yl)-6-bromo-4-[(3S)-pyrrolidin-3-ylamino]quinolin-2(1H)-one | 425.3 |
| 1189 | 3-(1H-benzimidazol-2-yl)-6-bromo-4-[(3R)-pyrrolidin-3-ylamino]quinolin-2(1H)-one | 425.3 |
| 1190 | 3-(1H-benzimidazol-2-yl)-6-bromo-4-[(piperidin-2-ylmethyl)amino]quinolin-2(1H)-one | 453.4 |
| 1191 | 4-amino-N-[(3S)-1-azabicyclo[2.2.2]oct-3-yl]-3-[5-(4-methylpiperazin-1-yl)-1H-benzimidazol-2-yl]-2-oxo-1,2-dihydroquinoline-6-carboxamide | 527.6 |
| 1192 | 4-amino-N-methyl-3-[5-(4-methylpiperazin-1-yl)-1H-benzimidazol-2-yl]-N-(1-methylpiperidin-4-yl)-2-oxo-1,2-dihydroquinoline-6-carboxamide | 529.7 |
| 1193 | 4-amino-3-[5-(4-methylpiperazin-1-yl)-1H-benzimidazol-2-yl]-2-oxo-N-(tetrahydrofuran-2-ylmethyl)-1,2-dihydroquinoline-6-carboxamide | 502.6 |
| 1194 | 3-(1H-benzimidazol-2-yl)-6-chloro-4-[(3R)-pyrrolidin-3-ylamino]quinolin-2(1H)-one | 380.8 |
| 1195 | 3-(1H-benzimidazol-2-yl)-6-chloro-4-{[(2R)-piperidin-2-ylmethyl]amino}quinolin-2(1H)-one | 408.9 |
| 1196 | 4-amino-3-{6-[(3R)-3,4-dimethylpiperazin-1-yl]-1H-benzimidazol-2-yl}-5-fluoroquinolin-2(1H)-one | 407.5 |
| 1197 | 6-chloro-3-(6-chloro-5-fluoro-1H-benzimidazol-2-yl)-4-{[2-(dimethylamino)ethyl]amino}quinolin-2(1H)-one | 435.3 |
| 1198 | 4-{[(1R,2R)-2-aminocyclohexyl]amino}-6-chloro-3-(6-chloro-5-fluoro-1H-benzimidazol-2-yl)quinolin-2(1H)-one | 461.3 |

TABLE 3-continued

Table of Examples 339-1273.

| Example | Name | LC/MS m/z (MH+) |
|---|---|---|
| 1199 | 6-chloro-3-(6-chloro-5-fluoro-1H-benzimidazol-2-yl)-4-[(piperidin-4-ylmethyl)amino]quinolin-2(1H)-one | 461.3 |
| 1200 | 4-[(4-aminocyclohexyl)amino]-6-chloro-3-(6-chloro-5-fluoro-1H-benzimidazol-2-yl)quinolin-2(1H)-one | 461.3 |
| 1201 | 6-chloro-3-(6-chloro-5-fluoro-1H-benzimidazol-2-yl)-4-{[2-(methylamino)ethyl]amino}quinolin-2(1H)-one | 421.3 |
| 1202 | 6-chloro-3-(6-chloro-5-fluoro-1H-benzimidazol-2-yl)-4-[(3S)-pyrrolidin-3-ylamino]quinolin-2(1H)-one | 433.3 |
| 1203 | 6-chloro-3-(6-chloro-5-fluoro-1H-benzimidazol-2-yl)-4-[(3R)-pyrrolidin-3-ylamino]quinolin-2(1H)-one | 433.3 |
| 1204 | 6-chloro-3-(6-chloro-5-fluoro-1H-benzimidazol-2-yl)-4-[(piperidin-2-ylmethyl)amino]quinolin-2(1H)-one | 461.3 |
| 1205 | 4-[(3S)-1-azabicyclo[2.2.2]oct-3-ylamino]-6-chloro-3-(6-chloro-5-fluoro-1H-benzimidazol-2-yl)quinolin-2(1H)-one | 473.3 |
| 1206 | 4-[(3R)-1-azabicyclo[2.2.2]oct-3-ylamino]-6-chloro-3-(6-chloro-5-fluoro-1H-benzimidazol-2-yl)quinolin-2(1H)-one | 473.3 |
| 1207 | 4-amino-6-fluoro-3-[6-(4-methylpiperazin-1-yl)-1H-benzimidazol-2-yl]quinolin-2(1H)-one | 393.4 |
| 1208 | 4-amino-3-(1H-benzimidazol-2-yl)-5-(methylamino)quinolin-2(1H)-one | 306.3 |
| 1209 | 4-amino-3-{6-[(2S)-2,4-dimethylpiperazin-1-yl]-1H-benzimidazol-2-yl}-5-fluoroquinolin-2(1H)-one | 407.5 |
| 1210 | 4-amino-5-fluoro-3-{6-[(2S)-2-methylpiperazin-1-yl]-1H-benzimidazol-2-yl}quinolin-2(1H)-one | 393.4 |
| 1211 | 4-amino-3-{6-[(2S)-4-isopropyl-2-methylpiperazin-1-yl]-1H-benzimidazol-2-yl}quinolin-2(1H)-one | 417.5 |
| 1212 | 4-amino-5,7-difluoro-3-[5-(4-methylpiperazin-1-yl)-1H-benzimidazol-2-yl]quinolin-2(1H)-one | 411.4 |
| 1213 | 3-(1H-benzimidazol-2-yl)-6-bromo-4-{[(2S)-piperidin-2-ylmethyl]amino}quinolin-2(1H)-one | 453.4 |
| 1214 | 3-(1H-benzimidazol-2-yl)-6-bromo-4-{[(2R)-piperidin-2-ylmethyl]amino}quinolin-2(1H)-one | 453.4 |
| 1215 | 4-amino-3-{6-[methyl(1,3-thiazol-2-ylmethyl)amino]-1H-benzimidazol-2-yl}quinolin-2(1H)-one | 403.5 |
| 1216 | 4-amino-3-{6-[(1-ethylpiperidin-4-yl)(methyl)amino]-1H-benzimidazol-2-yl}quinolin-2(1H)-one | 417.5 |
| 1217 | 4-amino-3-[6-(4-morpholin-4-ylpiperidin-1-yl)-1H-benzimidazol-2-yl]quinolin-2(1H)-one | 445.5 |
| 1218 | 4-amino-3-[6-(4-isopropylpiperazin-1-yl)-1H-benzimidazol-2-yl]-5-(methylamino)quinolin-2(1H)-one | 432.5 |
| 1219 | 4-amino-3-{6-[methyl(pyridin-2-ylmethyl)amino]-1H-benzimidazol-2-yl}quinolin-2(1H)-one | 397.5 |
| 1220 | 4-amino-3-{6-[(2S)-2,4-dimethylpiperazin-1-yl]-1H-benzimidazol-2-yl}quinolin-2(1H)-one | 389.5 |
| 1221 | 4-amino-3-{6-[(2S)-2-methylpiperazin-1-yl]-1H-benzimidazol-2-yl}quinolin-2(1H)-one | 375.4 |
| 1222 | N-[2-(4-amino-2-oxo-1,2-dihydroquinolin-3-yl)-1H-benzimidazol-6-yl]-N-methylacetamide | 348.4 |
| 1223 | 4-amino-5-fluoro-3-{6-[(2S)-4-isopropyl-2-methylpiperazin-1-yl]-1H-benzimidazol-2-yl}quinolin-2(1H)-one | 435.5 |
| 1224 | 4-amino-3-{6-[(3R)-3,4-dimethylpiperazin-1-yl]-1H-benzimidazol-2-yl}quinolin-2(1H)-one | 389.5 |
| 1225 | 4-[(3S)-1-azabicyclo[2.2.2]oct-3-ylamino]-3-(1H-benzimidazol-2-yl)-6-(dimethylamino)quinolin-2(1H)-one | 429.5 |
| 1226 | 4-amino-3-{6-[(2S)-4-cyclobutyl-2-methylpiperazin-1-yl]-1H-benzimidazol-2-yl}quinolin-2(1H)-one | 429.5 |
| 1227 | 4-amino-5-fluoro-3-[6-(methylamino)-1H-benzimidazol-2-yl]quinolin-2(1H)-one | 324.3 |
| 1228 | 4-amino-3-(1H-benzimidazol-2-yl)-5-(dimethylamino)quinolin-2(1H)-one | 320.4 |
| 1229 | 4-amino-3-(1H-benzimidazol-2-yl)-5-{[2-(dimethylamino)ethyl]amino}quinolin-2(1H)-one | 363.4 |
| 1230 | 4-amino-5-fluoro-3-(5-piperazin-1-yl-1H-benzimidazol-2-yl)quinolin-2(1H)-one | 379.4 |
| 1231 | 4-amino-3-{5-[[2-(dimethylamino)ethyl](methyl)amino]-1H-benzimidazol-2-yl}-5-fluoroquinolin-2(1H)-one | 395.5 |
| 1232 | 4-amino-5-fluoro-3-{5-[methyl(piperidin-3-ylmethyl)amino]-1H-benzimidazol-2-yl}quinolin-2(1H)-one | 421.5 |
| 1233 | 4-amino-3-(1H-benzimidazol-2-yl)-5-[[2-(dimethylamino)ethyl](methyl)amino]quinolin-2(1H)-one | 377.5 |

TABLE 3-continued

Table of Examples 339-1273.

| Example | Name | LC/MS m/z (MH+) |
|---|---|---|
| 1234 | 4-amino-5-fluoro-3-{5-[(2R)-4-isopropyl-2-methylpiperazin-1-yl]-1H-benzimidazol-2-yl}quinolin-2(1H)-one | 435.5 |
| 1235 | 4-amino-3-{5-[(2S)-4-ethyl-2-methylpiperazin-1-yl]-1H-benzimidazol-2-yl}-5-fluoroquinolin-2(1H)-one | 421.5 |
| 1236 | 4-amino-3-(5-{[(1-ethylpyrrolidin-2-yl)methyl]amino}-1H-benzimidazol-2-yl)-5-fluoroquinolin-2(1H)-one | 421.5 |
| 1237 | 4-amino-3-(5-{[2-(dimethylamino)-1-methylethyl]amino}-1H-benzimidazol-2-yl)-5-fluoroquinolin-2(1H)-one | 395.5 |
| 1238 | 4-amino-3-{5-[[2-(dimethylamino)-1-methylethyl](methyl)amino]-1H-benzimidazol-2-yl}-5-fluoroquinolin-2(1H)-one | 409.5 |
| 1239 | 4-amino-3-(1H-benzimidazol-2-yl)-5-(1,2-dimethylhydrazino)quinolin-2(1H)-one | 335.4 |
| 1240 | 4-amino-5-fluoro-3-{6-[4-(2-methoxyethyl)piperazin-1-yl]-1H-benzimidazol-2-yl}quinolin-2(1H)-one | 437.5 |
| 1241 | 4-amino-5-fluoro-3-{6-[methyl(1-methylpiperidin-4-yl)amino]-1H-benzimidazol-2-yl}quinolin-2(1H)-one | 421.5 |
| 1242 | 4-amino-5-fluoro-3-(6-{[3-(4-methylpiperazin-1-yl)propyl]amino}-1H-benzimidazol-2-yl)quinolin-2(1H)-one | 450.5 |
| 1243 | 4-amino-5-fluoro-3-(6-{methyl[3-(4-methylpiperazin-1-yl)propyl]amino}-1H-benzimidazol-2-yl)quinolin-2(1H)-one | 464.6 |
| 1244 | N-[2-(4-amino-5-fluoro-2-oxo-1,2-dihydroquinolin-3-yl)-1H-benzimidazol-6-yl]-N-methylacetamide | 366.4 |
| 1245 | 4-amino-6-fluoro-3-(5-{[(2R)-2-(pyrrolidin-1-ylmethyl)pyrrolidin-1-yl]carbonyl}-1H-benzimidazol-2-yl)quinolin-2(1H)-one | 475.5 |
| 1246 | 4-amino-3-(1H-benzimidazol-2-yl)-5-(ethylamino)quinolin-2(1H)-one | 320.4 |
| 1247 | 4-amino-3-{5-[(2R)-2,4-dimethylpiperazin-1-yl]-1H-benzimidazol-2-yl}-5-fluoroquinolin-2(1H)-one | 407.5 |
| 1248 | 4-amino-5-fluoro-3-{5-[(2R)-2-methylpiperazin-1-yl]-1H-benzimidazol-2-yl}quinolin-2(1H)-one | 393.4 |
| 1249 | 4-amino-3-{5-[(2R)-4-cyclobutyl-2-methylpiperazin-1-yl]-1H-benzimidazol-2-yl}-5-fluoroquinolin-2(1H)-one | 447.5 |
| 1250 | 4-amino-5-(dimethylamino)-3-[6-(4-isopropylpiperazin-1-yl)-1H-benzimidazol-2-yl]quinolin-2(1H)-one | 446.6 |
| 1251 | 4-amino-5-{[2-(dimethylamino)ethyl]amino}-3-[6-(4-isopropylpiperazin-1-yl)-1H-benzimidazol-2-yl]quinolin-2(1H)-one | 489.6 |
| 1252 | 4-amino-5-[[2-(dimethylamino)ethyl](methyl)amino]-3-[6-(4-isopropylpiperazin-1-yl)-1H-benzimidazol-2-yl]quinolin-2(1H)-one | 503.7 |
| 1253 | 4-amino-5-(ethylamino)-3-[6-(4-isopropylpiperazin-1-yl)-1H-benzimidazol-2-yl]quinolin-2(1H)-one | 446.6 |
| 1254 | N-[2-(4-amino-2-oxo(3-hydroquinolyl))benzimidazol-6-yl]-2-(dimethylamino)-N-methylacetamide | 391.4 |
| 1255 | 4-amino-5-fluoro-3-[6-(9-isopropyl-1-oxa-4,9-diazaspiro[5.5]undec-4-yl)-1H-benzimidazol-2-yl]quinolin-2(1H)-one | 491.6 |
| 1256 | 4-amino-7-fluoro-3-[6-fluoro-5-(4-methylpiperazin-1-yl)-1H-benzimidazol-2-yl]quinolin-2(1H)-one | 411.4 |
| 1257 | 4-amino-3-(5-{(2S,5S)-2-[(dimethylamino)methyl]-5-methylmorpholin-4-yl}-6-fluoro-1H-benzimidazol-2-yl)-5-fluoroquinolin-2(1H)-one | 469.5 |
| 1258 | 4-amino-3-(5-{(2S,5S)-2-[(dimethylamino)methyl]-5-methylmorpholin-4-yl}-6-fluoro-1H-benzimidazol-2-yl)quinolin-2(1H)-one | 451.5 |
| 1259 | 4-amino-5-methyl-3-[5-(4-methylpiperazin-1-yl)-1H-benzimidazol-2-yl]quinolin-2(1H)-one | 389.5 |
| 1260 | 4-amino-3-[5-(4-methylpiperazin-1-yl)-1H-benzimidazol-2-yl]-5-(trifluoromethyl)quinolin-2(1H)-one | 443.4 |
| 1261 | 4-amino-5-fluoro-3-[6-(2-isopropyl-5-oxa-2,8-diazaspiro[3.5]non-8-yl)-1H-benzimidazol-2-yl]quinolin-2(1H)-one | 463.5 |
| 1262 | 4-amino-6-fluoro-3-[5-(4-isopropylpiperazin-1-yl)-1H-benzimidazol-2-yl]quinolin-2(1H)-one | 421.5 |
| 1263 | N-[2-(4-amino-5-fluoro-2-oxo-1,2-dihydroquinolin-3-yl)-1H-benzimidazol-6-yl]-N-methyl-2-(4-methylpiperazin-1-yl)acetamide | 464.5 |
| 1264 | N-[2-(4-amino-5-fluoro-2-oxo-1,2-dihydroquinolin-3-yl)-1H-benzimidazol-6-yl]-N-methyl-2-morpholin-4-ylacetamide | 451.5 |

TABLE 3-continued

Table of Examples 339-1273.

| Example | Name | LC/MS m/z (MH+) |
|---|---|---|
| 1265 | N-[2-(4-amino-5-fluoro-2-oxo(3-hydroquinolyl))benzimidazol-6-yl]-N-methyl-2-morpholin-4-ylacetamide | 492.6 |
| 1266 | 4-amino-5-fluoro-3-(6-methyl-1H-benzimidazol-2-yl)quinolin-2(1H)-one | 309.3 |
| 1267 | 4-amino-3-[5-(4-ethylpiperazin-1-yl)-1H-benzimidazol-2-yl]-5-methylquinolin-2(1H)-one | 403.5 |
| 1268 | 4-amino-3-{6-[(4-methylpiperazin-1-yl)methyl]-1H-benzimidazol-2-yl}quinolin-2(1H)-one | 389.5 |
| 1269 | 4-amino-3-[6-(1,4-diazepan-1-yl)-1H-benzimidazol-2-yl]-5-fluoroquinolin-2(1H)-one | 393.4 |
| 1270 | 4-amino-5-fluoro-3-[6-(4-methyl-1,4-diazepan-1-yl)-1H-benzimidazol-2-yl]quinolin-2(1H)-one | 407.5 |
| 1271 | 3-[6-(4-acetylpiperazin-1-yl)-1H-benzimidazol-2-yl]-4-amino-5-fluoroquinolin-2(1H)-one | 421.4 |
| 1272 | 4-amino-3-[6-(4-ethyl-1,4-diazepan-1-yl)-1H-benzimidazol-2-yl]-5-fluoroquinolin-2(1H)-one | 421.5 |
| 1273 | 4-amino-5-fluoro-3-[6-(4-isopropyl-1,4-diazepan-1-yl)-1H-benzimidazol-2-yl]quinolin-2(1H)-one | 435.5 |

Examples 1274-1404

Examples 1274 to 1404 listed in Table 4 were synthesized using the methods described above such as Methods 1-24 and those set forth in the Schemes and other Examples or modified as apparent to one of reasonable skill in the art using commercially available materials.

TABLE 4

Table of Examples 1274-1415.

| Example | Name | LC/MS m/z (MH+) |
|---|---|---|
| 1274 | 4-amino-5-fluoro-3-{6-[(4-methylpiperazin-1-yl)methyl]-1H-benzimidazol-2-yl}quinolin-2(1H)-one | 407.4 |
| 1275 | N-[2-(4-amino-5-fluoro-2-oxo-1,2-dihydroquinolin-3-yl)-1H-benzimidazol-6-yl]-N-(1-methylpiperidin-4-yl)acetamide | 449.2 |
| 1276 | N-[2-(4-amino-5-fluoro-2-oxo-1,2-dihydroquinolin-3-yl)-1H-benzimidazol-6-yl]-2-[(2R,6S)-2,6-dimethylmorpholin-4-yl]-N-methylacetamide | 479.3 |
| 1277 | N-[2-(4-amino-5-fluoro-2-oxo-1,2-dihydroquinolin-3-yl)-1H-benzimidazol-6-yl]-N-methyl-2-piperidin-1-ylacetamide | 449.2 |
| 1278 | N-[2-(4-amino-5-fluoro-2-oxo-1,2-dihydroquinolin-3-yl)-1H-benzimidazol-6-yl]-N-methyl-2-pyrrolidin-1-ylacetamide | 435.2 |
| 1279 | N-[2-(4-amino-5-fluoro-2-oxo-1,2-dihydroquinolin-3-yl)-1H-benzimidazol-6-yl]-2-[(2S)-2-(methoxymethyl)pyrrolidin-1-yl]-N-methylacetamide | 479.2 |
| 1280 | N~1~-[2-(4-amino-5-fluoro-2-oxo-1,2-dihydroquinolin-3-yl)-1H-benzimidazol-6-yl]-N~1~-methyl-N~2~-(1-methylpiperidin-4-yl)glycinamide | 478.6 |
| 1281 | N-[2-(4-amino-5-fluoro-2-oxo-1,2-dihydroquinolin-3-yl)-1H-benzimidazol-6-yl]-2-{(2R,5S)-2-[(dimethylamino)methyl]-5-methylmorpholin-4-yl}-N-methylacetamide | 522.7 |
| 1282 | N-[2-(4-amino-5-fluoro-2-oxo-1,2-dihydroquinolin-3-yl)-1H-benzimidazol-6-yl]-N-methyl-2-(4-methyl-1,4-diazepan-1-yl)acetamide | 478.6 |
| 1283 | N-[2-(4-amino-5-fluoro-2-oxo-1,2-dihydroquinolin-3-yl)-1H-benzimidazol-6-yl]-2-[3-(dimethylamino)pyrrolidin-1-yl]-N-methylacetamide | 478.6 |
| 1284 | 4-amino-5-fluoro-3-{6-[4-(methylsulfonyl)piperazin-1-yl]-1H benzimidazol-2-yl}quinolin-2(1H)-one | 457.3 |
| 1285 | N-[2-(4-amino-5-fluoro-2-oxo-1,2-dihydroquinolin-3-yl)-1H-benzimidazol-6-yl]-N-[3-(4-methylpiperazin-1-yl)propyl]acetamide | 492.2 |
| 1286 | 4-amino-5-fluoro-3-(6-{[4-(methylsulfonyl)piperazin-1-yl]methyl}-1H-benzimidazol-2-yl)quinolin-2(1H)-one | 471.1 |
| 1287 | 4-amino-5-fluoro-3-(6-{[(2-methoxyethyl)amino]methyl}-1H-benzimidazol-2-yl)quinolin-2(1H)-one | 382.2 |

TABLE 4-continued

Table of Examples 1274-1415.

| Example | Name | LC/MS m/z (MH+) |
|---|---|---|
| 1288 | 4-amino-3-{6-[(4-cyclohexylpiperazin-1-yl)methyl]-1H-benzimidazol-2-yl}-5-fluoroquinolin-2(1H)-one | 475.2 |
| 1289 | 4-amino-3-{6-[(3,5-dimethylpiperazin-1-yl)methyl]-1H-benzimidazol-2-yl}-5-fluoroquinolin-2(1H)-one | 421.1 |
| 1290 | 4-amino-5-fluoro-3-(6-{[(2-morpholin-4-ylethyl)amino]methyl}-1H-benzimidazol-2-yl)quinolin-2(1H)-one | 437.2 |
| 1291 | 4-amino-5-fluoro-3-[6-({[2-(2-oxoimidazolidin-1-yl)ethyl]amino}methyl)-1H-benzimidazol-2-yl]quinolin-2(1H)-one | 436.3 |
| 1292 | 4-amino-5-fluoro-3-[6-({[3-(1H-imidazol-1-yl)propyl]amino}methyl)-1H-benzimidazol-2-yl]quinolin-2(1H)-one | 432.3 |
| 1293 | 4-amino-5-fluoro-3-{6-[(4-pyrrolidin-1-ylpiperidin-1-yl)methyl]-1H-benzimidazol-2-yl}quinolin-2(1H)-one | 461.4 |
| 1294 | 4-amino-3-[6-({[(3R)-1-benzylpyrrolidin-3-yl]amino}methyl)-1H-benzimidazol-2-yl]-5-fluoroquinolin-2(1H)-one | 483.3 |
| 1295 | 4-amino-5-fluoro-3-(6-{[(1-methylpiperidin-4-yl)amino]methyl}-1H-benzimidazol-2-yl)quinolin-2(1H)-one | 421.5 |
| 1296 | 4-amino-5-fluoro-3-(6-{[4-(hydroxymethyl)piperidin-1-yl]methyl}-1H-benzimidazol-2-yl)quinolin-2(1H)-one | 422.4 |
| 1297 | 4-amino-5-fluoro-3-[6-({[2-(1H-imidazol-4-yl)ethyl]amino}methyl)-1H-benzimidazol-2-yl]quinolin-2(1H)-one | 418.4 |
| 1298 | 4-amino-5-fluoro-3-(6-{[(2-pyridin-4-ylethyl)amino]methyl}-1H-benzimidazol-2-yl)quinolin-2(1H)-one | 429.4 |
| 1299 | 4-amino-5-fluoro-3-(6-{[(2-pyridin-3-ylethyl)amino]methyl}-1H-benzimidazol-2-yl)quinolin-2(1H)-one | 429.3 |
| 1300 | 4-amino-5-fluoro-3-(6-{[methyl(2-pyridin-2-ylethyl)amino]methyl}-1H-benzimidazol-2-yl)quinolin-2(1H)-one | 443.3 |
| 1301 | 4-amino-5-fluoro-3-(6-{[(pyridin-4-ylmethyl)amino]methyl}-1H-benzimidazol-2-yl)quinolin-2(1H)-one | 415.3 |
| 1302 | 4-amino-5-fluoro-3-(6-{[(pyridin-3-ylmethyl)amino]methyl}-1H-benzimidazol-2-yl)quinolin-2(1H)-one | 415.4 |
| 1303 | 4-amino-5-fluoro-3-(6-{[(pyridin-2-ylmethyl)amino]methyl}-1H-benzimidazol-2-yl)quinolin-2(1H)-one | 415.4 |
| 1304 | 4-amino-3-[6-(anilinomethyl)-1H-benzimidazol-2-yl]-5-fluoroquinolin-2(1H)-one | 400.4 |
| 1305 | 4-amino-5-fluoro-3-[6-(morpholin-4-ylmethyl)-1H-benzimidazol-2-yl]quinolin-2(1H)-one | 394.4 |
| 1306 | N~1~-[2-(4-amino-5-fluoro-2-oxo-1,2-dihydroquinolin-3-yl)-1H-benzimidazol-6-yl]-N~2~-(2-methoxyethyl)-N~1~-methylglycinamide | 439.4 |
| 1307 | N-[2-(4-amino-5-fluoro-2-oxo-1,2-dihydroquinolin-3-yl)-1H-benzimidazol-6-yl]-2-(4-cyclohexylpiperazin-1-yl)-N-methylacetamide | 532.5 |
| 1308 | N-[2-(4-amino-5-fluoro-2-oxo-1,2-dihydroquinolin-3-yl)-1H-benzimidazol-6-yl]-2-(3,5-dimethylpiperazin-1-yl)-N-methylacetamide | 478.4 |
| 1309 | N~1~-[2-(4-amino-5-fluoro-2-oxo-1,2-dihydroquinolin-3-yl)-1H-benzimidazol-6-yl]-N~1~-methyl-N~2~-(2-morpholin-4-ylethyl)glycinamide | 494.4 |
| 1310 | N~1~-[2-(4-amino-5-fluoro-2-oxo-1,2-dihydroquinolin-3-yl)-1H-benzimidazol-6-yl]-N~1~-methyl-N~2~-[2-(2-oxoimidazolidin-1-yl)ethyl]glycinamide | 493.4 |
| 1311 | N~1~-[2-(4-amino-5-fluoro-2-oxo-1,2-dihydroquinolin-3-yl)-1H-benzimidazol-6-yl]-N~2~-[3-(1H-imidazol-1-yl)propyl]-N~1~-methylglycinamide | 489.4 |
| 1312 | N-[2-(4-amino-5-fluoro-2-oxo-1,2-dihydroquinolin-3-yl)-1H-benzimidazol-6-yl]-N-methyl-2-(4-pyrrolidin-1-ylpiperidin-1-yl)acetamide | 518.4 |
| 1313 | N~1~-[2-(4-amino-5-fluoro-2-oxo-1,2-dihydroquinolin-3-yl)-1H-benzimidazol-6-yl]-N~2~-[(3R)-1-benzylpyrrolidin-3-yl]-N~1~-methylglycinamide | 540.4 |
| 1314 | N-[2-(4-amino-5-fluoro-2-oxo-1,2-dihydroquinolin-3-yl)-1H-benzimidazol-6-yl]-2-[4-(hydroxymethyl)piperidin-1-yl]-N-methylacetamide | 479.4 |
| 1315 | N~1~-[2-(4-amino-5-fluoro-2-oxo-1,2-dihydroquinolin-3-yl)-1H-benzimidazol-6-yl]-N~2~-[2-(1H-imidazol-4-yl)ethyl]-N~1~-methylglycinamide | 475.4 |

TABLE 4-continued

Table of Examples 1274-1415.

| Example | Name | LC/MS m/z (MH+) |
|---|---|---|
| 1316 | N~1~-[2-(4-amino-5-fluoro-2-oxo-1,2-dihydroquinolin-3-yl)-1H-benzimidazol-6-yl]-N~1~-methyl-N~2~-(2-pyridin-4-ylethyl)glycinamide | 486.4 |
| 1317 | N~1~-[2-(4-amino-5-fluoro-2-oxo-1,2-dihydroquinolin-3-yl)-1H-benzimidazol-6-yl]-N~1~-methyl-N~2~-(2-pyridin-3-ylethyl)glycinamide | 486.4 |
| 1318 | N~1~-[2-(4-amino-5-fluoro-2-oxo-1,2-dihydroquinolin-3-yl)-1H-benzimidazol-6-yl]-N~1~,N~2~-dimethyl-N~2~-(2-pyridin-2-ylethyl)glycinamide | 500.4 |
| 1319 | N~1~-[2-(4-amino-5-fluoro-2-oxo-1,2-dihydroquinolin-3-yl)-1H-benzimidazol-6-yl]-N~1~-methyl-N~2~-(pyridin-4-ylmethyl)glycinamide | 472.4 |
| 1320 | N~1~-[2-(4-amino-5-fluoro-2-oxo-1,2-dihydroquinolin-3-yl)-1H-benzimidazol-6-yl]-N~1~-methyl-N~2~-(pyridin-3-ylmethyl)glycinamide | 472.4 |
| 1321 | N~1~-[2-(4-amino-5-fluoro-2-oxo-1,2-dihydroquinolin-3-yl)-1H-benzimidazol-6-yl]-N~1~-methyl-N~2~-(pyridin-2-ylmethyl)glycinamide | 472.4 |
| 1322 | N~1~-[2-(4-amino-5-fluoro-2-oxo-1,2-dihydroquinolin-3-yl)-1H-benzimidazol-6-yl]-N~2~-[(1-ethylpyrrolidin-3-yl)methyl]-N~1~-methylglycinamide | 492.3 |
| 1323 | N~1~-[2-(4-amino-5-fluoro-2-oxo-1,2-dihydroquinolin-3-yl)-1H-benzimidazol-6-yl]-N~1~-methyl-N~2~-[3-(4-methylpiperazin-1-yl)propyl]glycinamide | 521.3 |
| 1324 | N~1~-[2-(4-amino-5-fluoro-2-oxo-1,2-dihydroquinolin-3-yl)-1H-benzimidazol-6-yl]-N~1~-methyl-N~2~-1,3-thiazol-2-ylglycinamide | 464.2 |
| 1325 | N~1~-[2-(4-amino-5-fluoro-2-oxo-1,2-dihydroquinolin-3-yl)-1H-benzimidazol-6-yl]-N~1~-methyl-N~2~-[2-(1-methylpyrrolidin-3-yl)ethyl]glycinamide | 492.4 |
| 1326 | N~1~-[2-(4-amino-5-fluoro-2-oxo-1,2-dihydroquinolin-3-yl)-1H-benzimidazol-6-yl]-N~1~-methyl-N~2~-(2-pyrrolidin-1-ylethyl)glycinamide | 478.3 |
| 1327 | N~1~-[2-(4-amino-5-fluoro-2-oxo-1,2-dihydroquinolin-3-yl)-1H-benzimidazol-6-yl]-N~1~,N~2~-dimethyl-N~2~-[2-(methylamino)ethyl]glycinamide | 452.4 |
| 1328 | N~1~-[2-(4-amino-5-fluoro-2-oxo-1,2-dihydroquinolin-3-yl)-1H-benzimidazol-6-yl]-N~2~-(2-hydroxyethyl)-N~1~-methylglycinamide | 425.3 |
| 1329 | N~1~-[2-(4-amino-5-fluoro-2-oxo-1,2-dihydroquinolin-3-yl)-1H-benzimidazol-6-yl]-N~1~-methyl-N~2~-(2-piperidin-1-ylethyl)glycinamide | 492.4 |
| 1330 | N~1~-[2-(4-amino-5-fluoro-2-oxo-1,2-dihydroquinolin-3-yl)-1H-benzimidazol-6-yl]-N~1~-methyl-N~2~-(3-piperidin-1-ylpropyl)glycinamide | 506.4 |
| 1331 | N~1~-[2-(4-amino-5-fluoro-2-oxo-1,2-dihydroquinolin-3-yl)-1H-benzimidazol-6-yl]-N~1~-methyl-N~2~-(3-pyrrolidin-1-ylpropyl)glycinamide | 492.4 |
| 1332 | N~1~-[2-(4-amino-5-fluoro-2-oxo-1,2-dihydroquinolin-3-yl)-1H-benzimidazol-6-yl]-N~2~-(3-methoxypropyl)-N~1~-methylglycinamide | 453.4 |
| 1333 | N~1~-[2-(4-amino-5-fluoro-2-oxo-1,2-dihydroquinolin-3-yl)-1H-benzimidazol-6-yl]-N~2~,N~2~-diisopropyl-N~1~-methylglycinamide | 465.4 |
| 1334 | N-[2-(4-amino-5-fluoro-2-oxo-1,2-dihydroquinolin-3-yl)-1H-benzimidazol-6-yl]-N-methyl-2-(2-methylaziridin-1-yl)acetamide | 421.3 |
| 1335 | 4-amino-3-[6-({[(1-ethylpyrrolidin-3-yl)methyl]amino}methyl)-1H-benzimidazol-2-yl]-5-fluoroquinolin-2(1H)-one | 435.4 |
| 1336 | 4-amino-5-fluoro-3-[6-({[3-(4-methylpiperazin-1-yl)propyl]amino}methyl)-1H-benzimidazol-2-yl]quinolin-2(1H)-one | 464.4 |
| 1337 | 4-amino-5-fluoro-3-{6-[(1,3-thiazol-2-ylamino)methyl]-1H-benzimidazol-2-yl}quinolin-2(1H)-one | 407.3 |
| 1338 | 4-amino-5-fluoro-3-[6-({[2-(1-methylpyrrolidin-3-yl)ethyl]amino}methyl)-1H-benzimidazol-2-yl]quinolin-2(1H)-one | 435.4 |
| 1339 | 4-amino-5-fluoro-3-(6-{[(2-pyrrolidin-1-ylethyl)amino]methyl}-1H-benzimidazol-2-yl)quinolin-2(1H)-one | 421.4 |
| 1340 | 4-amino-5-fluoro-3-[6-({methyl[2-(methylamino)ethyl]amino}methyl)-1H-benzimidazol-2-yl]quinolin-2(1H)-one | 395.4 |

TABLE 4-continued

Table of Examples 1274-1415.

| Example | Name | LC/MS m/z (MH+) |
|---|---|---|
| 1341 | 4-amino-5-fluoro-3-(6-{[(2-hydroxyethyl)amino]methyl}-1H-benzimidazol-2-yl)quinolin-2(1H)-one | 368.3 |
| 1342 | 4-amino-5-fluoro-3-(6-{[(2-piperidin-1-ylethyl)amino]methyl}-1H-benzimidazol-2-yl)quinolin-2(1H)-one | 435.4 |
| 1343 | 4-amino-5-fluoro-3-(6-{[(3-piperidin-1-ylpropyl)amino]methyl}-1H-benzimidazol-2-yl)quinolin-2(1H)-one | 449.4 |
| 1344 | 4-amino-5-fluoro-3-(6-{[(3-pyrrolidin-1-ylpropyl)amino]methyl}-1H-benzimidazol-2-yl)quinolin-2(1H)-one | 435.4 |
| 1345 | 4-amino-5-fluoro-3-(6-{[(3-methoxypropyl)amino]methyl}-1H-benzimidazol-2-yl)quinolin-2(1H)-one | 396.4 |
| 1346 | N-[2-({[2-(4-amino-5-fluoro-2-oxo-1,2-dihydroquinolin-3-yl)-1H-benzimidazol-6-yl]methyl}amino)ethyl]acetamide | 409.4 |
| 1347 | 4-amino-3-{6-[(diisopropylamino)methyl]-1H-benzimidazol-2-yl}-5-fluoroquinolin-2(1H)-one | 408.4 |
| 1348 | 4-amino-3-{6-[(dimethylamino)methyl]-1H-benzimidazol-2-yl}-5-fluoroquinolin-2(1H)-one | 352.3 |
| 1349 | 4-amino-3-{6-[(4-ethylpiperazin-1-yl)methyl]-1H-benzimidazol-2-yl}-5-fluoroquinolin-2(1H)-one | 421.1 |
| 1350 | 4-amino-5-fluoro-3-{6-[methyl(piperidin-4-yl)amino]-1H-benzimidazol-2-yl}quinolin-2(1H)-one | 407.2 |
| 1351 | 4-amino-5-fluoro-3-[6-(piperazin-1-ylmethyl)-1H-benzimidazol-2-yl]quinolin-2(1H)-one | 493.2 |
| 1352 | 4-amino-5-fluoro-3-[5-(4-pyrrolidin-1-ylpiperidin-1-yl)-1H-benzimidazol-2-yl]quinolin-2(1H)-one | 447.1 |
| 1353 | 4-amino-5-fluoro-3-{5-[4-(trifluoromethyl)piperidin-1-yl]-1H-benzimidazol-2-yl}quinolin-2(1H)-one | 446.1 |
| 1354 | 4-amino-5-fluoro-3-{6-[3-(trifluoromethyl)piperidin-1-yl]-1H-benzimidazol-2-yl}quinolin-2(1H)-one | 446.1 |
| 1355 | 4-amino-7-fluoro-3-{6-[3-(trifluoromethyl)piperidin-1-yl]-1H-benzimidazol-2-yl}quinolin-2(1H)-one | 446.1 |
| 1356 | 4-amino-5-fluoro-3-[5-fluoro-6-(4-isopropylpiperazin-1-yl)-1H-benzimidazol-2-yl]quinolin-2(1H)-one | 439.1 |
| 1357 | 4-amino-3-[5-fluoro-6-(4-isopropylpiperazin-1-yl)-1H-benzimidazol-2-yl]quinolin-2(1H)-one | 421.4 |
| 1358 | 4-amino-3-[6-(4,4-difluoropiperidin-1-yl)-1H-benzimidazol-2-yl]-5-fluoroquinolin-2(1H)-one | 414.1 |
| 1359 | 4-amino-6-fluoro-3-[5-fluoro-6-(4-isopropylpiperazin-1-yl)-1H-benzimidazol-2-yl]quinolin-2(1H)-one | 439.2 |
| 1360 | 4-amino-3-[5,7-difluoro-6-(4-isopropylpiperazin-1-yl)-1H-benzimidazol-2-yl]-6-fluoroquinolin-2(1H)-one | 457.1 |
| 1361 | 4-amino-3-[5,7-difluoro-6-(4-isopropylpiperazin-1-yl)-1H-benzimidazol-2-yl]quinolin-2(1H)-one | 439.1 |
| 1362 | 4-amino-3-[5-(4-methylpiperazin-1-yl)-1H-benzimidazol-2-yl]-5-(2,2,2-trifluoroethoxy)quinolin-2(1H)-one | 473.3 |
| 1363 | 4-amino-3-[5-(4-methylpiperazin-1-yl)-1H-benzimidazol-2-yl]-6-(2,2,2-trifluoroethoxy)quinolin-2(1H)-one | 473.3 |
| 1364 | 4-amino-3-[5-(4-methylpiperazin-1-yl)-1H-benzimidazol-2-yl]-7-(2,2,2-trifluoroethoxy)quinolin-2(1H)-one | 473.3 |
| 1365 | 4-amino-3-{5-[2-(dimethylamino)ethoxy]-6-methoxy-1H-benzimidazol-2-yl}-5-fluoroquinolin-2(1H)-one | 412.3 |
| 1366 | 3-[6-(4-acetyl-1,4-diazepan-1-yl)-1H-benzimidazol-2-yl]-4-amino-5-fluoroquinolin-2(1H)-one | 435.3 |
| 1367 | 4-amino-5-fluoro-3-{6-[(2-methoxyethyl)(methyl)amino]-1H-benzimidazol-2-yl}quinolin-2(1H)-one | 382.3 |
| 1368 | 4-amino-6-fluoro-3-[5-fluoro-6-(4-methylpiperazin-1-yl)-1H-benzimidazol-2-yl]quinolin-2(1H)-one | 411.3 |
| 1369 | 4-amino-3-{6-[4-(N,N-dimethylglycyl)-1,4-diazepan-1-yl]-1H-benzimidazol-2-yl}-5-fluoroquinolin-2(1H)-one | 478.3 |
| 1370 | 4-amino-5-fluoro-3-{5-fluoro-6-[methyl(1-methylpiperidin-4-yl)amino]-1H-benzimidazol-2-yl}quinolin-2(1H)-one | 439.3 |
| 1371 | 4-amino-3-{5-[3-(dimethylamino)propyl]-1H-benzimidazol-2-yl}-5-fluoroquinolin-2(1H)-one | 380.3 |
| 1372 | 4-amino-3-{5-fluoro-6-[methyl(1-methylpiperidin-4-yl)amino]-1H-benzimidazol-2-yl}quinolin-2(1H)-one | 421.3 |
| 1373 | 4-amino-5-fluoro-3-{6-[4-(2-furoyl)piperazin-1-yl]-1H-benzimidazol-2-yl}quinolin-2(1H)-one | 473.3 |
| 1374 | 4-amino-5-fluoro-3-[5-(3-morpholin-4-ylpropyl)-1H-benzimidazol-2-yl]quinolin-2(1H)-one | 422.3 |
| 1375 | 4-amino-3-{6-[4-(N,N-dimethylglycyl)piperazin-1-yl]-1H-benzimidazol-2-yl}-5-fluoroquinolin-2(1H)-one | 464.3 |

TABLE 4-continued

Table of Examples 1274-1415.

| Example | Name | LC/MS m/z (MH+) |
|---|---|---|
| 1376 | 2-{4-[2-(4-amino-5-fluoro-2-oxo-1,2-dihydroquinolin-3-yl)-1H-benzimidazol-6-yl]piperazin-1-yl}-N,N-dimethylacetamide | 464.3 |
| 1377 | 3-{5-[3-(4-acetylpiperazin-1-yl)propyl]-1H-benzimidazol-2-yl}-4-amino-5-fluoroquinolin-2(1H)-one | 463.3 |
| 1378 | 4-amino-3-{5-[3-(4-ethylpiperazin-1-yl)propyl]-1H-benzimidazol-2-yl}-5-fluoroquinolin-2(1H)-one | 449.4 |
| 1379 | 4-amino-3-(6-{(2R,5R)-2-[(diethylamino)methyl]-5-methylmorpholin-4-yl}-1H-benzimidazol-2-yl)-5-fluoroquinolin-2(1H)-one | 479.3 |
| 1380 | 4-amino-3-[5-(4-ethylpiperazin-1-yl)-6-fluoro-1H-benzimidazol-2-yl]-5-fluoroquinolin-2(1H)-one | 425.1 |
| 1381 | 4-amino-3-{6-[(2R,5R)-5-methyl-2-(pyrrolidin-1-ylmethyl)morpholin-4-yl]-1H-benzimidazol-2-yl}-1,7-naphthyridin-2(1H)-one | 460.2 |
| 1382 | 4-amino-3-[5-(4-ethylpiperazin-1-yl)-6-fluoro-1H-benzimidazol-2-yl]-6-fluoroquinolin-2(1H)-one | 425.1 |
| 1383 | 4-amino-3-[5-(4-ethylpiperazin-1-yl)-6-fluoro-1H-benzimidazol-2-yl]-1,7-naphthyridin-2(1H)-one | 408.2 |
| 1384 | 4-amino-5-fluoro-3-{6-[(2R,5R)-5-methyl-2-(pyrrolidin-1-ylmethyl)morpholin-4-yl]-1H-benzimidazol-2-yl}quinolin-2(1H)-one | 477.2 |
| 1385 | 4-amino-8-fluoro-3-[5-(4-methylpiperazin-1-yl)-1H-benzimidazol-2-yl]quinolin-2(1H)-one | 393.3 |
| 1386 | 4-amino-5-fluoro-3-[6-(4-methyl-5-oxo-1,4-diazepan-1-yl)-1H-benzimidazol-2-yl]quinolin-2(1H)-one | 421.1 |
| 1387 | 4-amino-3-(5-{(2R,5S)-2-[(dimethylamino)methyl]-5-methylmorpholin-4-yl}-6-fluoro-1H-benzimidazol-2-yl)-1,7-naphthyridin-2(1H)-one | 452.1 |
| 1388 | 4-amino-5-fluoro-3-{5-[3-(4-methylpiperazin-1-yl)-3-oxopropyl]-1H-benzimidazol-2-yl}quinolin-2(1H)-one | 449.2 |
| 1389 | 4-amino-3-{5-[3-(4-ethylpiperazin-1-yl)-3-oxopropyl]-1H-benzimidazol-2-yl}-5-fluoroquinolin-2(1H)-one | 463.2 |
| 1390 | ethyl {[2-(4-amino-5-fluoro-2-oxo-1,2-dihydroquinolin-3-yl)-1H-benzimidazol-6-yl]oxy}acetate | 397.1 |
| 1391 | 4-amino-3-[5-(4-ethylpiperazin-1-yl)-1H-benzimidazol-2-yl]-6-fluoro-1,7-naphthyridin-2(1H)-one | 408.3 |
| 1392 | 4-amino-3-(5-{(2S,5R)-2-[(dimethylamino)methyl]-5-methylmorpholin-4-yl}-1H-benzimidazol-2-yl)-1,7-naphthyridin-2(1H)-one | 434.2 |
| 1393 | 4,5-diamino-3-[5-(4-methylpiperazin-1-yl)-1H-benzimidazol-2-yl]quinolin-2(1H)-one | 390.2 |
| 1394 | N-{4-amino-3-[6-(4-methylpiperazin-1-yl)-1H-benzimidazol-2-yl]-2-oxo-1,2-dihydroquinolin-5-yl}methanesulfonamide | 468.1 |
| 1395 | 4-amino-5-fluoro-3-{5-[3-(4-methylpiperazin-1-yl)propyl]-1H-benzimidazol-2-yl}quinolin-2(1H)-one | 435.2 |
| 1396 | 4-amino-5-fluoro-3-[5-(2-pyrrolidin-1-ylethoxy)-1H-benzimidazol-2-yl]quinolin-2(1H)-one | 408.1 |
| 1397 | N-({(2R,5S)-4-[2-(4-amino-5-fluoro-2-oxo-1,2-dihydroquinolin-3-yl)-1H-benzimidazol-5-yl]-5-methylmorpholin-2-yl}methyl)-N-methylacetamide | 479.2 |
| 1398 | 4-amino-5-fluoro-3-(5-{(2S,5S)-5-methyl-2-[(methylamino)methyl]morpholin-4-yl}-1H-benzimidazol-2-yl)quinolin-2(1H)-one | 437.2 |
| 1399 | 4-amino-3-(5-{(1E)-3-[benzyl(methyl)amino]prop-1-enyl}-1H-benzimidazol-2-yl)-5-fluoroquinolin-2(1H)-one | 454.2 |
| 1400 | 4-amino-3-(5-{3-[benzyl(methyl)amino]propyl}-1H-benzimidazol-2-yl)-5-fluoroquinolin-2(1H)-one | 456.3 |
| 1401 | 4-amino-5-fluoro-3-(5-{3-[methyl(piperidin-4-yl)amino]propyl}-1H-benzimidazol-2-yl)quinolin-2(1H)-one | 449.2 |
| 1402 | 4-amino-5-fluoro-3-(5-{3-[(1-isopropylpiperidin-4-yl)(methyl)amino]propyl}-1H-benzimidazol-2-yl)quinolin-2(1H)-one | 491.3 |
| 1403 | 4-amino-3-(5-{3-[(1-ethylpiperidin-4-yl)(methyl)amino]propyl}-1H-benzimidazol-2-yl)-5-fluoroquinolin-2(1H)-one | 477.3 |
| 1404 | 4-amino-5-fluoro-3-[5-(1-methylpiperidin-4-yl)-1H-benzimidazol-2-yl]quinolin-2(1H)-one | 392.1 |
| 1405 | 4-amino-5-fluoro-3-[5-(4-methyl-4-oxidopiperazin-1-yl)-1H-benzimidazol-2-yl]quinolin-2(1H)-one | 409.2 |
| 1406 | N-[2-(4-amino-5-fluoro-2-oxo-1,2-dihydroquinolin-3-yl)-1H-benzimidazol-6-yl]-N,4-dimethylpiperazine-1-carboxamide | 450.1 |
| 1407 | 4-amino-3-(5-{2-[(dimethylamino)methyl]morpholin-4-yl}-1H-benzimidazol-2-yl)-5-fluoroquinolin-2(1H)-one | 437.2 |

TABLE 4-continued

Table of Examples 1274-1415.

| Example | Name | LC/MS m/z (MH+) |
|---|---|---|
| 1408 | 4-amino-5-ethoxy-3-[6-(4-methylpiperazin-1-yl)-1H-benzimidazol-2-yl]quinolin-2(1H)-one | 419.3 |
| 1409 | 4-amino-3-[5-(4-ethylpiperazin-1-yl)-6-fluoro-1H-benzimidazol-2-yl]-6,7-dimethoxyquinolin-2(1H)-one | 467.3 |
| 1410 | 4-amino-6,7-dimethoxy-3-[5-(4-methylpiperazin-1-yl)-1H-benzimidazol-2-yl]quinolin-2(1H)-one | 435.3 |
| 1411 | 4-amino-3-[6-(4-methylpiperazin-1-yl)-1H-benzimidazol-2-yl]-7-(trifluromethyl)quinolin-2(1H)-one | 443.3 |
| 1412 | 4-amino-3-(5-{(2R,5S)-2-[(dimethylamino)methyl]-5-methylmorpholin-4-yl}-6-flouro-1H-benzimidazol-2-yl)-6,7-dimethoxyquinolin-2(1H)-one | 511.4 |
| 1413 | 4-amino-3-[5-(4-ethyl-1,4-diazepan-1-yl)-1H-benzimidazol-2-yl]-6,7-dimethoxyquinolin-2(1H)-one | 463.3 |
| 1414 | 4-amino-3-{6-[(1-ethylpiperidin-4-yl)methyl]-1H-benzimidazol-2-yl}-5-fluoroquinolin-2(1H)-one | 420.5 |
| 1415 | 4-[(3R)-1-azabicyclo[2.2.2]oct-3-ylamino]-3-(1H-benzimidazol-2-yl)-1,7-naphthyridin-2(1H)-one | 387.4 |

Examples 1416-1457

Examples 1416 to 1457 listed in Table 5 were synthesized using the methods described above such as Methods 1-24 and those set forth in the Schemes and other Examples or modified as apparent to one of reasonable skill in the art using commercially available materials.

TABLE 5

Table of Examples 1416-1457.

| Example | Name | LC/MS m/z (MH +) |
|---|---|---|
| 1416 | 3-(1H-benzimidazol-2-yl)-6-chloro-4-[(pyridin-2-ylmethyl)amino]quinolin-2(1H)-one | 402.9 |
| 1417 | 4-[(3S)-1-azabicyclo[2.2.2]oct-3-ylamino]-3-(1H-benzimidazol-2-yl)-6,7-dimethoxyquinolin-2(1H)-one | 446.5 |
| 1418 | 4-[4-[(3R)-1-azabicyclo[2.2.2]oct-3-ylamino]-3-(1H-benzimidazol-2-yl)-2-oxo-1,2-dihydroquinolin-6-yl]benzonitrile | 487.6 |
| 1419 | 4-[(3S)-1-azabicyclo[2.2.2]oct-3-ylamino]-3-(1H-benzimidazol-2-yl)-6-(3-methoxyphenyl)quinolin-2(1H)-one | 492.6 |
| 1420 | 4-[(3S)-1-azabicyclo[2.2.2]oct-3-ylamino]-3-(1H-benzimidazol-2-yl)-6-(2-methoxyphenyl)quinolin-2(1H)-one | 492.6 |
| 1421 | 4-[(3R)-1-azabicyclo[2.2.2]oct-3-ylamino]-3-(1H-benzimidazol-2-yl)-6-(4-methoxyphenyl)quinolin-2(1H)-one | 492.6 |
| 1422 | 4-[(3S)-1-azabicyclo[2.2.2]oct-3-ylamino]-3-(1H-benzimidazol-2-yl)-6-fluoro-7-(isobutylamino)quinolin-2(1H)-one | 475.6 |
| 1423 | 4-[4-[(3R)-1-azabicyclo[2.2.2]oct-3-ylamino]-3-(1H-benzimidazol-2-yl)-2-oxo-1,2-dihydroquinolin-6-yl]benzamide | 505.6 |
| 1424 | 4-[(3R)-1-azabicyclo[2.2.2]oct-3-ylamino]-3-(1H-benzimidazol-2-yl)-6-fluoro-7-methoxyquinolin-2(1H)-one | 434.5 |
| 1425 | 4-[(3S)-1-azabicyclo[2.2.2]oct-3-ylamino]-3-(1H-benzimidazol-2-yl)-6-fluoro-7-[(2-piperidin-1-ylethyl)amino]quinolin-2(1H)-one | 530.7 |
| 1426 | 4-[(3R)-1-azabicyclo[2.2.2]oct-3-ylamino]-3-(1H-benzimidazol-2-yl)-2-oxo-1,2-dihydroquinoline-7-carboxylic acid | 430.5 |
| 1427 | 3-amino-4-[4-[(3R)-1-azabicyclo[2.2.2]oct-3-ylamino]-3-(1H-benzimidazol-2-yl)-7-(1H-imidazol-1-yl)-2-oxo-1,2-dihydroquinolin-6-yl]benzoic acid | 587.7 |
| 1428 | 4-[(3R)-1-azabicyclo[2.2.2]oct-3-ylamino]-3-(1H-benzimidazol-2-yl)-6-fluoro-7-{[3-(1H-imidazol-1-yl)propyl]amino}quinolin-2(1H)-one | 527.6 |
| 1429 | 4-[(3R)-1-azabicyclo[2.2.2]oct-3-ylamino]-3-(1H-benzimidazol-2-yl)-6-fluoro-7-[(2-pyridin-3-ylethyl)amino]quinolin-2(1H)-one | 524.6 |
| 1430 | 4-[(3R)-1-azabicyclo[2.2.2]oct-3-ylamino]-3-(1H-benzimidazol-2-yl)-7-methoxyquinolin-2(1H)-one | 416.5 |
| 1431 | 6-chloro-3-(5-morpholin-4-yl-1H-benzimidazol-2-yl)-4-[(pyridin-2-ylmethyl)amino]quinolin-2(1H)-one | 488.0 |
| 1432 | 4-{[(1S)-2-amino-1-benzylethyl]amino}-6-chloro-3-(5-morpholin-4-yl-1H-benzimidazol-2-yl)quinolin-2(1H)-one | 530.0 |

TABLE 5-continued

Table of Examples 1416-1457.

| Example | Name | LC/MS m/z (MH +) |
|---|---|---|
| 1433 | 4-[(1-benzylpiperidin-4-yl)amino]-6-chloro-3-(5-morpholin-4-yl-1H-benzimidazol-2-yl)quinolin-2(1H)-one | 570.1 |
| 1434 | 4-[(3S)-1-azabicyclo[2.2.2]oct-3-ylamino]-3-(1H-benzimidazol-2-yl)-2-oxo-1,2-dihydroquinoline-7-carboxylic acid | 430.5 |
| 1435 | 4-{[4-(aminomethyl)benzyl]amino}-6-chloro-3-[5-(4-methylpiperazin-1-yl)-1H-benzimidazol-2-yl]quinolin-2(1H)-one | 529.1 |
| 1436 | 4-[(1-benzylpiperidin-4-yl)amino]-6-chloro-3-[5-(4-methylpiperazin-1-yl)-1H-benzimidazol-2-yl]quinolin-2(1H)-one | 583.1 |
| 1437 | 4-[(3R)-1-azabicyclo[2.2.2]oct-3-ylamino]-3-(1H-benzimidazol-2-yl)-7-methoxy-6-[4-(methylsulfonyl)phenyl]quinolin-2(1H)-one | 570.7 |
| 1438 | 3-(1H-benzimidazol-2-yl)-6-chloro-4-[(3S)-pyrrolidin-3-ylamino]quinolin-2(1H)-one | 380.8 |
| 1439 | 4-[(3R)-1-azabicyclo[2.2.2]oct-3-ylamino]-6-bromo-3-(3H-imidazo[4,5-b]pyridin-2-yl)quinolin-2(1H)-one | 466.3 |
| 1440 | 4-[(3S)-1-azabicyclo[2.2.2]oct-3-ylamino]-6-bromo-3-(3H-imidazo[4,5-b]pyridin-2-yl)quinolin-2(1H)-one | 466.3 |
| 1441 | 6-bromo-3-(3H-imidazo[4,5-b]pyridin-2-yl)-4-(piperidin-3-ylamino)quinolin-2(1H)-one | 440.3 |
| 1442 | 4-[(3S)-1-azabicyclo[2.2.2]oct-3-ylamino]-6,7-difluoro-3-(3H-imidazo[4,5-b]pyridin-2-yl)quinolin-2(1H)-one | 423.4 |
| 1443 | 6,7-difluoro-3-(3H-imidazo[4,5-b]pyridin-2-yl)-4-(piperidin-3-ylamino)quinolin-2(1H)-one | 397.4 |
| 1444 | 4-[4-[(3R)-1-azabicyclo[2.2.2]oct-3-ylamino]-3-(3H-imidazo[4,5-b]pyridin-2-yl)-2-oxo-1,2-dihydroquinolin-6-yl]benzoic acid | 507.6 |
| 1445 | 4-[(3R)-1-azabicyclo[2.2.2]oct-3-ylamino]-3-(3H-imidazo[4,5-b]pyridin-2-yl)-6-[2-(trifluoromethyl)phenyl]quinolin-2(1H)-one | 531.6 |
| 1446 | 4-[(3R)-1-azabicyclo[2.2.2]oct-3-ylamino]-3-(3H-imidazo[4,5-b]pyridin-2-yl)-6-(2-methoxyphenyl)quinolin-2(1H)-one | 493.6 |
| 1447 | 4-[(3R)-1-azabicyclo[2.2.2]oct-3-ylamino]-7-(dimethylamino)-6-fluoro-3-(3H-imidazo[4,5-b]pyridin-2-yl)quinolin-2(1H)-one | 448.5 |
| 1448 | 5-(1-azabicyclo[2.2.2]oct-3-ylamino)-6-(1H-benzimidazol-2-yl)-2-(methylthio)pyrido[2,3-d]pyrimidin-7(8H)-one | 434.5 |
| 1449 | 5-(1-azabicyclo[2.2.2]oct-3-ylamino)-6-(1H-benzimidazol-2-yl)-2-hydroxypyrido[2,3-d]pyrimidin-7(8H)-one | 404.4 |
| 1450 | 5-[(3S)-1-azabicyclo[2.2.2]oct-3-ylamino]-6-(1H-benzimidazol-2-yl)-2-hydroxypyrido[2,3-d]pyrimidin-7(8H)-one | 404.4 |
| 1451 | 4-[(3S)-1-azabicyclo[2.2.2]oct-3-ylamino]-3-(1H-benzimidazol-2-yl)-6-fluoro-1,7-naphthyridin-2(1H)-one | 405.4 |
| 1452 | 4-[(3R)-1-azabicyclo[2.2.2]oct-3-ylamino]-3-(1H-benzimidazol-2-yl)-6-fluoro-1,7-naphthyridin-2(1H)-one | 405.4 |
| 1453 | 4-[(3R)-1-azabicyclo[2.2.2]oct-3-ylamino]-3-(1H-benzimidazol-2-yl)-6-chloro-1,7-naphthyridin-2(1H)-one | 421.9 |
| 1454 | 3-(1H-benzimidazol-2-yl)-6-chloro-4-{[2-(dimethylamino)ethyl]amino}-1,7-naphthyridin-2(1H)-one | 383.9 |
| 1455 | 4-{[(1R,2R)-2-aminocyclohexyl]amino}-3-(1H-benzimidazol-2-yl)-6-chloro-1,7-naphthyridin-2(1H)-one | 409.9 |
| 1456 | 3-(1H-benzimidazol-2-yl)-6-chloro-4-[(piperidin-3-ylmethyl)amino]-1,7-naphthyridin-2(1H)-one | 409.9 |
| 1457 | 3-(1H-benzimidazol-2-yl)-6-chloro-4-[(3S)-pyrrolidin-3-ylamino]-1,7-naphthyridin-2(1H)-one | 381.8 |

Assay Procedures

Serine/Threonine Kinases

The kinase activity of various protein serine/threonine kinases was measured by providing ATP and a suitable peptide or protein containing a serine or threonine amino acid residue for phosphorylation, and assaying for the transfer of phosphate moiety to the serine or threonine residue. Recombinant proteins containing the kinase domains of GSK-3, RSK-2, PAR-1, NEK-2, and CHK1 enzymes were expressed in Sf9 insect cells using a Baculovirus expression system (InVitrogen) and purified via Glu antibody interaction (for Glu-epitope tagged constructs) or by Metal Ion Chromatography (for $His_6$ (SEQ ID NO: 1) tagged constructs). Cdc2 (GST fusion construct) and cyclin B were co-expressed in Sf9 insect cells using a Baculovirus expression system. Recombinant, active Cdk2/cyclin A is available commercially and was purchased from Upstate Biotechnology. The purified Cdc2 enzyme used in the assay was commercially available, and it may be purchased from New England Bio Labs. For each assay, test compounds were serially diluted in DMSO and then mixed with the appropriate kinase reaction buffer plus 5-10 nM of $^{33}P$ gamma-labeled ATP. The kinase protein and the appropriate biotinylated peptide substrate were added to give a final volume of 150 µL. Reactions were incubated for 3-4 hours at room temperature and then stopped by transferring to a streptavidin-coated white microtiter plate (Thermo Labsystems) containing 100 µL of stop reaction buffer. The stop reaction buffer consists of 50 mM unlabeled ATP and 30 mM EDTA. After 1 hour of incubation, streptavidin plates were washed with PBS, and 200 µL Microscint 20 scintillation fluid was added per well. The plates were sealed and counted using TopCount. The concentration of each compound for 50% inhibition ($IC_{50}$) was calculated employing non-linear regression using XL Fit data analysis software.

The reaction buffer contained 30 mM Tris-$HCl_2$ pH 7.5, 10 mM $MgCl_2$, 2 mM DTT, 4 mM EDTA, 25 mM beta-glycerophosphate, 5 mM $MnCl_2$, 0.01% BSA/PBS, 0.5 µM peptide substrate, and 1 µM unlabeled ATP. GSK-3 enzyme was used at 27 nM, CHK1 at 5 nM, Cdc2 at 1 nM, Cdk2 at 5 nM, and Rsk2 at 0.044 units/mL. For the GSK-3 assay, biotin-CREB peptide (Biotin-SGSGKRREILSRRP(pS)YR-$NH_2$ (SEQ ID NO: 4)) was used. For the CHK1 assay, a biotin-Cdc25c peptide (Biotin-[AHX]SGSGSGLYRSPSMPENLNRPR [$CONH_2$] (SEQ ID NO: 5)) was used. For the Cdc2 and the Cdk2 assays, a biotin-Histone H1 peptide ([IcBiotin]GGGG-PKTPKKAKKL[$CONH_2$] (SEQ ID NO: 6)) was used. In the Rsk2 assay, a biotin-p70 peptide, 15 mM $MgCl_2$, 1 mM DTT, 5 mM EDTA, 2.7 µM PKC inhibitor peptide, and 2.7 µM PKA inhibitor peptide were used.

Tyrosine Kinases

The kinase activity of a number of protein tyrosine kinases was measured by providing ATP and an appropriate peptide or protein containing a tyrosine amino acid residue for phosphorylation, and assaying for the transfer of phosphate moiety to the tyrosine residue. Recombinant proteins corresponding to the cytoplasmic domains of the FLT-1 (VEGFR1), VEGFR2, VEGFR3, Tie-2, PDGFRα, PDGFRβ, and FGFR1 receptors were expressed in Sf9 insect cells using a Baculovirus expression system (InVitrogen) and may be purified via Glu antibody interaction (for Glu-epitope tagged constructs) or by Metal Ion Chromatography (for $His_6$ (SEQ ID NO: 1) tagged constructs). For each assay, test compounds were serially diluted in DMSO and then mixed with an appropriate kinase reaction buffer plus ATP. Kinase protein and an appropriate biotinylated peptide substrate were added to give a final volume of 50-100 µL, reactions were incubated for 1-3 hours at room temperature and then stopped by addition of 25-50 µL of 45 mM EDTA, 50 mM Hepes pH 7.5. The stopped reaction mixture (75 µL) was transferred to a streptavidin-coated microtiter plate (Boehringer Mannheim) and incubated for 1 hour. Phosphorylated peptide product was measured with the DELFIA time-resolved fluorescence system (Wallac or PE Biosciences), using a Europium labeled anti-phosphotyrosine antibody PT66 with the modification that the DELFIA assay buffer was supplemented with 1 mM $MgCl_2$ for the antibody dilution. Time resolved fluorescence was read on a Wallac 1232 DELFIA fluorometer or a PE Victor II multiple signal reader. The concentration of each compound for 50% inhibition ($IC_{50}$) was calculated employing non-linear regression using XL Fit data analysis software.

FLT-1, VEGFR2, VEGFR3, FGFR3, Tie-2, and FGFR1 kinases were assayed in 50 mM Hepes pH 7.0, 2 mM $MgCl_2$, 10 mM $MnCl_2$, 1 mM NaF, 1 mM DTT, 1 mg/mL BSA, 2 µM ATP, and 0.20-0.50 µM corresponding biotinylated peptide substrate. FLT-1, VEGFR2, VEGFR3, Tie-2, and FGFR1 kinases were added at 0.1 µg/mL, 0.05 µg/mL, or 0.1 µg/mL respectively. For the PDGFR kinase assay, 120 µg/mL enzyme with the same buffer conditions as above was used except for changing ATP and peptide substrate concentrations to 1.4 µM ATP, and 0.25 µM biotin-GGLFDDPSYVN-VQNL-$NH_2$ (SEQ ID NO: 2) peptide substrate. Each of the above compounds displayed an $IC_{50}$ value of less than 10 µM with respect to FLT-1, VEGFR2, VEGFR3, and FGFR1.

Recombinant and active tyrosine kinases Fyn, and Lck are available commercially and were purchased from Upstate Biotechnology. For each assay, test compounds were serially diluted in DMSO and then mixed with an appropriate kinase reaction buffer plus 10 nM $^{33}P$ gamma-labeled ATP. The kinase protein and the appropriate biotinylated peptide substrate were added to give a final volume of 150 µL. Reactions were incubated for 3-4 hours at room temperature and then stopped by transferring to a streptavidin-coated white microtiter plate (Thermo Labsystems) containing 100 µL of stop reaction buffer of 100 mM EDTA and 50 µM unlabeled ATP. After 1 hour incubation, the streptavidin plates were washed with PBS and 200 µL Microscint 20 scintillation fluid was added per well. The plates were sealed and counted using TopCount. The concentration of each compound for 50% inhibition ($IC_{50}$) was calculated employing non-linear regression using XL Fit data analysis software.

The kinase reaction buffer for Fyn, Lck, and c-ABL contained 50 mM Tris-HCl pH 7.5, 15 mM MgCl2, 30 mM $MnCl_2$, 2 mM DTT, 2 mM EDTA, 25 mM beta-glycerol phosphate, 0.01% BSA/PBS, 0.5 µM of the appropriate peptide substrate (biotinylated Src peptide substrate: biotin-GGGGKVEKIGEGTYGWYK-$NH_2$ (SEQ ID NO: 3) for Fyn and Lck), 1 µM unlabeled ATP, and 1 nM kinase.

The kinase activity of c-Kit and FLT-3 were measured by providing ATP and a peptide or protein containing a tyrosine amino acid residue for phosphorylation, and assaying for the transfer of phosphate moiety to the tyrosine residue. Recombinant proteins corresponding to the cytoplasmic domains of the c-Kit and FLT-3 receptors were purchased (Proquinase). For testing, an exemplary compound, for example 4-amino-5-fluoro-3-[5-(4-methylpiperazin-1-yl)-1H-benzimidazol-2-yl]quinolin-2(1H)-one, was diluted in DMSO and then mixed with the kinase reaction buffer described below plus ATP. The kinase protein (c-Kit or FLT-3) and the biotinylated peptide substrate (biotin-GGLFDDPSWNVQNL-NH2 (SEQ ID NO: 2)) were added to give a final volume of 100 µL. These reactions were incubated for 2 hours at room temperature and then stopped by addition of 50 µL of 45 mM EDTA, 50 mM HEPES, pH 7.5. The stopped reaction mixture (75 µL) was transferred to a streptavidin-coated microtiter plate (Boehringer Mannheim) and incubated for 1 hour. Phosphorylated peptide product was measured with the DELPHIA time-resolved fluorescence system (Wallac or PE Biosciences), using a Europium-labeled anti-phosphotyrosine antibody, PT66, with the modification that the DELFIA assay buffer was supplemented with 1 mM $MgCl_2$ for the antibody dilution. Time resolved fluorescence values were determined on a Wallac 1232 DELFIA fluorometer or a PE Victor II multiple signal reader. The concentration of each compound for 50% inhibition ($IC_{50}$) was calculated employing non-linear regression using XL Fit data analysis software.

FLT-3 and c-Kit kinases were assayed in 50 mM Hepes pH 7.5, 1 mM NaF, 2 mM $MgCl_2$, 10 mM $MnCl_2$ and 1 mg/mL BSA, 8 µM ATP and 1 µM of corresponding biotinylated peptide substrate (biotin-GGLFDDPSYVNVQNL-NH2 (SEQ ID NO: 2)). The concentration of FLT-3 and c-Kit kinases were assayed at 2 nM.

Each of the compounds produced in the Examples was synthesized and assayed using the procedures described above. The majority of the exemplary compounds displayed an IC$_{50}$ value of less than 10 µM with respect to VEGFR1, VEGFR2, VEGFR3, FGFR1, CHK1, Cdc2, GSK-3, NEK-2, Cdk2, Cdk4, MEK1, NEK-2, CHK2, CK1ε, Raf, Fyn, Lck, Rsk2, PAR-1, c-Kit, c-ABL, p60src, FGFR3, FLT-3, PDGFRα, and PDGFRβ. In addition, many of the exemplary compounds exhibited IC$_{50}$ values in the nM range and show potent activity with respect to VEGFR1, VEGFR2, VEGFR3, FGFR1, FGFR3, c-Kit, c-ABL, FLT-3, CHK1, Cdc2, GSK-3, NEK-2, Cdk2, MEK1, NEK-2, CHK2, Fyn, Lck, Rsk2, PAR-1, PDGFRα, and PDGFRβ with IC$_{50}$ values of less than 1 µM. The other examples also exhibited such activity with respect to VEGFR1, VEGFR2, VEGFR3, FGFR1, FGFR3, c-Kit, c-ABL, p60src, FLT-3, CHK1, Cdc2, GSK-3, NEK-2, Cdk2, Cdk4, MEK1, NEK-2, CHK2, CK1ε, Raf, Fyn, Lck, Rsk2, PAR-1, PDGFRα, and PDGFRβ or will be shown to exhibit such activity. The exemplary compounds also exhibited inhibition activity with respect to VEGFR2. In some embodiments, the invention provides a compound, a tautomer of the compound, a pharmaceutically acceptable salt of the compound, a pharmaceutically acceptable salt of the tautomer, an enantiomer or diastereomer of the compound, an enantiomer or diastereomer of the tautomer, an enantiomer or diastereomer of the pharmaceutically acceptable salt of the compound, an enantiomer or diastereomer of the pharmaceutically acceptable salt of the tautomer, or a mixture of the compounds, enantiomers, tautomers, or salts, wherein the compound is selected from the group consisting of the title compounds of Examples 51-90, Examples 93-100, Example 102, Example 104, Example 105, and Examples 339-1457. Such embodiments are directed to the specific compound, salts, enantiomers, and mixtures of the title compounds and are not limited to the procedures used to make such compounds, for example, the procedures described in Examples 51-90, 93-100, 102, 104, and 105. In some such embodiments, the invention provides the compound, the tautomer of the compound, the pharmaceutically acceptable salt of the compound, or the pharmaceutically acceptable salt of the tautomer, wherein the compound is selected from the group consisting of Examples 51-90, Examples 93-100, Example 102, Example 104, Example 105, and Examples 339-1457. In some such embodiments, the compound is selected from those named in Table 3, Table 4, and Table 5. In some embodiments, the compound is selected from those named in Table 3. In other embodiments, the compound is selected from those named in Table 4. In other embodiments, the compound is selected from those named in Table 5. The invention further provides the use of such compounds in the manufacture of a medicament or pharmaceutical formulation for inhibiting the kinase activity of the serine/threonine or tyrosine kinases described herein; the use of such compounds in the manufacture of a medicament or pharmaceutical formulation for treating a biological condition mediated by any of the of the serine/threonine or tyrosine kinases described herein. The invention further provides methods for inhibiting any of the serine/threonine kinases or tyrosine kinases described herein utilizing these compounds and methods of treating biological conditions mediated by any of the serine/threonine kinases or tyrosine kinases described herein utilizing these compounds.

In one embodiment, the invention provides a method of inhibiting FLT-1 (VEGFR1). The method includes administering an effective amount of a compound, or a pharmaceutically acceptable salt thereof, of any of the embodiments of the compounds of Structure I or IB to a subject, such as a human, in need thereof.

In one embodiment, the invention provides a method of inhibiting VEGFR2 (KDR (human), Flk-1 (mouse)). The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting VEGFR3 (FLT4). The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting FGFR1. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting NEK-2. The method includes administering an effective amount of a compound of compounds of Structure I or IB to a subject, such as a human, in need thereof.

In one embodiment, the invention provides a method of inhibiting PDGFRα and PDGFRβ. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting FGFR3. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting FLT-3. The method includes administering an effective amount of a compound, or a pharmaceutically acceptable salt thereof, of any of the embodiments of compounds of Structure I or IB to a subject, such as a human, in need thereof.

In another embodiment, the invention provides a method of inhibiting FLT-3 or Stat5 phosphorylation. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting c-Kit. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting c-ABL. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting p60src. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting FGFR3. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting ErB2. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting Cdk 2. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting Cdk 4. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting MEK1. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting NEK-2. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting CHK2. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting CK1ε. The method includes administering an effective amount of a compound, or a pharmaceutically acceptable salt thereof, of any of the embodiments of compounds of Structure I or IB to a subject, such as a human, in need thereof.

In one embodiment, the invention provides a method of inhibiting Raf. The method includes administering an effective amount of a compound, or a pharmaceutically acceptable salt thereof, of any of the embodiments of compounds of Structure I or IB to a subject, such as a human, in need thereof.

As noted above, the exemplary compounds exhibited activity in one or more important assay or will be found to exhibit such activity. For this reason, each of the exemplary compounds is both individually preferred and is preferred as a group. One, two, or more compounds of the invention may be used in combination in pharmaceutical formulations, medicaments, and in methods of treating subjects. Furthermore, each of the $R^1$-$R^{10}$ groups of the exemplary compounds is preferred individually and as a member of a group.

Small Molecule Inhibitors of Growth Factor Tyrosine Kinase Receptors Involved in Angiogenesis and Tumor Cell Proliferation Inhibition of Kinases 4-Amino-5-fluoro-3-[5-(4-methylpiperazin-1-yl)-1H-benzimidazol-2-yl]quinolin-2(1H)-one is an orally bioavailable benzimidazole-quinolinone that exhibits potent inhibition of receptor tyrosine kinases that drive both endothelial and tumor cell proliferation. The inhibitory effect of 4-amino-5-fluoro-3-[5-(4-methylpiperazin-1-yl)-1H-benzimidazol-2-yl]quinolin-2(1H)-one on nine tyrosine kinases, FGFR1, FGFR3, VEGFR1, VEGFR2, VEGFR3, PDGFRβ, c-Kit, p60src, and FLT-3 was determined using the assay procedures described above. The $IC_{50}$s for these tyrosine kinases were found to be less than 30 nM. The compound also displays $IC_{50}$s of less than 1 μM against fyn, $p^{56}$lck, c-ABL, CHK1, CHK2, PAR-1, MEK, and RSK2. 4-Amino-5-fluoro-3-[5-(4-methylpiperazin-1-yl)-1H-benzimidazol-2-yl]quinolin-2(1H)-one does not significantly inhibit EGFR family kinases or insulin receptor kinase at these concentrations ($IC_{50}$s>2 μM). The inhibitory effect of 4-Amino-5-fluoro-3-[5-(4-methylpiperazin-1-yl)-1H-benzimidazol-2-yl]quinolin-2(1H)-one on phosphorylation of FLT-3 in MV4-11 cells, a tumor cell line, is described below.

Antiproliferative Effects in Cell Lines

The antiproliferative activity of 4-Amino-5-fluoro-3-[5-(4-methylpiperazin-1-yl)-1H-benzimidazol-2-yl]quinolin-2(1H)-one (Example 166) was assessed in 27 different cancer and primary cell lines and displayed $EC_{50}$ values of less than 10 μM in 26 out of the 27 cell lines. The antiproliferative activity of the exemplary compound was tested by adding a MTS tetrazolium compound (available from Promega, Madison, Wis.) that is bioreduced by metabolically-active cells into a soluble colored formazan product, which was recorded by measuring the absorbance at 490 nm with a spectrophotometer. In order to determine $EC_{50}$ values for the exemplary compound in each of the cell lines, the appropriate number of cells was determined to give an optimal signal (see Table 6) and plated in 100 μL of growth media in a 96 well plate. Serially-diluted exemplary compound in a DMSO stock solution was added to the plate in 100 μL growth media typically at a starting concentration of 20 μM and incubated for 72 hours at 37° C. and 5% $CO_2$. The final DMSO concentration was 0.5% or less for each cell line (see Table 6). The cell lines used to determine $EC_{50}$ values of the exemplary compounds are listed in Table 6 and were of human origin unless otherwise noted. For the HMVEC and TF-1 cell lines, the $EC_{50}$ were determined as inhibition of VEGF and SCF (Stem cell factor) mediated proliferation, respectively. After the 72 hours of incubation, 40 μL of MTS solution was added to the wells and the OD measured after 3-5 hours at 490 nm. The $EC_{50}$ values were calculated using nonlinear regression. The exemplary compound had antiproliferative effects with $EC_{50}$s<10 μM for all the cell lines tested with the exception of the U87MG cell line in which the $EC_{50}$ was calculated to be about 10 μM for the exemplary compound.

TABLE 6

Cell Lines and Conditions Employed to Determine the Antiproliferative Activity of Exemplary Compounds.

| Cell Line | Origin* | Cells/well of 96 well plate | Final DMSO conc. (%) | MTS incubation | Medium |
|---|---|---|---|---|---|
| 4T1 | mouse breast | 500 | 0.5 | 4-5 H | DMEM + 10% FBS + Pen/Strep + Sodium Pyruvate + 2 mM L-Glut |
| ARH-77 | blood | 10,000 | 0.5 | 4 H | RPMI-1640 + 10% Heat Inactivated FBS + 2 mM L-Glut + Pen/Strep |
| DU145 | prostate | 500 | 0.5 | 3-4 H | EMEM + 10% FBS + 2 mM L-Glut + Pen/Strep |
| HCT-116 | colon | 500 | 0.5 | 5 H | McCoy's 5A with 2 mM L-Glut + 10% FBS + Pen/Strep |
| HMVECd | endothelium | 2,000 | 0.5 | 4 H | EGM-2-MV (Biowhittaker #cc-3202) |
| K-562 | blood | 5,000 | 0.2 | 3 H | RPMI-1640 + 10% FBS + 2 mM L-Glut + Pen/Strep |
| KM12L4A | colon | 500 | 0.5 | 5 H | EMEM + 10% FBS + 2 mM L-Glut + 2xVitamins + NEAA + Sodium Pyruvate + Pen/Strep |
| KU812 | blood | 10,000 | 0.2 | 6 H | RPMI-1640 + 10% FBS + 2 mM L-Glut + Pen/Strep |
| MOLT4 | blood | 5,000 | 0.5 | 4 H | RPMI-1640 + 10% FBS + 2 mM L-Glut + Pen/Strep |
| MV4-11 | blood | 10,000 | 0.2 | 6 H | IMDM + 10% FBS + 5 ng/ml GM-CSF + 2 mM L-Gut + Pen/Strep |
| NCI-H209 | lung | 10,000 | 0.5 | 5 H | IMDM + 10% FBS + 2 mM L-Glut + Pen/Strep |
| NCI-H526 | lung | 10,000 | 0.5 | 5 H | RPMI-1640 + 10% FBS + 2 mM L-Glut + Pen/Strep |
| PC-3P | prostate | 500 | 0.5 | 5 H | EMEM + 10% FBS + vit 2% 100x + L-L-Glut 200 mM 1% + NaPy 100 mM 1% + NEAA100x 1% |
| RS4;11 | blood | 10,000 | 0.2 | 6 H | RPMI-1640 + 10% FBS + 10 mM HEPES + 1 mM Sodium Pyruvate + Pen/Strep |
| SK-OV-3 | ovary | 2,500 | 0.5 | 4 H | McCoy's 5A + 10% FBS + 2 mM L-Glut + Pen/Strep |
| TF-1 | blood | 10,000 | 0.2 | 6 H | RPMI-1640 + 10% FBS + 0.044 mM BME + 2 mM L-Glut + Pen/Strep + 5 ng/ml GM-CSF |
| U-87MG | brain | 500 | 0.5 | 5 H | EMEM + 10% FBS + NEAA + Sodium Pyruvate + Earle's BSS |
| HL60 | blood | 12,500 | 0.5 | 5 H | RPMI-1640 + 10% FBS + 2 mM L-Glut + Pen/Strep |
| M-NFS-60 | blood | 5,000 | 0.5 | 4-5 H | RPMI-1640 + 10% FBS + 0.044 mM BME + 2 mM L-Glut + Pen/Strep + 67.1 ng/ml GM-CSF |
| GH3 | rat pituitary | 10,000 | 0.5 | 4 H | Ham's F10 + 2 mM L-Glut + 15% Horse Serum (HS) + 2.5% Fetal Bovine Serum (FBS) |
| HP75 | pituitary | 5,000 | 0.5 | 4 H | DMEM 15% Horse Serum, 2.5% Fetal Bovine Serum, 1 µg/ml Insulin, Pen/Strep |
| HMEC | mammary epithelium | 2,000 | 0.5 | 4 H | MEGM (Biowhittaker #CC-3051) |
| PrEC | prostate epithelium | 2,000 | 0.5 | 4 H | PrEGM (Cambrex #CC3166) |
| MDA-MB435 | breast | 500 | 0.5 | 4 H | DMEM/F12 (1:1) 10% FBS |
| SW620 | colon | 500 | 0.5 | 4 H | Leibovitz's L-15 medium with 2 mM L-Glut 10% fetal bovine serum |
| HT29 | colon | 5,000 | 0.5 | 4 H | McCoy's 5A + 10% FBS |

*Origin was human unless otherwise noted.

Significant anti-proliferative effects were observed in endothelial cells and a subset of tumor cell lines. Several human cancer cell lines have been identified that are at least 10 fold more sensitive to the anti-proliferative effects of 4-amino-5-fluoro-3-[5-(4-methylpiperazin-1-yl)-1H-benzimidazol-2-yl]quinolin-2(1H)-one than the rest of the cell lines tested. The compound inhibited VEGF mediated proliferation in HMVEC (human microvascular endothelial cells) with an $IC_{50}$ of 25 nM and the compound inhibited KM12L4a, a human colon cancer cell line, in a dose-dependent manner with an $EC_{50}$ of 9 nM. SCF (Stem Cell Factor) mediated proliferation of TF-1 cells was inhibited by 4-amino-5-fluoro-3-[5-(4-methylpiperazin-1-yl)-1H-benzimidazol-2-yl]quinolin-2(1H)-one indicating that c-Kit RTK activity is modulated. The compound displayed antiproliferative activity in FLT-3 mutant and wild-type cells: $EC_{50}$s of 13 nM against MV4-11 (FLT-3 ITD mutant), and 510 nM against RS4 (FLT-3 wild-type). Reduced tumor cell proliferation was documented in vivo by immunohistochemistry staining with Ki67. Thus, 4-amino-5-fluoro-3-[5-(4-methylpiperazin-1-yl)-1H-benzimidazol-2-yl]quinolin-2(1H)-one is not a general "non-specific" cytotoxic agent, but has potent activity against many cancer cell lines.

Inhibition of Phosphorylation in Cell-Based Assays

Studies with plasma and tumors collected from mice following treatment with 4-amino-5-fluoro-3-[5-(4-methylpiperazin-1-yl)-1H-benzimidazol-2-yl]quinolin-2(1H)-one were performed to evaluate potential pharmacodynamic endpoints. Analysis of target modulation in KM12L4a tumors after 4-amino-5-fluoro-3-[5-(4-methylpiperazin-1-yl)-1H-benzimidazol-2-yl]quinolin-2(1H)-one treatment indicated that phosphorylation of VEGFR1, VEGFR2, PDGFRβ, and FGFR1 were inhibited in a time- and dose-dependent manner. For example, HMVEC cells showed inhibition of VEGF mediated VEGFR2 phosphorylation with an $IC_{50}$ of about 0.1 µM. In addition, treatment of endothelial cells with 4-amino-5-fluoro-3-[5-(4-methylpiperazin-1-yl)-1H-benzimidazol-2-yl]quinolin-2(1H)-one inhibited MAPK and Akt phosphorylation mediated by VEGF.

Furthermore, a time- and dose-dependent inhibition of ERK (MAPK) activation, a downstream target of receptor tyrosine kinases, was observed with $IC_{50}$s ranging from 0.1 to 0.5 µM in KM12L4A cells. (KM12L4A cells express PDGFRβ and VEGFR1/2 on their surfaces.) The inhibitory effects of 4-amino-5-fluoro-3-[5-(4-methylpiperazin-1-yl)-1H-benzimidazol-2-yl]quinolin-2(1H)-one on receptor phosphorylation and ERK activation were maintained for 24 hours after treatment. Phosphorylation of ERK1/2 in MV4-11 cells was inhibited by the exemplary compound at $IC_{50}$s of 0.01 to 0.1 µM in a dose-dependent manner.

FLT-3 and Stat5 phosphorylation was inhibited at concentrations of 0.1 and 0.5 µM of 4-amino-5-fluoro-3-[5-(4-methylpiperazin-1-yl)-1H-benzimidazol-2-yl]quinolin-2(1H)-one when MV4-11 cells are treated for 1 hour. A dose response study of the exemplary compound showed full inhibition of Stat5 phosphorylation in MV4-11 cells at 0.1 µM. A pulse-washout experiment in MV4-11 cells with the exemplary compound showed full inhibition of Stat5 phosphorylation for at least 4 hours and partial inhibition at 24 and 44 hours. FLT-3 phosphorylation in RS4 cells was inhibited at 0.1, 1 and 3 µM concentrations of the exemplary compound.

Significant activity was observed in vivo in the HCT116 human colon tumor model. In HCT116 tumors, 4-amino-5-fluoro-3-[5-(4-methylpiperazin-1-yl)-1H-benzimidazol-2-yl]quinolin-2(1H)-one inhibited the phosphorylation of ERK (MAPK) in a dose- and time-dependent manner and significant changes in histology analyses of the tumors was observed.

These PK/PD evaluations in preclinical models indicate that 4-amino-5-fluoro-3-[5-(4-methylpiperazin-1-yl)-1H-benzimidazol-2-yl]quinolin-2(1H)-one showed a dose- and time-dependent inhibition of both the target receptors and the downstream signaling molecule, ERK (MAPK). These studies will aid in the identification of potential biomarkers to support the monitoring of biological activity of 4-amino-5-fluoro-3-[5-(4-methylpiperazin-1-yl)-1H-benzimidazol-2-yl]quinolin-2(1H)-one in clinical trials.

In Vivo Tumor Model Studies

In vivo daily oral dosing of 4-amino-5-fluoro-3-[5-(4-methylpiperazin-1-yl)-1H-benzimidazol-2-yl]quinolin-2(1H)-one resulted in significant anti-tumor activity in a broad range of human and murine tumor models. Established tumor xenografts of prostate, colon, ovarian and hematologically-derived cancer cells have all demonstrated responsiveness to treatment in a dose-dependent manner, with $ED_{50s}$ ranging from 4-65 mg/kg/d. The in vivo activity ranges from growth inhibition to stable disease and tumor regressions. For example, the compound induces regression and growth inhibition in subcutaneous KM12L4a human colon tumor xenografts in nu/nu mice. FIG. 1 shows tumor volume over time at various doses of 4-amino-5-fluoro-3-[5-(4-methylpiperazin-1-yl)-1H-benzimidazol-2-yl]quinolin-2(1H)-one. Dosing started when tumor xenografts reached 125 mm³. The results show significant tumor growth inhibition after 4 doses of greater than or equal to 30 mg/kg, and tumor regressions at 60 and 100 mg/kg. Similar results were observed in 90-100% of animals with larger KM12L4a colon tumor xenografts. Treatment started when tumor size reached 500 and 1000 mm³. Tissue concentration studies showed that 4-amino-5-fluoro-3-[5-(4-methylpiperazin-1-yl)-1H-benzimidazol-2-yl]quinolin-2(1H)-one was retained in the tumor with levels up to 65-300 fold higher than plasma at 24 hours after dosing. In addition, target modulation studies showed inhibition was maintained for more than 24 hours.

Figure 11:
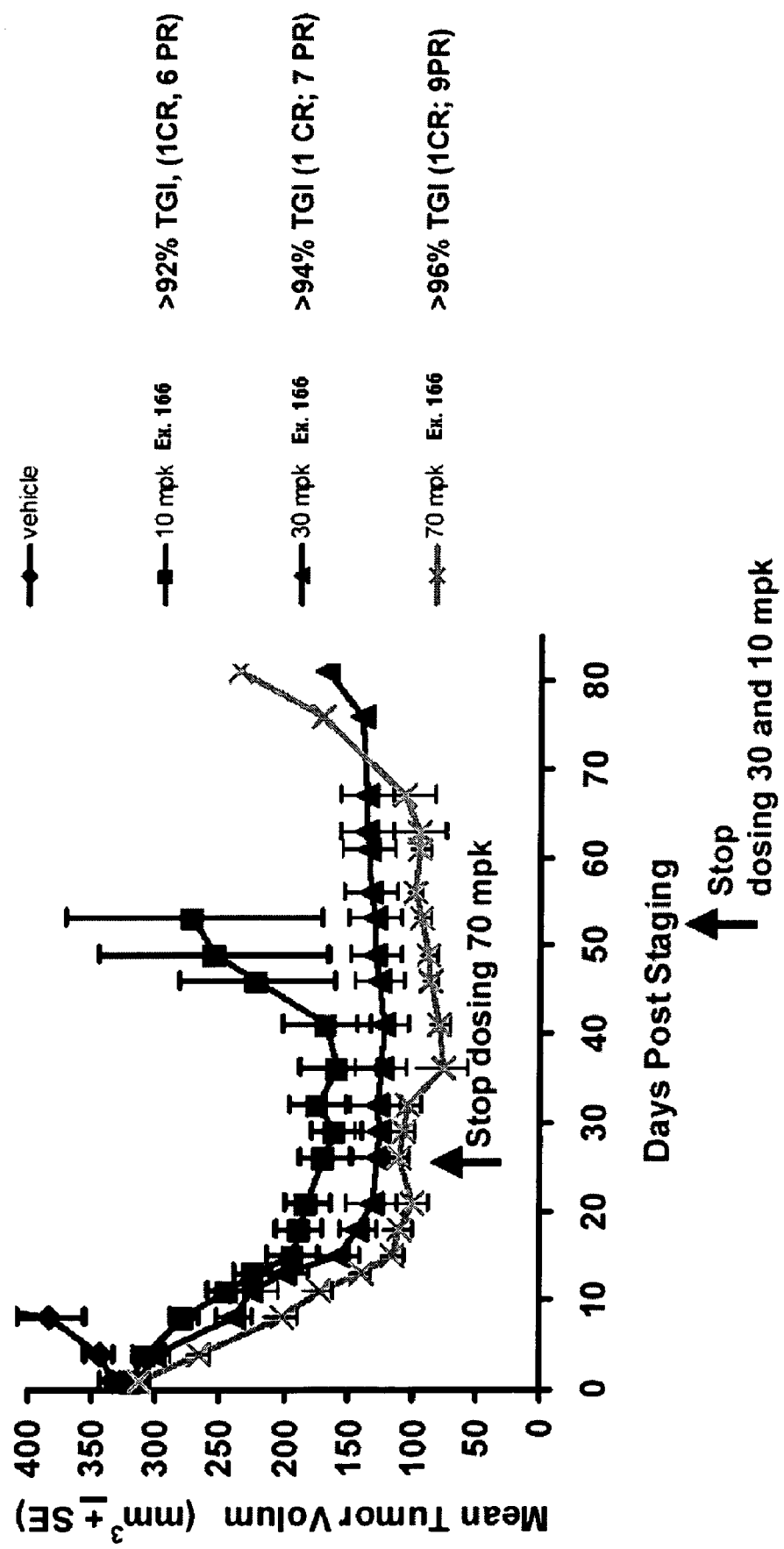
FIG. 11 is a graph of tumor growth inhibition in the presence of 10, 30, and 70 mg/kg/d 4-amino-5-fluoro-3-[5-(4-methylpiperazin-1-yl)-1H-benzimidazol-2-yl]quinolin-2(1H)-one in the MV4-11 (FLT-3 ITD mutant) tumor model in SCID-NOD mice.
Figure 12:
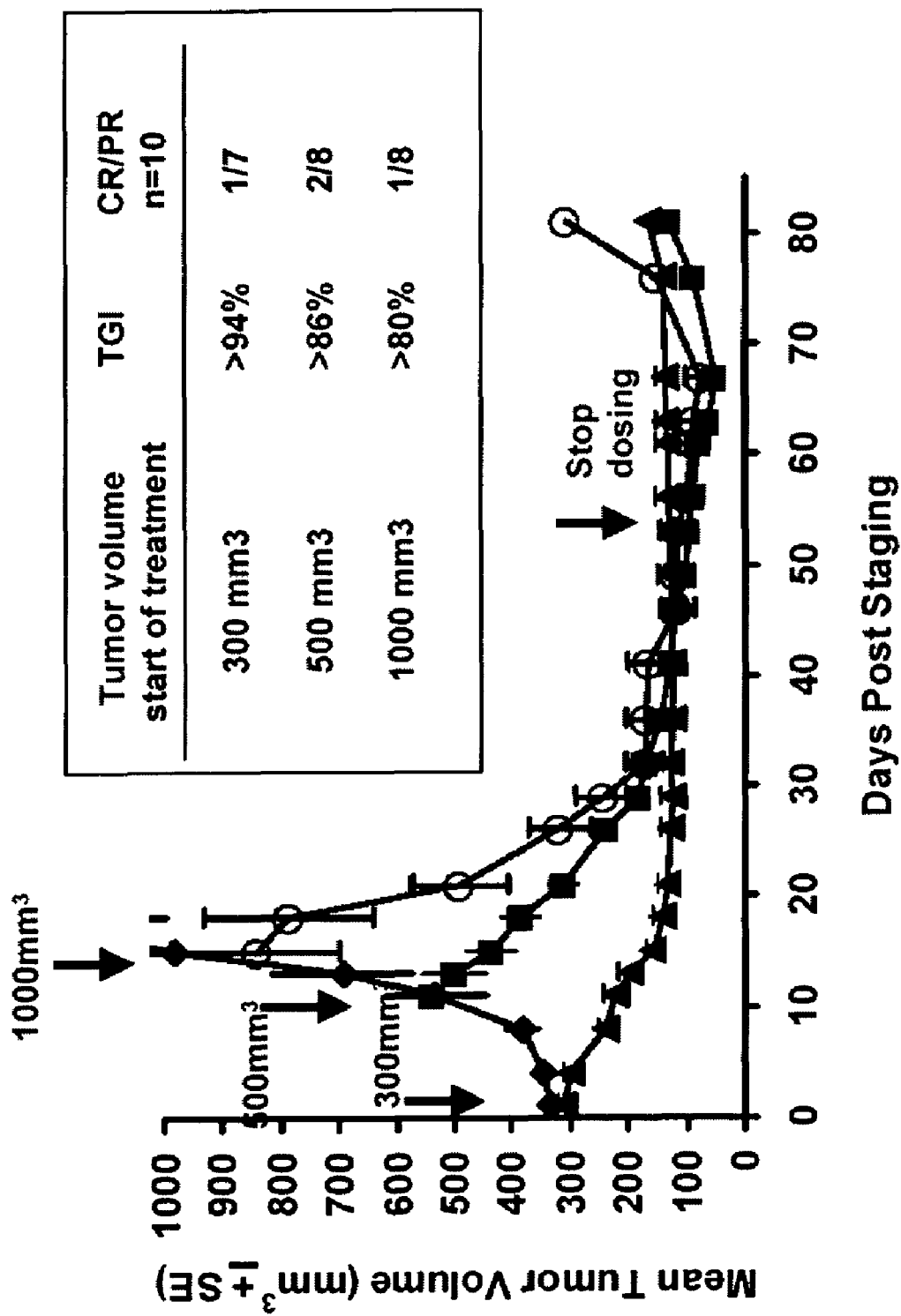
FIG. 12 is a graph of tumor growth inhibition starting with different tumor sizes (300, 500, 1000 mm$^3$) in the presence of 30 mg/kg/d 4-amino-5-fluoro-3-[5-(4-methylpiperazin-1-yl)-1H-benzimidazol-2-yl]quinolin-2(1H)-one in the MV4-11 (FLT-3 ITD mutant) tumor model in SCID-NOD mice.

Example 166 also displayed an $ED_{50}$ of 4 mg/kg/d in a subcutaneous MV4-11 (FLT-3 ITD mutant) tumor model in SCID-NOD mice (treatment initiated when tumor volume at 300 mm³; see FIG. 11). A dose of 30 mg/kg/d inhibited the growth of larger MV4-11 tumors (>86% for 500 mm³; >80% for 1000 mm³ tumor volume at treatment start) and resulted in several complete regressions (see FIG. 12). Regressions were found to be stable after cessation of dosing. In those tumors that recurred, a second cycle of 30 mg/kg/d of the exemplary compound again caused partial regression, indicating a lack of acquired resistance to the compound.

4-Amino-5-fluoro-3-[5-(4-methylpiperazin-1-yl)-1H-benzimidazol-2-yl]quinolin-2(1H)-one also proved efficacious in a tumor metastasis study in which 4T1 murine breast tumor cells were implanted subcutaneously in BALB/c mice. Treatment was begun when the tumors reached 150 mm³, and the mice were given oral daily doses for 17 days. Study endpoints at 30 days after cell implant were primary tumor growth inhibition versus vehicle and macroscopic counts of gross liver metastases. Example 166 inhibited the primary tumor up to 82% and inhibited liver metastases by more than 75% at all doses above 10 mg/kg/d.

Antiangiogenic Effects

Figure 9A:
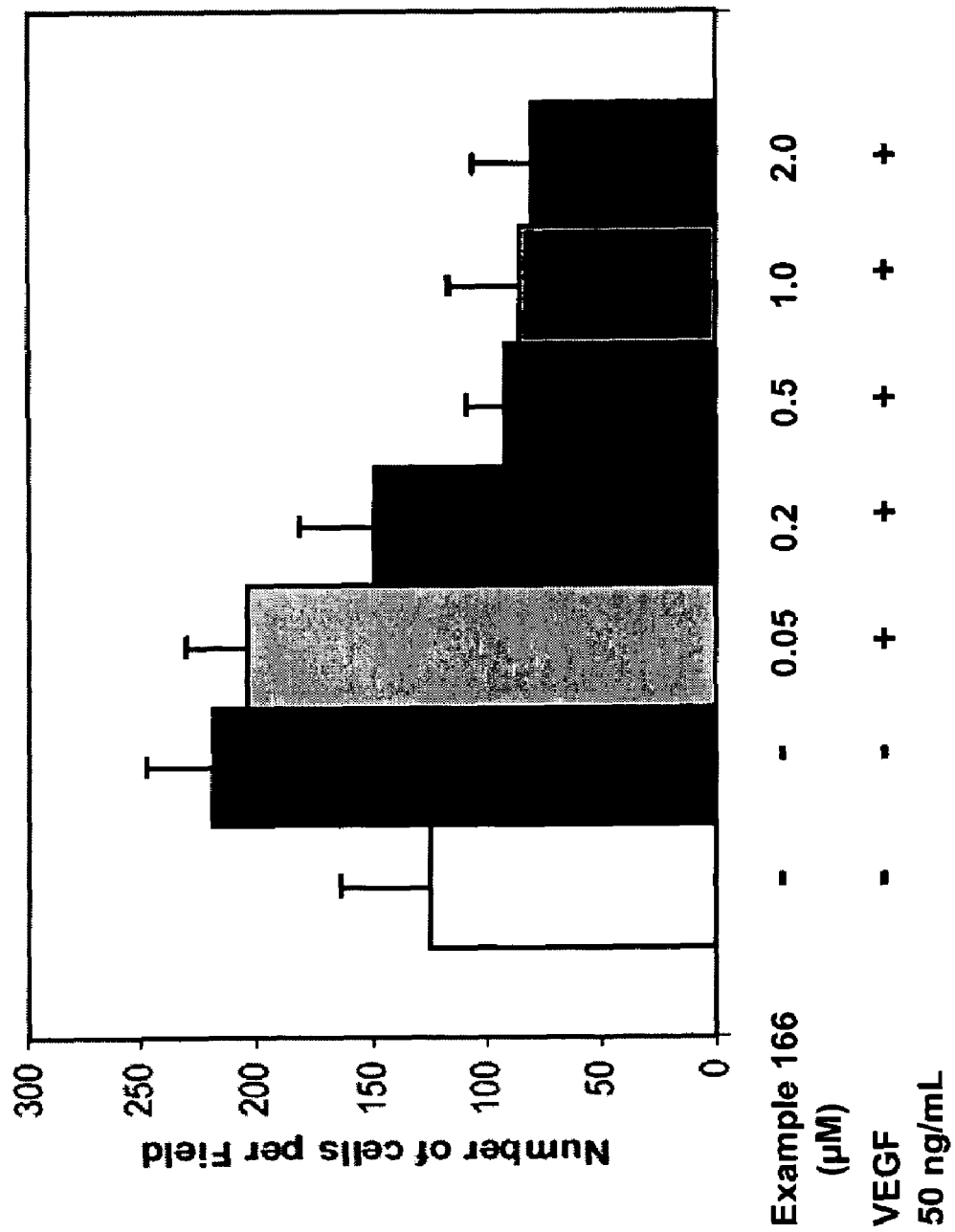
Figure 10:
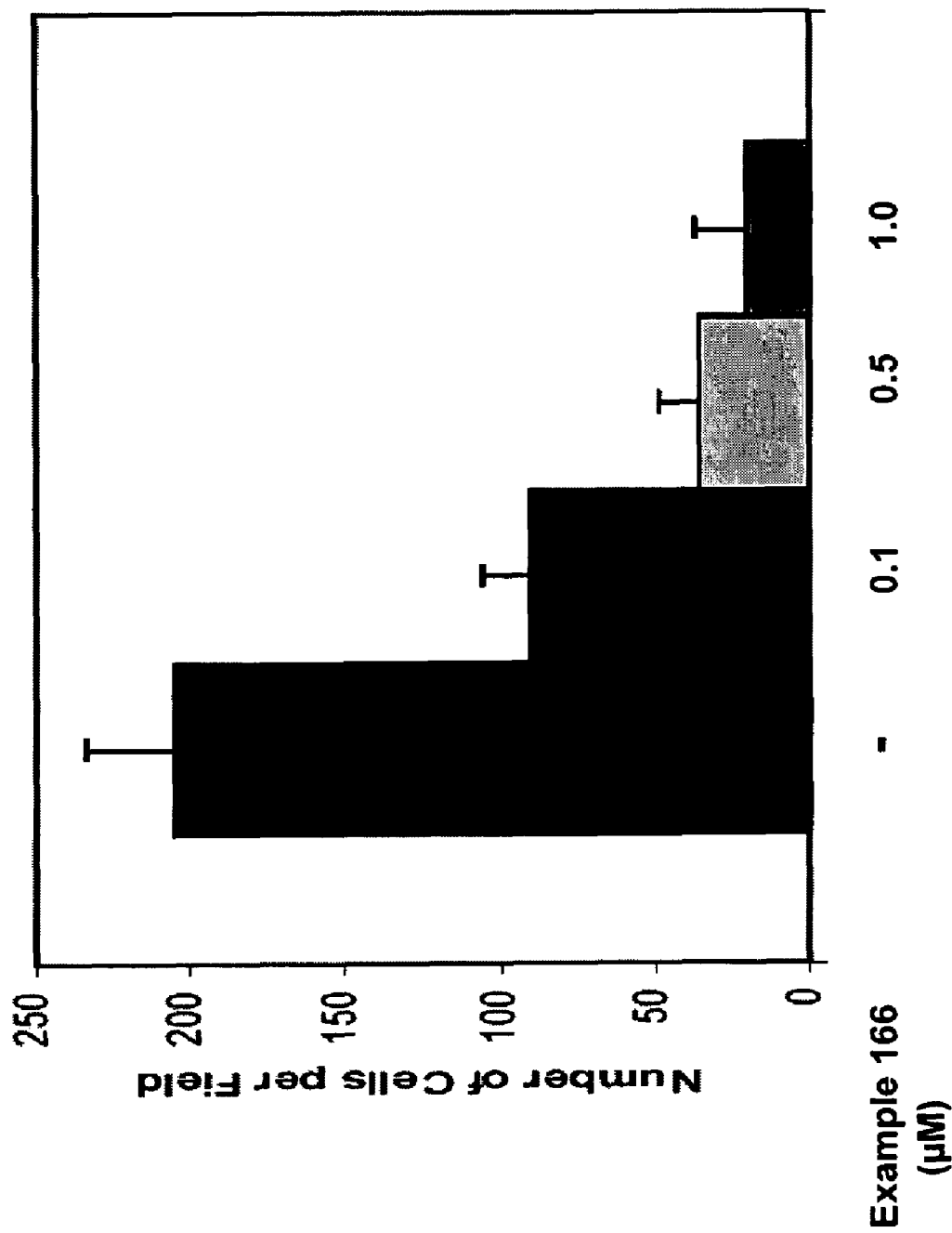
FIG. 10 is a graph showing inhibition of the sprouting of endothelial cells from rat aortic rings in the presence of 4-amino-5-fluoro-3-[5(4-methylpiperazin-1-yl)-1H-benzimidazol-2-yl]quinolin-2(1H)-one.

4-Amino-5-fluoro-3-[5-(4-methylpiperazin-1-yl)-1H-benzimidazol-2-yl]quinolin-2(1H)-one was assayed in several in vitro angiogenesis assays including endothelial cell migration and tube formation on fibrin gels (see FIGS. 9A and 9B) as well as in the ex vivo rat aortic ring assay (see FIG. 10). It showed dose-dependent inhibition of the respective assay endpoints compared to the control.

Figure 2:
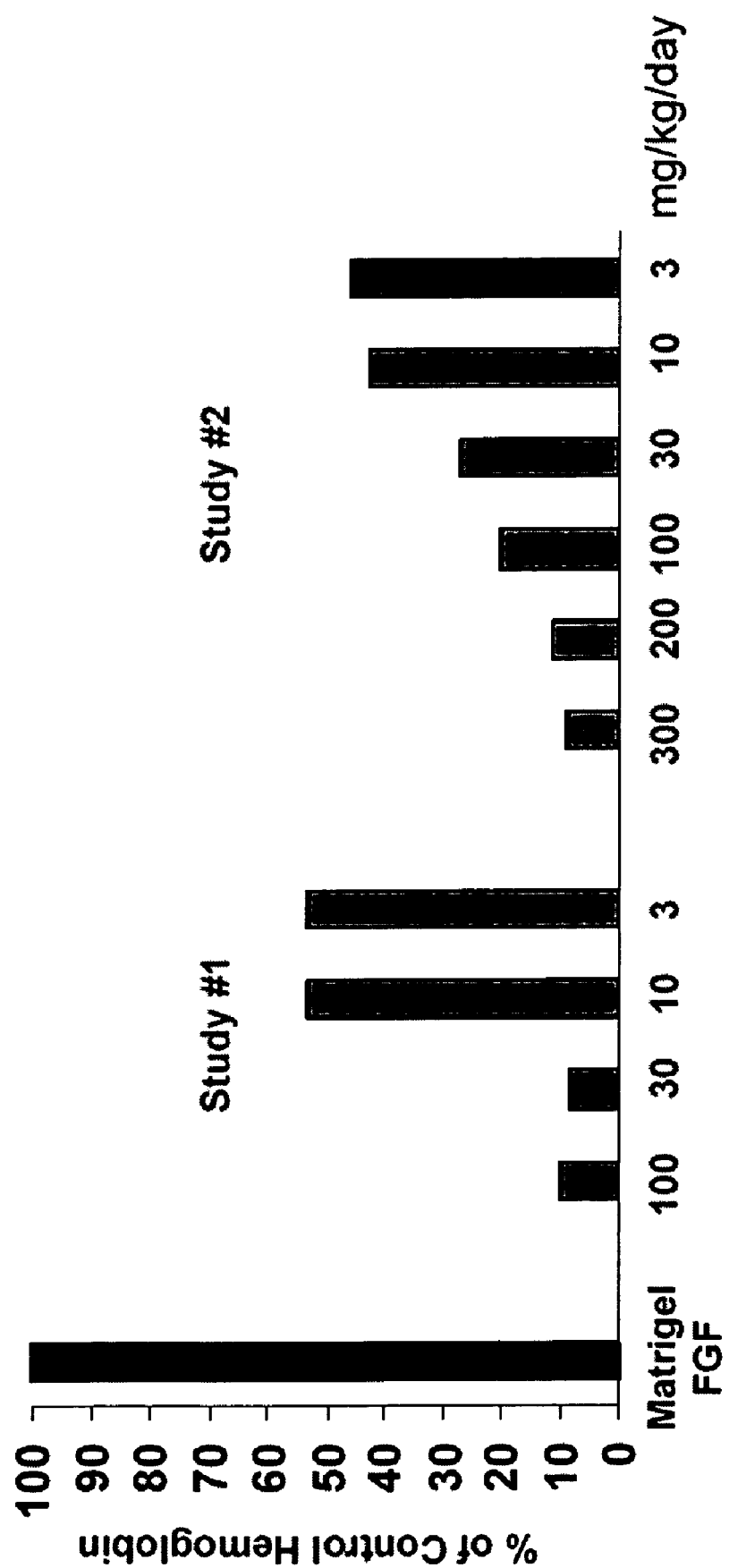
FIG. 2 is a graph of inhibition of angiogenesis in the presence of 4-amino-5-fluoro-3-[5-(4-methylpiperazin-1-yl)-1H-benzimidazol-2-yl]quinolin-2(1H)-one in the in vivo matrigel angiogenesis model.

4-Amino-5-fluoro-3-[5-(4-methylpiperazin-1-yl)-1H-benzimidazol-2-yl]quinolin-2(1H)-one induces dose-dependent inhibition of angiogenesis in the in vivo matrigel model. Matrigel supplemented with bFGF was injected subcutaneously into mice. The compound was orally administered to the mice for 8 days. The matrigel plug was removed and the hemoglobin concentration therein was quantitated. As shown in FIG. 2, significant inhibition of neovascularization was observed, with an $ED_{50}$ of 3 mg/kg/day. In addition, all doses were well tolerated by the animals in the 8-day studies.

Dosing Scheduling Effects

Figure 3:
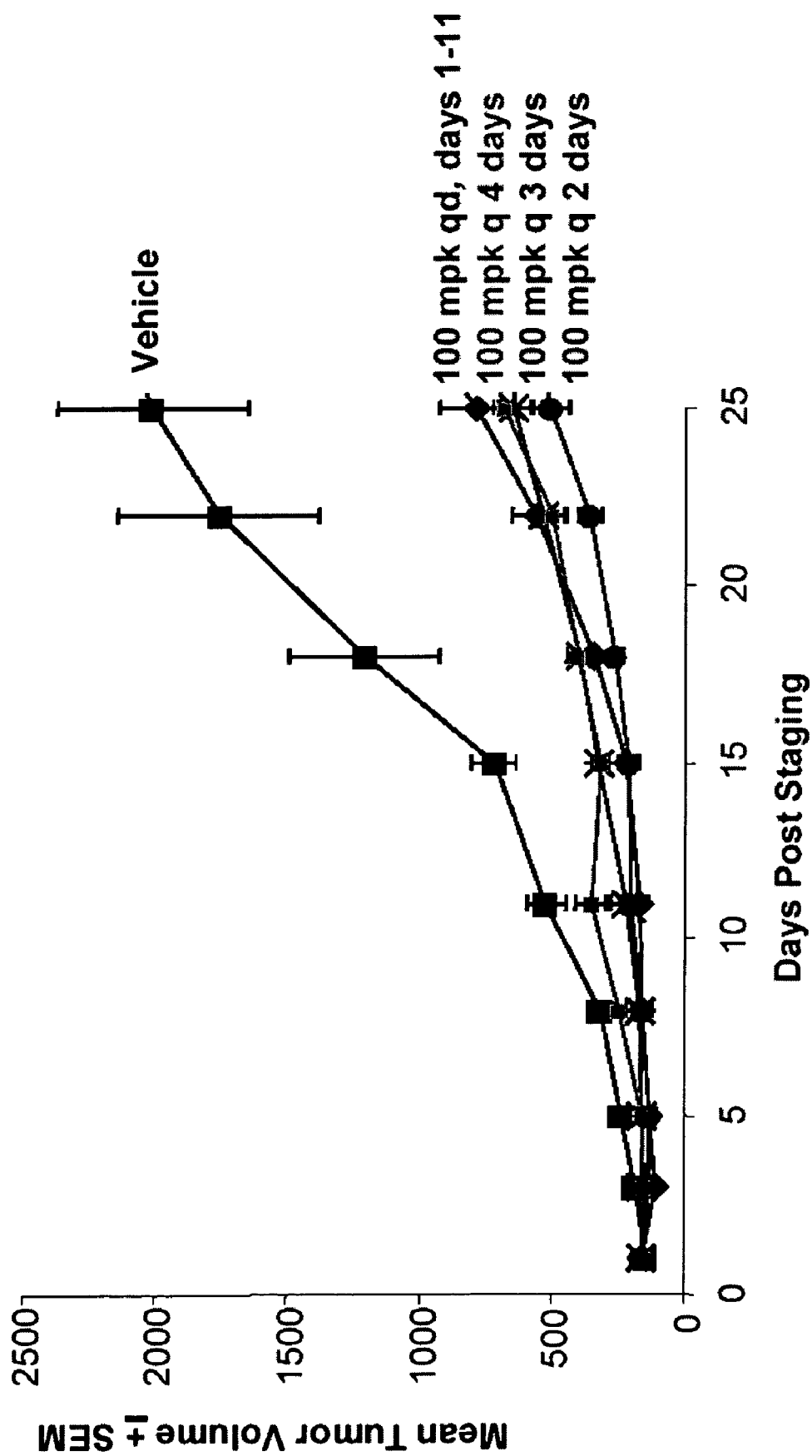
FIG. 3 is a graph of tumor growth inhibition in the presence of 4amino-5-fluoro-3-[5-(4-methylpiperazin-1-yl)-1H-benzimidazol-2-yl]quinolin-2(1H)-one administered intermittently in the PC3 human prostate tumor model in SCID mice.
Figure 4:
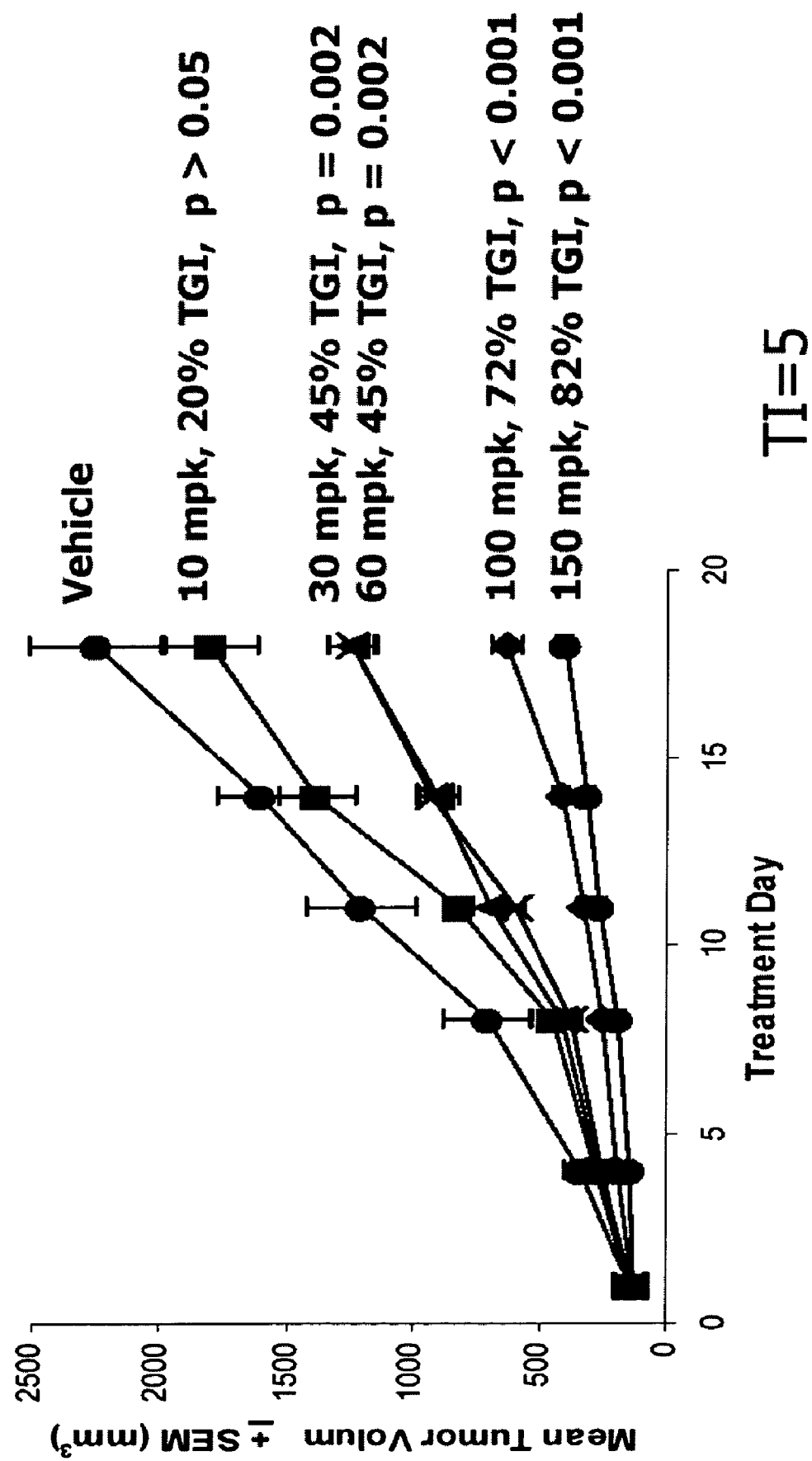
FIG. 4 is a graph of tumor growth inhibition in the presence of 4amino-5-fluoro-3-[5-(4-methylpiperazin-1-yl)-1H-benzimidazol-2-yl]quinolin2(1H)-one.

Dose scheduling studies were done to evaluate the relationship of the extended tumor half-life and prolonged biological activity to the antitumor efficacy. Significant activity was observed with several intermittent and cyclic dosing regimens. For example, in an intermittent dosing regime, 4-amino-5-fluoro-3-[5-(4-methylpiperazin-1-yl)-1H-benzimidazol-2-yl]quinolin-2(1H)-one was administered to SCID mice having subcutaneous PC3 human prostate tumor xenografts. Treatment was started when tumors reached 150 mm³ in size. Dosing was performed at 100 mg/kg orally qd, q2d, q3d, and q4d. Significant and similar tumor inhibition was observed in all treatment groups as shown in FIG. 3.

Figure 13:
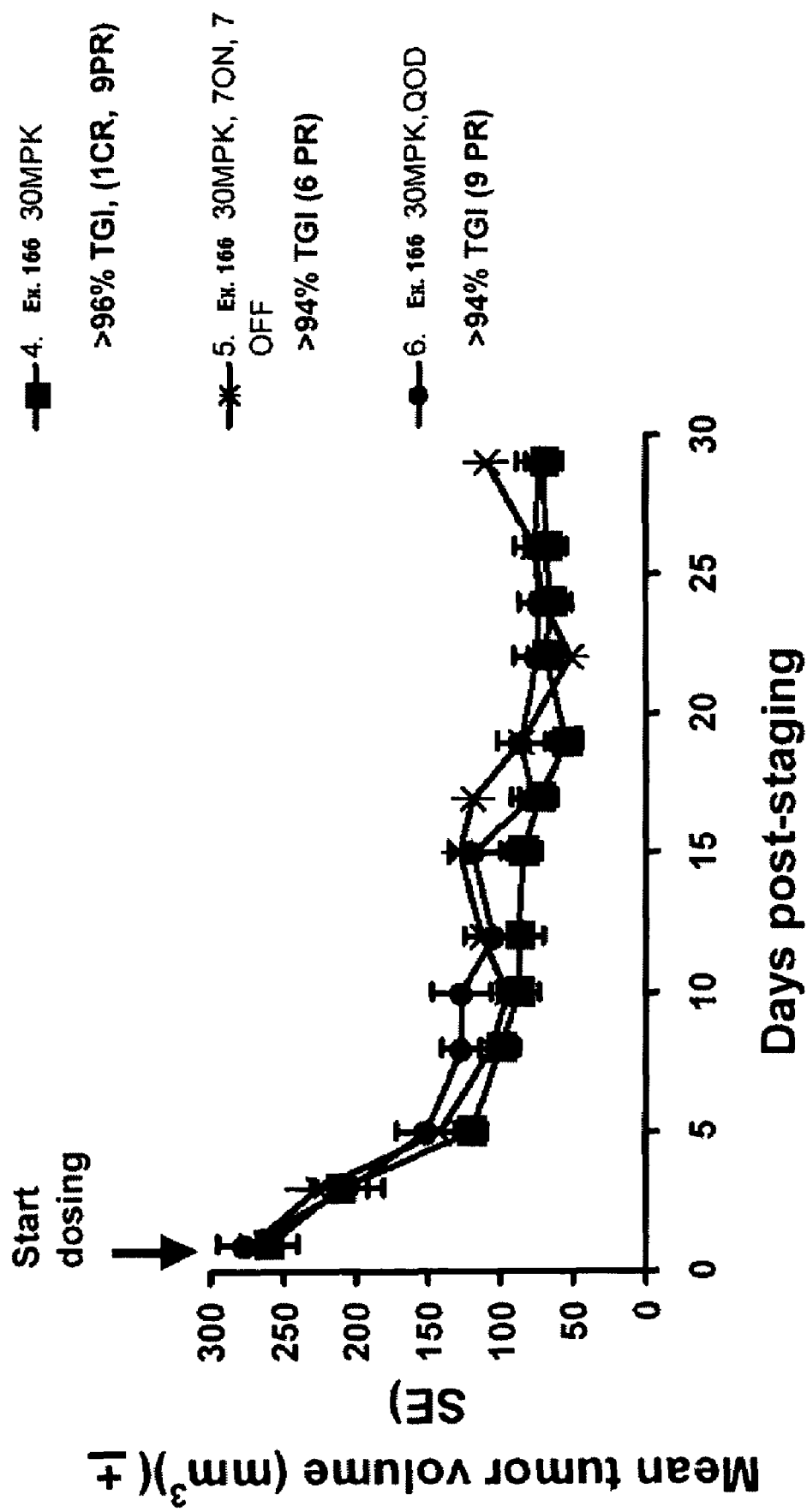
FIG. 13 is a graph of tumor growth inhibition in the presence of 30 mg/kg/d 4-amino-5-fluoro-3-[5-(4-methylpiperazin-1-yl)-1H-benzimidazol-2yl]quinolin-2(1H)-one administered daily, q.o.d., or 7 days on/7 off in the MV4-11 (FLT-3 ITD mutant) tumor model in SCID-NOD mice.

In a cyclic dosing experiment, 4-amino-5-fluoro-3-[5-(4-methylpiperazin-1-yl)-1H-benzimidazol-2-yl]quinolin-2 (1H)-one was administered to nu/nu mice having KM12L4a human colon tumor xenografts. Treatment was started when tumors reached 500 mm³. Doses were administered at 100 or 150 mg/kg on days 1-5, 18-22, and 26-30. Compared to vehicle, tumor regression of 50% or more was seen. At the higher dose, tumors continued to regress and then stabilize for about 10 days. In another dosing study, the effect of the exemplary compound was examined in the human MV4-11 (FLT-3 ITD mutant) subcutaneous tumor model in SCID-NOD mice. Alternate dosing schedules (q.o.d. or 7days on/7 off) of 30 mg/kg 4-amino-5-fluoro-3-[5-(4-methylpiperazin-1-yl)-1H-benzimidazol-2-yl]quinolin-2(1H)-one were equally potent (see FIG. 13).

Combination Therapy Results

Figure 5:
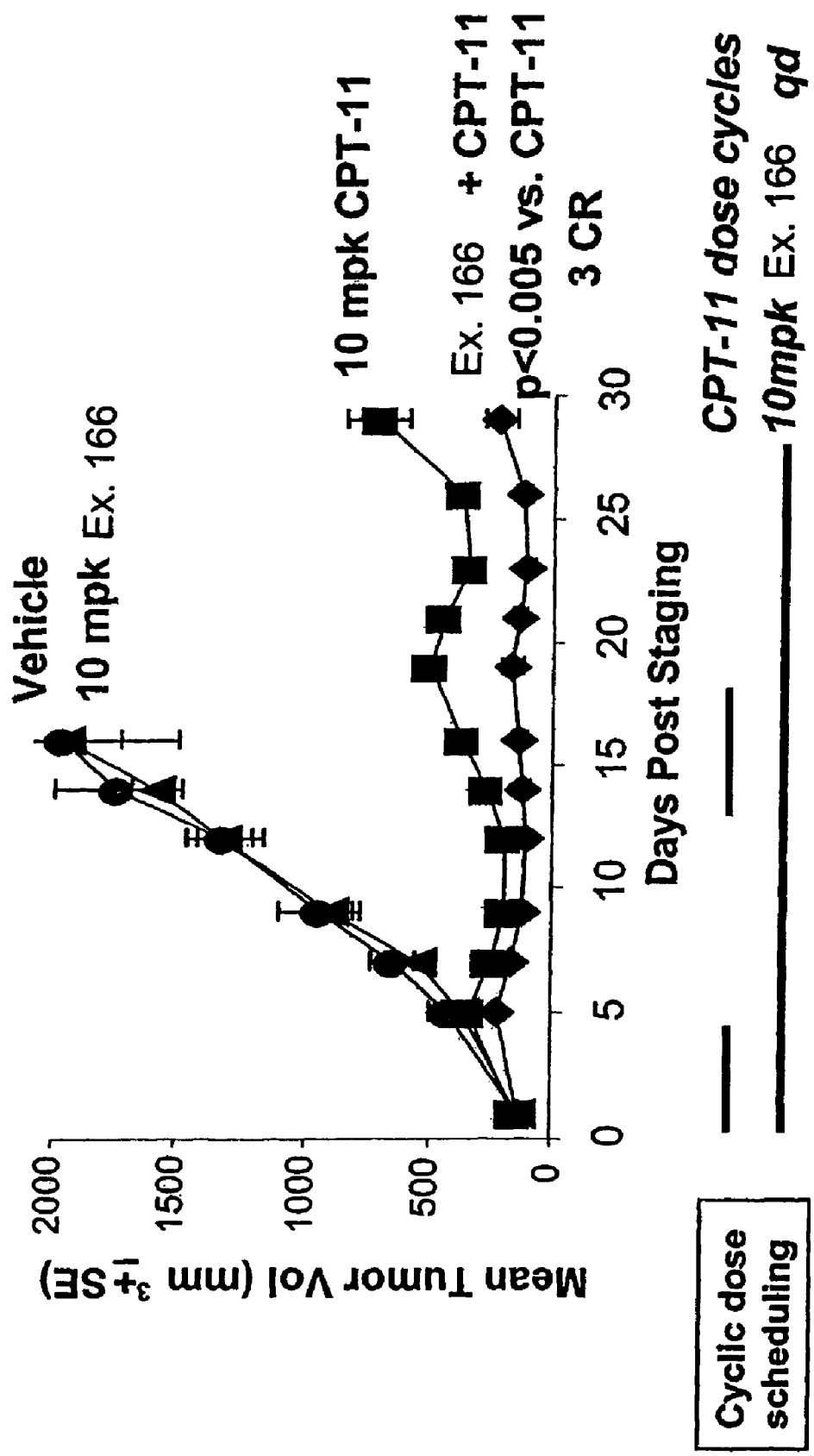
FIG. 5 is a graph of tumor growth inhibition in the presence of 10 mg/kg/d 4-amino-5-fluoro-3-[5-(4-methylpiperazin-1-yl)-1H-benzimidazol-2-yl]quinolin-2(1H)-one administered in combination with irinotecan in the KM12L4a colon tumor model in nu/nu mice.
Figure 6:
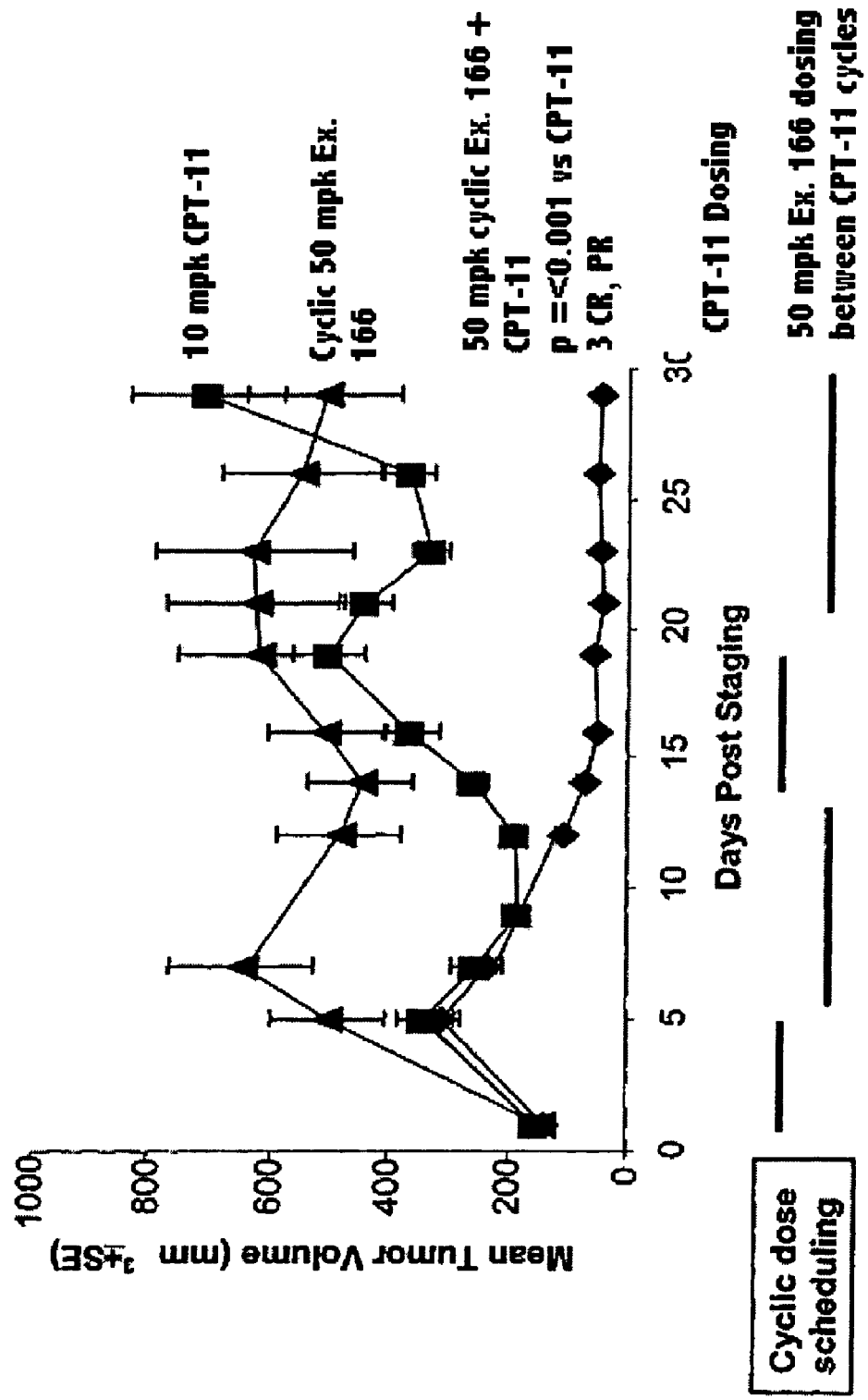
FIG. 6 is a graph of tumor growth inhibition in the presence of 50 mg/kg/d 4-amino-5-fluoro-3-[5-(4-methylpiperazin-1-yl)-1H-benzimidazol-2-yl]quinolin-2(1H)-one administered in combination with irinotecan in the KM12L4a colon tumor model in nu/nu mice.
Figure 7:
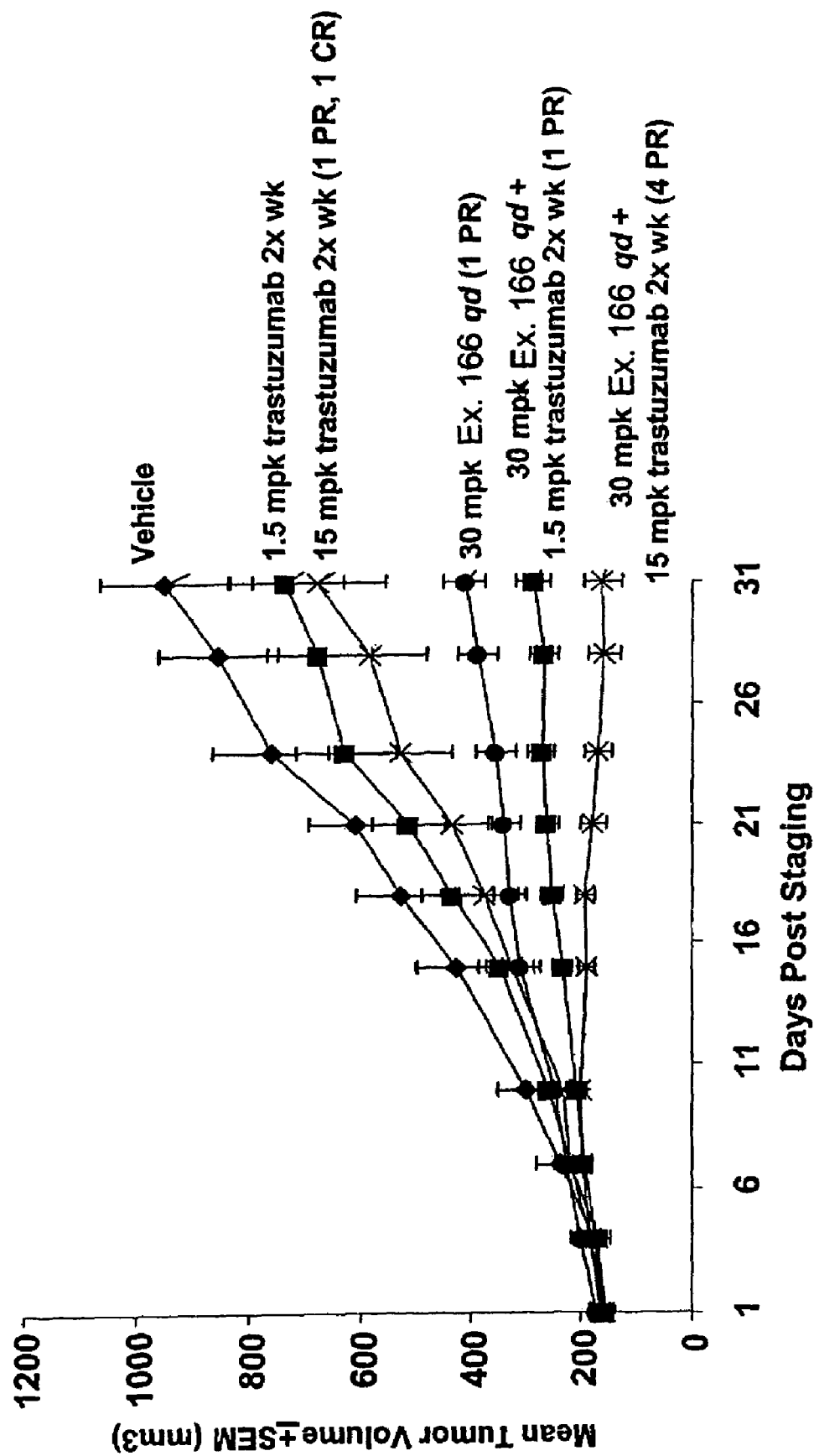
FIG. 7. is a graph of tumor growth inhibition in the presence of 50 mg/kg/d 4-amino-5-fluoro-3-[5-(4-methylpiperazin-1-yl)-1H-benzimidazol-2-yl]quinolin-2(1H)-one administered in combination with trastuzumab in the erbB2-overexpressing ovarian tumor model, SKOV3ip1.
Figure 8:
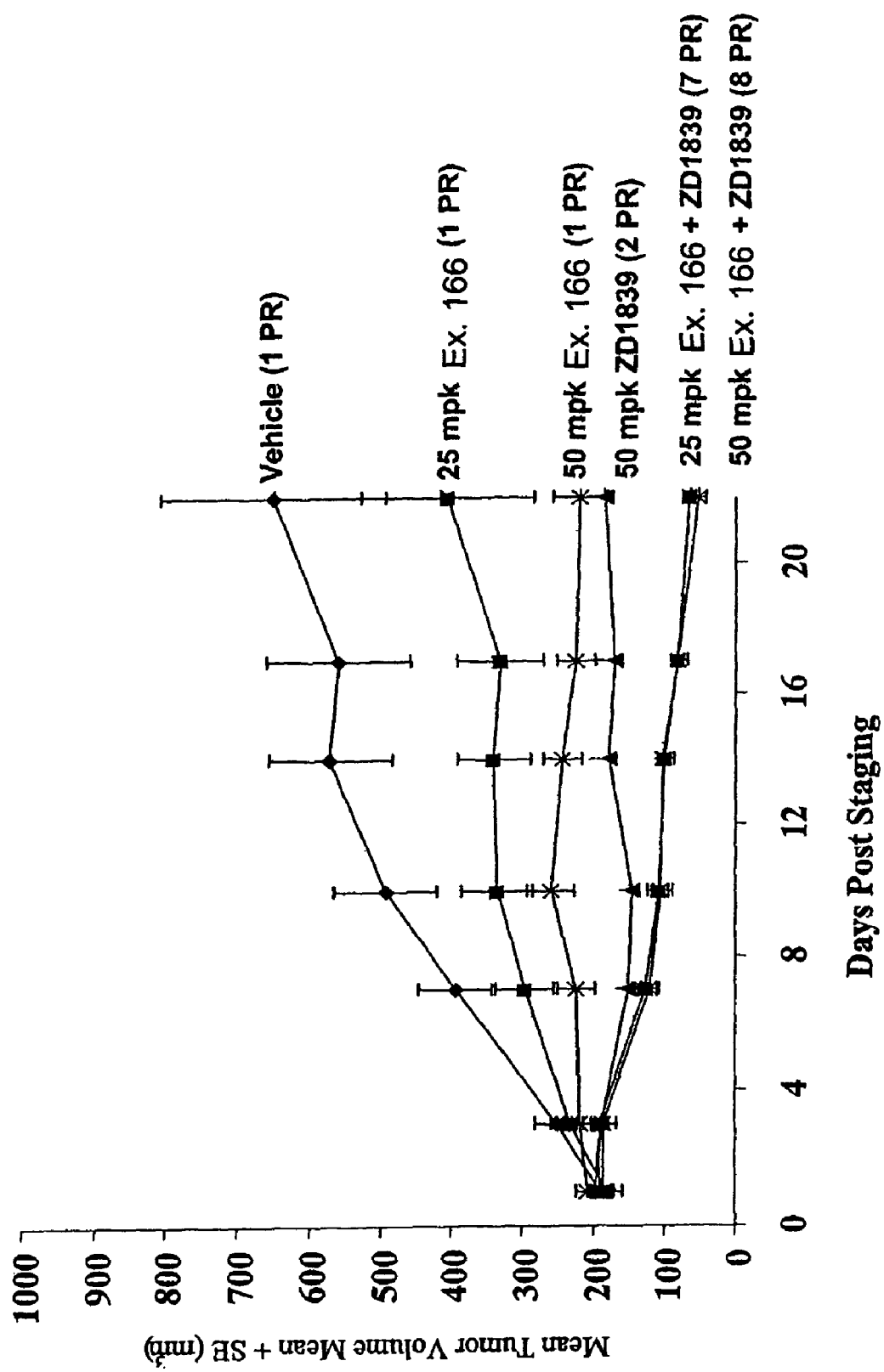
FIG. 8 is a graph of tumor growth inhibition in the presence of 50 mg/kg/d 4-amino-5-fluoro-3-[5-(4-methylpiperazin-1-yl)-1H-benzimidazol-2-yl]quinolin-2(1H)-one administered in combination with ZD1839 in the A431 epidermoid tumor model.

Combination therapy studies were done using the standard cytotoxics, irinotecan and 5-FU, in the KM12L4a colon tumor model. Significant potentiation of activity was seen, with the most dramatic effects at low, inactive doses of 4-amino-5-fluoro-3-[5-(4-methylpiperazin-1-yl)-1H-benzimidazol-2-yl]quinolin-2(1H)-one as shown in FIG. 5. A cyclic dosing regimen of the compound at 50 mg/kg in combination with irinotecan gave excellent results, with 3 complete regressions and 7 partial regressions, as shown in FIG. 6. Synergistic and greater than additive effects were also seen with trastuzumab combined with 4-amino-5-fluoro-3-[5-(4-methylpiperazin-1-yl)-1H-benzimidazol-2-yl]quinolin-2 (1H)-one in the erbB2-overexpressing ovarian tumor model, SKOV3ip1 (see FIG. 7). Additionally, tumor responses and regressions were significantly improved over each single agent treatment in the A431 epidermoid tumor model when 4-amino-5-fluoro-3-[5-(4-methylpiperazin-1-yl)-1H-benzimidazol-2-yl]quinolin-2(1H)-one was combined with ZD1839 (Iressa) (see FIG. 8). These data suggest that 4-amino-5-fluoro-3-[5-(4-methylpiperazin-1-yl)-1H-benzimidazol-2-yl]quinolin-2(1H)-one has the potential to be a broadly applicable and effective therapy for solid and hematological cancers.

Metabolism and Pharmacokinetic Studies

Metabolism and pharmacokinetic studies were carried out on 4-amino-5-fluoro-3-[5-(4-methylpiperazin-1-yl)-1H-benzimidazol-2-yl]quinolin-2(1H)-one. The compound was stable in human liver microsomes. It did not demonstrate a significant potential for inhibition of five common cDNA derived CYP isozymes (1A2, 2C9, 2C19, 2D6, 3A4) having $IC_{50}$s of greater than 25 µM for each. In addition, the compound displays a half life adequate for once daily dosing. Thus, the compound displays favorable metabolic and pharmacokinetic properties.

Each of the following compounds was synthesized and was assayed using the procedures described herein:

3-{5-[2-(ethylanilino)ethoxy]-1H-benzimidazol-2-yl}-4-hydroxy-2(1H)-quinolinone; 3-[5-(4-aminophenoxy)-1H-benzimidazol-2-yl]-4-hydroxy-2(1H)-quinolinone; 3-{6-[[2-(dimethylamino)ethyl](methyl)amino]-1H-benzimidazol-2-yl}-4-hydroxy-2(1H)-quinolinone; 4-hydroxy-3-[5-(4-morpholinyl)-1H-benzimidazol-2-yl]-2(1H)-quinolinone; 3-[5-(3-amino-1-pyrrolidinyl)-1H-benzimidazol-2-yl]4-hydroxy-2(1H)-quinolin; N,N-dimethyl-2-(2-oxo-1,2-dihydro-3-quinolinyl)-1H-benzimidazole-5-carboxamide; 3-{5-[2-(4-morpholinyl)ethoxy]-1H-benzimidazol-2-yl}-2(1H)-quinolinone; 3-{5-[3-(dimethylamino)-1-pyrrolidinyl]-1H-benzimidazol-2-yl}-2(1H)-quinolinone; 3-(1H-benzimidazol-2-yl)-2-oxo-1,2-dihydro-4-quinolinecarbonitrile; 4-amino-3-{5-[2-(4morpholinyl)ethoxy]-1H-benzimidazol-2-yl}-2(1H)-quinolinone; 4-amino-3-[6-(4-morpholinyl)-1H-benzimidazol-2-yl]-2(1H)-quinolinone; 4-amino-3-[6-(3-amino-1-pyrrolidinyl)-1H-benzimidazol-2-yl]-2(1H)-quinolinone; 2-(4-amino-2-oxo-1,2-dihydro-3-quinolinyl)-1H-benzimidazole-5-carbonitrile; 2-(4-amino-2-oxo-1,2-dihydro-3-quinolinyl)-N,N-dimethyl-1H-benzimidazole-5-carboxamide; 4-amino-3-{5-[3-(dimethylamino)-1-pyrrolidinyl]-1H-benzimidazol-2-yl}-2(1H)-quinolinone; 2-(4-amino-2-oxo-1,2-dihydro-3-quinolinyl)-1H-benzimidazole-6-carboximidamide; 4-amino-3-[5-(4-morpholinylcarbonyl)-1H-benzimidazol-2-yl]-2(1H)-quinolinone; 4-amino-3-[5-(1H-1,2,4-triazol-1-yl)-1H-benzimidazol-2-yl]-2(1H)-quinolinone; 4-amino-3-[5-(dimethylamino)-1H-benzimidazol-2-yl]-2(1H)-quinolinone; 4-amino-3-[5-(1-piperidinyl)-1H-benzimidazol-2-yl]-2(1H)-quinolinone; 4-amino-3-[5-(2-thienyl)-1H-benzimidazol-2-yl]-2(1H)-quinolinone; 4amino-3-{5-[3-(1-pyrrolidinyl)propoxy]-1H-benzimidazol-2-yl}-2(1H)-quinolinone; 4-amino-3-{5-[3-(4-morpholinyl)propoxy]-1H-benzimidazol-2-yl}-2(1H)-quinolinone; 4-amino-3-[5-(3,5-dimethyl-1-piperazinly)-1H-benzimidazol-2-yl]-2(1H)-quinoli016; 4-amino-3-[5-(2,6-dimethly-4-morpholiny)-1H-benzimidazol-2-yl]-2 (1H)-quinolinone; 4-amino-3-[5-(4-methyl-1-piperazinyl)-1H-benzimidazol-2-yl]-2(1H)-quinolinone; 4-amimo-3-(1H-benzimidazol-2-yl)-6-[hydroxy(oxido)amino]-2(1H)-quinolinone; 4-amino-3-(1H-benzimidazol-2yl)-5-[2-(4-morpholinyl)ethoxy]-2(1H)-quinolinone; 4-amino-3-(1H-benzimidazol-2-yl)-6-(4-methyl-1-piperazinyl)-2(1H)-quinolinone; 4-amino-3-(1-benzimidazol-2-yl)-5-[(1-methyl-3-piperidinyl)oxy]-2(1H)-quinolinone; 4-amino-6-chloro-3-[5-(4-morpholinyl)-1H-benzimidazol-2-yl]-2(1H)-quinolinone; 4-amino-6-chloro-3-{5-[3-(dimethylamino)-1-pyrrolidinyl]-1H-benzimidazol-2-yl}-2(1H)-quinolinone; 4-amino-6-[hydroxy(oxido)amino]-3-{5-[2-(4-morpholinyl)ethoxy]-1H- benzimidazol-2-yl}-2(1H)-quinolinone; 4-amino-5-[2-(4-morpholinyl)ethoxy]-3-{5-[2-(4-morpholinyl)ethoxy]-1H-benzimidazol-2-yl}-2(1H)-quinolinone; 4-amino-3-(1H-benzimidazol-2-yl)-6-(2-pyridinylmethoxy)-2(1H)-quinolinone; 4-amino-6-fluoro-3-[5-(4-morpholinyl)-1H-benzimidazol-2-yl]-2(1H)-quinolinone; 4-amino-3-{5-[3-(dimethylamino)-1-pyrrolidinyl]-1H-benzimidazol-2-yl}-6-fluoro-2(1H)-quinolinone; 3-(1H-benzimidazol-2-yl)-4-[(tetrahydro-2-furanylmethyl)amino]-2(1H)-quinolinone; 3-(1H-benzimidazol-2-yl)-4-(methylamino)-2(1H)-quinolinone; 3-(1H-benzimidazol-2-yl)-4-(ethylamino)-2(1H)-quinolinone; 3-(1H-benzimidazol-2-yl)-4-{[2-(1-methyl-2-pyrrolidinyl)ethyl]amino}-2(1H)-quinolinone; 3-(1H-benzimidazol-2-yl)-4-[(4-piperidinylmethyl)amino]-2(1H)-quinolinone; 3-(1H-benzimidazol-2-yl)-4-(4-fluoroanilino)-2(1H)-quinolinone; 4-(1-azabicyclo[2.2.2]oct-3-ylamino)-3-(1H-benzimidazol-2-yl)-2(1H)-quinolinone; 3-(1H-benzimidazol-2-yl)-4-(1H-benzimidazol-6-ylamino)-2(1H)-quinolinone; 4-anilino-3-(1H-benzimidazol-2-yl)-2(1H)-quinolinone; 3-(1H-benzimidazol-2-yl)-4-(methoxyamino)-2(1H)-quinolinone; 3-(1H-benzimidazol-2-yl)-4-[(1H-imidazol-5-ylmethyl)amino]-2(1H)-quinolinone; 3-(1H-benzimidazol-2-yl)-4-(4-morpholinylamino)-2(1H)quinolinone; 3-(1H-benzimidazol-2-yl)-4-hydrazino-2(1H)-quinolinone; 4-(1-azabicyclo[2.2.2]oct-3-ylamino)-3-(1H-benzimidazol-2-yl)-2(1H)-quinolinone; 4-(1-azabicyclo[2.2.2]oct-3-ylamino)-3-(1H-benzimidazol-2-yl)-2(1H)-quinolinone; 4-[(2-methoxyethyl)amino]-3-[6-(4-morpholinyl)-1H-benzimidazol-2-yl]-2(1H)-quinolinone; 4-[(2-hydroxyethyl)amino]-3-[5-(4-morpholinyl)-1H-benzimidazol-2-yl]-2(1H)-quinolinone; 4-(methoxyamino)-3-[5-(4-morpholinyl)-1H-benzimidazol-2-yl]-2(1H)-quinolinone; 3-[5-(4-morpholinyl)-1H-benzimidazol-2-yl]-4-(3-piperidinylamino)-2(1H)-quinolinone; 3-[5-(4-morpholinyl)-1H-benzimidazol-2-yl]-4-[(3-piperidinylmethyl)amino]-2(1H)-quinolinone; 4-{[2-(dimethylamino)ethyl]amino}-3-[5-(4-morpholinyl)-1H-benzimidazol-2-yl]-2(1H)-quinolinone; 3-[5-(4-morpholinyl)-1H-benzimidazol-2-yl]-4-[(tetrahydro-2-furanylmethyl)amino]-2(1H)-quinolinone; 4-{[2-(methylamino)ethyl]amino}-3-[5-(4-morpholinyl)-1H-benzimidazol-2-yl]-2(1H)-quinolinone; 3-[5-(4-morpholinyl)-1H-benzimidazol-2-yl]-4-(3-pyrrolidinylamino)-2(1H)-quinolinone; 4-[(2-amino-4-methylpentyl)amino]-3-[5-(4-morpholinyl)-1H-benzimidazol-2-yl]-2(1H)-quinolinone; 4-[(2-amino-3-methylbutyl)amino]-3-[5-(4-morpholinyl)-1H-benzimidazol-2-yl]-2(1H)-quinolinone; 3-(5,6-dimethyl-1H-benzimidazol-2-yl)-4-(3-piperidinylamino)-2(1H)-quinolinone; 4-[(2-aminocyclohexyl)amino]-3-[5-(4-morpholinyl)-1H-benzimidazol-2-yl]-2(1H)-quinolinone; 4-[(2-aminocyclohexyl)amino]-3-[5-(4-morpholinyl)-1H-benzimidazol-2-yl]-2(1H)-quinolinone; 3-(1H-benzimidazol-2-yl)-4-hydroxybenzo[g]quinolin-2(1H)-one; 4-amino-3-(3H-imidazo[4,5-b]pyridin-2-yl)quinolin-2(1H)-one; 4-amino-3-(5-morpholin-4-yl-3H-imidazo[4,5-b]pyridin-2-yl)quinolin-2(1H)-one; 4-amino-5-[(2R,6S)-2,6-dimethylmorpholin-4-yl]-3-(3H-imidazo[4,5-b]pyridin-2-yl)quinolin-2(1H)-one; 4-amino-3-{5-[3-(dimethylamino)pyrrolidin-1-yl]-3H-imidazo[4,5-b]pyridin-2-yl}quinolin-2(1H)-one; 4-amino-3-{5-[(3S)-3-(dimethylamino)pyrrolidin-1-yl]-1H-benzimidazol-2-yl}quinolin-2(1H)-one; 4-[(3S)-1-azabicyclo[2.2.2]oct-3-ylamino]-3-(1H-benzimidazol-2-yl)-6-chloroquinolin-2(1H)-one; 4-[(3R)-1-azabicyclo[2.2.2]oct-3-ylamino]-3-(1H-benzimidazol-2-yl)-6-chloroquinolin-2(1H)-one; 3-(1H-benzimidazol-2-yl)-4-[(3R)-3-(dimethylamino)pyrrolidin-1-yl]quinolin-2(1H)-one; 3-(1H-benzimidazol-2-yl)-6-chloro-4-[(3R)-3-(dimethylamino)pyrrolidin-1-yl]quinolin-2(1H)-one; 4-amino-3-[5-(4-ethylpiperazin-1-yl)-1H-benzimidazol-2-yl]-1-methylquinolin-2(1H)-one; 4-amino-3-(6-piperazin-1-yl-1H-benzimidazol-2-yl)quinolin-2(1H)-one; 4-amino-3-[6-(pyridin-4-ylmethyl)-1H-benzimidazol-2-yl]quinolin-2(1H)-one; 4-amino-3-{5-[(3R,5S)-3,5-dimethylpiperazin-1-yl]-1H-benzimidazol-2-yl}quinolin-2(1H)-one; 4-amino-3-[5-(4-methylpiperazin-1-yl)-1H-benzimidazol-2-yl]quinolin-2(1H)-one; 4-amino-3-(6-methyl-5-morpholin-4-yl-1H-benzimidazol-2-yl)quinolin-2(1H)-one; 4-amino-3-{5-[(1-methylpiperidin-3-yl)oxy]-1H-benzimidazol-2-yl}quinolin-2(1H)-one; 4-amino-3-{5-[(2R,6S)-2,6-dimethylmorpholin-4-yl]-6-fluoro-1H-benzimidazol-2-yl}quinolin-2(1H)-one; 4-amino-3-{5-[(1-methylpyrrolidin-3-yl)oxy]-1H-benzimidazol-2-yl}quinolin-2(1H)-one; 4-amino-3-[5-(4-methyl-1,4-diazepan-1-yl)-1H-benzimidazol-2-yl]quinolin-2(1H)-one; 4-amino-3-{5-[(3R)-3-(dimethylamino)pyrrolidin-1-yl]-1H-benzimidazol-2-yl}quinolin-2(1H)-one; 4-amino-6-chloro-3-{5-[(3R)-3-(dimethylamino)pyrrolidin-1-yl]-1H-benzimidazol-2-yl}quinolin-2(1H)-one; ethyl{4-[2-(4-amino-2-oxo-1,2-dihydroquinolin-3-yl)-1H-benzimidazol-6-yl]piperazin-1-yl}acetate; 4-amino-3-{6-[methyl(1-methylpiperidin-4-yl)amino]-1H-benzimidazol-2-yl}quinolin-2(1H)-one; 3-[6-(4-acetylpiperazin-1-yl)-1H-benzimidazo-2-yl]-4-aminoquinolin-2(1H)-one; 4-amino-3-[6-(1,4'-bipiperidin-1'-yl)-1H-benzimidazol-2-yl]quinolin-2(1H)-one; 2-(4-amino-2-oxo-1,2-dihydroquinolin-3-yl)-1H-benzimidazole-6-carboxylic acid; 4-amino-5-(methyloxy)-3-[6-(4-methylpiperazin-1-yl)-1H-benzimidazol-2-yl]quinolin-2(1H)-one; 4-amino-3-{6-[4-(1-methylethyl)piperazin-1-yl]-1H-benzimidazol-2-yl}quinolin-2(1H)-one; {4-[2-(4-amino-2-oxo-1,2-dihydroquinolin-3-yl)-1H-benzimidazol-6-yl]piperazin-1-yl}acetic acid; 4-[(3S)-1-azabicyclo[2.2.2]oct-3-ylamino]-3-(1H-benzimidazol-2-yl)quinolin-2(1H)-one; 4-[(3R)-1-azabicyclo[2.2.2]oct-3-ylamino]-3-(1H-benzimidazol-2-yl)quinolin-2(1H)-one; 4-amino-3-[5-(4-ethylpiperazin-1-yl)-1H-benzimidazol-2-yl]quinolin-2(1H)-one; 4-amino-3-(5-{(2S,5S)-2-[(dimethylamino)methyl]-5-methylmorpholin-4-yl}-1H-benzimidazol-2-yl)quinolin-2-(1H)-one; 4-amino-6-chloro-3-[5-(4-methylpiperazin-1-yl)-1H-benzimidazol-2-yl]quinolin-2(1H)-one; 4-amino-6-chloro-3-{5-[(3S)-3(dimethylamino)pyrrolidin-1-yl]-1H-benzimidazol-2-yl}quinolin-2(1H)-one; 4-amino-5,6-dichloro-3-{5-[(3S)-3-(dimethylamino)pyrrolidin-1-yl]-1H-benzimidazol-2-yl}quinolin-2(1H)-one; 4-amino-5,6-dichloro-3-[5-(4-methylpiperazin-1-yl)-1H-benzimidazol-2-yl]quinolin-2(1H )-one; 4-amino-3-(1H-benzimidazol-2-yl)-6-[(pyridin-2-ylmethyl)oxy]quinolin-2(1H)-one; 4-amino-3-(1H-benzimidazol-2-yl)-6-[(2R,6S)-2,6-dimethylmorpholin-4-yl]quinolin-2(1H)-one; 4-amino-3-(1H-benzimidazol-2-yl)-6-morpholin-4-ylquinolin-2(1H)-one; 4-amino-3-(1H-benzimidazol-2-yl)-5-[(1-methylpiperidin-3-yl)oxy]

quinolin-2(1H)-one; 4-amino-3-(1H-benzimidazol-2-yl)-5-[(pyridin-2-ylmethyl)oxy]quinolin-2(1H)-one; 4-amino-3-(5-morpholin-4-yl-1H-benzimidazol-2-yl)-5-[(pyridin-4-ylmethyl)oxy]quinolin-2(1H)-one; 4-amino-3-(1H-benzimidazol-2-yl)-5-(methyloxy)quinolin-2(1H)-one; 4-amino-3-(5-methyl-1H-benzimidazol-2-yl)-5-(methyloxy)quinolin-2(1H)-one; 4-amino-3-{5-[(2R,6S)-2,6-dimethylmorpholin-4-yl]-1H-benzimidazol-2-yl}-5-(methyloxy)quinolin-2(1H)-one; 4-amino-3-(1H-benzimidazol-2-yl)-5-morpholin-4-ylquinolin-2(1H)-one; 4-amino-3-(1H-benzimidazol-2-yl)-5-[(2R,6S)-2,6-dimethylmorpholin-4-yl]quinolin-2(1H)-one; 4-amino-3-(1H-benzimidazol-2-yl)-5-(4-methylpiperazin-1-yl)quinolin-2(1H)-one; 4-amino-5,6-dichloro-3-(5-morpholin-4-yl-1H-benzimidazol-2-yl)quinolin-2(1H)-one; 3-{5-[(2-morpholin-4-ylethyl)oxy]-1H-benzimidazol-2-yl}quinolin-2(1H)-one; 4-amino-3-{5-[(3-pyrrolidin-1-ylpropyl)oxy]-1H-benzimidazol-2-yl}quinolin-2(1H)-one; 4-amino-3-{5-[(3-morpholin-4-ylpropyl)oxy]-1H-benzimidazol-2-yl}quinolin-2(1H)-one; 4-amino-6-fluoro-3-(5-morpholin-4-yl-1H-benzimidazol-2-yl)quinolin-2(1H)-one; 4-amino-3-{5-[3-(dimethylamino)pyrrolidin-1-yl]-1H-benzimidazol-2-yl}-6-fluoroquinolin-2(1H)-one; 4-amino-3-(1H-benzimidazol-2-yl)-6-fluoroquinolin-2(1H)-one; 4-amino-3-(6-fluoro-5-morpholin-4-yl-1H-benzimidazol-2-yl)quinolin-2(1H)-one; 4-amino-3-{5-[(tetrahydrofuran-2-ylmethyl)oxy]-1H-benzimidazol-2-yl}quinolin-2(1H)-one; 4-amino-6-fluoro-3-(6-fluoro-5-morpholin-4-yl-1H-benzimidazol-2-yl)quinolin-2(1H)-one; 4-amino-3-[6-fluoro-5-(4-methylpiperazin-1-yl)-1H-benzimidazol-2-yl]quinolin-2(1H)-one; 4-amino-3-(5-{[2-(methyloxy)ethyl]oxy}-1H-benzimidazol-2-yl)quinolin-2(1H)-one; 4-amino-3-[4,6-difluoro-5-(4-methylpiperazin-1-yl)-1H-benzimidazol-2-yl]quinolin-2(1H)-one; 4-amino-3-{5-[3-(dimethylamino)pyrrolidin-1-yl]-1H-benzimidazol-2-yl}-5-fluoroquinolin-2(1H)-one; 4-amino-5-fluoro-3-[5-(4-methylpiperazin-1-yl)-1H-benzimidazol-2-yl]quinolin-2(1H)-one; 4-amino-5-chloro-3-[5-(4-methylpiperazin-1-yl)-1H-benzimidazol-2-yl]quinolin-2(1H)-one; 4-amino-3-{5-[3-(dimethylamino)pyrrolidin-1-yl]-6-fluoro-1H-benzimidazol-2-yl}quinolin-2(1H)-one; 4-amino-5-chloro-3-{5-[3-(dimethylamino)pyrrolidin-1-yl]-1H-benzimidazol-2-yl}quinolin-2(1H)-one; 4-amino-6-chloro-3-{5-[3-(dimethylamino)pyrrolidin-1-yl]-6-fluoro-1H-benzimidazol-2-yl}quinolin-2(1H)-one; 4-amino-5-[(2R,6S)-2,6-dimethylmorpholin-4-yl]-3-(3H-imidazo[4,5-b]pyridin-2-yl)quinolin-2(1H)-one; 4-amino-3-(6-thiomorpholin-4-yl-1H-benzimidazol-2-yl)quinolin-2(1H)-one; 4-amino-3-[5-(4-cyclohexylpiperazin-1-yl)-1H-benzimidazol-2-yl]quinolin-2(1H)-one; 4-amino-3-{6-[3-(diethylamino)pyrrolidin-1-yl]-1H-benzimidazol-2-yl}quinolin-2(1H)-one; 4-amino-3-[6-(4-pyridin-2-ylpiperazin-1-yl)-1H-benzimidazol-2-yl]quinolin-2(1H)-one; 4-amino-3-[5-(4-methylpiperazin-1-yl)-3H-imidazo[4,5-b]pyridin-2-yl]quinolin-2(1H)-one; 4-amino-6-chloro-3-[5-(4-methylpiperazin-1-yl)-1H-imidazo[4,5-b]pyridin-2-yl]quinolin-2(1H)-one; 2-(4-amino-2-oxo-1,2-dihydroquinolin-3-yl)-N-methyl-N-(1-methylpiperidin-4-yl)-1H-benzimidazole-5-carboxamide; 4-amino-3-(5-{[4-(1-methylethyl)piperazin-1-yl]carbonyl}-1H-benzimidazol-2-yl)quinolin-2(1H)-one; 4-amino-3-[5-(4-methylpiperazin-1-yl)-1H-benzimidazol-2-yl]-6-nitroquinolin-2(1H)-one; 4-amino-3-[5-(1,4'-bipiperidin-1'-ylcarbonyl)-1H-benzimidazol-2-yl]quinolin-2(1H)-one; 4-amino-3-{5-[(4-methylpiperazin-1-yl)carbonyl]-1H-benzimidazol-2-yl}quinolin-2(1H)-one; 4-amino-3-[5-(1-oxidothiomorpholin-4-yl)-1H-benzimidazol-2-yl]quinolin-2(1H)-one; 3-{5-[(4-acetylpiperazin-1-yl)carbonyl]-1H-benzimidazol-2-yl}-4-aminoquinolin-2(1H)-one; 4-amino-3-(5-{[(3R)-3-(dimethylamino)pyrrolidin-1-yl]carbonyl}-1H-benzimidazol-2-yl)quinolin-2(1H)-one; 4-amino-3-(5-{[(3S)-3-(dimethylamino)pyrrolidin-1-yl]carbonyl}-1H-benzimidazol-2-yl)quinolin-2(1H)-one; 4-amino-3-(5-{[4-(dimethylamino)piperidin-1-yl]carbonyl}-1H-benzimidazol-2-yl)quinolin-2(1)H-one; methyl 2-(4-amino-5-fluoro-2-oxo-1,2-dihydroquinolin-3-yl)-1H-benzimidazole-6-carboxylate; 4-amino-3-[5-(1,3'-bipyrrolidin-1'-yl)-1H-benzimidazol-2-yl]quinolin-2(1H)-one; 4-amino-3-[5-(pyridin-3-yloxy)-1H-benzimidazol-2-yl]quinolin-2(1H)-one; 4-amino-5,6-bis(methyloxy)-3-[5-(4-methylpiperazin-1-yl)-1H-benzimidazol-2-yl]quinolin-2(1H)-one; 2-(4-amino-2-oxo-1,2-dihydroquinolin-3-yl)-N-[2-(dimethylamino)ethyl]-N-methyl-1H-benzimidazole-5-carboxamide; 2-(4-amino-2-oxo-1,2-dihydroquinolin-3-yl)-N-methyl-N-(1-methylpyrrolidin-3-yl)-1H-benzimidazole-5-carboxamide; 4-amino-3-{5-[(5-methyl-2,5-diazabicyclo[2.2.1]hept-2-yl)carbonyl]-1H-benzimidazol-2-yl}quinolin-2(1H)-one; 4-amino-3-{5-[(4-cyclohexylpiperazin-1-yl)carbonyl]-1H-benzimidazol-2-yl}quinolin-2(1H)-one; 4-amino-3-{5-[(2-piperidin-1-ylethyl)amino]-1H-benzimidazol-2-yl}quinolin-2(1H)-one; ethyl 4-{[2-(4-amino-2-oxo-1,2-dihydroquinolin-3-yl)-1H-benzimidazol-5-yl]amino}piperidine-1-carboxylate; 4-amino-3-[5-({(5R)-5-[(methyloxy)methyl]pyrrolidin-3-yl}amino)-1H-benzimidazol-2-yl]quinolin-2(1H)-one; 4-amino-3-{5-[(pyridin-2-ylmethyl)amino]-1H-benzimidazol-2-yl}quinolin-2(1H)-one; 4-amino-3-[5-(piperidin-3-ylamino)-1H-benzimidazol-2-yl]quinolin-2(1H)-one; 4-amino-5-fluoro-3-{5-[(pyridin-2-ylmethyl)amino]-1H-benzimidazol-2-yl}quinolin-2(1H)-one; ethyl 4-{[2-(4-amino-5-fluoro-2-oxo-1,2-dihydroquinolin-3-yl)-1H-benzimidazol-5-yl]amino}piperidin-1-carboxylate; 4-amino-5-fluoro-3-[5-(piperidin-3-ylamino)-1H-benzimidazol-2-yl]quinolin-2(1H)-one; 4-amino-3-(1H-benzimidazol-2-yl)-6-bromoquinolin-2(1H)-one; 4-amino-3-(1H-benzimidazol-2-yl)-7-bromoquinolin-2(1H)-one; 4-amino-3-(5-bromo-1H-benzimidazol-2-yl)quinolin-2(1H)-one; N,N-dimethyl-2-(2-oxo-1,2-dihydroquinolin-3-yl)-1H-benzimidazole-5-carboxamide; 4-amino-3-(5-thien-2-yl-1H-benzimidazol-2-yl)quinolin-2(1H)-one; 2-(4-amino-2-oxo-1,2-dihydroquinolin-3-yl)-N,N-dimethyl-1H-benzimidazole-5-sulfonamide; 4-amino-6-iodo-3-[5-(4-methylpiperazin-1-yl)-1H-benzimidazol-2-yl]quinolin-2(1H)-one; 4-amino-3-(5-{2-[(dimethylamino)methyl]morpholin-4-yl}-1H-benzimidazol-2-yl)quinolin-2(1H)-one; 4-[(3R)-1-azabicyclo[2.2.2]oct-3-ylamino]-3-(1H-benzimidazol-2-yl)-7-chloro-6-iodoquinolin-2(1H)-one; 4-[(3R)-1-azabicyclo[2.2.2]oct-3-ylamino]-3-(1H-benzimidazol-2-yl)-6-nitroquinolin-2(1H)-one; 4-[(3R)-1-azabicyclo[2.2.2]oct-3-ylamino]-3-(1H-benzimidazol-2-yl)-6-methylquinolin-2(1H)-one; 4-[(3R)-1-azabicyclo[2.2.2]oct-3-ylamino]-3-(1H-benzimidazol-2-yl)-6,7-difluoroquinolin-2(1H)-one; 4-[(3S)-1-azabicyclo[2.2.2]oct-3-ylamino]-3-(1H-benzimidazol-2-yl)-7- chloroquinolin-2(1H)-one; 4-[(3R)-1-azabicyclo[2.2.2]oct-3-ylamino]-3-(1H-benzimidazol-2-yl)-6-bromoquinolin-2-(1H)-one; 4-[(3R)-1-azabicyclo[2.2.2]oct-3-ylamino]-3-(1H-benzimidazol-2-yl)-2-oxo-1,2-dihydroquinoline-6-carbonitrile; 4-[(3R)-1-azabicyclo[2.2.2]oct-3-ylamino]-3-(1H-benzimidazol-2-yl)-6-fluoroquinolin-2(1H)-one; 4-[(3S)-1-azabicyclo[2.2.2]oct-3-ylamino]-3-(1H-benzimidazol-2-yl)-6,7-bis(methyloxy)quinolin-2(1H)-one; 4-[(3R)-1-azabicyclo[2.2.2]oct-3-ylamino]-3-(1H-benzimidazol-2-yl)-6,7-dichloroquinolin-2(1H)-one; 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-4-carboxamide; 4-[(3S)-1-azabicyclo[2.2.2]oct-3-ylamino]-3-(1H-benzimidazol-2-yl)-6-fluoro-7-[(3-hydroxypropyl)amino]quinolin-2(1H)-one; 4-[(3S)-1-azabicyclo[2.2.2]oct-3-ylamino]-3-(1H-benzimidazol-2-yl)-7-(dimethylamino)-6-fluoroquinolin-2(1H)-one; 4-[(3R)-1-azabicyclo[2.2.2]oct-3-ylamino]-3-(1H-benzimidazol-2-yl)-5-fluoroquinolin-2(1H)-one; 4-[(3R)-1-azabicyclo[2.2.2]oct-3-ylamino]-3-(1H-benzimidazol-2-yl)-6-(4-nitrophenyl)quinolin-2(1H)-one; 4-[(3S)-1-azabicyclo[2.2.2]oct-3-ylamino]-3-(1H-benzimidazol-2-yl)-7-{[2-(dimethylamino)ethyl]amino}-6-fluoroquinolin-2(1H)-one; 4-[(3S)-1-azabicyclo[2.2.2]oct-3-ylamino]-3-(1H-benzimidazol-2-yl)-6-fluoro-7-(1H-imidazol-1-yl)quinolin-2(1H)-one; 4-[(3R)-1-azabicyclo[2.2.2]oct-3-ylamino]-3-(1H-benzimidazol-2-yl)-6-[4-(methyloxy)phenyl]quinolin-2(1H)-one; 4-[(3S)-1-azabicyclo[2.2.2]oct-3-ylamino]-3-(1H-benzimidazol-2-yl)-6-fluoro-7-morpholin-4-ylquinolin-2(1H)-one; 4-[(3R)-1-azabicyclo[2.2.2]oct-3-ylamino]-6,7-difluoro-3-(3H-imidazo[4,5-b]pyridin-2-yl)quinolin-2(1H)-one; 4-[(3R)-1-azabicyclo[2.2.2]oct-3-ylamino]-3-(1H-benzimidazol-2-yl)-6-(3-nitrophenyl)quinolin-2(1H)-one; 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-3-carboxamide; 4-[(3S)-1-azabicyclo[2.2.2]oct-3-ylamino]-3-(1H-benzimidazol-2-yl)-5-methylquinolin-2(1H)-one; 6-(3-acetylphenyl)-4-[(3R)-1-azabicyclo[2.2.2]oct-3-ylamino]-3-(3H-imidazo[4,5-b]pyridin-2yl)quinolin-2(1H)-one; 4-[(3S)-1-azabicyclo[2.2.2]oct-3-ylamino]-3-(1H-benzimidazol-2-yl)-5-chloroquinolin-2(1H)-one; 4-[(3R)-1-azabicyclo[2.2.2]oct-3-ylamino]-6-fluoro-3-(3H-imidazo[4,5-b]pyridin-2-yl)-7-morpholin-4-ylquinolin-2(1H)-one; 4-[(3S)-1-azabicyclo[2.2.2]oct-3-ylamino]-3-(1H-benzimidazol-2-yl)-7-(cyclopropylamino)-6-fluoroquinolin-2(1H)-one; N-{3-[4-[(3R)-1-azabicyclo[2.2.2]oct-3-ylamino]-3-(3H-imidazo[4,5]pyridin-2yl)-2-oxo-1,2-dihydroquinolin-6-yl]phenyl}acetamide; 4-[(3S)-1-azabicyclo[2.2.2]oct-3-ylamino]-3-(1H-benzimidazol-2-yl)-6-fluoro-7-(4-methylpiperazin-1-yl)quinolin-2(1H)-one; 4-[(3R)-1-azabicyclo[2.2.2]oct-3-ylamino]-6-fluoro-7-(1H-imidazol-1-yl)-3-(3H-imidazo[4,5-b]pyridin-2-yl)quinolin-2(1H)-one; 4-[(3S)-1-azabicyclo[2.2.2]oct-3-ylamino]-3-(1H-benzimidazol-2-yl)-6-fluoro-7-[(2-pyridin-2-ylethyl)amino]quinolin-2(1H)-one; 4-[(3S)-1-azabicyclo[2.2.2]oct-3-ylamino]-3-(1H-benzimidazol-2-yl)-6-fluoro-7-piperidin-1-ylquinolin-2(1H)-one; 6-chloro-3-(3H-imidazo[4,5-b]pyridin-2-yl)quinolin-2(1H)-one; ethyl 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-4-carboxylate; 4-[(3R)-1-azabicyclo[2.2.2]oct-3-ylamino]-3-(1H-benzimidazol-2-yl)-6-(1-benzothien-2-yl)quinolin-2(1H)-one; 4-[(3S)-1-azabicyclo[2.2.2]oct-3-ylamino]-3-(1H-benzimidazol-2-yl)-6-fluoro-7-pyrrolidin-1-ylquinolin-2(1H)-one; 4-[(3R)-1-azabicyclo[2.2.2]oct-3-ylamino]-3-(3H-imidazo[4,5-b]pyridin-2-yl)-6-[2-(trifluoromethyl)phenyl]quinolin-2(1H)-one; 4-[(3R)-1-azabicyclo[2.2.2]oct-3-ylamino]-3-(3H-imidazo[4,5-b]pyridin-2-yl)-6-[2-(methyloxy)phenyl]quinolin-2(1H)-one; ethyl 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-3-carboxylate; 4-[(3R)-1-azabicyclo[2.2.2]oct-3-ylamino]-3-(1H-benzimidazol-2-yl)-6-(4-ethylphenyl)quinolin-2(1H)-one; 4-[(3S)-1-azabicyclo[2.2.2]oct-3-ylamino]-3-(1H-benzimidazol-2-yl)-6-fluoro-7-[(2-methylpropyl)amino]quinolin-2(1H)-one; 4-[(3R)-1-azabicyclo[2.2.2]oct-3-ylamino]-3-(1H-benzimidazol-2-yl)-5-methylquinolin-2(1H)-one; 4-[(3R)-1-azabicyclo[2.2.2]oct-3-ylamino]-6-(2,4-dichlorophenyl)-3-(3H-imidazo[4,5-b]pyridin-2-yl)quinolin-2(1H)-one; 4-[(3R)-1-azabicyclo[2.2.2]oct-3-ylamino]-3-(1H-benzimidazol-2-yl)-6-[3-(trifluoromethyl)phenyl]quinolin-2(1H)-one; 3-(1H-benzimidazol-2-yl)-4-(dimethylamino)quinolin-2(1H)-one; 4-hydroxy-3-(1H-imidazo[4,5-f]quinolin-2-yl)quinolin-2(1H)-one; 4-hydroxy-3-(1H-imidazo[4,5-b]pyridin-2-yl)quinolin-2(1H)-one; 4-[4-[(3R)-1-azabicyclo[2.2.2]oct-3-ylamino]-3-(1H-benzimidazol-2-yl)-5-fluoro-2-oxo-1,2-dihydroquinolin-6-yl]benzoic acid; 4-[4-[(3R)-1-azabicyclo[2.2.2]oct-3-ylamino]-3-(1H-benzimidazol-2-yl)-5-fluoro-2-oxo-1,2-dihydroquinolin-6-yl-]benzamide; N-{3-[4-[(3R)-1-azabicyclo[2.2.2]oct-3-ylamino]-3-(1H-benzimidazol-2-yl)-5-fluoro-2-oxo-1,2-dihydroquinolin-6-yl]phenyl}acetamide; 3-[4-[(3R)-1-azabicyclo[2.2.2]oct-3-ylamino]-3-(1H-benzimidazol-2-yl)-5-fluoro-2-oxo-1,2-dihydroquinolin-6-yl]benzoic acid; 4-[4-[(3R)-1-azabicyclo[2.2.2]oct-3-ylamino]-3-(1H-benzimidazol-2-yl)-7-fluoro-2-oxo-1,2-dihydroquinolin-6-yl]benzoic acid; N-{3-[4-[(3R)-1-azabicyclo[2.2.2]oct-3-ylamino]-3-(1H-benzimidazol-2-yl)-7-fluoro-2-oxo-1,2-dihydroquinolin-6-yl]phenyl}acetamide; 4-[(3R)-1-azabicyclo[2.2.2]oct-3-ylamino]-3-(1H-benzimidazol-2-yl)-7-chloro-6-(2-methylphenyl)quinolin-2(1H)-one; 4-[(3R)-1-azabicyclo[2.2.2]oct-3-ylamino]-3-(1H-benzimidazol-2-yl)-2-oxo-1,2-dihydroquinolin-7-carbonitrile; 4-[(3R)-1-azabicyclo[2.2.2]oct-3-ylamino]-3-(1H-benzimidazol-2-yl)-7-(methyloxy)quinolin-2(1H)-one; 4-[4-[(3R)-1-azabicyclo[2.2.2]oct-3-ylamino]-3-(1H-benzimidazol-2-yl)-2-oxo-1,2-dihydroquinolin-7-yl]benzamide; 4-[(3R)-1-azabicyclo[2.2.2]oct-3-ylamino]-3-(1H-benzimidazol-2-yl)-6-fluoro-7-(methyloxy)quinolin-2(1H)-one; 4-[(3R)-1-azabicyclo[2.2.2oct-3-ylamino]-3-(1H-benzimidazol-2-yl)-6-chloro-7-(dimethylamino)quinolin-2(1H)-one; 4-[(3R)-1-azabicyclo[2.2.2]oct-3-ylamino]-3-(1H-benzimidazol-2-yl)-7-(dimethylamino)-6-iodoquinolin-2(1H)-one; 3-[4-[(3R)-1-azabicyclo[2.2.2]oct-3-ylamino]-3-(1H-benzimidazol-2-yl)-7-(1H-imidazol-1-yl)-2-oxo-1,2-dihydroquinolin-6-yl]benzoic acid; 4-[4-[(3R)-1-azabicyclo[2.2.2]oct-3-ylamino]-3-(1H-benzimidazol-2-yl)-2-oxo-7-piperidin-1-yl-1,2-dihydroquinolin-6-yl]benzoic acid; 4-[(3R)-1-azabicyclo[2.2.2]oct-3-ylamino]-3-(1H-benzimidazol-2-yl)-7-(methyloxy)-6-[4-(methylsulfonyl)phenyl]quinolin-2(1H)-one; 4-[(3R)-1-azabicyclo[2.2.2]oct-3-ylamino]-3-(1H-benzimidazol-2-yl)-8-methylquinolin-2(1H)- one; 4-[(3S)-1-azabicyclo[2.2.2]oct-3-ylamino]-3-(1H-benzimidazol-2-yl)-6,7-difluoroquinolin-2(1H)-one; 3-(1H-benzimidazol-2-yl)-6-methyl4-(piperidin-3-ylamino)quinolin-2(1H)-one; 4-[(3S)-1-azabicyclo[2.2.2]oct-3-ylamino]-3-(1H-benzimidazol-2-yl)-6-[2-(methyloxy)phenyl]quinolin-2(1H)-one; 4-[(3S)-1-azabicyclo[2.2.2]oct-3-ylamino]-3-(1H-benzimidazol-2-yl)-6-[3-(methyloxy)phenyl]quinolin-2(1H)-one; 3-(1H-benzimidazol-2-yl)-6,7-difluoro-4-(piperidin-4-ylamino)quinolin-2(1H)-one; 3-(1H-benzimidazol-2-yl)-6,7-difluoro-4-(pyrrolidin-3-ylamino)quinolin-2(1H)-one; 3-(1H-benzimidazol-2-yl)-6-chloro-4-[(3-morpholin-4-ylpropyl)amino]quinolin-2(1H)-one; 6-chloro-3-(5-morpholin-4-yl-1H-benzimidazol-2-yl)-4-(piperidin-4-ylamino)quinolin-2(1H)-one; 6-chloro-3-(5-morpholin-4-yl-1H-benzimidazol-2-yl)-4-[(piperidin-2-ylmethyl)amino]quinolin-2(1H)-one; 4-[(3S)-1-azabicyclo[2.2.2]oct-3-ylamino]-6-chloro-3-(5-morpholin-4-yl-1H-benzimidazol-2-yl)quinolin-2(1H)-one; 6-chloro-3-(5-morpholin-4-yl-1H-benzimidazol-2-yl)-4-(piperidin-3-ylamino)quinolin-2(1H)-one; 6-chloro-4-{[2-(dimethylamino)ethyl]amino}-3-(5-morpholin-4-yl-1H-benzimidazol-2-yl)quinolin-2(1H)-one; 4-[(3R)-1-azabicyclo[2.2.2]oct-3-ylamino]-6-chloro-3-(5-morpholin-4-yl-1H-benzimidazol-2-yl)quinolin-2(1H)-one; 6-chloro-3-(5-morpholin-4-yl-1H-benzimidazol-2-yl)-4-[(piperidin-3-ylmethyl)amino]quinolin-2(1H)-one; 6-chloro-3-(5-morpholin-4-yl-1H-benzimidazol-2-yl)-4-[(piperidin-4-ylmethyl)amino]quinolin-2(1H)-one; 4-{[(1R,2R)-2-aminocyclohexyl]amino}-6-chloro-3-(5-morpholin-4-yl-1H-benzimidazol-2-yl)quinolin-2(1H)-one; 4-[(4-aminocyclohexyl)amino]-6-chloro-3-(5-morpholin-4-yl-1H-benzimidazol-2-yl)quinolin-2(1H)-one; 4-{[(2S)-2-amino-3-methylbutyl]amino}-6-chloro-3-(5-morpholin-4-yl-1H-benzimidazol-2-yl)quinolin-2(1H)-one; 4-({[4-(aminomethyl)phenyl]methyl}amino)-6-chloro-3-(5-morpholin-4-yl-1H-benzimidazol-2-yl)quinolin-2(1H)-one; 6-chloro-3-(5-morpholin-4-yl-1H-benzimidazol-2-yl)-4-[(pyrrolidin-2-ylmethyl)amino]quinolin-2(1H)-one; 4-{[(1R)-1-(aminomethyl)propyl]amino}-6-chloro-3-(5-morpholin-4-yl-1H-benzimidazol-2-yl)quinolin-2(1H)-one; 4-{[(1S)-2-amino-1-(phenylmethyl)ethyl]amino}-6-chloro-3-(5-morpholin-4-yl-1H-benzimidazol-2-yl)quinolin-2(1H)-one; 6-chloro-4-{[3-(4-methylpiperazin-1-yl)propyl]amino}-3-(5-morpholin-4-yl-1H-benzimidazol-2-yl)quinolin-2(1H)-one; 6-chloro-3-(5-morpholin-4-yl-1H-benzimidazol-2-yl)-4-{[1-(phenylmethyl)piperidin-4-yl]amino}quinolin-2(1H)-one; 6-chloro-3-(5-morpholin-4-yl-1H-benzimidazol-2-yl)-4-[(3-morpholin-4-ylpropyl)amino]quinolin-2(1H)-one; 6-chloro-3-(5-morpholin-4-yl-1H-benzimidazol-2-yl)-4-[(2-piperidin-1-ylethyl)amino]quinolin-2(1H)-one; 6-chloro-3-(5-morpholin-4-yl-1H-benzimidazol-2-yl)-4-[(pyridin-3-ylmethyl)amino]quinolin-2(1H)-one; 6-chloro-4-{[3-(1H-imidazol-1-yl)propyl]amino}-3-(5-morpholin-4-yl-1H-benzimidazol-2-yl)quinolin-2(1H)-one; 6-chloro-3-(5-morpholin-4-yl-1H-benzimidazol-2-yl)-4-[(pyridin-4-ylmethyl)amino]quinolin-2(1H)-one; 6-chloro-4-{[2-(methylamino)ethyl]amino}-3-(5-morpholin-4-yl-1H-benzimidazol-2-yl)quinolin-2(1H)-one; 6-chloro-4-{[(2-methyl-1-piperidin-4-yl-1H-benzimidazol-5-yl)methyl]amino}-3-(5-morpholin-4-yl-1H-benzimidazol-2-yl)quinolin-2(1H)-one; 6-chloro-3-(5-morpholin-4-yl-1H-benzimidazol-2-4-[(2-pyrrolidin-1-ylethyl)amino]quinolin-2(1H)-one; 6-chloro-3-(5-morpholin-4-yl-1H-benzimidazol-2-yl)-4-(pyrrolidin-3-ylamino)quinolin-2(1H)-one; 4-{[(1R,2R)-2-aminocyclohexyl]amino}-6-chloro-3-[5-(4-methylpiperazin-1-yl)-1H-benzimidazol-2-yl]quinolin-2(1H)-one; 4-[(4-aminocyclohexyl)amino]-6-chloro-3-[5-(4-methylpiperazin-1-yl)-1H-benzimidazol-2-yl]quinolin-2(1H)-one; 4-({[4-(aminomethyl)phenyl]methyl}amino)-6-chloro-3-[5-(4-methylpiperazin-1-yl)-1H-benzimidazol-2-yl]quinolin-2(1H)-one; 6-chloro-4-{[2-(methylamino)ethyl]amino}-3-[5-4-methylpiperazin-1-yl)-1H-benzimidazol-2-yl]quinolin-2(1H)-one; 6-chloro-3-[5-(4-methylpiperazin-1-yl)-1H-benzimidazol-2-yl]-4-{[3-(4-methylpiperazin-1-yl)propyl]amino}quinolin-2(1H)-one; 6-chloro-3-[5-(4-methylpiperazin-1-yl)-1H-benzimidazol-2-yl]-4-{[1-(phenylmethyl)piperidin-4-yl]amino}quinolin-2(1H)-one; 6-chloro-3-[5-(4-methylpiperazin-1-yl)-1H-benzimidazol-2-yl]-4-[(2-pyrrolidin-1-ylethyl)amino]quinolin-2(1H)-one; 6-chloro-3-[5-(4-methylpiperazin-1-yl)-1-benzimidazol-2-yl]-4-(pyrrolidin-3-ylamino)quinolin-2(1H)-one; 6-chloro-3-[5-(4-methylpiperazin-1-yl)-1H-benzimidazol-2-yl]-4-(piperidin-4-ylamino)quinolin-2(1H)-one; 6-chloro-3-(5-morpholin-4-yl-1H-benzimidazol-2-yl)-4-[(2-piperidin-2-ylethyl)amino]quinolin-2(1H)-one; 4-[(3S)-1-azabicyclo[2.2.2]oct-3-ylamino]-7-chloro-3-(5-morpholin-4-yl-1H-benzimidazol-2-yl)quinolin-2(1H)-one; 7-chloro-3-(5-morpholin-4-yl-1H-benzimidazol-2-yl)-4-(piperidin-3-ylamino)quinolin-2(1H)-one; 6-chloro-3-[5-(4-methylpiperazin-1-yl)-1H-benzimidazol-2-yl]-4-[(piperidin-2-ylmethyl)amino]quinolin-2(1H)-one; 6-chloro-3-[5-(4-methylpiperazin-1-yl)-1H-benzimidazol-2-yl]-4-{[(2S)-pyrrolidin-2-ylmethyl]amino}quinolin-2-(1H)-one; 6-chloro-3-[5-(4-methylpiperazin-1-yl)-1H-benzimidazol-2-yl]-4-{[(2R)-pyrrolidin-2-ylmethyl]amino}quinolin-2(1H)-one; 6-chloro-4-({[(2S)-1-ethylpyrrolidin-2-yl]methyl}amino)-3-[5-(4-methylpiperazin-1-yl)-1H-benzimidazol-2-yl]quinolin-2(1H)-one; 6-chloro-4-({[(2R)-1-ethylpyrrolidin-2-yl]methyl}amino)-3-[5-(4-methylpiperazin-1-yl)-1H-benzimidazol-2-yl]quinolin-2(1H)-one; 4-[(3S)-1-azabicyclo[2.2.2]oct-3-ylamino]-3-(1H-benzimidazol-2-yl)-6-[4-(methyloxy)phenyl]quinolin-2(1H)-one; and 6-(3-aminophenyl)-4-[(3S)-1-azabicyclo[2.2.2]oct-3-ylamino]-3-(1H-benzimidazol-2-yl)quinolin-2(1H)-one.

In some embodiments, the invention provides: a method of inhibiting a serine/threonine kinase or a tyrosine kinase, the tyrosine kinase selected from Fyn, Lck, c-Kit, c-ABL, p60src, FGFR3, VEGFR3, PDGFRα, PDGFRβ, FLT-3, or Tie-2; a method of treating a biological condition mediated by a serine/threonine kinase or a tyrosine kinase, the tyrosine kinase selected from Fyn, Lck, c-Kit, c-ABL, p60src, FGFR3, VEGFR3, PDGFRα, PDGFRβ, FLT-3, or Tie-2; and the use in the manufacture of a medicament for inhibiting, or treating a biological condition mediated by, a serine/threonine kinase or a tyrosine kinase, the tyrosine kinase selected from Fyn, Lck, c-Kit, c-ABL, p60src, FGFR3, VEGFR3, PDGFRα, PDGFRβ, FLT-3, or Tie-2. In such embodiments, the compound is selected from one of the above-listed compounds, a tautomer of the compound, a pharmaceutically acceptable salt of the compound, a pharmaceutically acceptable salt of the tautomer, an enantiomer or diastereomer of the compound, an enantiomer or diastereomer of the tautomer, an enantiomer or diastereomer of the pharmaceutically acceptable salt of the compound, an enantiomer or diastereomer of the pharmaceutically acceptable salt of the tautomer, or a mixture of the compounds, enantiomers, tautomers, or salts. In some such embodiments, the invention provides the compound, the tautomer of the compound, the pharmaceutically acceptable salt of the compound, or the pharmaceutically acceptable salt of the tautomer, or mixtures thereof. The invention further provides methods for inhibiting any of the serine/threonine kinases described herein utilizing these compounds and methods of treating biological conditions mediated by any of the serine/threonine kinases utilizing these compounds.

It is understood that the invention is not limited to the embodiments set forth herein for illustration, but embraces all such forms thereof as come within the scope of the following claims.

What is claimed is:

1. A method of treating cancer comprising: administering to a cancer patient an effective amount of a compound of Structure I, a tautomer of the compound, a pharmaceutically acceptable salt of the compound, a pharmaceutically acceptable salt of the tautomer, or mixtures thereof, wherein the cancer is selected from hematologic cancers, acute myelogenous leukemia, ovarian carcinoma, breast carcinoma, lung cancer, colon cancer, prostate cancer, pituitary cancer, chronic myelogenous leukemia, or acute lymphoblastic leukemia, and Structure I has the following formula:

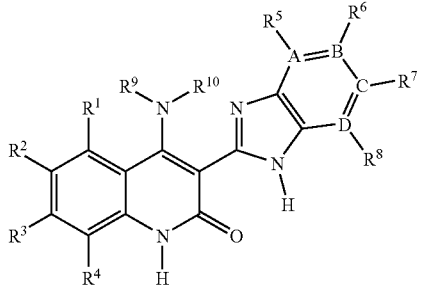

wherein,

A, B, C, and D are all carbon or one of A or D is nitrogen, and B and C are both carbon;

$R^1$ is selected from the group consisting of —H, —F, —Cl, —Br, —I, substituted and unsubstituted straight and branched chain alkyl groups having from 1 to 8 carbon atoms, substituted and unsubstituted cycloalkyl groups, substituted and unsubstituted heterocyclyl groups, substituted and unsubstituted heterocyclylalkyl groups, substituted and unsubstituted alkoxy groups, substituted and unsubstituted heterocyclyloxy groups, or substituted and unsubstituted heterocyclylalkoxy groups;

$R^2$ is selected from —H, —F, —Cl, —Br, —I, —NO$_2$, —CN, substituted and unsubstituted straight and branched chain alkyl groups having from 1 to 12 carbon atoms, substituted and unsubstituted cycloalkyl groups, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted heterocyclylalkoxy groups, —NH$_2$, substituted and unsubstituted —N(H)(alkyl) groups, substituted and unsubstituted —N(alkyl)$_2$ groups, —C(=O)—NH$_2$, substituted and unsubstituted —C(=O)—N(H)

(aryl) groups, substituted and unsubstituted —C(=O)—N(alkyl)(aryl) groups, substituted and unsubstituted —C(=O)—N(aryl)$_2$ groups, substituted and unsubstituted —C(=O)—N(H)(aralkyl) groups, substituted and unsubstituted —C(=O)—N(alkyl)(aralkyl) groups, substituted and unsubstituted —C(=O)—N(aralkyl)$_2$ groups, or —CO$_2$H;

$R^3$ is selected from —H, —F, —Cl, —Br, —I, —CN, substituted and unsubstituted straight or branched chain alkyl groups having from 1 to 8 carbon atoms, substituted and unsubstituted cycloalkyl groups, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted heterocyclyloxy groups, substituted and unsubstituted heterocyclylalkoxy groups, substituted and unsubstituted —N(H)(alkyl) groups, substituted and unsubstituted —N(alkyl)$_2$ groups, or substituted and unsubstituted —N(H)(heterocyclylalkyl) groups;

$R^4$ is selected from the group consisting of —H and substituted and unsubstituted alkyl groups having from 1 to 12 carbon atoms;

$R^5$ and $R^8$ are independently selected from —H, —F, —OH, or saturated heterocyclyl groups; or $R^5$ is absent if A is nitrogen; or $R^8$ is absent if D is nitrogen;

$R^6$ and $R^7$ are independently selected from —H, —F, —Cl, —Br, —I, —CN, substituted and unsubstituted straight and branched chain alkyl groups having from 1 to 8 carbon atoms, substituted and unsubstituted heterocyclyl groups, substituted and unsubstituted heterocyclylalkyl groups, substituted and unsubstituted —S(=O)$_2$—N(H)(alkyl) groups, substituted and unsubstituted —S(=O)$_2$—N(alkyl)$_2$ groups, —OH, substituted and unsubstituted alkoxy groups, substituted and unsubstituted heterocyclyloxy groups, substituted and unsubstituted heterocyclylalkoxy groups, substituted and unsubstituted —N(H)(alkyl) groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(H)(heterocyclylalkyl) groups, substituted and unsubstituted —N(alkyl)(heterocyclylalkyl) groups, substituted and unsubstituted —C(=O)—heterocyclyl groups, substituted and unsubstituted —C(=O)—N(H)(alkyl) groups, substituted and unsubstituted —C(=O)—N(alkyl)$_2$ groups, substituted and unsubstituted —C(=O)—N(H)(heterocyclyl) groups, or substituted and unsubstituted —C(=O)—N(alkyl)(heterocyclyl) groups;

$R^9$ is selected from the group consisting of —H, substituted and unsubstituted alkyl groups having from 1 to 12 carbon atoms, substituted and unsubstituted alkenyl groups having from 1 to 12 carbons, substituted and unsubstituted aryl groups, substituted and unsubstituted aralkyl groups, substituted and unsubstituted heterocyclyl groups, substituted and unsubstituted heterocyclylalkyl groups, —OH, substituted and unsubstituted alkoxy groups, substituted and unsubstituted heterocyclyloxy groups, —NH$_2$, and substituted and unsubstituted heterocyclylaminoalkyl; and $R^{10}$ is —H.

2. The method of claim 1, wherein $R^9$ is H.

3. The method of claim 1, wherein $R^1$ is selected from —H, —F, —Cl, substituted and unsubstituted straight or branched chain alkoxy, substituted and unsubstituted piperidinyloxy, substituted and unsubstituted morpholinyl, or substituted and unsubstituted piperazinyl.

4. The method of claim 1, wherein $R^1$ is —F.

5. The method of claim 1, wherein $R^2$ is selected from —H, —F, —Cl, —Br, —I, methyl, methoxy, or —CO$_2$H.

6. The method of claim 1, wherein $R^3$ is selected from —H, —F, —Cl, —Br, methoxy, and dimethylamino groups.

7. The method of claim 1, wherein $R^4$ is selected from —H or —CH$_3$.

8. The method of claim 1, wherein $R^5$ and $R^8$ are independently selected from —H, —F, —OH, or saturated heterocyclyl groups; or $R^5$ is absent if A is nitrogen; or $R^8$ is absent if D is nitrogen.

9. The method of claim 1, wherein A and D are both carbon, $R^5$ is —H, and $R^8$ is —H.

10. The method of claim 1, wherein $R^6$ and $R^7$ are independently selected from —H, —F, —Cl, —CN, substituted and unsubstituted straight and branched chain alkyl groups having from 1 to 8 carbon atoms, substituted and unsubstituted pyrrolidinyl groups, substituted and unsubstituted morpholinyl groups, substituted and unsubstituted piperazinyl groups, substituted and unsubstituted diazepinyl groups, substituted and unsubstituted triazolyl groups, substituted and unsubstituted thiomorpholine 1-oxide groups, substituted and unsubstituted pyridinylalkyl groups, substituted and unsubstituted —S(=O)$_2$—N(alkyl)$_2$ groups, —OH, substituted and unsubstituted straight and branched chain alkoxy groups, substituted and unsubstituted heterocyclyloxy groups, substituted and unsubstituted heterocyclylalkoxy groups, substituted and unsubstituted —N(alkyl)$_2$ groups, substituted and unsubstituted —N(H)(heterocyclyl) groups, substituted and unsubstituted —N(alkyl)(heterocyclyl) groups, substituted and unsubstituted —N(H)(heterocyclylalkyl) groups, substituted and unsubstituted —C(=O)—N(alkyl)$_2$ groups, substituted and unsubstituted —C(=O)—N(alkyl)(piperidinyl) groups, substituted and unsubstituted —C(=O)-(morpholin-4-yl) groups, or substituted and unsubstituted —C(=O)-(piperazin-1-yl) groups; or $R^6$ is absent if B is nitrogen; or $R^7$ absent if C is nitrogen.

11. The method of claim 1, wherein the compound has the following formula:

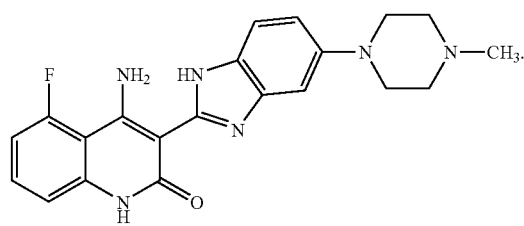

12. The method of claim 1, wherein the cancer is acute myelogenous leukemia, ovarian carcinoma, breast carcinoma, lung cancer, colon cancer, prostate cancer, or chronic myelogenous leukemia.

13. The method of claim 1, wherein the cancer is acute myelogenous leukemia.

14. The method of claim 12, wherein the compound has the following formula:

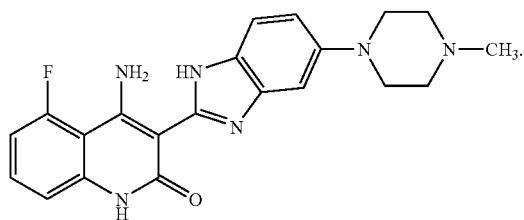

15. The method of claim 13, wherein the compound has the following formula:

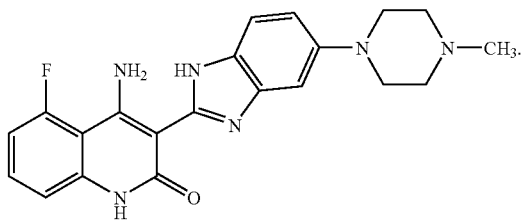

16. The method of claim 1, wherein the cancer is acute myelogenous leukemia, ovarian carcinoma, breast carcinoma, colon cancer, or prostate cancer.

17. The method of claim 11, wherein the cancer is acute myelogenous leukemia, ovarian carcinoma, breast carcinoma, colon cancer, or prostate cancer.

* * * * *

UNITED STATES PATENT AND TRADEMARK OFFICE
CERTIFICATE OF CORRECTION

| | | |
|---|---|---|
| PATENT NO. | : 7,470,709 B2 | Page 1 of 1 |
| APPLICATION NO. | : 10/644055 | |
| DATED | : October 19, 2003 | |
| INVENTOR(S) | : Barsanti et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 810 days.

Signed and Sealed this

Sixteenth Day of November, 2010

David J. Kappos
*Director of the United States Patent and Trademark Office*

```
SEQUENCE LISTING

<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His His His His His His
 1               5

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 2

Gly Gly Leu Phe Asp Asp Pro Ser Tyr Val Asn Val Gln Asn Leu
 1               5                  10                  15

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 3

Gly Gly Gly Gly Lys Val Glu Lys Ile Gly Glu Gly Thr Tyr Gly Val
 1               5                  10                  15

Val Tyr Lys

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)
<223> OTHER INFORMATION: phosphorylated Ser
<220> FEATURE:
<223> OTHER INFORMATION: c-term amidated
```

```
<400> SEQUENCE: 4

Ser Gly Ser Gly Lys Arg Arg Glu Ile Leu Ser Arg Arg Pro Ser Tyr
1               5                   10                  15

Arg

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: AHX
<220> FEATURE:
<223> OTHER INFORMATION: c-term amidated

<400> SEQUENCE: 5

Xaa Ser Gly Ser Gly Ser Gly Leu Tyr Arg Ser Pro Ser Met Pro Glu
1               5                   10                  15

Asn Leu Asn Arg Pro Arg
            20

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 6

Gly Gly Gly Gly Pro Lys Thr Pro Lys Lys Ala Lys Lys Leu
1               5                   10
```